United States Patent
Meng et al.

(10) Patent No.: US 12,221,442 B2
(45) Date of Patent: *Feb. 11, 2025

(54) HETEROCYCLIC GLP-1 AGONISTS

(71) Applicant: Gasherbrum Bio, Inc., South San Francisco, CA (US)

(72) Inventors: Qinghua Meng, Shanghai (CN); Weiqiang Xing, Shanghai (CN); Haizhen Zhang, Shanghai (CN); Xichen Lin, Shanghai (CN); Hui Lei, Shanghai (CN); Andrew Jennings, San Francisco, CA (US)

(73) Assignee: Gasherbrum Bio, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/424,580

(22) Filed: Jan. 26, 2024

(65) Prior Publication Data

US 2024/0246962 A1 Jul. 25, 2024

Related U.S. Application Data

(63) Continuation of application No. 17/950,073, filed on Sep. 21, 2022, now Pat. No. 11,926,626, which is a continuation of application No. PCT/CN2021/115064, filed on Aug. 27, 2021.

(30) Foreign Application Priority Data

Aug. 28, 2020 (WO) ................ PCT/CN2020/112149

(51) Int. Cl.
    C07D 471/04 (2006.01)
    A61K 45/06 (2006.01)
    C07D 405/14 (2006.01)
    C07D 417/14 (2006.01)

(52) U.S. Cl.
    CPC ............ C07D 471/04 (2013.01); A61K 45/06 (2013.01); C07D 405/14 (2013.01); C07D 417/14 (2013.01)

(58) Field of Classification Search
    CPC .................................................. C07D 471/04
    USPC ....................................................... 514/303
    See application file for complete search history.

(56) References Cited

U.S. PATENT DOCUMENTS

| | | | |
|---|---|---|---|
| 11,926,626 B2 * | 3/2024 | Meng | A61K 45/06 |
| 2008/0280933 A1 | 11/2008 | Efremov et al. | |
| 2018/0170908 A1 | 6/2018 | Aspnes et al. | |
| 2019/0276465 A1 | 9/2019 | Xu | |
| 2023/0071840 A1 | 3/2023 | Meng et al. | |
| 2023/0107793 A1 | 4/2023 | Meng et al. | |
| 2023/0165846 A1 | 6/2023 | Meng et al. | |
| 2023/0192633 A1 | 6/2023 | Meng et al. | |
| 2023/0295154 A1 | 9/2023 | Meng et al. | |

FOREIGN PATENT DOCUMENTS

| | | |
|---|---|---|
| CN | 108017636 | 5/2018 |
| CN | 108430998 | 8/2018 |
| CN | 109790161 | 5/2019 |
| CN | 110325530 | 10/2019 |
| CN | 113480534 | 10/2021 |
| CN | 113493447 | 10/2021 |
| CN | 113773310 | 12/2021 |
| CN | 113801136 | 12/2021 |
| CN | 113816948 | 12/2021 |
| CN | 113831337 | 12/2021 |
| CN | 114591296 | 6/2022 |
| CN | 114591308 | 6/2022 |
| CN | 114634510 | 6/2022 |
| CN | 114716423 | 7/2022 |
| CN | 114763352 | 7/2022 |
| CN | 114907351 | 8/2022 |
| CN | 115594669 A | 1/2023 |
| WO | WO 2008153701 | 12/2008 |
| WO | WO 2011/068821 | 6/2011 |
| WO | WO 2018/056453 A1 | 3/2018 |
| WO | WO 2018/109607 | 6/2018 |
| WO | WO 2019/239319 | 12/2019 |
| WO | WO 2019/239371 | 12/2019 |
| WO | WO 2020/103815 | 5/2020 |

(Continued)

OTHER PUBLICATIONS

American Chemical Society STN. RN 12901 10-76-7, 1228633-44-0, 1228554-41-3. STN Registry. May 4, 2011, 3 pages.
International Search Report and Written Opinion for PCT/CN2021/115064 dated Dec. 1, 2021, 12 pages.
GLP-1 Receptor Agonists—The Johns Hopkins Patient guide to Diabetes. Hopkinsdiabetesinfo.org/medications-for-type-2-diabetes-glp-1-agonists/. Retrieved May 15, 2023. 2 pages.

(Continued)

*Primary Examiner* — Niloofar Rahmani
(74) *Attorney, Agent, or Firm* — Sheppard Mullin Richter & Hampton LLP

(57) ABSTRACT

This disclosure relates to GLP-1 agonists of Formula (I), including pharmaceutically acceptable salts and solvates thereof, and pharmaceutical compositions including the same.

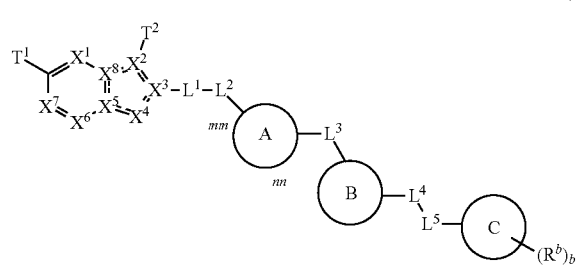

(I)

4 Claims, No Drawings

(56) References Cited

FOREIGN PATENT DOCUMENTS

| | | |  |  |
|---|---|---|---|---|
| WO | WO 2020/207474 | 10/2020 | | |
| WO | WO 2020/234726 | 11/2020 | | |
| WO | WO 2020/263695 | 12/2020 | | |
| WO | WO 2021/018023 | 2/2021 | | |
| WO | WO 2021/081207 | 4/2021 | | |
| WO | WO 2021/096304 | 5/2021 | | |
| WO | WO-2021096284 A1 * | 5/2021 | ......... | A61K 31/4439 |
| WO | WO 2021/112538 | 6/2021 | | |
| WO | WO 2021/154796 | 8/2021 | | |
| WO | WO 2021/160127 | 8/2021 | | |
| WO | WO 2021/187886 | 9/2021 | | |
| WO | WO 2021/197464 | 10/2021 | | |
| WO | WO 2021/219019 | 11/2021 | | |
| WO | WO 2021/244645 | 12/2021 | | |
| WO | WO 2021/249492 | 12/2021 | | |
| WO | WO 2021/254470 | 12/2021 | | |
| WO | WO 2022/007979 | 1/2022 | | |
| WO | WO 2022/028572 | 2/2022 | | |
| WO | WO 2022/031994 | 2/2022 | | |
| WO | WO 2022/040600 | 2/2022 | | |
| WO | WO 2022/068772 | 4/2022 | | |
| WO | WO 2022/078152 | 4/2022 | | |
| WO | WO 2022/078380 | 4/2022 | | |
| WO | WO 2022/078407 | 4/2022 | | |
| WO | WO 2022/109182 | 5/2022 | | |
| WO | WO 2022/111624 | 6/2022 | | |
| WO | WO 2022/135572 | 6/2022 | | |
| WO | WO 2022/165076 | 8/2022 | | |
| WO | WO 2022/192428 | 9/2022 | | |
| WO | WO 2022/192430 | 9/2022 | | |
| WO | WO 2022/199458 | 9/2022 | | |
| WO | WO 2022/199661 | 9/2022 | | |
| WO | WO 2022/202864 | 9/2022 | | |
| WO | WO 2022/216094 | 10/2022 | | |
| WO | WO 2022/219495 | 10/2022 | | |

OTHER PUBLICATIONS

Castro. GLP-1 Agonists: Diabetes drugs and weight loss. Mayo Clinic. Mayoclinic.org/diseaes-conditions/type-2-diabetes/expert-answers/byetta/faq-20057955. Jun. 29, 2022. 2 pages.

* cited by examiner

HETEROCYCLIC GLP-1 AGONISTS

CROSS REFERENCE TO RELATED APPLICATION

This application is a continuation of U.S. patent application Ser. No. 17/950,073, which is a continuation of International Patent Application Number PCT/CN2021/115064, filed on Aug. 27, 2021, which claims the benefit of International Patent Application Number PCT/CN2020/112149, filed on Aug. 28, 2020 which is incorporated herein by reference in its entirety.

TECHNICAL FIELD

This disclosure relates to GLP-1 agonists, pharmaceutical compositions, and methods of use thereof.

BACKGROUND

Incretin metabolic hormones, including glucagon-like peptide-1 (GLP-1) and glucose-dependent insulinotropic polypeptide (GIP), are important in the regulation of glucose homeostasis. Medicaments targeting this family of intestinal peptides, such as GLP-1 agonists, have been shown to suppress glucagon production, decrease gastric motility, and increase satiety.

Diabetes mellitus refers to a group of metabolic disorders characterized by persistent hyperglycemia. The most common form, type 2 diabetes mellitus (T2DM) is an acquired condition that accounts for more than 90% of diabetes cases. Typical onset occurs in obese or otherwise sedentary adults and begins with insulin resistance. Though lifestyle changes can be useful in management of this disorder, patients with T2DM may be required to take antidiabetic medications, including dipeptidyl peptidase-4 inhibitors, SGLT2 inhibitors, and sulfonylureas, among others.

In healthy individuals, the incretin hormones glucose-dependent insulinotropic polypeptide (GIP) and glucagon-like peptide 1 (GLP-1) provide tandem modulation of insulin secretory response to glucose ingestion. While this incretin effect is significantly diminished (if at all present) in cases of T2DM, GLP-1 retains insulinotropic properties, even as endocrine pancreatic response to GIP is effectively halted. As such, incretin mimetics and other GLP-1-based therapies can help stimulate insulin production in T2DM patients.

SUMMARY

The present application describes heterocyclic GLP-1 agonists, as well as pharmaceutical compositions comprising the compounds disclosed herein. Also provided are methods for treating GLP-1-associated diseases, disorders, and conditions.

Accordingly, provided herein are compounds of Formula I:

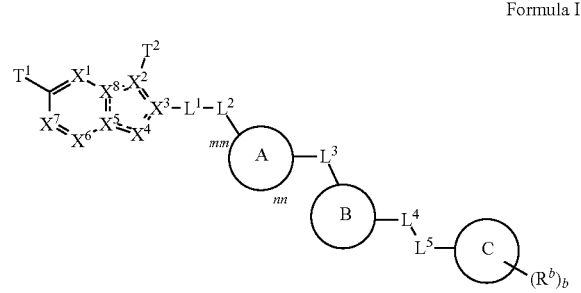

Formula I or a pharmaceutically acceptable salt or solvate thereof, wherein:

- -- indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;

$T^1$ is C(=O)OH or a carboxylic acid bioisostere;

$T^2$ is hydrogen or $(C_1$-$C_6)$alkyl which is optionally substituted with $(C_1$-$C_6)$alkoxy, $(C_1$-$C_6)$thioalkoxy, $(C_1$-$C_6)$haloalkoxy, $S(O)_2(C_1$-$C_6$ alkyl), $(C_3$-$C_6)$cycloalkyl, 3- to 6-membered heterocycloalkyl, phenyl, or 5- to 6-membered heteroaryl, wherein each of the $(C_3$-$C_6)$cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, $(C_1$-$C_6)$alkyl, $(C_2$-$C_6)$alkenyl, $(C_2$-$C_6)$alkynyl, $(C_1$-$C_6)$haloalkyl, $(C_1$-$C_6)$cyanoalkyl, $(C_1$-$C_6)$hydroxyalkyl, $(C_1$-$C_6)$alkoxy, $(C_1$-$C_6)$haloalkoxy, $(C_3$-$C_6)$cycloalkyl, amino, $(C_1$-$C_6)$alkylamino, and di$(C_1$-$C_6)$alkylamino;

$L^1$ is a bond or $(C_1$-$C_3)$alkylene which is optionally substituted with 1-3 $R^L$;

$L^2$ is a bond, —O—, —$S(O)_{0-2}$—, or —NH—;

each $R^L$ is independently selected from the group consisting of: halogen, $(C_1$-$C_3)$alkyl, and $(C_1$-$C_3)$haloalkyl; or a pair of $R^L$ on the same or on adjacent carbon atoms, taken together with the atom(s) to which each is attached, forms a $(C_3$-$C_6)$cycloalkyl ring;

Ring A is selected from the group consisting of: (A-1), (A-2), and (A-3):

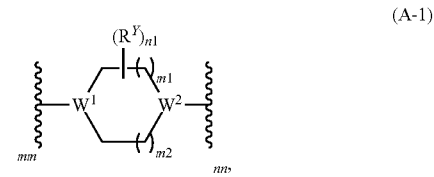

(A-1)

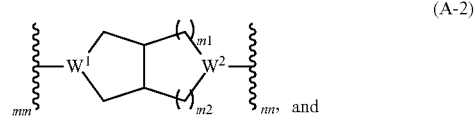

(A-2)

and

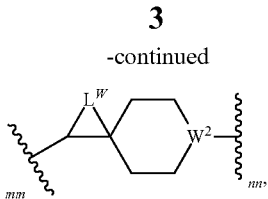

(A-3)

wherein mm represents the point of attachment to $L^2$, and nn represents the point of attachment to $L^3$;

n1 is 0, 1, or 2, m1 and m2 are independently 0 or 1;

$W^1$ is $CR^{Y1}$ or N, provided that when $L^2$ is —O—, —S—, or —N(H)—, then $W^1$ is $CR^{Y1}$;

$W^2$ is $CR^Y$ or N, provided that when $L^3$ is —O—, —S—, —N(H)—, or —N($C_{1-3}$ alkyl)-, then $W^2$ is $CR^{Y2}$;

further provided that when Ring A is (A-1), and at least one of m1 and m2 is 0, then $W^1$ and $W^2$ are not simultaneously N;

$L^w$ is ($C_1$-$C_3$)alkylene;

each occurrence of $R^Y$ is independently selected from the group consisting of halogen, CN, —OH, oxo, ($C_1$-$C_6$) alkyl, ($C_1$-$C_3$)haloalkyl, ($C_1$-$C_3$)alkoxy, and ($C_1$-$C_3$) haloalkoxy;

$R^{Y1}$ and $R^{Y2}$ are independently selected from the group consisting of hydrogen, halogen, CN, —OH, ($C_1$-$C_6$) alkyl, ($C_1$-$C_3$)haloalkyl, ($C_1$-$C_3$)alkoxy, and ($C_1$-$C_3$) haloalkoxy; or when $W^1$ is $CR^{Y1}$; and $W^2$ is $CR^{Y2}$, the $R^{Y1}$ and $R^{Y2}$ groups taken together form ($C_1$-$C_4$)alkylene, wherein one of the $CH_2$ units of the ($C_1$-$C_4$)alkylene is optionally replaced by a heteroatom selected from the group consisting of O, S, NH, and N($C_{1-3}$)alkyl;

$L^3$ is selected from the group consisting of: —O—; —S—; —C($R^aR^a$)—; —N(H)—; —N($C_{1-3}$ alkyl)-; —C(=O)—; and —S(O)$_{1-2}$—, each occurrence of $R^a$ is independently selected from the group consisting of: hydrogen, halogen, CN, —OH, ($C_1$-$C_6$)alkyl, ($C_1$-$C_3$)haloalkyl, ($C_3$-$C_8$)cycloalkyl, ($C_1$-$C_3$)alkoxy, and ($C_1$-$C_3$)haloalkoxy; or a pair of $R^a$ taken together with the carbon atom to which each is attached forms a ($C_3$-$C_8$)cycloalkyl ring; or when $W^2$ is $CR^{Y2}$; and $L^3$ is —C($R^aR^a$)—, one $R^a$ combines with $R^{Y2}$ to form a double bond between $W^2$ and $L^3$, wherein the remaining $R^a$ is selected from the group consisting of: hydrogen, halogen, CN, ($C_1$-$C_6$) alkyl, ($C_1$-$C_3$)haloalkyl, and ($C_3$-$C_8$)cycloalkyl;

Ring B is selected from the group consisting of: (B-I), (B-II), and (B-II):

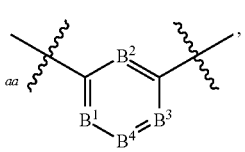

(B-I)

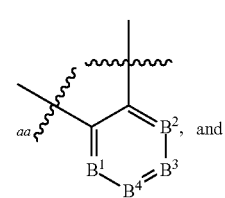

(B-II)

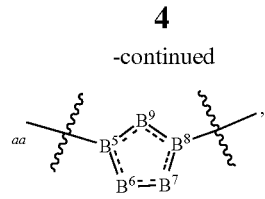

(B-III)

wherein aa represents the point of attachment to $L^3$;

each of $B^1$, $B^2$, $B^3$, and $B^4$ is independently selected from the group consisting of $CR^1$ and N;

each of $B^5$ and $B^8$ is independently selected from the group consisting of: C and N, provided that:

when $L^3$ is —O—, —S—, —N(H)—, or —N($C_{1-3}$ alkyl)-, and Ring B is (B-III), then $B^5$ is C, and when $L^4$ is —O—, —S—, —N(H)—, or —N($C_{1-3}$ alkyl)-, and Ring B is (B-III), then $B^8$ is C;

each of $B^6$, $B^7$, and $B^9$ is independently selected from the group consisting of: O, S, $CR^1$, NR, and N, each ═ (B-III) is independently a single bond or a double bond, provided that at least one of $B^5$, $B^6$, $B^7$, $B^8$, and $B^9$ is an independently selected heteroatom, at least one of $B^5$, $B^6$, $B^7$, $B^8$, and $B^9$ is C or $CR^1$, and the ring including $B^5$, $B^6$, $B^7$, $B^8$, and $B^9$ is heteroaryl;

each $R^1$ is selected from the group consisting of hydrogen, halogen, CN, ($C_1$-$C_6$)alkyl, ($C_1$-$C_6$)haloalkyl; ($C_1$-$C_3$) alkyl($C_3$-$C_6$)cycloalkyl, ($C_1$-$C_3$)alkyl(3- to 5-membered heterocycloalkyl), and —C(O)N$R^2R^3$;

each $R^2$ and $R^3$ is independently selected from the group consisting of hydrogen and ($C_1$-$C_6$)alkyl;

each RN is selected from the group consisting of hydrogen, ($C_1$-$C_6$)alkyl, ($C_1$-$C_6$)haloalkyl, C(=O)($C_1$-$C_6$) alkyl, S(O)$_2$($C_1$-$C_6$)alkyl, and C(=O)O($C_1$-$C_6$)alkyl;

$L^4$ is selected from the group consisting of: —C($R^cR^c$)—; —O—; —S—; —N(H)—; —N($C_{1-3}$ alkyl)-; —C(=O)—; and —S(O)$_{1-2}$—, $L^5$ is selected from the group consisting of: a bond; —C($R^cR^c$)—; —O—; —S—; —N(H)—; —N($C_{1-3}$ alkyl)-; —C(=O)—; and —S(O)$_{1-2}$—, provided that when $L^4$ is —O—, —S—, —N(H)—, or —N($C_{1-3}$ alkyl)-, then $L^5$ is a bond, —C($R^cR^c$)—, —C(=O)—, or —S(O)$_{1-2}$—, and provided that when $L^5$ is —O—, —S—, —N(H)—, or —N($C_{1-3}$ alkyl)-, then $L^4$ is —C($R^cR^c$)—, —C(=O), or —S(O)$_{1-2}$—, each occurrence of $R^c$ is independently selected from the group consisting of: hydrogen, halogen, CN, —OH, ($C_1$-$C_6$)alkyl, ($C_1$-$C_3$)haloalkyl, ($C_3$-$C_8$)cycloalkyl, ($C_1$-$C_3$)alkoxy, and ($C_1$-$C_3$)haloalkoxy; or a pair of $R^c$ taken together with the carbon atom to which each is attached forms a ($C_3$-$C_8$)cycloalkyl ring;

Ring C is selected from the group consisting of phenyl, 5- to 6-membered heteroaryl, ($C_3$-$C_6$)cycloalkyl, ($C_5$-$C_{10}$) bicycloalkyl, 5- to 10-membered bicycloheteroaryl, and 3- to 6-membered heterocycloalkyl;

each $R^b$ is independently selected from the group consisting of ($C_1$-$C_6$)alkyl, ($C_1$-$C_6$)haloalkyl, ($C_1$-$C_6$)alkoxy, ($C_1$-$C_6$)haloalkoxy, halogen, ($C_3$-$C_6$)cycloalkyl, and CN; and b is an integer selected from 0-3.

Further provided herein are compounds of Formula I:

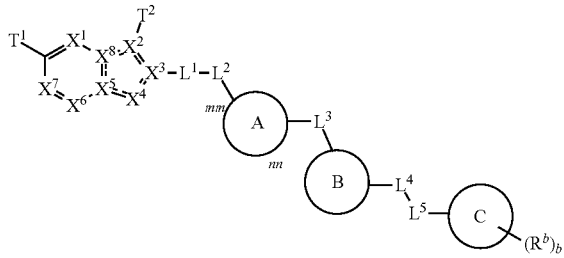

Formula I or a pharmaceutically acceptable salt or solvate thereof, wherein:

- ⌇ indicates an optional single or double bond, as allowed by valence;
- each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;
- $T^1$ is C(=O)OH, C(=O)NH$_2$, NHC(=O)—C$_1$-C$_6$ alkyl, or a carboxylic acid bioisostere;
- $T^2$ is hydrogen or (C$_1$-C$_6$)alkyl which is optionally substituted with (C$_1$-C$_6$)alkoxy, (C$_1$-C$_6$)thioalkoxy, (C$_1$-C$_6$)haloalkoxy, S(O)$_2$(C$_1$-C$_6$ alkyl), (C$_3$-C$_6$)cycloalkyl, 3- to 6-membered heterocycloalkyl, phenyl, or 5- to 6-membered heteroaryl, wherein each of the (C$_3$-C$_6$)cycloalkyl, 3- to 6-membered heterocycloalkyl, phenyl, or 5- to 6-membered heteroaryl is optionally substituted with 1-4 $R^T$;
- each $R^T$ is independently selected from the group consisting of OH, SH, CN, NO$_2$, halogen, (C$_1$-C$_6$)alkyl, (C$_2$-C$_6$)alkenyl, (C$_2$-C$_6$)alkynyl, (C$_1$-C$_6$)haloalkyl, (C$_1$-C$_6$)cyanoalkyl, (C$_1$-C$_6$)hydroxyalkyl, (C$_1$-C$_6$)alkoxy, (C$_1$-C$_6$)haloalkoxy, (C$_3$-C$_6$)cycloalkyl, amino, (C$_1$-C$_6$)alkylamino, and di(C$_1$-C$_6$)alkylamino;
- $L^1$ is a bond or (C$_1$-C$_3$)alkylene which is optionally substituted with 1-3 $R^L$;
- $L^2$ is a bond, —O—, —S(O)$_{0-2}$—, or —NH—;
- each $R^L$ is independently selected from the group consisting of: halogen, (C$_1$-C$_3$)alkyl, and (C$_1$-C$_3$)haloalkyl; or a pair of $R^L$ on the same or on adjacent carbon atoms, taken together with the atom(s) to which each is attached, forms a (C$_3$-C$_6$)cycloalkyl ring;
- Ring A is selected from the group consisting of (A-1), (A-2), (A-3), C$_6$-C$_{10}$ arylene, and 5-10 membered heteroarylene; wherein each of (A-1), (A-2), and (A-3) has the formula shown below:

(A-1)

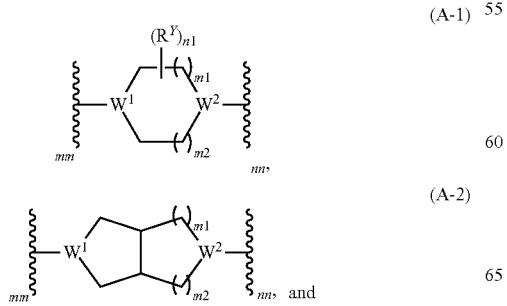

(A-2)

, and (A-3)

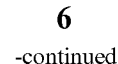

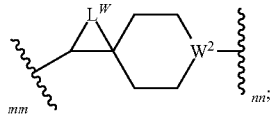

and wherein mm represents the point of attachment to $L^2$, and nn represents the point of attachment to U; and wherein the C$_6$-C$_{10}$ arylene, and 5-10 membered heteroarylene are each optionally substituted with 1-4 $R^T$,

- n1 is 0, 1, or 2; m1 and m2 are independently 0 or 1;
- $W^1$ is CR$^{Y1}$ or N, provided that when $L^2$ is —O—, —S—, or —N(H)—, then $W^1$ is CR$^{Y1}$;
- $W^2$ is CR$^{Y2}$ or N, provided that when $L^3$ is —O—, —S—, —N(H)—, or —N(C$_{1-3}$ alkyl)-, then $W^2$ is CR$^{Y1}$;
- further provided that when Ring A is (A-1), and at least one of m1 and m2 is 0, then $W^1$ and $W^2$ are not simultaneously N;
- $L^w$ is (C$_1$-C$_3$)alkylene;
- each occurrence of $R^Y$ is independently selected from the group consisting of halogen, CN, —OH, oxo, (C$_1$-C$_6$)alkyl, (C$_1$-C$_3$)haloalkyl, (C$_1$-C$_3$)alkoxy, and (C$_1$-C$_3$)haloalkoxy;
- $R^{Y1}$ and $R^{Y2}$ are independently selected from the group consisting of hydrogen, halogen, CN, —OH, (C$_1$-C$_6$)alkyl, (C$_1$-C$_3$)haloalkyl, (C$_1$-C$_3$)alkoxy, and (C$_1$-C$_3$)haloalkoxy; or
- when $W^1$ is CR$^{Y1}$; and $W^2$ is CR$^{Y2}$, the R$^{Y1}$ and R$^{Y2}$ groups taken together form (C$_1$-C$_4$)alkylene, wherein one of the CH$_2$ units of the (C$_1$-C$_4$)alkylene is optionally replaced by a heteroatom selected from the group consisting of O, S, NH, and N(C$_{1-3}$)alkyl;
- $L^3$ is selected from the group consisting of: —O—; —S—; —C(R$^a$R$^a$)—; —N(H)—; —N(C$_{1-3}$ alkyl)-; —C(=O)—; and —S(O)$_{1-2}$—,
- each occurrence of $R^a$ is independently selected from the group consisting of: hydrogen, halogen, CN, —OH, (C$_1$-C$_6$)alkyl, (C$_1$-C$_3$)haloalkyl, (C$_3$-C$_8$)cycloalkyl, (C$_1$-C$_3$)alkoxy, and (C$_1$-C$_3$)haloalkoxy; or
- a pair of R$^a$ taken together with the carbon atom to which each is attached forms a (C$_3$-C$_8$)cycloalkyl ring; or
- when $W^2$ is CR$^{Y2}$; and $L^3$ is —C(R$^a$R$^a$)—, one R$^a$ combines with R$^{Y2}$ to form a double bond between $W^2$ and $L^3$, wherein the remaining R$^a$ is selected from the group consisting of: hydrogen, halogen, CN, (C$_1$-C$_6$)alkyl, (C$_1$-C$_3$)haloalkyl, and (C$_3$-C$_8$)cycloalkyl;
- Ring B is selected from the group consisting of: (B-I), (B-II), and (B-III):

(B-I)

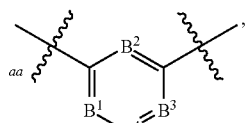

(B-II)

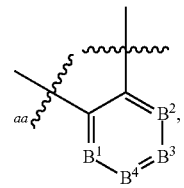

-continued

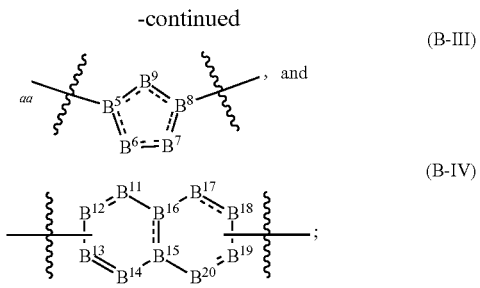

(B-III)

(B-IV)

wherein aa represents the point of attachment to $L^3$;
each of $B^1$, $B^2$, $B^3$, and $B^4$ is independently selected from the group consisting of $CR^1$ and N;
each of $B^5$ and $B^8$ is independently selected from the group consisting of C and N, provided that:
when $L^3$ is —O—, —S—, —N(H)—, or —N($C_{1-3}$ alkyl)-, and Ring B is (B-III), then $B^5$ is C, and
when $L^4$ is —O—, —S—, —N(H)—, or —N($C_{1-3}$ alkyl)-, and Ring B is (B-III), then $B^8$ is C;
each of $B^6$, $B^7$, and $B^9$ is independently selected from the group consisting of: O, S, CR, $NR^N$, and N,
each ═══ in (B-III) is independently a single bond or a double bond, provided that at least one of $B^5$, $B^6$, $B^7$, $B^8$, and $B^9$ is an independently selected heteroatom, at least one of $B^5$, $B^6$, $B^7$, $B^8$, and $B^9$ is C or $CR^1$, and the ring including $B^5$, $B^6$, $B^7$, $B^8$, and $B^9$ is heteroaryl;
each of $B^{11}$, $B^{12}$, $B^{13}$, and $B^{14}$ is independently selected from the group consisting of $CR^1$, C and N;
each of $B^{15}$ and $B^{16}$ is independently C or N;
each of $B^{17}$ and $B^{20}$ is, independently, O, S, C, $CR^1$, $NR^N$, or N;
each of $B^{18}$ and $B^{19}$ is, independently, O, S, C, $CR^1$, $NR^N$, N, or is absent, provided that only one of $B^{18}$ and $B^{19}$ can be absent;
each ═══ in (B-IV) is independently a single bond or a double bond,
provided that:
the 6-membered ring and the 5-membered ring in (B-IV) are both aromatic rings,
when $L^3$ is —O—, —S—, —N(H)—, or —N($C_{1-3}$ alkyl)-, and Ring B is (B-IV), then the ring B ring atom that is directly attached to $L^3$ is C, and
when $L^4$ is —O—, —S—, —N(H)—, or —N($C_{1-3}$ alkyl)-, and Ring B is (B-IV), then the ring B ring atom that is directly attached to $L^4$ is C;
each $R^1$ is selected from the group consisting of hydrogen, halogen, CN, ($C_1$-$C_6$)alkyl, ($C_1$-$C_6$)haloalkyl; ($C_1$-$C_3$)alkyl($C_3$-$C_6$)cycloalkyl, ($C_1$-$C_3$)alkyl(3- to 5-membered heterocycloalkyl), and —C(O)$NR^2R^3$;
each $R^2$ and $R^3$ is independently selected from the group consisting of hydrogen and ($C_1$-$C_6$)alkyl;
each $R^N$ is selected from the group consisting of hydrogen, ($C_1$-$C_6$)alkyl, ($C_1$-$C_6$)haloalkyl, C(═O)($C_1$-$C_6$)alkyl, $S(O)_2$($C_1$-$C_6$)alkyl, and C(═O)O($C_1$-$C_6$)alkyl;
$L^4$ is selected from the group consisting of: —C($R^cR^c$)—; —O—; —S—; —N(H)—; —N($C_{1-3}$ alkyl)-; —C(═O)—; and —S(O)$_{1-2}$—,
$L^5$ is selected from the group consisting of: a bond; —C($R^cR^c$)—; —O—; —S—; —N(H)—; —N($C_{1-3}$ alkyl)-; —C(═O)—; and —S(O)$_{1-2}$—,
provided that when $L^4$ is —O—, —S—, —N(H)—, or —N($C_{1-3}$ alkyl)-, then $L^5$ is a bond, —C(RR)—, —C(═O)—, or —S(O)$_{1-2}$—, and provided that when $L^5$ is —O—, —S—, —N(H)—, or —N($C_{1-3}$ alkyl)-, then $L^4$ is —C($R^cR^c$)—, —C(═O), or —S(O)$_{1-2}$—,
each occurrence of $R^c$ is independently selected from the group consisting of: hydrogen, halogen, CN, —OH, ($C_1$-$C_6$)alkyl, ($C_1$-$C_3$)haloalkyl, ($C_3$-$C_8$)cycloalkyl, ($C_1$-$C_3$)alkoxy, and ($C_1$-$C_3$)haloalkoxy; or
a pair of $R^4$ taken together with the carbon atom to which each is attached forms a ($C_3$-$C_8$)cycloalkyl ring;
Ring C is selected from the group consisting of phenyl, 5- to 6-membered heteroaryl, ($C_3$-$C_6$)cycloalkyl, ($C_5$-$C_{10}$) bicycloalkyl, 5- to 10-membered bicycloheteroaryl, and 3- to 6-membered heterocycloalkyl;
each $R^b$ is independently selected from the group consisting of ($C_1$-$C_6$)alkyl, ($C_1$-$C_6$)haloalkyl, ($C_1$-$C_6$)alkoxy, ($C_1$-$C_6$)haloalkoxy, halogen, ($C_3$-$C_6$)cycloalkyl, and CN; and
b is an integer selected from 0-3.

Also provided herein are pharmaceutical compositions comprising a compound of Formula I, or a pharmaceutically acceptable salt or solvate thereof, and a pharmaceutically acceptable excipient.

Also provided herein are methods for treating type 2 diabetes mellitus in a patient in need thereof, the methods comprising administering to the patient a therapeutically effective amount of a compound of Formula I, or a pharmaceutically acceptable salt or solvate thereof, or a pharmaceutical composition thereof.

Also provided herein are methods for treating type 2 diabetes mellitus in a patient, the methods comprising administering to a patient identified or diagnosed as having type 2 diabetes mellitus a therapeutically effective amount of a compound of Formula I, or a pharmaceutically acceptable salt or solvate thereof, or a pharmaceutical composition thereof.

Also provided herein are methods for treating diabetes mellitus in a patient, the methods comprising determining that the patient has type 2 diabetes mellitus; and administering to the patient a therapeutically effective amount of a compound of Formula I, or a pharmaceutically acceptable salt or solvate thereof, or a pharmaceutical composition thereof. In some embodiments, the step of determining that the patient has type 2 diabetes mellitus includes performing an assay to determine the level of an analyte in a sample from the patient, wherein the analyte is selected from the group consisting of hemoglobin A1c (HbA1c), fasting plasma glucose, non-fasting plasma glucose, or any combination thereof. In some embodiments, the level of HbA1c is greater than or about 6.5%. In some embodiments, the level of fasting plasma glucose is greater than or about 126 mg/dL. In some embodiments, the level of non-fasting plasma glucose is greater than or about 200 mg/dL.

In some embodiments, the methods further comprise obtaining a sample from the patient. In some embodiments, the sample is a body fluid sample. In some embodiments, the patient is about 40 to about 70 years old and is overweight or obese. In some embodiments, the patient has a body mass index (BMI) greater than or about 22 kg/m². In some embodiments, the patient has a BMI greater than or about 30 kg/m².

In some embodiments, the methods for the treatment of type 2 diabetes mellitus comprise a reduction in fasting plasma glucose levels. In some embodiments, the fasting plasma glucose levels are reduced to about or below 100 mg/dL.

In some embodiments, the methods for the treatment of type 2 diabetes mellitus comprise a reduction in HbA1c levels. In some embodiments, the HbA1c levels are reduced to about or below 5.7%.

In some embodiments, the methods for the treatment of type 2 diabetes mellitus comprise a reduction in glucagon levels.

In some embodiments, the methods for the treatment of type 2 diabetes mellitus comprise an increase in insulin levels.

In some embodiments, the methods for the treatment of type 2 diabetes mellitus comprise a decrease in BMI. In some embodiments, the BMI is decreased to about or below 25 kg/m$^2$.

In some embodiments, the compound of Formula I, or a pharmaceutically acceptable salt or solvate thereof, or a pharmaceutical composition thereof, is administered orally.

In some embodiments, the methods of treatment for type 2 diabetes mellitus further comprise administering an additional therapy or therapeutic agent to the patient. In some embodiments, the additional therapy or therapeutic agent is selected from the group consisting of an antidiabetic agent, an anti-obesity agent, a GLP-1 receptor agonist, an agent to treat non-alcoholic steatohepatitis (NASH), anti-emetic agent, gastric electrical stimulation, dietary monitoring, physical activity, or any combinations thereof. In some embodiments, the antidiabetic agent is selected from the group consisting of a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor, or any combinations thereof. In some embodiments, the biguanide is metformin. In some embodiments, the anti-obesity agent is selected from the group consisting of neuropeptide Y receptor type 2 (NPYR2) agonist, a NPYR1 or NPYR5 antagonist, a human proislet peptide (HIP), a cannabinoid receptor type 1 (CB1R) antagonist, a lipase inhibitor, a melanocortin receptor 4 agonist, a farnesoid X receptor (FXR) agonist, phentermine, zonisamide, a norepinephrine/dopamine reuptake inhibitor, a GDF-15 analog, an opioid receptor antagonist, a cholecystokinin agonist, a serotonergic agent, a methionine aminopeptidase 2 (MetAP2) inhibitor, diethylpropion, phendimetrazine, benzphetamine, a fibroblast growth factor receptor (FGFR) modulator, an AMP-activated protein kinase (AMPK) activator, or any combinations thereof. In some embodiments, the GLP-1 receptor agonist is selected from the group consisting of liraglutide, exenatide, dulaglutide, albiglutide, taspoglutide, lixisenatide, semaglutide, or any combinations thereof. In some embodiments, the agent to treat NASH is selected from the group consisting of an FXR agonist, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21) agonist, a niacin analogue, a leukotriene D4 (LTD4) receptor antagonist, an acetyl-CoA carboxylase (ACC) inhibitor, a ketohexokinase (KHK) inhibitor, an ileal bile acid transporter (IBAT) inhibitor, an apoptosis signal-regulating kinase 1 (ASK1) inhibitor, or any combinations thereof. In some embodiments, the compound of Formula I, or a pharmaceutically acceptable salt or solvate thereof, or a pharmaceutical composition thereof, and the additional therapeutic agent are administered as separate dosages sequentially in any order.

Also provided herein are methods for modulating insulin levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in an increase of insulin levels.

Also provided herein are methods for modulating glucose levels in a patient in need of such modulating, the method comprising administering to the patient an effective amount of a compound of Formula I, or a pharmaceutically acceptable salt or solvate thereof, or a pharmaceutical composition thereof. In some embodiments, the modulation results in a decrease of glucose levels.

Also provided herein are methods for treating a GLP-1 associated disease, disorder, or condition, the method comprising administering to a patient in need thereof an effective amount of a compound of Formula I, or a pharmaceutically acceptable salt or solvate thereof, or a pharmaceutical composition thereof. In some embodiments, the disease, disorder, or condition is selected from the group consisting of type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, Polycystic Ovary Syndrome (PCOS), or any combination thereof. In some embodiments, the disease, disorder, or condition is selected from the group consisting of type 2 diabetes mellitus, early onset type 2 diabetes mellitus, obesity, weight gain from use of other agents, gout, excessive sugar craving, hypertriglycerdiemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof. In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the invention will be apparent from the following detailed description and figures, and from the claims.

DETAILED DESCRIPTION

Provided herein are heterocyclic GLP-1 agonists for use in the management of T2DM and other conditions where activation of GLP-1 activity is useful.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "halo" or "halogen" means —F (sometimes referred to herein as "fluoro" or "fluoros"), —Cl (sometimes referred to herein as "chloro" or "chloros"), —Br (sometimes referred to herein as "bromo" or "bromos"), and —I (sometimes referred to herein as "iodo" or "iodos").

As used herein, the term "alkyl" refers to saturated linear or branched-chain monovalent hydrocarbon radicals, containing the indicated number of carbon atoms. For example, "$(C_1-C_6)$alkyl" refers to saturated linear or branched-chain monovalent hydrocarbon radicals of one to six carbon atoms. Non-limiting examples of alkyl include methyl, ethyl, 1-propyl, isopropyl, 1-butyl, isobutyl, sec-butyl, tert-butyl, 2-methyl-2-propyl, pentyl, neopentyl, and hexyl.

As used herein, the term "alkylene" refers to a divalent alkyl containing the indicated number of carbon atoms. For example, "$(C_1-C_3)$alkylene" refers to a divalent alkyl having one to three carbon atoms (e.g., —$CH_2$—, —$CH(CH_3)$—, —$CH_2CH_2$—, or —$CH_2CH_2CH_2$—). Similarly, the terms "cycloalkylene", "heterocycloalkylene", "arylene", and "heteroarylene" mean divalent cycloalkyl, heterocycloalkyl, aryl, and heteroaryl, respectively.

As used herein, the term "alkenyl" refers to a linear or branched mono-unsaturated hydrocarbon chain, containing the indicated number of carbon atoms. For example, "$(C_2-C_6)$alkenyl" refers a linear or branched mono unsaturated hydrocarbon chain of two to six carbon atoms. Non-limiting examples of alkenyl include ethenyl, propenyl, butenyl, or pentenyl.

As used herein, the term "alkynyl" refers to a linear or branched di-unsaturated hydrocarbon chain, containing the indicated number of carbon atoms. For example, "$(C_2-C_6)$alkynyl" refers to a linear or branched di-unsaturated hydrocarbon chain having two to six carbon atoms. Non-limiting examples of alkynyl include ethynyl, propynyl, butynyl, or pentynyl.

As used herein, the term "cycloalkyl" refers to a saturated or partially unsaturated cyclic hydrocarbon, containing the indicated number of carbon atoms. For example, "$(C_3-C_6)$cycloalkyl" refers to a saturated or partially unsaturated cyclic hydrocarbon having three to six ring carbon atoms. Non-limiting examples of cycloalkyl include cyclopropyl, cyclobutyl, cyclopentyl, and cyclohexyl. Cycloalkyl may be partially unsaturated. Non-limiting examples of partially unsaturated cycloalkyl include cyclohexenyl, cyclopentenyl, cycloheptenyl, cyclooctenyl, and the like. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

As used herein, the term "heterocycloalkyl" refers to a mon-, bi-, tri-, or polycyclic nonaromatic ring system containing indicated number of ring atoms (e.g., 3-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, the heteroatoms selected from O, N, S, or $S(O)_{1-2}$ (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkyl groups include piperazinyl, pyrrolidinyl, dioxanyl, morpholinyl, tetrahydrofuranyl, and the like. Heterocycloalkyl groups may be partially unsaturated. Non-limiting examples of partially unsaturated heterocycloalkyl include dihydropyrrolyl, dihydropyridinyl, tetrahydropyridinyl, dihydrofuranyl, dihydropyranyl, and the like. Heterocycloalkyl may include multiple fused and bridged rings. Non-limiting examples of fused/bridged heterocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo

[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocycloalkyl also includes spirocyclic rings (e.g., spirocyclic bicycle wherein two rings are connected through just one atom). Non-limiting examples of spirocyclic heterocycloalkyl include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, the term "aryl" refers to a mono-, bi-, tri- or polycyclic hydrocarbon group containing the indicated numbers of carbon atoms, wherein at least one ring in the system is aromatic (e.g., $C_6$ monocyclic, $C_{10}$ bicyclic, or $C_{14}$ tricyclic aromatic ring system). Examples of aryl groups include phenyl, naphthyl, tetrahydronaphthyl, and the like.

As used herein, the term "heteroaryl" refers to a mono-, bi-, tri- or polycyclic group having indicated numbers of ring atoms (e.g., 5-6 ring atoms; e.g., 5, 6, 9, 10, or 14 ring atoms); and having 6, 10, or 14 pi electrons shared in a cyclic array; wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others.

As used herein, the term "haloalkyl" refers to an alkyl radical as defined herein, wherein one or more hydrogen atoms is replaced with one or more halogen atoms. Non-limiting examples include fluoromethyl, difluoromethyl, trifluoromethyl, 2-fluoroethyl, 2,2-difluoroethyl, 2,2,2-trifluoroethyl, chloromethyl, dichloromethyl, chloroethyl, trichloroethyl, bromomethyl, and iodomethyl.

As used herein, the term "alkoxy" refers to an —O-alkyl radical, wherein the radical is on the oxygen atom. For example, "$C_{1-6}$ alkoxy" refers to an —O—($C_{1-6}$ alkyl) radical, wherein the radical is on the oxygen atom. Examples of alkoxy include methoxy, ethoxy, propoxy, isopropoxy, butoxy and tert-butoxy. Accordingly, as used herein, the term "haloalkoxy" refers to an —O-haloalkyl radical, wherein the radical is on the oxygen atom.

As used herein, "⚯" indicates an optional single or double bond, as allowed by valence. As used herein, "⚬" indicates the point of attachment to the parent molecule.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

As used herein, when a ring is described as being "aromatic", it means the ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like. When a ring system comprising at least two rings is described as "aromatic", it means the ring system comprises one or more aromatic ring(s). Accordingly, when a ring system comprising at least two rings is described as "non-aromatic", none of the constituent rings of the ring system is aromatic.

As used herein, when a ring is described as being "partially unsaturated", it means the ring has one or more additional degrees of unsaturation (in addition to the degree of unsaturation attributed to the ring itself; e.g., one or more double bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like. When a ring system comprising at least two rings is described as "partially unsaturated", it means the ring system comprises one or more partially unsaturated ring(s), provided that none of the constituent rings of the ring system is aromatic.

As used herein, the term "carboxylic acid bioisostere" means a group which has chemical and physical similarities producing broadly similar biological properties to a carboxylic acid (see Lipinski, Annual Reports in Medicinal Chemistry, 1986, 21, p 283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 25 "Bioisosteric Replacement And Development Of Lead Compounds In Drug Design"; Graham, Theochem, 1995, 343, pages 105-109 "Theoretical Studies Applied To Drug Design: ab initio Electronic Distributions In Bioisosteres"). Examples of suitable carboxylic acid bioisostere include: sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydroxy-1-methylpyrazolyl.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "GLP-1R" or "GLP-1 receptor" as used herein is meant to include, without limitation, nucleic acids, polynucleotides, oligonucleotides, sense and antisense polynucleotide strands, complementary sequences, peptides, polypeptides, proteins, homologous, and/or orthologous GLP-1R molecules, isoforms, precursors, mutants, variants, derivatives, splice variants, alleles, different species, and active fragments thereof.

The term "GLP-1 associated disease" as used herein is meant to include, without limitation, all those diseases, disorders, or conditions in which modulating glucagon-like peptide-1 (GLP-1) receptor signaling can alter the pathology and/or symptoms and/or progression of the disease, disorder, or condition.

The term "GLP-1 agonist" or "GLP-1 RA" as used herein refers to an agonist of the glucagon-like peptide-1 (GLP-1) receptor. GLP-1 RAs enhance glucose-dependent insulin secretion; suppress inappropriately elevated glucagon levels, both in fasting and postprandial states; and slow gastric emptying. Karla et al., Glucagon-like peptide-1 receptor agonists in the treatment of type 2 diabetes: Past, present, and future, *Indian J Endocrinol Metab.* 2016 March-April; 20(2): 254-267. GLP-1 RAs have been shown to treat type 2 diabetes. Examples of GLP-1 RAs include, but are not limited to, albiglutide (TANZEUM®), dulaglutide (LY2189265, TRULICITY®), efpeglenatide, exenatide (BYETTA®, BYDUREON®, Exendin-4), liraglutide (VICTOZA®, NN2211), lixisenatide (LYXUMIA®), semaglutide (OZEMPIC®), tirzepatide, ZP2929, NNC0113-0987, BPI-3016, and TT401. See, also, for example, additional GLP-1 receptor agonists described in U.S. Pat. Nos. 10,370,426; 10,308,700; 10,259,823; 10,208,019; 9,920,106; 9,839,664; 8,129,343; 8,536,122; 7,919,598; 6,414,126; 6,628,343; and RE45313.

The term "pharmaceutically acceptable" as used herein indicates that the compound, or salt or composition thereof is compatible chemically and/or toxicologically with the other ingredients comprising a formulation and/or the patient being treated therewith.

The term "therapeutic compound" as used herein is meant to include, without limitation, all compounds of Formula I, or pharmaceutically acceptable salts or solvates thereof (e.g., a compound of any one of Formulas IA, IB, IC, and ID, or a pharmaceutically acceptable salt or solvate thereof), and all compositions (e.g., pharmaceutical compositions) wherein a compound of Formula I, or a pharmaceutically acceptable salt or solvate thereof (e.g., a compound of any one of Formulas IA, IB, IC, and ID, or a pharmaceutically acceptable salt or solvate thereof) is a component of the composition.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof (e.g., a compound of any one of Formulas IA, IB, IC, and ID, or a pharmaceutically acceptable salt or solvate thereof)) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, P A, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009.

The term "pharmaceutical composition" refers to a mixture of a compound of Formula I, or a pharmaceutically acceptable salt or solvate thereof (e.g., a compound of any one of Formulas IA, TB, IC, and ID or a pharmaceutically acceptable salt or solvate thereof) as described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing", as used herein, is the prevention of the onset, recurrence or spread, in whole or in part, of the disease or condition as described herein, or a symptom thereof.

The terms "subject", "patient" or "individual", as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the patient is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination of the invention.

The term "pharmaceutical combination", as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulation", as used herein, refers to a regulation or an adjustment (e.g., increase or decrease) and can include, for example agonism, partial agonism or antagonism.

Compounds

Accordingly, provided herein are compounds of Formula I.

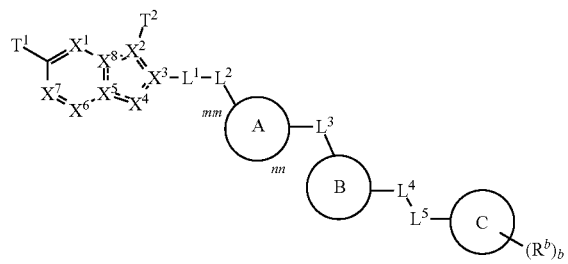

Formula I or a pharmaceutically acceptable salt or solvate thereof, wherein:

- $\sim$ indicates an optional single or double bond, as allowed by valence;
- each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;
- $T^1$ is C(=O)OH or a carboxylic acid bioisostere;
- $T^2$ is hydrogen or $(C_1-C_6)$alkyl which is optionally substituted with $(C_1-C_6)$alkoxy, $(C_1-C_6)$thioalkoxy, $(C_1-C_6)$haloalkoxy, $S(O)_2(C_1-C_6$ alkyl), $(C_3-C_6)$cycloalkyl, 3- to 6-membered heterocycloalkyl, phenyl, or 5- to 6-membered heteroaryl, wherein each of the $(C_3-C_6)$cycloalkyl, 3- to 6-membered heterocycloalkyl, phenyl, or 5- to 6-membered heteroaryl is optionally substituted with 1-4 $R^T$;
- each $R^T$ is independently selected from the group consisting of OH, SH, CN, $NO_2$, halogen, $(C_1-C_6)$alkyl, $(C_2-C_6)$alkenyl, $(C_2-C_6)$alkynyl, $(C_1-C_6)$haloalkyl, $(C_1-C_6)$cyanoalkyl, $(C_1-C_6)$hydroxyalkyl, $(C_1-C_6)$alkoxy, $(C_1-C_6)$haloalkoxy, $(C_3-C_6)$cycloalkyl, amino, $(C_1-C_6)$alkylamino, and di$(C_1-C_6)$alkylamino;
- $L^1$ is a bond or $(C_1-C_3)$alkylene which is optionally substituted with 1-3 $R^L$;
- $L^2$ is a bond, —O—, —S(O)$_{0-2}$, or —NH—;
- each $R^L$ is independently selected from the group consisting of: halogen, $(C_1-C_3)$alkyl, and $(C_1-C_3)$haloalkyl; or a pair of $R^L$ on the same or on adjacent carbon atoms, taken together with the atom(s) to which each is attached, forms a $(C_3-C_6)$cycloalkyl ring;
- Ring A is selected from the group consisting of: (A-1), (A-2), and (A-3):

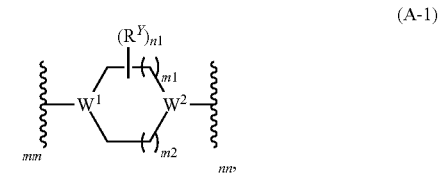

(A-1)

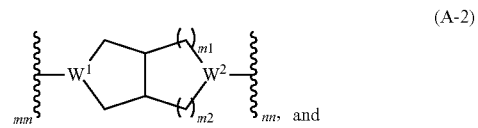

(A-2)

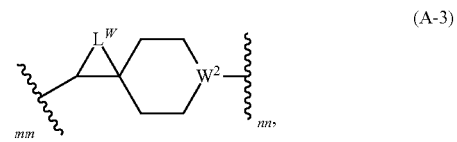

(A-3)

wherein mm represents the point of attachment to $L^2$, and nn represents the point of attachment to $L^3$;

n1 is 0, 1, or 2; m1 and m2 are independently 0 or 1;

$W^1$ is $CR^{Y1}$ or N, provided that when $L^2$ is —O—, —S—, or —N(H)—, then $W^1$ is $CR^{Y1}$;

$W^2$ is $CR^{Y2}$ or N, provided that when $L^3$ is —O—, —S—, —N(H)—, or —N($C_{1-3}$ alkyl)-, then $W^2$ is $CR^2$;

further provided that when Ring A is (A-1), and at least one of m1 and m2 is 0, then $W^2$ and $W^2$ are not simultaneously N;

$L^w$ is $(C_1-C_3)$alkylene;

each occurrence of $R^Y$ is independently selected from the group consisting of halogen, CN, —OH, oxo, $(C_1-C_6)$alkyl, $(C_1-C_3)$haloalkyl, $(C_1-C_3)$alkoxy, and $(C_1-C_3)$haloalkoxy;

$R^{Y1}$ and $R^{Y2}$ are independently selected from the group consisting of hydrogen, halogen, CN, —OH, $(C_1-C_6)$alkyl, $(C_1-C_3)$haloalkyl, $(C_1-C_3)$alkoxy, and $(C_1-C_3)$haloalkoxy; or when $W^1$ is $CR^{Y1}$; and $W^2$ is $CR^{Y2}$, the $R^{Y1}$ and $R^{Y2}$ groups taken together form $(C_1-C_4)$alkylene, wherein one of the $CH_2$ units of the $(C_1-C_4)$alkylene is optionally replaced by a heteroatom selected from the group consisting of O, S, NH, and N($C_{1-3}$)alkyl;

$L^3$ is selected from the group consisting of: —O—; —S—; —C($R^aR^a$)—; —N(H)—; —N($C_{1-3}$ alkyl)-; —C(=O)—; and —S(O)$_{1-2}$—, each occurrence of $R^a$ is independently selected from the group consisting of: hydrogen, halogen, CN, —OH, $(C_1-C_6)$alkyl, $(C_1-C_3)$haloalkyl, $(C_3-C_8)$cycloalkyl, $(C_1-C_3)$alkoxy, and $(C_1-C_3)$haloalkoxy; or a pair of $R^a$ taken together with the carbon atom to which each is attached forms a $(C_3-C_8)$cycloalkyl ring; or when $W^2$ is $CR^{Y2}$; and $L^3$ is —C($R^aR^a$)—, one $R^a$ combines with $R^{Y2}$ to form a double bond between $W^2$ and $L^3$, wherein the remaining $R^a$ is selected from the group consisting of: hydrogen, halogen, CN, $(C_1-C_6)$alkyl, $(C_1-C_3)$haloalkyl, and $(C_3-C_8)$cycloalkyl;

Ring B is selected from the group consisting of (B-I), (B-II), and (B-III):

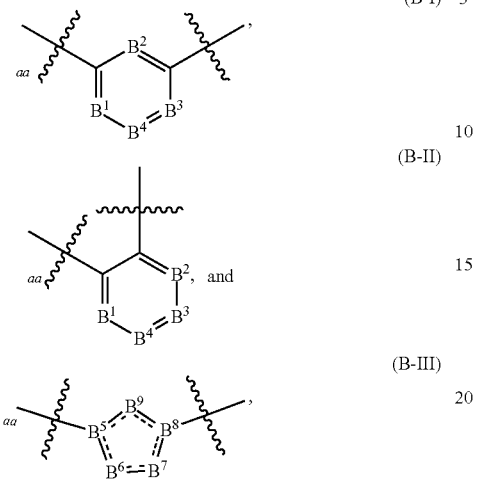

wherein aa represents the point of attachment to $L^3$;

each of $B^1$, $B^2$, $B^3$, and $B^4$ is independently selected from the group consisting of $CR^1$ and N;

each of $B^5$ and $B^8$ is independently selected from the group consisting of: C and N, provided that:

when $L^3$ is —O—, —S—, —N(H)—, or —N($C_{1-3}$ alkyl)-, and Ring B is (B-III), then $B^5$ is C, and when $L^4$ is —O—, —S—, —N(H)—, or —N($C_{1-3}$ alkyl)-, and Ring B is (B-III), then $B^8$ is C;

each of $B^6$, $B^7$, and $B^9$ is independently selected from the group consisting of: O, S, CR, $NR^N$, and N, each ═══ in (B-III) is independently a single bond or a double bond, provided that at least one of $B^5$, $B^6$, $B^7$, $B^8$, and $B^9$ is an independently selected heteroatom, at least one of $B^5$, $B^6$, $B^7$, $B^8$, and $B^9$ is C or $CR^1$, and the ring including $B^5$, $B^6$, $B^7$, $B^8$, and $B^9$ is heteroaryl;

each $R^1$ is selected from the group consisting of hydrogen, halogen, CN, ($C_1$-$C_6$)alkyl, ($C_1$-$C_6$)haloalkyl; ($C_1$-$C_3$) alkyl($C_3$-$C_6$)cycloalkyl, ($C_1$-$C_3$)alkyl(3- to 5-membered heterocycloalkyl), and —C(O)$NR^2R^3$;

each $R^2$ and $R^3$ is independently selected from the group consisting of hydrogen and ($C_1$-$C_6$)alkyl;

each $R^N$ is selected from the group consisting of hydrogen, ($C_1$-$C_6$)alkyl, ($C_1$-$C_6$)haloalkyl, C(=O)($C_1$-$C_6$) alkyl, S(O)$_2$($C_1$-$C_6$)alkyl, and C(=O)O($C_1$-$C_6$)alkyl;

$L^4$ is selected from the group consisting of: —C($R^cR^c$)—; —O—; —S—; —N(H)—; —N($C_{1-3}$ alkyl)-; —C(=O)—; and —S(O)$_{1-2}$—, $L^5$ is selected from the group consisting of: a bond; —C($R^cR^c$)—; —O—; —S—; —N(H)—; —N($C_{1-3}$ alkyl)-; —C(=O)—; and —S(O)$_{1-2}$—, provided that when $L^4$ is —O—, —S—, —N(H)—, or —N($C_{1-3}$ alkyl)-, then $L^5$ is a bond, —C($R^cR^c$)—, —C(=O), or —S(O)$_{1-2}$—, and provided that when $L^5$ is —O—, —S—, —N(H)—, or —N($C_{1-3}$ alkyl)-, then $L^4$ is —C($R^cR^c$)—, —C(=O), or —S(O)$_{1-2}$—, each occurrence of $R^c$ is independently selected from the group consisting of: hydrogen, halogen, CN, —OH, ($C_1$-$C_6$)alkyl, ($C_1$-$C_3$)haloalkyl, ($C_3$-$C_8$)cycloalkyl, ($C_1$-$C_3$)alkoxy, and ($C_1$-$C_3$)haloalkoxy; or a pair of $R^c$ taken together with the carbon atom to which each is attached forms a ($C_3$-$C_8$)cycloalkyl ring;

Ring C is selected from the group consisting of phenyl, 5- to 6-membered heteroaryl, ($C_3$-$C_6$)cycloalkyl, ($C_5$-$C_{10}$) bicycloalkyl, 5- to 10-membered bicycloheteroaryl, and 3- to 6-membered heterocycloalkyl;

each $R^b$ is independently selected from the group consisting of ($C_1$-$C_6$)alkyl, ($C_1$-$C_6$)haloalkyl, ($C_1$-$C_6$)alkoxy, ($C_1$-$C_6$)haloalkoxy, halogen, ($C_3$-$C_6$)cycloalkyl, and CN; and b is an integer selected from 0-3.

Further provided herein are compounds of Formula I:

Formula I

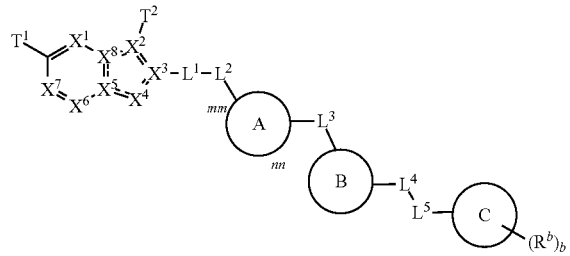

or a pharmaceutically acceptable salt or solvate thereof, wherein:

╌╌ indicates an optional single or double bond, as allowed by valence;

each of $X^1$, $X^2$, $X^3$, $X^4$, $X^5$, $X^6$, $X^7$, and $X^8$ is independently selected from the group consisting of C, CH, and N, provided that at least two and no more than four of $X^1$, $X^2$, $X^3$, $X^4$, $X^5$, $X^6$, $X^7$, and $X^8$ are N;

$T^1$ is C(=O)OH, C(=O)$NH_2$, NHC(=O)—$C_1$-$C_6$ alkyl, or a carboxylic acid bioisostere;

$T^2$ is hydrogen or ($C_1$-$C_6$)alkyl which is optionally substituted with ($C_1$-$C_6$)alkoxy, ($C_1$-$C_6$)thioalkoxy, ($C_1$-$C_6$)haloalkoxy, S(O)$_2$($C_1$-$C_6$ alkyl), ($C_3$-$C_6$)cycloalkyl, 3- to 6-membered heterocycloalkyl, phenyl, or 5- to 6-membered heteroaryl, wherein each of the ($C_3$-$C_6$) cycloalkyl, 3- to 6-membered heterocycloalkyl, phenyl, or 5- to 6-membered heteroaryl is optionally substituted with 1-4 $R^T$;

each $R^T$ is independently selected from the group consisting of OH, SH, CN, $NO_2$, halogen, ($C_1$-$C_6$)alkyl, ($C_2$-$C_6$)alkenyl, ($C_2$-$C_6$)alkynyl, ($C_1$-$C_6$)haloalkyl, ($C_1$-$C_6$)cyanoalkyl, ($C_1$-$C_6$)hydroxyalkyl, ($C_1$-$C_6$) alkoxy, ($C_1$-$C_6$)haloalkoxy, ($C_3$-$C_6$)cycloalkyl, amino, ($C_1$-$C_6$)alkylamino, and di($C_1$-$C_6$)alkylamino;

$L^1$ is a bond or ($C_1$-$C_3$)alkylene which is optionally substituted with 1-3 $R^L$;

$L^2$ is a bond, —O—, —S(O)$_{0-2}$—, or —NH—;

each $R^L$ is independently selected from the group consisting of: halogen, ($C_1$-$C_3$)alkyl, and ($C_1$-$C_3$)haloalkyl; or a pair of $R^L$ on the same or on adjacent carbon atoms, taken together with the atom(s) to which each is attached, forms a ($C_3$-$C_6$)cycloalkyl ring;

Ring A is selected from the group consisting of (A-1), (A-2), (A-3), $C_6$-$C_{10}$ arylene, and 5-10 membered heteroarylene; wherein each of (A-1), (A-2), and (A-3) has the formula shown below:

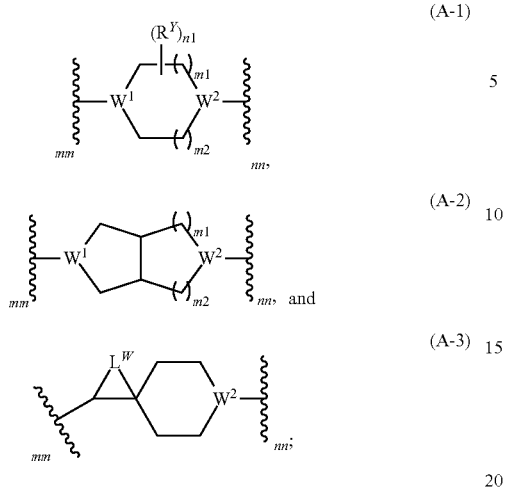

(A-1)

(A-2)

(A-3)

and wherein mm represents the point of attachment to $L^2$, and nn represents the point of attachment to U; and wherein the $C_6$-$C_{10}$ arylene, and 5-10 membered heteroarylene are each optionally substituted with 1-4 $R^T$;

n1 is 0, 1, or 2; m1 and m2 are independently 0 or 1;

$W^1$ is $CR^{Y1}$ or N, provided that when $L^2$ is —O—, —S—, or —N(H)—, then $W^1$ is $CR^{Y1}$;

$W^2$ is $CR^{Y2}$ or N, provided that when $L^3$ is —O—, —S—, —N(H)—, or —N($C_{1-3}$ alkyl)-, then $W^2$ is $CR^{Y1}$;

further provided that when Ring A is (A-1), and at least one of m1 and m2 is 0, then $W^1$ and $W^2$ are not simultaneously N;

$L^w$ is ($C_1$-$C_3$)alkylene;

each occurrence of $R^Y$ is independently selected from the group consisting of halogen, CN, —OH, oxo, ($C_1$-$C_6$) alkyl, ($C_1$-$C_3$)haloalkyl, ($C_1$-$C_3$)alkoxy, and ($C_1$-$C_3$) haloalkoxy;

$R^{Y1}$ and $R^{Y2}$ are independently selected from the group consisting of hydrogen, halogen, CN, —OH, ($C_1$-$C_6$) alkyl, ($C_1$-$C_3$)haloalkyl, ($C_1$-$C_3$)alkoxy, and ($C_1$-$C_3$) haloalkoxy; or when $W^1$ is $CR^{Y1}$; and $W^2$ is $CR^{Y2}$, the $R^{Y1}$ and $R^{Y2}$ groups taken together form ($C_1$-$C_4$)alkylene, wherein one of the $CH_2$ units of the ($C_1$-$C_4$)alkylene is optionally replaced by a heteroatom selected from the group consisting of O, S, NH, and N($C_{1-3}$)alkyl;

$L^3$ is selected from the group consisting of: —O—; —S—; —C($R^aR^a$)—; —N(H)—; —N($C_{1-3}$ alkyl)-; —C(=O)—; and —S(O)$_{1-2}$—, each occurrence of $R^a$ is independently selected from the group consisting of: hydrogen, halogen, CN, —OH, ($C_1$-$C_6$)alkyl, ($C_1$-$C_3$)haloalkyl, ($C_3$-$C_8$)cycloalkyl, ($C_1$-$C_3$)alkoxy, and ($C_1$-$C_3$)haloalkoxy; or a pair of $R^a$ taken together with the carbon atom to which each is attached forms a ($C_3$-$C_8$)cycloalkyl ring; or when $W^2$ is $CR^{Y2}$; and $L^3$ is —C($R^aR^a$)—, one $R^a$ combines with $R^{Y2}$ to form a double bond between $W^2$ and $L^3$, wherein the remaining $R^a$ is selected from the group consisting of: hydrogen, halogen, CN, ($C_1$-$C_6$) alkyl, ($C_1$-$C_3$)haloalkyl, and ($C_3$-$C_8$)cycloalkyl;

Ring B is selected from the group consisting of: (B-I), (B-II), and (B-III):

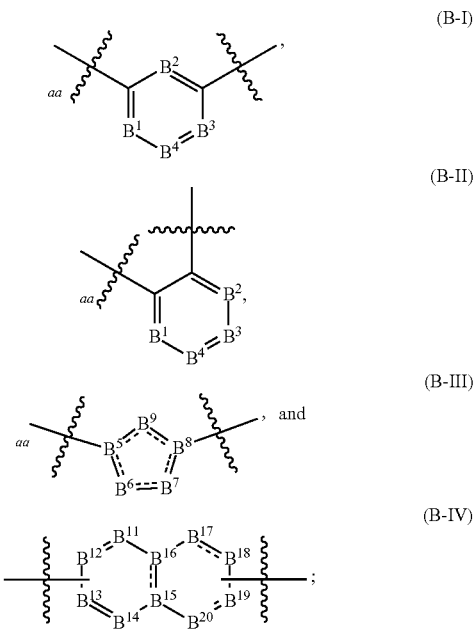

(B-I)

(B-II)

(B-III)

(B-IV)

wherein aa represents the point of attachment to $L^3$;

each of $B^1$, $B^2$, $B^3$, and $B^4$ is independently selected from the group consisting of CR and N;

each of $B^5$ and $B^8$ is independently selected from the group consisting of C and N, provided that:

when $L^3$ is —O—, —S—, —N(H)—, or —N($C_{1-3}$ alkyl)-, and Ring B is (B-III), then $B^5$ is C, and when $L^4$ is —O—, —S—, —N(H)—, or —N($C_{1-3}$ alkyl)-, and Ring B is (B-III), then $B^8$ is C;

each of $B^6$, $B^7$, and $B^9$ is independently selected from the group consisting of: O, S, CR, $NR^N$, and N, each ⸺ in (B-III) is independently a single bond or a double bond, provided that at least one of $B^5$, $B^6$, $B^7$, $B^8$, and $B^9$ is an independently selected heteroatom, at least one of $B^5$, $B^6$, $B^7$, $B^8$, and $B^9$ is C or $CR^1$, and the ring including $B^5$, $B^6$, $B^7$, $B^8$, and $B^9$ is heteroaryl;

each of $B^{11}$, $B^{12}$, $B^{13}$, and $B^{14}$ is independently selected from the group consisting of $CR^1$, C and N;

each of $B^{15}$ and $B^{16}$ is independently C or N;

each of $B^{17}$ and $B^{20}$ is, independently, O, S, C, $CR^1$, $NR^N$, or N;

each of $B^{18}$ and $B^{19}$ is, independently, O, S, C, $CR^1$, $NR^N$, N, or is absent, provided that only one of $B^{18}$ and $B^{19}$ can be absent;

each ⸺ in (B-IV) is independently a single bond or a double bond, provided that:

the 6-membered ring and the 5-membered ring in (B-IV) are both aromatic rings, when $L^3$ is —O—, —S—, —N(H)—, or —N($C_{1-3}$ alkyl)-, and Ring B is (B-IV), then the ring B ring atom that is directly attached to $L^3$ is C, and when $L^4$ is —O—, —S—, —N(H)—, or —N($C_{1-3}$ alkyl)-, and Ring B is (B-IV), then the ring B ring atom that is directly attached to $L^4$ is C;

each R¹ is selected from the group consisting of hydrogen, halogen, CN, $(C_1-C_6)$alkyl, $(C_1-C_6)$haloalkyl; $(C_1-C_3)$ alkyl$(C_3-C_6)$cycloalkyl, $(C_1-C_3)$alkyl(3- to 5-membered heterocycloalkyl), and —C(O)NR²R³;

each R² and R³ is independently selected from the group consisting of hydrogen and $(C_1-C_6)$alkyl;

each $R^N$ is selected from the group consisting of hydrogen, $(C_1-C_6)$alkyl, $(C_1-C_6)$haloalkyl, C(=O)$(C_1-C_6)$alkyl, S(O)₂$(C_1-C_6)$alkyl, and C(=O)O$(C_1-C_6)$alkyl;

L⁴ is selected from the group consisting of: —C(R$^c$R$^c$)—; —O—; —S—; —N(H)—; —N($C_{1-3}$ alkyl)-; —C(=O)—; and —S(O)$_{1-2}$—, L⁵ is selected from the group consisting of: a bond; —C(R$^c$R$^c$)—; —O—; —S—; —N(H)—; —N($C_{1-3}$ alkyl)-; —C(=O)—; and —S(O)$_{1-2}$—, provided that when L⁴ is —O—, —S—, —N(H)—, or —N($C_{1-3}$ alkyl)-, then L⁵ is a bond, —C(RR)—, —C(=O), or —S(O)$_{1-2}$—, and provided that when L⁵ is —O—, —S—, —N(H)—, or —N($C_{1-3}$ alkyl)-, then L⁴ is —C(R$^c$R$^c$)—, —C(=O), or —S(O)$_{1-2}$—, each occurrence of R$^c$ is independently selected from the group consisting of: hydrogen, halogen, CN, —OH, $(C_1-C_6)$alkyl, $(C_1-C_3)$haloalkyl, $(C_3-C_8)$cycloalkyl, $(C_1-C_3)$alkoxy, and $(C_1-C_3)$haloalkoxy; or a pair of R⁴ taken together with the carbon atom to which each is attached forms a $(C_3-C_8)$cycloalkyl ring;

Ring C is selected from the group consisting of phenyl, 5- to 6-membered heteroaryl, $(C_3-C_6)$cycloalkyl, $(C_5-C_{10})$ bicycloalkyl, 5- to 10-membered bicycloheteroaryl, and 3- to 6-membered heterocycloalkyl;

each R$^b$ is independently selected from the group consisting of $(C_1-C_6)$alkyl, $(C_1-C_6)$haloalkyl, $(C_1-C_6)$alkoxy, $(C_1-C_6)$haloalkoxy, halogen, $(C_3-C_6)$cycloalkyl, and CN; and b is an integer selected from 0-3.

In some embodiments, X⁸ is C; and X⁵ is C.
In some embodiments, X³ is C.
In some embodiments, X² is N.
In some embodiments, X⁴ is N.
In some embodiments, X² is N; X³ is C; and X⁴ is N.
In some embodiments, X² is N; X³ is C; X⁴ is N; X⁸ is C; and X⁵ is C.
In some embodiments, X⁷ is CH.
In some embodiments, X¹ and X⁶ are CH. In some embodiments, X¹ is N; and X⁶ is CH. In some embodiments, X¹ is CH; and X⁶ is N.
In some embodiments, X⁸, X⁵, and X³ are C; X² and X⁴ are N; X⁷ is CH; and X¹ and X⁶ are independently CH or N.
In some embodiments, X⁸, X⁵, and X³ are C; X² and X⁴ are N; X⁷ is CH; and X¹ and X⁶ are CH.
In some embodiments, X⁸, X⁵, and X³ are C; X² and X⁴ are N; X⁷ is CH; X¹ is N; and X⁶ is CH.
In some embodiments, X⁸, X⁵, and X³ are C; X² and X⁴ are N; X¹ is CH; X¹ is CH; and X⁶ is N.
In some embodiments, the

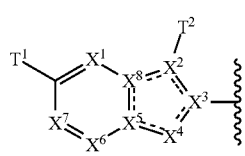

moiety has the formula:

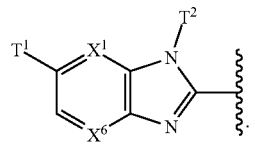

In some embodiments, the

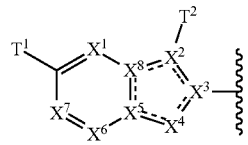

moiety has the formula:

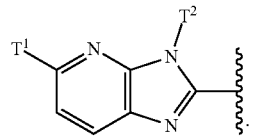

In some embodiments, the

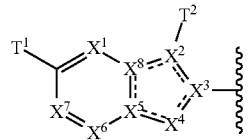

moiety has the formula:

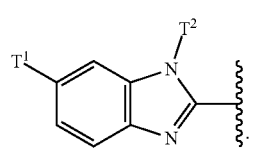

In some embodiments, T¹ is C(=O)OH.

In some embodiments, T¹ is C(=O)NH₂. In some embodiments, T¹ is NHC(=O)—$C_1-C_6$ alkyl (e.g., NHC(=O)—CH₃).

In some embodiments, T¹ is a carboxylic acid bioisostere.

In some embodiments (when T₁ is a carboxylic acid bioisostere), T¹ is a 5-membered heteroaryl including from 2-4 heteroatoms each independently selected from the group consisting of N, O, and S, wherein the heteroaryl is optionally substituted with from 1-4 substituents each independently selected from the group consisting of hydroxy, $(C_1-C_6)$alkyl, $(C_1-C_6)$haloalkyl, and halogen.

In some embodiments, T₁ is tetrazolyl, which is optionally substituted with from 1-2 substituents each independently selected from the group consisting of hydroxy, $(C_1-C_6)$alkyl, $(C_1-C_6)$haloalkyl, and halogen. For example, T¹ is selected from the group consisting of:

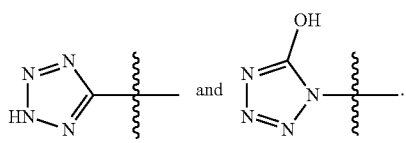 [SMILES: *c1nn[nH]n1 ; *n1nnnc1O] and

In some embodiments, $T^1$ is triazolyl or oxadiazolyl, which is optionally substituted with from 1-2 substituents each independently selected from $(C_1-C_6)$alkyl and hydroxy. For example, $T^1$ is

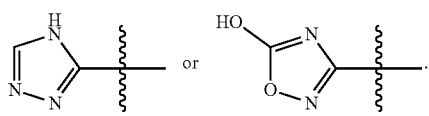 [SMILES: *c1nnc[nH]1 ; *c1noc(O)n1]

In some embodiments, $T^1$ is a ring (e.g., a 4-6 membered ring, e.g., a 5-membered ring) including from 0-3 heteroatoms each independently selected from the group consisting of N, O, and S, wherein the ring is substituted with from 1-2 oxo and further optionally substituted from 1-2 substituent each independently selected from the group consisting of hydroxy, $(C_1-C_6)$alkyl, $(C_1-C_6)$haloalkyl, and halogen. For example, $T^1$ is

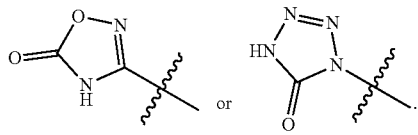 [SMILES: *c1noc(=O)[nH]1 ; *n1nn[nH]c1=O]

In some embodiments, $T^1$ is $(C_1-C_6)$alkyl which is substituted with from 1-3 hydroxy and further optionally substituted with from 1-10 fluoro. In certain of these embodiments, $T^1$ is $(C_1-C_6)$alkyl which is substituted with from 1-3 hydroxy and further substituted with from 1-10 fluoro. For example, $T^1$ is

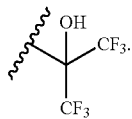

In some embodiments, $T^1$ is $C(=O)NHS(O)_2(C_1-C_4)$alkyl. For example, $T^1$ is $C(=O)NHS(O)_2Me$.

In some embodiments, $T^1$ is selected from the group consisting of the following:

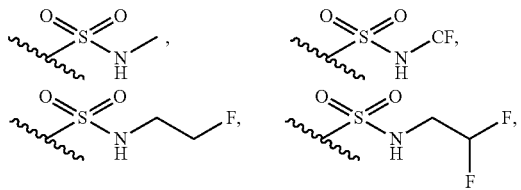

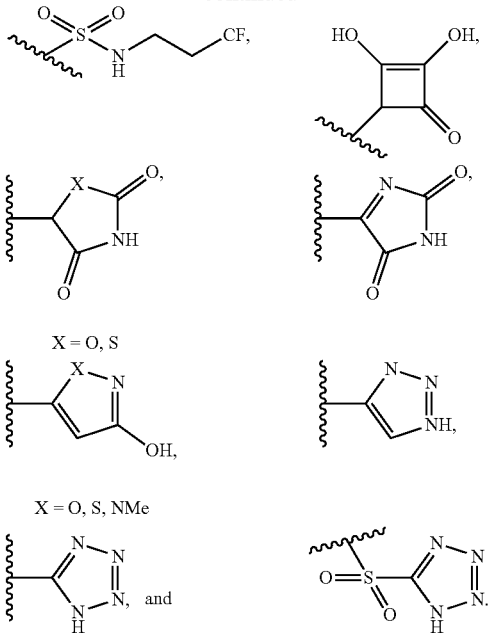

In some embodiments, $T^2$ is $(C_1-C_6)$alkyl which is optionally substituted with $(C_1-C_6)$alkoxy, $(C_1-C_6)$thioalkoxy, $(C_1-C_6)$haloalkoxy, $S(O)_2(C_1-C_6$ alkyl), $(C_3-C_6)$cycloalkyl, 3- to 6-membered heterocycloalkyl, phenyl, or 5- to 6-membered heteroaryl, wherein each of the $(C_3-C_6)$cycloalkyl, 3- to 6-membered heterocycloalkyl, phenyl, or 5- to 6-membered heteroaryl is optionally substituted with 1-4 $R^T$.

In some embodiments, $T^2$ is $(C_1-C_3)$alkyl which is substituted with $(C_1-C_6)$alkoxy, $(C_3-C_6)$cycloalkyl, 3- to 6-membered heterocycloalkyl, phenyl, or 5- to 6-membered heteroaryl.

In some embodiments, $T^2$ is $(C_1-C_3)$alkyl which is substituted with $(C_3-C_6)$cycloalkyl or 3- to 6-membered heterocycloalkyl. In some embodiments, $T^2$ is $(C_1-C_3)$alkyl which is substituted with 3- to 6-membered heterocycloalkyl. In some embodiments, $T^2$ is $(C_1-C_3)$alkyl which is substituted with 4- to 6-membered heterocycloalkyl. In some embodiments, $T^2$ is $(C_1-C_3)$alkyl which is substituted with oxetanyl. In some embodiments, $T^2$ is

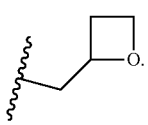 [SMILES: *CC1CCO1]

In some embodiments, the stereocenter in

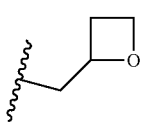

has (S)-configuration.

In some embodiments, $L^1$ is $CH_2$. In some embodiments, $L^1$ is a bond.

In some embodiments, $L^2$ is a bond.

In some embodiments, $L^1$ is $CH_2$, and $L^2$ is a bond.

In some embodiments L$^1$ is a bond; and L$^2$ is a bond. For avoidance of doubt, when L$^1$ is a bond; and L$^2$ is a bond, X$^3$ is directly bonded to Ring A.

In some embodiments, Ring A

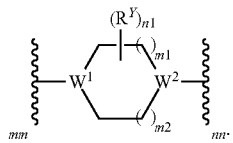

(A-1)

In some embodiments, m1 is 1. In some embodiments, m2 is 1. In some embodiments, m2 is 0. In some embodiments, W$^1$ is N. In some embodiments, W$^1$ is CR$^{Y1}$. In some embodiments, W$^1$ is CH. In some embodiments, W$^2$ is N. In some embodiments, W$^2$ is CR$^{Y2}$. In some embodiments, W$^2$ is CH. In some embodiments, n1 is 0. In some embodiments, n1 is 1. In some embodiments, R is (C$_1$-C$_6$)alkyl. In some embodiments, R is (C$_1$-C$_3$)alkyl, such as methyl. In some embodiments, R is ortho to W$^1$.

In some embodiments, Ring A is

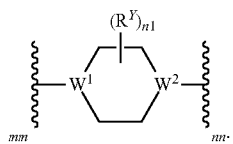

In some embodiments, W$^1$ is N. In some embodiments, W$^1$ is CR$^{Y1}$. In some embodiments, W$^1$ is CH. In some embodiments, W$^2$ is N. In some embodiments, W$^2$ is CR$^{Y2}$. In some embodiments, W$^2$ is CH. In some embodiments, n1 is 0. In some embodiments, n1 is 1. In some embodiments, R$^Y$ is (C$_1$-C$_6$)alkyl. In some embodiments, R is (C$_1$-C$_3$)alkyl, such as methyl. In some embodiments, R$^Y$ is ortho to W$^1$.

In some embodiments, Ring A is

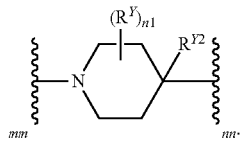

As a non-limiting example of the foregoing embodiments, Ring A can be

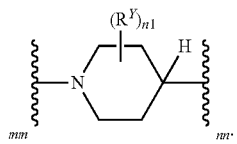

In some embodiments, n1 is 0. In some embodiments, n1 is 1. In some embodiments, R$^Y$ is (C$_1$-C$_6$)alkyl. In some embodiments, R is (C$_1$-C$_3$)alkyl, such as methyl.

In some embodiments, Ring A is

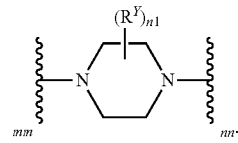

In some embodiments, n1 is 0. In some embodiments, n1 is 1. In some embodiments, R$^Y$ is (C$_1$-C$_6$)alkyl. In some embodiments, R$^Y$ is (C$_1$-C$_3$)alkyl, such as methyl.

In some embodiments, Ring A is

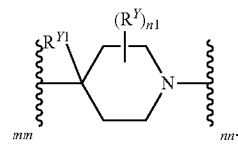

As a non-limiting example of the foregoing embodiments, Ring A can be

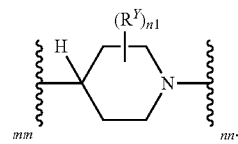

In some embodiments, n1 is 0. In some embodiments, n1 is 1. In some embodiments, R$^Y$ is (C$_1$-C$_6$)alkyl. In some embodiments, R is (C$_1$-C$_3$)alkyl, such as methyl.

In some embodiments, Ring A is

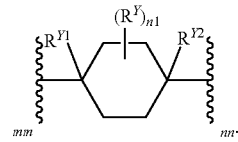

As a non-limiting example of the foregoing embodiments, Ring A can be

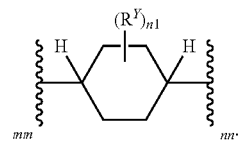

In some embodiments, n1 is 0. In some embodiments, n1 is 1. In some embodiments, R$^Y$ is (C$_1$-C$_6$)alkyl. In some embodiments, R is (C$_1$-C$_3$)alkyl, such as methyl.

In some embodiments, Ring A is

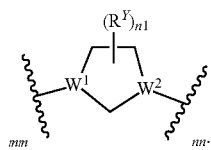

In some embodiments, $W^1$ is N, provided that $W^1$ and $W^2$ are not simultaneously N. In some embodiments, $W^1$ is $CR^{Y1}$. In some embodiments, $W^1$ is CH. In some embodiments, $W^2$ is N, provided that $W^1$ and $W^2$ are not simultaneously N. In some embodiments, $W^2$ is $CR^Y$. In some embodiments, $W^2$ is CH. In some embodiments, n1 is 0. In some embodiments, n1 is 1. In some embodiments, $R^Y$ is $(C_1$-$C_3)$alkyl. In some embodiments, $R^Y$ is $(C_1$-$C_3)$alkyl, such as methyl. In some embodiments, R is ortho to $W^1$.

In some embodiments, Ring A is

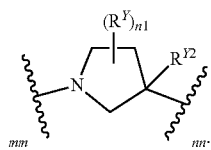

As a non-limiting example of the foregoing embodiments, Ring A can be

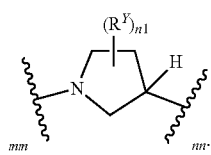

In some embodiments, n1 is 0. In some embodiments, n1 is 1. In some embodiments, $R^Y$ is $(C_1$-$C_6)$alkyl. In some embodiments, $R^Y$ is $(C_1$-$C_3)$alkyl, such as methyl.

In some embodiments, Ring A is

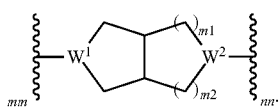

In some embodiments, m1 is 0; and m2 is 0. In some embodiments, W is N. In some embodiments, $W^2$ is $CR^{Y2}$. In some embodiments, $W^2$ is CH.

As a non-limiting example of the foregoing embodiments, Ring A can be

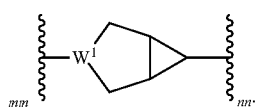

In some embodiments, $L^3$ is selected from the group consisting of —O—; —S—; —N(H)—; and —N($C_{1-3}$ alkyl)-. As a non-limiting example of the foregoing embodiments, $L^3$ can be —O—.

In some embodiments, $L^3$ is selected from the group consisting of —C($R^aR^a$)—; C(=O); and S(O)$_{1-2}$. As a non-limiting example of the foregoing embodiments, $L^3$ can be C(=O). As another non-limiting example, $L^3$ can be —C($R^aR^a$)—.

In some embodiments, $L^3$ is —C($R^aR^a$)—; and each $R^a$ is hydrogen. In some embodiments, $L^3$ is —CH$_2$—.

In some embodiments, Ring A is

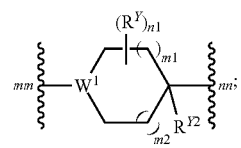

and $L^3$ is selected from the group consisting of —O—; —S—; —N(H)—; and —N($C_{1-3}$ alkyl)-. In some of these embodiments, $L^3$ is —O—. In some embodiments, $R^{Y2}$ is hydrogen. In some embodiments, m1 is 1. In some embodiments, m2 is 1. In some embodiments, $W^1$ is N. In some embodiments, $W^1$ is $CR^{Y1}$. In some embodiments, $W^1$ is CH. In some embodiments, n1 is 0. In some embodiments, n1 is 1; and R is $(C_1$-$C_6)$alkyl, such as $(C_1$-$C_3)$alkyl (e.g., methyl). In some embodiments, R is ortho to $W^1$.

In some embodiments, Ring A is

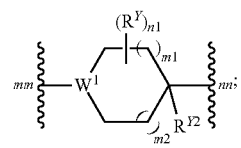

and $L^3$ is selected from the group consisting of: —C($R^aR^a$)—; C(=O); and S(O)$_{1-2}$. In some of these embodiments, $L^3$ is —C($R^aR^a$)—. In some embodiments, $L^3$ is —CH$_2$—. In some embodiments, $R^{Y2}$ is hydrogen. In some embodiments, m1 is 1. In some embodiments, m2 is 1. In some embodiments, $W^1$ is N. In some embodiments, $W^1$ is $CR^{Y1}$. In some embodiments, $W^1$ is CH. In some embodiments, n1 is 0. In some embodiments, n1 is 1; and R is $(C_1$-$C_6)$alkyl, such as $(C_1$-$C_3)$alkyl (e.g., methyl). In some embodiments, R is ortho to $W^1$.

In some embodiments when Ring A is

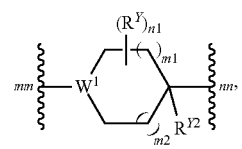

$L^3$ is —C($R^aR^a$), wherein one $R^a$ combines with $R^{Y2}$ to form a double bond; and the other $R^a$ is selected from the group consisting of hydrogen, halogen, CN, $(C_1$-$C_6)$alkyl, $(C_1$-$C_3)$ haloalkyl, and $(C_3$-$C_8)$cycloalkyl. For example, the other $R^a$ can be hydrogen. In some embodiments, m1 is 1. In some embodiments, m2 is 1. In some embodiments, $W^1$ is N. In some embodiments, $W^1$ is $CR^{Y1}$. In some embodiments, $W^1$ is CH. In some embodiments, n1 is 0. In some embodiments, n1 is 1; and R is $(C_1$-$C_6)$alkyl, such as $(C_1$-$C_3)$alkyl (e.g., methyl). In some embodiments, $R^7$ is ortho to $W^1$.

In some embodiments, Ring A is

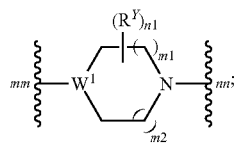

and $L^3$ is selected from the group consisting of: —C($R^a R^a$)—; C(=O); and S(O)$_{1-2}$. In some of these embodiments, $L^3$ is C(=O). In some embodiments, m1 is 1. In some embodiments, m2 is 1. In some embodiments, $W^1$ is N. In some embodiments, $W^1$ is CR$^{Y1}$. In some embodiments, $W^1$ is CH. In some embodiments, n1 is 0. In some embodiments, n1 is 1; and R is (C$_1$-C$_6$)alkyl, such as (C$_1$-C$_3$)alkyl (e.g., methyl). In some embodiments, R is ortho to $W^1$.

In some embodiments, Ring A is

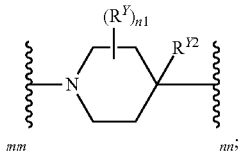

and $L^3$ is —O—. In some embodiments, $R^{Y2}$ is H. In some embodiments, n1 is 0. In some embodiments, n1 is 1; and $R^Y$ is (C$_1$-C$_6$)alkyl, such as (C$_1$-C$_3$)alkyl (e.g., methyl).

In some embodiments, Ring A is

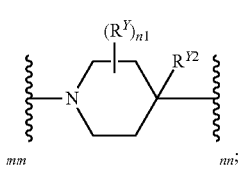

and $L^3$ is —C($R^a R^a$)—. In some embodiments, $L^3$ is —CH$_2$—. In some embodiments, $R^{Y2}$ is H. In some embodiments, n1 is 0. In some embodiments, n1 is 1; and R is (C$_1$-C$_6$)alkyl, such as (C$_1$-C$_3$)alkyl (e.g., methyl).

In some embodiments, Ring A is

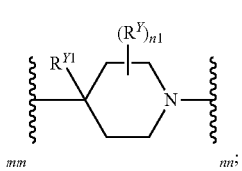

and $L^3$ is C(=O). In some embodiments, $R^{Y1}$ is hydrogen. In some embodiments, n1 is 0. In some embodiments, n1 is 1; and $R^Y$ is (C$_1$-C$_6$)alkyl, such as (C$_1$-C$_3$)alkyl (e.g., methyl).

In some embodiments, Ring A is

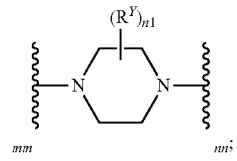

and $L^3$ is C(=O). In some embodiments, n1 is 0. In some embodiments, n1 is 1; and $R^Y$ is (C$_1$-C$_6$)alkyl, such as (C$_1$-C$_3$)alkyl (e.g., methyl).

In some embodiments, ring A is C$_6$-C$_{10}$ arylene, e.g., phenylene.

In some embodiments, $B^2$ is N. In some embodiments, $B^2$ is CR$^1$. For example, $B^2$ can be CH.

In some embodiments, $B^1$ is N. In some embodiments, $B^1$ is CR$^1$. For example, $B^2$ can be CH. As another non-limiting example, $B^1$ can be C-halogen, such as CF.

In some embodiments, $B^4$ is CR$^1$. For example, $B^4$ can be CH.

In some embodiments, $B^3$ is N. In some embodiments, $B^3$ is CR$^1$. For example, $B^3$ can be CH.

In some embodiments, $B^2$ is N; and $B^1$, $B^3$, and $B^4$ are independently CR$^1$. In some of these embodiments, $B^1$, $B^3$, and $B^4$ are CH. In some embodiments, $B^1$ is C-halogen; and $B^3$ and $B^4$ are CH.

In some embodiments, $B^2$ is N; $B^1$ is N; and $B^3$ and $B^4$ are independently CR$^1$.

In some of these embodiments, $B^3$ and $B^4$ are CH.

In some embodiments, $B^2$ is N; $B^3$ is N; and $B^1$ and $B^4$ are independently CR$^1$.

In some of these embodiments, $B^1$ and $B^4$ are CH.

In some embodiments, $B^1$, $B^2$, $B^3$, and $B^4$ are independently CR$^1$. In some of these embodiments, $B^1$ is CH or C-halogen; and $B^2$, $B^3$, and $B^4$ are CH.

In some embodiments, Ring B is

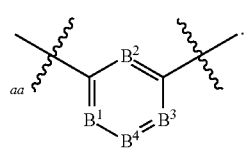

(B-I)

In some embodiments, $B^2$ is N. In some embodiments, $B^2$ is CR$^1$. For example, $B^2$ can be CH. In some embodiments, $B^1$ is N. In some embodiments, $B^1$ is CR$^1$. For example, $B^1$ can be CH. As another non-limiting example, $B^1$ can be C-halogen, such as CF. In some embodiments, $B^4$ is CR$^1$. For example, $B^4$ can be CH. In some embodiments, $B^3$ is N. In some embodiments, $B^3$ is CR$^1$. For example, $B^3$ can be CH.

In some embodiments, Ring B is

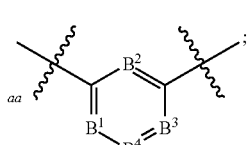

(B-I)

$B^2$ is N; and $B^1$, $B^3$, and $B^4$ are independently CR$^1$. In some of these embodiments, $B^1$, $B^3$, and $B^4$ are CH. In some embodiments, $B^1$ is C-halogen; and $B^3$ and $B^4$ are CH.

In some embodiments, Ring B is

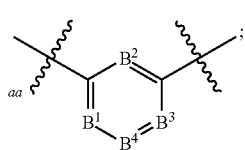
(B-I)

$B^2$ is N; $B^1$ is N; and $B^3$ and $B^4$ are independently $CR^1$. In some of these embodiments, $B^3$ and $B^4$ are CH.

In some embodiments, Ring B is

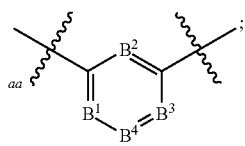
(B-I)

$B^2$ is N; $B^3$ is N; and $B^1$ and $B^4$ are independently $CR^1$. In some of these embodiments, $B^1$ and $B^4$ are CH.

In some embodiments, Ring B is

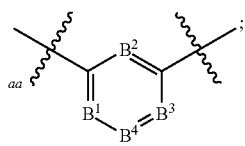
(B-I)

$B^1$, $B^2$, $B^3$, and $B^4$ are independently $CR^1$. In some of these embodiments, $B^1$ is CH or C-halogen; and $B^2$, $B^3$, and $B^4$ are CH.

In some embodiments, Ring B is

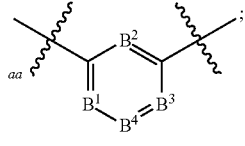
(B-II)

In some embodiments, $B^1$, $B^2$, $B^3$, and $B^4$ are independently $CR^1$. In some of these embodiments, B, $B^2$, $B^3$ and $B^4$ are CH.

In some embodiments, Ring B is

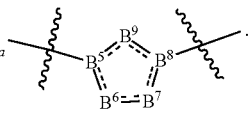
(B-III)

In some embodiments, $B^9$ is N. In some embodiments, $B^9$ is S. In some embodiments, $B^8$ is C. In some embodiments, $B^8$ is N. In some embodiments, $B^5$ is C.

In some embodiments, Ring B is

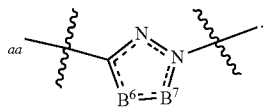

As a non-limiting example of the foregoing embodiments, Ring B can be

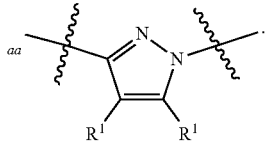

For example, Ring B can be

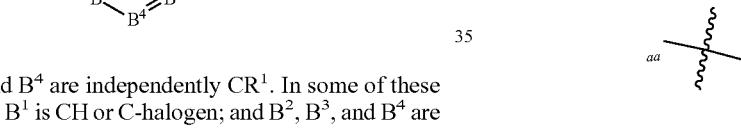

wherein $R^{1a}$ is $(C_1-C_3)$alkyl.

In some embodiments, Ring B is

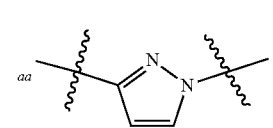

For example, Ring B can be

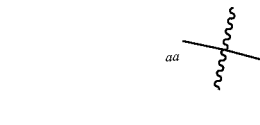

As another non-limiting example, Ring B can be

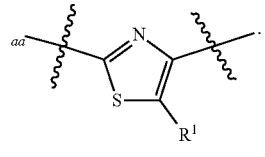

In some embodiments, Ring B has

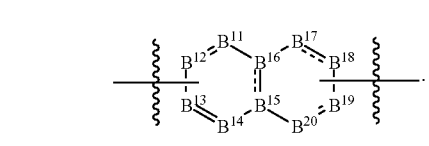
(B-IV)

In certain embodiments, one of $B^{11}$, $B^{12}$, $B^{13}$, and $B^{14}$ is C, and the other three of $B^{11}$, $B^{12}$, $B^{13}$, and $B^{14}$ are independently selected from N and $CR^1$.

In certain embodiments, one of $B^{11}$, $B^{12}$, $B^{13}$, and $B^{14}$ is C, and the other three of $B^{11}$, $B^{12}$, $B^{13}$, and $B^{14}$ are each an independently selected $CR^1$ (e.g., CH or CF).

In certain of these embodiments, $B^{11}$ or $B^{14}$ is C.

In certain of these embodiments, $B^{11}$ or $B^{14}$ is the point of attachment of ring B to ring A.

In other embodiments, $B^{12}$ or $B^{13}$ is C.

In certain of these embodiments, $B^{12}$ or $B^{13}$ is the point of attachment of ring B to ring C.

In certain embodiments, each of $B^{15}$ and $B^{16}$ is C. In other embodiments, one of $B^{15}$ and $B^{16}$ is C, and the other is N.

In certain embodiments, one of $B^{18}$ and $B^{19}$ is absent.

In certain embodiments, from 1-2 of $B^{17}$, $B^{18}$ or $B^{19}$, and $B^{20}$ are selected from the group consisting of O, S, $NR^N$, and N; and the others are independently C or $CR^1$.

In certain of these embodiments, $B^7$ or $B^{20}$ is N or C.

In certain of these embodiments, $B^1$ or $B^{20}$ is the point of attachment of ring B to ring A.

In other embodiments, $B^{18}$ or $B^{19}$ is N or C.

In certain of these embodiments, $B^{18}$ or $B^{19}$ is the point of attachment of ring B to ring C.

In certain embodiments, $B^{11}$ or $B^{14}$ is C and is the point of attachment of ring B to ring A; and $B^{18}$ or $B^{19}$ is C or N and is the point of attachment of ring B to ring C.

In certain of these embodiments, one of $B^{18}$ or $B^{19}$ is absent.

In certain embodiments, $B^{11}$ is C and is the point of attachment of ring B to ring A; and $B^{18}$ is C or N and is the point of attachment of ring B to ring C. In certain of these embodiments, $B^{19}$ is absent.

In certain embodiments, $B^{14}$ is C and is the point of attachment of ring B to ring A; and $B^{19}$ is C or N and is the point of attachment of ring B to ring C. In certain of these embodiments, $B^{18}$ is absent.

In certain embodiments, $B^{12}$ or $B^{13}$ is C and is the point of attachment of ring B to ring C; and $B^{17}$ or $B^{20}$ is C or N and is the point of attachment of ring B to ring A.

In certain of these embodiments, one of $B^{18}$ or $B^{19}$ is absent.

In certain embodiments, $B^{12}$ is C and is the point of attachment of ring B to ring C; and $B^{17}$ is C or N and is the point of attachment of ring B to ring A. In certain of these embodiments, one of $B^{18}$ or $B^{19}$ is absent.

In certain embodiments, $B^{13}$ is C and is the point of attachment of ring B to ring C; and $B^{20}$ is C or N and is the point of attachment of ring B to ring A. In certain of these embodiments, one of $B^{18}$ or $B^{19}$ is absent.

In certain embodiments, ring B has formula B-IVa:

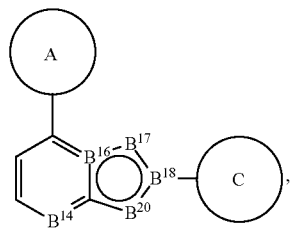

B-IVva in which:
$B^{14}$ is $CR^1$ (e.g., CH or CF) or N;
$B^{16}$ is N or C (e.g., C);

$B^{17}$ is CR (e.g., CH), N, S, or O (e.g., N or O);
$B^{18}$ is N or C; and
$B^{20}$ is CR (e.g., CH), N, S, or O (e.g., N, S, or CH).

In certain embodiments, ring B has formula B-IVb:

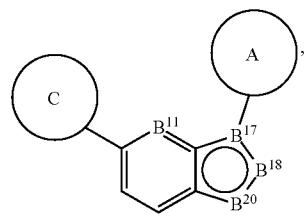

B-IVb in which:
$B^{11}$ is $CR^1$ (e.g., CH) or N;
$B^{17}$ is N or C;
$B^{18}$ is $CR^1$ (e.g., CH) or N; and
$B^{20}$ is $CR^1$ (e.g., CH), N, S, or O (e.g., N, S, or CH).

Non-limiting examples of ring B having formula (B-IV) include:

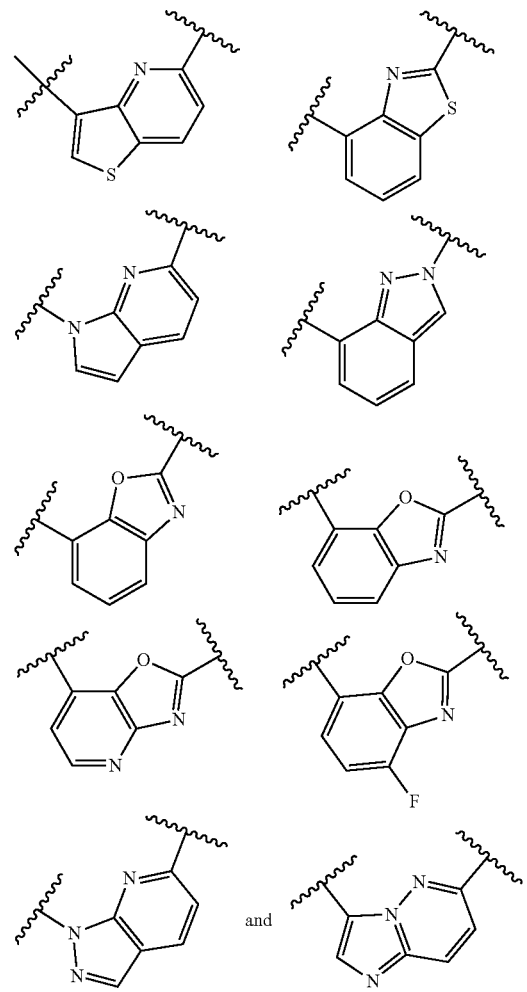

In some embodiments, $L^4$ is —O—.
In some embodiments, $L^4$ is —$C(R^cR^c)$—. In some embodiments, each $R^c$ is hydrogen. In some embodiments, each $R^c$ is halogen. For example, each $R^c$ can be —F. In some embodiments, one $R^c$ is hydrogen; and the other $R^c$ is $(C_1-C_3)$alkyl. In some embodiments, a pair of $R^c$ taken together with the carbon atom to which each is attached forms a $(C_3-C_8)$cycloalkyl ring. For example, a pair of $R^c$ taken together with the carbon atom to which each is attached can form a $(C_3-C_4)$cycloalkyl (e.g., cyclopropyl) ring.

In some embodiments, $L^4$ is —CH$_2$—. In some embodiments, $L^4$ is —CF$_2$—, —CH(Me)-, or

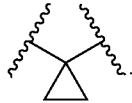 [SMILES: *C1(*)CC1]

In some embodiments, $L^5$ is a bond.
In some embodiments, $L^4$ is —O—; and $L^5$ is a bond.
In some embodiments, $L^4$ is —C(RR)—; and $L^5$ is a bond.
In some embodiments, $L^4$ is selected from the group consisting of: —CH$_2$—, —CF$_2$—, —CH(Me)-, and

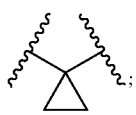 [SMILES: *C1(*)CC1]

and $L^5$ is a bond.

In some embodiments, Ring C is selected from the group consisting of: phenyl, 5- to 6-membered heteroaryl, and 5- to 10-membered bicycloheteroaryl. In some embodiments, b is 1-3. For example, b can be 2. As another non-limiting example, b can be 1. In some embodiments, b is 0.

In some embodiments, Ring C is phenyl. In some embodiments, b is 1-3. For example, b can be 2. As another non-limiting example, b can be 1. In some embodiments, b is 0.

In some embodiments, Ring C is phenyl; and b is 2. In some embodiments,

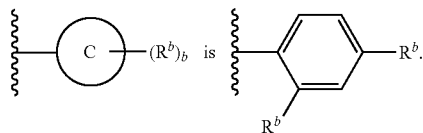

In some embodiments, Ring C is phenyl; and b is 1. In some embodiments,

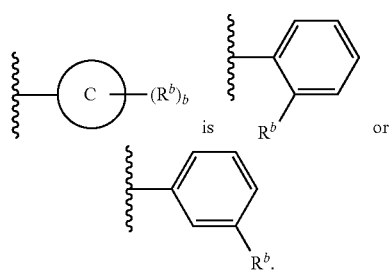

In some embodiments

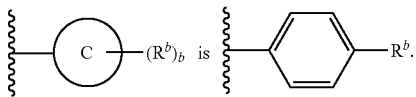

In some embodiments, Ring C is phenyl; and b is 0.

In some embodiments, Ring C is pyridyl. In some embodiments, b is 1-3. For example, b can be 2. As another non-limiting example, b can be 1. In some embodiments, b is 0.

In some embodiments, Ring C is pyridyl; and b is 1. In some embodiments,

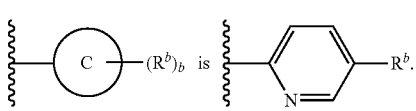

In some embodiments, each occurrence of $R^b$ is independently selected from the group consisting of: $(C_1-C_6)$alkyl, $(C_1-C_6)$haloalkyl, $(C_1-C_6)$alkoxy, halogen, and CN.

In some embodiments, each occurrence of $R^b$ is independently selected from the group consisting of —F, —Cl, —CH$_3$, —CF$_3$, and CN.

In some embodiments, each occurrence of $R^b$ is independently selected from the group consisting of —F, —Cl, and —CN.

In some embodiments, the compound is a compound of Formula (I-A):

Formula I-A

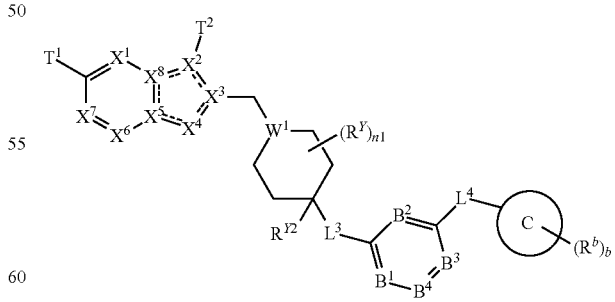

or a pharmaceutically acceptable salt thereof, wherein:
$L^3$ is selected from the group consisting of —O—; —S—; —N(H)—; and —N(C$_{1-3}$ alkyl)-.

In some embodiments of Formula (I-A), $L^3$ is —O—.

In some embodiments, the compound is a compound of Formula (I-B):

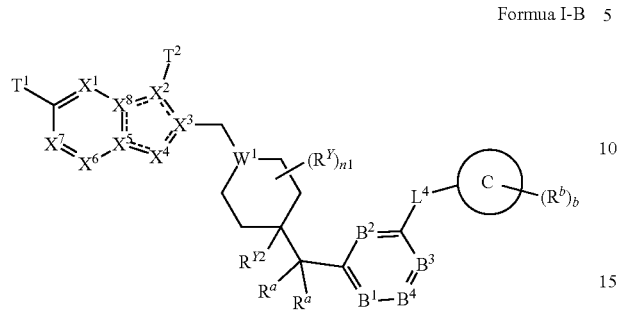

Formula I-B or a pharmaceutically acceptable salt thereof.

In some embodiments of Formula (I-B), each $R^a$ is hydrogen.

In some embodiments of Formula (I-B), one $R^a$ combines with $R^{y2}$ to form a double bond; and the other $R^a$ is selected from the group consisting of: hydrogen, halogen, CN, ($C_1$-$C_6$)alkyl, ($C_1$-$C_3$)haloalkyl, and ($C_3$-$C_8$)cycloalkyl. In some embodiments, the other $R^a$ is hydrogen.

In some embodiments of Formulae (I-A) or (I-B), $B^2$ is N; and $B^1$, $B^3$, and $B^4$ are independently $CR^1$. In some embodiments, $B^1$ is CH or C-halogen; and $B^3$ and $B^4$ are CH.

In some embodiments of Formulae (I-A) or (I-B), $B^2$ is N; B is N; and $B^3$ and $B^4$ are independently $CR^1$. In some embodiments, $B^3$ and $B^4$ are CH.

In some embodiments of Formulae (I-A) or (I-B), $B^2$ is N; $B^3$ is N; and $B^1$ and $B^4$ are independently $CR^1$. In some embodiments, $B^1$ and $B^4$ are CH.

In some embodiments of Formulae (I-A) or (I-B), $B^1$, $B^2$, $B^3$, and $B^4$ are independently $CR^1$, such as CH.

In some embodiments, the compound is a compound of Formula (I-C):

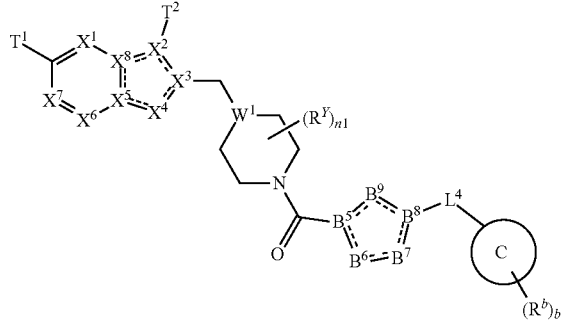

Formula I-C or a pharmaceutically acceptable salt thereof.

In some embodiments of Formula (I-C), $B^9$ is N.

In some embodiments of Formula (I-C), $B^5$ is C; and $B^8$ is C. In some embodiments of Formula (I-C), $B^5$ is C; and $B^8$ is N.

In some embodiments of Formula (I-C), the ring including $B^5$-$B^9$ is

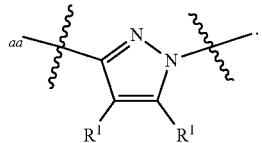

In some embodiments of Formula (I-C), the ring including $B^5$-$B^9$ is

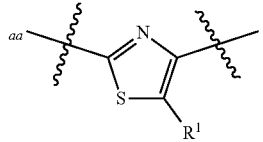

In some embodiments of Formulae (I-A), (I-B), or (I-C), $W^1$ is $CR^{Y1}$. For example, $W^1$ can be CH.

In some embodiments of Formulae (I-A), (I-B), or (I-C), $W^1$ is N.

In some embodiments of Formulae (I-A), (I-B), or (I-C), n1 is 0.

In some embodiments of Formulae (I-A), (I-B), or (I-C), n1 is 1.

In some embodiments of Formulae (I-A), (I-B), or (I-C), $R^Y$ is ortho to $W^1$.

In some embodiments of Formulae (I-A), (I-B), or (I-C), $R^Y$ is ($C_1$-$C_3$)alkyl, such as methyl.

In some embodiments of Formulae (I-A), (I-B), or (I-C), $L^4$ is —O—.

In some embodiments of Formulae (I-A), (I-B), or (I-C), $L^4$ is —C($R^cR^c$)—. For example, $L^4$ can be —$CH_2$—.

In some embodiments of Formulae (I-A), (I-B), or (I-C), $L^4$ is —C($R^cR^c$)—; and one or both $R^c$ is other than hydrogen. As non-limiting examples of the foregoing embodiments, $L^4$ can be selected from the group consisting of: —$CH_2$—, —$CF_2$—, —CH(Me)-, and

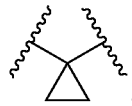

In some embodiments of Formulae (I-A), (I-B), or (I-C), $X^8$, $X^5$, and $X^3$ are C; $X^2$ and $X^4$ are N; $X^7$ is CH; and $X^1$ and $X^6$ are independently CH or N.

In some embodiments of Formulae (I-A), (I-B), or (I-C), $X^8$, $X^5$, and $X^3$ are C; $X^2$ and $X^4$ are N; $X^7$ is CH; $X^1$ is N; and $X^6$ is CH.

In some embodiments of Formulae (I-A), (I-B), or (I-C), $X^8$, $X^5$, and $X^3$ are C; $X^2$ and $X^4$ are N; $X^7$ is CH; $X^1$ is CH; and $X^6$ is CH.

In some embodiments of Formulae (I-A), (I-B), or (I-C), $T^1$ is C(=O)OH.

In some embodiments of Formulae (I-A), (I-B), or (I-C), $T^2$ is ($C_1$-$C_3$)alkyl which is substituted with 4- to 6-membered heterocycloalkyl.

In some embodiments of Formulae (I-A), (I-B), or (I-C), $T^2$ is ($C_1$-$C_3$)alkyl which is substituted with oxetanyl.

In some embodiments of Formulae (I-A), (I-B), or (I-C), T² is

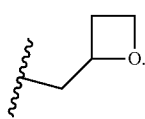 [SMILES: *CC1CCO1]

In some embodiments, the stereocenter of T² has (S)-configuration.

In some embodiments of Formulae (I-A), (I-B), or (I-C),

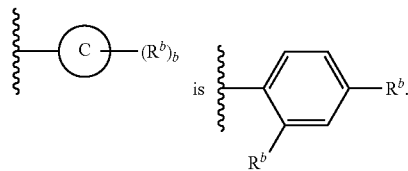

In some embodiments of Formulae (I-A), (I-B), or (I-C),

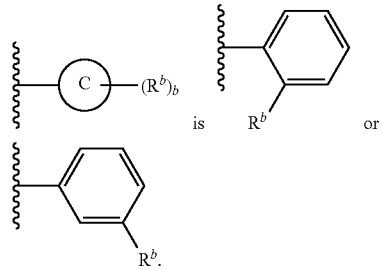

In some embodiments of Formulae (I-A), (I-B), or (I-C),

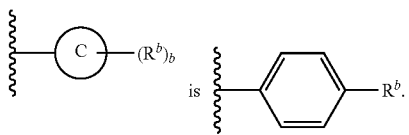

In some embodiments of Formulae (I-A), (I-B), or (I-C),

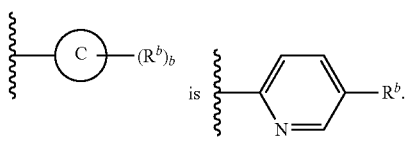

In some embodiments of Formulae (I-A), (I-B), or (I-C), each occurrence of $R^b$ is independently selected from the group consisting of: $(C_1-C_6)$alkyl, $(C_1-C_6)$haloalkyl, $(C_1-C_6)$alkoxy, halogen, and CN. As non-limiting examples of the foregoing embodiments, each occurrence of $R^b$ can be independently selected from the group consisting of —F, —Cl, and CN.

In some embodiments, the compound is selected from the group consisting of the compounds in Table $C_1$ or a pharmaceutically acceptable salt or solvate thereof.

TABLE C1

| Compound No. | Structure |
|---|---|
| 101 | (structure shown) |

TABLE C1-continued

| Compound No. | Structure |
|---|---|
| 102 | 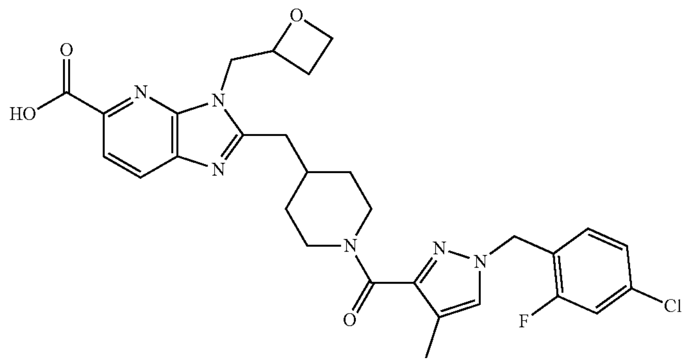 [SMILES: Cc1cn(Cc2ccc(Cl)cc2F)nc1C(=O)N1CCC(Cc2nc3ccc(C(=O)O)nc3n2CC2CCO2)CC1] |
| 103 | 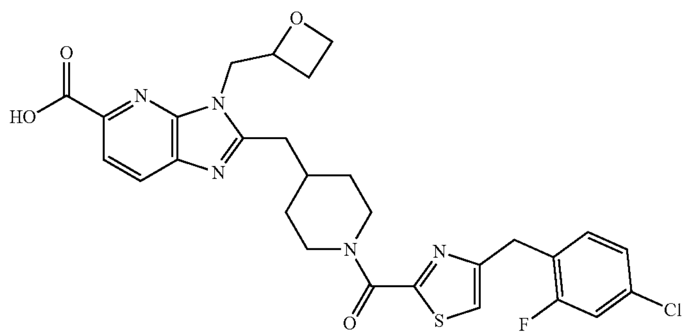 [SMILES: O=C(O)c1ccc2nc(CC3CCN(C(=O)c4nc(Cc5ccc(Cl)cc5F)cs4)CC3)n(CC3CCO3)c2n1] |
| 104 | 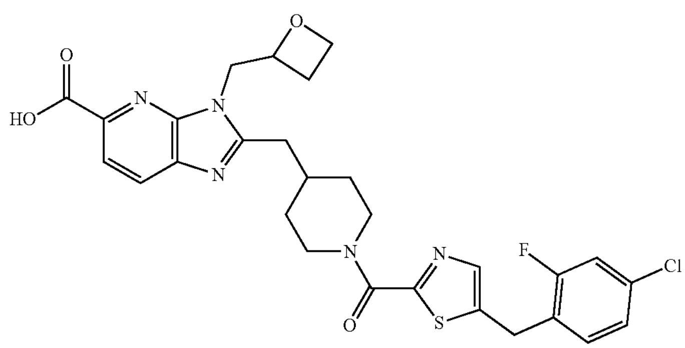 [SMILES: O=C(O)c1ccc2nc(CC3CCN(C(=O)c4ncc(Cc5ccc(Cl)cc5F)s4)CC3)n(CC3CCO3)c2n1] |
| 105 | 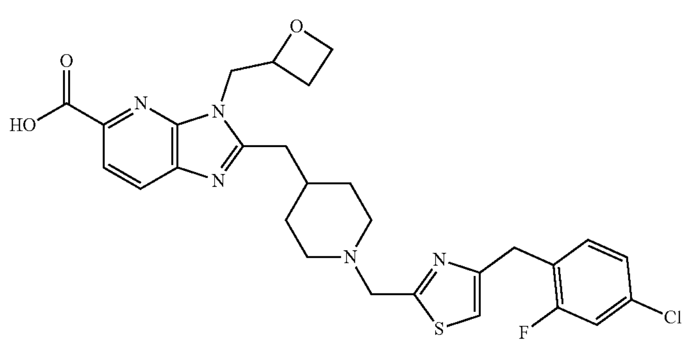 [SMILES: O=C(O)c1ccc2nc(CC3CCN(Cc4nc(Cc5ccc(Cl)cc5F)cs4)CC3)n(CC3CCO3)c2n1] |

TABLE C1-continued

| Compound No. | Structure |
|---|---|
| 106 | 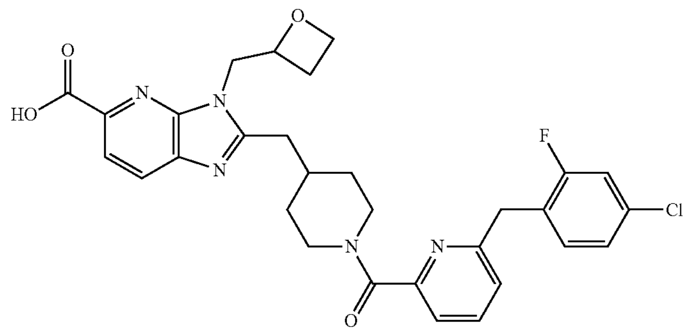 [SMILES: O=C(O)c1ccc2nc(CC3CCN(C(=O)c4cccc(Cc5ccc(Cl)cc5F)n4)CC3)n(CC3CCO3)c2n1] |
| 107 | 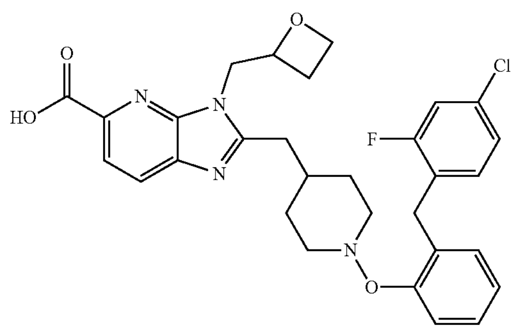 [SMILES: O=C(O)c1ccc2nc(CC3CCN(Oc4ccccc4Cc4ccc(Cl)cc4F)CC3)n(CC3CCO3)c2n1] |
| 108 | 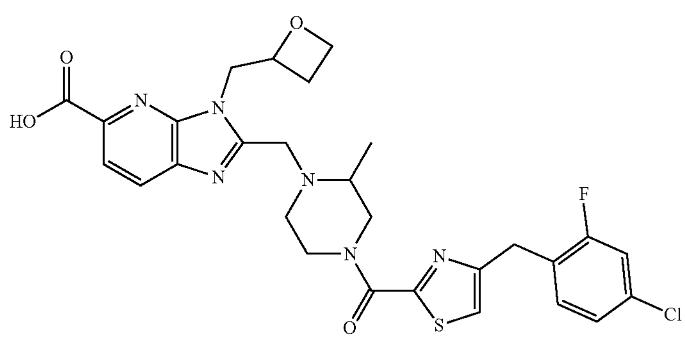 [SMILES: CC1CN(C(=O)c2nc(Cc3ccc(Cl)cc3F)cs2)CCN1Cc1nc2ccc(C(=O)O)nc2n1CC1CCO1] |
| 109 | 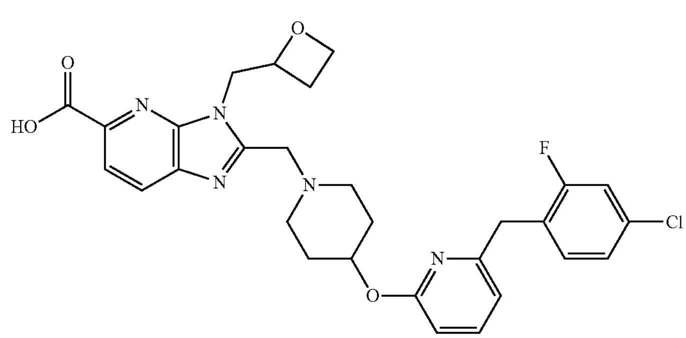 [SMILES: O=C(O)c1ccc2nc(CN3CCC(Oc4cccc(Cc5ccc(Cl)cc5F)n4)CC3)n(CC3CCO3)c2n1] |

TABLE C1-continued
| Compound No. | Structure |
|---|---|
| 110 | 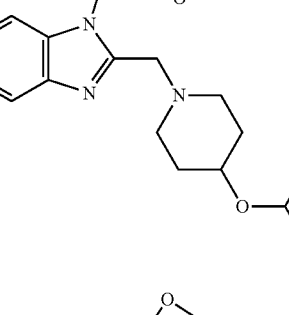 |
| 111 | 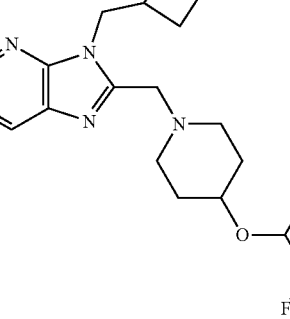 |
| 112 | 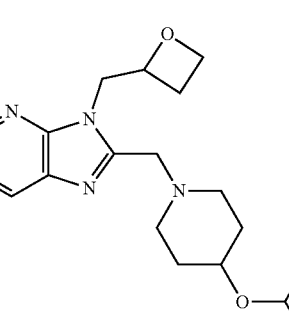 |
| 113 | 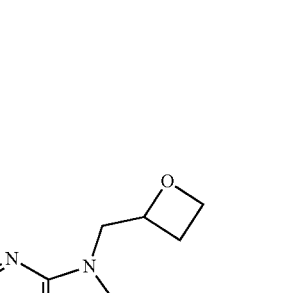 |

TABLE C1-continued
| Compound No. | Structure |
|---|---|
| 114 | 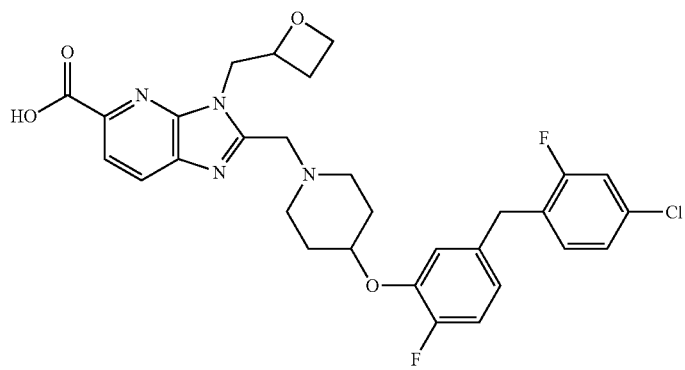 [SMILES: O=C(O)c1ccc2nc(CN3CCC(Oc4nc(Cc5ccc(Cl)cc5F)ccc4F)CC3)n(CC3CCO3)c2n1] |
| 115 | 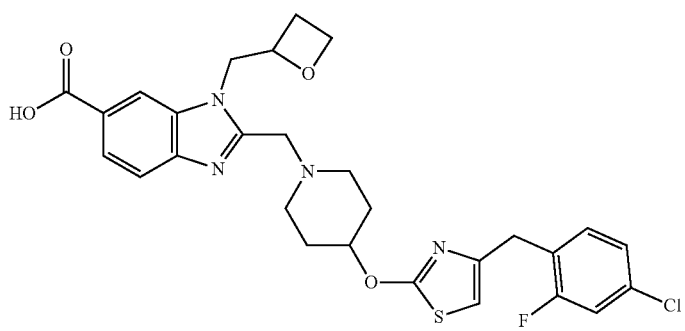 [SMILES: O=C(O)c1ccc2nc(CN3CCC(Oc4nc(Cc5ccc(Cl)cc5F)cs4)CC3)n(CC3CCO3)c2c1] |
| 116 | 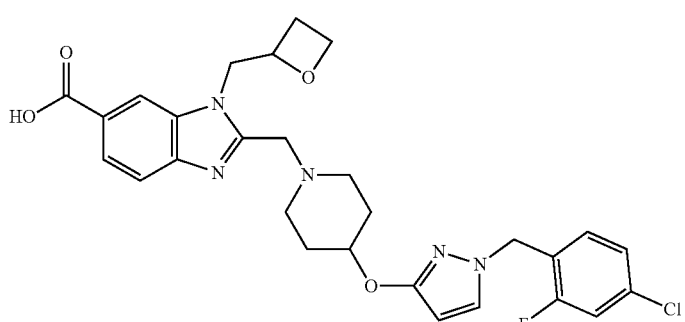 |
| 117 | 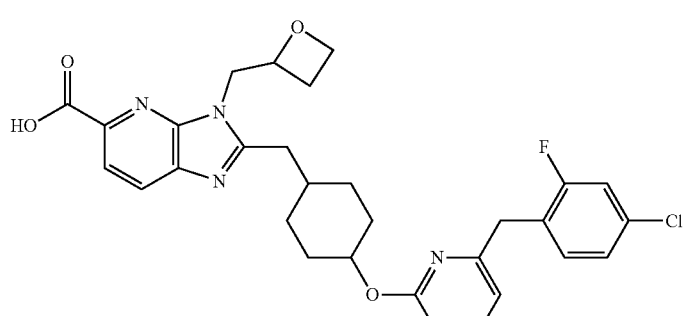 |

TABLE C1-continued

| Compound No. | Structure |
|---|---|
| 118 | (structure) |
| 119 | (structure) |
| 120 | (structure) |
| 121 | (structure) |

TABLE C1-continued
| Compound No. | Structure |
|---|---|
| 122 | 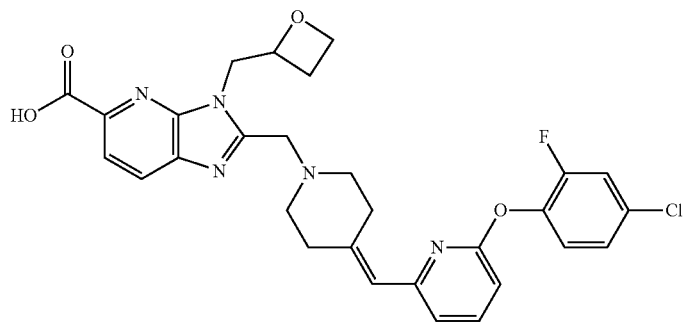 [SMILES: O=C(O)c1ccc2nc(CN3CCC(=Cc4cccc(Cc5ccc(Cl)cc5F)n4)CC3)n(CC3CCO3)c2n1] |
| 123 | 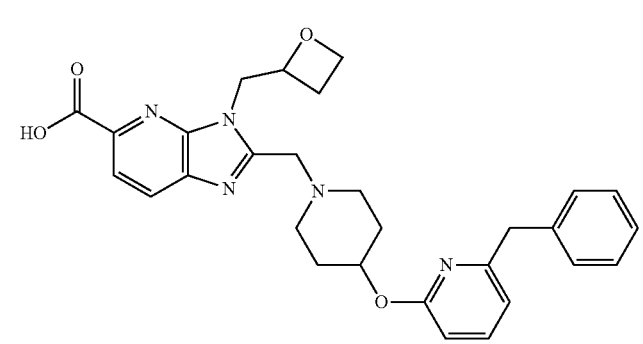 [SMILES: O=C(O)c1ccc2nc(CN3CCC(Oc4cccc(Cc5ccccc5)n4)CC3)n(CC3CCO3)c2n1] |
| 124 | 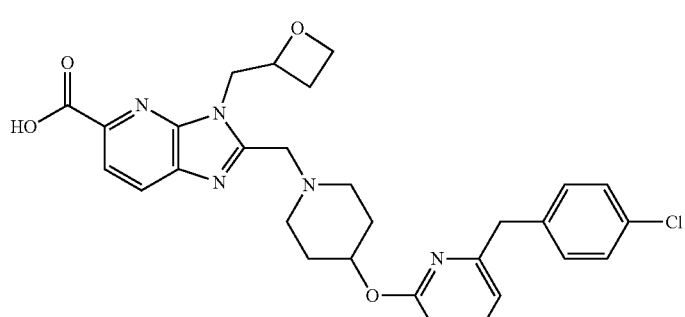 |
| 125 | 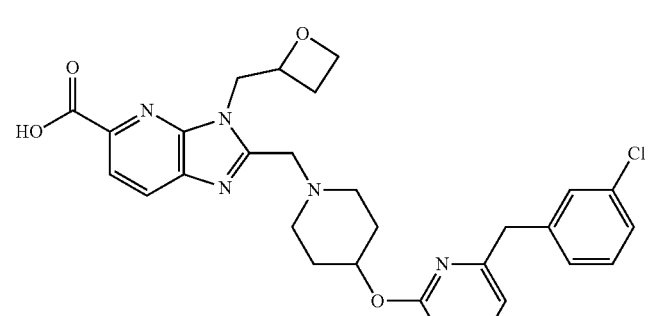 |

TABLE C1-continued
| Compound No. | Structure |
|---|---|
| 126 | 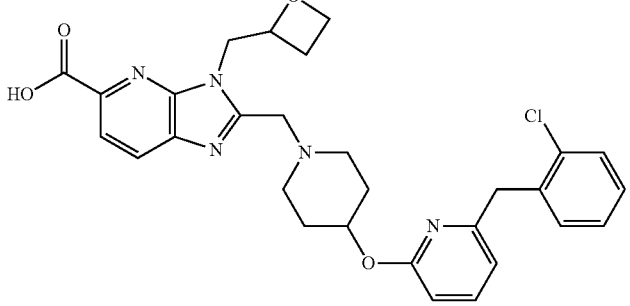 |
| 127 | 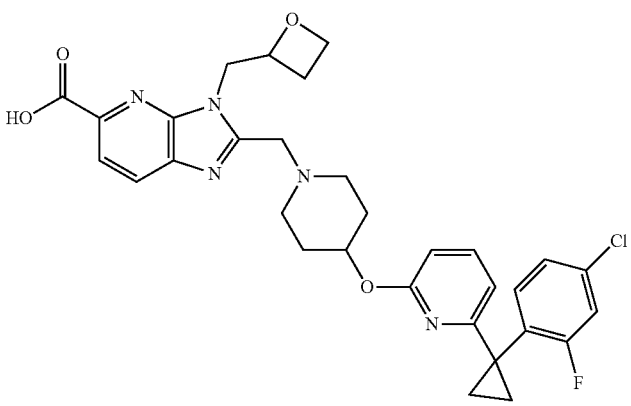 [SMILES: O=C(O)c1ccc2nc(CN3CCC(Oc4cccc(C5(c6ccc(Cl)cc6F)CC5)n4)CC3)n(CC3CCO3)c2n1] |
| 128 | 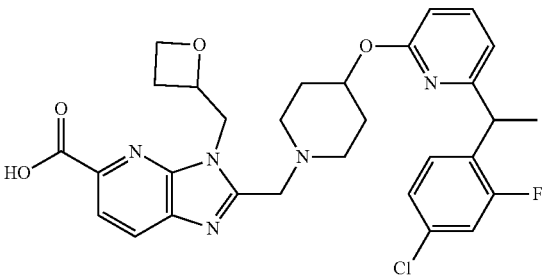 [SMILES: CC(c1cccc(OC2CCN(Cc3nc4ccc(C(=O)O)nc4n3CC3CCO3)CC2)n1)c1ccc(Cl)cc1F] |
| 129 | 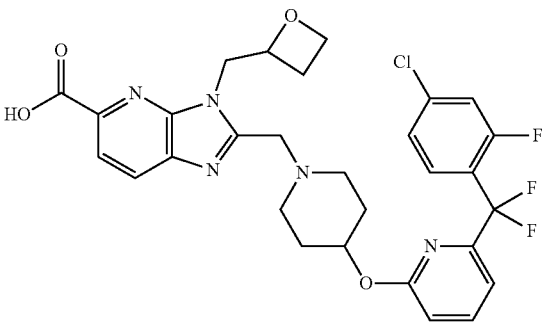 [SMILES: O=C(O)c1ccc2nc(CN3CCC(Oc4cccc(C(F)(F)c5ccc(Cl)cc5F)n4)CC3)n(CC3CCO3)c2n1] |
| 130 | 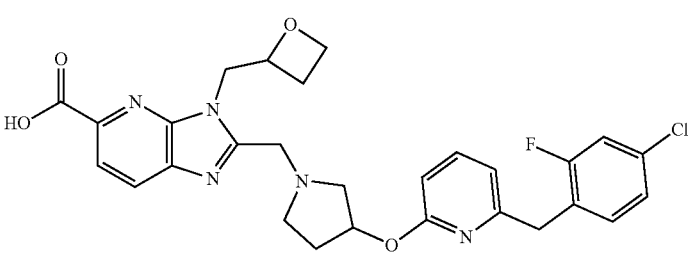 [SMILES: O=C(O)c1ccc2nc(CN3CCC(Oc4cccc(Cc5ccc(Cl)cc5F)n4)C3)n(CC3CCO3)c2n1] |

TABLE C1-continued

| Compound No. | Structure |
|---|---|
| 131 | 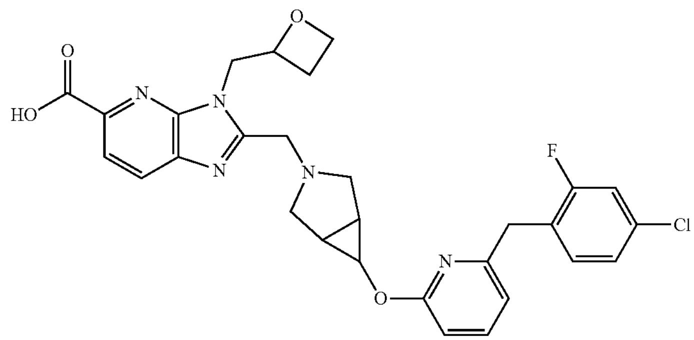 [SMILES: O=C(O)c1ccc2nc(CN3CC4C(C3)C4Oc3cccc(Cc4ccc(Cl)cc4F)n3)n(CC3CCO3)c2n1] |
| 132 | 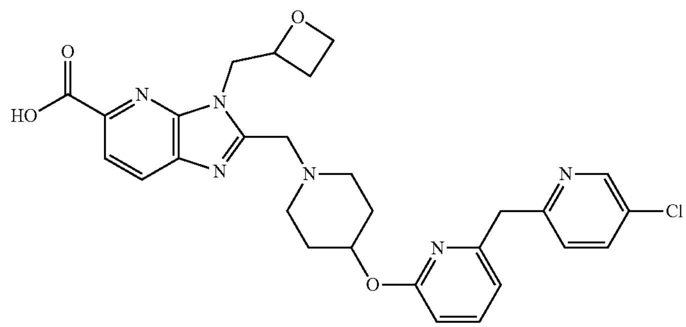 [SMILES: O=C(O)c1ccc2nc(CN3CCC(Oc4cccc(Cc5ccc(Cl)cn5)n4)CC3)n(CC3CCO3)c2n1] |
| 133 | 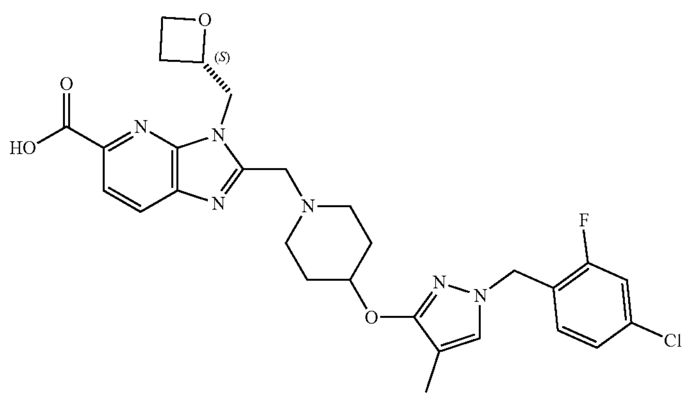 |
| 134 | 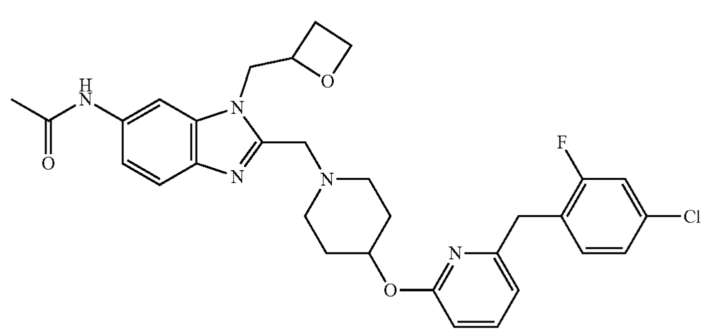 [SMILES: CC(=O)Nc1ccc2nc(CN3CCC(Oc4cccc(Cc5ccc(Cl)cc5F)n4)CC3)n(CC3CCO3)c2c1] |

TABLE C1-continued
| Compound No. | Structure |
|---|---|
| 135 | 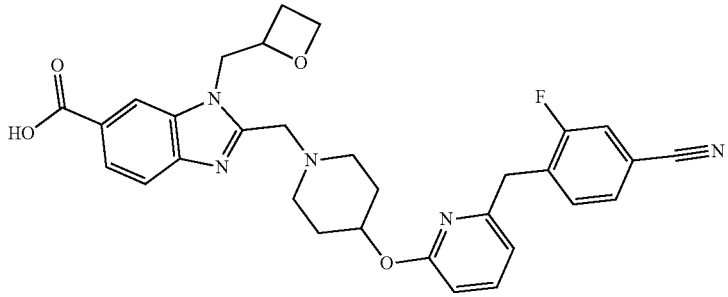 [SMILES: N#Cc1ccc(Cc2cccc(OC3CCN(Cc4nc5ccc(C(=O)O)cc5n4CC4CCO4)CC3)n2)c(F)c1] |
| 136 | 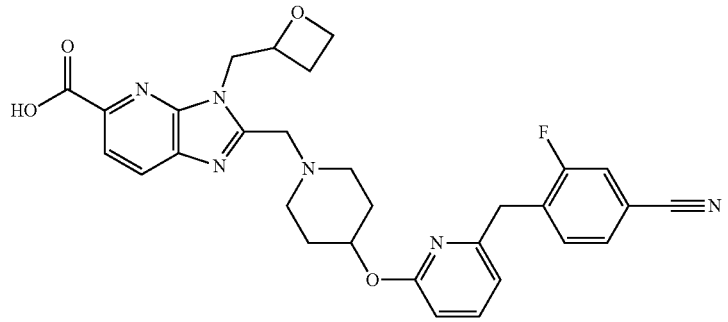 [SMILES: N#Cc1ccc(Cc2cccc(OC3CCN(Cc4nc5ccc(C(=O)O)nc5n4CC4CCO4)CC3)n2)c(F)c1] |
| 137 | 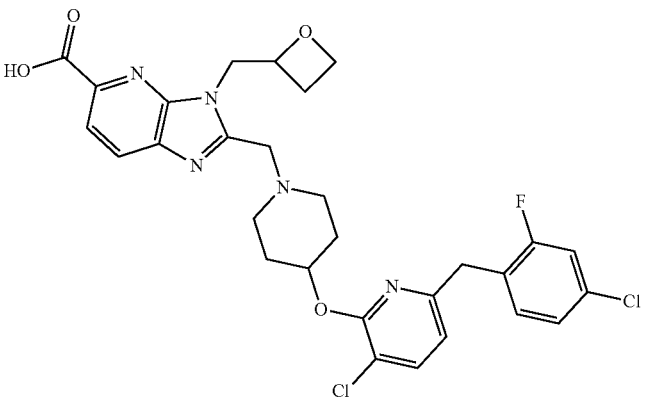 [SMILES: O=C(O)c1ccc2nc(CN3CCC(Oc4nc(Cc5ccc(Cl)cc5F)ccc4Cl)CC3)n(CC3CCO3)c2n1] |
| 138 | 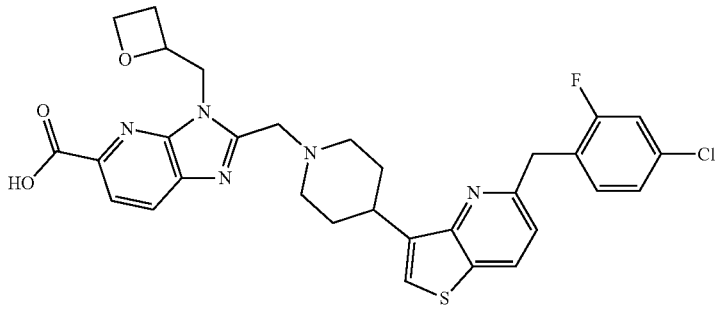 [SMILES: O=C(O)c1ccc2nc(CN3CCC(c4csc5ccc(Cc6ccc(Cl)cc6F)nc45)CC3)n(CC3CCO3)c2n1] |

TABLE C1-continued

| Compound No. | Structure |
|---|---|
| 139 | 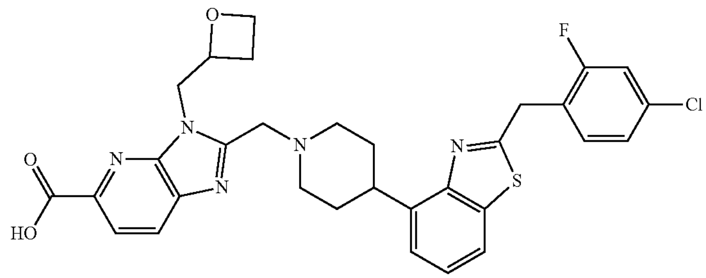 [SMILES: O=C(O)c1ccc2nc(CN3CCC(c4cccc5sc(Cc6ccc(Cl)cc6F)nc45)CC3)n(CC3CCO3)c2n1] |
| 140 | 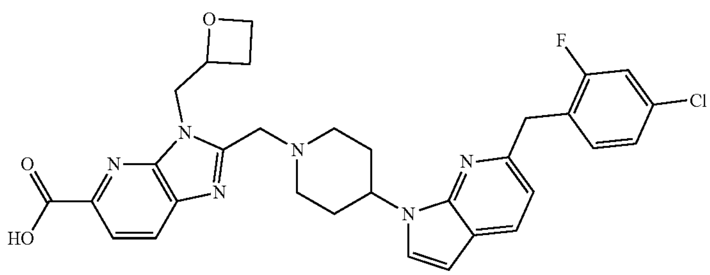 [SMILES: O=C(O)c1ccc2nc(CN3CCC(n4ccc5ccc(Cc6ccc(Cl)cc6F)nc54)CC3)n(CC3CCO3)c2n1] |
| 141 | 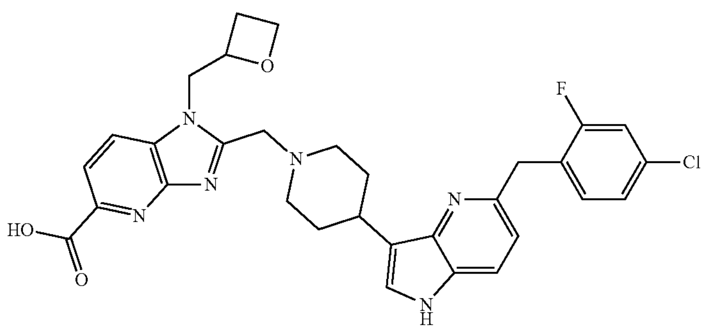 [SMILES: O=C(O)c1ccc2c(n1)nc(CN1CCC(c3c[nH]c4ccc(Cc5ccc(Cl)cc5F)nc34)CC1)n2CC1CCO1] |
| 142 | 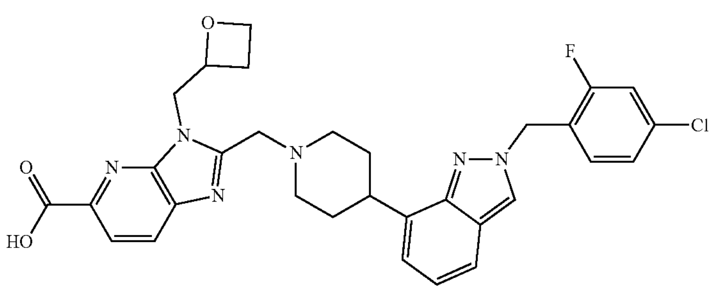 [SMILES: O=C(O)c1ccc2nc(CN3CCC(c4cccc5cn(Cc6ccc(Cl)cc6F)nc45)CC3)n(CC3CCO3)c2n1] |
| 143 | 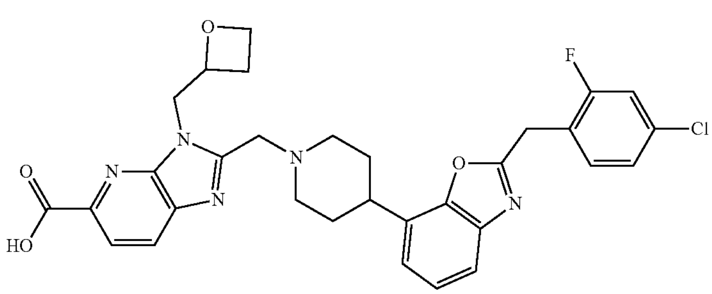 [SMILES: O=C(O)c1ccc2nc(CN3CCC(c4cccc5nc(Cc6ccc(Cl)cc6F)oc45)CC3)n(CC3CCO3)c2n1] |

TABLE C1-continued

| Compound No. | Structure |
|---|---|
| 144 | 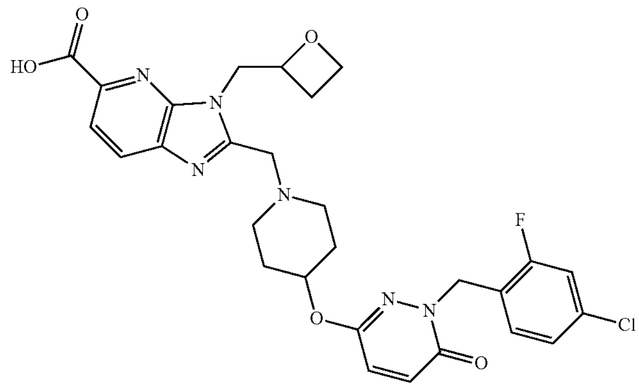 [SMILES: O=C(O)c1ccc2nc(CN3CCC(Oc4ccc(=O)n(Cc5ccc(Cl)cc5F)n4)CC3)n(CC3CCO3)c2n1] |
| 145 | 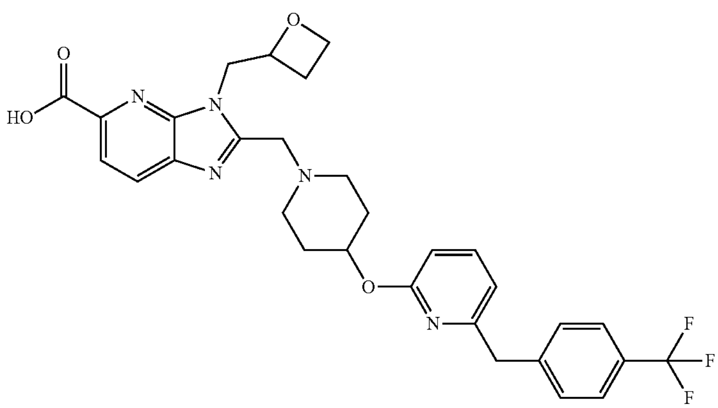 [SMILES: O=C(O)c1ccc2nc(CN3CCC(Oc4cccc(Cc5ccc(C(F)(F)F)cc5)n4)CC3)n(CC3CCO3)c2n1] |
| 146 | 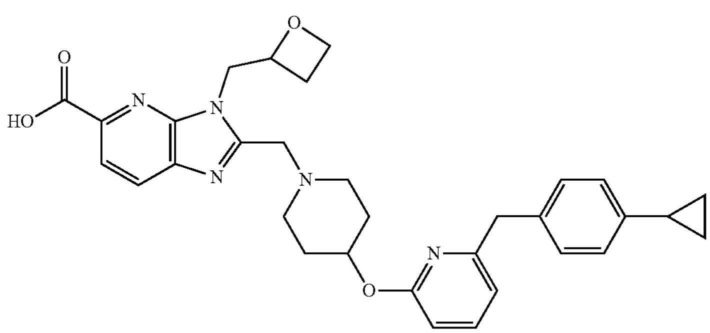 [SMILES: O=C(O)c1ccc2nc(CN3CCC(Oc4cccc(Cc5ccc(C6CC6)cc5)n4)CC3)n(CC3CCO3)c2n1] |
| 147 | 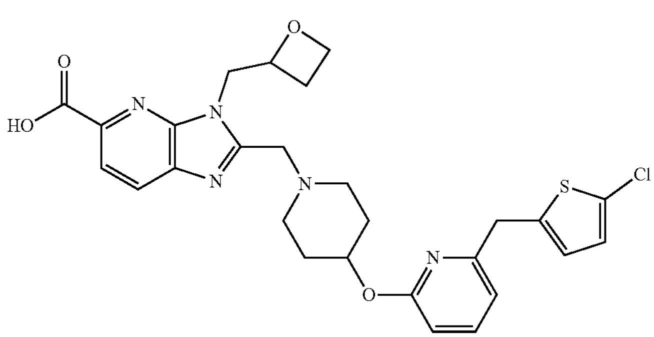 [SMILES: O=C(O)c1ccc2nc(CN3CCC(Oc4cccc(Cc5ccc(Cl)s5)n4)CC3)n(CC3CCO3)c2n1] |

TABLE C1-continued
| Compound No. | Structure |
|---|---|
| 148 | 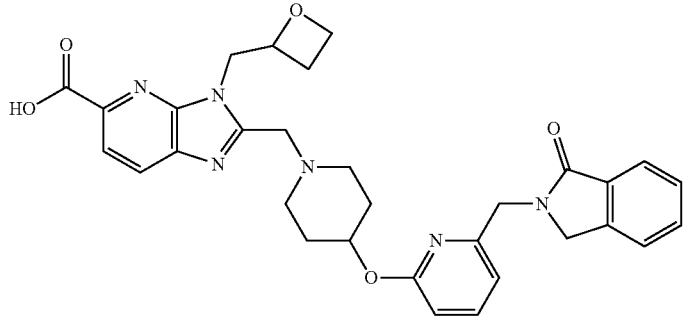 [SMILES: O=C(O)c1ccc2nc(CN3CCC(Oc4cccc(CN5Cc6ccccc6C5=O)n4)CC3)n(CC3CCO3)c2n1] |
| 149 | 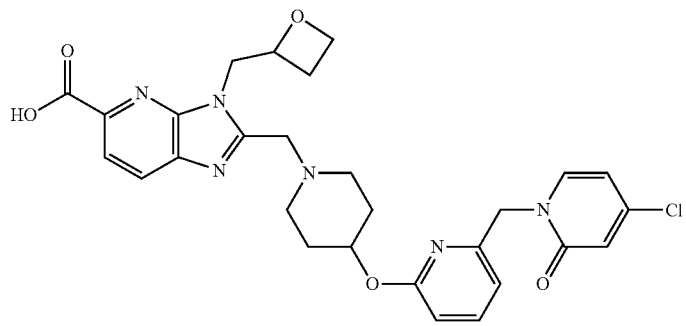 [SMILES: O=C(O)c1ccc2nc(CN3CCC(Oc4cccc(Cn5ccc(Cl)cc5=O)n4)CC3)n(CC3CCO3)c2n1] |
| 150 | 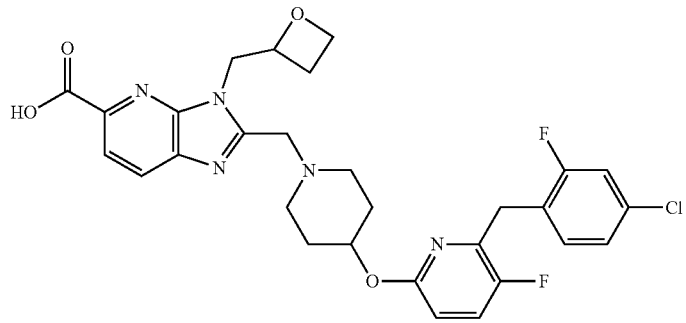 [SMILES: O=C(O)c1ccc2nc(CN3CCC(Oc4ccc(F)c(Cc5ccc(Cl)cc5F)n4)CC3)n(CC3CCO3)c2n1] |
| 151 | 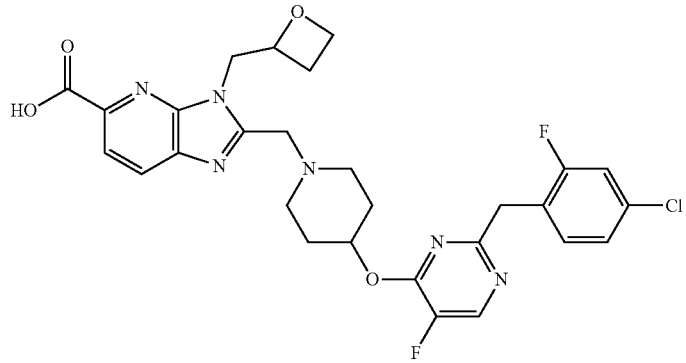 [SMILES: O=C(O)c1ccc2nc(CN3CCC(Oc4nc(Cc5ccc(Cl)cc5F)ncc4F)CC3)n(CC3CCO3)c2n1] |

TABLE C1-continued

| Compound No. | Structure |
|---|---|
| 152 | 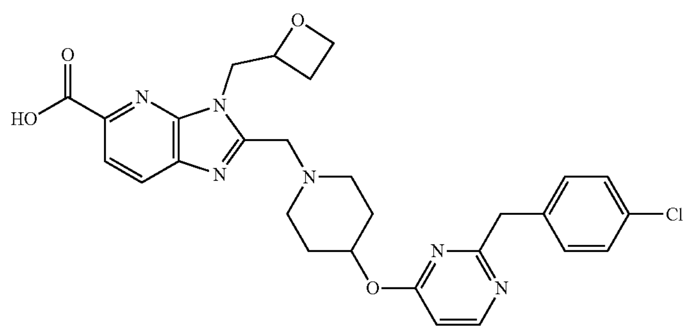 |
| 153 | 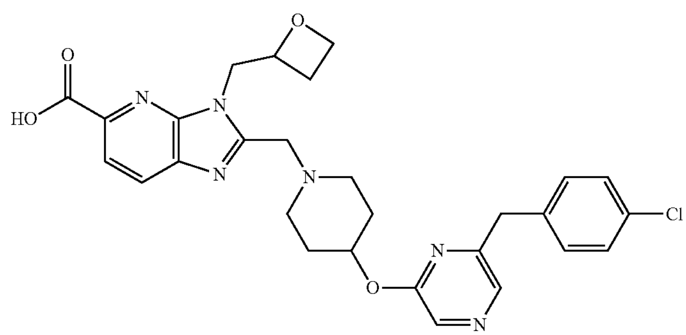 [SMILES: O=C(O)c1ccc2nc(CN3CCC(Oc4cncc(Cc5ccc(Cl)cc5)n4)CC3)n(CC3CCO3)c2n1] |
| 154 | 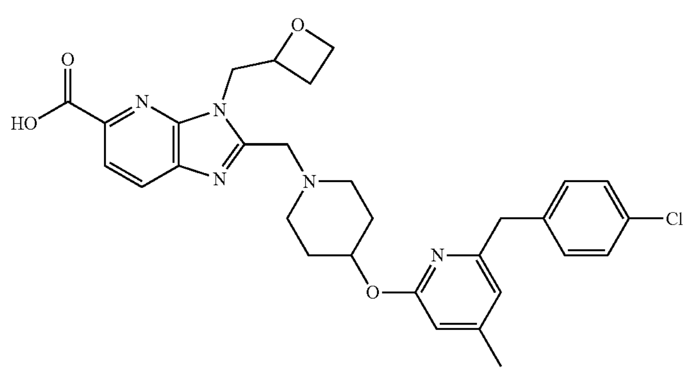 [SMILES: Cc1cc(Cc2ccc(Cl)cc2)nc(OC2CCN(Cc3nc4ccc(C(=O)O)nc4n3CC3CCO3)CC2)c1] |
| 155 | 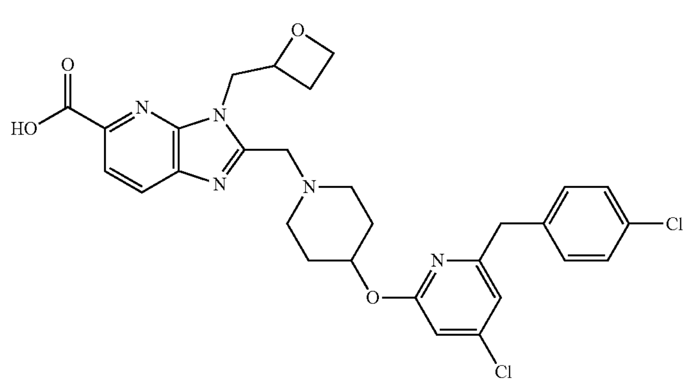 [SMILES: O=C(O)c1ccc2nc(CN3CCC(Oc4cc(Cl)cc(Cc5ccc(Cl)cc5)n4)CC3)n(CC3CCO3)c2n1] |

TABLE C1-continued
| Compound No. | Structure |
|---|---|
| 156 | 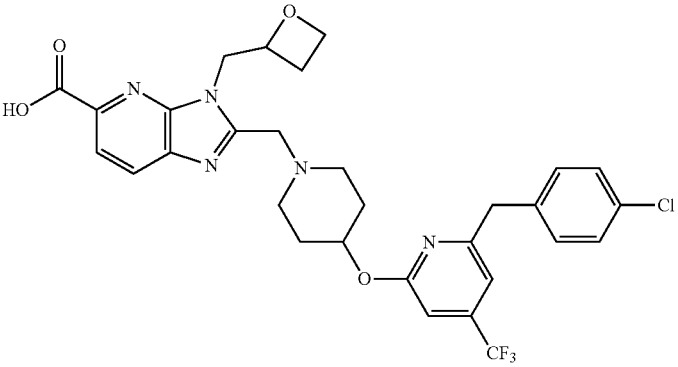 [SMILES: O=C(O)c1ccc2nc(CN3CCC(Oc4cc(C(F)(F)F)cc(Cc5ccc(Cl)cc5)n4)CC3)n(CC3CCO3)c2n1] |
| 157 | 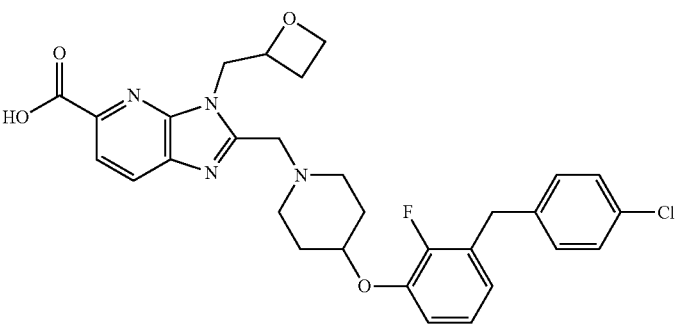 [SMILES: O=C(O)c1ccc2nc(CN3CCC(Oc4cccc(Cc5ccc(Cl)cc5)c4Cl)CC3)n(CC3CCO3)c2n1] |
| 158 | 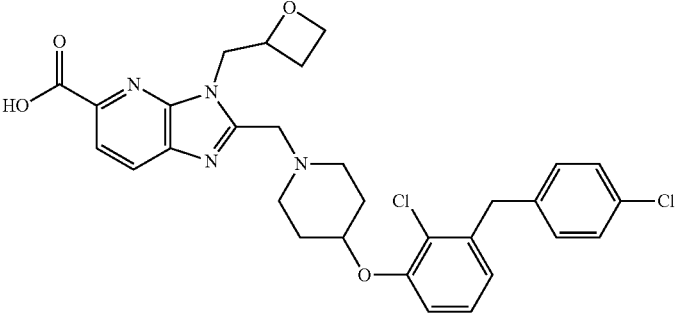 |
| 159 | 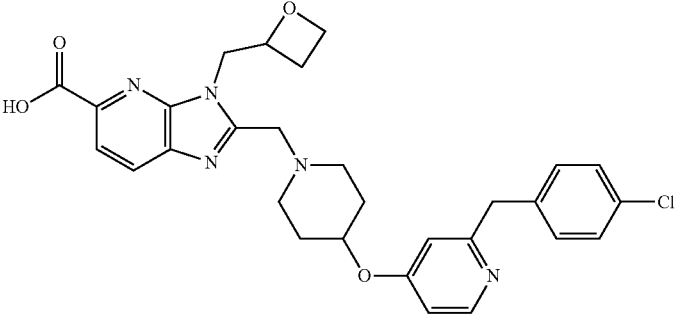 [SMILES: O=C(O)c1ccc2nc(CN3CCC(Oc4ccnc(Cc5ccc(Cl)cc5)c4)CC3)n(CC3CCO3)c2n1] |

TABLE C1-continued

| Compound No. | Structure |
|---|---|
| 160 | 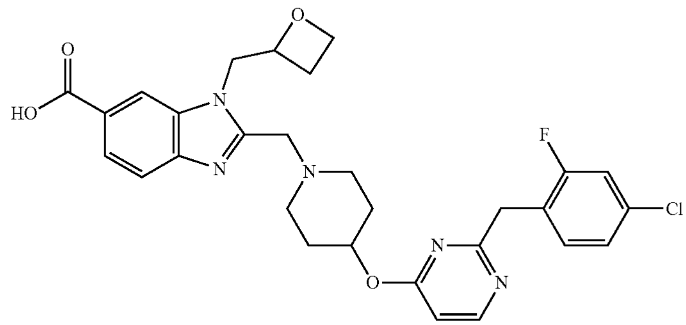 [SMILES: O=C(O)c1ccc2nc(CN3CCC(Oc4ccnc(Cc5ccc(Cl)cc5F)n4)CC3)n(CC3CCO3)c2c1] |
| 161 | 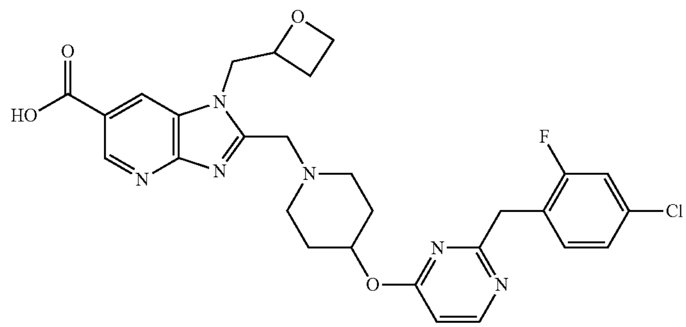 [SMILES: O=C(O)c1cnc2nc(CN3CCC(Oc4ccnc(Cc5ccc(Cl)cc5F)n4)CC3)n(CC3CCO3)c2c1] |
| 162 | 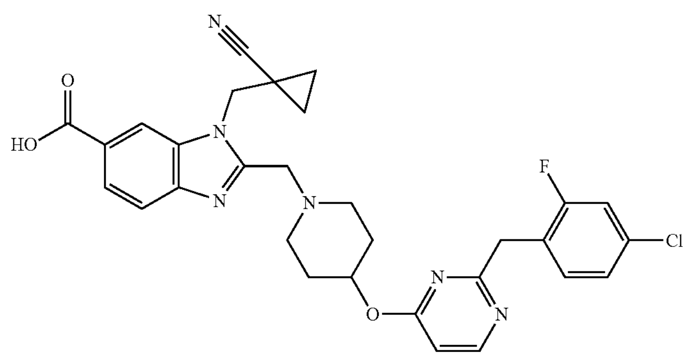 [SMILES: N#CC1(Cn2c(CN3CCC(Oc4ccnc(Cc5ccc(Cl)cc5F)n4)CC3)nc3ccc(C(=O)O)cc32)CC1] |
| 163 | 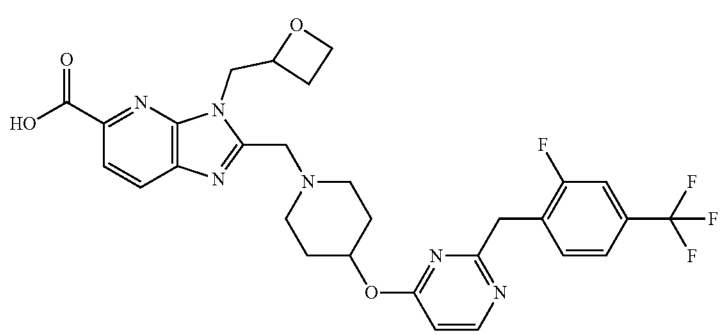 [SMILES: O=C(O)c1ccc2nc(CN3CCC(Oc4ccnc(Cc5ccc(C(F)(F)F)cc5F)n4)CC3)n(CC3CCO3)c2n1] |

TABLE C1-continued
| Compound No. | Structure |
|---|---|
| 164 | 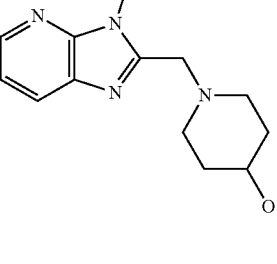 |
| 165 | 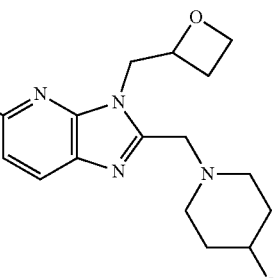 |
| 166 | 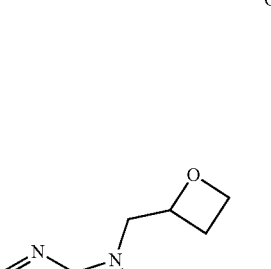 |
| 167 | 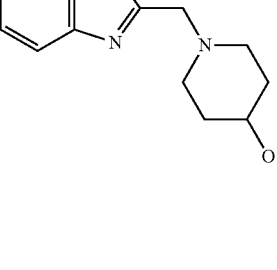 |

TABLE C1-continued

| Compound No. | Structure |
|---|---|
| 168 | 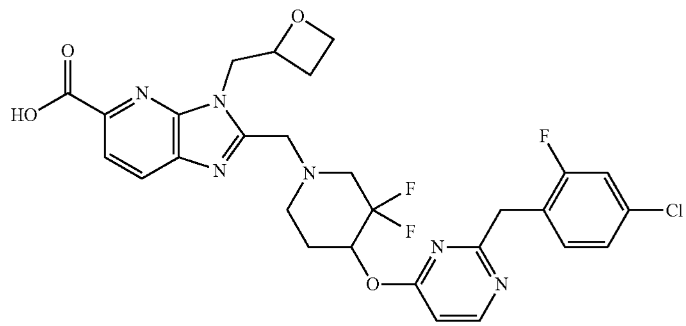 [SMILES: O=C(O)c1ccc2nc(CN3CCC(Oc4ccnc(Cc5ccc(Cl)cc5F)n4)C(F)(F)C3)n(CC3CCO3)c2n1] |
| 169 | 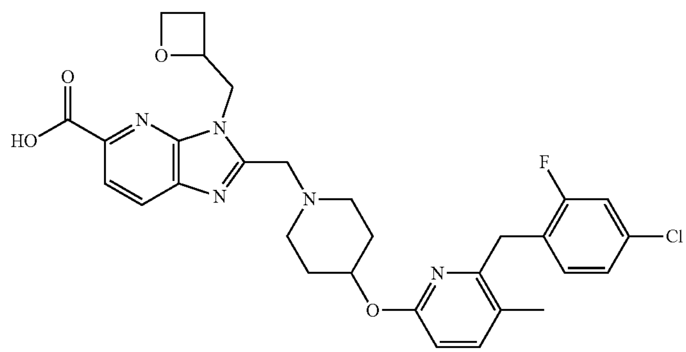 [SMILES: Cc1ccc(OC2CCN(Cc3nc4ccc(C(=O)O)nc4n3CC3CCO3)CC2)nc1Cc1ccc(Cl)cc1F] |
| 170 | 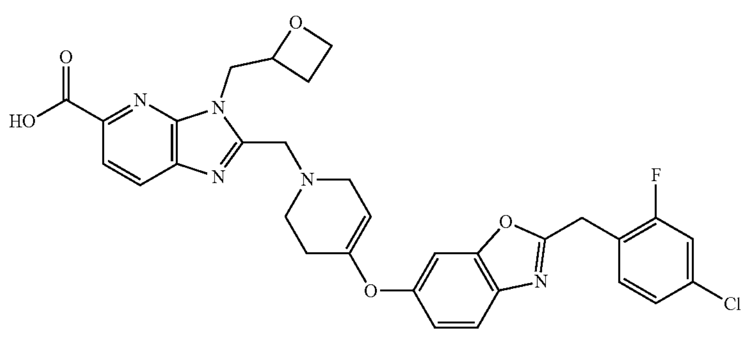 [SMILES: O=C(O)c1ccc2nc(CN3CC=C(Oc4ccc5nc(Cc6ccc(Cl)cc6F)oc5c4)CC3)n(CC3CCO3)c2n1] |
| 171 | 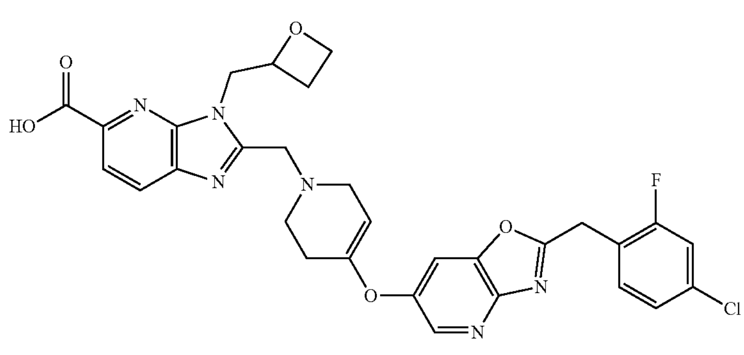 [SMILES: O=C(O)c1ccc2nc(CN3CC=C(Oc4cnc5nc(Cc6ccc(Cl)cc6F)oc5c4)CC3)n(CC3CCO3)c2n1] |

TABLE C1-continued

| Compound No. | Structure |
|---|---|
| 172 | 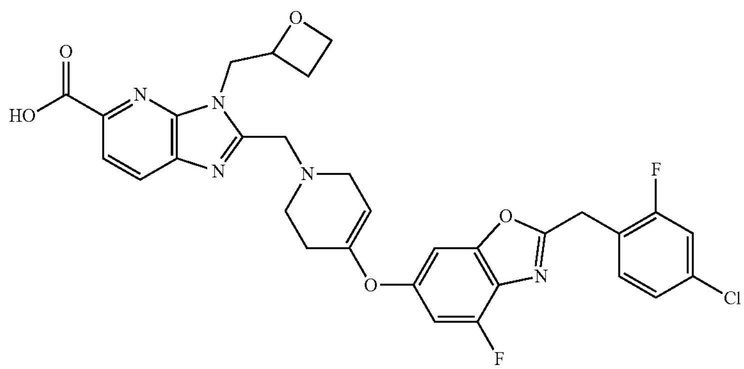 [SMILES: O=C(O)c1ccc2nc(CN3CC=C(Oc4cc(F)c5nc(Cc6ccc(Cl)cc6F)oc5c4)CC3)n(CC3CCO3)c2n1] |
| 173 | 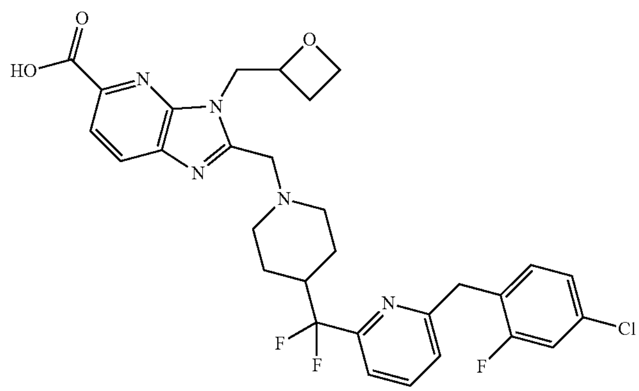 [SMILES: O=C(O)c1ccc2nc(CN3CCC(C(F)(F)c4cccc(Cc5ccc(Cl)cc5F)n4)CC3)n(CC3CCO3)c2n1] |
| 174 | 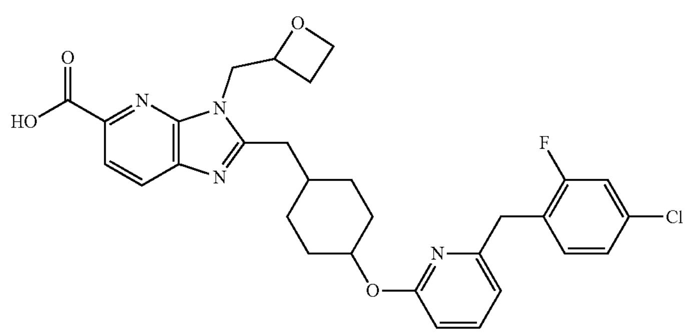 |
| 175 | 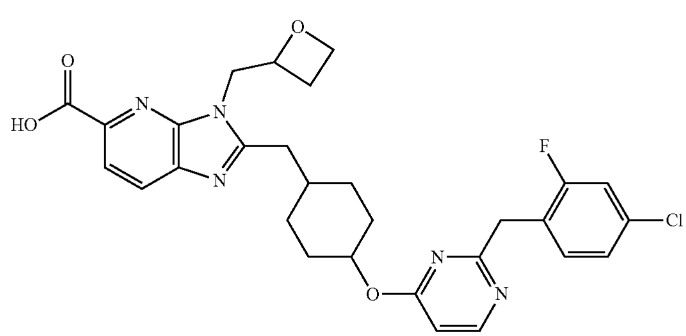 |

TABLE C1-continued

| Compound No. | Structure |
|---|---|
| 176 | 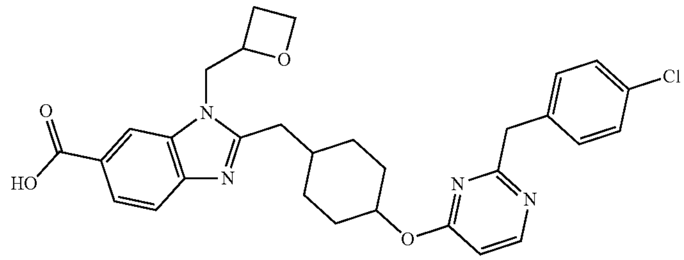 [SMILES: O=C(O)c1ccc2nc(CC3CCC(Oc4ccnc(Cc5ccc(Cl)cc5)n4)CC3)n(CC3CCO3)c2c1] |
| 177 | 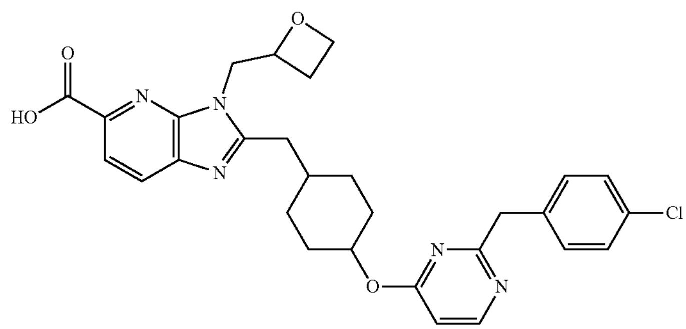 |
| 178 | 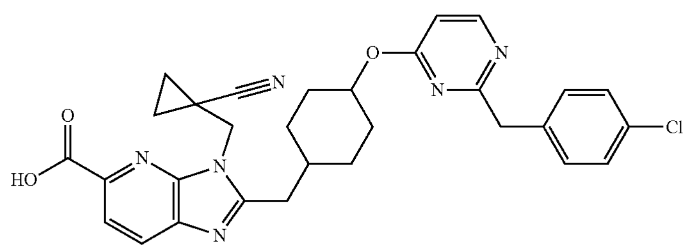 [SMILES: N#CC1(Cn2c(CC3CCC(Oc4ccnc(Cc5ccc(Cl)cc5)n4)CC3)nc3ccc(C(=O)O)nc32)CC1] |
| 179 | 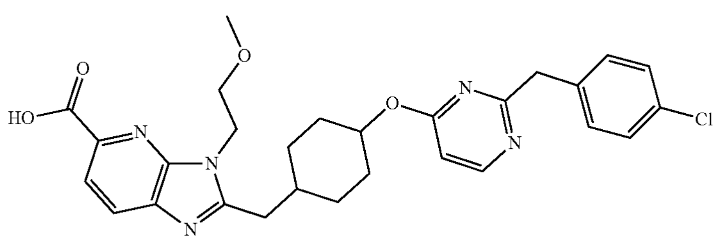 [SMILES: COCCn1c(CC2CCC(Oc3ccnc(Cc4ccc(Cl)cc4)n3)CC2)nc2ccc(C(=O)O)nc21] |
| 180 | 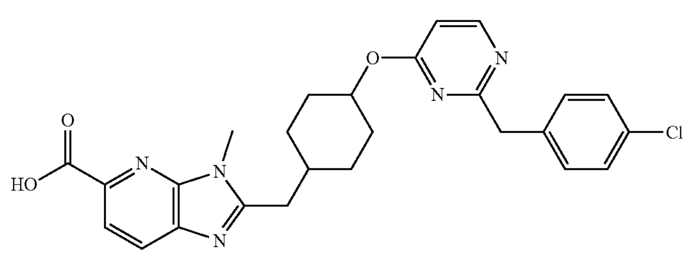 [SMILES: Cn1c(CC2CCC(Oc3ccnc(Cc4ccc(Cl)cc4)n3)CC2)nc2ccc(C(=O)O)nc21] |

TABLE C1-continued

| Compound No. | Structure |
|---|---|
| 181 | 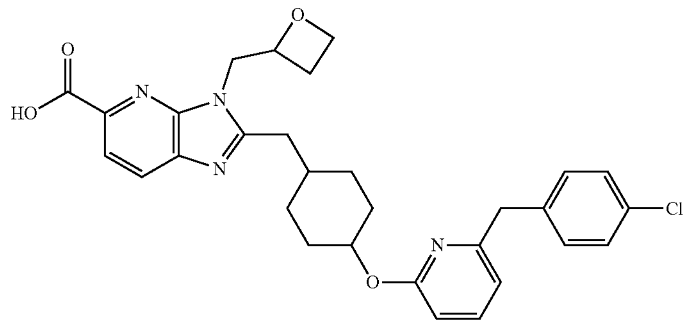 [SMILES: O=C(O)c1ccc2nc(CC3CCC(Oc4cccc(Cc5ccc(Cl)cc5)n4)CC3)n(CC3CCO3)c2n1] |
| 182 | 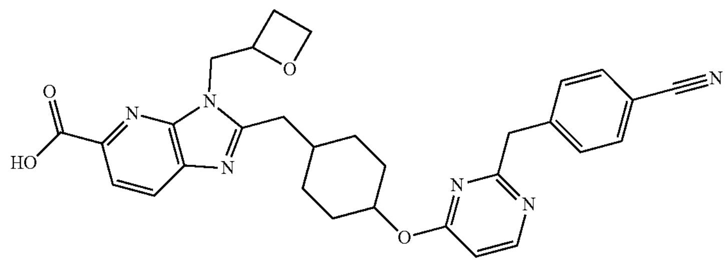 [SMILES: N#Cc1ccc(Cc2nccc(OC3CCC(Cc4nc5ccc(C(=O)O)nc5n4CC4CCO4)CC3)n2)cc1] |
| 183 | 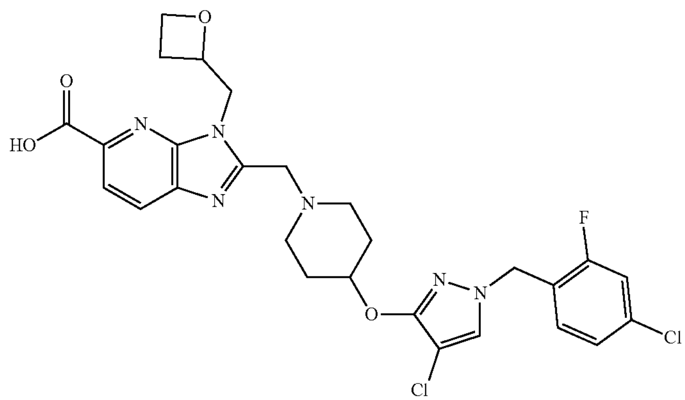 [SMILES: O=C(O)c1ccc2nc(CN3CCC(Oc4nn(Cc5ccc(Cl)cc5F)cc4Cl)CC3)n(CC3CCO3)c2n1] |
| 184 | 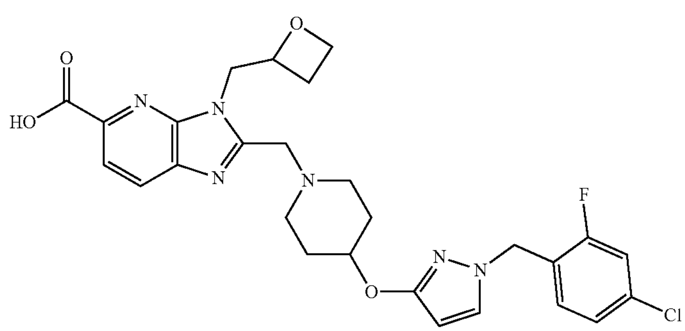 [SMILES: O=C(O)c1ccc2nc(CN3CCC(Oc4ccn(Cc5ccc(Cl)cc5F)n4)CC3)n(CC3CCO3)c2n1] |
| 185 | 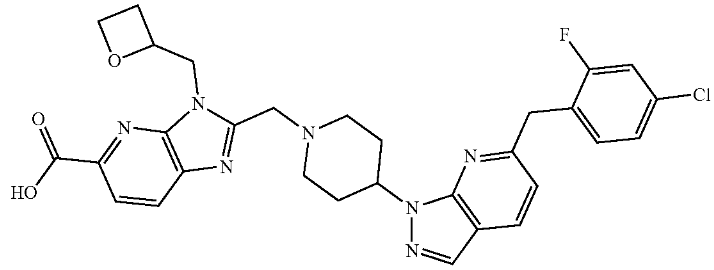 [SMILES: O=C(O)c1ccc2nc(CN3CCC(n4ncc5ccc(Cc6ccc(Cl)cc6F)nc54)CC3)n(CC3CCO3)c2n1] |

TABLE C1-continued

| Compound No. | Structure |
|---|---|
| 186 | 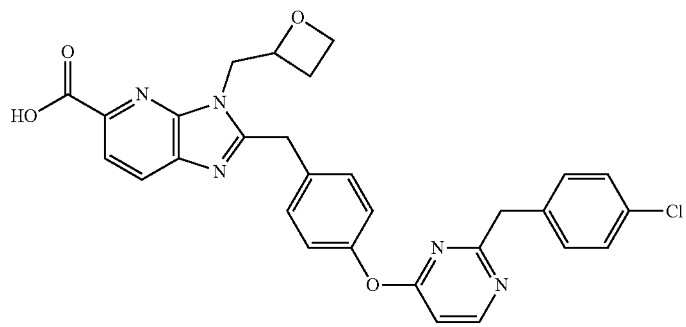 [SMILES: O=C(O)c1ccc2nc(Cc3ccc(Oc4ccnc(Cc5ccc(Cl)cc5)n4)cc3)n(CC3CCO3)c2n1] |
| 187 | 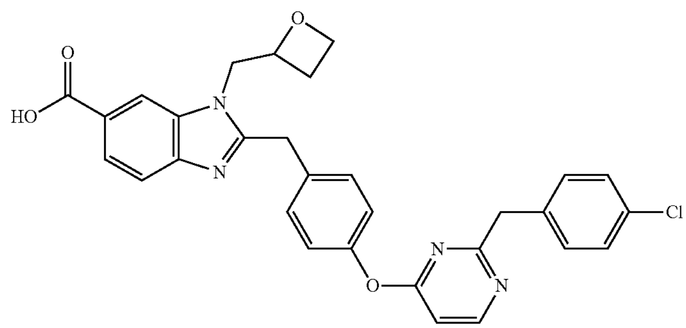 [SMILES: O=C(O)c1ccc2nc(Cc3ccc(Oc4ccnc(Cc5ccc(Cl)cc5)n4)cc3)n(CC3CCO3)c2c1] |
| 188 | 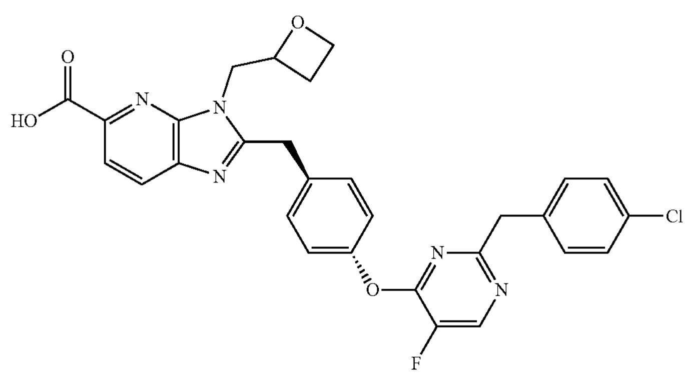 |
| 189 | 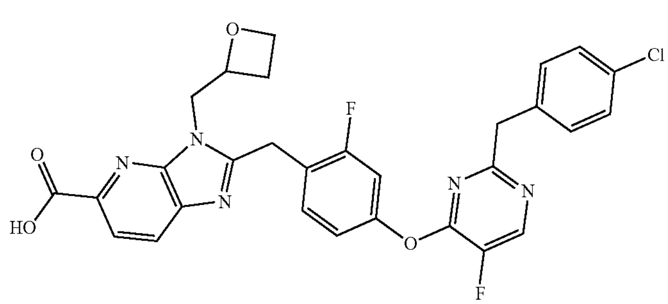 [SMILES: O=C(O)c1ccc2nc(Cc3ccc(Oc4nc(Cc5ccc(Cl)cc5)ncc4F)cc3F)n(CC3CCO3)c2n1] |

TABLE C1-continued
| Compound No. | Structure |
|---|---|
| 190 | 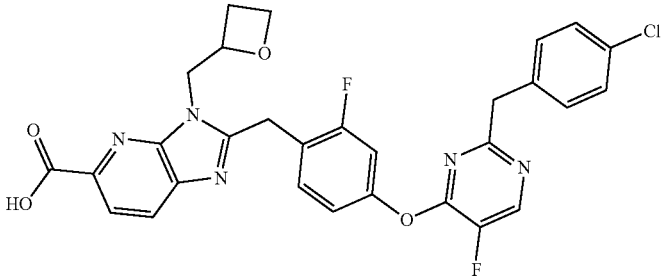 [SMILES: O=C(O)c1ccc2nc(Cc3ccc(Oc4nc(Cc5ccc(Cl)cc5)ncc4F)cc3F)n(CC3CCO3)c2n1] |
| 191 | 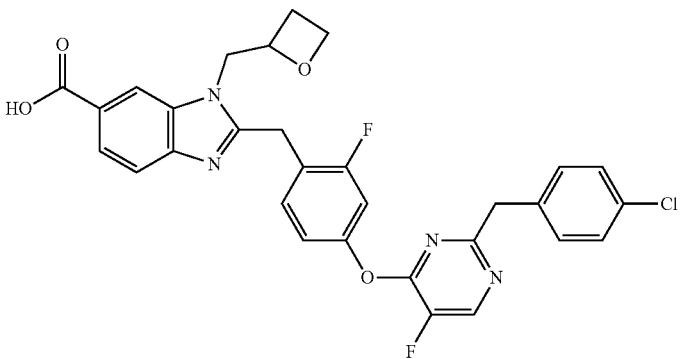 [SMILES: O=C(O)c1ccc2nc(Cc3ccc(Oc4nc(Cc5ccc(Cl)cc5)ncc4F)cc3F)n(CC3CCO3)c2c1] |
| 192 | 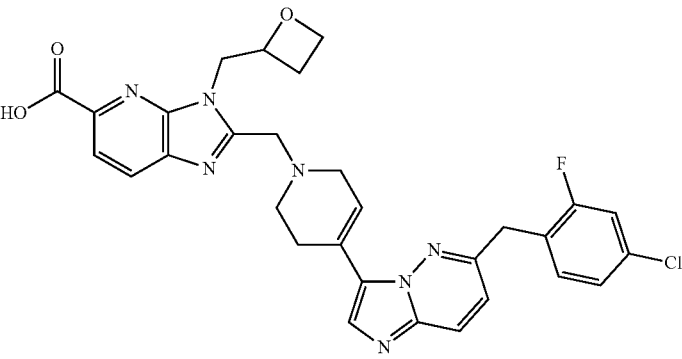 [SMILES: O=C(O)c1ccc2nc(CN3CC=C(c4cnc5ccc(Cc6ccc(Cl)cc6F)nn45)CC3)n(CC3CCO3)c2n1] |
| 193 | 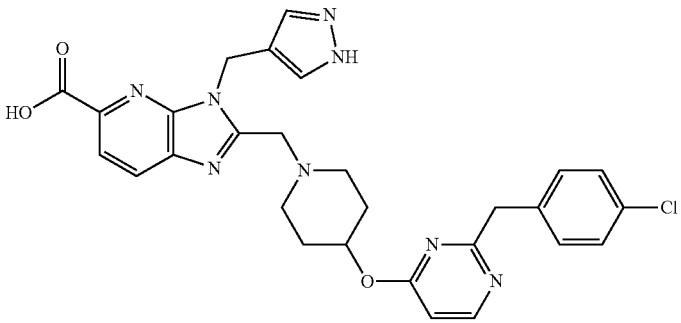 [SMILES: O=C(O)c1ccc2nc(CN3CCC(Oc4ccnc(Cc5ccc(Cl)cc5)n4)CC3)n(Cc3cn[nH]c3)c2n1] |

TABLE C1-continued

| Compound No. | Structure |
|---|---|
| 194 | 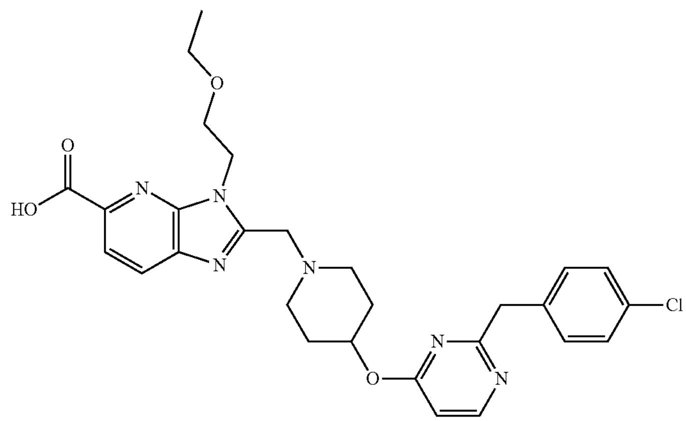 [SMILES: CCOCCn1c(CN2CCC(Oc3ccnc(Cc4ccc(Cl)cc4)n3)CC2)nc2ccc(C(=O)O)nc21] |
| 195 | 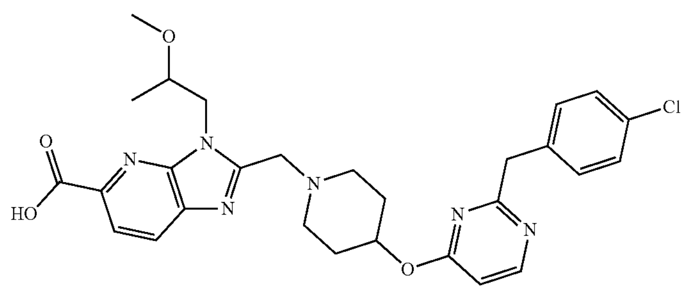 [SMILES: COC(C)Cn1c(CN2CCC(Oc3ccnc(Cc4ccc(Cl)cc4)n3)CC2)nc2ccc(C(=O)O)nc21] |
| 196 | 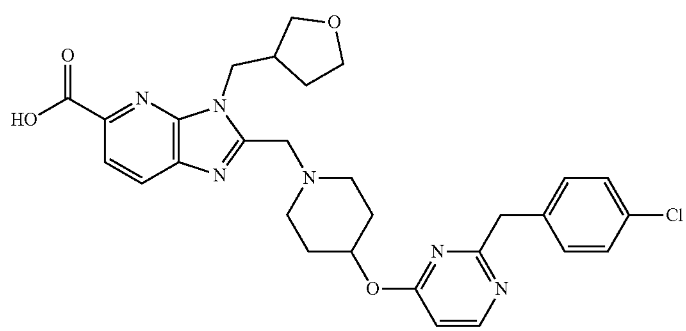 [SMILES: O=C(O)c1ccc2nc(CN3CCC(Oc4ccnc(Cc5ccc(Cl)cc5)n4)CC3)n(CC3CCOC3)c2n1] |
| 197 | 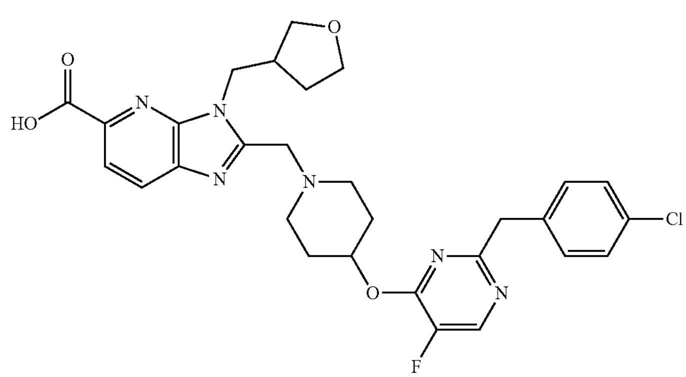 [SMILES: O=C(O)c1ccc2nc(CN3CCC(Oc4nc(Cc5ccc(Cl)cc5)ncc4F)CC3)n(CC3CCOC3)c2n1] |

TABLE C1-continued

| Compound No. | Structure |
|---|---|
| 198 | 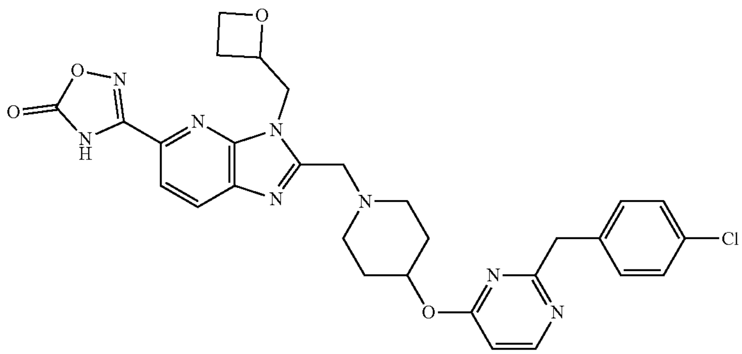 [SMILES: O=c1[nH]c(-c2ccc3nc(CN4CCC(Oc5ccnc(Cc6ccc(Cl)cc6)n5)CC4)n(CC4CCO4)c3n2)no1] |
| 199 | 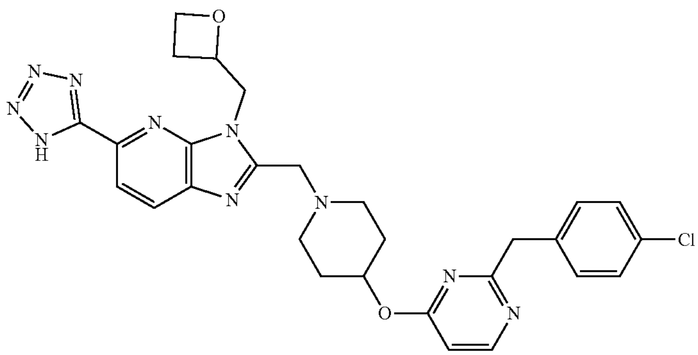 [SMILES: Clc1ccc(Cc2nccc(OC3CCN(Cc4nc5ccc(-c6nnn[nH]6)nc5n4CC4CCO4)CC3)n2)cc1] |
| 200 | 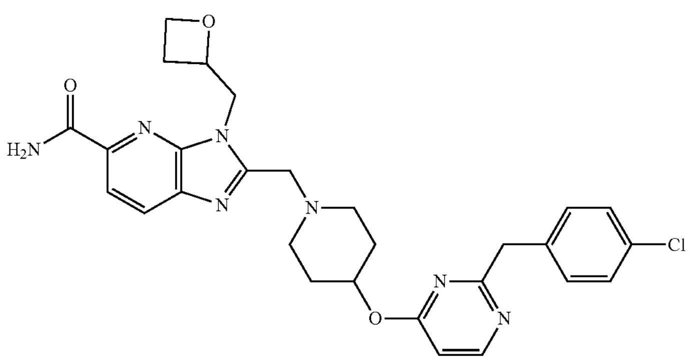 [SMILES: NC(=O)c1ccc2nc(CN3CCC(Oc4ccnc(Cc5ccc(Cl)cc5)n4)CC3)n(CC3CCO3)c2n1] |
| 201 | 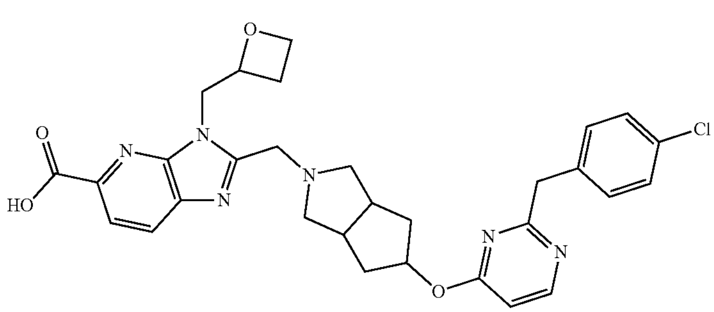 [SMILES: O=C(O)c1ccc2nc(CN3CC4CC(Oc5ccnc(Cc6ccc(Cl)cc6)n5)CC4C3)n(CC3CCO3)c2n1] |

In some embodiments, the compound is selected from the group consisting of the compounds in Table C2 or a pharmaceutically acceptable salt or solvate thereof.

TABLE C2

| Compound No. | Structure |
| --- | --- |
| 101a | 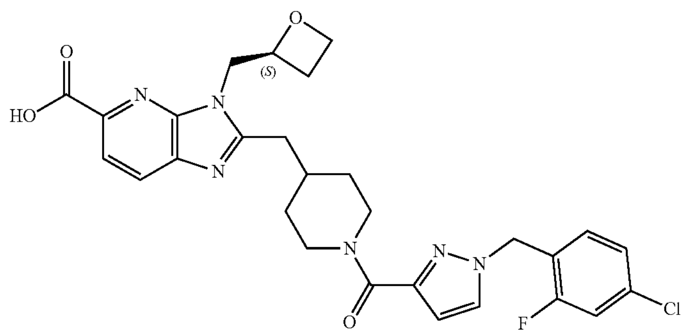 |
| 102a | 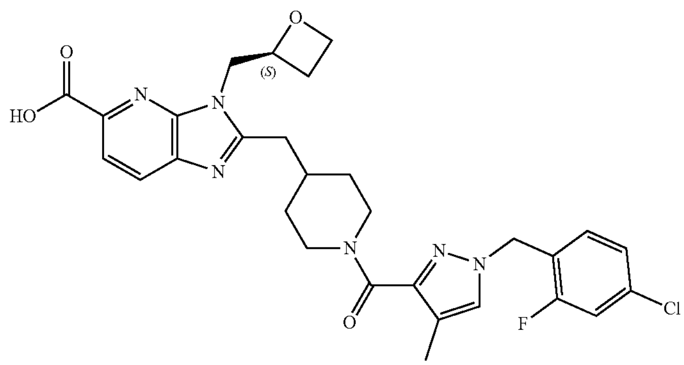 |
| 103a | 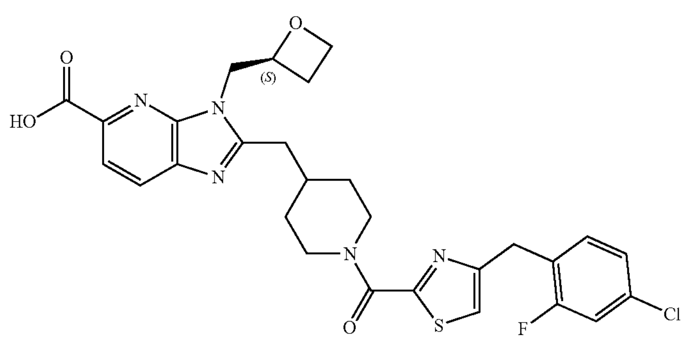 |
| 104a | 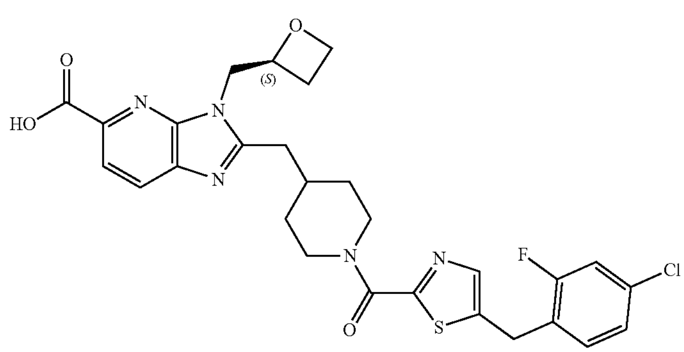 |

TABLE C2-continued

| Compound No. | Structure |
|---|---|
| 105a | 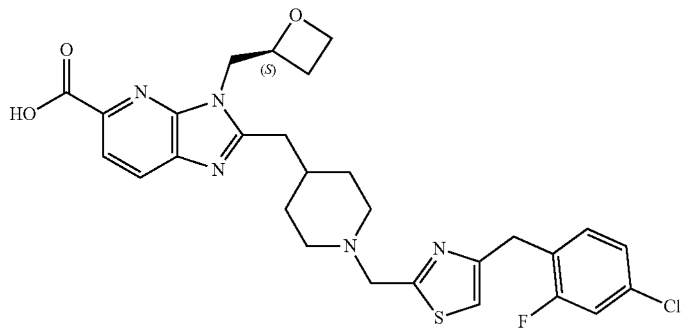 |
| 106a | 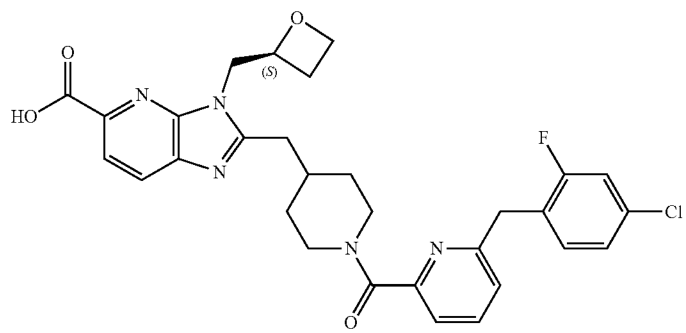 |
| 107a | 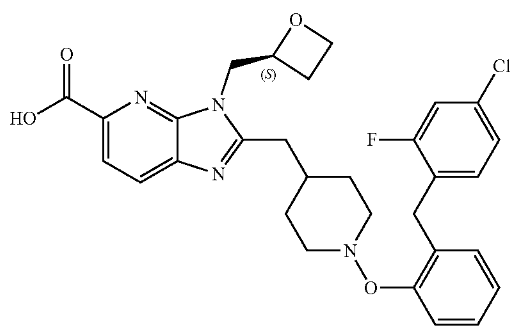 |
| 108a | 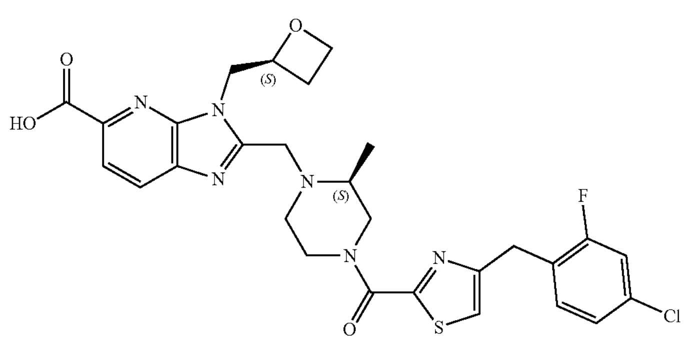 |

TABLE C2-continued

| Compound No. | Structure |
|---|---|
| 109a | 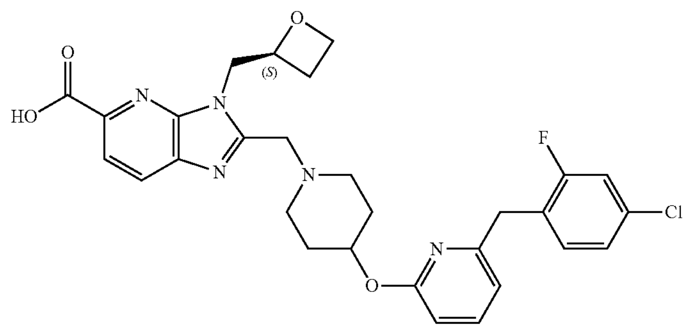 |
| 110a | 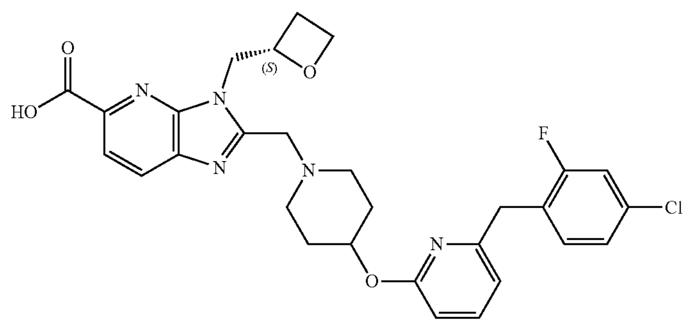 |
| 111a | 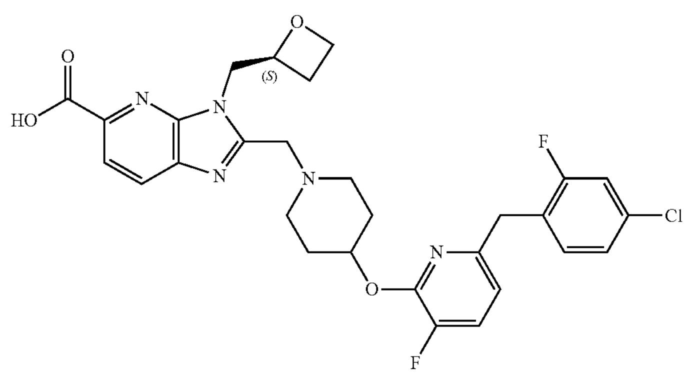 |
| 112a | 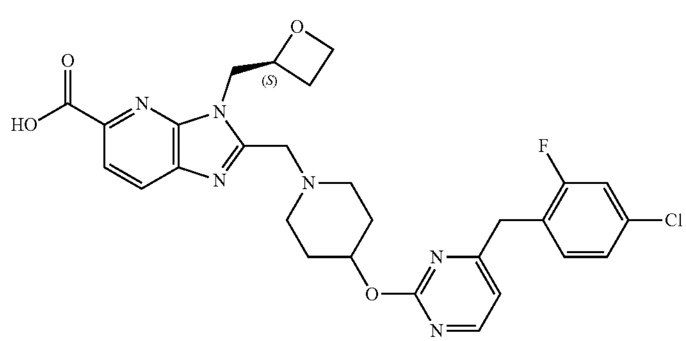 |

TABLE C2-continued

| Compound No. | Structure |
|---|---|
| 113a | 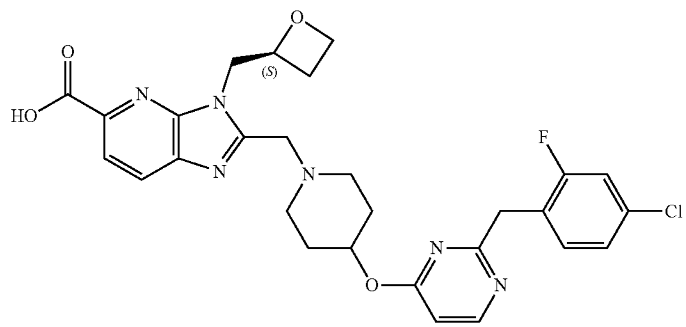 |
| 114a | 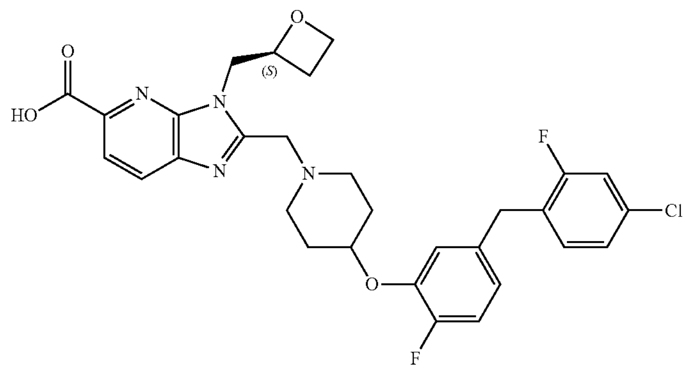 |
| 115a | 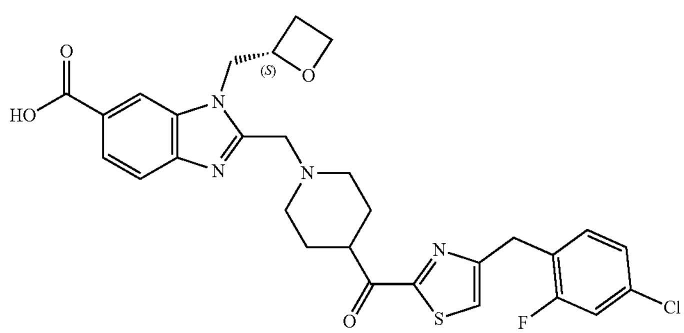 |
| 116a | 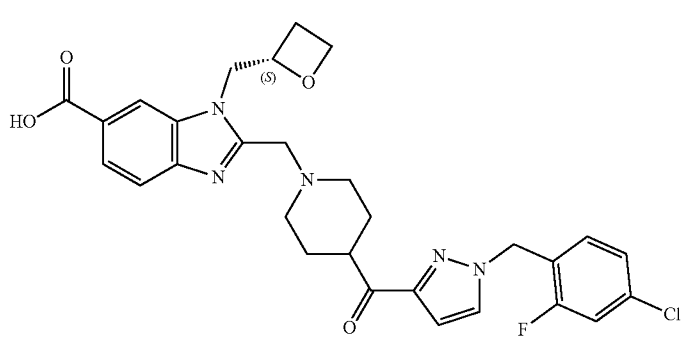 |

TABLE C2-continued

| Compound No. | Structure |
|---|---|
| 117a | 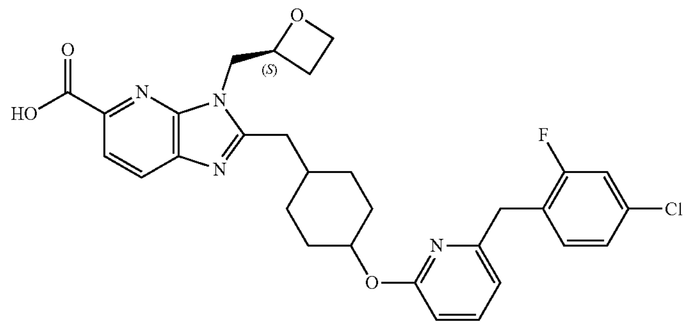 |
| 118a | 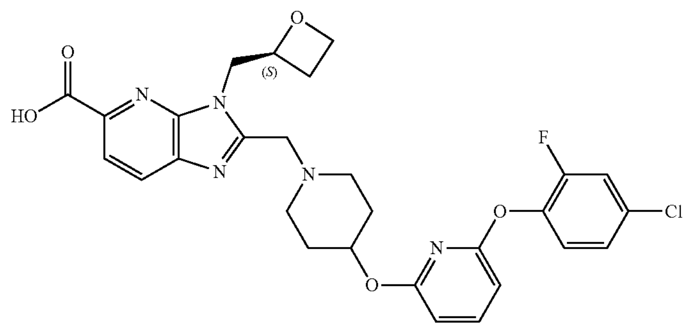 |
| 119a | 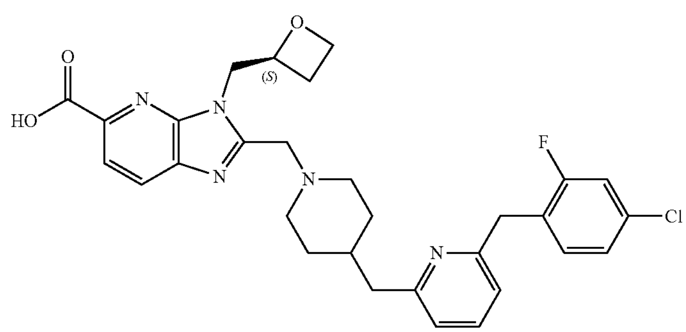 |
| 120a | 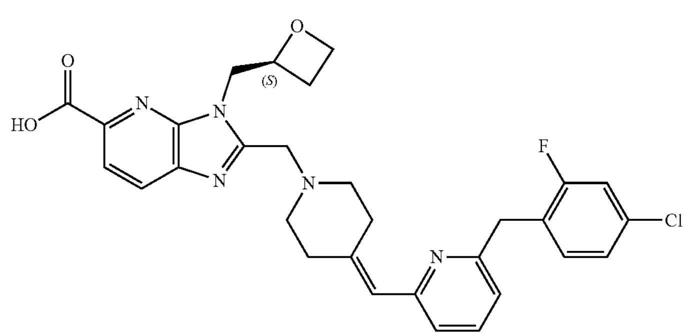 |

TABLE C2-continued

| Compound No. | Structure |
| --- | --- |
| 121a | 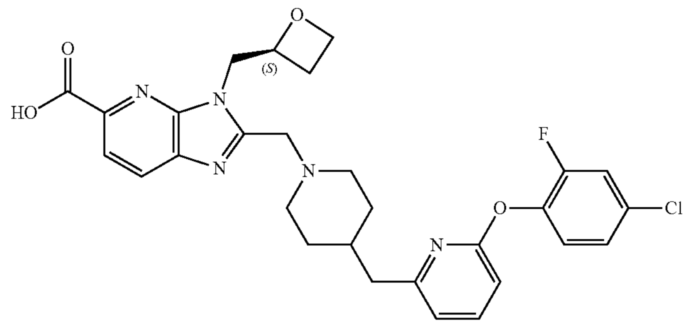 |
| 122a | 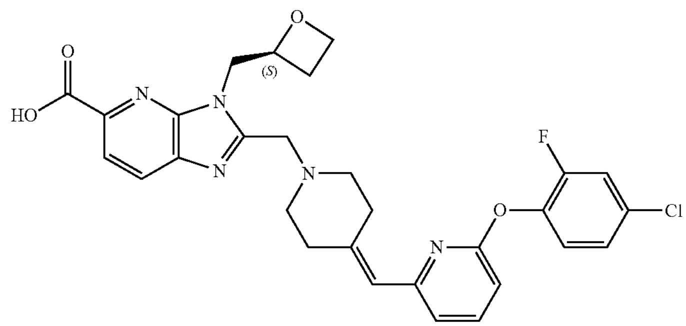 |
| 123a | 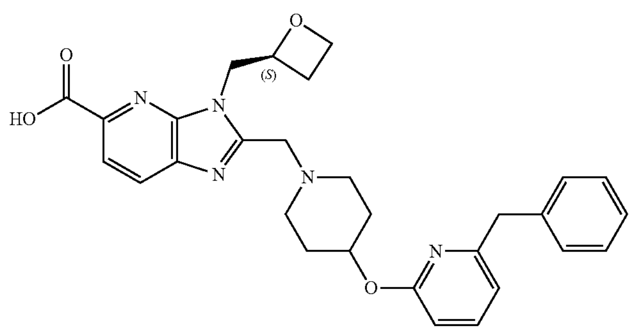 |
| 124a | 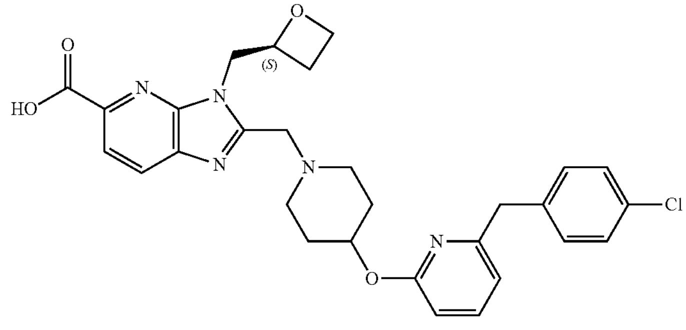 |

TABLE C2-continued
| Compound No. | Structure |
|---|---|
| 125a | 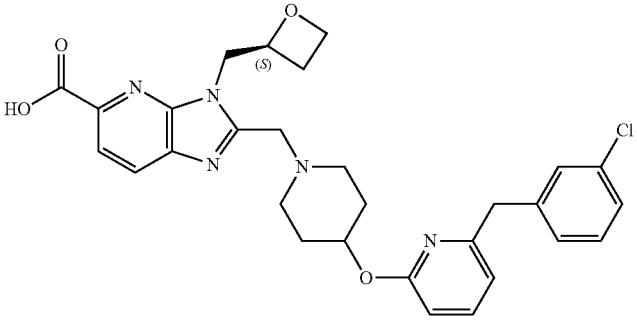 |
| 126a | 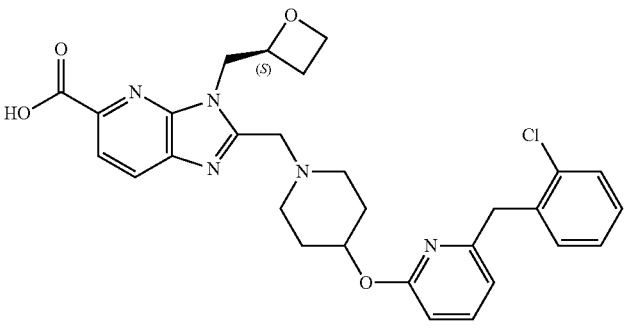 |
| 127a | 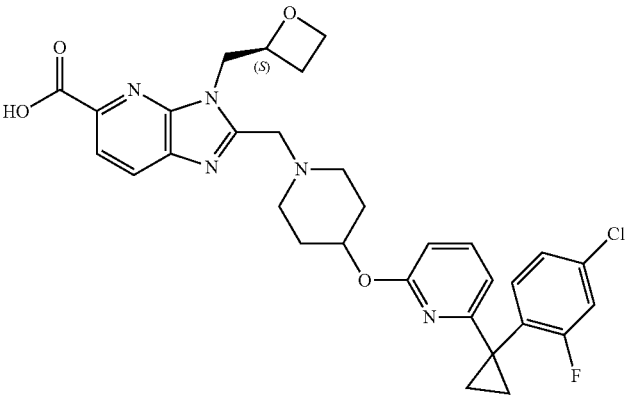 |
| 128a | 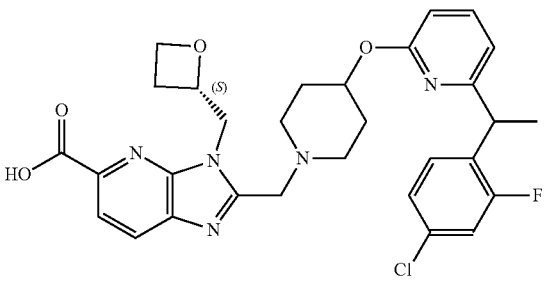 |

TABLE C2-continued
| Compound No. | Structure |
|---|---|
| 129a | 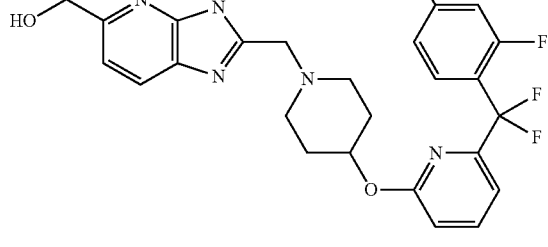 |
| 130a | 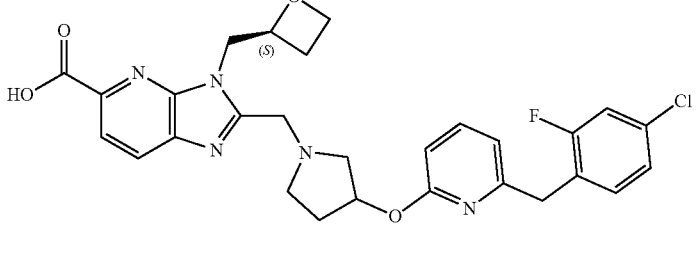 |
| 131a | 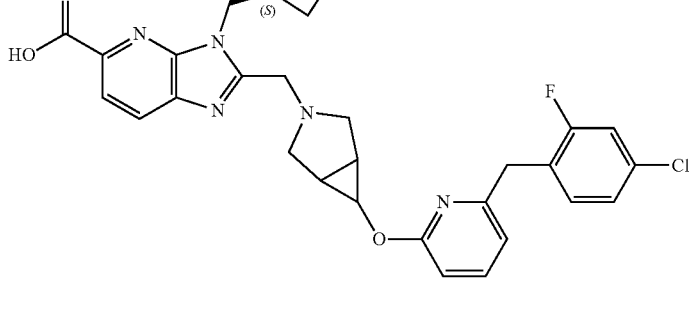 |
| 132a | 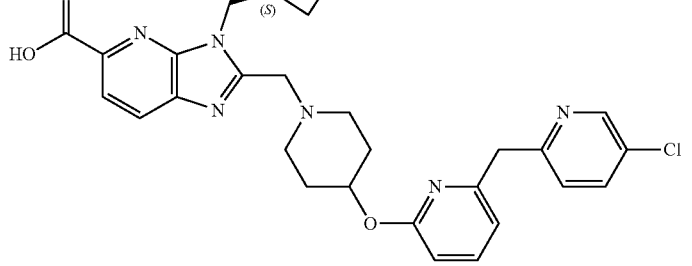 |

TABLE C2-continued

| Compound No. | Structure |
|---|---|
| 133a | 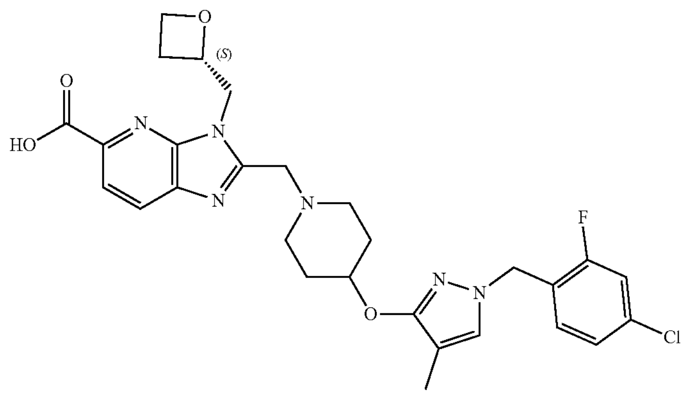 |
| 134a | 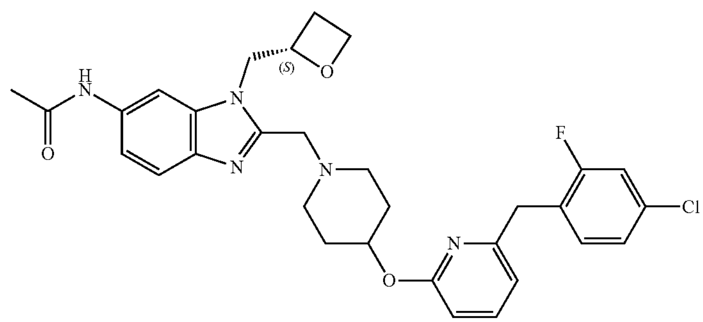 |
| 135a | 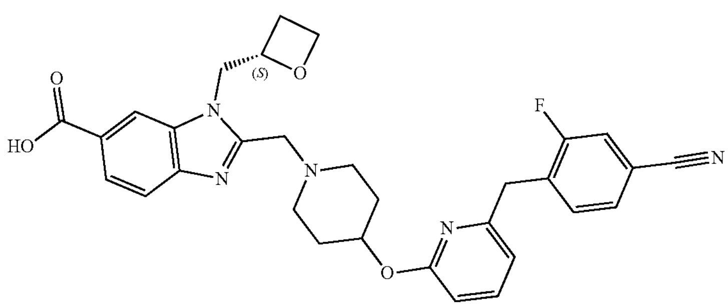 |
| 136a | 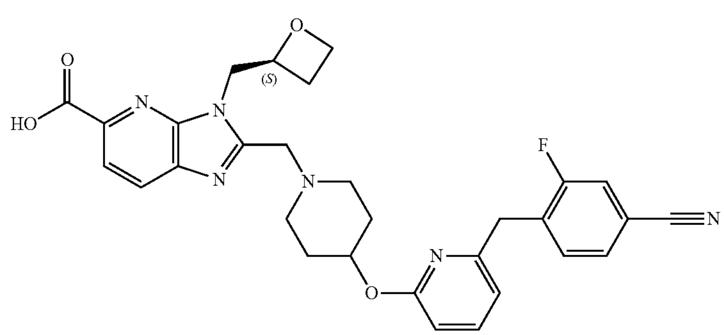 |

TABLE C2-continued

| Compound No. | Structure |
|---|---|
| 137a | 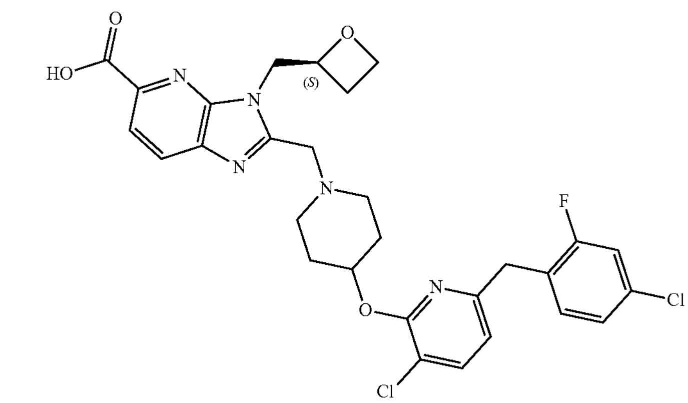 |
| 138a | 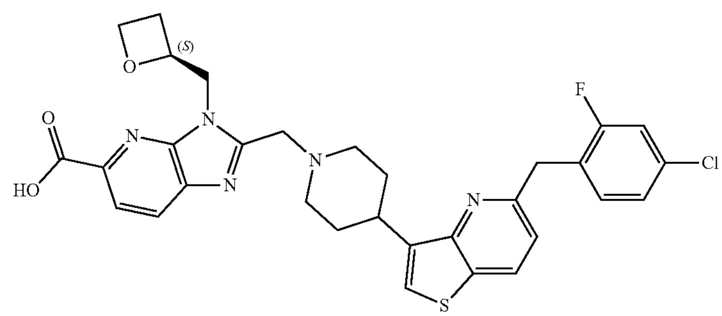 |
| 139a | 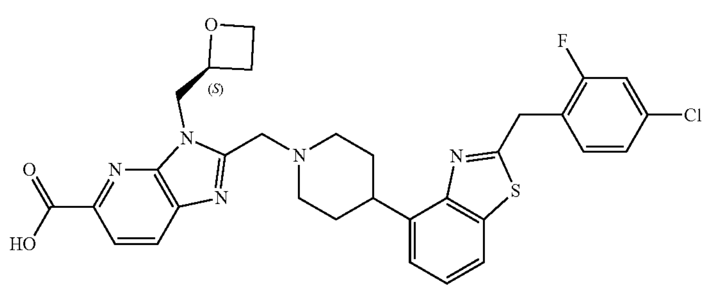 |
| 140a | 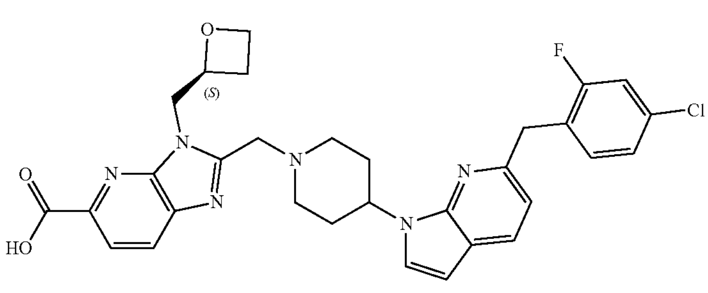 |

TABLE C2-continued

| Compound No. | Structure |
|---|---|
| 141a | (chemical structure) |
| 142a | (chemical structure) |
| 143a | (chemical structure) |
| 144a | (chemical structure) |

TABLE C2-continued

| Compound No. | Structure |
| --- | --- |
| 145a | 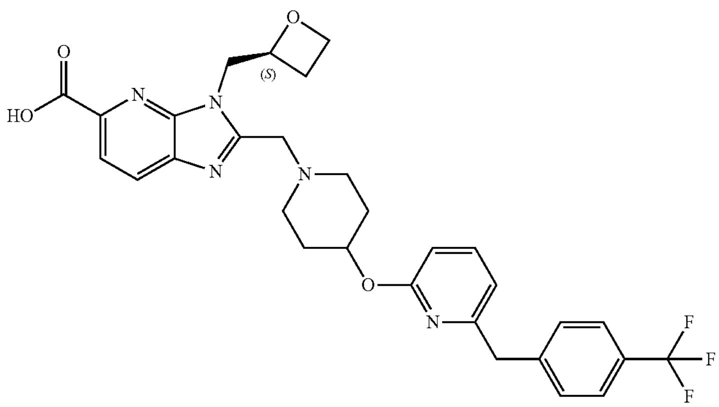 |
| 146a | 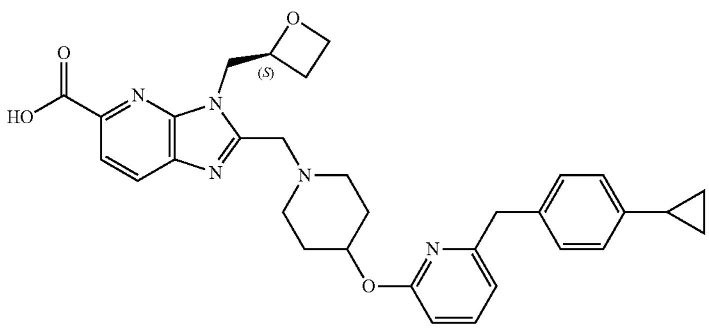 |
| 147a | 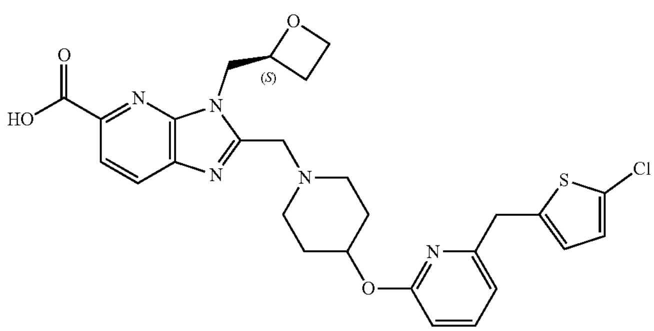 |
| 148a | 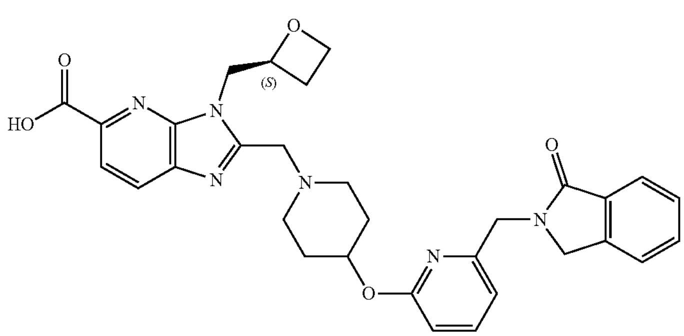 |

TABLE C2-continued

| Compound No. | Structure |
|---|---|
| 149a | 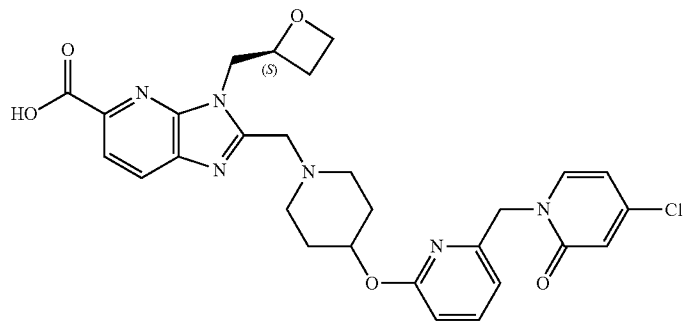 |
| 150a | 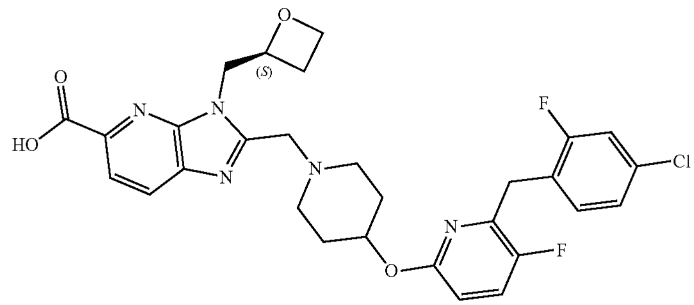 |
| 151a | 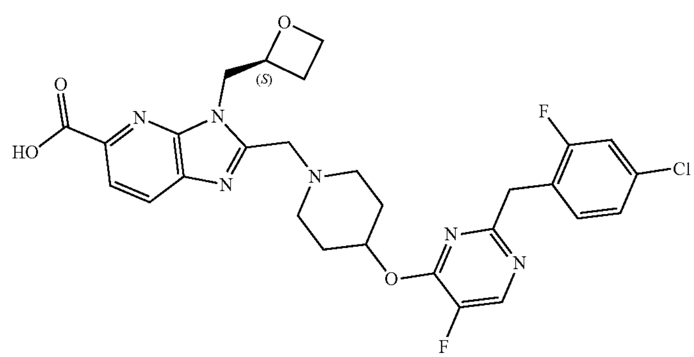 |
| 152a | 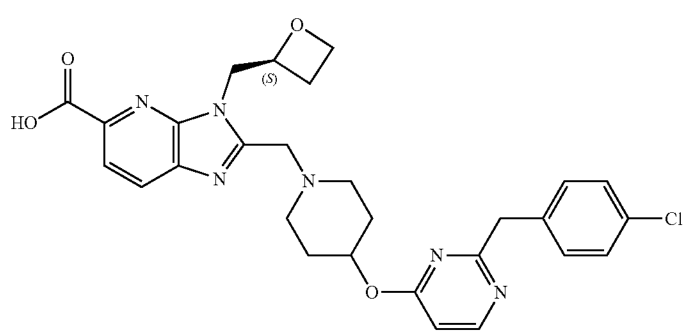 |

TABLE C2-continued

| Compound No. | Structure |
|---|---|
| 153a | 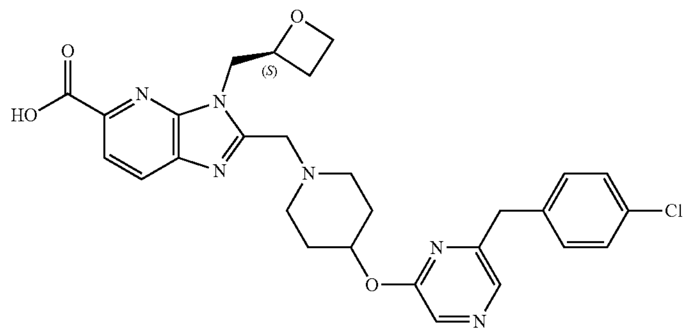 |
| 154a | 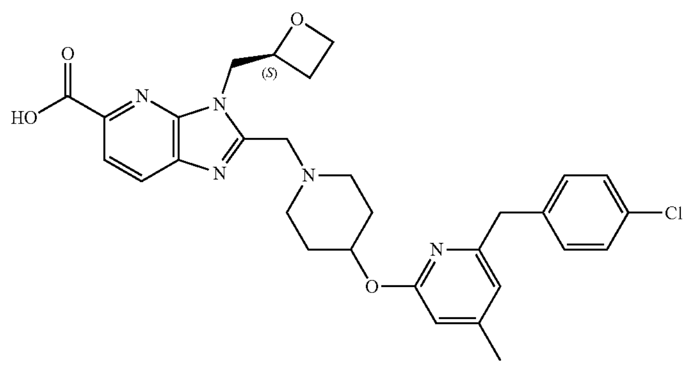 |
| 155a | 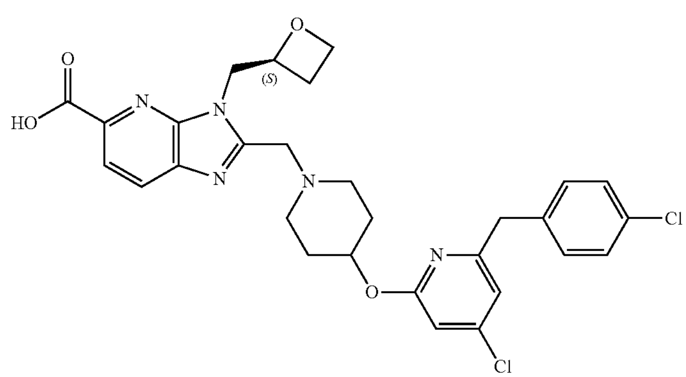 |
| 156a | 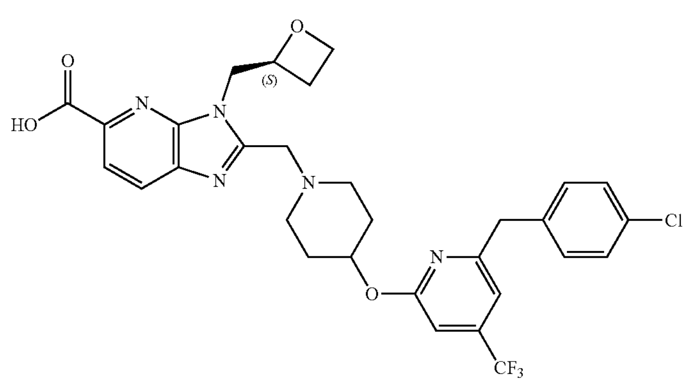 |

TABLE C2-continued

| Compound No. | Structure |
|---|---|
| 157a | 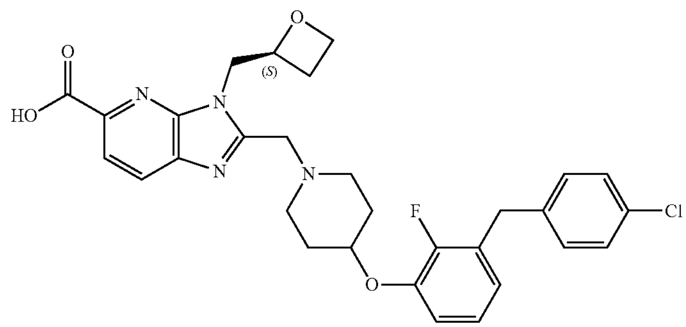 |
| 158a | 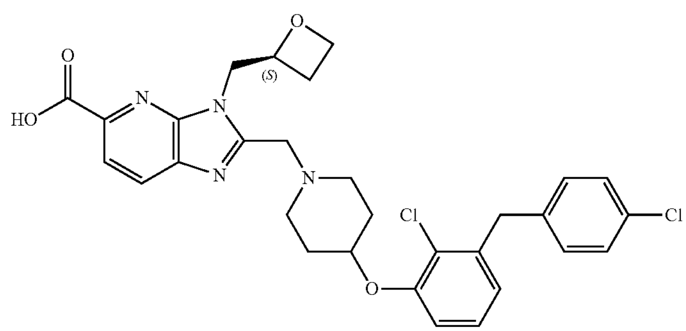 |
| 159a | 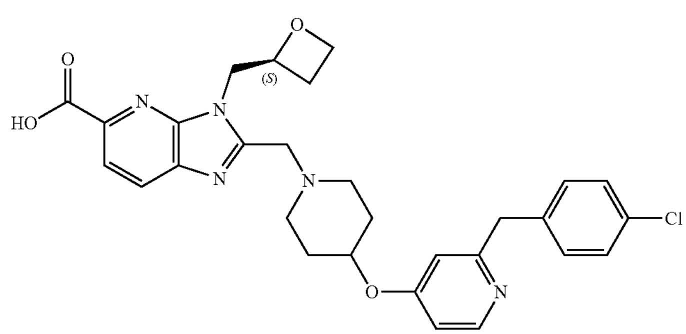 |
| 160a | 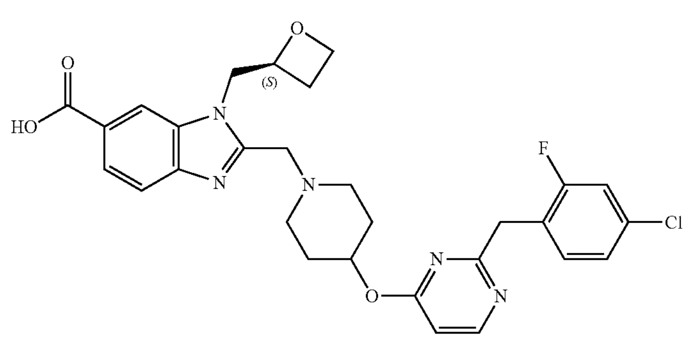 |

TABLE C2-continued
| Compound No. | Structure |
|---|---|
| 161a | 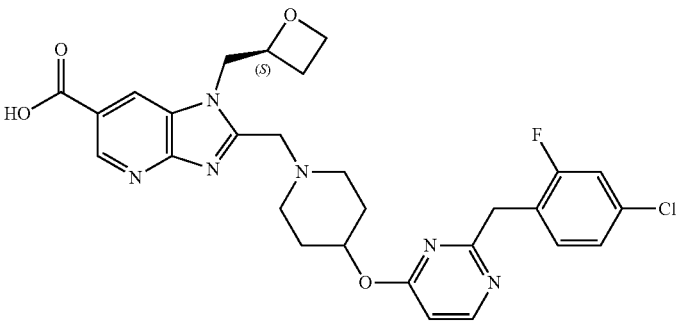 |
| 163a | 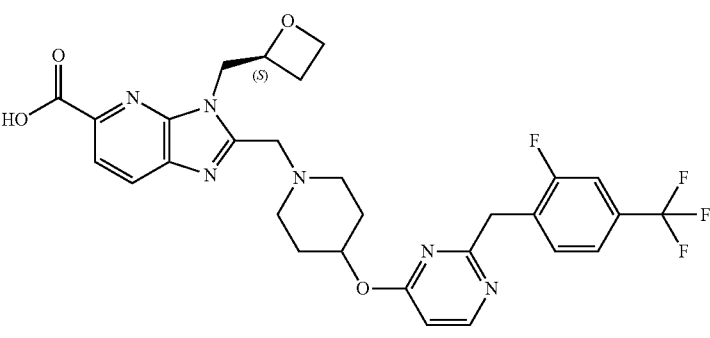 |
| 164a | 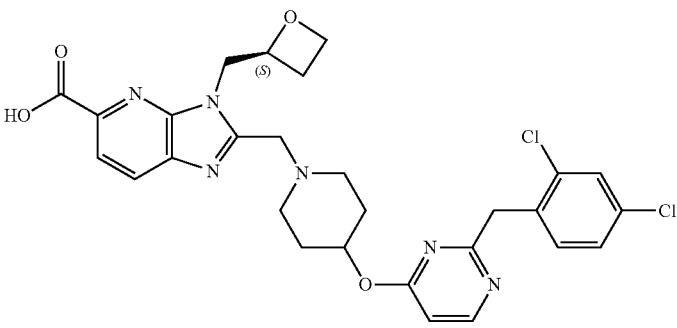 |
| 165a | 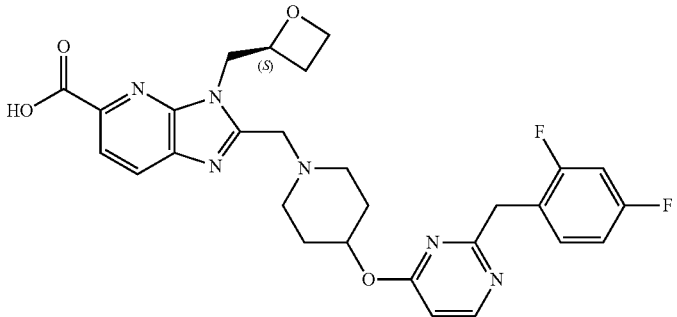 |

TABLE C2-continued

| Compound No. | Structure |
|---|---|
| 166a | 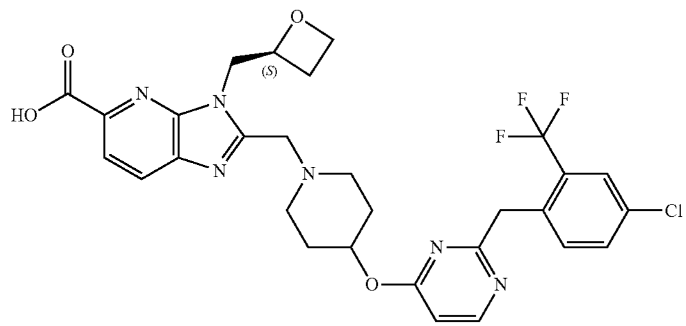 |
| 167a | 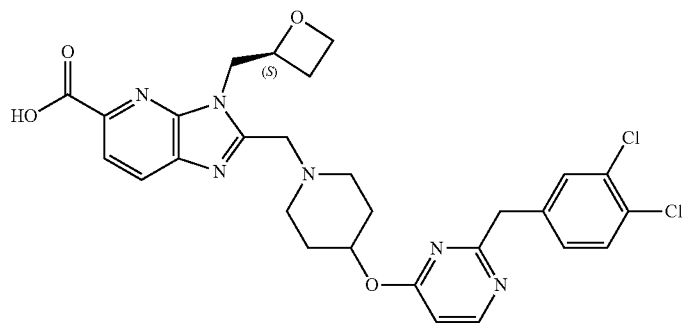 |
| 168a | 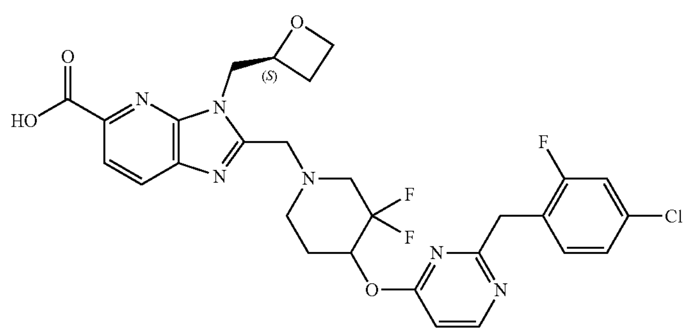 |
| 169a | 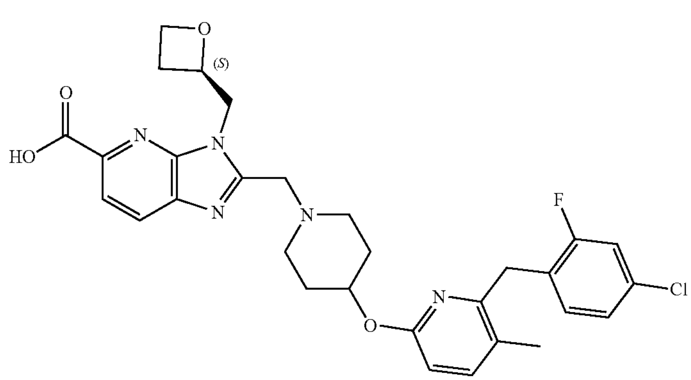 |

TABLE C2-continued
| Compound No. | Structure |
|---|---|
| 170a | 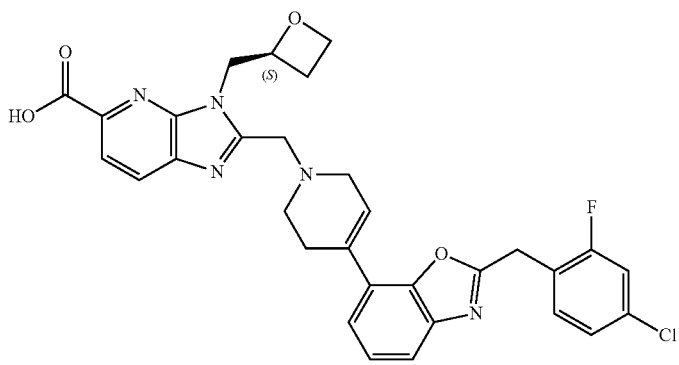 |
| 171a | 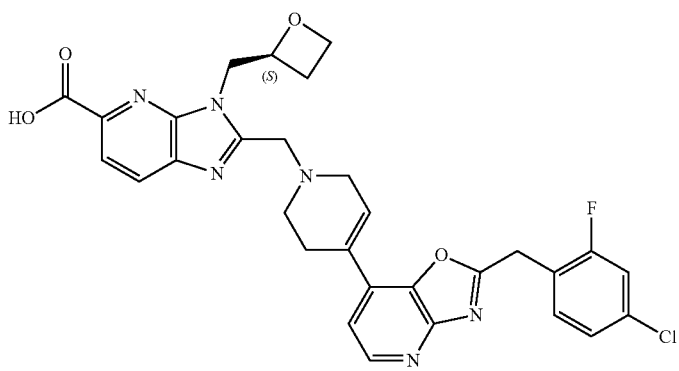 |
| 172a | 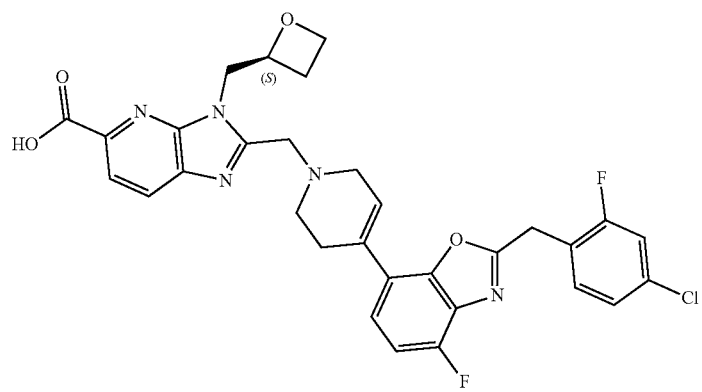 |
| 173a | 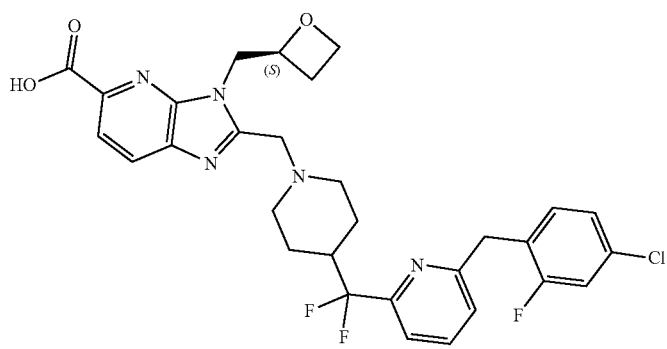 |

TABLE C2-continued
| Compound No. | Structure |
|---|---|
| 174a | 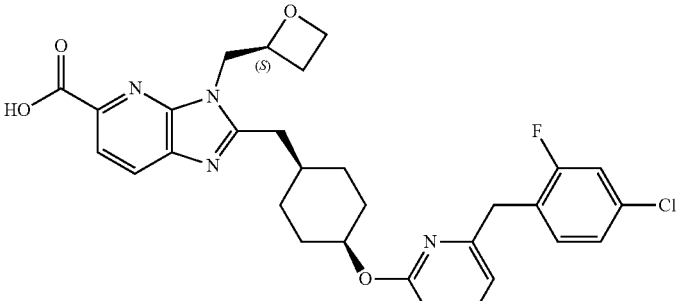 |
| 174b | 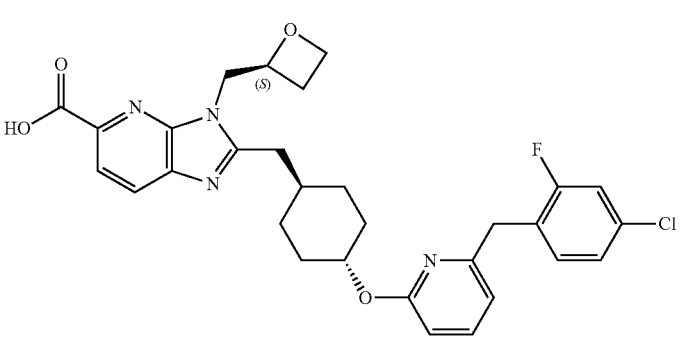 |
| 175a | 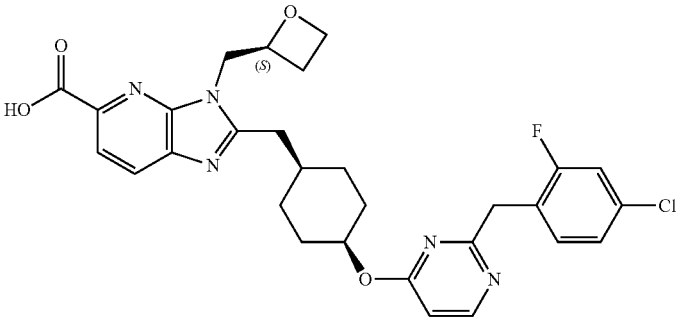 |
| 175b | 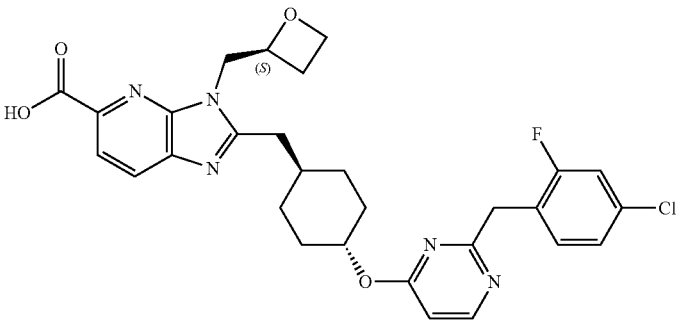 |
| 176a | 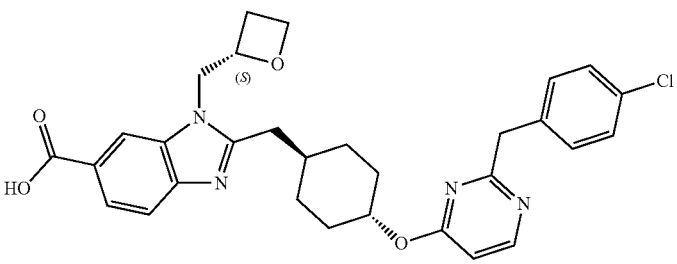 |

TABLE C2-continued

| Compound No. | Structure |
|---|---|
| 177a | 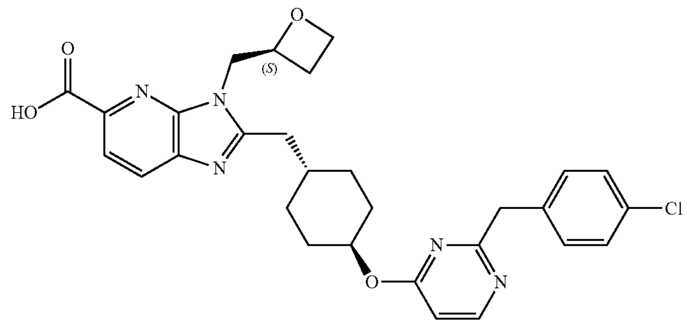 |
| 178a | 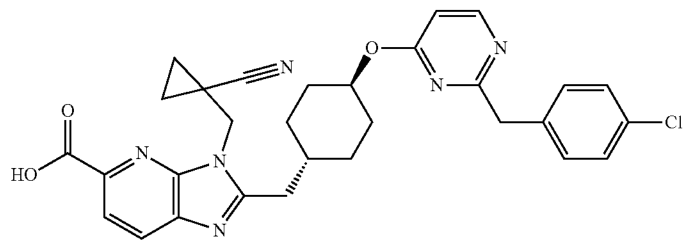 [SMILES: N#CC1(Cn2c(C[C@H]3CC[C@H](Oc4ccnc(Cc5ccc(Cl)cc5)n4)CC3)nc3ccc(C(=O)O)nc32)CC1] |
| 179a | 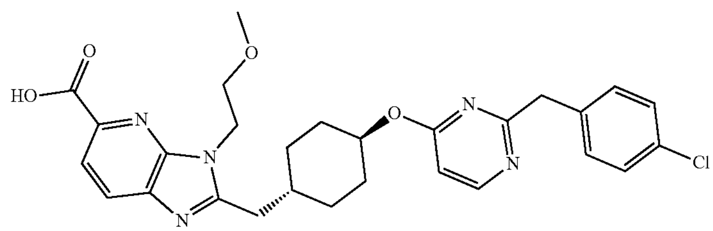 [SMILES: COCCn1c(C[C@H]2CC[C@H](Oc3ccnc(Cc4ccc(Cl)cc4)n3)CC2)nc2ccc(C(=O)O)nc21] |
| 180a | 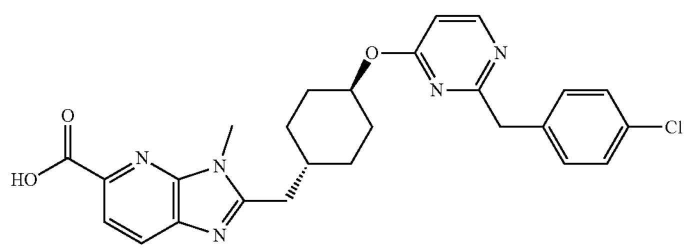 [SMILES: Cn1c(C[C@H]2CC[C@H](Oc3ccnc(Cc4ccc(Cl)cc4)n3)CC2)nc2ccc(C(=O)O)nc21] |
| 181a | 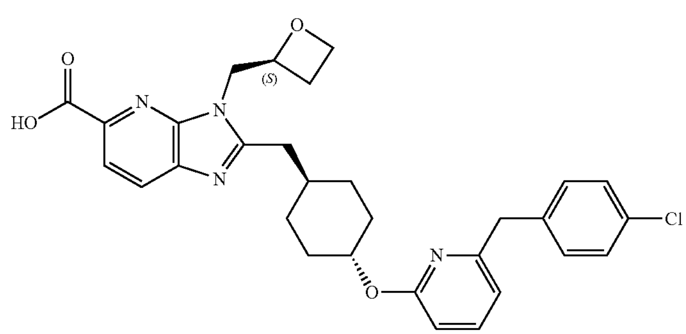 |

TABLE C2-continued
| Compound No. | Structure |
|---|---|
| 182a | 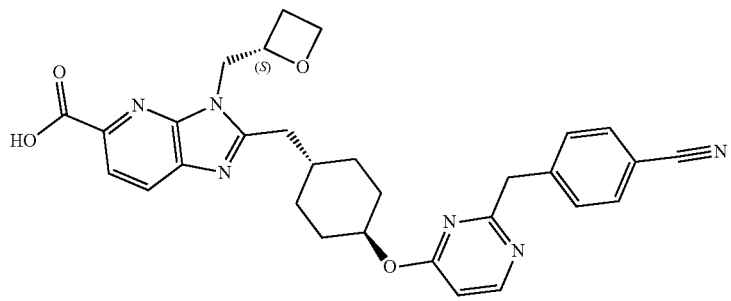 |
| 183a | 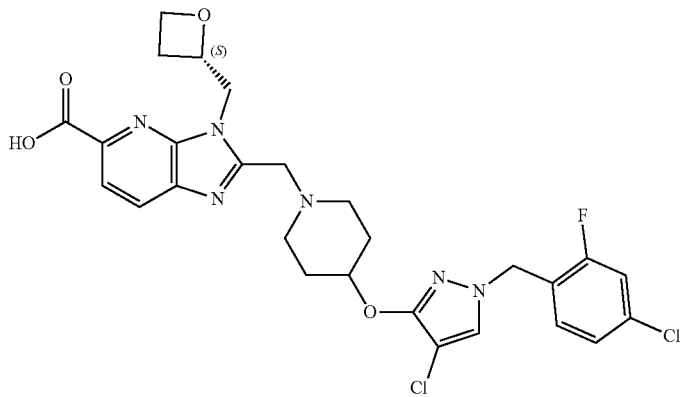 |
| 184a | 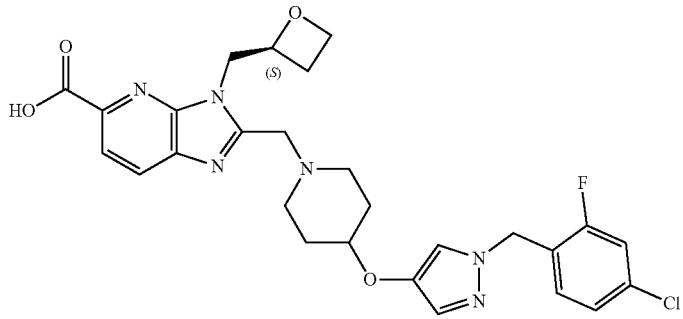 |
| 185a | 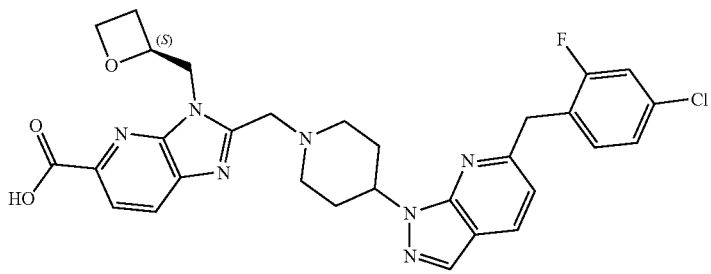 |

TABLE C2-continued
| Compound No. | Structure |
| --- | --- |
| 186a | 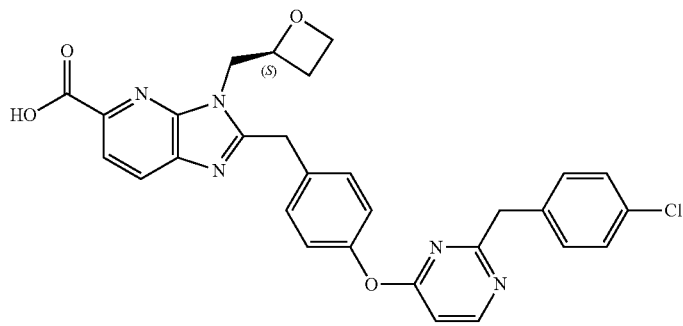 |
| 187a | 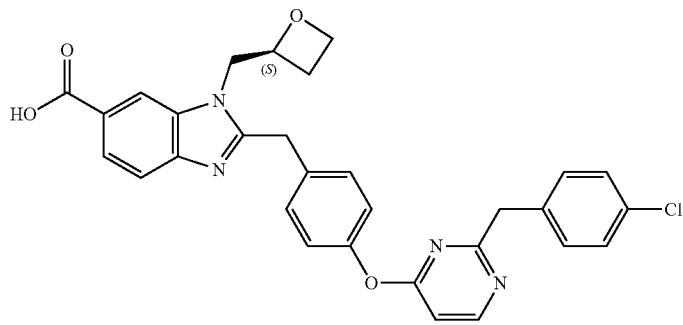 |
| 188a | 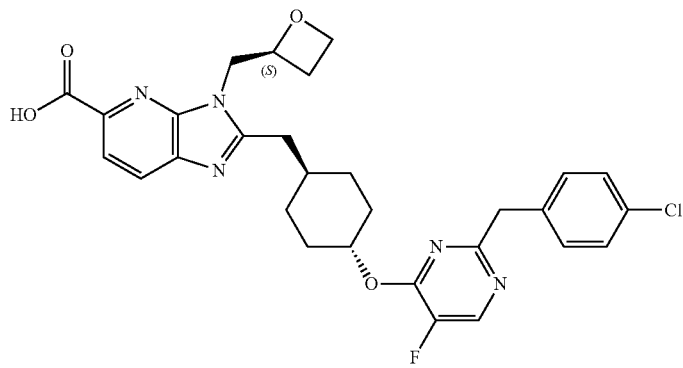 |
| 189a | 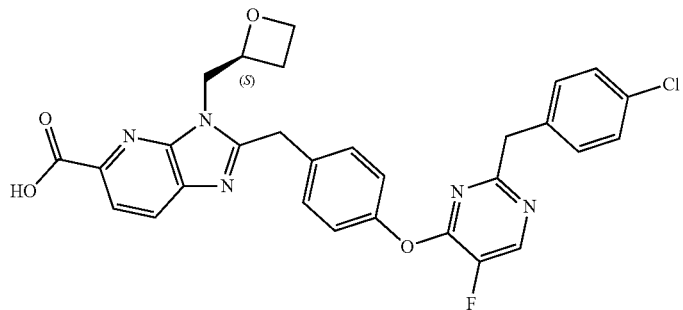 |

TABLE C2-continued
| Compound No. | Structure |
|---|---|
| 190a | 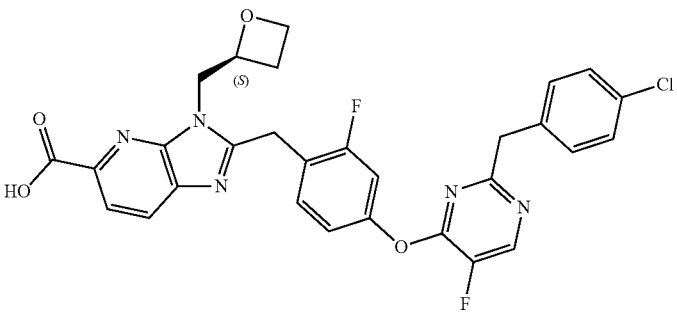 |
| 191a | 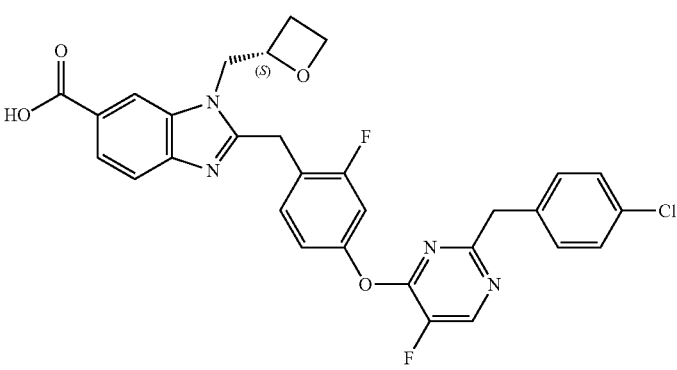 |
| 192a | 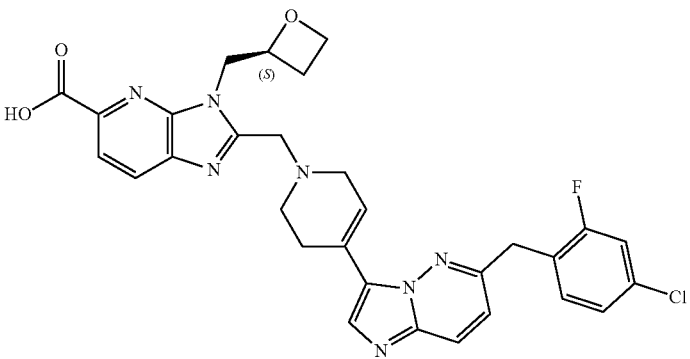 |
| 196a | 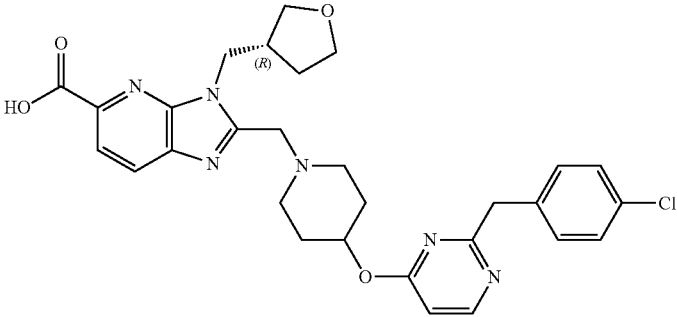 |

TABLE C2-continued
| Compound No. | Structure |
|---|---|
| 197a | 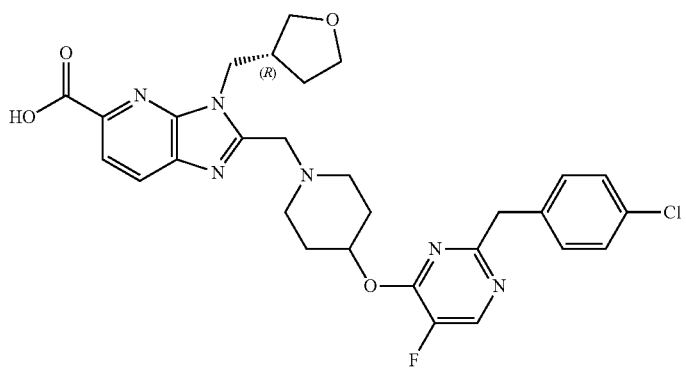 |
| 198a | 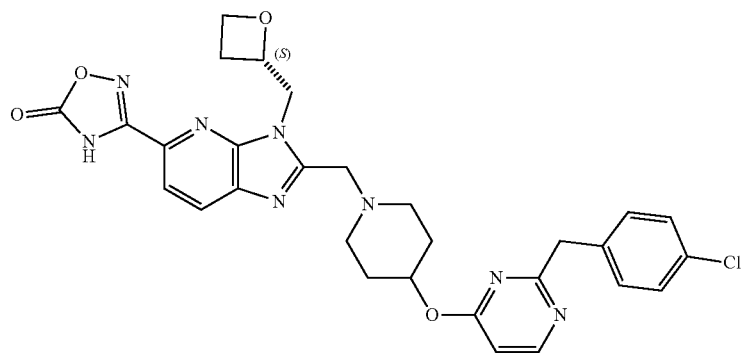 |
| 199a | 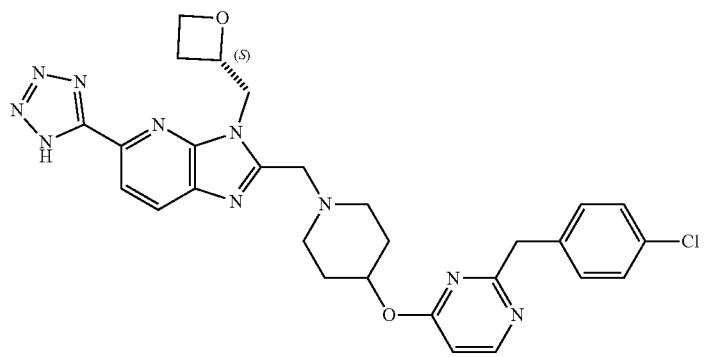 |
| 200a | 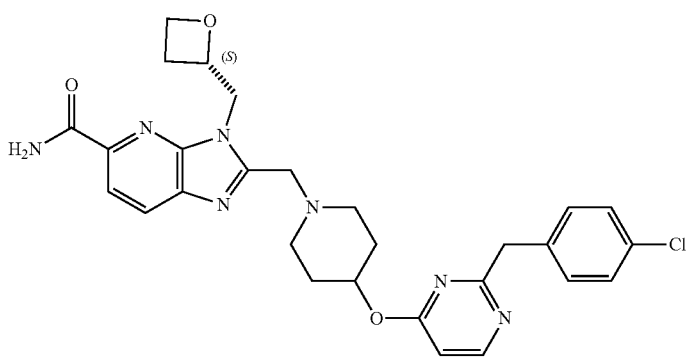 |

TABLE C2-continued

| Compound No. | Structure |
|---|---|
| 201a | 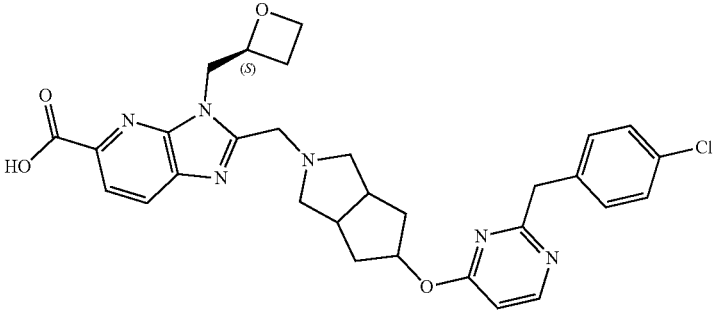 |

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

Pharmaceutical Compositions and Administration

When employed as pharmaceuticals, the compounds of Formula I, including pharmaceutically acceptable salts or solvates thereof can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, or a pharmaceutically acceptable salt or solvate thereof, in combination with one or more pharmaceutically acceptable excipients (carriers). For example, a pharmaceutical composition prepared using a compound of Formula I, or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, or a pharmaceutically acceptable salt or solvate thereof with a pharmaceutically acceptable excipient. Pharmaceutical compositions containing a compound of Formula I, or a pharmaceutically acceptable salt or solvate thereof as the active ingredient can be prepared by intimately mixing the compound of Formula I, or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In some embodiments, the compound or pharmaceutical composition can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

In some embodiments, the compounds and pharmaceutical compositions described herein or a pharmaceutical composition thereof can be administered to patient in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intramenlingeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound of Formula I, or a pharmaceutically acceptable salt or solvate thereof (e.g., a compound of any one of Formulas IA, IB, IC, and ID, or a pharmaceutically acceptable salt or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound of Formula I, or a pharmaceutically acceptable salt or solvate thereof (e.g., a compound of any one of Formulas IA, IB, IC, and ID, or a pharmaceutically acceptable salt or solvate thereof) or pharmaceutical compositions as described herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound of Formula I, or a pharmaceutically acceptable salt or solvate thereof (e.g., a compound of any one of Formulas IA, IB, IC, and ID, or a pharmaceutically acceptable salt or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein or a pharmaceutical composition thereof is formulated for ocular administration. In some embodiments, ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating and non-sensitizing.

In any of the foregoing embodiments, pharmaceutical compositions as described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments, the dosage for a compound of Formula I, or a pharmaceutically acceptable salt or solvate thereof (e.g., a compound of any one of Formulas IA, IB, IC, and ID, or a pharmaceutically acceptable salt or solvate thereof), is determined based on a multiple factors including, but not limited to, type, age, weight, sex, medical condition of the patient, severity of the medical condition of the patient, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) as described herein is administered as a dosage of about 100 mg/Kg.

In some embodiments, the foregoing dosages of a compound of Formula I, or a pharmaceutically acceptable salt or solvate thereof (e.g., a compound of any one of Formulas IA, IB, IC, and ID, or a pharmaceutically acceptable salt or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound of Formula I, or a pharmaceutically acceptable salt or solvate thereof (e.g., a compound of any one of Formulas IA, IB, IC, and ID, or a pharmaceutically acceptable salt or solvate thereof) as described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) is administered to a patient for a period of time followed by a separate period of time where administration of the compound of Formula I, or a pharmaceutically acceptable salt or solvate thereof (e.g., a compound of any one of Formulas IA, IB, IC, and ID, or a pharmaceutically acceptable salt or solvate thereof) is stopped. In some embodiments, a compound of Formula I, or a pharmaceutically acceptable salt or solvate thereof (e.g., a compound of any one of Formulas IA, IB, IC, and ID, or a pharmaceutically acceptable salt or solvate thereof) is administered for a first period and a second period following the first period, with administration stopped during the second period, followed by a third period where administration of the compound of Formula I, or a pharmaceutically acceptable salt or solvate thereof (e.g., a compound of any one of Formulas IA, IB, IC, and ID, or a pharmaceutically acceptable salt or solvate thereof) is started and then a fourth period following the third period where administration is stopped. For example, the period of administration of a compound of Formula I, or a pharmaceutically acceptable salt or solvate thereof (e.g., a compound of any one of Formulas IA, IB, IC, and ID, or a pharmaceutically acceptable salt or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, months, 6 months, 7 months, 8 months, 9 months, 10 months, 11 months, 12 months, or more.

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof), is orally administered to the patient one or more times per day (e.g., one time per day, two times per day, three times per day, four times per day per day or a single daily dose).

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof), is administered by parenteral administration to the patient one or more times per day (e.g., 1 to 4 times one time per day, two times per day, three times per day, four times per day or a single daily dose).

In some embodiments, a compound of Formula I, or a pharmaceutically acceptable salt or solvate thereof (e.g., a compound of any one of Formulas IA, IB, IC, and ID, or a pharmaceutically acceptable salt or solvate thereof), is administered by parenteral administration to the patient weekly.

Methods of Treatment

In some embodiments, this disclosure features methods for treating a patient (e.g., a human) having a disease, disorder, or condition in which modulation of GLP-1R (e.g., repressed or impaired and/or elevated or unwanted GLP-1R) is beneficial for the treatment of the underlying pathology and/or symptoms and/or progression of the disease, disorder, or condition. In some embodiments, the methods described herein can include or further include treating one or more conditions associated, co-morbid or sequela with any one or more of the conditions described herein.

Provided herein is a method for treating a GLP-1 associated disease, disorder, or condition, the method comprising administering to a patient in need thereof an effective amount of a compound of Formula I, or a pharmaceutically acceptable salt or solvate thereof (e.g., a compound of any one of Formulas IA, IB, IC, and ID, or a pharmaceutically acceptable salt or solvate thereof), or a pharmaceutical composition as disclosed herein.

In some embodiments, the disease, disorder, or condition includes, but is not limited to type 1 diabetes mellitus, type 2 diabetes mellitus, early onset type 2 diabetes mellitus, idiopathic type 1 diabetes mellitus (Type 1b), youth-onset atypical diabetes (YOAD), maturity onset diabetes of the young (MODY), latent autoimmune diabetes in adults (LADA), obesity, weight gain from use of other agents, gout, excessive sugar craving, hypertriglyceridemia, dyslipidemia, malnutrition-related diabetes, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, traumatic brain injury, peripheral vascular disease, endothelial dysfunction, impaired vascular compliance, vascular restenosis, thrombosis, hypertension, pulmonary hypertension, restenosis after angioplasty, intermittent claudication, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, macular degeneration, cataract, glomerulosclerosis, arthritis, osteoporosis, treatment of addiction, cocaine dependence, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), ulcerative colitis, inflammatory bowel disease, colitis, irritable bowel syndrome, Crohn's disease, short bowel syndrome, Parkinson's, Alzheimer's disease, impaired cognition, schizophrenia, and Polycystic Ovary Syndrome (PCOS).

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, kidney disease, adipocyte dysfunction, sleep apnea, visceral adipose deposition, eating disorders, cardiovascular disease, congestive heart failure, myocardial infarction, left ventricular hypertrophy, peripheral arterial disease, stroke, hemorrhagic stroke, ischemic stroke, transient ischemic attacks, atherosclerotic cardiovascular disease, hyperglycemia, post-prandial lipemia, metabolic acidosis, ketosis, hyperinsulinemia, impaired glucose metabolism, insulin resistance, hepatic insulin resistance, alcohol use disorder, chronic renal failure, metabolic syndrome, syndrome X, smoking cessation, premenstrual syndrome, angina pectoris, diabetic nephropathy, impaired glucose tolerance, diabetic neuropathy, diabetic retinopathy, bipolar disorder/major depressive disorder, skin and connective tissue disorders, foot ulcerations, psoriasis, primary polydipsia, non-alcoholic steatohepatitis (NASH), non-alcoholic fatty liver disease (NAFLD), short bowel syndrome, Parkinson's disease, Polycystic Ovary Syndrome (PCOS), or any combination thereof.

In some embodiments, the disease, disorder, or condition includes, but is not limited to type 2 diabetes mellitus, early onset type 2 diabetes mellitus, obesity, weight gain from use of other agents, gout, excessive sugar craving, hypertriglyceridemia, dyslipidemia, gestational diabetes, adipocyte dysfunction, visceral adipose deposition, myocardial infarction, peripheral arterial disease, stroke, transient ischemic attacks, hyperglycemia, post-prandial lipemia, metabolic acidosis, ketosis, hyperinsulinemia, impaired glucose metabolism, insulin resistance, hepatic insulin resistance, chronic renal failure, syndrome X, angina pectoris, diabetic nephropathy, impaired glucose tolerance, diabetic neuropathy, diabetic retinopathy, skin and connective tissue disorders, foot ulcerations, or any combination thereof.

In some embodiments, the compounds and pharmaceutical compositions and methods for treating a patient described herein induce one or more of blood glucose reduction (e.g., reduce blood glucose levels), reduce blood hemoglobin A1c (HbA1c) levels, promote insulin synthesis, stimulate insulin secretion, increase the mass of β-cells, modulate gastric acid secretion, modulate gastric emptying, decrease the body mass index (BMI), and/or decrease glucagon production (e.g., level). In certain embodiments, the compounds and pharmaceutical compositions and methods for treating a patient described herein stabilize serum glucose and serum insulin levels (e.g., serum glucose and serum insulin concentrations). Also provided herein are methods for modulating glucose or insulin levels in a patient in need of such modulating, the method comprising administering to the patient an effective amount of a compound of Formula I, or a pharmaceutically acceptable salt or solvate thereof (e.g., a compound of any one of Formulas IA, IB, IC, and ID, or a pharmaceutically acceptable salt or solvate thereof), or a pharmaceutical composition as disclosed herein.

In some embodiments, provided herein is a method for reducing the risk (e.g., by about at least 20%, at least 30%, at least 40%, at least 50%, at least 60%, at least 70%, or at least 80%) of major adverse cardiovascular events (MACE) in a patient in need thereof, the method comprising administering to the patient an effective amount of a compound of Formula I, or a pharmaceutically acceptable salt or solvate thereof (e.g., a compound of any one of Formulas IA, IB, IC, and ID, or a pharmaceutically acceptable salt or solvate thereof), or a pharmaceutical composition as disclosed herein. In certain of these embodiments, the patient is an adult that has been diagnosed with type 2 diabetes (T2D). In certain embodiments, the patient is an adult that has been diagnosed with a heart disease. In certain embodiments, the patient is an adult that has been diagnosed with type 2 diabetes (T2D) and a heart disease. In certain embodiments, the patient is an adult that has type 2 diabetes (T2D). In certain embodiments, the patient is an adult that has a heart disease. In certain embodiments, the patient has type 2 diabetes (T2D) and a heart disease.

Indications

Obesity

In some embodiments, the condition, disease or disorder is obesity and conditions, diseases or disorders that are associated with or related to obesity. Non-limiting examples of obesity and obesity related conditions include symptomatic obesity, simple obesity, childhood obesity, morbid obesity, and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudohypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, diseases or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In some embodiments, the chemical compound and pharmaceutical compositions described herein can be used to treat patients exhibiting symptoms of both obesity and insulin deficiency.

Diabetes

In some embodiments, the condition, disease or disorder is diabetes. Non-limiting examples of diabetes include type 1 diabetes mellitus, type 2 diabetes mellitus (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes. In some embodiments, the condition, disease or disorder is type 2 diabetes mellitus (e.g., diet-treated type 2-diabetes, sulfonylurea-treated type 2-diabetes, a far-advanced stage type 2-diabetes, long-term insulin-treated type 2-diabetes).

Provided herein is a method of treating a diabetes mellitus in a patient, the method comprising (a) determining that the patient has type 2 diabetes mellitus, and (b) administering to the patient a therapeutically effective amount of a compound of Formula I, or a pharmaceutically acceptable salt or solvate thereof (e.g., a compound of any one of a compound of any one of Formulas IA, IB, IC, and ID, or a pharmaceutically acceptable salt or solvate thereof, or a pharmaceutically acceptable salt or solvate thereof) or a pharmaceutical composition as disclosed herein.

Provided herein is a method for treating type 2 diabetes mellitus in a patient, the method comprising administering to a patient identified or diagnosed as having type 2 diabetes mellitus a therapeutically effective amount of a compound of Formula I, or a pharmaceutically acceptable salt or solvate thereof (e.g., a compound of any one of a compound of any one of Formulas IA, IB, IC, and ID, or a pharmaceutically acceptable salt or solvate thereof, or a pharmaceutically acceptable salt or solvate thereof), or a pharmaceutical composition as disclosed herein.

Also provided herein is a method of treating type 2 diabetes mellitus in a patient in need thereof, the method comprising administering to the patient a therapeutically effective amount of a compound of Formula I, or a pharmaceutically acceptable salt or solvate thereof (e.g., a compound of any one of a compound of any one of Formulas IA, IB, IC, and ID, or a pharmaceutically acceptable salt or solvate thereof, or a pharmaceutically acceptable salt or solvate thereof), or a pharmaceutical composition as disclosed herein.

In some embodiments, the compounds and pharmaceutical compositions and methods for treating a patient with a condition, disease, or disorder (e.g., type 2 diabetes mellitus) described herein reduce fasting plasma glucose levels. In some embodiments, the compounds and pharmaceutical compositions and methods for treating a patient with a condition, disease, or disorder (e.g., type 2 diabetes mellitus) described herein reduce non-fasting plasma glucose levels. In some embodiments, the compounds and pharmaceutical compositions and methods for treating a patient with a condition, disease, or disorder (e.g., type 2 diabetes mellitus) described herein reduce HbA1c levels. In some embodiments, the compounds and pharmaceutical compositions and methods for treating a patient with a condition, disease, or disorder (e.g., type 2 diabetes mellitus) described herein reduce glucagon levels. In some embodiments, the compounds and pharmaceutical compositions and methods for treating a patient with a condition, disease, or disorder (e.g., type 2 diabetes mellitus) described herein increase insulin levels. In some embodiments, the compounds and pharmaceutical compositions and methods for treating a patient with a condition, disease, or disorder (e.g., type 2 diabetes mellitus) described herein reduce BMI.

In some embodiments, a reduction in fasting plasma glucose levels of about 5% to about 95% indicates treatment of type 2 diabetes mellitus. In some embodiments, a reduction in fasting plasma glucose levels of about 15% to about 80% indicates treatment of type 2 diabetes mellitus. In some embodiments, a reduction in fasting plasma glucose levels of about 25% to about 60% indicates treatment of type 2 diabetes mellitus. In some embodiments, a reduction in fasting plasma glucose levels to about or below 126 mg/dL, about or below 110 mg/dL, or about or below 90 mg/dL indicates treatment of the type 2 diabetes mellitus.

In some embodiments, a reduction in non-fasting plasma glucose levels of about 5% to about 95% indicates treatment of type 2 diabetes mellitus. In some embodiments, a reduction in non-fasting plasma glucose levels of about 15% to about 80% indicates treatment of type 2 diabetes mellitus. In some embodiments, a reduction in non-fasting plasma glucose levels of about 25% to about 60% indicates treatment of type 2 diabetes mellitus. In some embodiments, a reduction in non-fasting plasma glucose levels to about or below 200 mg/dL, about or below 150 mg/dL, or about or below 130 mg/dL indicates treatment of type 2 diabetes mellitus.

In some embodiments, a reduction in HbA1c levels of about 5% to about 95% indicates treatment of type 2 diabetes mellitus. In some embodiments, a reduction in HbA1c levels of about 15% to about 80% indicates treatment of type 2 diabetes mellitus. In some embodiments, a reduction in HbA1c levels of about 25% to about 60% indicates treatment of type 2 diabetes mellitus. In some embodiments, reduction in HbA1c levels to about or below 6.5%, about or below 6.0%, or about or below 5.0% indicates treatment of type 2 diabetes mellitus.

In some embodiments, a reduction in glucagon levels of about 5% to about 95% indicates treatment of type 2 diabetes mellitus. In some embodiments, a reduction in glucagon levels of about 15% to about 80% indicates treatment of type 2 diabetes mellitus. In some embodiments, a reduction in glucagon levels of about 25% to about 60% indicates treatment of type 2 diabetes mellitus. In some embodiments, an increase in insulin levels of about 5% to about 95% indicates treatment of type 2 diabetes mellitus. In some embodiments, an increase in insulin levels of about 15% to about 80% indicates treatment of type 2 diabetes mellitus. In some embodiments, an increase in insulin levels of about 25% to about 60% indicates treatment of type 2 diabetes mellitus.

In some embodiments, a reduction in BMI of about 5% to about 95% indicates treatment of type 2 diabetes mellitus. In some embodiments, a reduction in BMI of about 15% to about 80% indicates treatment of the type 2 diabetes mellitus. In some embodiments, a reduction in BMI of about 25% to about 60% indicates treatment of type 2 diabetes mellitus. In some embodiments, a reduction in BMI of about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of type 2 diabetes mellitus. In some embodiments, a reduction in BMI to about or below 40, about or below 30, or about or below 20 indicates treatment of type 2 diabetes mellitus.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture, and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In some embodiments, the compounds described herein are also useful in improving the therapeutic effectiveness of metformin.

Disorders of Metabolically Important Tissues

In some embodiments, the condition, disease or disorder is a disorder of a metabolically important tissue. Non-limiting examples of metabolically important tissues include liver, fat, pancreas, kidney, and gut.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., *J Hepatol* 2001; 35: 195-9; Chitturi et al., *Hepatology* 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., *J Gastroenterol Hepatol* 2002; 17 Suppl: S186-90). In some embodiments, the patient is a pediatric patient. The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age. In some embodiments, the patient is an adult patient.

Other non-limiting examples of disorders in metabolically important tissues include joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutrition polycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction), and geriatric syndrome. In some embodiments, the compounds and pharmaceutical compositions described herein can be used for treating surgical trauma by improving recovery after surgery and/or by preventing the catabolic reaction caused by surgical trauma.

Cardiovascular and Vascular Diseases

In some embodiments, the condition, disease or disorder is a cardiovascular disease. Non-limiting examples of cardiovascular disease include congestive heart failure, atherosclerosis, arteriosclerosis, coronary heart disease, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

In some embodiments, the condition, disease or disorder is related to a vascular disease. Non-limiting examples of vascular diseases include peripheral vascular disease, macrovascular complications (e.g., stroke), vascular dysfunction, peripheral artery disease, abdominal aortic aneurysm, carotid artery disease, cerebrovascular disorder (e.g., cerebral infarction), pulmonary embolism, chronic venous insufficiency, critical limb ischemia, retinopathy, nephropathy, and neuropathy.

Neurological Diseases

In some embodiments, the condition, disease or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome). See, e.g., US20060275288A1.

Non-limiting examples of psychiatric disorders include drug dependence/addiction (narcotics and amphetamines and attention deficit/hyperactivity disorder (ADHD). The compounds and pharmaceutical compositions described herein can be useful in improving behavioral response to addictive drugs, decreasing drug dependence, prevention drug abuse relapse, and relieving anxiety caused by the absence of a given addictive substance. See, e.g., US20120021979A1.

In some embodiments, the compounds and pharmaceutical compositions described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In some embodiments, the compounds and pharmaceutical compositions described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., US20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, and cachexia caused by acquired immunodeficiency syndrome).

Body Weight

In some embodiments, the compounds and pharmaceutical compositions described herein can be used to reduce body weight (e.g., excess body weight), prevent body weight gain, induce weight loss, decrease body fat, or reduce food intake in a patient (e.g., a patient in need thereof). In some embodiments, the weight increase in a patient may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). In some embodiments, the weight increase may be weight increase before reaching obesity, or may be weight increase in an obese patient. In some embodiments, the weight increase may also be medication-induced weight gain or weight gain subsequent to cessation of smoking.

In some embodiments, the condition, disease or disorder is an eating disorder, such as hyperphagia, binge eating, bulimia, or compulsive eating.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Hypothalamic-Pituitary Disorders

In some embodiments, the condition, disease or disorder is related to the hypothalamic-pituitary-gonadal axis. For example, the condition, disease or disorder is related to the hypothalamus-pituitary-ovary axis. In another example, the condition, disease or disorder is related to the hypothalamus-pituitary-testis axis. Hypothalamic-pituitary-gonadal axis diseases include, but are not limited to, hypogonadism, polycystic ovary syndrome, hypothyroidism, hypopituitarism, sexual dysfunction, and Cushing's disease.

In some embodiments, the condition, disease or disorder associated with diabetes is related to the hypothalamic-pituitary-gonadal axis.

Pulmonary Disease

In some embodiments, the condition, disease or disorder is related to a pulmonary disease. Pulmonary diseases include, but are not limited to, asthma, idiopathic pulmonary fibrosis, pulmonary hypertension, obstructive sleep apnoea-hypopnea syndrome, and chronic obstructive pulmonary disease (COPD) (e.g., emphysema, chronic bronchitis, and refractory (non-reversible) asthma).

In some embodiments, the condition, disease or disorder associated with diabetes is a pulmonary disease.

Combination Therapy

In some embodiments, this disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., dietary monitoring, diet therapy for diabetes), an exercise therapy (e.g., physical activity), blood sugar monitoring, gastric electrical stimulation (e.g., TANTALUS®), and diet modifications.

In some embodiments, the compounds of X, or a pharmaceutically acceptable salt or solvate thereof as described herein can be administered in combination with one or more additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, therapeutic agents for NASH, therapeutic agents for dysuria and anti-emetic agents.

In some embodiments, the one or more additional therapeutic agents include those useful, for example, as anti-obesity agents. Non-limiting examples include monoamine uptake inhibitors (e.g., tramadol, phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), including GABA receptor agonists (e.g., gabapentin, pregabalin), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11-hydroxysteroid dehydrogenase inhibitors (e.g., AZD-4017, BVT-3498, INCB-13739), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), sodium-glucose cotransporter 2 (SGLT-2) inhibitors (e.g., JNJ-28431754, dapagliflozin, AVE2268, TS-033, YM543, TA-7284, ASP1941, remogliflozin), NFK inhibitors (e.g., IHE-3286), PPAR agonists (e.g., GFT-505, DRF-11605, gemfibrozil and fenofibrate), phosphotyrosine phosphatase inhibitors (e.g., sodium vanadate, trodusquemin), GPR119 agonists (e.g., PSN-821, MBX-2982, APD597), glucokinase activators (e.g., piragliatin, AZD-1656, AZD6370, TTP-355, compounds described in WO006/112549, WO007/028135, WO008/047821, WO008/050821, WO008/136428 and WO008/156757), leptin, leptin derivatives (e.g., metreleptin), leptin resistance improving drugs, CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin (OXM) preparations, appetite suppressants (e.g. ephedrine), FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57), human proislet peptide (HIP), farnesoid X receptor (FXR) agonist, phentermine, zonisamide, norepinephrine/dopamine reuptake inhibitor, GDF-15 analog, methionine aminopeptidase 2 (MetAP2) inhibitor, diethylpropion, phendimetrazine, benzphetamine, fibroblast growth factor receptor (FGFR) modulator, and AMP-activated protein kinase (AMPK) activator.

In some embodiments, the one or more additional therapeutic agents include those useful, for example, as anti-diabetic agents. Non-limiting examples include insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin), insulin sensitizers (e.g., pioglitazone or a salt thereof), biguanides (e.g., metformin, buformin or a salt thereof (e.g., hydrochloride, fumarate, succinate)), glucagon analogs (e.g., any of glucagon analogs described, e.g., in WO 2010/011439), agents which antagonize the actions of or reduce secretion of glucagon, sulfonylurea agents (e.g., chlorpropamide, tolazamide, gliclazide, glimepiride, tolbutamide, glibenclamide, gliclazide, acetohexamide, glyclopyramide, glybuzole, glyburide), thiazolidinedione agents (e.g. rosiglitazone or pioglitazone), α-glucosidase inhibitors (e.g., voglibose, acarbose, miglitol, emiglitate), insulin secretagogues, such as prandial glucose regulators (sometimes called "short-acting secretagogues"), e.g., meglitinides (e.g. repaglinide and nateglinide), cholinesterase inhibitors (e.g., donepezil, galantamine, rivastigmine, tacrine), NMDA receptor antagonists, dual GLP-1/GIP receptor agonists (e.g., LBT-2000, ZPD1-70), GLP-1R agonists (e.g., exenatide, liraglutide, albiglutide, dulaglutide, abiglutide, taspoglutide, lixisenatide, semaglutide, AVE-0010, S4P and Boc5), and dipeptidyl peptidase IV (DPP-4) inhibitors (e.g., vildagliptin, dutogliptin, gemigliptin, alogliptin, saxagliptin, sitagliptin, linagliptin, berberine, adogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, for example, for treating NAFL and NASH. Non-limiting examples include FXR agonists, PF-05221304, a synthetic fatty acid-bile conjugate, an anti-lysyl oxidase homologue 2 (LOXL2) monoclonal antibody, a caspase inhibitor, a MAPK5 inhibitor, a galectin 3 inhibitor, a fibroblast growth factor 21 (FGF21), a niacin analogue, a leukotriene D4 (LTD4) receptor antagonist, an acetyl-CoA carboxylase (ACC) inhibitor, a ketohexokinase (KHK) inhibitor, an apoptosis signal-regulating kinase 1 (ASK1) inhibitor, an ileal bile acid transporter (IBAT) inhibitor, glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, for example, for treating diabetic complications. Non-limiting examples include aldose reductase inhibitors (e.g., tolrestat, epalrestat, zopolrestat, fidarestat, CT-112, ranirestat, lidorestat), neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

In some embodiments, the one or more additional therapeutic agents include those useful, for example, for treating hyperlipidemia. Non-limiting examples include HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid), fibrate compounds (e.g., bezafibrate, clofibrate, simfibrate, clinofibrate), anion exchange resin (e.g., colestyramine), nicotinic acid drugs (e.g., nicomol, niceritrol, niaspan), phytosterols (e.g., soysterol, gamma oryzanol (γ-oryzanol)), cholesterol absorption inhibitors (e.g., zechia), CETP inhibitors (e.g., dalcetrapib, anacetrapib) and ω-3 fatty acid preparations (e.g., ω-3-fatty acid ethyl esters 90).

In some embodiments, the one or more additional therapeutic agents include those useful, for example, as antihypertensive agents. Non-limiting examples include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine) and β-blockers (e.g., metoprolol, atenolol, propranolol, carvedilol, pindolol).

In some embodiments, the one or more additional therapeutic agents include those useful, for example, as diuretics. Non-limiting examples include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene), carbonic anhydrase inhibitors (e.g., acetazolamide) and chlorobenzenesulfonamide agents (e.g., chlortalidone, mefruside, indapamide).

In some embodiments, the one or more additional therapeutic agents include those useful, for example, as immunotherapeutic agents. Non-limiting examples include microbial or bacterial compounds (e.g., muramyl dipeptide derivative, picibanil), polysaccharides having immunoenhancing activity (e.g., lentinan, sizofiran, krestin), cytokines obtained by genetic engineering approaches (e.g., interferon, interleukin (IL) such as IL-1, IL-2, IL-12), and colony-stimulating factors (e.g., granulocyte colony-stimulating factor, erythropoietin).

In some embodiments, the one or more additional therapeutic agents include those useful, for example, as anti-thrombotic agents. Non-limiting examples include heparins (e.g., heparin sodium, heparin calcium, enoxaparin sodium, dalteparin sodium) warfarin (e.g., warfarin potassium); antithrombin drugs (e.g., aragatroban, dabigatran) FXa inhibitors (e.g., rivaroxaban, apixaban, edoxaban, YM150, compounds described in WO02/06234, WO2004/048363, WO2005/030740, WO2005/058823, and WO2005/113504) thrombolytic agents (e.g., urokinase, tisokinase, alteplase, nateplase, monteplase, pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

In some embodiments, the one or more additional therapeutic agents include those useful, for example, for treating osteoporosis. Non-limiting examples include alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavoxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other exemplary additional therapeutic agents include agents that modulate hepatic glucose balance (e.g., fructose 1,6-bisphosphatase inhibitors, glycogen phosphorylase inhibitors, glycogen synthase kinase inhibitors, glucokinase activators), agents designed to treat the complications of prolonged hyperglycemia, such as aldose reductase inhibitors (e.g. epalrestat and ranirestat), agents used to treat complications related to micro-angiopathies, anti-dyslipidemia agents, such as HMG-CoA reductase inhibitors (statins, e.g. rosuvastatin), cholesterol-lowering agents, bile acid sequestrants (e.g., cholestyramine), cholesterol absorption inhibitors (e.g. plant sterols such as phytosterols), cholesteryl ester transfer protein (CETP) inhibitors, inhibitors of the ileal bile acid transport system (IBAT inhibitors), bile acid binding resins, nicotinic acid (niacin) and analogues thereof, anti-oxidants (e.g., probucol), omega-3 fatty acids, antihypertensive agents, including adrenergic receptor antagonists, such as beta blockers (e.g. atenolol), alpha blockers (e.g. doxazosin), and mixed alpha/beta blockers (e.g. labetalol), adrenergic receptor agonists, including alpha-2 agonists (e.g. clonidine), angiotensin converting enzyme (ACE) inhibitors (e.g. lisinopril), calcium channel blockers, such as dihydropridines (e.g. nifedipine), phenylalkylamines (e.g. verapamil), and benzothiazepines (e.g. diltiazem), angiotensin II receptor antagonists (e.g. candesartan), aldosterone receptor antagonists (e.g. eplerenone), centrally acting adrenergic drugs, such as central alpha agonists (e.g. clonidine), diuretic agents (e.g. furosemide), haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban), antiplatelet agents (e.g., cyclooxygenase inhibitors (e.g. aspirin)), adenosine diphosphate (ADP) receptor inhibitors (e.g. clopidogrel), phosphodiesterase inhibitors (e.g. cilostazol), glycoprotein IIB/IIA inhibitors (e.g. tirofiban), adenosine reuptake inhibitors (e.g. dipyridamole), noradrenergic agents (e.g. phentermine), serotonergic agents (e.g. sibutramine), diacyl glycerolacyltransferase (DGAT) inhibitors, feeding behavior modifying agents, pyruvate dehydrogenase kinase (PDK) modulators, serotonin receptor modulators, monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine), compounds described in WO007/013694, WO2007/018314, WO2008/093639 and WO2008/099794, GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931), SGLT1 inhibitors, adiponectin or agonist thereof, IKK inhibitors (e.g., AS-2868), somatostatin receptor agonists, ACC2 inhibitors, cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M, metabolism-modifying proteins or peptides such as glucokinase (GK), glucokinase regulatory protein (GKRP), uncoupling proteins 2 and 3 (UCP2 and UCP3), peroxisome proliferator-activated receptor α (PPARα), MC4r agonists, insulin receptor agonist, PDE 5 inhibitors, glycation inhibitors (e.g., ALT-711), nerve regeneration-promoting drugs (e.g., Y-128, VX853, prosaptide), antidepressants (e.g., desipramine, amitriptyline, imipramine), antiepileptic drugs (e.g., lamotrigine, trileptal, keppra, zonegran, pregabalin, harkoseride, carbamazepine), antiarrhythmic drugs (e.g., mexiletine), acetylcholine receptor ligands (e.g., ABT-594), endothelin receptor antagonists (e.g., ABT-627), narcotic analgesics (e.g., morphine), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), cytotoxic antibodies (e.g., T-cell receptor and IL-2 receptor-specific antibodies), B cell depleting therapies (e.g., anti-CD20 antibody (e.g., rituxan), i-BLyS antibody), drugs affecting T cell migration (e.g., anti-integrin alpha 4/beta 1 antibody (e.g., tysabri), drugs that act on immunophilins (e.g., cyclosporine, tacrolimus, sirolimus, rapamicin), interferons (e.g., IFN-β), immunomodulators (e.g., glatiramer), TNF-binding proteins (e.g., circulating receptors), immunosupressants (e.g., mycophenolate), and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide.

In some embodiments, the one or more additional therapeutic agents include those useful, for example, as antiemetic agents. As used herein, an "anti-emetic" agent refers to any agent that counteracts (e.g., reduces or removes) nausea or emesis (vomiting). While not wishing to be bound by theory, it is believed that administering one or more anti-emetic agents in combination with the formula (I) compounds described herein may allow higher dosages of the formula (I) compounds to be administered, e.g., because the patient may be able to have a normal food intake and thereby respond faster to the treatment.

Non-limiting examples of anti-emetic agents include 5HT3-receptor antagonists (serotonin receptor antagonists), neuroleptics/anti-psychotics, antihistamines, anticholinergic agents, steroids (e.g., corticosteroids), NK1-receptor antagonists (e.g., Neurokinin 1 substance P receptor antagonists), antidopaminergic agents/dopamine receptor antagonists, benzodiazepines, cannabinoids.

For example, the antiemetic agent can be selected from the group consisting of; neuroleptics, antihistamines, anticholinergic agents, steroids, 5HT-3-receptor antagonists, NK1-receptor antagonists, anti-dopaminergic agents/dopamine receptor antagonists, benzodiazepines and non-psychoactive cannabinoids.

In some embodiments, the anti-emetic agent is a 5HT3-receptor antagonist (serotonin receptor antagonist). Non-limiting examples of 5HT3-receptor antagonists (serotonin receptor antagonists) include: Granisetron (Kytril), Dolasetron, Ondansetron (Zofran), Tropisetron, Ramosetron, Palonosetron, Alosetron, azasetron, Bemesetron, Zatisetron, Batanopirde, MDL-73147EF; Metoclopramide, N-3389 (endo-3,9-dimethyl-3,9-diazabicyclo[3,3,1]non-7-yl-1H-indazole-3-carboxamide dihydrochloride), Y-25130 hydrochloride, MDL 72222, Tropanyl-3,5-dimethylbenzoate, 3-(4-Allylpiperazin-1-yl)-2-quinoxalinecarbonitrile maleate, Zacopride hydrochloride, and Mirtazapine. Other non-limiting examples of 5HT3-receptor antagonists (serotonin receptor antagonists) include: cilansetron, clozapine, cyproheptadine, dazopride, hydroxyzine, lerisetron, metoclopramide, mianserin, olanzapine, palonosetron (+netupitant), quetiapine, qamosetron, ramosteron, ricasetron, risperidone, ziprasidone, and zatosetron.

In certain embodiments, the 5HT-3-receptor antagonist is Granisetron, Dolasetron, Ondansetron hydrochloride, Tropisetron, Ramosetron, Palonosetron, Alosetron, Bemesetron, Zatisetron, Batanopirde, MDL-73147EF, Metoclopramide, N-3389, Y-25130 hydrochloride, MDL 72222, Tropanyl-3, 5-dimethylbenzoate 3-(4-Allyl-piperazin-1-yl)-2-quinoxalinecarbonitrile maleate, Zacopride hydrochloride and Mirtazepine.

In certain embodiments, the 5HT-3-receptor antagonist is Granisetron, Dolasetron, Ondansetron hydrochloride, Tropisetron, Ramosetron, Palonosetron, Alosetron, Bemesetron, and Zatisetron.

In certain embodiments, the 5HT-3-receptor antagonist is Granisetron, Dolasetron and Ondansetron.

In certain embodiments, the 5HT-3-receptor antagonist is Granisetron.

In certain embodiments, the 5HT-3-receptor antagonist is Ondansetron.

In some embodiments, the anti-emetic agent is an antihistamine. Non-limiting examples of antihistamines include: piperazine derivatives (e.g., cyclizine, meclizine, and cinnarizine); Promethazine; Dimenhydrinate (Dramamine, Gravol); Diphenhydramine; Hydroxyzine; Buclizine; and Meclizine hydrochloride (Bonine, Antivert), doxylamine, and mirtazapine.

In some embodiments, the anti-emetic agent is an anticholinergic agent (Inhibitors of the acetylcholine receptors). Non-limiting examples of anticholinergic agents include: atropine, Scopolamine, Glycopyrron, Hyoscine, Artane (Trihexy-5 trihexyphenidyl hydrochloride), Cogentin (benztropine mesylate), Akineton (biperiden hydrochloride), Disipal (Norflex orphenadrine citrate), diphenhydramine, hydroxyzine, hyoscyamine, and Kemadrin (procyclidine hydrochloride).

In some embodiments, the anti-emetic agent is a steroid (e.g., a corticosteroid). Non-limiting examples of steroids include: betamethasone, Dexamethasone, Methylprednisolone, Prednisone®, and Trimethobenzamide (Tigan).

In some embodiments, the anti-emetic agent is an NK1-receptor antagonists (e.g., Neurokinin 1 substance P receptor antagonists). Non-limiting examples of NK1-receptor antagonists include: aprepitant, casopitant, ezlopitant, fosaprepitant, maropitant, netupitant, rolapitant, and vestipitant.

Other non-limiting examples of NK1-receptor antagonists include: MPC-4505, GW597599, MPC-4505, GR205171, L-759274, SR 140333, CP-96,345, BIIF 1149, NKP 608C, NKP 608A, CGP 60829, SR 140333 (Nolpitantium besilate/chloride), LY 303870 (Lanepitant), MDL-105172A, MDL-103896, MEN-11149, MEN-11467, DNK 333A, YM-49244, YM-44778, ZM-274773, MEN-10930, S-19752, Neuronorm, YM-35375, DA-5018, MK-869, L-754030, CJ-11974, L-758298, DNK-33A, 6b-1, CJ-11974 j. Benserazide and carbidopa k. TAK-637 [(aR, 9R)-7-[3,5-bis(trifluoromethyl)benzyl]-8,9,10,11-tetrahydro-9-methyl-5-(4-methylphenyl)-7H-[1,4]diazocino[2, 1-g] [1,7]naphthyridine-6,13-dione], PD 154075, ([(2-benzofuran)-CH2OCO]—(R)-alpha-MeTrp-(S)—NHCH (CH3) Ph), FK888, and (D-Pro4, D-Trp7,9,10, Phe11)SP4-11.

In some embodiments, the anti-emetic agent is an antidopaminergic agents/dopamine receptor antagonist (e.g., dopamine receptor antagonist, e.g., D2 or D3 antagonists). Non-limiting examples include phenothiazines (e.g., promethazine, chlorpromazine, prochlorperazine, perphenazine, hydroxyzine, thiethylperazine, metopimazine,); benzamides (e.g., Metoclopramide, domperidone), butyrophenones (e.g., haloperidol, droperidol); alizapride, bromopride, clebopride, domperidone, itopride, metoclopramide, trimethobenzamide, and amisulpride.

In some embodiments, the anti-emetic agent is a non-psychoactive cannabinoids (e.g., Cannabidiol (CBD), Cannabidiol dimethylheptyl (CBD-DMH), Tetra-hydro-cannabinol (THC), Cannabinoid agonists such as WIN 55-212 (a CB1 and CB2 receptor agonist), Dronabinol (Marinol®), and Nabilone (Cesamet)).

Other exemplary anti-emetic agents include: c-9280 (Merck); benzodiazepines (diazepam, midazolam, lorazepam); neuroleptics/anti-psychotics (e.g., dixyrazine, haloperidol, and Prochlorperazine (Compazine®)); cerium oxalate; propofol; sodium citrate; dextrose; fructose (Nauzene); orthophosphoric acid; fructose; glucose (Emetrol); bismuth subsalicylate (Pepto Bismol); ephedrine; vitamin B6; peppermint, lavender, and lemon essential oils; and ginger.

Still other exemplary anti-emetic agents include those disclosed in US 20120101089A1; U.S. Pat. No. 10,071,088 B2; U.S. Pat. No. 6,673,792 B1; U.S. Pat. No. 6,197,329 B1; U.S. Pat. No. 10,828,297 B2; U.S. Pat. No. 10,322,106 B2; U.S. Pat. No. 10,525,033 B2; WO 2009080351 A1; WO 2019203753 A2; WO 2002020001 A2; U.S. Pat. No. 8,119,697 B2; U.S. Pat. No. 5,039,528; US20090305964A1; and WO 2006/111169, each of which is incorporated by reference in its entirety.

In some embodiments, the additional therapeutic agent or regimen is administered to the patient prior to contacting with or administering the compounds and pharmaceutical compositions (e.g., about one hour prior, or about 6 hours prior, or about 12 hours prior, or about 24 hours prior, or about 48 hours prior, or about 1 week prior, or about 1 month prior).

In some embodiments, the additional therapeutic agent or regimen is administered to the patient at about the same time as contacting with or administering the compounds and pharmaceutical compositions. By way of example, the additional therapeutic agent or regimen and the compounds and pharmaceutical compositions are provided to the patient simultaneously in the same dosage form. As another example, the additional therapeutic agent or regimen and the compounds and pharmaceutical compositions are provided to the patient concurrently in separate dosage forms.

Patient Selection

In some embodiments, the methods described herein further include the step of identifying a patient (e.g., a subject) in need of such treatment (e.g., by way of blood assay, body mass index, or other conventional method known in the art).

In some embodiments, the methods described herein further include the step of identifying a patient (e.g., patient) that has a disease, disorder, or condition as provided here (e.g., a GLP-1 associated disease, disorder, or condition).

In some embodiments, the methods described herein further include the step of identifying a patient (e.g., patient) that has type 2 diabetes mellitus. In some embodiments, determining if the patient has type 2 diabetes mellitus includes performing an assay to determine the level of hemoglobin A1c (HbA1c), fasting plasma glucose, non-fasting plasma glucose, or any combination thereof. In some embodiments, the level of HbA1c is about 6.5% to about 24.0%. In some embodiments, the level of HbA1c is greater than or about 6.5%. In some embodiments, the level of HbA1c is greater than or about 8.0%. In some embodiments, the level of HbA1c is greater than or about 10.0%. In some embodiments, the level of HbA1c is greater than or about 12.0%. In some embodiments, the level of HbA1c is greater than or about 14.0%. In some embodiments, the level of HbA1c is greater than or about 16.0%. In some embodiments, the level of HbA1c is greater than or about 18.0%. In some embodiments, the level of HbA1c is greater than or about 20.0%. In some embodiments, the level of HbA1c is greater than or about 22.0%. In some embodiments, the level of HbA1c is greater than or about 24.0%.

In some embodiments, the level of fasting plasma glucose is greater than or about 120 mg/dL to greater than or about 750 mg/dL. In some embodiments, the level of fasting plasma glucose is greater than or about 200 mg/dL to greater than or about 500 mg/dL. In some embodiments, the level of fasting plasma glucose is greater than or about 300 mg/dL to greater than or about 700 mg/dL.

In some embodiments, the level of non-fasting plasma glucose is greater than or about 190 mg/dL to greater than or about 750 mg/dL. In some embodiments, the level of non-fasting plasma glucose is greater than or about 250 mg/dL to greater than or about 450 mg/dL. In some embodiments, the level of non-fasting plasma glucose is greater than or about 400 mg/dL to greater than or about 700 mg/dL.

In some embodiments, determining if the patient has type 2 diabetes mellitus further includes determining the patient's BMI. In some embodiments, the BMI of the patient is greater than or about 22 kg/m$^2$ to greater than or about 100 kg/m$^2$. In some embodiments, the BMI of the patient is greater than or about 30 kg/m$^2$ to greater than or about 90 kg/m$^2$. In some embodiments, the BMI of the patient is greater than or about 40 kg/m$^2$ to greater than or about 80 kg/m$^2$. In some embodiments, the BMI of the patient is greater than or about 50 kg/m$^2$ to greater than or about 70 kg/m$^2$.

In some embodiments, additional factors (e.g. risk factors) used for determining if the patient has type 2 diabetes mellitus further includes age and ethnicity of the patient. In some embodiments, the patient's age is greater than or about 10 years. In some embodiments, the patient's age is greater than or about 15 years. In some embodiments, the patient's age is greater than or about 20 years. In some embodiments, the patient's age is greater than or about 25 years. In some embodiments, the patient's age is greater than or about 30 years. In some embodiments, the patient's age is greater than or about 35 years. In some embodiments, the patient's age is greater than or about 40 years. In some embodiments, the patient's age is greater than or about 42 years. In some embodiments, the patient's age is greater than or about 44 years. In some embodiments, the patient's age is greater than or about 46 years. In some embodiments, the patient's age is greater than or about 48 years. In some embodiments, the patient's age is greater than or about 50 years. In some embodiments, the patient's age is greater than or about 52 years. In some embodiments, the patient's age is greater than or about 54 years. In some embodiments, the patient's age is greater than or about 56 years. In some embodiments, the patient's age is greater than or about 58 years. In some embodiments, the patient's age is greater than or about 60 years. In some embodiments, the patient's age is greater than or about 62 years. In some embodiments, the patient's age is greater than or about 64 years. In some embodiments, the patient's age is greater than or about 66 years. In some embodiments, the patient's age is greater than or about 68 years. In some embodiments, the patient's age is greater than or about 70 years. In some embodiments, the patient's age is greater than or about 72 years. In some embodiments, the patient's age is greater than or about 74 years. In some embodiments, the patient's age is greater than or about 76 years. In some embodiments, the patient's age is greater than or about 78 years. In some embodiments, the patient's age is greater than or about 80 years. In some embodiments, the patient's age is greater than or about 85 years. In some embodiments, the patient's age is greater than or about 90 years. In some embodiments, the patient's age is greater than or about 95 years. In some embodiments, the ethnicity of the patient may be African American, American Indian or Alaska Native, Asian American, Hispanics or Latinos, or Native Hawaiian or Pacific Islander.

EXAMPLES

The invention is further described in the following examples, which do not limit the scope of the invention described in the claims.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. $^1$H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Example 1: Synthesis of (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylic acid (Compound 101a)

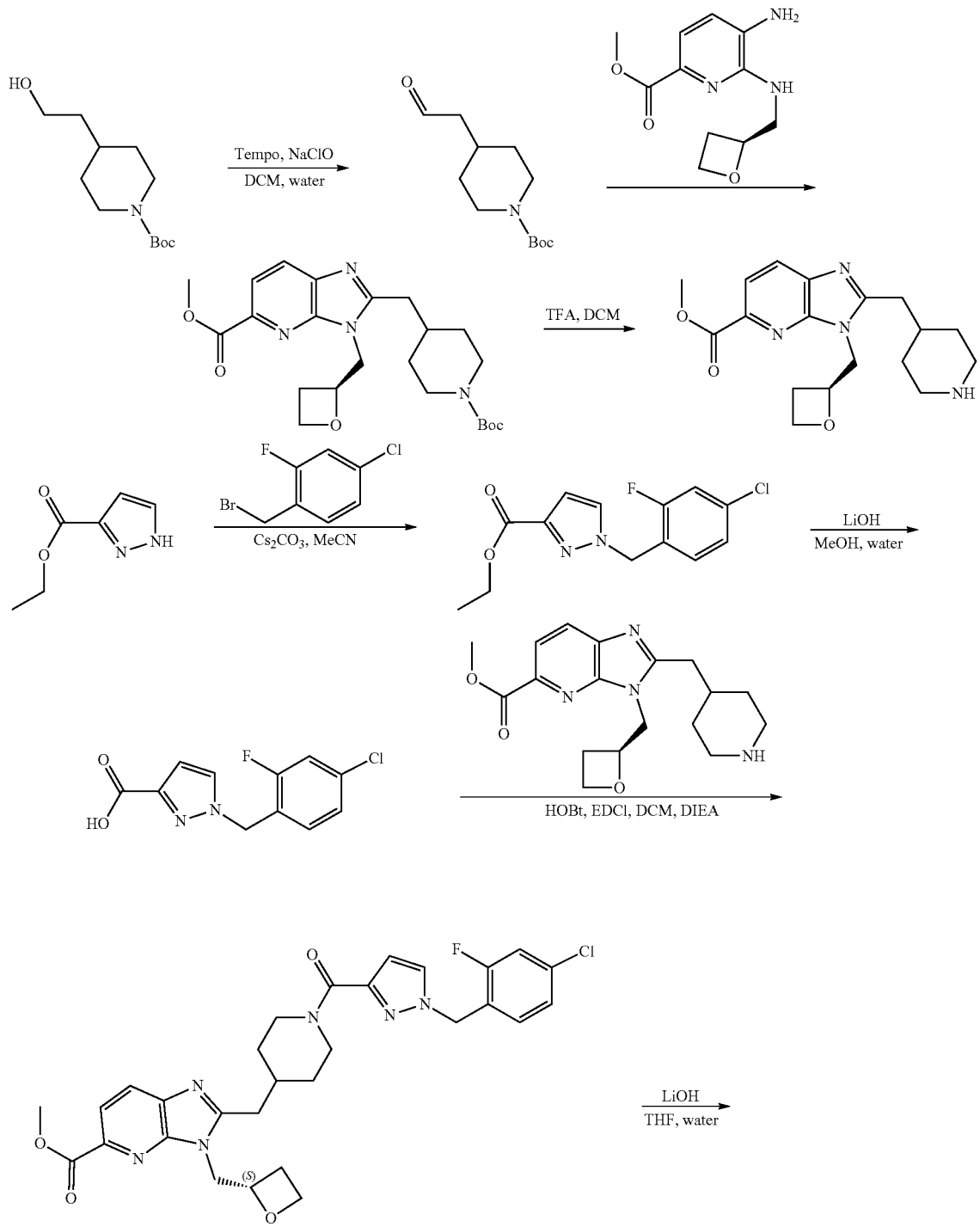

-continued

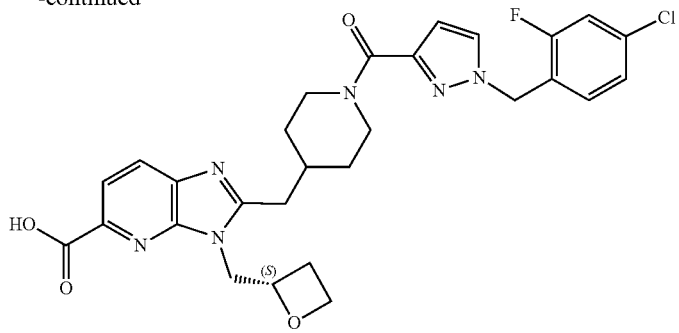

Compound 101a

Step A: tert-Butyl 4-(2-oxoethyl)piperidine-1-carboxylate

To a mixture of tert-butyl 4-(2-hydroxyethyl)piperidine-1-carboxylate (3 g, 13 mmol), TEMPO (20 mg, 0.13 mmol), NaHCO$_3$ (1.09 g, 13 mmol), NaCl (754 mg, 13 mmol) and KBr (154 mg, 1.3 mmol) in DCM (20 mL) and H$_2$O (20 mL) was added NaClO water solution (11.5 mL, 11.7 mmol) dropwise over 50 min at 0° C. The resulting mixture was stirred at 0° C. for 20 min. The aqueous layer was separated and extracted with DCM (10 mL*2). The combined organic layers were washed with saturated Na$_2$S$_2$O$_3$ aqueous solution (15 mL), saturated NaHCO$_3$ aqueous solution (15 mL) and brine (15 mL). The resulting organic solution was dried over Na$_2$SO$_4$, filtered and concentrated. The residue was purified by flash column chromatography eluting with DCM/MeOH (80/1-40/1) to give methyl tert-Butyl 4-(2-oxoethyl)piperidine-1-carboxylate (2.5 g, yield: 85%) as colorless oil. MS Calcd.: 227.1. MS Found: 172.1 [M+H-56]$^+$.

Step B: Methyl (S)-2-((1-(tert-butoxycarbonyl)piperidin-4-yl)methyl)-3-(oxetan-2-ylmethyl)-3H-imidazo[4,5-b]pyridine-5-carboxylate A mixture of methyl (S)-5-amino-6-((oxetan-2-ylmethyl) amino) picolinate (2.5 g, 11 mmol), methyl (S)-5-amino-6-((oxetan-2-ylmethyl) amino) picolinate (3 g, 13 mmol) and Molecular sieves (5 g) in Toluene (30 mL) was stirred at 90° C. under O$_2$ atmosphere for 48 hrs. The reaction mixture was filtered, and then the filtrate was concentrated under reduced pressure. The crude was purified by flash silica column chromatography (eluent=20%-80% EA in PE) to give desired product methyl (S)-2-((1-(tert-butoxycarbonyl) piperidin-4-yl) methyl)-3-(oxetan-2-ylmethyl)-3H-imidazo [4,5-b]pyridine-5-carboxylate (2.5 g, yield: 51%) as white solid. MS Calcd.: 444.2. MS Found: 445.0 [M+H]$^+$.

Step C: Methyl (S)-3-(oxetan-2-ylmethyl)-2-(piperidin-4-ylmethyl)-3H-imidazo[4,5-b]pyridine-5-carboxylate A solution of methyl (S)-2-((1-(tert-butoxycarbonyl) piperidin-4-yl)methyl)-3-(oxetan-2-ylmethyl)-3H-imidazo[4,5-b]pyridine-5-carboxylate (2.5 g, 5.6 mmol) and TFA (3 mL) in DCM (10 mL) was stirred at room temperature for 5 hours. The reaction mixture was concentrated in vacuo to give methyl (S)-3-(oxetan-2-ylmethyl)-2-(piperidin-4-ylmethyl)-3H-imidazo [4,5-b]pyridine-5-carboxylate (1.9 g) as a crude product, which was used in next steps without further purification. MS Calcd.: 344.2. MS Found: 345.0 [M+H]$^+$.

Step D: Ethyl 1-(4-chloro-2-fluorobenzyl)-1H-pyrazole-3-carboxylate

A mixture of ethyl 1H-pyrazole-3-carboxylate (275 mg, 1.97 mmol), 1-(bromomethyl)-4-chloro-2-fluorobenzene (400 mg, 1.79 mmol), and Cesium carbonate (874 mg, 2.68 mmol) in MeCN (5 ml) was stirred at room temperature for 16 hours. After the reaction was completed, the mixture was extracted with ethyl acetate (15 ml×3), washed with brine (15 ml×2), dried over sodium sulfate, filtered and concentrated in vacuum, the residue was purified by column chromatography to give ethyl 1-(4-chloro-2-fluorobenzyl)-1H-pyrazole-3-carboxylate (230 mg, yield: 45%) as white solid. MS Calcd.: 282.1. MS Found: 283.0 [M+H]$^+$.

Step E: 1-(4-Chloro-2-fluorobenzyl)-1H-pyrazole-3-carboxylic acid

A mixture of ethyl 1-(4-chloro-2-fluorobenzyl)-1H-pyrazole-3-carboxylate (230 mg, 0.8 mmol) and lithium hydroxide (60 mg, 2.4 mmol) in MeOH (3 ml) and water (1 ml) was stirred at room temperature for 6 hours. The mixture was poured into cold water and extracted with EtOAc (3×15 ml), the combined organic layer was washed with water (30 ml), dried over sodium sulfate, filtered and concentrated under reduced pressure to furnish 1-(4-chloro-2-fluorobenzyl)-1H-pyrazole-3-carboxylic acid (149 mg, yield: 72%) as white solid. MS Calcd.: 254.0. MS Found: 255.1 [M+H]$^+$.

Step F: Methyl (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylate A mixture of 1-(4-chloro-2-fluorobenzyl)-1H-pyrazole-3-carboxylic acid (149 mg, 0.6 mmol), methyl (S)-3-(oxetan-2-ylmethyl)-2-(piperidin-4-ylmethyl)-3H-imidazo[4,5-b] pyridine-5-carboxylate (300 mg), HOBt (132 mg, 0.9 mmol), EDCI (250 mg, 1.3 mmol) and DIEA (253 mg, 1.9 mmol) in DCM (5 ml) was stirred at room temperature for 16 hours. The mixture was poured into cold water and extracted with DCM (3×15 ml), dried over sodium sulfate, filtered and concentrated under reduced pressure, the residue was purified by silica gel column chromatography to furnish methyl (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylate (78 mg, yield: 21%) as yellow oil. MS Calcd.: 580.2. MS Found: 581.2 [M+H]$^+$.

Step G: (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylic acid (Compound 101a)

A mixture of methyl (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylate (78 mg, 0.13 mmol) and lithium hydroxide (15 mg, 0.6 mmol) in THF (3 ml) and water (0.5 ml) was stirred at room temperature for 6 hours. The reaction mixture was purified by prep-HPLC directly to give (S)-2-((1-(1-(4-chloro-2-fluorobenzyl)-1H-pyrazole-3-carbonyl)piperidin-4-yl)methyl)-3-(oxetan-2-ylmethyl)-3H-imidazo[4,5-b]pyridine-5-carboxylic acid (16.8 mg, yield: 22%) as white solid.

MS Calcd.: 566.1. MS Found: 567.2 [M+H]$^+$.

$^1$H NMR (400 MHz, MeOD) δ 8.14 (d, J=8.4 Hz, 1H), 8.07 (d, J=8.4 Hz, 1H), 7.76 (d, J=2.4 Hz, 1H), 7.33-7.15 (m, 3H), 6.62 (d, J=2.3 Hz, 1H), 5.43 (s, 2H), 5.34-5.22 (m, 1H), 4.83-4.52 (m, 5H), 4.48-4.33 (m, 1H), 3.22-3.02 (m, 3H), 2.93-2.73 (m, 2H), 2.60-2.40 (m, 2H), 1.93 (d, J=12.2 Hz, 1H), 1.79 (d, J=12.2 Hz, 1H), 1.49-1.33 (m, 2H).

Example 2: Synthesis of (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylic acid (Compound 102a)

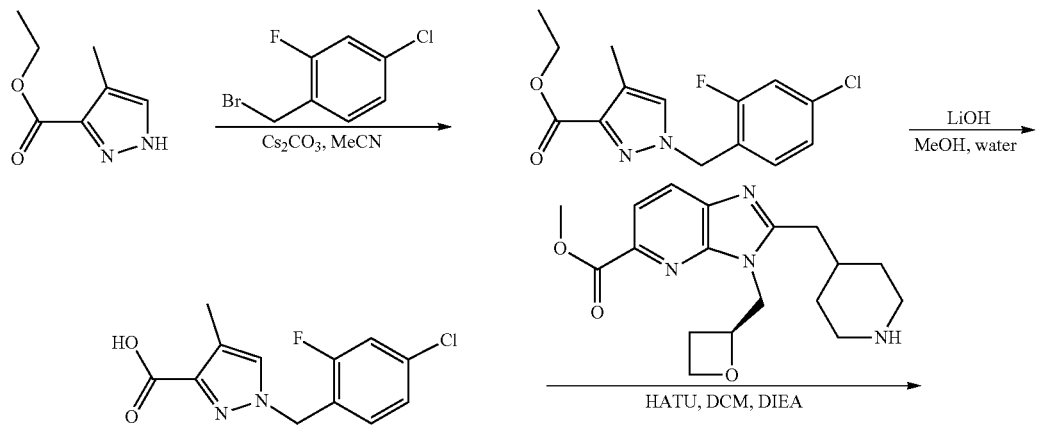

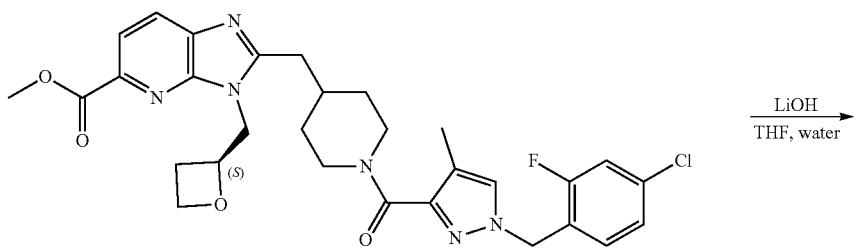

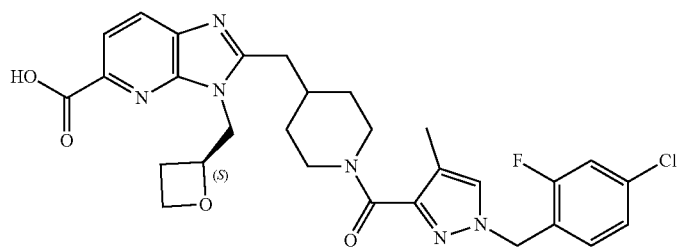

Compound 102a

Step A: Ethyl 1-(4-chloro-2-fluorobenzyl)-4-methyl-1H-pyrazole-3-carboxylate A mixture of ethyl 4-methyl-1H-pyrazole-3-carboxylate (303 mg, 1.9 mmol), 1-(bromomethyl)-4-chloro-2-fluorobenzene (400 mg, 1.7 mmol), and Cesium carbonate (874 mg, 2.6 mmol) in MeCN (5 ml) was stirred at room temperature for 16 hours. After the reaction was completed, the mixture was extracted with ethyl acetate (15 ml×3), washed with brine (15 ml×2), dried over sodium sulfate, filtered and concentrated in vacuum, the residue was purified by column chromatography to give ethyl 1-(4-chloro-2-fluorobenzyl)-4-methyl-1H-pyrazole-3-carboxylate (300 mg) as white solid. MS Calcd.: 296.1. MS Found: 297.0 [M+H]$^+$.

Step B: 1-(4-Chloro-2-fluorobenzyl)-4-methyl-1H-pyrazole-3-carboxylic acid

A mixture of ethyl 1-(4-chloro-2-fluorobenzyl)-4-methyl-1H-pyrazole-3-carboxylate (300 mg) and lithium hydroxide (72 mg, 3.03 mmol) in MeOH (3 ml) and water (1 ml) was stirred at room temperature for 6 hours. The mixture was poured into cold water and extracted with EtOAc (3×15 ml), the combined organic layer was washed with water (30 ml), dried over sodium sulfate, filtered and concentrated under reduced pressure to furnish 1-(4-chloro-2-fluorobenzyl)-4-methyl-1H-pyrazole-3-carboxylic acid (218 mg, yield: 80%) as white solid. MS Calcd.: 268.0. MS Found: 269.0 [M+H]$^+$.

Step C: Methyl (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylate A mixture of 1-(4-chloro-2-fluorobenzyl)-4-methyl-1H-pyrazole-3-carboxylic acid (205 mg, 0.7 mmol), methyl (S)-3-(oxetan-2-ylmethyl)-2-(piperidin-4-ylmethyl)-3H-imidazo[4,5-b]pyridine-5-carboxylate (350 mg), HOBt (154 mg, 1.1 mmol), EDCI (292 mg, 1.5 mmol) and DIEA (296 mg, 2.3 mmol) in DCM (5 ml) was stirred at room temperature for 16 hours. The mixture was poured into cold water and extracted with DCM (3×15 ml), dried over sodium sulfate, filtered and concentrated under reduced pressure, the residue was purified by silica gel column chromatography to furnish methyl (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylate (59 mg, yield: 12%) as yellow oil. MS Calcd.: 594.2. MS Found: 595.0 [M+H]$^+$.

Step D: (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylic acid (Compound 102a)

A mixture of methyl (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylate (59 mg, 0.09 mmol) and lithium hydroxide (10 mg, 0.39 mmol) in THF (3 ml) and water (0.5 ml) was stirred at room temperature for 6 hours. The reaction mixture was purified by prep-HPLC directly to give (S)-2-((1-(1-(4-chloro-2-fluorobenzyl)-4-methyl-1H-pyrazole-3-carbonyl)piperidin-4-yl)methyl)-3-(oxetan-2-ylmethyl)-3H-imidazo[4,5-b]pyridine-5-carboxylic acid (30.5 mg, yield: 51.5%) as white solid. MS Calcd.: 580.2. MS Found: 581.2 [M+H]$^+$.

$^1$H NMR (400 MHz, MeOD) δ 8.15 (d, J=8.4 Hz, 1H), 8.07 (d, J=8.4 Hz, 1H), 7.55 (s, 1H), 7.30-7.12 (m, 3H), 5.35 (s, 2H), 5.34-5.22 (m, 1H), 4.82-4.57 (m, 4H), 4.37-4.43 (d, J=6.5 Hz, 1H), 4.04 (d, J=13.6 Hz, 1H), 3.24-3.05 (m, 3H), 2.98-2.75 (m, 2H), 2.60-2.37 (m, 2H), 2.10 (s, 3H), 1.94 (d, J=11.5 Hz, 1H), 1.76 (d, J=12.9 Hz, 1H), 1.48-1.30 (m, 2H).

Example 3: Synthesis of (S)-2-((1-(5-(4-chloro-2-fluorobenzyl)thiazole-2-carbonyl)piperidin-4-yl)methyl)-3-(oxetan-2-ylmethyl)-3H-imidazo[4,5-b]pyridine-5-carboxylic acid (Compound 103a)

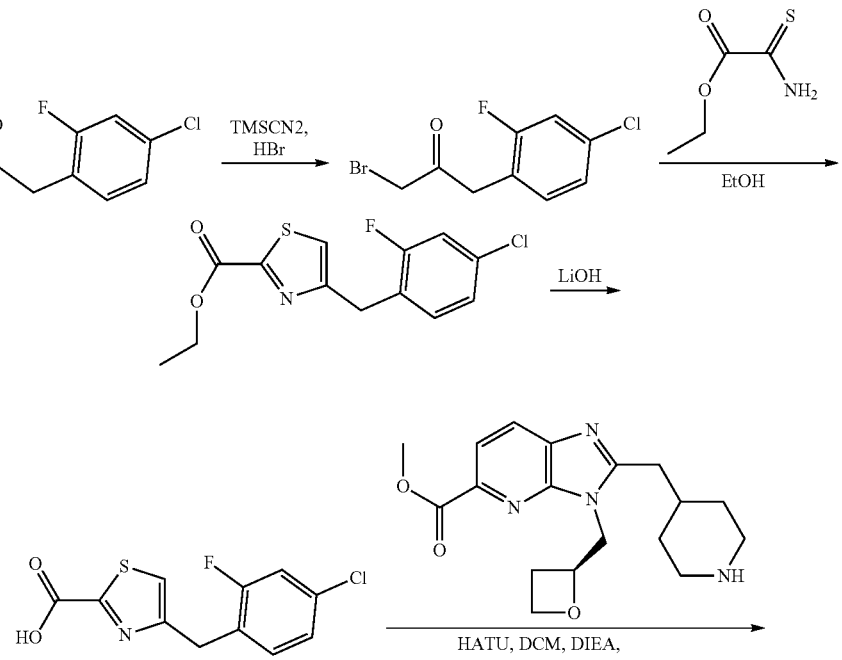

-continued

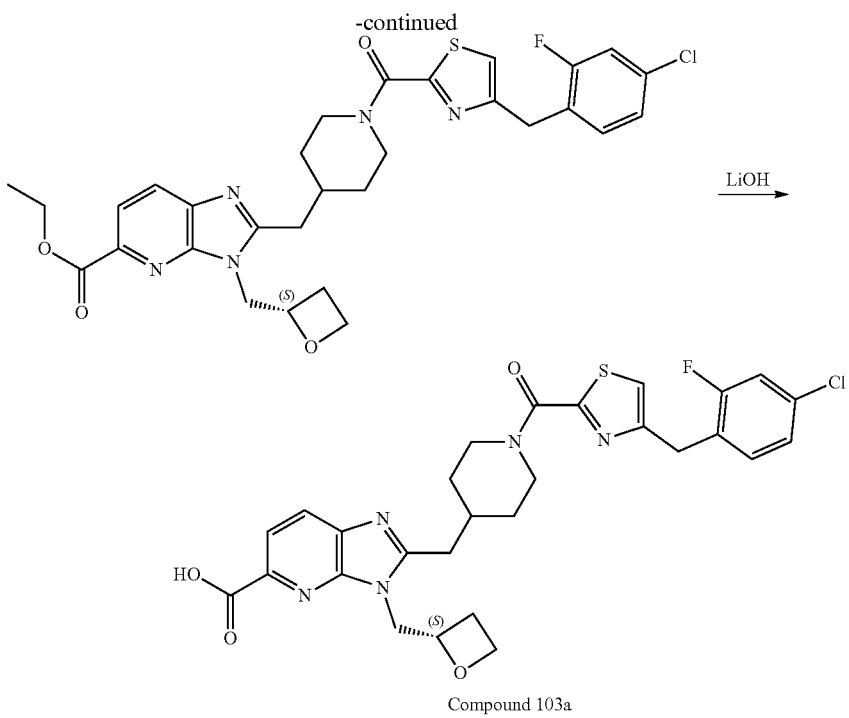

Compound 103a

Step A: 1-Bromo-3-(4-chloro-2-fluorophenyl)propan-2-one

To a solution of 2-(4-chloro-2-fluorophenyl)acetic acid (740 mg, 3.9 mmol) in dry DCM (15 mL) was added oxalyl chloride (0.6 g, 4.7 mmol) dropwise at 0° C. followed by 3 drops of dry DMF. The mixture was then stirred at rt for 3 hrs. The mixture was concentrated under reduced pressure. The residue was dissolved in THF (3 mL) and added dropwise to a solution of TMSN$_2$ (1N, 7.8 mL) in THF—CH$_3$CN (1:1, 15 mL) at 0° C. The resulting mixture was stirred at rt for 1 h and then cooled to 0° C. 30% HBr in acetic acid (1.57 g, 5.9 mmol) was added dropwise. After stirring 15 min, the mixture was concentrated in vacuo and purified by flash column chromatography eluting with PE/EtOAc (10/1-3/1) to give 1-bromo-3-(4-chloro-2-fluorophenyl)propan-2-one (0.5 g, yield: 48.5%) as yellow oil.

$^1$H NMR (400 MHz, CDCl$_3$) δ 7.17-7.06 (m, 3H), 4.17 (s, 2H), 3.92 (s, 2H).

Step B: Ethyl 4-(4-chloro-2-fluorobenzyl)thiazole-2-carboxylate

To a solution of 1-bromo-3-(4-chloro-2-fluorophenyl)propan-2-one (0.5 g, 1.89 mmol) in EtOH (10 mL) was ethyl 2-amino-2-thioxoacetate (251 mg, 1.89 mmol). The mixture was refluxed for 65 hrs. Then the mixture was concentrated under vacuum and the residue was diluted with water (15 mL) and extracted with EA (20 mL*3). The organic phase was concentrated under vacuum and the residue was purified by flash column (silica, UV254 nm, PE/EA=3/1) to afford ethyl 4-(4-chloro-2-fluorobenzyl)thiazole-2-carboxylate (0.32 g, yield: 56.7%) as yellow oil. Calcd.: 299.0. MS Found: 299.9 [M+H]$^+$.

Step C: 4-(4-Chloro-2-fluorobenzyl)thiazole-2-carboxylic acid

To a solution of ethyl 4-(4-chloro-2-fluorobenzyl)thiazole-2-carboxylate (300 mg, 1.0 mmol) in MeOH (10 mL) were added water (2 mL) and LiOH (72 mg, 3 mmol). The mixture was stirred at RT for 2 hrs. Then the mixture was acidified with diluted aqueous HCl solution (0.5 M) to pH=4-5 and extracted with DCM (20 mL*4). The combined organic layers were dried over Na$_2$SO$_4$, filtered and the filtrate was concentrated to give 4-(4-chloro-2-fluorobenzyl)thiazole-2-carboxylic acid (200 mg, yield: 74%) as yellow solid. MS Calcd.: 271.0. MS Found: 272.0 [M+H]$^+$.

Step D: Methyl (S)-2-((1-(5-(4-chloro-2-fluorobenzyl)thiazole-2-carbonyl)piperidin-4-yl)methyl)-3-(oxetan-2-ylmethyl)-3H-imidazo[4,5-b]pyridine-5-carboxylate To a solution of 4-(4-chloro-2-fluorobenzyl)thiazole-2-carboxylic acid (180 mg) in DCM (10 mL) was added HATU (380 mg, 1.0 mmol), DIPEA (419 mg, 3.3 mmol) and methyl (S)-3-(oxetan-2-ylmethyl)-2-(piperidin-4-ylmethyl)-3H-imidazo [4,5-b]pyridine-5-carboxylate (344 mg, 1.0 mmol). The mixture was stirred at RT for 12 hrs under N$_2$ protection. Then mixture was diluted with water (20 mL) and extracted with DCM (20 mL*3). The organic phase was concentrated under vacuum and purified with flash column (silica, UV254 nm, DCM/MEOH=35/1) to give methyl (S)-2-((1-(5-(4-chloro-2-fluorobenzyl)thiazole-2-carbonyl)piperidin-4-yl)methyl)-3-(oxetan-2-ylmethyl)-3H-imidazo [4,5-b]pyridine-5-carboxylate (200 mg, yield: 51%) as yellow solid. MS Calcd.: 597.2. MS Found: 597.8 [M+H]$^+$.

Step E: (S)-2-((1-(5-(4-Chloro-2-fluorobenzyl)thiazole-2-carbonyl)piperidin-4-yl)methyl)-3-(oxetan-2-ylmethyl)-3H-imidazo[4,5-b]pyridine-5-carboxylic Acid (Compound 103a)

To a solution of methyl (S)-2-((1-(5-(4-chloro-2-fluorobenzyl)thiazole-2-carbonyl)piperidin-4-yl)methyl)-3-(oxetan-2-ylmethyl)-3H-imidazo[4,5-b]pyridine-5-carboxylate (200 mg, 0.35 mmol) in THF (10 mL) and water (2 mL) was added LiOH (24 mg, 1.0 mmol). The mixture was stirred at RT for 4 hrs. Then mixture was filtered and the filtrate was purified by prep-HPLC (high-pH method) to give (S)-2-((1-(5-(4-chloro-2-fluorobenzyl)thiazole-2-carbonyl)piperidin-4-yl)methyl)-3-(oxetan-2-ylmethyl)-3H-imidazo[4,5-b]pyridine-5-carboxylic acid (30 mg, yield: 20%) as white solid. MS Calcd.: 583.1. MS Found: 584.1 [M+H]$^+$.

$^1$H NMR (400 MHz, MeOD) δ 8.13 (d, J=8.3 Hz, 1H), 8.07 (d, J=8.3 Hz, 1H), 7.41 (s, 1H), 7.28 (t, J=8.1 Hz, 1H), 7.19-7.06 (m, 2H), 5.32-5.11 (m, 2H), 4.82-4.52 (m, 4H), 4.47-4.32 (m, 1H), 4.14 (s, 2H), 3.25-3.07 (m, 3H), 2.92 (t, J=12.2 Hz, 1H), 2.83-2.70 (m, 1H), 2.58-2.40 (m, 2H), 2.00-1.75 (m, 2H), 1.50-1.32 (m, 2H).

Example 4: Synthesis of (S)-2-((1-(5-(4-Chloro-2-fluorobenzyl)thiazole-2-carbonyl)piperidin-4-yl)methyl)-3-(oxetan-2-ylmethyl)-3H-imidazo[4,5-b]pyridine-5-carboxylic acid (Compound 104a)

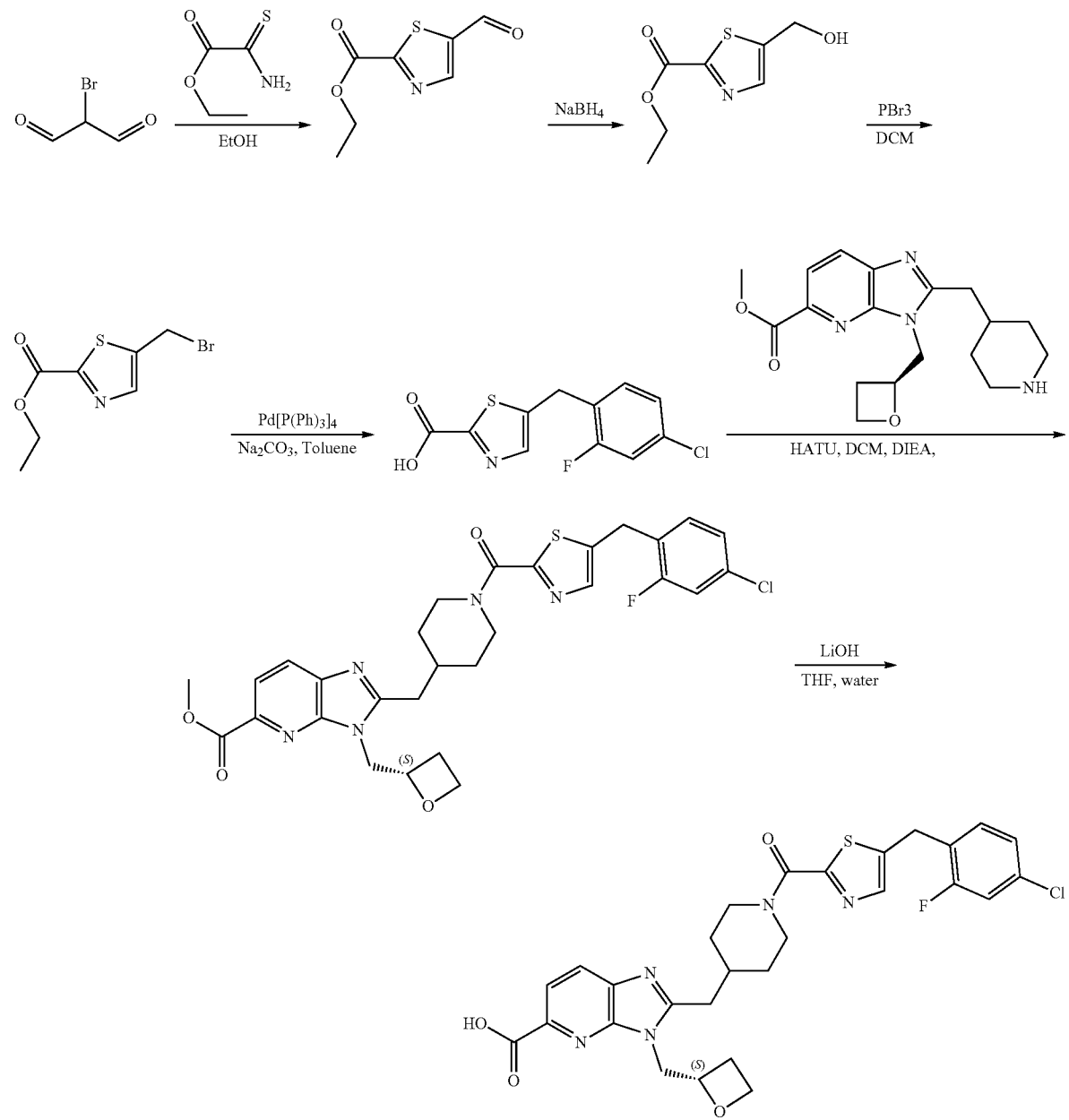

Compound 104a

Step A: Ethyl 5-formylthiazole-2-carboxylate

To a solution of 2-bromomalonaldehyde (10.0 g, 66 mmol) in EtOH (100 mL) was ethyl 2-amino-2-thioxoacetate (9.0 g, 68 mmol) and. The mixture was refluxed for 3.5 h, then stirred at RT for 65 hrs. Then the mixture was concentrated under vacuum and the residue was diluted with water (50 mL) and extracted with EA (100 mL*3). The organic phase was concentrated under vacuum and the residue was purified by flash column (silica, UV254 nm, PE/EA=3/1) to afford ethyl 5-formylthiazole-2-carboxylate (2.2 g, yield: 18%) as yellow oil. Calcd.: 185.0; MS Found: 186.0 [M+H]+.

Step B: Ethyl 5-(hydroxymethyl)thiazole-2-carboxylate

To a solution of ethyl 5-formylthiazole-2-carboxylate (2.1 g, 11.4 mmol) in methanol (75 mL) was added NaBH4 (866 mg, 22.8 mmol) at 0° C. The mixture was stirred at 0° C. for 2 hrs. Then the mixture was concentrated under vacuum and the residue was diluted with water (30 mL) and extracted with EA (50 mL*3). The organic phase was concentrated under vacuum and the residue was purified by flash column (silica, UV254 nm, PE/EA=1/1) to afford ethyl 5-(hydroxymethyl)thiazole-2-carboxylate (1.2 g, yield: 59%) as white solid. MS Calcd.: 187.0. MS Found: 188.0 [M+H]+.

Step C: Ethyl 5-(bromomethyl)thiazole-2-carboxylate

To a mixture of ethyl 5-(hydroxymethyl)thiazole-2-carboxylate (1.1 g, 5.9 mmol) in dry DCM (80 mL) was added dropwise PBr3 (3.25 g, 12 mmol). The mixture was stirred at RT for 2 hrs, under N2 protection. Then the mixture was washed with aq·NaHCO3 and the organic was concentrated under vacuum and the residue was purified by prep-TLC (silica, UV254 nm, PE/EA=1/1) to afford ethyl 5-(bromomethyl)thiazole-2-carboxylate (700 mg, yield: 48%) as yellow oil. MS Calcd.: 249.0. MS Found: 249.8 [M+H]+.

Step D: 5-(4-Chloro-2-fluorobenzyl)thiazole-2-carboxylic acid

To a solution of ethyl 5-(bromomethyl)thiazole-2-carboxylate (600 mg, 2.4 mmol) in toluene (4 mL), was added (4-chloro-2-fluorophenyl)boronic acid (503 mg, 2.89 mmol), Na2CO3 (509 mg, 4.8 mmol) and Pd[P(Ph)3]4 (136 mg, 0.12 mmol). The mixture was stirred at 80° C. for 12 hrs, under N2 protection. Then mixture was diluted with water (20 mL) and EA (20 mL). The aqueous phase was acidified with diluted aqueous HCl solution (0.5 M) to pH=4-5 and extracted with DCM (20 mL*4). Then the organic phase was dried over Na2SO4 and concentrated to give 5-(4-chloro-2-fluorobenzyl)thiazole-2-carboxylic acid (200 mg, yield: 28%) as yellow solid. MS Calcd.: 271.0. MS Found: 271.9 [M+H]+.

Step E: (S)-2-((1-(5-(4-Chloro-2-fluorobenzyl)thiazole-2-carbonyl)piperidin-4-yl)methyl)-3-(oxetan-2-ylmethyl)-3H-imidazo[4,5-b]pyridine-5-carboxylate (Compound 104a)

To a solution of 5-(4-chloro-2-fluorobenzyl)thiazole-2-carboxylic acid (200 mg) in DCM (10 mL) was added HATU (422 mg, 1.1 mmol), DIPEA (474 mg, 3.7 mmol) and methyl (S)-3-(oxetan-2-ylmethyl)-2-(piperidin-4-ylmethyl)-3H-imidazo [4,5-b]pyridine-5-carboxylate (382 mg, 1.11 mmol). The mixture was stirred at RT for 12 h, under N2 protection. Then mixture was diluted with water (20 mL) and extracted with DCM (20 mL*3). The organic phase was concentrated under vacuum and purified with flash column (silica, UV254 nm, DCM/MEOH=40/1) to give methyl (S)-2-((1-(5-(4-chloro-2-fluorobenzyl)thiazole-2-carbonyl) piperidin-4-yl)methyl)-3-(oxetan-2-ylmethyl)-3H-imidazo [4,5-b]pyridine-5-carboxylate (160 mg, yield: 36%) as yellow oil. MS Calcd.: 597.2. MS Found: 597.8 [M+H]+.

Step F: (S)-2-((1-(5-(4-chloro-2-fluorobenzyl)thiazole-2-carbonyl)piperidin-4-yl)methyl)-3-(oxetan-2-ylmethyl)-3H-imidazo[4,5-b]pyridine-5-carboxylic acid To a solution of 1376-7 (130 mg, 0.22 mmol) in THF (5 mL) and water (1 mL) was added LiOH (27 mg). The mixture was stirred at RT for 4 h. Then mixture was filtered and the filtrate was purified by prep-HPLC (high-pH) to give (S)-2-((1-(5-(4-chloro-2-fluorobenzyl)thiazole-2-carbonyl) piperidin-4-yl)methyl)-3-(oxetan-2-ylmethyl)-3H-imidazo [4,5-b]pyridine-5-carboxylic acid (25 mg, yield: 20%) as white solid. MS Calcd.: 583.1. MS Found: 584.1 [M+H]+.
1H NMR (400 MHz, MeOD) δ 8.09 (d, J=8.3 Hz, 1H), 8.02 (d, J=8.2 Hz, 1H), 7.69 (s, 1H), 7.36 (t, J=8.1 Hz, 1H), 7.23 (t, J=10.8 Hz, 2H), 5.38-5.20 (m, 2H), 4.80-4.52 (m, 4H), 4.46-4.37 (m, 1H), 4.27 (s, 2H), 3.25 (t, J=12.6 Hz, 1H), 3.20-3.03 (m, 2H), 2.94 (t, J=11.8 Hz, 1H), 2.85-2.72 (m, 1H), 2.58-2.41 (m, 2H), 2.03-1.83 (m, 2H), 1.52-1.35 (m, 2H).

Example 5: Synthesis of (S)-2-((1-((4-(4-Chloro-2-fluorobenzyl)thiazol-2-yl)methyl)piperidin-4-yl)methyl)-3-(oxetan-2-ylmethyl)-3H-imidazo[4,5-b]pyridine-5-carboxylic acid (Compound 105a)

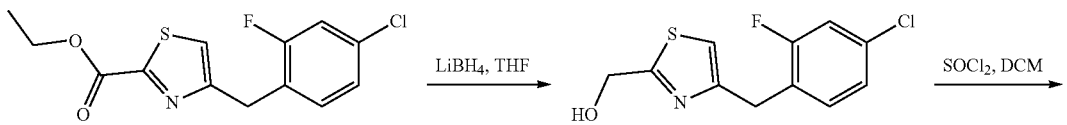

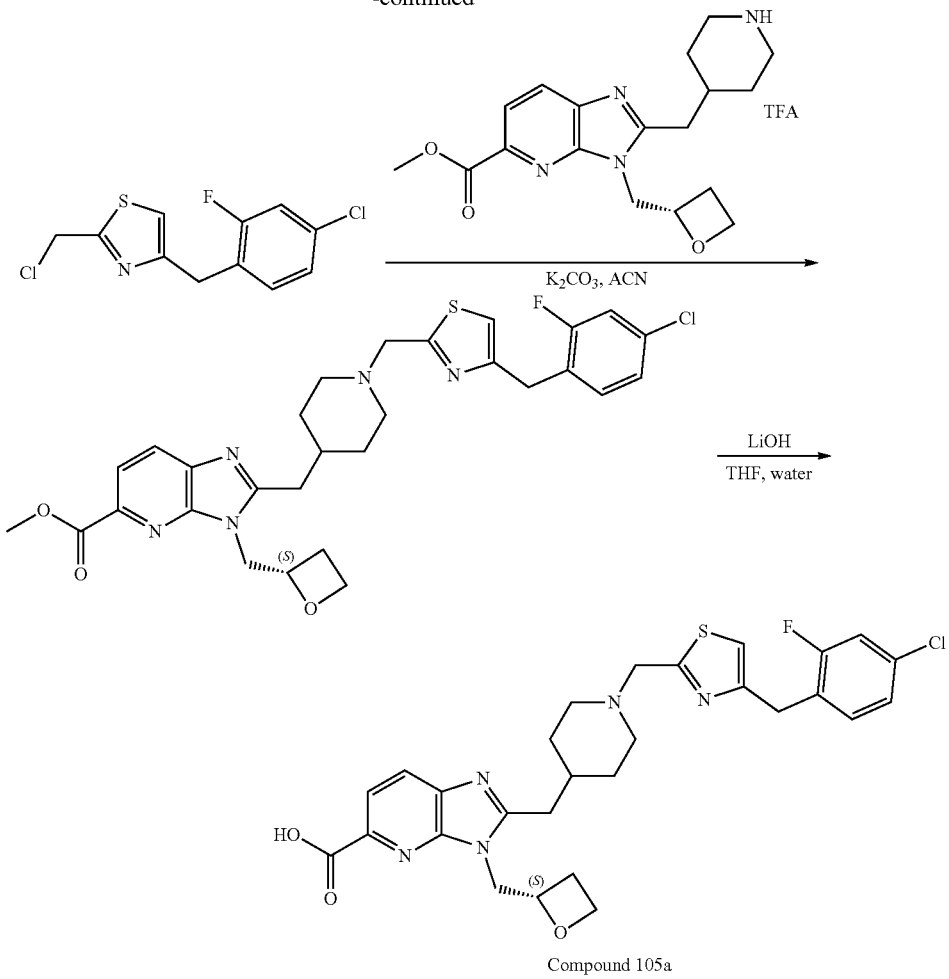

Compound 105a

Step A: (4-(4-chloro-2-fluorobenzyl)thiazol-2-yl)methanol

To a solution of 4-(4-Chloro-2-fluorobenzyl)thiazole-2-carboxylic acid (230 mg) in THF (10 mL) was added LiBH4 (2M in THF, 0.8 mL). The mixture was stirred under refluxing for 12 hours under N2. Then the reaction was quenched with $H_2O$ (10 mL) and then extracted with ethyl acetate (20 mL*3). The organic phase was combined; and then the residue was purified with flash column (silica, UV254 nm, PE/EA=5/1) to afford (4-(4-chloro-2-fluorobenzyl)thiazol-2-yl)methanol (100 mg, 60% yield). LCMS: m/z 258.0 (M+H)$^+$.

Step B: 4-(4-chloro-2-fluorobenzyl)-2-(chloromethyl)thiazole

To a solution of (4-(4-chloro-2-fluorobenzyl)thiazol-2-yl)methanol (53.0 mg, 0.206 mmol) in DCM (2 mL) was added thionyl chloride (49.0 mg, 0.412 mmol) at 0° C. The resulting mixture was stirred at room temperature for 3 hours. The solvent and thionyl chloride was removed in vacuo to afford 4-(4-chloro-2-fluorobenzyl)-2-(chloromethyl)thiazole as an oil (54.0 mg, 95% yield), which was used in next step directly. LCMS: m/z 276.1 (M+H)$^+$.

Step C: methyl (S)-2-((1-((4-(4-chloro-2-fluorobenzyl)thiazol-2-yl)methyl)piperidin-4-yl)methyl)-3-(oxetan-2-ylmethyl)-3H-imidazo[4,5-b]pyridine-5-carboxylate To a solution of 4-(4-chloro-2-fluorobenzyl)-2-(chloromethyl)thiazole (53.0 mg) in ACN (2 mL) was added methyl (S)-3-(oxetan-2-ylmethyl)-2-(piperidin-4-ylmethyl)-3H-imidazo[4,5-b]pyridine-5-carboxylate (77.0 mg, TFA salt) and $K_2CO_3$ (83.0 mg, 0.600 mmol). The resulting mixture was stirred at 60° C. overnight. The reaction mixture was quenched with water (5 mL) and extracted with EtOAc (3×5 mL). The combined organic phase was washed with brine (30 mL), dried over anhydrous $Na_2SO_4$ and concentrated. The residue was purified by Perp-TLC (DCM/MeOH=15/1) to afford methyl (S)-2-((1-((4-(4-chloro-2-fluorobenzyl)thiazol-2-yl)methyl)piperidin-4-yl)methyl)-3-(oxetan-2-ylmethyl)-3H-imidazo[4,5-b]pyridine-5-carboxylate (92.0 mg, 82% yield). LCMS: m/z 584.1 (M+H)$^+$.

Step D: (S)-2-((1-((4-(4-chloro-2-fluorobenzyl)thiazol-2-yl)methyl)piperidin-4-yl)methyl)-3-(oxetan-2-ylmethyl)-3H-imidazo[4,5-b]pyridine-5-carboxylic Acid (Compound 105a)

To a solution of methyl (S)-2-((1-((4-(4-chloro-2-fluorobenzyl)thiazol-2-yl)methyl)piperidin-4-yl)methyl)-3-

(oxetan-2-ylmethyl)-3H-imidazo[4,5-b]pyridine-5-carboxylate (92.0 mg) in THF/H$_2$O (2 mL/0.5 mL) was added LiOH (15.0 mg). The resulting mixture was stirred at room temperature overnight. Then the reaction mixture was adjusted to pH=5 with HCOOH and concentrated. The residue was purified by prep-HPLC to afford (S)-2-((1-((4-(4-chloro-2-fluorobenzyl)thiazol-2-yl)methyl)piperidin-4-yl)methyl)-3-(oxetan-2-ylmethyl)-3H-imidazo[4,5-b]pyridine-5-carboxylic acid as a white solid (39.9 mg, 44% yield). $^1$H NMR (400 MHz, DMSO-d$_6$) δ 13.06 (br.s, 1H), 8.09 (d, J=8.0 Hz, 1H), 7.96 (d, J=8.4 Hz, 1H), 7.39 (dd, J=9.6, 2.0 Hz, 1H), 7.32 (t, J=8.0 Hz, 1H), 7.24 (dd, J=8.4, 2.0 Hz, 1H), 7.18 (s, 1H), 5.03-5.14 (m, 1H), 4.64 (dd, J=15.2, 6.8 Hz, 1H), 4.43-4.54 (m, 2H), 4.29-4.34 (m, 1H), 4.02 (s, 2H), 3.72 (s, 2H), 2.93-3.05 (m, 2H), 2.87 (d, J=11.2 Hz, 2H), 2.62-2.74 (m, 1H), 2.39-2.47 (m, 1H), 1.99-2.14 (m, 3H), 1.74 (d, J=11.6 Hz, 2H), 1.31-1.40 (m, 2H). LCMS: m/z 570.2 (M+H)$^+$.

Example 6: Synthesis of (S)-2-((1-(6-(4-Chloro-2-fluorobenzyl)picolinoyl)piperidin-4-yl)methyl)-3-(oxetan-2-ylmethyl)-3H-imidazo[4,5-b]pyridine-5-carboxylic Acid (Compound 106a)

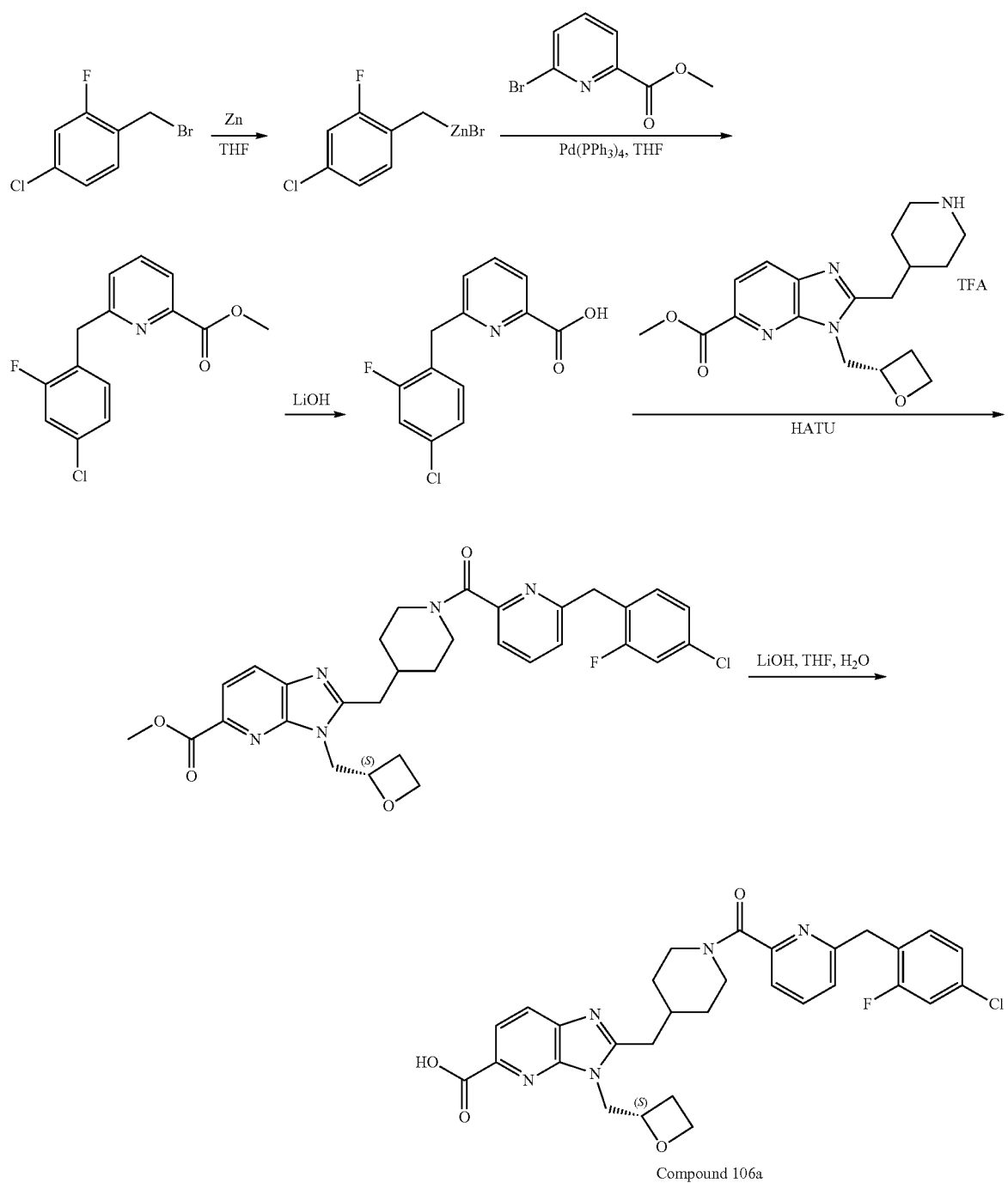

Compound 106a

Step A: Methyl 6-(4-chloro-2-fluorobenzyl)picolinate

To a solution of 1-(bromomethyl)-4-chloro-2-fluorobenzene (1.5 g, 6.7 mmol) in THF (20 mL) was added Zn powder (529.6 mg, 8.1 mmol) at RT. The mixture was stirred under refluxing for 1 hour under $N_2$ atmosphere. The resulting mixture was filtered and the filtrate was treated with methyl 6-bromopicolinate (1.4 g, 6.7 mmol) and Pd(PPh$_3$)$_4$ (387.1 mg, 0.34 mmol) under $N_2$ atmosphere. The reaction mixture was stirred under refluxing for 2 hours under $N_2$ atmosphere. The mixture was filtered through a pad of silica gel, eluted with ethyl acetate (100 mL) and the organic filtrate was concentrated to give crude product, which was purified by silica gel column chromatography to afford the title compound (1.5 g, 80% yield). MS Calcd.: 279.0. MS Found: 279.9 [M+1]$^+$.

Step B: 6-(4-Chloro-2-fluorobenzyl)picolinic acid

To a solution of methyl 6-(4-chloro-2-fluorobenzyl)picolinate (500 mg, 1.78 mmol) in THF (8 mL) and $H_2O$ (4 mL) was added LiOH·$H_2O$ (256.6 mg). The mixture was stirred at 20° C. for 3 hours. The mixture was acidified with diluted aqueous HCl solution (1 M) to pH=2-3. The precipitate was collected by filtration and dried to give crude product (400 mg, Crude), which was used for next step reaction without further purification. MS Calcd.: 265.0. MS Found: 265.9[M+1]$^+$.

Step C: (S)-2-((1-(6-(4-Chloro-2-fluorobenzyl)picolinoyl)piperidin-4-yl)methyl)-3-(oxetan-2-ylmethyl)-3H-imidazo[4,5-b]pyridine-5-carboxylate To a solution of 6-(4-chloro-2-fluorobenzyl)picolinic acid (150 mg) and methyl (S)-3-(oxetan-2-ylmethyl)-2-(piperidin-4-ylmethyl)-3H-imidazo[4,5-b]pyridine-5-carboxylate (291.7 mg, 0.84 mmol) in DMF (5 mL) was added HATU (425.86 mg, 1.12 mmol) and DIPEA (144.76 mg, 1.12 mmol) at RT. The mixture was stirred at RT for 3 hours. The mixture was diluted with water (10 mL) and extracted with ethyl acetate (20 mL*3). Combined organic layers were washed with brine (30 mL*2), dried over $Na_2SO_4$ and filtered. The filtrate was concentrated to give crude product, which was purified on silica gel to give (S)-2-((1-(6-(4-Chloro-2-fluorobenzyl)picolinoyl)piperidin-4-yl)methyl)-3-(oxetan-2-ylmethyl)-3H-imidazo[4,5-b]pyridine-5-carboxylate (126 mg, 42% yield) as off-yellow solid.

1H NMR (400 MHz, CDCl$_3$) δ 8.10 (d, J=8.1 Hz, 1H), 8.04 (dd, J=8.2 Hz, 1H), 7.69 (t, J=7.7 Hz, 1H), 7.46 (d, J=7.7 Hz, 1H), 7.15-7.21 (m, 2H), 7.09-7.01 (m, 2H), 5.18-5.22 (m, 1H), 4.73 (d, J=13.0 Hz, 1H), 4.61 (d, J=3.8 Hz, 3H), 4.41-4.28 (m, 1H), 4.13 (s, 2H), 4.00 (s, 3H), 3.84 (d, J=14.3 Hz, 1H), 3.49-3.38 (m, 1H), 3.12-2.93 (m, 3H), 2.88-2.70 (m, 3H), 2.47 (d, J=7.2 Hz, 2H), 1.95-2.01 (m, 1H), 1.26-1.31 (m, 1H).

Step D: (S)-2-((1-(6-(4-chloro-2-fluorobenzyl)picolinoyl)piperidin-4-yl)methyl)-3-(oxetan-2-ylmethyl)-3H-imidazo[4,5-b]pyridine-5-carboxylic Acid (Compound 106a)

To a solution of methyl (S)-2-((1-(6-(4-Chloro-2-fluorobenzyl)picolinoyl)piperidin-4-yl)methyl)-3-(oxetan-2-ylmethyl)-3H-imidazo[4,5-b]pyridine-5-carboxylate (46.0 mg, 0.0780 mmol) in THF/$H_2O$ (2 mL/0.5 mL) was added LiOH (7.50 mg, 0.311 mmol). The resulting mixture was stirred at room temperature overnight. Then the reaction mixture was adjusted to pH=5 with HCOOH and concentrated. The residue was purified by prep-HPLC to afford (S)-2-((1-(6-(4-chloro-2-fluorobenzyl)picolinoyl)piperidin-4-yl)methyl)-3-(oxetan-2-ylmethyl)-3H-imidazo[4,5-b]pyridine-5-carboxylic acid as a white solid (5.00 mg, 11% yield). $^1$H NMR (400 MHz, DMSO-d$_6$) δ 8.09 (d, J=8.4 Hz, 1H), 7.97 (d, J=8.0 Hz, 1H), 7.85 (t, J=7.6 Hz, 1H), 7.33-7.40 (m, 4H), 7.19-7.21 (m, 1H), 5.05-5.17 (m, 1H), 4.60-4.71 (m, 1H), 4.40-4.59 (m, 2H), 4.31-4.36 (m, 1H), 4.15 (s, 2H), 2.87-3.07 (m, 3H), 2.66-2.80 (m, 2H), 2.42-2.46 (m, 1H), 2.32-2.34 (m, 1H), 1.96-2.03 (m, 1H), 1.87 (d, J=12.0 Hz, 1H), 1.44-1.55 (m, 2H), 1.29-1.34 (m, 1H), 1.10-1.16 (m, 1H). LCMS: m/z 578.2 (M+H)$^+$.

Example 7: Synthesis of (S)-2-((4-(2-(4-Chloro-2-fluorobenzyl)phenoxy)piperidin-1-yl)methyl)-3-(oxetan-2-ylmethyl)-3H-imidazo[4,5-b]pyridine-5-carboxylic Acid (Compound 107a)

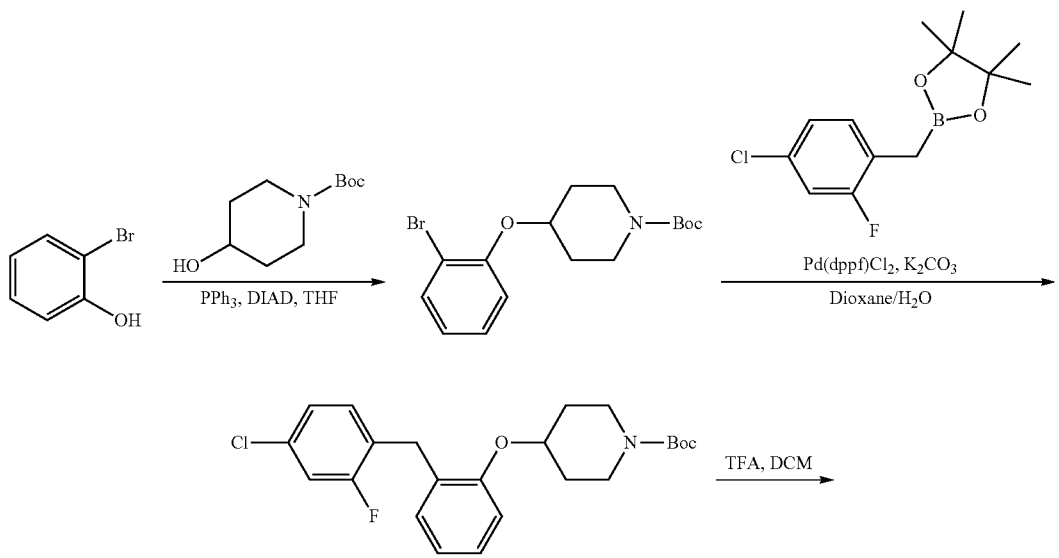

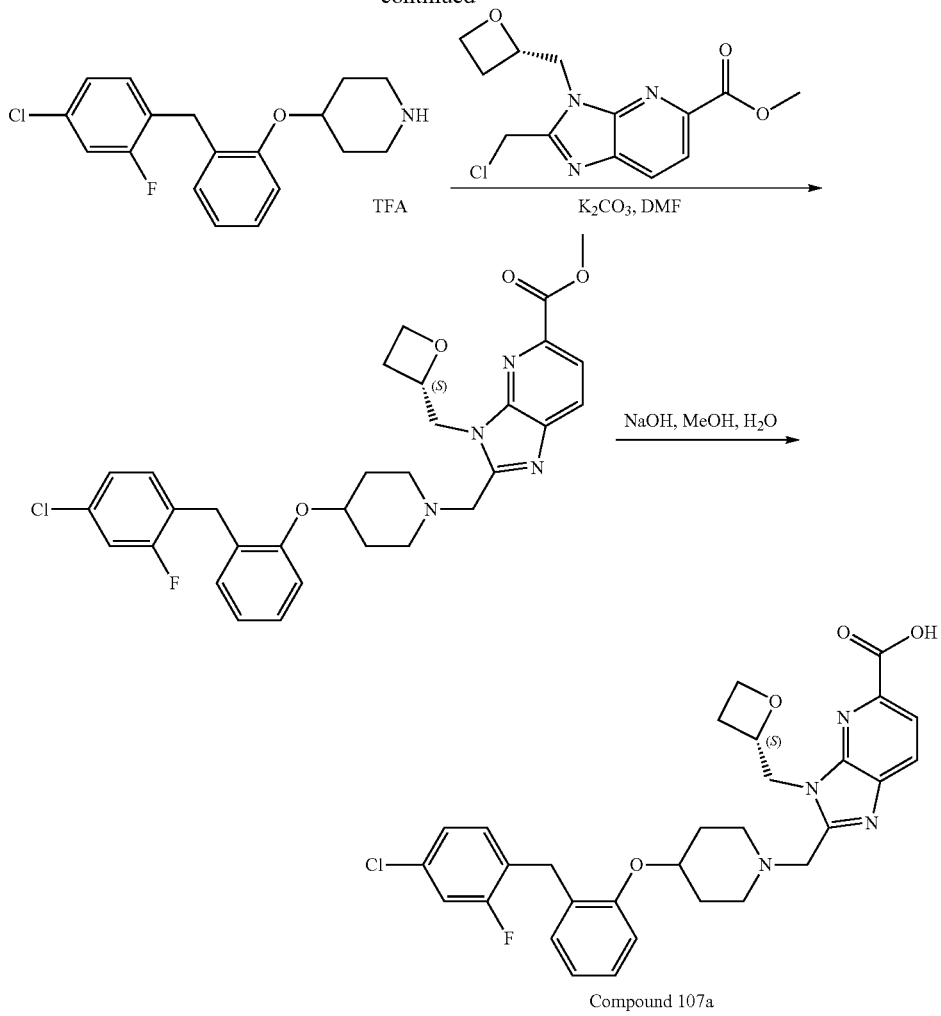

Compound 107a

Step A: tert-Butyl 4-(2-bromophenoxy)piperidine-1-carboxylate

A mixture of 2-bromophenol (1.5 g, 8.7 mmol), tert-butyl 4-hydroxypiperidine-1-carboxylate (2.1 g, 10.4 mmol), $PPh_3$ (3.4 g, 12.9 mmol) in THF (50 mL) was cooled to 0° C., DIAD (2.64 g, 13.1 mmol) was added dropwise, The mixture was stirred at room temperature for 3 hs, The mixture was poured into cold water and extracted with EtOAc (2×50 ml). The combined organic layer was dried over sodium sulfate, filtered, and concentrated under reduced pressure. The residue was purified by column chromatography to give tert-butyl 4-(2-bromophenoxy)piperidine-1-carboxylate (2.8 g, yield: 92%) as colorless oil. MS Calcd.: 355.1. MS Found: 301.9 [M-56+H]$^+$.

Step B: tert-Butyl 4-(2-(4-chloro-2-fluorobenzyl) phenoxy)piperidine-1-carboxylate A mixture of 2-(4-chloro-2-fluorobenzyl)-4,4,5,5-tetramethyl-1,3,2-dioxaborolane (600 mg, 2.22 mmol), tert-butyl 4-(2-bromophenoxy)piperidine-1-carboxylate (791 mg, 2.22 mmol), $PdCl_2(dppf)$ (163 mg, 0.22 mmol), $K_2CO_3$ (919 mg, 6.66 mmol) in dioxane/$H_2O$ (10 mL/1 mL) was stirred at 85° C. for 3 hours under Ar. The mixture was extracted with DCM (3×20 ml). The combined organic layer was dried over sodium sulfate, filtered and concentrated under reduced pressure, the residue was purified by silica gel column chromatography to give tert-butyl 4-(2-(4-chloro-2-fluorobenzyl)phenoxy)piperidine-1-carboxylate (660 mg, yield: 70%) as colorless oil. MS Calcd.: 419.2. MS Found: 461.1 [M+41+H]$^+$.

Step C: 4-(2-(4-Chloro-2-fluorobenzyl)phenoxy)piperidine

A mixture of tert-butyl 4-(2-(4-chloro-2-fluorobenzyl) phenoxy)piperidine-1-carboxylate (660 mg, 1.57 mmol) in DCM (6 mL), TFA (2 mL) was added and stirred at rt for 2 h. After the reaction was completed, The mixture was concentrated under reduced pressure to give 4-(2-(4-chloro-2-fluorobenzyl)phenoxy)piperidine TFA salt (530 mg) as colorless oil. MS Calcd.: 319.1. MS Found: 320.1 [M+H]$^+$.

Step D: Methyl (S)-2-((4-(2-(4-chloro-2-fluorobenzyl)phenoxy)piperidin-1-yl)methyl)-3-(oxetan-2-ylmethyl)-3H-imidazo[4,5-b]pyridine-5-carboxylate A mixture of 4-(2-(4-chloro-2-fluorobenzyl)phenoxy)piperidine TFA salt (244 mg), methyl (S)-2-(chloromethyl)-

3-(oxetan-2-ylmethyl)-3H-imidazo[4,5-b]pyridine-5-carboxylate (150 mg, 0.51 mmol), $K_2CO_3$ (210 mg, 1.52 mmol) in DMF (5 mL) was stirred at 50° C. for 3 h under Ar. The mixture was cooled to rt and extracted with EA (20 ml). The organic layer was washed with brine (2×20 ml), dried over sodium sulfate, filtered and concentrated under reduced pressure. The residue was purified by silica gel column chromatography to give methyl (S)-2-((4-(2-(4-chloro-2-fluorobenzyl)phenoxy)piperidin-1-yl)methyl)-3-(oxetan-2-ylmethyl)-3H-imidazo[4,5-b]pyridine-5-carboxylate (270 mg, yield: 91%) as a white solid. MS Calcd.: 578.2. MS Found: 579.2 [M+H]$^+$.

Step E: (S)-2-((4-(2-(4-Chloro-2-fluorobenzyl)phenoxy)piperidin-1-yl)methyl)-3-(oxetan-2-ylmethyl)-3H-imidazo[4,5-b]pyridine-5-carboxylic Acid (Compound 107a)

A mixture of methyl (S)-2-((4-(2-(4-chloro-2-fluorobenzyl)phenoxy)piperidin-1-yl)methyl)-3-(oxetan-2-ylmethyl)-3H-imidazo[4,5-b]pyridine-5-carboxylate (270 mg, 0.47 mmol) and NaOH (56 mg, 1.41 mmol) in MeOH (5 ml) and water (1 ml) was stirred at room temperature for 2 h. The reaction mixture was purified by prep-HPLC to give (S)-2-((4-(2-(4-Chloro-2-fluorobenzyl)phenoxy)piperidin-1-yl)methyl)-3-(oxetan-2-ylmethyl)-3H-imidazo[4,5-b]pyridine-5-carboxylic acid (147.3 mg, yield: 56%) as a white solid. MS Calcd.: 564.2. MS Found: 565.2 [M+H]$^+$.

$^1$H NMR (400 MHz, DMSO-d$_6$): δ 8.11 (d, J=8.0 Hz, 1H), 7.98 (d, J=8.4 Hz, 1H), 7.38 (d, J=10.0 Hz, 1H), 7.21-7.11 (m, 4H), 7.00 (d, J=8.4 Hz, 1H), 6.86 (t, J=7.2 Hz, 1H), 5.19-5.12 (m, 1H), 4.85-4.80 (m, 1H), 4.73-4.68 (m, 1H), 4.51-4.43 (m, 2H), 4.37-4.32 (m, 1H), 3.94-3.83 (m, 4H), 2.70-2.57 (m, 3H), 2.49-2.35 (m, 3H), 1.88-1.82 (m, 2H), 1.62-1.52 (m, 2H).

Example 8: Synthesis of 2-(((S)-4-(4-(4-Chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylic acid (Compound 108a)

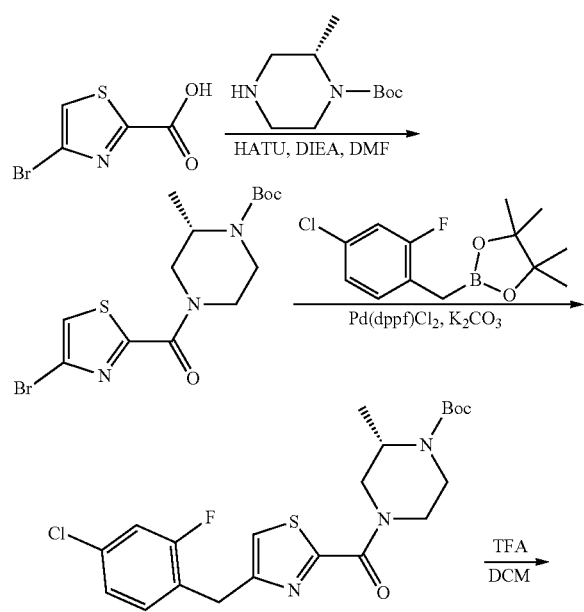

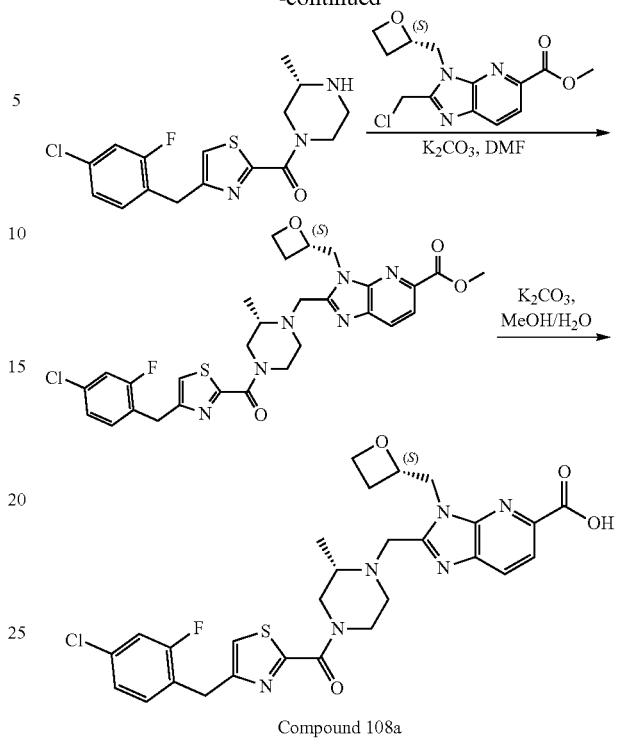

Compound 108a

Step A: tert-Butyl (S)-4-(4-bromothiazole-2-carbonyl)-2-methylpiperazine-1-carboxylate To a solution of 4-bromothiazole-2-carboxylic acid (500 mg, 2.4 mmol), tert-butyl (S)-2-methylpiperazine-1-carboxylate (480 mg, 2.4 mmol), and DIEA (620 mg, 4.8 mmol) in DMF (5 mL) was added HATU (1.096 g, 2.88 mmol) at room temperature. The mixture was stirred at room temperature for 2 hours. After the reaction was completed, the mixture was extracted with ethyl acetate (30 mL×3). The organic layer was washed with brine (30 mL×2), dried over sodium sulfate, filtered, and concentrated in vacuum. The residue was purified by column chromatography to give tert-butyl (S)-4-(4-bromothiazole-2-carbonyl)-2-methylpiperazine-1-carboxylate (900 mg, yield: 95%) as a white solid. MS Calcd.: 389.4. MS Found: 289.9 [M+H-100].

Step B: tert-Butyl(S)-4-(4-(4-chloro-2-fluorobenzyl)thiazole-2-carbonyl)-2-methylpiperazine-1-carboxylate A mixture of tert-butyl (S)-4-(4-bromothiazole-2-carbonyl)-2-methylpiperazine-1-carboxylate (500 mg, 1.28 mmol), 2-(4-chloro-2-fluorobenzyl)-4,4,5,5-tetramethyl-1,3,2-dioxaborolane (416 mg, 1.54 mmol), Pd(dppf)Cl$_2$·CH$_2$Cl$_2$ (52 mg, 0.064 mmol) and K$_2$CO$_3$ (355 mg, 2.56 mmol) in dioxane (10 mL) and water (2 mL) was purged with N$_2$ for 3 times. The mixture was stirred at 90° C. under N$_2$ for 16 hours. The reaction was quenched with 30 mL H$_2$O and extracted with EtOAc (30 mL×3). The combined organic layer was dried over sodium sulfate, filtered and concentrated. The residue was purified by column chromatography to give tert-butyl (S)-4-(4-(4-chloro-2-fluorobenzyl)thiazole-2-carbonyl)-2-methyl piperazine-1-carboxylate (230 mg, yield: 40%) as a yellow solid. MS Calcd.: 453.13. MS Found: 454.0 [M+H]$^+$.

Step C: (S)-(4-(4-Chloro-2-fluorobenzyl)thiazol-2-yl)(3-methylpiperazin-1-yl)methanone To a solution of tert-butyl (S)-4-(4-(4-chloro-2-fluorobenzyl)thiazole-2-carbonyl)-2-methylpiperazine-1-carboxylate (230 mg, 0.5 mmol) in DCM (5 mL) was added TFA (2 mL) at room temperature. The reaction was stirred at room temperature for 1 hour. The reaction was concentrated under reduced pressure to furnish (S)-(4-(4-chloro-2-fluorobenzyl)thiazol-2-yl)(3-methylpiperazin-1-yl)methanone TFA salt (300 mg, crude) as yellow oil. MS Calcd.: 353.08. MS Found: 354.1 [M+H]+.

Step D: Methyl 2-(((S)-4-(4-(4-chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylate A mixture of (S)-(4-(4-chloro-2-fluorobenzyl)thiazol-2-yl)(3-methylpiperazin-1-yl)methanone TFA salt (50 mg), methyl (S)-2-(chloromethyl)-3-(oxetan-2-ylmethyl)-3H-imidazo[4,5-b]pyridine-5-carboxylate (40 mg, 0.14 mmol) and K$_2$CO$_3$ (58 mg, 0.42 mmol) in DMF (2 mL) was stirred at 60° C. for 3 hours. The reaction was quenched with 30 mL H$_2$O and extracted with EtOAc (30 mL×3). The combined organic layer was dried over sodium sulfate, filtered and concentrated under reduced pressure to afford methyl 2-(((S)-4-(4-(4-chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylate (70 mg, crude). MS Calcd.: 612.17. MS Found: 613.0 [M+H]+.

Step E: 2-(((S)-4-(4-(4-chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylic acid (Compound 108a)

To a solution of methyl 2-(((S)-4-(4-(4-chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylate (70 mg, crude) in MeOH (3 mL) and water (1 mL) was added K$_2$CO$_3$. The reaction was stirred at room temperature for 3 hours. The reaction mixture was purified by prep-HPLC directly to give 2-(((S)-4-(4-(4-chloro-2-fluorobenzyl)thiazole-2-carbonyl)-2-methylpiperazin-1-yl)methyl)-3-(((S)-oxetan-2-yl)methyl)-3H-imidazo[4,5-b]pyridine-5-carboxylic acid (2.95 mg) as white solid. MS Calcd.: 598.16. MS Found: 599.1 [M+H]+.

$^1$H NMR (400 MHz, DMSO-d$_6$): δ 8.15 (d, J=8.2 Hz, 1H), 8.00 (d, J=8.4 Hz, 1H), 7.70-7.61 (m, 1H), 7.39-7.35 (m, 2H), 7.30-7.15 (m, 1H), 5.23-5.19 (m, 1H), 4.79-4.77 (m, 2H), 4.68-4.61 (m, 1H), 4.47-4.41 (m, 2H), 4.25-4.19 (m, 1H), 4.14-4.10 (m, 2H), 3.96-3.73 (m, 2H), 3.58-3.48 (m, 2H), 2.71-2.65 (m, 3H), 2.49-2.36 (m, 2H), 1.22-1.12 (m, 2H), 0.99 (d, J=5.2 Hz, 1H).

Example 9: Synthesis of (S)-2-((4-((6-(4-Chloro-2-fluorobenzyl)pyridin-2-yl)oxy)piperidin-1-yl)methyl)-3-(oxetan-2-ylmethyl)-3H-imidazo[4,5-b]pyridine-5-carboxylic acid (Compound 109a)

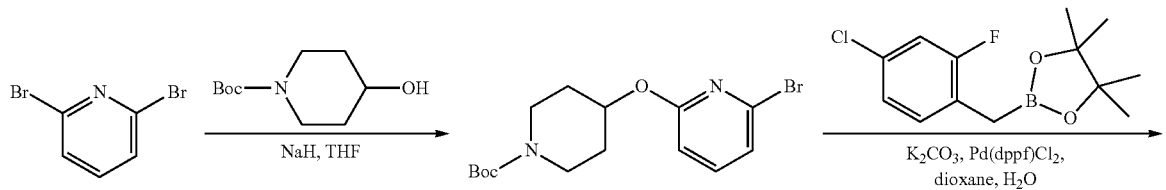

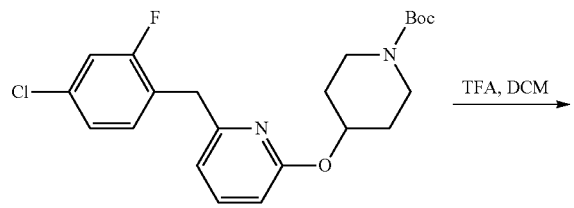

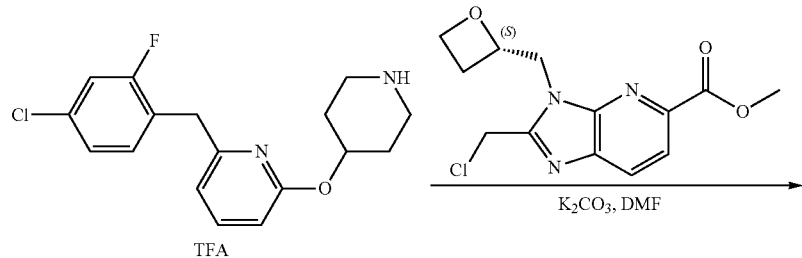

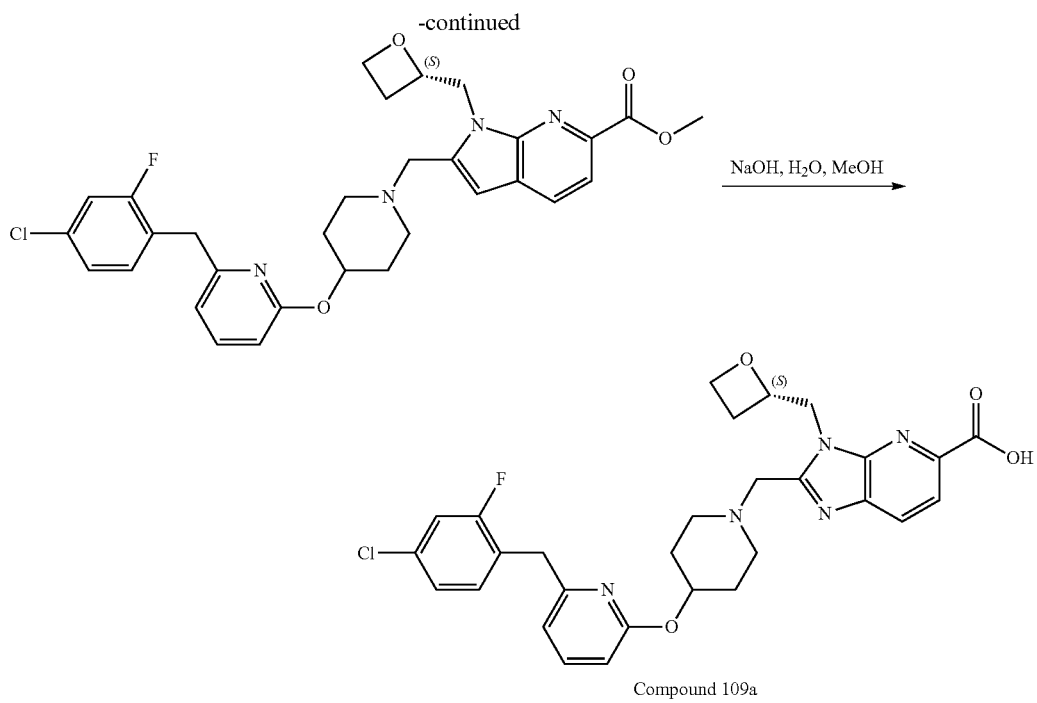

Compound 109a

Step A: tert-Butyl 4-((6-bromopyridin-2-yl)oxy)piperidine-1-carboxylate

To a solution of tert-butyl 4-hydroxypiperidine-1-carboxylate (424 mg, 2.11 mmol) in THF (5 mL) was added NaH (126.6 mg, 3.165 mmol) at room temperature. The mixture was heated to 50° C. for 0.5 h, then added with 2,6-dibromopyridine (500 mg, 2.11 mmol). The mixture was stirred at 50° C. for 2 hours. The reaction was quenched by the addition of water, extracted with EA. The organic layers were combined, dried over $Na_2SO_4$, filtered, and concentrated under vacuum. The residue was applied on a silica gel column and eluted with PE:EtOAc=15:1 to give tert-butyl 4-((6-bromopyridin-2-yl)oxy)piperidine-1-carboxylate (340 mg, 45% yield) as colorless oil. MS Calcd.: 356.07. MS Found: 358.1 [M+H]$^+$.

Step B: tert-Butyl 4-((6-(4-chloro-2-fluorobenzyl)pyridin-2-yl)oxy) piperidine-1-carboxylate A mixture of tert-butyl 4-((6-bromopyridin-2-yl)oxy)piperidine-1-carboxylate (200 mg, 0.56 mmol), 2-(4-chloro-2-fluorobenzyl)-4,4,5,5-tetramethyl-1,3,2-dioxaborolane (226 mg, 0.84 mmol), Pd(dppf)Cl$_2$ (20 mg, 0.028 mmol), $K_2CO_3$ (193 mg, 1.4 mmol) in dioxane (8 mL) and $H_2O$ (0.8 mL) was stirred at 100° C. for 12 hours under an atmosphere of nitrogen. The reaction mixture was concentrated under vacuum, The residue was purified by silica gel column and Prep-HPLC to afford tert-butyl 4-((6-(4-chloro-2-fluorobenzyl)pyridin-2-yl)oxy)piperidine-1-carboxylate (30 mg, yield: 13%) as a white solid. MS Calcd.: 420.1. MS Found: 421.2 [M+H]$^+$.

Step C: 2-(4-chloro-2-fluorobenzyl)-6-(piperidin-4-yloxy)pyridine

To a solution of tert-butyl 4-((6-(4-chloro-2-fluorobenzyl)pyridin-2-yl)oxy)piperidine-1-carboxylate (30 mg, 0.071 mmol) in DCM (1 mL) was added TFA (0.4 mL). The resulting mixture was stirred at room temperature for 2 hours. The solvent was removed under vacuum to obtain 2-(4-chloro-2-fluorobenzyl)-6-(piperidin-4-yloxy)pyridine TFA salt as a brown oil (30 mg, crude). The crude product was directly used for next step without further purification. MS Calcd.: 320.1. MS Found: 321.0 [M+H]$^+$.

Step D: Methyl 2-((4-((6-(4-chloro-2-fluorobenzyl)pyridin-2-yl)oxy)piperidin-1-yl)methyl)-1-(cyclobutylmethyl)-1H-pyrrolo[2,3-b]pyridine-6-carboxylate To a mixture of 2-(4-chloro-2-fluorobenzyl)-6-(piperidin-4-yloxy)pyridine TFA salt (30 mg) in DMF (2 mL) was added $K_2CO_3$ (51.7 mg, 0.375 mmol), then methyl (S)-2-(chloromethyl)-3-(oxetan-2-ylmethyl)-3H-imidazo[4,5-b]pyridine-5-carboxylate (27 mg, 0.0937 mmol) was added. The resulting mixture was stirred at 60° C. for 3 hours. The reaction mixture was quenched by the addition of water, extracted with EA. The organic layers were combined, dried over $Na_2SO_4$, filtered and concentrated under vacuum to afford methyl 2-((4-((6-(4-chloro-2-fluorobenzyl)pyridin-2-yl)oxy)piperidin-1-yl)methyl)-1-(cyclobutylmethyl)-1H-pyrrolo[2,3-b]pyridine-6-carboxylate as a light brown oil (20 mg, crude). The crude product was directly used for next step without further purification. MS Calcd.: 579.2. MS Found: 580.3 [M+H]$^+$.

Step E: (S)-2-((4-((6-(4-Chloro-2-fluorobenzyl pyridin-2-yl)oxy)piperidin-1-yl)methyl)-3-(oxetan-2-ylmethyl)-3H-imidazo[4,5-b]pyridine-5-carboxylic Acid (Compound 109a)

A mixture of methyl 2-((4-((6-(4-chloro-2-fluorobenzyl)pyridin-2-yl)oxy)piperidin-1-yl)methyl)-1-(cyclobutylmethyl)-1H-pyrrolo[2,3-b]pyridine-6-carboxylate (20 mg) and NaOH (5.4 mg, 0.136 mmol) in MeOH (2 ml) and water (0.5 ml) was stirred at room temperature for 1 h. The reaction mixture was purified by Prep-HPLC to obtain (S)-2-((4-((6-(4-chloro-2-fluorobenzyl)pyridin-2-yl)oxy)piperidin-1-yl)methyl)-3-(oxetan-2-ylmethyl)-3H-imidazo[4,5-b]pyridine-5-carboxylic acid (5 mg) as a white solid. MS Calcd.: 565.2. MS Found: 566.3 [M+H]$^+$.

$^1$H NMR (400 MHz, DMSO-d$_6$): δ 8.05 (d, J=8.4 Hz, 1H), 7.94 (d, J=8.0 Hz 1H), 7.61-7.55 (m, 1H), 7.38-7.34 (m, 2H), 7.25-7.22 (m, 1H), 6.81 (d, J=7.2 Hz, 1H), 6.58 (d, J=8.4 Hz, 1H), 5.20-5.13 (m, 1H), 4.84-4.79 (m, 2H), 4.71-4.66 (m, 1H), 4.49-4.45 (m, 1H), 4.38-4.34 (m. 1H), 4.00-3.87 (m, 4H), 2.78-2.65 (m, 4H), 2.31-2.25 (m, 2H), 1.87-1.85 (m, 2H), 1.59-1.54 (m, 2H).

Example 10: 2-{[4-({6-[1-(4-chloro-2-fluorophenyl) ethyl]pyridin-2-yl}oxy)piperidin-1-yl]methyl}-3-{[(2S)-oxetan-2-yl]methyl}-3H-imidazo[4,5-b]pyridine-5-carboxylic acid (Compound 128a)

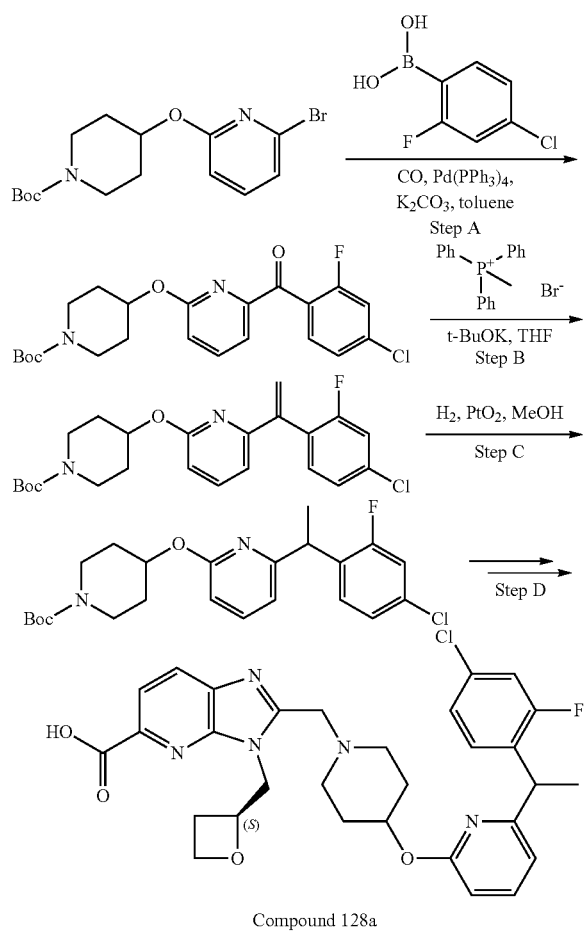

Compound 128a

Step A: The Synthesis of tert-butyl 4-((6-(4-chloro-2-fluorobenzoyl)pyridin-2-yl)oxy)piperidine-1-carboxylate To a solution of tert-butyl 4-((6-bromopyridin-2-yl)oxy) piperidine-1-carboxylate (3.0 g, 8.4 mmol) in toluene (50 mL) was added (4-chloro-2-fluorophenyl)boronic acid (3.6 g, 21.1 mmol), K$_2$CO$_3$ (3.5 g, 25.3 mmol) and Pd(PPh$_3$)$_4$ (970 mg, 20.8 mmol). The flask was evacuated and flushed three times with CO. The mixture was stirred at 95° C. for 16 hours under an atmosphere of CO (balloon). The solvent was removed in vacuo. The residue was applied on a silica gel column and eluted with ethyl acetate/n-hexane (1/10) to give tert-butyl 4-((6-(4-chloro-2-fluorobenzoyl)pyridin-2-yl)oxy)piperidine-1-carboxylate (0.9 g, yield: 25%) as a colorless oil. MS Calcd.: 434.1. MS Found: 435.1 [M+H]$^+$.

Step B: The Synthesis of tert-butyl 4-((6-(1-(4-chloro-2-fluorophenyl)vinyl)pyridin-2-yl)oxy)piperidine-1-carboxylate To a solution of methyltriphenylphosphonium bromide (395 mg, 1.1 mmol) in dry THF (10 mL) was added t-BuOK (206 mg, 1.8 mmol) at 0° C. Then a solution of tert-butyl 4-((6-(4-chloro-2-fluorobenzoyl)pyridin-2-yl)oxy)piperidine-1-carboxylate (400 mg, 0.92 mmol) in dry THF (1 mL) was added dropwise. The resulting mixture was stirred at room temperature for 4 hours. Add water quenching the reaction, extracted with ethyl acetate. The organic layer was dried over Na$_2$SO$_4$, filtered and concentrated. The residue was applied on a silica gel column and eluted with ethyl acetate/n-hexane (1/5) to give tert-butyl 4-((6-(1-(4-chloro-2-fluorophenyl)vinyl)pyridin-2-yl)oxy)piperidine-1-carboxylate (150 mg, yield: 38%) as a colorless oil. MS Calcd.: 432.2. MS Found: 433.0 [M+H]$^+$.

Step C: The Synthesis of tert-butyl 4-((6-(1-(4-chloro-2-fluorophenyl)ethyl)pyridin-2-yl)oxy)piperidine-1-carboxylate To a solution of tert-butyl 4-((6-(1-(4-chloro-2-fluorophenyl)vinyl)pyridin-2-yl)oxy)piperidine-1-carboxylate (120 mg, 0.28 mmol) in MeOH (3 mL) was added PtO$_2$ (19 mg, 0.083 mmol). The flask was evacuated and flushed three times with hydrogen. The mixture was stirred at room temperature for 60 minutes under an atmosphere of hydrogen (balloon). The reaction mixture was filtered through a celite pad. The filtrate was concentrated under vacuum to afford tert-butyl 4-((6-(1-(4-chloro-2-fluorophenyl)ethyl) pyridin-2-yl)oxy)piperidine-1-carboxylate (110 mg, yield: 92%) as a colorless oil. MS Calcd.: 434.2. MS Found: 435.0 [M+H]$^+$.

Step D: The Synthesis of 2-{[4-({6-[1-(4-chloro-2-fluorophenyl)ethyl]pyridin-2-yl}oxy)piperidin-1-yl] methyl}-3-{[(2S)-oxetan-2-yl]methyl}-3H-imidazo [4,5-b]pyridine-5-carboxylic acid 2-{[4-({6-[1-(4-chloro-2-fluorophenyl)ethyl]pyridin-2-yl}oxy)piperidin-1-yl]methyl}-3-{[(2S)-oxetan-2-yl] methyl}-3H-imidazo[4,5-b]pyridine-5-carboxylic acid (43.2 mg) was obtained as a white solid by the similar procedure of Compound 109a. MS Calcd.: 579.2. MS Found: 580.1 [M+H]+.

$^1$H NMR (400 MHz, DMSO-d6): δ 7.90-8.00 (m, 2H), 7.59 (dd, J=8.4 Hz, 7.6 Hz, 1H), 7.40-7.48 (m, 1H), 7.33 (dd, J=10.4, 2.4 Hz, 1H), 7.25-7.29 (m, 2H), 6.84 (d, J=7.2 Hz, 1H), 6.58 (d, J=8.4 Hz, 1H), 5.09-5.15 (m, 1H), 4.80-4.89 (m, 2H), 4.60-4.67 (m, 1H), 4.44-4.51 (m, 1H), 4.37-4.43 (m, 1H), 4.29-4.36 (m, 1H), 3.92-4.00 (m, 1H), 3.72-3.80 (m, 1H), 2.57-2.84 (m, 3H), 2.48-2.55 (m, 1H), 2.24-2.33

(m, 2H), 1.80-1.96 (m, 2H), 1.48-1.63 (m, 5H). $^{19}$F NMR (377 MHz, DMSO-d6): δ −115.03.

Example 11: 2-{[4-({6-[(4-chloro-2-fluorophenyl) difluoromethyl]pyridin-2-yl}oxy)piperidin-1-yl] methyl}-3-{[(2S)-oxetan-2-yl]methyl}-3H-imidazo [4,5-b]pyridine-5-carboxylic acid (Compound 129a)

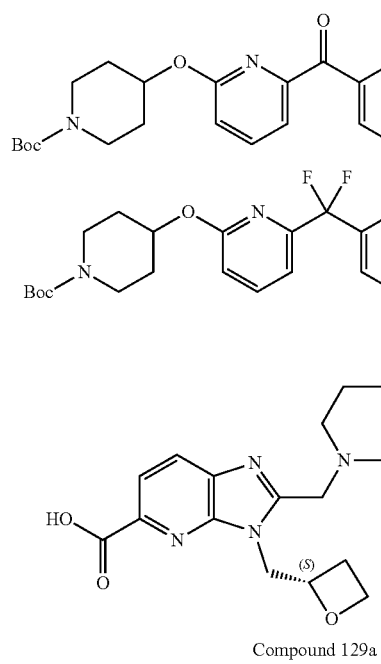

Compound 129a

A mixture of tert-butyl 4-((6-(4-chloro-2-fluorobenzoyl) pyridin-2-yl)oxy)piperidine-1-carboxylate (200 mg, 10.5 mmol) in Bis(2-methoxyethyl)aminosulfur trifluoride (BAST) (2 mL) was heated to 45° C. for 48 hours. The reaction was carefully poured into ice-water and the resulting mixture was extracted with ethyl acetate. The organic layer was dried over Na$_2$SO$_4$, filtered and concentrated. The residue was applied on a silica gel column and eluted with ethyl acetate/n-hexane (1/8) to give tert-butyl 4-((6-((4-chloro-2-fluorophenyl)difluoromethyl)pyridin-2-yl)oxy)piperidine-1-carboxylate (130 mg, yield: 62%) as a colorless oil. MS Calcd.: 456.1. MS Found: 457.0 [M+H]$^+$. 2-{[4-({6-[(4-chloro-2-fluorophenyl)difluoromethyl]pyridin-2-yl}oxy)piperidin-1-yl]methyl}-3-{[(2S)-oxetan-2-yl] methyl}-3H-imidazo[4,5-b]pyridine-5-carboxylic acid (41.6 mg, yield: 46%) was then obtained as a white solid by the similar procedure of Compound 109a. MS Calcd.: 601.2. MS Found: 602.4 [M+H]$^+$.

$^1$H NMR (400 MHz, DMSO-d$_6$): δ 8.06 (d, J=8.4 Hz, 1H), 7.94 (d, J=8.4 Hz, 1H), 7.90 (d, J=8.0 Hz, 1H), 7.70 (t, J=8.4 Hz, 1H), 7.59 (dd, J=10.8 Hz, 2.0 Hz, 1H), 7.47 (dd, J=8.4 Hz, 1.6 Hz, 1H), 7.44 (d, J=7.2 Hz, 1H), 6.94 (d, J=8.4 Hz, 1H), 5.11-5.17 (m, 1H), 4.77-4.83 (m, 1H), 4.64-4.71 (m, 1H), 4.52-4.61 (m, 1H), 4.45-4.51 (m, 1H), 4.30-4.37 (m, 1H), 3.94 (d, J=13.6 Hz, 1H), 3.87 (d, J=13.6 Hz, 1H), 2.60-2.75 (m, 3H), 2.42-2.52 (m, 1H), 2.14-2.21 (m, 2H), 1.70-1.80 (m, 2H), 1.47-1.58 (m, 2H). $^{19}$F NMR (377 MHz, DMSO-d6): δ−92.65, −110.98.

Example 12: 2-{[4-({6-[1-(4-chloro-2-fluorophenyl) cyclopropyl]pyridin-2-yl}oxy)piperidin-1-yl] methyl}-3-{[(2S)-oxetan-2-yl]methyl}-3H-imidazo [4,5-b]pyridine-5-carboxylic acid (Compound 127a)

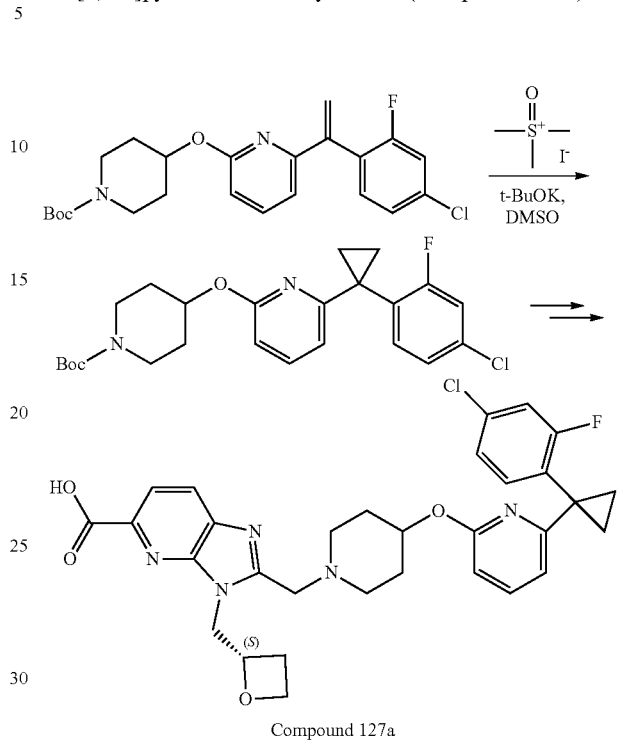

Compound 127a

To a solution of t-BuOK (11.6 mg, 0.10 mmol) in DMSO (1.5 mL) was added trimethylsulfoxonium iodide (23 mg, 0.10 mmol) under nitrogen. Then a solution of tert-butyl 4-((6-(1-(4-chloro-2-fluorophenyl)vinyl)pyridin-2-yl)oxy) piperidine-1-carboxylate (30 mg, 0.069 mmol) in DMSO (0.5 mL) was added. The resulting mixture was stirred at room temperature for 2 hours under an atmosphere of nitrogen. Add water quenching the reaction, extracted with ethyl acetate. The organic layer was dried over Na$_2$SO$_4$, filtered and concentrated. The residue was purified by Prep-TLC (ethyl acetate/n-hexane=1/10) to give tert-butyl 4-((6-(1-(4-chloro-2-fluorophenyl)cyclopropyl)pyridin-2-yl)oxy) piperidine-1-carboxylate (22 mg, yield: 71%) as a colorless oil. 2-{[4-({6-[1-(4-chloro-2-fluorophenyl)cyclopropyl] pyridin-2-yl}oxy)piperidin-1-yl]methyl}-3-{[(2S)-oxetan-2-yl]methyl}-3H-imidazo[4,5-b]pyridine-5-carboxylic acid (2.6 mg) was then obtained as a white solid by the similar procedure of Compound 109a. MS Calcd.: 591.2. MS Found: 592.0 [M+H]$^+$.

$^1$H NMR (400 MHz, DMSO-d$_6$): δ 7.98 (d, J=8.4 Hz, 1H), 7.92 (d, J=8.0 Hz, 1H), 7.42-7.50 (m, 3H), 7.31 (dd, J=8.4 Hz, 2.4 Hz, 1H) 6.51 (d, J=8.0 Hz, 1H), 6.30 (d, J=7.6 Hz, 1H), 5.11-5.18 (m, 1H), 4.79-4.86 (m, 2H), 4.62-4.71 (m, 1H), 4.47-4.53 (m, 1H), 4.30-4.38 (m, 1H), 3.96 (d, J=13.6 Hz, 1H), 3.82 (d, J=13.6 Hz, 1H), 2.60-2.82 (m, 3H), 2.44-2.51 (m, 1H), 2.25-2.34 (m, 2H), 1.88-1.97 (m, 2H), 1.55-1.69 (m, 4H), 1.23-1.28 (m, 2H). $^{19}$F NMR (377 MHz, DMSO-d6): δ −110.94.

Example 13: 2-[(4-{[6-(4-chloro-2-fluorophenoxy)pyridin-2-yl]oxy}piperidin-1-yl)methyl]-3-{[(2S)-oxetan-2-yl]methyl}-3H-imidazo[4,5-b]pyridine-5-carboxylic acid (Compound 118a)

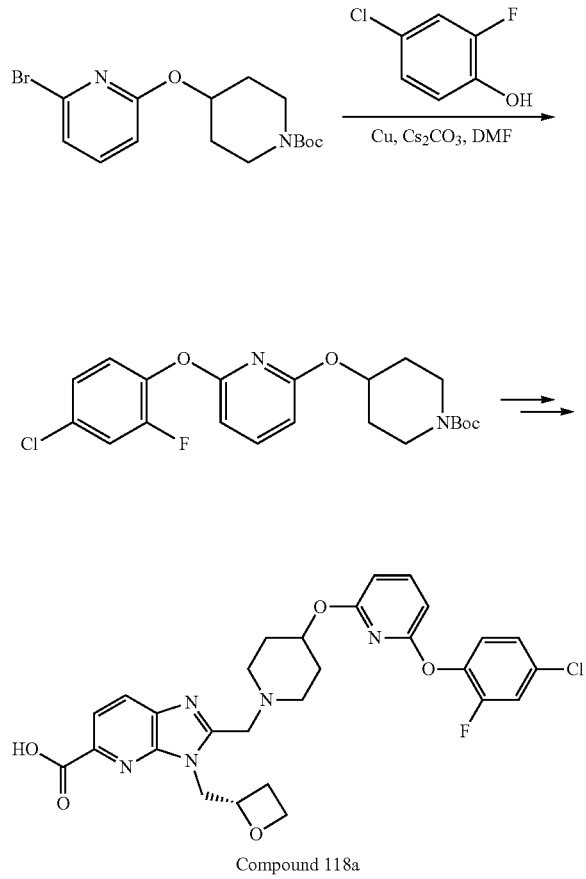

Compound 118a

A mixture of tert-butyl 4-((6-bromopyridin-2-yl)oxy)piperidine-1-carboxylate (400 mg, 1.12 mmol), 4-chloro-2-fluorophenol (197 mg, 1.34 mmol), Cu (108 mg, 1.68 mmol), Cs$_2$CO$_3$ (1.1 g, 3.36 mmol) in DMF (10 mL) was stirred at 100° C. for 16 hours under Ar. The mixture was quenched with H$_2$O (15 mL), extracted with DCM (2×20 mL). The combined organic layer was dried over Na$_2$SO$_4$, filtered, and concentrated under reduced pressure. The residue was purified by column chromatography on silica gel to give tert-butyl 4-((6-(4-chloro-2-fluorophenoxy)pyridin-2-yl)oxy)piperidine-1-carboxylate (500 mg) as a colorless oil. MS Calcd.: 422.1. MS Found: 422.9 [M+H]$^+$. 2-[(4-{[6-(4-chloro-2-fluorophenoxy)pyridin-2-yl]oxy}piperidin-1-yl)methyl]-3-{[(2S)-oxetan-2-yl]methyl}-3H-imidazo[4,5-b]pyridine-5-carboxylic acid (13.0 mg) was then obtained as a white solid by the similar procedure of Compound 109a. MS Calcd.: 567.2. MS Found: 568.3 [M+H]$^+$.

$^1$H NMR (400 MHz, DMSO-d6): δ 8.07 (d, J=8.4 Hz, 1H), 7.95 (d, J=8.4 Hz, 1H), 7.76 (t, J=8.0 Hz, 1H), 7.62 (dd, J=10.4 Hz, 2.0 Hz, 1H), 7.32-7.41 (m, 2H), 6.64 (d, J=7.6 Hz, 1H), 6.51 (d, J=8.0 Hz, 1H), 5.10-5.17 (m, 1H), 4.78-4.83 (m, 1H), 4.64-4.72 (m, 1H), 4.45-4.52 (m, 1H), 4.30-4.45 (m, 2H), 3.81-3.94 (m, 2H), 2.62-2.78 (m, 3H), 2.43-2.51 (m, 1H), 2.05-2.15 (m, 2H), 1.73-1.82 (m, 2H), 1.47-1.60 (m, 2H). 19F NMR (377 MHz, DMSO-d6): δ −125.16.

Example 14: 2-[(4-{[6-(4-chloro-2-fluorophenoxy)pyridin-2-yl]methyl}piperidin-1-yl)methyl]-3-{[(2S)-oxetan-2-yl]methyl}-3H-imidazo[4,5-b]pyridine-5-carboxylic acid (Compound 121a)

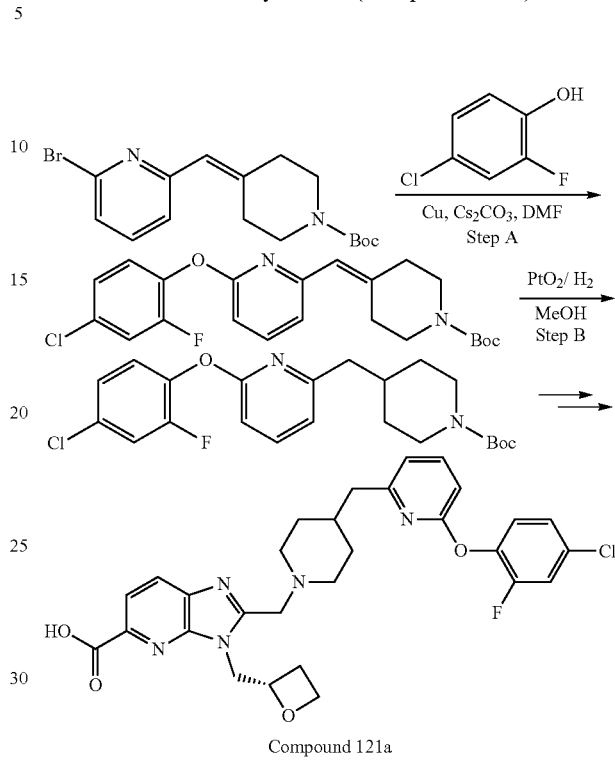

Compound 121a

Step A: The Synthesis of tert-butyl 4-((6-(4-chloro-2-fluorophenoxy)pyridin-2-yl)methylene)piperidine-1-carboxylate A mixture of tert-butyl 4-((6-bromopyridin-2-yl)methylene)piperidine-1-carboxylate (500 mg, 1.42 mmol), 4-chloro-2-fluorophenol (311 mg, 2.13 mmol), Cu (137 mg, 2.13 mmol), Cs$_2$CO$_3$ (1.4 g, 4.26 mmol) in DMF (2 mL) was stirred at 100° C. for 16 hours under Ar. The mixture was quenched with H$_2$O (15 mL), extracted with ethyl acetate (30 mL), washed with brine (20 mL). The combined organic layer was dried over Na$_2$SO$_4$, filtered, and concentrated under reduced pressure. The residue was purified by column chromatography on silica gel to give tert-butyl 4-((6-(4-chloro-2-fluorophenoxy)pyridin-2-yl)methylene)piperidine-1-carboxylate (420 mg, yield: 70%) as a yellow oil. MS Calcd.: 418.1. MS Found: 419.0 [M+H]$^+$.

Step B: The Synthesis of tert-butyl 4-((6-(4-chloro-2-fluorophenoxy)pyridin-2-yl)methyl)piperidine-1-carboxylate To a mixture of tert-butyl 4-((6-(4-chloro-2-fluorophenoxy)pyridin-2-yl)methylene)piperidine-1-carboxylate (250 mg, 0.6 mmol) in MeOH (10 mL), PtO$_2$ (25 mg) was added, the mixture was stirred at room temperature for 1 hour under H$_2$. After the reaction was completed, the mixture was filtered and concentrated under reduced pressure. The residue was purified by column chromatography to give tert-butyl 4-((6-(4-chloro-2-fluorophenoxy)pyridin-2-yl)methyl)piperidine-1-carboxylate (200 mg, yield: 80%) as a colorless oil. MS Calcd.: 420.2. MS Found: 421.1 [M+H]$^+$. 2-[(4-{

[6-(4-chloro-2-fluorophenoxy)pyridin-2-yl]methyl}piperidin-1-yl)methyl]-3-{[(2S)-oxetan-2-yl]methyl}-3H-imidazo[4,5-b]pyridine-5-carboxylic acid (62.6 mg) was then obtained as a white solid by the similar procedure of Compound 109a. MS Calcd.: 565.2. MS Found: 566.3 [M+H]+.

¹H NMR (400 MHz, DMSO-d6): δ 8.07 (d, J=8.4 Hz, 1H), 7.96 (d, J=8.0 Hz, 1H), 7.76 (t, J=8.0 Hz, 1H), 7.58 (dd, J=10.8 Hz, 2.4 Hz, 1H), 7.29-7.36 (m, 2H), 6.98 (d, J=7.2 Hz, 1H), 6.92 (d, J=8.0 Hz, 1H), 5.10-5.16 (m, 1H), 4.77-4.85 (m, 1H), 4.65-4.72 (m, 1H), 4.44-4.50 (m, 1H), 4.30-4.37 (m, 1H), 3.77-3.92 (m, 2H), 2.60-2.81 (m, 3H), 2.42-2.51 (m, 3H), 1.90-2.02 (m, 2H), 1.40-1.62 (m, 3H), 1.05-1.19 (m, 2H). 19F NMR (377 MHz, DMSO-d6): δ −124.76.

Example 15: 2-{[4-({6-[(4-chloro-2-fluorophenyl)methyl]pyridin-2-yl}difluoromethyl)piperidin-1-yl]methyl}-3-{[(2S)-oxetan-2-yl]methyl}-3H-imidazo[4,5-b]pyridine-5-carboxylic acid (Compound 173a)

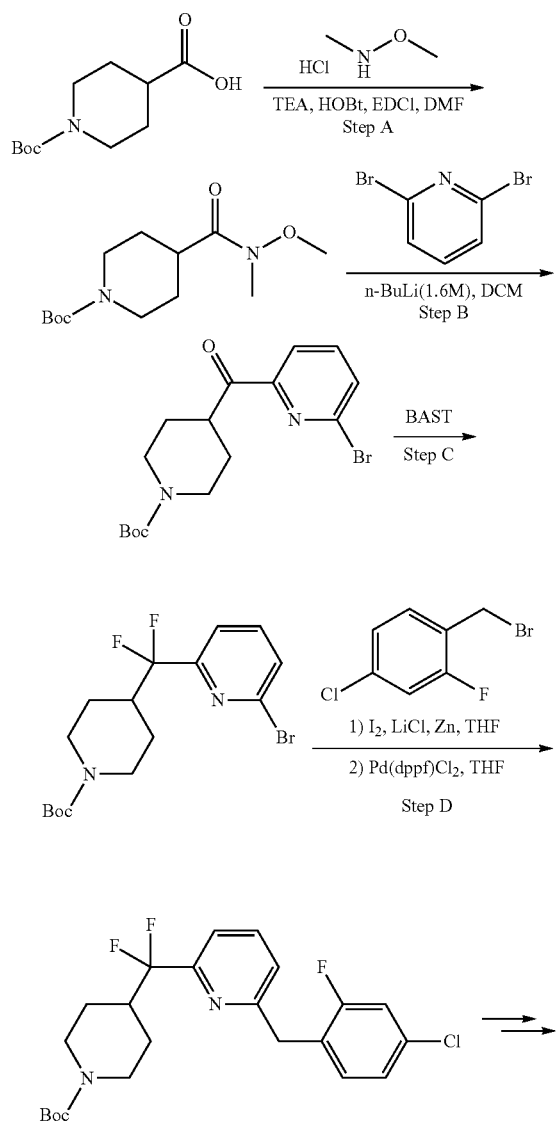

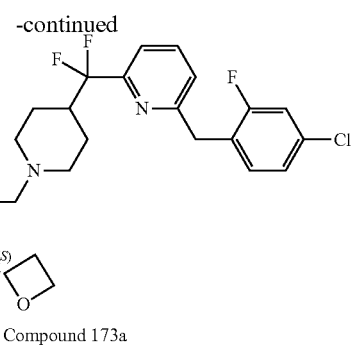

Compound 173a

Step A: The Synthesis of tert-butyl 4-(methoxy(methyl)carbamoyl)piperidine-1-carboxylate To a solution of 1-(tert-butoxycarbonyl)piperidine-4-carboxylic acid (1.0 g, 4.37 mmol) in DMF (15 ml) was added N,O-dimethylhydroxylamine hydrochloride (635 mg, 6.55 mmol) and TEA (882 mg, 8.73 mmol). After stirring 10 minutes, HOBt (707 mg, 5.24 mmol) and EDCI (1.0 g, 5.24 mmol) were added to the above reaction mixture. The mixture was stirred at room temperature for 2 hours, then brine was added. The mixture was extracted with ethyl acetate. The organic layer was dried over Na₂SO₄, filtered and concentrated. The residue was applied on a silica gel column and eluted with ethyl acetate/n-hexane (2/3) to give tert-butyl 4-(methoxy(methyl)carbamoyl)piperidine-1-carboxylate (1.07 g, yield: 90%) as a colorless oil. ¹H NMR (400 MHz, DMSO-d₆): δ 3.93-3.96 (m, 2H), 3.68 (s, 3H), 3.09 (s, 3H), 2.79-2.88 (m, 3H), 1.62-1.65 (m, 2H), 1.32-1.42 (m, 11H).

Step B: The Synthesis of tert-butyl 4-(6-bromopicolinoyl)piperidine-1-carboxylate To a solution of 2,6-dibromopyridine (3.6 g, 15.2 mmol) in dry DCM (80 mL) was added n-BuLi (10.4 mL, 16.7 mmol, 1.6 M solution in hexane) at −60° C. under an atmosphere of nitrogen, and the reaction mixture was stirred at this temperature for 60 minutes. Then a solution of tert-butyl 4-(methoxy(methyl) carbamoyl)piperidine-1-carboxylate (2.0 g, 7.6 mmol) in dry DCM (10 mL) was added and the mixture was stirred for 3 hours. The reaction was quenched with ice-water, extracted with ethyl acetate. The organic layer was dried over Na₂SO₄, filtered and concentrated. The residue was applied on a silica gel column and eluted with ethyl acetate/n-hexane (1/4) to give tert-butyl 4-(6-bromopicolinoyl)piperidine-1-carboxylate (1.8 g, yield: 66%) as a light-brown solid.

Step C: The Synthesis of tert-butyl 4-((6-bromopyridin-2-yl)difluoromethyl)piperidine-1-carboxylate A mixture of tert-butyl 4-(6-bromopicolinoyl)piperidine-1-carboxylate (500 mg, 1.36 mmol) in BAST (2 mL) was heated to 45° C. for 12 hours. The reaction was carefully poured into ice-water and the resulting mixture was extracted with ethyl acetate. The organic layer was dried over Na₂SO₄, filtered and concentrated. The residue was applied on a silica gel column and eluted with ethyl acetate/n-hexane (1/8) to give tert-butyl 4-((6-bromopyridin-2-yl)difluoromethyl)piperidine-1-carboxylate (410 mg, yield: 77%) as a white solid.

Step D: The Synthesis of tert-butyl 4-((6-(4-chloro-2-fluorobenzyl)pyridin-2-yl)difluoromethyl)piperidine-1-carboxylate A mixture of 1-(bromomethyl)-4-chloro-2-fluorobenzene (86 mg, 0.39 mmol), LiCl (8 mg, 0.19 mmol), I₂ (10 mg, 0.038 mmol) and Zn (75 mg, 1.15 mmol) in dry THF (4 mL) was heated to 50° C. for 1 hour under an atmosphere of nitrogen (balloon). Then tert-butyl 4-((6-bromopyridin-2-yl) difluoromethyl)piperidine-1-carboxylate (150 mg, 0.38 mmol) and Pd(dppf)Cl₂ (28 mg, 0.038 mmol) was added to the above reaction mixture. The resulted reaction mixture was stirred at 70° C. for 1 hour under nitrogen. The reaction was quenched with water and extracted with ethyl acetate. The organic layer was combined and washed with brine, dried over Na₂SO₄, filtered, and concentrated in vacuum. The residue was applied on a silica gel column and eluted with ethyl acetate/n-hexane (1/10) to give tert-butyl 4-((6-(4-chloro-2-fluorobenzyl) pyridine-2-yl)difluoromethyl)piperidine-1-carboxylate (90 mg, 51% yield) as a white solid. MS Calcd.: 454.2. MS Found: 455.4 [M+H]⁺. 2-{[4-({6-[(4-chloro-2-fluorophenyl)methyl]pyridin-2-yl}difluoromethyl)piperidin-1-yl]methyl}-3-{[(2S)-oxetan-2-yl]methyl}-3H-imidazo[4,5-b]pyridine-5-carboxylic acid (50.5 mg) was then obtained as a white solid by the similar procedure of Compound 109a. MS Calcd.: 599.2. MS Found: 600.4 [M+H]⁺.

¹H NMR (400 MHz, DMSO-d₆): δ 7.87-7.94 (m, 3H), 7.48 (d, J=7.6 Hz, 1H), 7.34-7.42 (m, 3H), 7.23 (dd, J=8.0 Hz, 1.6 Hz, 1H), 5.00-5.09 (m, 1H), 4.79-4.86 (m, 1H), 4.55-4.61 (m, 1H), 4.40-4.48 (m, 1H), 4.27-4.32 (m, 1H), 4.18 (s, 2H), 3.90 (d, J=13.6 Hz, 1H), 3.68 (d, J=13.6 Hz, 1H), 2.87-2.95 (m, 1H), 2.70-2.77 (m, 1H), 2.40-2.58 (m, 2H), 2.25-2.40 (m, 1H), 1.91-2.05 (m, 2H), 1.40-1.51 (m, 2H), 1.20-1.40 (m, 2H). ¹⁹F NMR (377 MHz, DMSO-d6): δ −105.36, −114.30.

Example 16: 2-{[4-({6-[(4-chloro-2-fluorophenyl)methyl]-3-fluoropyridin-2-yl}oxy)piperidin-1-yl]methyl}-3-{[(2S)-oxetan-2-yl]methyl}-3H-imidazo[4,5-b]pyridine-5-carboxylic acid (Compound 111a)

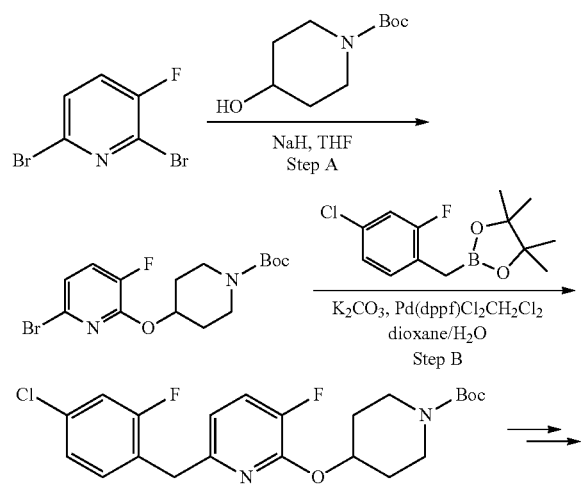

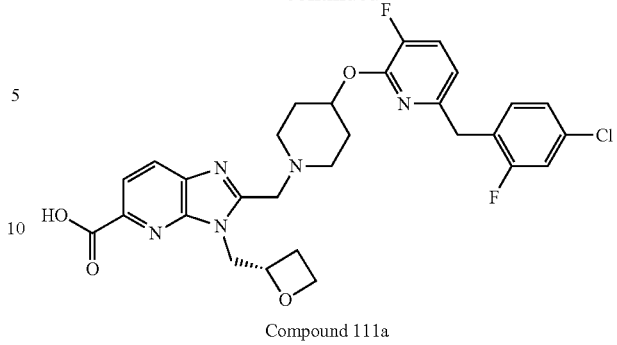

Compound 111a

Step A: The Synthesis of tert-butyl 4-((6-bromo-3-fluoropyridin-2-yl)oxy)piperidine-1-carboxylate To a solution of 2,6-dibromo-3-fluoropyridine (1.5 g, 5.9 mmol) and tert-butyl 4-hydroxypiperidine-1-carboxylate (1.8 g, 8.8 mmol) in THE (20 mL) was added NaH (353 mg, 8.8 mmol) at 0° C. The mixture was stirred at room temperature for 2 hours. After the reaction was completed, the mixture was extracted with ethyl acetate (30 mL×3). The organic layer was washed with brine (30 mL×2), dried over Na₂SO₄, filtered, and concentrated in vacuum. The residue was purified by column chromatography to give tert-butyl 4-((6-bromo-3-fluoropyridin-2-yl)oxy)piperidine-1-carboxylate (600 mg, yield: 27%) as a colorless oil. MS Calcd.: 374.1. MS Found: 318.9 [M+H-56]⁺.

Step B: The Synthesis of tert-butyl 4-((6-(4-chloro-2-fluorobenzyl)-3-fluoropyridin-2-yl)oxy)piperidine-1-carboxylate A mixture of tert-butyl 4-((6-bromo-3-fluoropyridin-2-yl)oxy)piperidine-1-carboxylate (100 mg, 0.3 mmol), 2-(4-chloro-2-fluorobenzyl)-4,4,5,5-tetramethyl-1,3,2-dioxaborolane (144 mg, 0.6 mmol), Pd(dppf) Cl₂ (22 mg, 0.03 mmol) and K₂CO₃ (111 mg, 0.9 mmol) in dioxane (2 mL) and water (0.5 mL) was purged with N₂ for 3 times. The mixture was stirred at 90° C. under N₂ for 16 hours. The reaction was quenched with 30 mL H₂O and extracted with EtOAc (30 mL×3). The combined organic layer was dried over Na₂SO₄, filtered, and concentrated. The residue was purified by column chromatography to give tert-butyl 4-((6-(4-chloro-2-fluorobenzyl)-3-fluoropyridin-2-yl)oxy)piperidine-1-carboxylate (90 mg, yield: 77%) as a yellow oil. MS Calcd.: 438.1. MS Found: 439.2 [M+H]⁺.

2-{[4-({6-[(4-chloro-2-fluorophenyl)methyl]-3-fluoropyridin-2-yl}oxy)piperidin-1-yl]methyl}-3-{[(2S)-oxetan-2-yl]methyl}-3H-imidazo[4,5-b]pyridine-5-carboxylic acid (9.7 mg) was then obtained as a white solid by the similar procedure of Compound 109a. MS Calcd.: 583.2. MS Found: 584.4 [M+H]⁺.

¹H NMR (400 MHz, DMSO-d₆): δ 8.12 (d, J=8.4 Hz, 1H), 7.98 (d, J=8.0 Hz, 1H), 7.57 (dd, J=10.8 Hz, 8.0 Hz, 1H), 7.34-7.39 (m, 2H), 7.23 (dd, J=8.4 Hz, 2.0 Hz, 1H), 6.86 (dd, J=8.0 Hz, 2.8 Hz, 1H), 5.13-5.20 (m, 1H), 4.78-4.92 (m, 2H), 4.67-4.75 (m, 1H), 4.46-4.52 (m, 1H), 4.30-4.40 (m, 1H), 3.85-4.00 (m, 4H), 2.64-2.79 (m, 3H), 2.44-2.51 (m, 1H), 2.27-2.35 (m, 2H), 1.84-1.92 (m, 2H), 1.52-1.69 (m, 2H). ¹⁹F NMR (377 MHz, DMSO-d6): δ −114.66, −143.71.

Example 17: 2-{[4-({2-[(4-chloro-2-fluorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (Compound 113a)

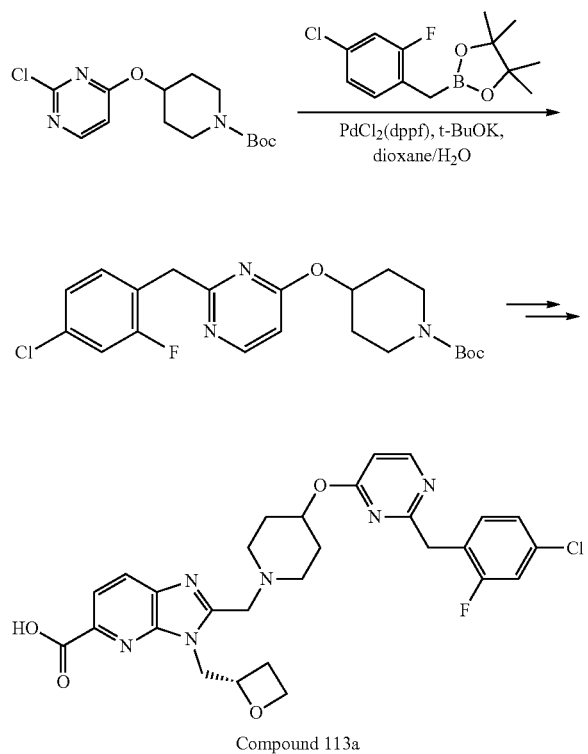

Compound 113a

A mixture of tert-butyl 4-((2-chloropyrimidin-4-yl)oxy)piperidine-1-carboxylate (2.0 g, 6.4 mmol), 2-(4-chloro-2-fluorobenzyl)-4,4,5,5-tetramethyl-1,3,2-dioxaborolane (3.45 g, 12.8 mmol), PdCl₂(dppf) (467 mg, 0.64 mmol), t-BuOK (2.15 g, 19.2 mmol) in dioxane/H₂O (20 mL/2 mL) was stirred at 90° C. for 4 hours under Ar. The mixture was cooled to room temperature and extracted with H₂O (20 mL)/DCM (2×30 mL). The combined organic layer was dried over Na₂SO₄, filtered, and concentrated under reduced pressure. The residue was purified by column chromatography on silica gel to give tert-butyl 4-((2-(4-chloro-2-fluorobenzyl)pyrimidin-4-yl)oxy)piperidine-1-carboxylate (450 mg, yield: 20%) as a yellow oil. MS Calcd.: 421.2. MS Found: 422.0 [M+H]⁺. 2-{[4-({2-[(4-chloro-2-fluorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (58 mg) was then obtained as a white solid by the similar procedure of Compound 109a. MS Calcd.: 566.2. MS Found: 567.4 [M+H]⁺.

$^1$H NMR (400 MHz, DMSO-d$_6$): δ 8.40 (d, J=6.0 Hz, 1H), 8.02 (d, J=8.0 Hz, 1H), 7.94 (d, J=8.4 Hz, 1H), 7.37-7.42 (m, 2H), 7.25 (dd, J=8.4 Hz, 2.0 Hz, 1H), 6.73 (d, J=6.0 Hz, 1H), 5.10-5.17 (m, 1H), 4.79-4.92 (m, 2H), 4.64-4.71 (m, 1H), 4.45-4.51 (m, 1H), 4.31-4.37 (m, 1H), 4.15 (s, 2H), 3.96 (d, J=13.6 Hz, 1H), 3.85 (d, J=13.6 Hz, 1H), 2.60-2.80 (m, 3H), 2.44-2.51 (m, 1H), 2.24-2.35 (m, 2H), 1.85-1.94 (m, 2H), 1.56-1.66 (m, 2H). $^{19}$F NMR (377 MHz, DMSO-d6): δ −114.06.

Example 18: 2-{[4-({2-[(4-chloro-2-fluorophenyl)methyl]pyrimidin-4-yl}oxy)piperidin-1-yl]methyl}-1-{[(2S)-oxetan-2-yl]methyl}-1H-1,3-benzodiazole-6-carboxylic acid (Compound 160a)

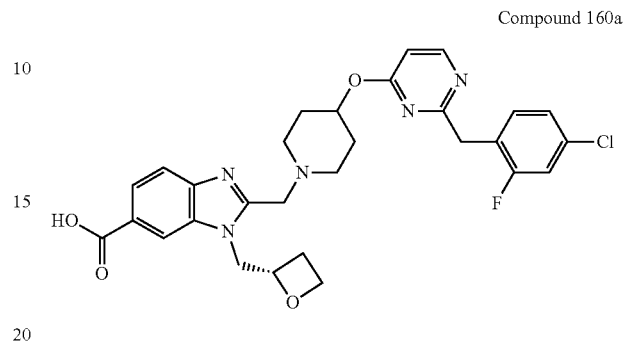

Compound 160a

MS Calcd.: 565.2, MS Found: 566.4 [M+H]⁺.

$^1$H NMR (400 MHz, DMSO-d$_6$): δ 8.40 (d, J=5.6 Hz, 1H), 8.25 (s, 1H), 7.80 (d, J=8.4 Hz, 1H), 7.63 (d, J=8.4 Hz, 1H), 7.37-7.42 (m, 2H), 7.24 (dd, J=8.0 Hz, 1.6 Hz, 1H), 6.73 (d, J=5.6 Hz, 1H), 5.05-5.11 (m, 1H), 4.84-4.92 (m, 1H), 4.72-4.80 (m, 1H), 4.59-4.66 (m, 1H), 4.46-4.52 (m, 1H), 4.34-4.40 (m, 1H), 4.15 (s, 2H), 3.93 (d, J=13.6 Hz, 1H), 3.77 (d, J=13.6 Hz, 1H), 2.66-2.80 (m, 3H), 2.35-2.50 (m, 1H), 2.20-2.32 (m, 2H), 1.82-1.92 (m, 2H), 1.50-1.64 (m, 2H). $^{19}$F NMR (377 MHz, DMSO-d6): δ −114.06.

Example 19: 2-{[4-({2-[(4-chloro-2-fluorophenyl)methyl]pyrimidin-4-yl}oxy)piperidin-1-yl]methyl}-1-[(1-cyanocyclopropyl)methyl]-1H-1,3-benzodiazole-6-carboxylic acid (Compound 162)

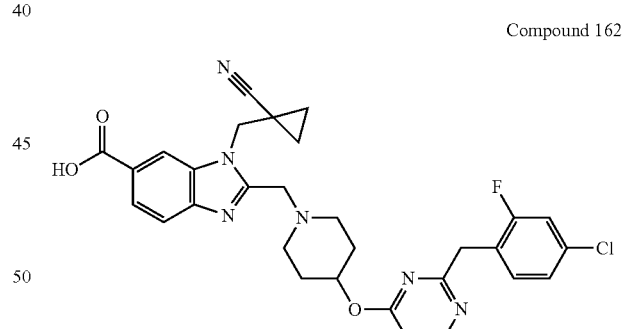

Compound 162

MS Calcd.: 574.19. MS Found: 575.4 [M+H]⁺.

$^1$H NMR (400 MHz, DMSO-d6): δ 8.42 (d, J=5.6 Hz, 1H), 8.38 (d, J=0.8 Hz, 1H), 8.06 (dd, J=8.8 Hz, J=1.6 Hz, 1H), 7.82 (d, J=8.4 Hz, 1H), 7.33 (t, J=8.4 Hz, 1H), 7.16-7.21 (m, 2H), 6.77 (d, J=5.6 Hz, 1H), 5.25-5.31 (m, 1H), 4.89 (s, 2H), 4.64 (s, 2H), 4.20 (s, 2H), 3.48-3.63 (m, 4H), 2.13-2.29 (m, 4H), 1.42-1.49 (m, 4H). $^{19}$F NMR (377 MHz, DMSO-d6): δ −116.01.

Example 20: 2-{[4-({2-[(4-chloro-2-fluorophenyl)methyl]pyrimidin-4-yl}oxy)piperidin-1-yl]methyl}-1-{[(2S)-oxetan-2-yl]methyl}-1H-imidazo[4,5-b]pyridine-6-carboxylic acid (Compound 161a)

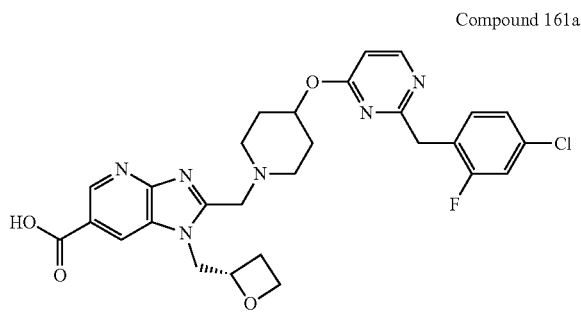 [SMILES: O=C(O)c1cnc2nc(CN3CCC(Oc4ccnc(Cc5ccc(Cl)cc5F)n4)CC3)n(C[C@@H]3CCO3)c2c1]

Compound 161a

MS Calcd.: 566.2. MS Found: 567.4 [M+H]$^+$.

$^1$H NMR (400 MHz, DMSO-d$_6$): δ 8.89 (d, J=1.6 Hz, 1H), 8.38-8.42 (m, 2H), 7.35-7.42 (m, 2H), 7.25 (dd, J=8.0 Hz, 2.0 Hz, 1H), 6.73 (d, J=5.6 Hz, 1H), 5.04-5.11 (m, 1H), 4.86-4.93 (m, 1H), 4.70-4.77 (m, 1H), 4.57-4.65 (m, 1H), 4.46-4.51 (m, 1H), 4.32-4.40 (m, 1H), 4.15 (s, 2H), 3.93 (d, J=13.6 Hz, 1H), 3.80 (d, J=13.6 Hz, 1H), 2.65-2.82 (m, 3H), 2.36-2.45 (m, 1H), 2.24-2.33 (m, 2H), 1.82-1.93 (m, 2H), 1.52-1.64 (m, 2H). $^{19}$F NMR (377 MHz, DMSO-d6): δ −114.06.

Example 21: 2-[(4-{5-[(4-chloro-2-fluorophenyl)methyl]-2-fluorophenoxy}piperidin-1-yl)methyl]-3-{[(2S)-oxetan-2-yl]methyl}-3H-imidazo[4,5-b]pyridine-5-carboxylic acid (Compound 114a)

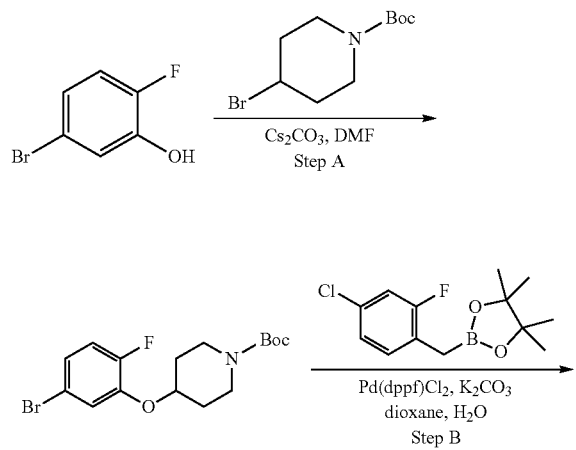

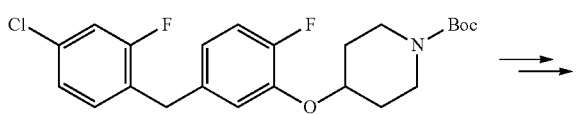

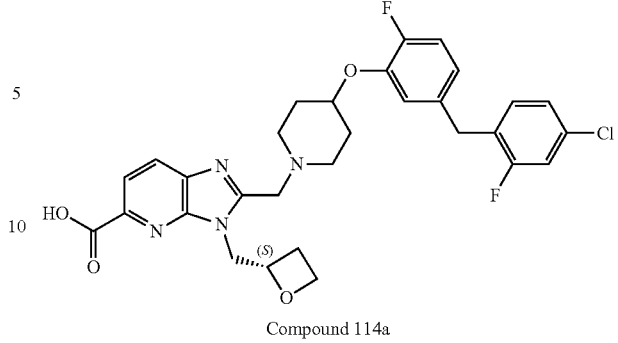

Compound 114a

Step A: The Synthesis of tert-butyl 4-(5-bromo-2-fluorophenoxy)piperidine-1-carboxylate A mixture of 5-bromo-2-fluorophenol (0.50 g, 2.62 mmol), tert-butyl 4-bromopiperidine-1-carboxylate (1.38 g, 5.24 mmol) and Cs$_2$CO$_3$ (2.13 g, 6.54 mmol) in DMF (12 mL) was heated to 100° C. for 12 hours. The reaction mixture was quenched with water, extracted with ethyl acetate. The organic layers were combined, washed with brine, dried over Na$_2$SO$_4$, filtered, and concentrated under vacuum. The residue was purified by column chromatography to give tert-butyl 4-(5-bromo-2-fluorophenoxy)piperidine-1-carboxylate (300 mg, yield: 32%) as a light-yellow oil.

$^1$H NMR (400 MHz, DMSO-d$_6$): δ 7.48-7.51 (m, 1H), 7.14-7.24 (m, 2H), 4.64-4.66 (m, 1H), 3.62-3.68 (m, 2H), 3.15-3.20 (m, 2H), 1.88-1.92 (m, 2H), 1.50-1.54 (m, 2H), 1.47 (s, 9H).

Step B: The Synthesis of tert-butyl 4-(5-(4-chloro-2-fluorobenzyl)-2-fluorophenoxy)piperidine-1-carboxylate To a solution of tert-butyl 4-(5-bromo-2-fluorophenoxy)piperidine-1-carboxylate (500 mg, 1.34 mmol) in dioxane (10 mL) and H$_2$O (1 mL) was added 2-(4-chloro-2-fluorobenzyl)-4,4,5,5-tetramethyl-1,3,2-dioxaborolane (540 mg, 2.01 mmol), Pd(dppf)Cl$_2$ (110 mg, 0.13 mmol) and K$_2$CO$_3$ (460 mg, 3.35 mmol). The resulting mixture was stirred at 80° C. for 12 hours. The solvent was removed in vacuo. The residue was purified by Flash (ethyl acetate/n-hexane=1/10) to give tert-butyl 4-(5-(4-chloro-2-fluorobenzyl)-2-fluorophenoxy)piperidine-1-carboxylate (170 mg, yield: 29%) as a colorless oil. MS Calcd.: 437.2. MS Found: 382.0 [M+H-56]$^+$. 2-[(4-{5-[(4-chloro-2-fluorophenyl)methyl]-2-fluorophenoxy}piperidin-1-yl)methyl]-3-{[(2S)-oxetan-2-yl]methyl}-3H-imidazo[4,5-b]pyridine-5-carboxylic acid (53.5 mg) was then obtained as a white solid by the similar procedure of Compound 109a.

MS Calcd.: 582.2. MS Found: 583.1 [M+H]$^+$.

$^1$H NMR (400 MHz, DMSO-d$_6$): δ 7.91-7.96 (m, 2H), 7.38 (dd, J=10.0 Hz, 2.0 Hz, 1H), 7.32 (t, J=8.4 Hz, 1H), 7.23 (dd, J=8.4 Hz, 2.0 Hz, 1H), 7.07-7.14 (m, 2H), 6.70-6.75 (m, 1H), 5.08-5.14 (m, 1H), 4.84-4.91 (m, 1H), 4.60-4.66 (m, 1H), 4.44-4.51 (m, 1H), 4.28-4.41 (m, 2H), 3.96 (d, J=13.6 Hz, 1H), 3.91 (s, 2H), 3.74 (d, J=13.6 Hz, 1H), 2.58-2.80 (m, 3H), 2.45-2.51 (m, 1H), 2.30-2.40 (m, 2H), 1.87-1.97 (m, 2H), 1.58-1.70 (m, 2H). $^{19}$F NMR (377 MHz, DMSO-d6): δ −114.84, −136.81.

Example 22: 2-{[4-({2-[(4-chlorophenyl)methyl]pyridin-4-yl}oxy)piperidin-1-yl]methyl}-3-{[(2S)-oxetan-2-yl]methyl}-3H-imidazo[4,5-b]pyridine-5-carboxylic acid (Compound 159a)

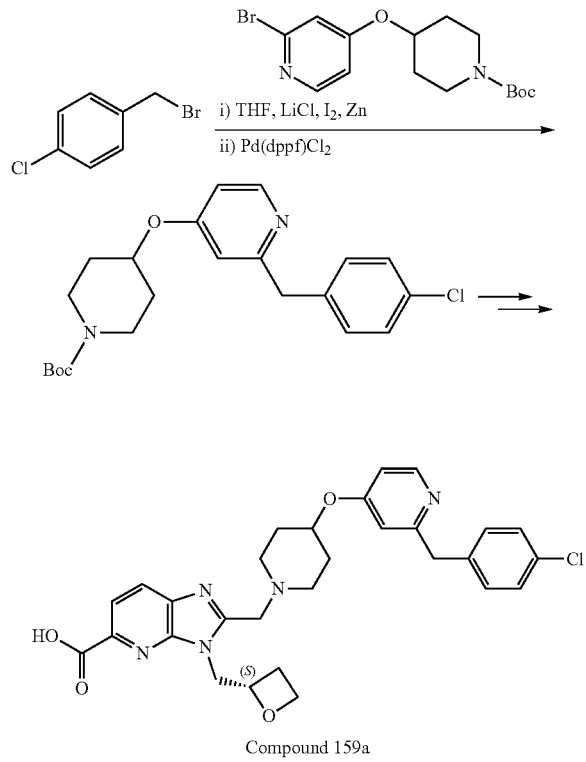

Compound 159a

Example 23: 2-[(4-{3-[(4-chlorophenyl)methyl]-2-fluorophenoxy}piperidin-1-yl)methyl]-3-{[(2S)-oxetan-2-yl]methyl}-3H-imidazo[4,5-b]pyridine-5-carboxylic acid (Compound 157a)

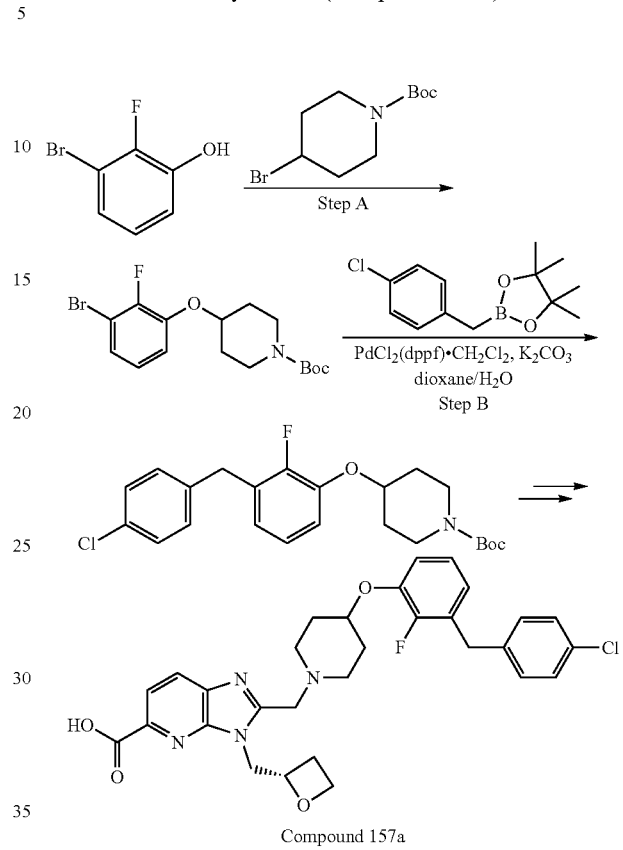

Compound 157a

A mixture of 1-(bromomethyl)-4-chlorobenzene (0.4 g, 1.95 mmol), LiCl (40 mg, 0.98 mmol), $I_2$ (24 mg, 0.10 mmol) and Zn (189 mg, 2.91 mmol) in dry THF (5 mL) was heated to 50° C. for 1 hour under an atmosphere of nitrogen (balloon). Then tert-butyl 4-((2-bromopyridin-4-yl)oxy)piperidine-1-carboxylate (276 mg, 0.78 mmol) and Pd(dppf)Cl$_2$ (70 mg, 0.10 mmol) was added to the above reaction mixture. The resulted reaction mixture was stirred at 70° C. for 3 hours under nitrogen. The reaction mixture was quenched with water and extracted with ethyl acetate. The organic layer was combined and washed with brine, dried over Na$_2$SO$_4$, filtered, and concentrated in vacuum. The residue was purified by column chromatography to give tert-butyl 4-((2-(4-chlorobenzyl)pyridin-4-yl)oxy)piperidine-1-carboxylate (230 mg, 74% yield) as a white solid.

MS Calcd.: 402.2, MS Found: 403.0 [M+H]$^+$. 2-{[4-({2-[(4-chlorophenyl)methyl]pyridin-4-yl}oxy)piperidin-1-yl]methyl}-3-{[(2S)-oxetan-2-yl]methyl}-3H-imidazo[4,5-b]pyridine-5-carboxylic acid (90 mg) was then obtained as a white solid by the similar procedure of Compound 109a. MS Calcd.: 547.2. MS Found: 548.4 [M+H]$^+$.

$^1$H NMR (400 MHz, DMSO-d$_6$): δ 8.25 (d, J=6.0, 1H), 7.94 (d, J=8.4 Hz, 1H), 7.88 (d, J=8.0 Hz, 1H), 7.28-7.34 (m, 4H), 6.89 (d, J=2.4 Hz, 1H), 6.82 (dd, J=6.0 Hz, 2.4 Hz, 1H), 5.10-5.17 (m, 1H), 4.76-4.82 (m, 1H), 4.62-4.69 (m, 1H), 4.45-4.57 (m, 2H), 4.31-4.38 (m, 1H), 3.92-4.00 (m, 3H), 3.83 (d, J=14.0 Hz, 1H), 2.61-2.79 (m, 3H), 2.30-2.45 (m, 3H), 1.90-1.99 (m, 2H), 1.58-1.70 (m, 2H).

Step A: The Synthesis of tert-butyl 4-(3-bromo-2-fluorophenoxy)piperidine-1-carboxylate A mixture of 3-bromo-2-fluorophenol (1.0 g, 5.3 mmol), tert-butyl 4-bromopiperidine-1-carboxylate (1.4 g, 5.3 mmol), and Cs$_2$CO$_3$ (3.4 g, 10.5 mmol) in DMF (10 mL) was stirred at 80° C. for 18 hours. After the reaction was completed, the mixture was extracted with ethyl acetate (15 mL×3), washed with brine (15 mL×2), dried over Na$_2$SO$_4$, filtered, and concentrated in vacuum, the residue was purified by column chromatography to give tert-butyl 4-(3-bromo-2-fluorophenoxy)piperidine-1-carboxylate (109 mg, yield: 5.6%) as dark oil.

MS Calcd.: 373.1. MS Found: 318.0 [M-56+H]$^+$.

Step B: The Synthesis of tert-butyl 4-(3-(4-chlorobenzyl)-2-fluorophenoxy)piperidine-1-carboxylate A mixture of tert-butyl 4-(3-bromo-2-fluorophenoxy)piperidine-1-carboxylate (109 mg, 0.29 mmol) and 2-(4-chlorobenzyl)-4,4,5,5-tetramethyl-1,3,2-dioxaborolane (74 mg, 0.29 mmol), PdCl$_2$(dppf)·CH$_2$Cl$_2$ (21 mg, 0.03 mmol) and K$_2$CO$_3$ (121 mg, 0.88 mmol) in dioxane (3 mL) and water (0.3 mL) was stirred at 80° C. under N$_2$ for 18 hours. The reaction mixture was filtered, the filtrate was concentrated in vacuum, purified by prep-TLC (PE/EA=10/1) to give tert-butyl 4-(3-bromo-2-fluorophenoxy)piperidine-1-carboxylate (31 mg, yield: 25%) as a yellow solid.

MS Calcd.: 419.2. MS Found: 364.1 [M-56+H]+. 2-[(4-{3-[(4-chlorophenyl)methyl]-2-fluorophenoxy}piperidin-1-yl)methyl]-3-{[(2S)-oxetan-2-yl]methyl}-3H-imidazo[4,5-b]pyridine-5-carboxylic acid (9.5 mg) was then obtained as a white solid by the similar procedure of Compound 109a. MS Calcd.: 564.2. MS Found: 565.2 [M+H]+.

$^1$H NMR (400 MHz, CD$_3$OD): δ 8.06 (d, J=8.4 Hz, 1H), 7.99 (d, J=8.4 Hz, 1H), 7.22-7.28 (m, 2H), 7.16-7.20 (m, 2H), 6.95-7.00 (m, 2H), 6.75-6.80 (m, 1H), 5.25-5.36 (m, 1H), 4.95-5.05 (m, 1H), 4.80-4.90 (m, 1H), 4.58-4.64 (m, 1H), 4.36-4.43 (m, 2H), 4.06 (d, J=14.0 Hz, 1H), 3.91-3.96 (m, 3H), 2.70-2.83 (m, 3H), 2.50-2.60 (m, 1H), 2.40-2.49 (m, 2H), 1.95-2.02 (m, 2H), 1.75-1.88 (m, 2H). $^{19}$F NMR (377 MHz, CD$_3$OD): δ −140.22.

Example 24: 2-[(4-{2-chloro-3-[(4-chlorophenyl)methyl]phenoxy}piperidin-1-yl)methyl]-3-{[(2S)-oxetan-2-yl]methyl}-3H-imidazo[4,5-b]pyridine-5-carboxylic acid (Compound 158a)

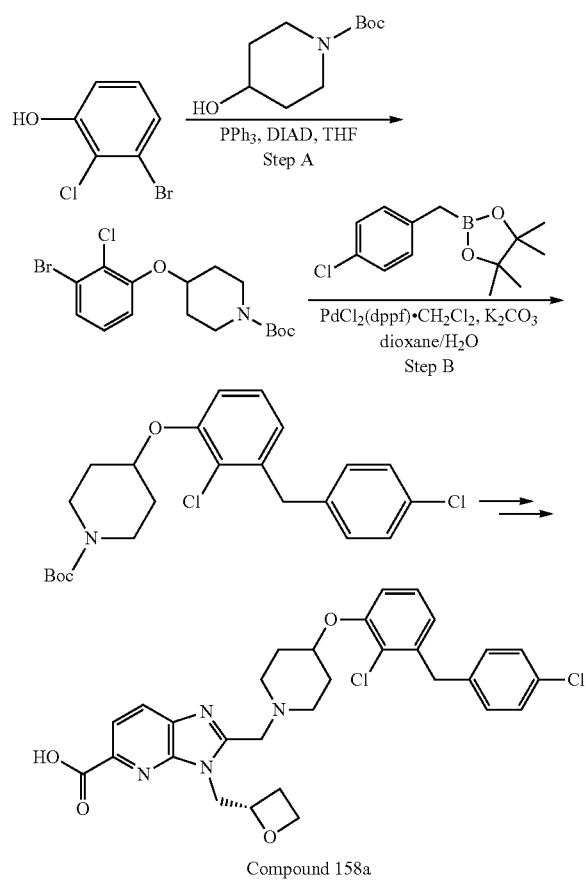

Compound 158a

Step A: The Synthesis of tert-butyl 4-(3-bromo-2-chlorophenoxy)piperidine-1-carboxylate To a solution 3-bromo-2-chlorophenol (1.0 g, 4.83 mmol) in THF (20 mL) was added tert-butyl 4-hydroxypiperidine-1-carboxylate (1.16 g, 5.80 mmol), PPh$_3$ (1.9 g, 7.24 mmol). The mixture was cooled to 0° C., DIAD (1.46 g, 7.24 mmol) was added dropwise at 0° C. under Ar. The reaction mixture was stirred at rt for 2 hours. After the reaction was completed, the reaction mixture was quenched with ice-water and extracted with ethyl acetate (50 mL*2). The organic layers were combined, dried over Na$_2$SO$_4$, filtered and concentrated. The residue was purified by silica gel column chromatography (PE/EA=10/1) to give tert-butyl 4-(3-bromo-2-chlorophenoxy)piperidine-1-carboxylate (1.8 g, 95% yield) as a colorless oil.

MS Calcd.: 389.0. MS Found: 335.8 [M+H-56]+.

Step B: The Synthesis of tert-butyl 4-(2-chloro-3-(4-chlorobenzyl)phenoxy)piperidine-1-carboxylate A mixture of tert-butyl 4-(3-bromo-2-chlorophenoxy)piperidine-1-carboxylate (150 mg, 0.38 mmol), 2-(4-chlorobenzyl)-4,4,5,5-tetramethyl-1,3,2-dioxaborolane (146 mg, 0.58 mmol), PdCl$_2$(dppf)·CH$_2$Cl$_2$ (31 mg, 0.04 mmol), K$_2$CO$_3$ (157 mg, 1.14 mmol) in dioxane/H$_2$O (3 mL/0.3 mL) was stirred at 90° C. for 3 hours under Ar. After the reaction was completed, the reaction mixture was quenched with water and extracted with ethyl acetate (10 mL*2). The organic layers were concentrated, dried over Na$_2$SO$_4$ and concentrated. The residue was purified by silica gel column chromatography (PE/EA=8/1) to give tert-butyl 4-(2-chloro-3-(4-chlorobenzyl)phenoxy)piperidine-1-carboxylate (190 mg, 85% yield) as a colorless oil.

MS Calcd.: 435.1. MS Found: 380.0 [M+H-56]+. 2-[(4-{2-chloro-3-[(4-chlorophenyl)methyl]phenoxy}piperidin-1-yl)methyl]-3-{[(2S)-oxetan-2-yl]methyl}-3H-imidazo[4,5-b]pyridine-5-carboxylic acid (63.6 mg) was then obtained as a white solid by the similar procedure of Compound 109a. MS Calcd.: 580.2. MS Found: 581.4 [M+H]+.

$^1$H NMR (400 MHz, DMSO-d6): δ 7.90-7.95 (m, 2H), 7.31-7.38 (m, 2H), 7.17-7.24 (m, 3H), 7.09 (d, J=7.2 Hz, 1H), 6.90 (dd, J=7.6 Hz, 0.8 Hz, 1H), 5.09-5.17 (m, 1H), 4.80-4.89 (m, 1H), 4.62-4.68 (m, 1H), 4.45-4.54 (m, 2H), 4.28-4.35 (m, 1H), 4.05 (s, 2H), 3.95 (d, J=13.6 Hz, 1H), 3.78 (d, J=13.6 Hz, 1H), 2.59-2.79 (m, 3H), 2.34-2.55 (m, 3H), 1.85-1.97 (m, 2H), 1.62-1.75 (m, 2H).

Example 25: 2-{[4-({6-[(4-chlorophenyl)methyl]-4-(trifluoromethyl)pyridin-2-yl}oxy)piperidin-1-yl]methyl}-3-{[(2S)-oxetan-2-yl]methyl}-3H-imidazo[4,5-b]pyridine-5-carboxylic acid (Compound 156a)

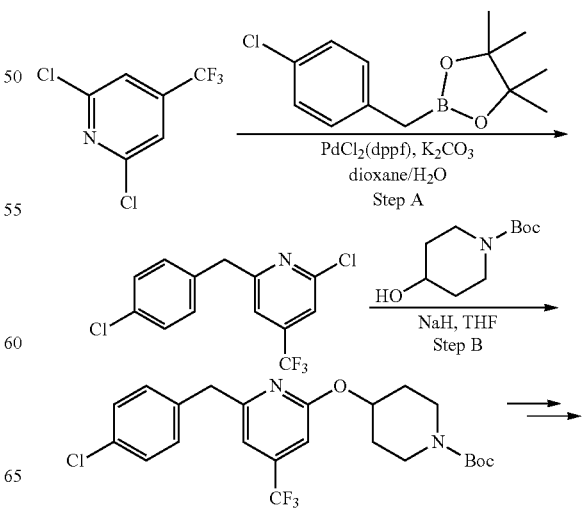

-continued

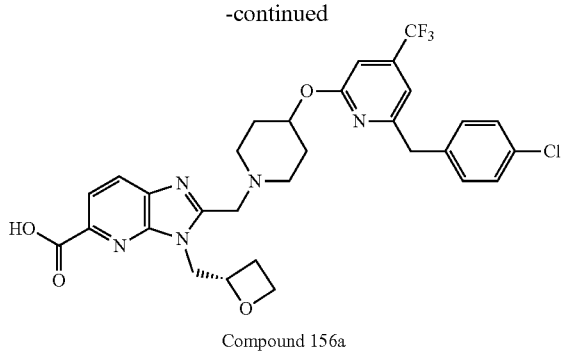

Compound 156a

Step A: The Synthesis of 2-chloro-6-(4-chlorobenzyl)-4-(trifluoromethyl)pyridine A mixture of 2,6-dichloro-4-(trifluoromethyl)pyridine (350 mg, 1.63 mmol) and 2-(4-chlorobenzyl)-4,4,5,5-tetramethyl-1,3,2-dioxaborolane (410 mg, 1.63 mmol), Pd(dppf)Cl$_2$ (119 mg, 0.16 mmol) and K$_2$CO$_3$ (674 mg, 4.88 mmol) in dioxane (10 mL) and water (1 mL) was stirred at 80° C. under N$_2$ for 16 hours. The reaction mixture was filtered, the filtrate was concentrated in vacuum, purified by prep-TLC (PE/EA=10/1) to give 2-chloro-6-(4-chlorobenzyl)-4-(trifluoromethyl)pyridine (110 mg, yield: 24%) as a yellow oil.

MS Calcd.: 305.0. MS Found: 306.0 [M+H]$^+$.

Step B: The Synthesis of tert-butyl 4-((6-(4-chlorobenzyl)-4-(trifluoromethyl)pyridin-2-yl)oxy)piperidine-1-carboxylate To a solution of tert-butyl 4-hydroxypiperidine-1-carboxylate (178 mg, 0.89 mmol) in THF (5 mL) was added NaH (60%) (35 mg, 0.89 mmol) at 25° C., and the mixture was stirred at 50° C. for 0.5 hour. 2-chloro-6-(4-chlorobenzyl)-4-(trifluoromethyl)pyridine (90 mg, 0.29 mmol) was then added to the above mixture. The mixture was stirred at 50° C. for 18 hours. After the reaction was completed, the mixture was poured into cold water (50 mL) and extracted with ethyl acetate (2×50 mL), the combined organic layer was washed with brine, dried over Na$_2$SO$_4$, filtered, and purified under by FCC (PE/EA=2/1) to give tert-butyl 4-((6-(4-chlorobenzyl)-4-(trifluoromethyl)pyridin-2-yl)oxy)piperidine-1-carboxylate (94 mg, yield: 68%) as a yellow oil.

MS Calcd.: 470.2. MS Found: 415.2 [M-56+H]$^+$. 2-{[4-({6-[(4-chlorophenyl)methyl]-4-(trifluoromethyl)pyridin-2-yl}oxy)piperidin-1-yl]methyl}-3-{[(2S)-oxetan-2-yl]methyl}-3H-imidazo[4,5-b]pyridine-5-carboxylic acid (3.1 mg) was then obtained as a white solid by the similar procedure of Compound 109a. MS Calcd.: 615.2. MS Found: 616.1 [M+H]$^+$.

$^1$H NMR (400 MHz, CD$_3$OD): δ 8.12-8.07 (m, 1H), 8.05-8.00 (m, 1H), 7.32-7.25 (m, 4H), 7.03 (s, 1H), 6.80 (s, 1H), 5.40-5.25 (m, 1H), 5.10-4.90 (m, 3H), 4.60-4.52 (m, 1H), 4.40-4.30 (m, 1H), 4.10-4.00 (m, 3H), 4.00-3.90 (m, 1H), 2.87-2.70 (m, 3H), 2.60-2.51 (m, 1H), 2.48-2.40 (m, 2H), 1.99-1.95 (m, 2H), 1.80-1.70 (m, 2H). $^{19}$F NMR (377 MHz, CD$_3$OD): δ −66.38.

Example 26: 2-{[4-({4-chloro-6-[(4-chlorophenyl)methyl]pyridin-2-yl}oxy)piperidin-1-yl]methyl}-3-{[(2S)-oxetan-2-yl]methyl}-3H-imidazo[4,5-b]pyridine-5-carboxylic acid (Compound 155a)

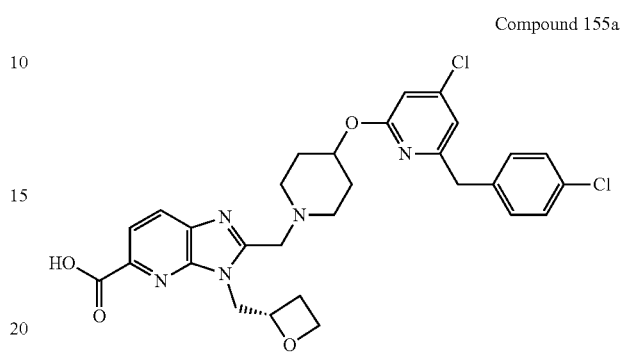

Compound 155a

MS Calcd.: 581.2. MS Found: 582.2 [M+H]$^+$.

$^1$H NMR (400 MHz, CD$_3$OD): δ 8.13-8.05 (m, 2H), 7.31-7.20 (m, 4H), 6.83 (d, J=1.2 Hz, 1H), 6.62 (d, J=1.2 Hz, 1H), 5.33-5.24 (m, 1H), 5.09-4.97 (m, 2H), 4.90-4.83 (m, 1H), 4.65-4.57 (m, 1H), 4.45-4.39 (m, 1H), 4.17-4.00 (m, 2H), 3.95 (s, 2H), 2.91-2.70 (m, 3H), 2.57-2.47 (m, 3H), 2.05-1.95 (m, 2H), 1.82-1.70 (m, 2H).

Example 27: 2-{[4-({6-[(4-chlorophenyl)methyl]-4-methylpyridin-2-yl}oxy)piperidin-1-yl]methyl}-3-{[(2S)-oxetan-2-yl]methyl}-3H-imidazo[4,5-b]pyridine-5-carboxylic acid (Compound 154a)

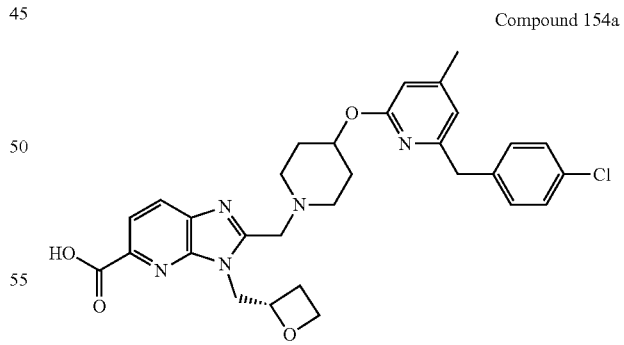

Compound 154a

MS Calcd.: 561.2. MS Found: 562.2 [M+H]$^+$.

$^1$H NMR (400 MHz, CD$_3$OD): δ 8.11-8.01 (m, 2H), 7.30-7.20 (m, 4H), 6.61 (s, 1H), 6.39 (s, 1H), 5.33-5.28 (m, 1H), 5.04-4.95 (m, 2H), 4.85-4.80 (m, 1H), 4.65-4.57 (m, 1H), 4.45-4.39 (m, 1H), 4.13 (d, J=14.0 Hz, 1H), 4.02 (d, J=14.0 Hz, 1H), 3.91 (s, 2H), 2.90-2.70 (m, 3H), 2.60-2.47 (m, 3H), 2.23 (s, 3H), 2.05-1.95 (m, 2H), 1.82-1.70 (m, 2H).

Example 28: 2-{[4-({6-[(4-chlorophenyl)methyl]pyrazin-2-yl}oxy)piperidin-1-yl]methyl}-3-{[(2S)-oxetan-2-yl]methyl}-3H-imidazo[4,5-b]pyridine-5-carboxylic acid (Compound 153a)

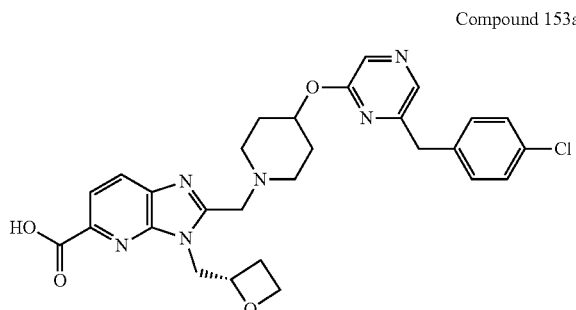

Compound 153a

MS Calcd.: 548.2. MS Found: 549.3 [M+H]$^+$.

$^1$H NMR (400 MHz, CD$_3$OD): δ 8.10-8.07 (m, 1H), 8.06-8.00 (m, 2H), 7.97 (s, 1H), 7.28 (br.s, 4H), 5.32-5.26 (m, 1H), 5.10-4.97 (m, 2H), 4.94-4.85 (m, 1H), 4.65-4.58 (m, 1H), 4.47-4.38 (m, 1H), 4.12-4.08 (m, 1H), 4.05-3.97 (m, 3H), 2.90-2.70 (m, 3H), 2.60-2.42 (m, 3H), 2.05-1.95 (m, 2H), 1.86-1.76 (m, 2H).

Example 29: (S)-2-((4-((6-(4-chloro-2-fluorobenzyl)-5-fluoropyridin-2-yl)oxy)piperidin-1-yl)methyl)-3-(oxetan-2-ylmethyl)-3H-imidazo[4,5-b]pyridine-5-carboxylic acid (Compound 150a)

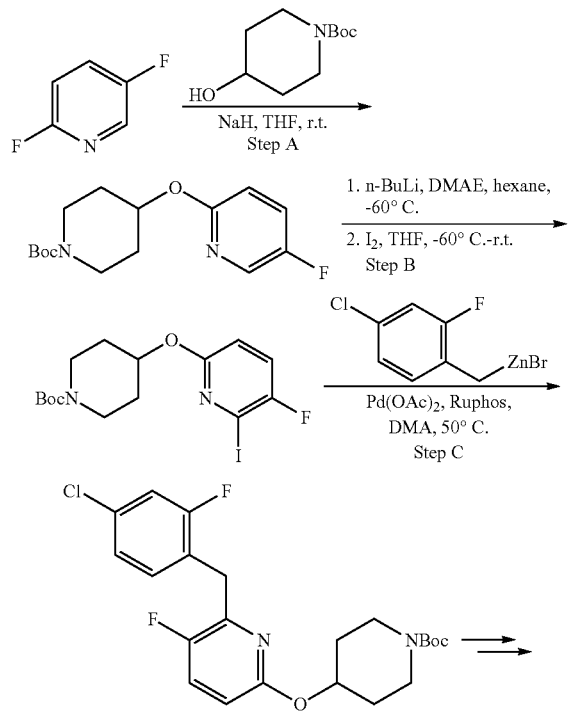

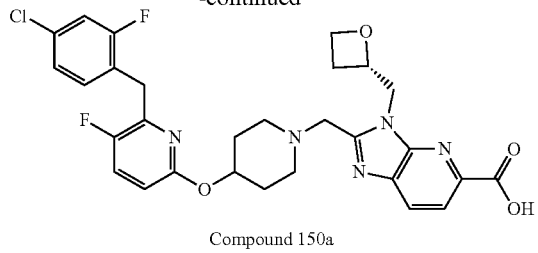

Compound 150a

Step A: tert-butyl 4-((5-fluoropyridin-2-yl)oxy)piperidine-1-carboxylate

To a suspension of NaH (261 mg, 6.52 mmol) in THF (5 mL) was added tert-butyl 4-hydroxypiperidine-1-carboxylate (1.31 g, 6.52 mmol). The resulting mixture was stirred at 25° C. for 10 mins, followed by the dropwise addition of 2,5-difluoropyridine (500 mg, 4.35 mmol). The resulting solution was stirred at 25° C. for 4 hours. The mixture was quenched with sat. NH$_4$Cl aqueous solution and extracted with EtOAc (30 mL*3). The organic phase was concentrated and purified by flash chromatography (PE/EtOAc=10/1) to give tert-butyl 4-((5-fluoropyridin-2-yl)oxy)piperidine-1-carboxylate as a yellow solid (831 mg, 64% yield). $^1$H NMR (400 MHz, CDCl$_3$) δ 7.95 (d, J=2.8 Hz, 1H), 7.29-7.36 (m, 1H), 6.68 (dd, J=9.2, 3.6 Hz, 1H), 5.09-5.17 (m, 1H), 3.80-3.90 (m, 2H), 3.70-3.80 (m, 2H), 1.91-2.01 (m, 2H), 1.79-1.89 (m, 2H), 1.46 (s, 9H).

Step B: tert-butyl 4-((5-fluoro-6-iodopyridin-2-yl)oxy)piperidine-1-carboxylate To a solution of tert-butyl 4-((5-fluoropyridin-2-yl)oxy)piperidine-1-carboxylate (180 mg, 2.02 mmol) in hexane (2 mL) was added n-BuLi (2.5 M in THF)(1.6 mL, 4.02 mmol) dropwise at −5° C. After stirred 30 mins at −5° C., a solution of tert-butyl 4-((5-fluoropyridin-2-yl)oxy)piperidine-1-carboxylate (200 mg, 0.673 mmol) in hexane (4 mL) was added dropwise at −60° C. The resulting mixture was stirred at −60° C. overnight. Then a solution of I$_2$ (680 mg, 2.68 mmol) in THF (3 mL) was introduced dropwise at −60° C. After addition, the reaction was allowed to warm to room temperature and stirred at 25° C. for 2 hours. The mixture was quenched with H$_2$O and extracted with EtOAc (30 mL*3). The organic phase was concentrated and purified by reverse-HPLC (0.1% NH$_3$·H$_2$O in water and methanol) to afford tert-butyl 4-((5-fluoro-6-iodopyridin-2-yl)oxy)piperidine-1-carboxylate (47.0 mg, 16% yield) as a yellow solid. LC-MS: m/z 367.1 (M-56+H)$^+$.

Step C: tert-butyl 4-((6-(4-chloro-2-fluorobenzyl)-5-fluoropyridin-2-yl)oxy)piperidine-1-carboxylate A mixture of tert-butyl 4-((5-fluoro-6-iodopyridin-2-yl)oxy)piperidine-1-carboxylate (47.0 mg, 0.11 mmol), Pd(OAc)$_2$ (5.00 mg, 0.022 mmol), Ruphos (21.0 mg, 0.044 mmol) in DMA (2 mL) was bubbled with N$_2$. Then (4-chloro-2-fluorobenzyl)zinc(II) bromide (1 M in DMA) (1.10 mL, 1.10 mmol) was added in one portion. The resulting mixture was stirred at 50° C. for 1 h. Then the mixture was diluted with H$_2$O and extracted with EtOAc (30 mL*3). The organic phase was concentrated and purified by prep-TLC (PE/EtOAc=5/1) to afford tert-butyl 4-((6-(4-chloro-2-fluorobenzyl)-5-fluoropyridin-2-yl)oxy)piperidine-1-carboxylate as a yellow solid (40.0 mg, 83% yield). LC-MS: m/z 383.1 (M-56+H)+.

(S)-2-((4-((6-(4-Chloro-2-fluorobenzyl)-5-fluoropyridin-2-yl)oxy)piperidin-1-yl)methyl)-3-(oxetan-2-ylmethyl)-3H-imidazo[4,5-b]pyridine-5-carboxylic acid as a white solid (30 mg, 76% yield) was obtained as a solid by the similar procedure of Compound 109a.

$^1$H NMR (400 MHz, CDCl$_3$) δ 8.19 (q, J=8.0 Hz, 2H), 7.89 (d, J=0.8 Hz, 1H), 7.07-7.17 (m, 3H), 6.41 (d, J=4.8 Hz, 1H), 5.20-5.28 (m, 1H), 4.88-5.05 (m, 2H), 4.77-4.85 (m, 1H), 4.63 (dd, J=14.4, 7.6 Hz, 1H), 4.34-4.44 (m, 1H), 4.06 (s, 2H), 3.92 (s, 2H), 2.79-2.90 (m, 3H), 2.41-2.54 (m, 3H), 1.98-2.12 (m, 2H), 1.70-1.85 (m, 2H). LC-MS: m/z 584.2 (M+H)+.

Example 30: (S)-2-((4-((2-(4-chloro-2-fluorobenzyl)-5-fluoropyrimidin-4-yl)oxy)piperidin-1-yl)methyl)-3-(oxetan-2-ylmethyl)-3H-imidazo[4,5-b]pyridine-5-carboxylic acid (Compound 151a)

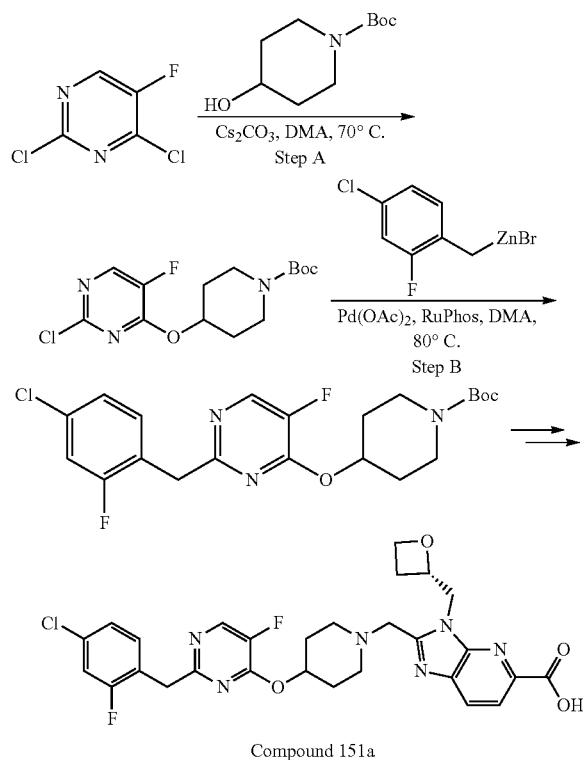

Compound 151a

Step A: tert-butyl 4-((2-chloro-5-fluoropyrimidin-4-yl)oxy)piperidine-1-carboxylate To a mixture of 2,4-dichloro-5-fluoropyrimidine (4.06 g, 24.3 mmol) in dry DMA (100 mL) were added tert-butyl 4-hydroxypiperidine-1-carboxylate (5.87 g, 29.2 mmol) and cesium carbonate (15.8 g, 48.6 mmol). The mixture was heated at 80° C. for 1 h and then at 70° C. overnight. TLC showed the reaction was completed. The mixture was diluted with ethyl acetate (100 mL) and washed with water (3×100 mL). The organic layer was dried over Na$_2$SO$_4$ and concentrated. The residue was purified with silica gel column chromatography (PE/EA=5/1) to afford tert-butyl 4-((2-chloro-5-fluoropyrimidin-4-yl)oxy)piperidine-1-carboxylate as a white solid (1.03 g, 13% yield). LC-MS: m/z 232.0 (M-100+H)+.

Step B: tert-butyl 4-((2-(4-chloro-2-fluorobenzyl)-5-fluoropyrimidin-4-yl)oxy)piperidine-1-carboxylate To a mixture of tert-butyl 4-((2-chloro-5-fluoropyrimidin-4-yl)oxy)piperidine-1-carboxylate (664 mg, 2.0 mmol), Pd(OAc)$_2$ (90.0 mg, 0.40 mmol) and RuPhos (373 mg, 0.80 mmol) was added dry DMA (5 mL). Then (4-chloro-2-fluorobenzyl)zinc(II) bromide (1.18 M in DMA, 7.0 mL, 8.26 mmol) was added dropwise. The mixture was degassed and refilled with argon for three times. The reaction mixture was heated at 80° C. for 1.5 hours under an atmosphere of argon. The reaction mixture was diluted with ethyl acetate (100 mL). The mixture was washed with water (3×50 mL), dried over Na$_2$SO$_4$ and concentrated. The residue was purified with reverse phase HPLC (0.1% ammonia in water and methanol) to afford tert-butyl 4-((2-(4-chloro-2-fluorobenzyl)-5-fluoropyrimidin-4-yl)oxy)piperidine-1-carboxylate as a yellow oil (188 mg, 21% yield). LC-MS: m/z 440.2 (M+H)+.

(S)-2-((4-((2-(4-Chloro-2-fluorobenzyl)-5-fluoropyrimidin-4-yl)oxy)piperidin-1-yl)methyl)-3-(oxetan-2-ylmethyl)-3H-imidazo[4,5-b]pyridine-5-carboxylic acid as a white solid (116 mg, 60% yield) was obtained as a solid by the similar procedure of Compound 109a.

$^1$H NMR (400 MHz, DMSO-d$^6$) δ 13.01 (s, 1H), 8.51 (d, J=3.2 Hz, 1H), 8.14-8.16 (m, 1H), 8.00 (d, J=8.4 Hz, 1H), 7.37-7.42 (m, 2H), 7.25 (dd, J=8.4, 1.6 Hz, 1H), 5.13-5.19 (m, 1H), 4.95-5.01 (m, 1H), 4.84 (dd, J=14.8, 6.4 Hz, 1H), 4.71 (dd, J=14.8, 4.4 Hz, 1H), 4.47-4.52 (m, 1H), 4.34-4.39 (m, 1H), 4.15 (s, 2H), 3.97 (dd, J=23.6, 13.6 Hz, 2H), 2.65-2.78 (m, 3H), 2.45-2.48 (m, 1H), 2.34 (t, J=9.6 Hz, 2H), 1.87-2.01 (m, 2H), 1.64-1.74 (m, 2H). LC-MS: m/z 585.2 (M+H).

Example 31: 2-{[4-({6-[(4-chloro-2-fluorophenyl)methyl]-5-methylpyridin-2-yl}oxy)piperidin-1-yl]methyl}-3-{[(2S)-oxetan-2-yl]methyl}-3H-imidazo[4,5-b]pyridine-5-carboxylic acid (Compound 169a)

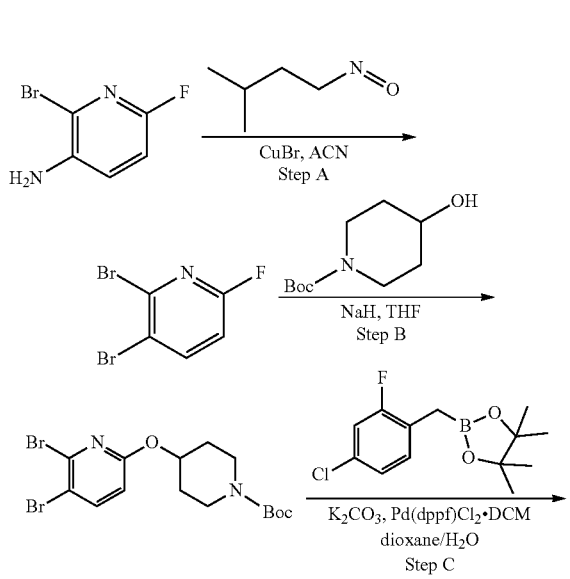

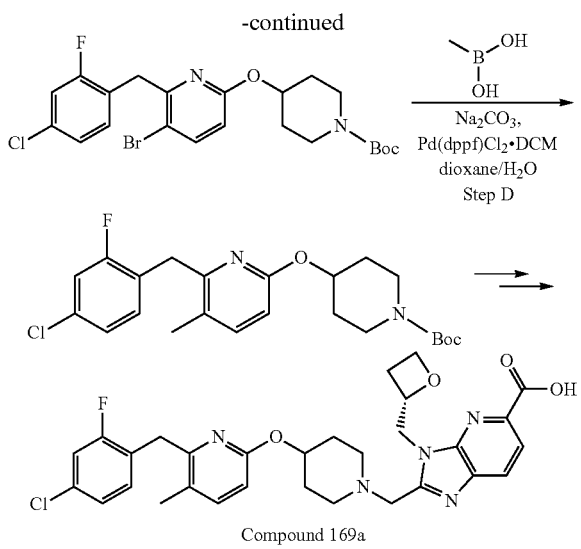

Compound 169a

Step A: The Synthesis of 2,3-dibromo-6-fluoropyridine

A mixture of 2-bromo-6-fluoropyridin-3-amine (5.0 g, 26 mmol), 3-methyl-1-nitroisobutane (6.1 g, 52 mmol), CuBr (7.5 g, 52 mmol) in ACN (100 mL) was stirred at room temperature for 6 hours. After the reaction was completed, the reaction mixture was quenched with water (100 mL) and extracted with ethyl acetate (200 mL*2). The organic layers were combined, dried over $Na_2SO_4$ and concentrated. The residue was purified by silica gel column chromatography (PE/EA=50/1) to give 2,3-dibromo-6-fluoropyridine (4.0 g, 61% yield) as colorless oil.

Step B: The Synthesis of tert-butyl 4-((5,6-dibromopyridin-2-yl)oxy)piperidine-1-carboxylate To a solution of tert-butyl 4-hydroxypiperidine-1-carboxylate (482 mg, 2.4 mmol) in THF (10 mL) was added NaH (120 mg, 3.0 mmol) at room temperature. After the mixture was heated to 50° C. and stirred for 20 min, 2,3-dibromo-6-fluoropyridine (510 mg, 2.0 mmol) was added and the mixture was stirred at 50° C. for 2 hours. The reaction was quenched with water (50 mL) and extracted with ethyl acetate (100 mL*2). The organic layers were dried over $Na_2SO_4$ and concentrated. The residue was purified by silica gel column chromatography (PE/EA=20/1) to give tert-butyl 4-((5,6-dibromopyridin-2-yl)oxy)piperidine-1-carboxylate (710 mg, 81% yield) as a colorless oil.

MS Calcd.: 434.0, MS Found: 378.8 [M+H-56]$^+$.

Step C: The Synthesis of tert-butyl 4-((5-bromo-6-(4-chloro-2-fluorobenzyl)pyridin-2-yl)oxy)piperidine-1-carboxylate A mixture of tert-butyl 4-((5,6-dibromopyridin-2-yl)oxy)piperidine-1-carboxylate (610 mg, 1.40 mmol), 2-(4-chloro-2-fluorobenzyl)-4,4,5,5-tetramethyl-1,3,2-dioxaborolane (455 mg, 1.69 mmol), Pd(dppf)Cl$_2$·DCM (61 mg, 0.07 mmol) and $K_2CO_3$ (620 mg, 4.20 mmol) in dioxane/H$_2$O (10 mL/1 mL) was stirred at 85° C. for 3 hours under Ar. The reaction mixture was quenched with water (40 mL) and extracted with DCM (3×20 ml). The combined organic layer was dried over $Na_2SO_4$, filtered, and concentrated under reduced pressure, the residue was purified by silica gel column chromatography (PE/EA=30/1) to give tert-butyl 4-((5-bromo-6-(4-chloro-2-fluorobenzyl)pyridin-2-yl)oxy) piperidine-1-carboxylate (142 mg, yield: 20%) as a colorless oil.

MS Calcd.: 498.1. MS Found: 498.9 [M+H]$^+$.

Step D: The Synthesis of tert-butyl 4-((6-(4-chloro-2-fluorobenzyl)-5-methylpyridin-2-yl)oxy)piperidine-1-carboxylate A mixture of tert-butyl 4-((5-bromo-6-(4-chloro-2-fluorobenzyl)pyridin-2-yl)oxy)piperidine-1-carboxylate (140 mg, 0.3 mmol), methylboronic acid (84 mg, 1.4 mmol), Pd(dppf)Cl$_2$·DCM (12 mg, 0.02 mmol) and $Na_2CO_3$ (148 mg, 1.4 mmol) in dioxane/H$_2$O (4 mL/0.4 mL) was stirred at 90° C. overnight under Ar. The reaction was quenched with water (40 mL) and extracted with DCM (3×20 mL). The combined organic layer was dried over $Na_2SO_4$, filtered, and concentrated under reduced pressure. The residue was purified by silica gel column chromatography (PE/EA=30/1) to give tert-butyl 4-((6-(4-chloro-2-fluorobenzyl)-5-methylpyridin-2-yl)oxy)piperidine-1-carboxylate (31 mg, yield: 22%) as a colorless oil.

MS Calcd.: 434.2, MS Found: 435.0 [M+H]$^+$. 2-{[4-({6-[(4-Chloro-2-fluorophenyl)methyl]-5-methylpyridin-2-yl}oxy)piperidin-1-yl]methyl}-3-{[(2S)-oxetan-2-yl]methyl}-3H-imidazo[4,5-b]pyridine-5-carboxylic acid (18.4 mg) was then obtained as a white solid by the similar procedure of Compound 109a. MS Calcd.: 579.2. MS Found: 580.7 [M+H]$^+$.

$^1$H NMR (400 MHz, DMSO-d$_6$): δ 8.13 (d, J=8.4 Hz, 1H), 7.99 (d, J=8.4 Hz, 1H), 7.45 (d, J=8.4 Hz, 1H), 7.36 (dd, J=10.0 Hz, 2.0 Hz, 1H), 7.28 (t, J=8.0 Hz, 1H), 7.20-7.23 (m, 1H), 6.50 (d, J=8.0 Hz, 1H), 5.10-5.19 (m, 1H), 4.79-4.86 (m, 1H), 4.66-4.74 (m, 1H), 4.45-4.60 (m, 2H), 4.33-4.40 (m, 1H), 4.00 (s, 2H), 3.95 (d, J=13.6 Hz, 1H), 3.88 (d, J=14.0 Hz, 1H), 2.64-2.79 (m, 3H), 2.42-2.55 (m, 1H), 2.23 (s, 3H), 2.10-2.20 (m, 2H), 1.72-1.80 (m, 2H), 1.40-1.55 (m, 2H). $^{19}$F NMR (377 MHz, DMSO-d6): δ −114.19.

Example 32: 2-{[4-({1-[(4-chloro-2-fluorophenyl)methyl]-6-oxo-1,6-dihydropyridazin-3-yl}oxy)piperidin-1-yl]methyl}-3-{[(2S)-oxetan-2-yl]methyl}-3H-imidazo[4,5-b]pyridine-5-carboxylic acid (Compound 144a)

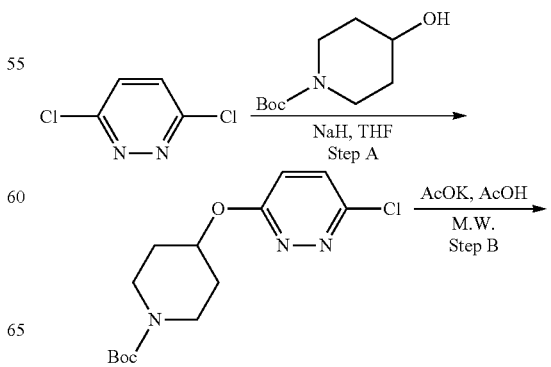

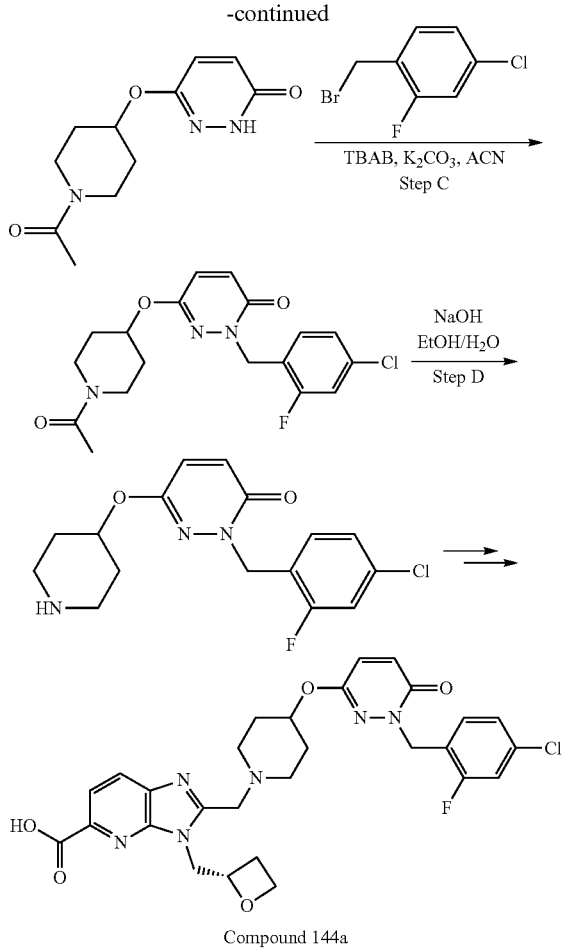

Compound 144a

Step A: The Synthesis of tert-butyl 4-((6-chloro-pyridazin-3-yl)oxy)piperidine-1-carboxylate To a stirred solution of tert-butyl 4-hydroxypiperidine-1-carboxylate (2.26 g, 11.2 mmol) in dry THF (10 mL) was added NaH (816 mg, 20.4 mmol) in portions at room temperature. The reaction mixture was stirred at room temperature for 1 hour. To the above reaction mixture was added 3,6-dichloropyridazine (1.51 g, 10.2 mmol) in portions at room temperature. The final reaction mixture was stirred at 80° C. for 16 hours. Upon cooling down, the reaction was quenched with $H_2O$ and extracted with ethyl acetate. The organic layers were combined and washed with brine, dried over anhydrous $Na_2SO_4$, filtered and concentrated under vacuum. The residue was purified by RFC to give tert-butyl 4-((6-chloropyridazin-3-yl)oxy)piperidine-1-carboxylate (710 mg, 22% yield) as a white solid.

MS Calcd.: 313.1. MS Found: 314.2 [M+H]+.

Step B: The Synthesis of 6-((1-acetylpiperidin-4-yl)oxy)pyridazin-3(2H)-one

A mixture of tert-butyl 4-((6-chloropyridazin-3-yl)oxy)piperidine-1-carboxylate (630 mg, 2.0 mmol) and AcOK (197 mg, 4.0 mmol) in AcOH (6 mL) was stirred at 120° C. for 1.5 hours with irradiation. Upon cooling down, the reaction mixture was adjusted pH to 8 with saturated $NaHCO_3$ solution and extracted with DCM/MeOH=10/1. The combined organic layers were dried over anhydrous $Na_2SO_4$ and concentrated under vacuum. The residue was purified by RFC to give 6-((1-acetylpiperidin-4-yl)oxy) pyridazin-3(2H)-one (185 mg, yield: 39%) as a white solid.

MS Calcd.: 237.1. MS Found: 238.2 [M+H]+.

Step C: The Synthesis of 6-((1-acetylpiperidin-4-yl) oxy)-2-(4-chloro-2-fluorobenzyl)pyridazin-3(2H)-one A mixture of 6-((1-acetylpiperidin-4-yl)oxy)pyridazin-3 (2H)-one (180 mg, 0.76 mmol), 1-(bromomethyl)-4-chloro-2-fluorobenzene (204 mg, 0.91 mmol), $K_2CO_3$ (263 mg, 1.9 mmol) and TBAB (12 mg, 0.038 mmol) in ACN (10 mL) was stirred at 90° C. for 16 hours. The mixture was filtered, the filtrate was concentrated under reduced pressure, purified by reversed column to give 6-((1-acetylpiperidin-4-yl) oxy)-2-(4-chloro-2-fluorobenzyl)pyridazin-3(2H)-one (138 mg, yield: 47%) as a white solid.

MS Calcd.: 379.1. MS Found: 380.0 [M+H]+.

Step D: The Synthesis of 2-(4-chloro-2-fluorobenzyl)-6-(piperidin-4-yloxy)pyridazin-3(2H)-one To a solution of 6-((1-acetylpiperidin-4-yl)oxy)-2-(4-chloro-2-fluorobenzyl)pyridazin-3(2H)-one (138 mg, 0.36 mmol) in EtOH/$H_2O$ (5 mL/0.5 mL) was added NaOH (146 mg, 3.6 mmol), the mixture was stirred at 80° C. for 16 hours. The mixture was concentrated under reduced pressure, diluted with DCM/MeOH (V/V=20/1), washed with water and brine, dried over $Na_2SO_4$, concentrated to give crude 2-(4-chloro-2-fluorobenzyl)-6-(piperidin-4-yloxy) pyridazin-3(2H)-one (143 mg) as brown solid and used directly for the next step.

MS Calcd.: 337.1. MS Found: 338.0 [M+H]+. 2-{[4-({1-[(4-Chloro-2-fluorophenyl)methyl]-6-oxo-1,6-dihydro-pyridazin-3-yl}oxy)piperidin-1-yl]methyl}-3-{[(2S)-oxetan-2-yl]methyl}-3H-imidazo[4,5-b]pyridine-5-carboxylic acid (76.3 mg) was then obtained as a white solid by the similar procedure of Compound 109a. MS Calcd.: 582.2. MS Found: 583.2 [M+H]+.

$^1$H NMR (400 MHz, $CD_3OD$): δ 8.14-8.09 (m, 2H), 7.35 (t, J=8.0 Hz, 1H), 7.24-7.15 (m, 2H), 7.12 (d, J=10.0 Hz, 1H), 6.99 (d, J=9.6 Hz, 1H), 5.30-5.24 (m, 1H), 5.22 (s, 2H), 5.04-4.95 (m, 1H), 4.90-4.80 (m, 1H), 4.71-4.58 (m, 2H), 4.45-4.39 (m, 1H), 4.14-4.02 (m, 2H), 2.90-2.70 (m, 3H), 2.60-2.40 (m, 3H), 2.00-1.91 (m, 2H), 1.81-1.71 (m, 2H).
$^{19}$F NMR (377 MHz, $CD_3OD$): δ 116.61.

Example 33: 2-{[4-({3-chloro-6-[(4-chloro-2-fluorophenyl)methyl]pyridin-2-yl}oxy)piperidin-1-yl] methyl}-3-{[(2S)-oxetan-2-yl]methyl}-3H-imidazo [4,5-b]pyridine-5-carboxylic acid (Compound 137a)

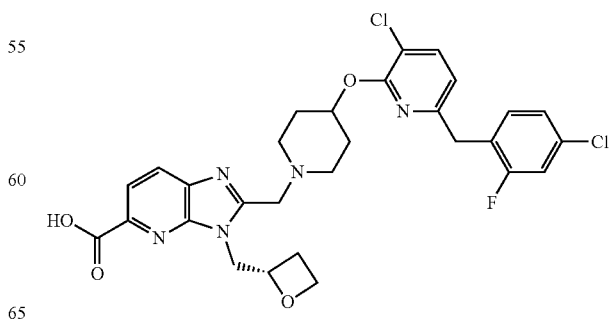

Compound 137a

MS Calcd.: 599.2. MS Found: 600.5 [M+H]+.

¹H NMR (400 MHz, CD₃OD): δ 7.95-8.10 (m, 2H), 7.61 (d, J=8.0 Hz, 1H), 7.10-7.28 (m, 3H), 6.57 (d, J=8.4 Hz, 1H), 5.25-5.35 (m, 1H), 4.90-5.08 (m, 2H), 4.55-4.70 (m, 2H), 4.35-4.45 (m, 1H), 4.15 (s, 2H), 4.00-4.10 (m, 1H), 3.91-3.97 (m, 1H), 2.70-2.83 (m, 3H), 2.45-2.60 (m, 1H), 2.20-2.30 (m, 2H), 1.78-1.90 (m, 2H), 1.55-1.70 (m, 2H). ¹⁹F NMR (377 MHz, CD₃OD): δ 116.08.

Example 34: 2-{[4-({1-[(4-chloro-2-fluorophenyl)methyl]-1H-pyrazol-3-yl}oxy)piperidin-1-yl]methyl}-1-{[(2S)-oxetan-2-yl]methyl}-1H-1,3-benzodiazole-6-carboxylic acid (Compound 116a)

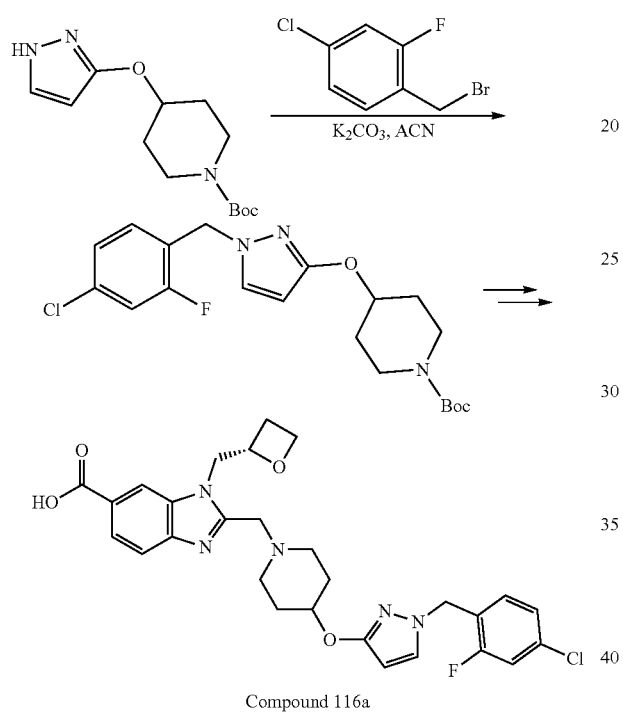

A mixture of tert-butyl 4-((1H-pyrazol-3-yl)oxy)piperidine-1-carboxylate (500 mg, 1.87 mmol), 1-(bromomethyl)-4-chloro-2-fluorobenzene (500 mg, 2.24 mmol), K₂CO₃ (774 mg, 5.61 mmol) in acetonitrile (20 mL) was stirred at 80° C. for 3 days. The reaction was filtered and concentrated under reduced pressure. The residue was purified by silica gel column chromatography to give tert-butyl 4-((1-(4-chloro-2-fluorobenzyl)-1H-pyrazol-3-yl)oxy)piperidine-1-carboxylate (430 mg, yield: 56%) as a colorless oil. MS Calcd.: 409.2. MS Found: 410.2 [M+H]⁺.

2-{[4-({1-[(4-Chloro-2-fluorophenyl)methyl]-1H-pyrazol-3-yl}oxy)piperidin-1-yl]methyl}-1-{[(2S)-oxetan-2-yl]methyl}-1H-1,3-benzodiazole-6-carboxylic acid (22.1 mg) was then obtained as a white solid by the similar procedure of Compound 109a. MS Calcd.: 553.2. MS Found: 554.2 [M+H]⁺.

¹H NMR (400 MHz, DMSO-d₆): δ 8.25 (d, J=0.8 Hz, 1H), 7.78-7.81 (m, 1H), 7.60-7.63 (m, 2H), 7.45 (dd, J=10.0 Hz, 2.0 Hz, 1H), 7.28 (dd, J=8.8 Hz, 2.0 Hz, 1H), 7.12 (t, 0.1=8.0 Hz, 1H), 5.71 (d, J=2.4 Hz, 1H), 5.17 (s, 2H), 5.04-5.12 (m, 1H), 4.74-4.81 (m, 1H), 4.59-4.65 (m, 1H), 4.42-4.51 (m, 1H), 4.34-4.41 (m, 2H), 3.92 (d, J=13.6 Hz, 1H), 3.75 (d, J=13.6 Hz, 1H), 2.64-2.78 (m, 3H), 2.37-2.47 (m, 1H), 2.26-2.36 (m, 2H), 1.87-1.96 (m, 2H), 1.52-1.66 (m, 2H). ¹⁹F NMR (377 MHz, DMSO-d6): δ −115.56.

Example 35: 2-{[4-({1-[(4-chloro-2-fluorophenyl)methyl]-4-methyl-1H-pyrazol-3-yl}oxy)piperidin-1-yl]methyl}-3-{[(2S)-oxetan-2-yl]methyl}-3H-imidazo[4,5-b]pyridine-5-carboxylic acid (Compound 133a)

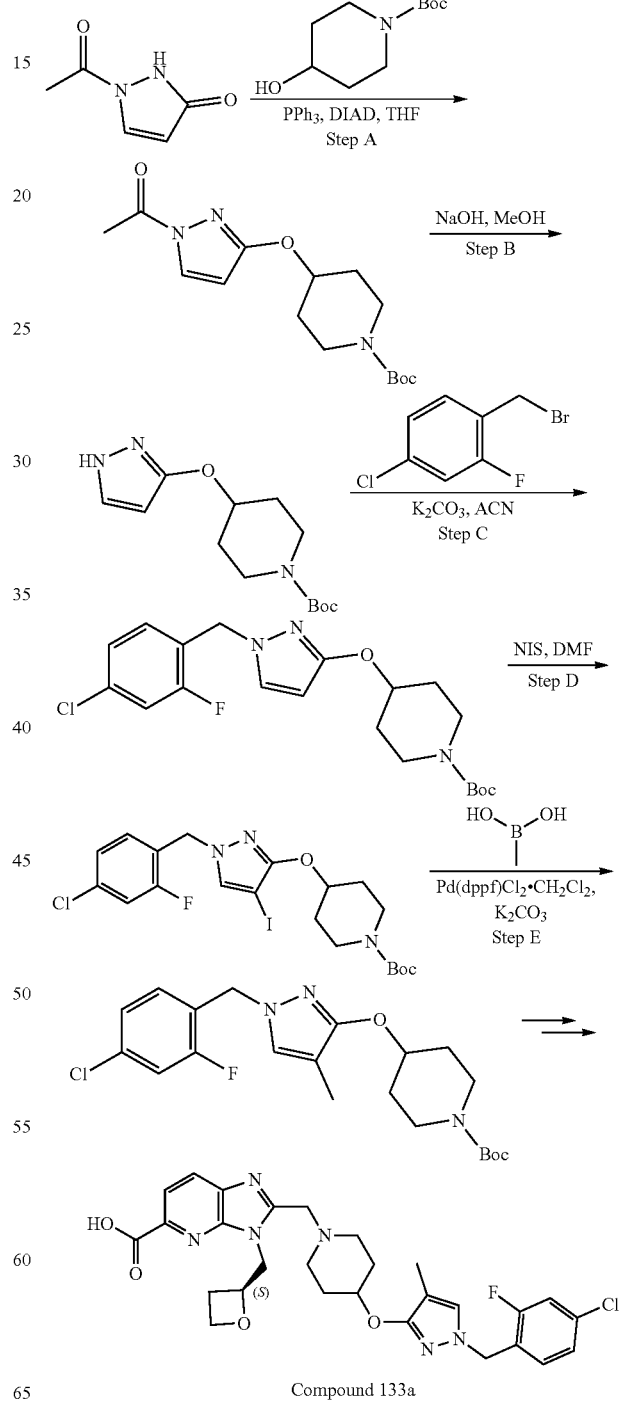

Step A: The Synthesis of tert-butyl 4-((1-acetyl-1H-pyrazol-3-yl)oxy)piperidine-1-carboxylate A mixture of 1-acetyl-1,2-dihydro-3H-pyrazol-3-one (2.1 g, 10.4 mmol), PPh$_3$ (3.4 g, 13.1 mmol) in THF (50 mL) was cooled to 0° C. and DIAD (2.64 g, 13.1 mmol) was added dropwise. The mixture was stirred at room temperature for 3 hours, poured into cold water and extracted with ethyl acetate (2×50 mL). The combined organic layer was dried over Na$_2$SO$_4$, filtered and concentrated under reduced pressure. The residue was purified by column chromatography to give tert-butyl 4-((1-acetyl-1H-pyrazol-3-yl)oxy)piperidine-1-carboxylate (1.7 g, yield: 63%) as a white solid.
MS Calcd.: 309.2. MS Found: 332.1 [M+Na]$^+$.

Step B: The Synthesis of tert-butyl 4-((1H-pyrazol-3-yl)oxy)piperidine-1-carboxylate A mixture of tert-butyl 4-((1-acetyl-1H-pyrazol-3-yl)oxy)piperidine-1-carboxylate (1.7 g, 5.5 mmol), NaOH (290 mg, 8.3 mmol) in MeOH (20 mL) was stirred at room temperature for 2 hours. After the reaction was completed, the reaction mixture was concentrated and purified by column chromatography to give tert-butyl 4-((1H-pyrazol-3-yl)oxy)piperidine-1-carboxylate (1.1 g, 76% yield) as a white solid.
MS Calcd.: 267.2. MS Found: 268.1 [M+H]$^+$.

Step C: The Synthesis of tert-butyl 4-((1-(4-chloro-2-fluorobenzyl)-1H-pyrazol-3-yl)oxy)piperidine-1-carboxylate A mixture of tert-butyl 4-((1H-pyrazol-3-yl)oxy)piperidine-1-carboxylate (500 mg, 1.87 mmol), 1-(bromomethyl)-4-chloro-2-fluorobenzene (500 mg, 2.24 mmol), K$_2$CO$_3$ (774 mg, 5.61 mmol) in acetonitrile (20 mL) was stirred at 80° C. for 3 days. The reaction was filtered and concentrated under reduced pressure. The residue was purified by silica gel column chromatography to give tert-butyl 4-((1-(4-chloro-2-fluorobenzyl)-1H-pyrazol-3-yl)oxy)piperidine-1-carboxylate (430 mg, yield: 56%) as a colorless oil.
MS Calcd.: 409.2. MS Found: 354.1 [M+H-56]$^+$.

Step D: The Synthesis of tert-butyl 4-((1-(4-chloro-2-fluorobenzyl)-4-iodo-1H-pyrazol-3-yl)oxy)piperidine-1-carboxylate To a solution of tert-butyl 4-((1-(4-chloro-2-fluorobenzyl)-1H-pyrazol-3-yl)oxy)piperidine-1-carboxylate (100 mg, 0.24 mmol) in DMF (2 mL) was added NIS (83 mg, 0.36 mmol). The reaction mixture was stirred at 60° C. for 5 hours. After the reaction was completed, the reaction mixture was quenched with water (20 mL) and extracted with ethyl acetate (30 mL×3). The organic layers were combined and washed with brine (50 mL×2), dried over Na$_2$SO$_4$, filtered, and concentrated in vacuum to give tert-butyl 4-((1-(4-chloro-2-fluorobenzyl)-4-iodo-1H-pyrazol-3-yl)oxy)piperidine-1-carboxylate (100 mg, 77% yield) as a yellow solid.
MS Calcd.: 535.0. MS Found: 479.8 [M+H-56].

Step E: The Synthesis of tert-butyl 4-((1-(4-chloro-2-fluorobenzyl)-4-methyl-1H-pyrazol-3-yl)oxy)piperidine-1-carboxylate To a solution of tert-butyl 4-((1-(4-chloro-2-fluorobenzyl)-4-iodo-1H-pyrazol-3-yl)oxy)piperidine-1-carboxylate (100 mg, 0.24 mmol) in dioxane (2 mL) was added methylboronic acid (20 mg, 0.33 mmol), Pd(dppf)Cl$_2$·CH$_2$Cl$_2$ (15 mg, 0.02 mmol) and K$_2$CO$_3$ (77 mg, 0.56 mmol). The reaction mixture was degassed and charged with N$_2$ and stirred at 100° C. for 16 hours. After the reaction was completed, the reaction mixture was quenched with water (20 mL) and extracted with ethyl acetate (30 mL×3). The organic layers were combined and washed with brine (50 mL×2), dried over Na$_2$SO$_4$, filtered, and concentrated in vacuum. The residue was purified by silica gel column chromatography to give tert-butyl 4-((1-(4-chloro-2-fluorobenzyl)-4-iodo-1H-pyrazol-3-yl)oxy)piperidine-1-carboxylate (80 mg, crude) as a yellow solid.
MS Calcd.: 423.2. MS Found: 424.0 [M+H]$^+$. 2-{[4-({1-[(4-Chloro-2-fluorophenyl)methyl]-4-methyl-1H-pyrazol-3-yl}oxy)piperidin-1-yl]methyl}-3-{[(2S)-oxetan-2-yl]methyl}-3H-imidazo[4,5-b]pyridine-5-carboxylic acid (3.3 mg) was obtained as a white solid by the similar procedure of Compound 109a. MS Calcd.: 568.2. MS Found: 569.4 [M+H]$^+$.
$^1$H NMR (400 MHz, DMSO-d$_6$): δ 8.08 (d, J=8.4 Hz, 1H), 7.96 (d, J=8.4 Hz, 1H), 7.43 (dd, J=9.6 Hz, 1.6 Hz, 1H), 7.38 (s, 1H), 7.26 (dd, J=8.4 Hz, 1.6 Hz, 1H), 7.06 (t, J=8.4 Hz, 1H), 5.13-5.20 (m, 1H), 5.12 (s, 2H), 4.83 (dd, J=14.0, 5.4 Hz, 1H), 4.70 (dd, J=15.2, 3.6 Hz, 1H), 4.42-4.52 (m, 2H), 4.30-4.39 (m, 1H), 3.95 (d, J=14.0 Hz, 1H), 3.88 (d, J=14.0 Hz, 1H), 2.64-2.75 (m, 3H), 2.43-2.51 (m, 1H), 2.32-2.38 (m, 2H), 1.85-1.97 (m, 2H), 1.82 (s, 3H), 1.58-1.70 (m, 2H).
$^{19}$F NMR (377 MHz, DMSO-d6): δ −115.62.

Example 36: 2-{[4-({4-chloro-1-[(4-chloro-2-fluorophenyl)methyl]-1H-pyrazol-3-yl}oxy)piperidin-1-yl]methyl}-3-{[(2S)-oxetan-2-yl]methyl}-3H-imidazo[4,5-b]pyridine-5-carboxylic acid (Compound 183a)

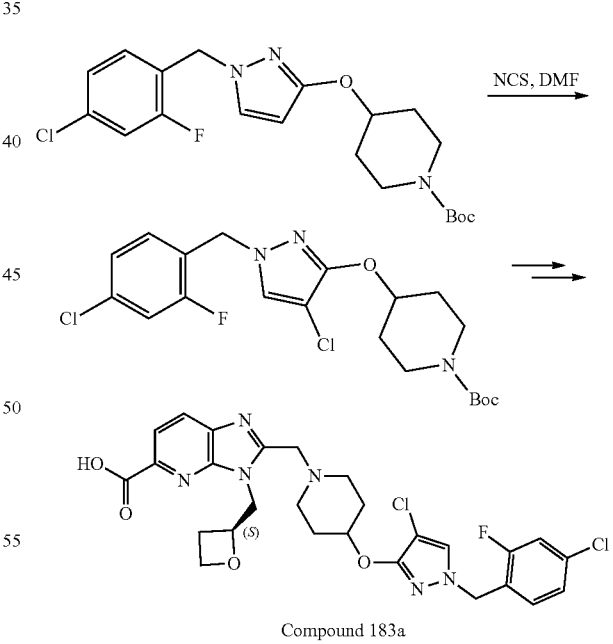

Compound 183a

To a solution of tert-butyl 4-((1-(4-chloro-2-fluorobenzyl)-1H-pyrazol-3-yl)oxy)piperidine-1-carboxylate (110 mg, 0.27 mmol) in DMF (2 mL) was added NCS (53 mg, 0.39 mmol). The reaction mixture was stirred at 80° C. for 16 hours. After the reaction was completed, the reaction mixture was quenched with water (20 mL) and extracted with ethyl acetate (30 mL×3). The organic layers were combined and washed with brine (50 mL×2), dried over Na₂SO₄, filtered, and concentrated in vacuum to give tert-butyl 4-((4-chloro-1-(4-chloro-2-fluorobenzyl)-1H-pyrazol-3-yl)oxy)piperidine-1-carboxylate (100 mg, 92% yield) as a yellow solid.

MS Calcd.: 443.1 MS Found: 387.9 [M+H-56]⁺. 2-{[4-({4-Chloro-1-[(4-chloro-2-fluorophenyl)methyl]-1H-pyrazol-3-yl}oxy)piperidin-1-yl]methyl}-3-{[(2S)-oxetan-2-yl]methyl}-3H-imidazo[4,5-b]pyridine-5-carboxylic acid (36.9 mg) was obtained as a white solid by the similar procedure of Compound 109a. MS Calcd.: 588.2. MS Found: 589.2 [M+H]⁺.

¹H NMR (400 MHz, DMSO-d₆): δ 8.07 (d, J=8.0 Hz, 1H), 7.95 (d, J=8.4 Hz, 1H), 7.91 (s, 1H), 7.46 (dd, J=10.0, 2.0 Hz, 1H), 7.29 (dd, J=8.0, 2.0 Hz, 1H), 7.17 (t, J=8.0 Hz, 1H), 5.19 (s, 2H), 5.10-5.18 (m, 1H), 4.78-4.86 (m, 1H), 4.65-4.72 (m, 1H), 4.45-4.54 (m, 2H), 4.33-4.39 (m, 1H), 3.96 (d, J=13.6 Hz, 1H), 3.89 (d, J=13.6 Hz, 1H), 2.64-2.76 (m, 3H), 2.45-2.48 (m, 1H), 2.31-2.40 (m, 2H), 1.91-1.97 (m, 2H), 1.63-1.73 (m, 2H). 19F NMR (377 MHz, DMSO-d6): δ −115.34.

Example 37: 2-{[4-({1-[(4-chloro-2-fluorophenyl)methyl]-1H-pyrazol-4-yl}oxy)piperidin-1-yl]methyl}-3-{[(2S)-oxetan-2-yl]methyl}-3H-imidazo[4,5-b]pyridine-5-carboxylic acid (Compound 184a)

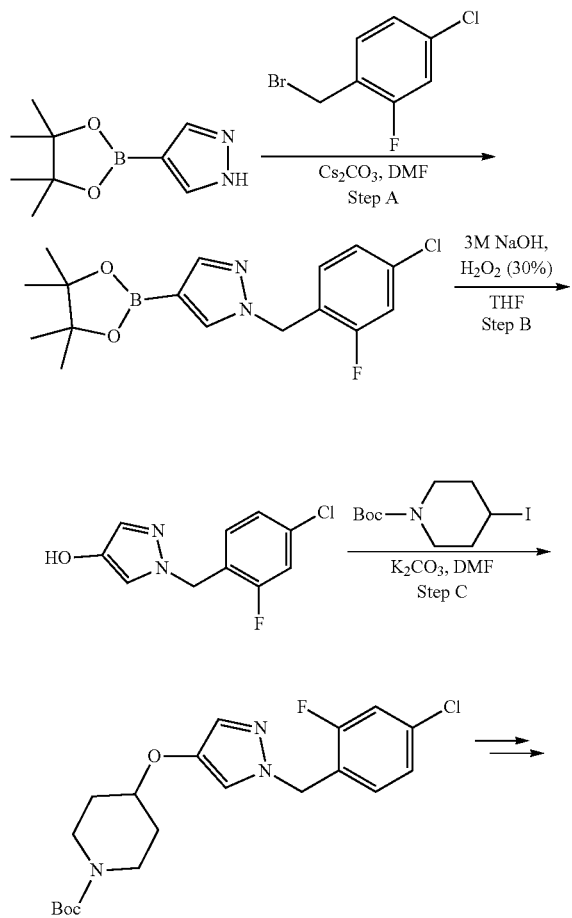

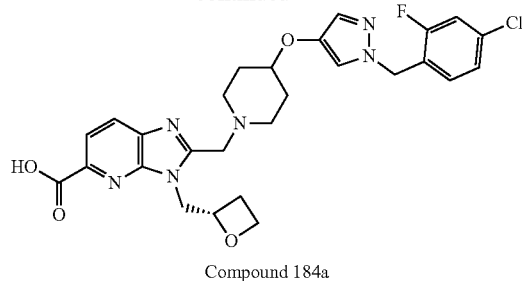

Compound 184a

Step A: The Synthesis of 1-(4-chloro-2-fluorobenzyl)-4-(4,4,5,5-tetramethyl-1,3,2-dioxaborolan-2-yl)-1H-pyrazole To a solution of 4-(4,4,5,5-tetramethyl-1,3,2-dioxaborolan-2-yl)-1H-pyrazole (600 mg, 3.1 mmol) and 1-(bromomethyl)-4-chloro-2-fluorobenzene (758 mg, 3.4 mmol) in DMF (10 mL) was added Cs₂CO₃ (1.51 g, 4.6 mmol) at room temperature. The reaction mixture was stirred at room temperature for 16 hours. After the reaction was completed, the reaction mixture was quenched with water (10 mL) and extracted with ethyl acetate (30 mL×3). The organic layer was combined and washed with brine (30 mL×5), dried over s Na₂SO₄, filtered, and concentrated in vacuum. The residue was purified by column chromatography (PE/EA=2/1) to give 1-(4-chloro-2-fluorobenzyl)-4-(4,4,5,5-tetramethyl-1,3,2-dioxaborolan-2-yl)-1H-pyrazole (600 mg, 58%) as a white solid.

Step B: The Synthesis of 1-(4-chloro-2-fluorobenzyl)-1H-pyrazol-4-ol

To a solution of 1-(4-chloro-2-fluorobenzyl)-4-(4,4,5,5-tetramethyl-1,3,2-dioxaborolan-2-yl)-1H-pyrazole (600 mg, 1.8 mmol) in THF (10 mL) was added NaOH solution (3 M, 1.6 mL) and H₂O₂ (30%, 1.6 mL) at 0° C. The reaction was stirred at room temperature for 1 hour. After the reaction was completed, the reaction mixture was quenched with water (5 mL) and extracted with ethyl acetate (20 mL×3). The organic layer was combined and washed with brine (10 mL), dried over Na₂SO₄, filtered, and concentrated in vacuum. The residue was purified by column chromatography (PE/EA=3/1) to give the impure 1-(4-chloro-2-fluorobenzyl)-1H-pyrazol-4-ol (436 mg) as a colorless oil.

MS Calcd.: 226.0. MS Found: 227.0 [M+H]⁺.

Step C: The Synthesis of tert-butyl 4-((1-(4-chloro-2-fluorobenzyl)-1H-pyrazol-4-yl)oxy)piperidine-1-carboxylate To a solution of 1-(4-chloro-2-fluorobenzyl)-1H-pyrazol-4-ol (286 mg, 1.3 mmol) in DMF (5 mL) was added tert-butyl 4-iodopiperidine-1-carboxylate (787 mg, 2.5 mmol) and K₂CO₃ (523 mg, 3.8 mmol) at room temperature. The reaction mixture was stirred at 60° C. for 16 hours. After the reaction was completed, the reaction mixture was quenched with water (10 mL) and extracted with ethyl acetate (20 mL×3). The organic layer was combined and washed with brine (20 mL×5), dried over Na₂SO₄, filtered, and concentrated in vacuum. The residue was purified by column chromatography (PE/EA=5/1) to give tert-butyl 4-((1-(4-chloro-2-fluorobenzyl)-1H-pyrazol-4-yl)oxy)piperidine-1-carboxylate (144 mg, 28% yield) as a colorless oil.

MS Calcd.: 409.2. MS Found: 354.0 [M+H-56]⁺. 2-{[4-({1-[(4-chloro-2-fluorophenyl)methyl]-1H-pyrazol-4-yl}oxy)piperidin-1-yl]methyl}-3-{[(2S)-oxetan-2-yl]methyl}-3H-imidazo[4,5-b]pyridine-5-carboxylic acid (15 mg) was obtained as a white solid by the similar procedure of Compound 109a. MS Calcd.: 554.2. MS Found: 555.3 [M+H]⁺.

$^1$H NMR (400 MHz, DMSO-d$_6$): 7.84-7.96 (m, 2H), 7.59 (s, 1H), 7.45 (dd, J=10.0 Hz, 2.0 Hz, 1H), 7.28 (dd, J=8.4 Hz, 2.0 Hz, 1H), 7.24 (s, 1H), 7.14 (t, J=8.0 Hz, 1H), 5.23 (s, 2H), 5.08-5.17 (m, 1H), 4.77-4.82 (m, 1H), 4.60-4.66 (m, 1H), 4.45-4.51 (m, 1H), 4.30-4.36 (m, 1H), 3.90-4.00 (m, 2H), 3.78 (d, J=13.2 Hz, 1H), 2.60-2.79 (m, 3H), 2.42-2.51 (m, 1H), 2.26-2.35 (m, 2H), 1.84-1.95 (m, 2H), 1.51-1.65 (m, 2H). $^{19}$F NMR (377 MHz, DMSO-d6): δ –115.38.

Example 38: 2-({4-[(6-benzylpyridin-2-yl)oxy]piperidin-1-yl}methyl)-3-{[(2S)-oxetan-2-yl]methyl}-3H-imidazo[4,5-b]pyridine-5-carboxylic acid (Compound 123a)

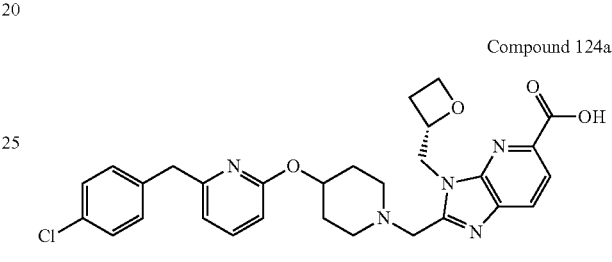

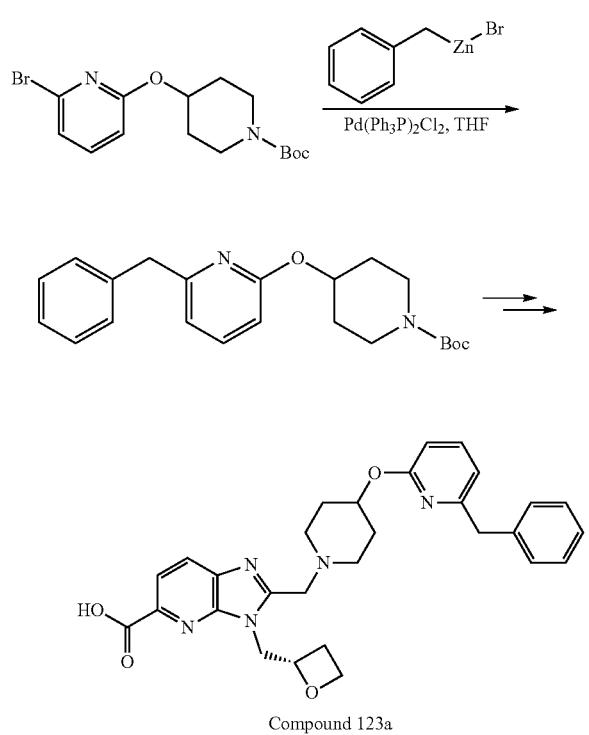

Compound 123a

A mixture of tert-butyl 4-((6-bromopyridin-2-yl)oxy)piperidine-1-carboxylate (300 mg, 0.84 mmol), benzylzinc(II) bromide (1.9 g, 8.4 mmol), Pd(Ph$_3$P)$_2$Cl$_2$ (118 mg, 0.17 mmol) in THF (10 mL) was stirred at 70° C. for 12 hours under an atmosphere of nitrogen. The reaction mixture was concentrated under vacuum, the residue was applied on a silica gel column and eluted with PE:EA=10:1 to give tert-butyl 4-((6-benzylpyridin-2-yl)oxy)piperidine-1-carboxylate (150 mg, crude, mixture of product and by-product). The crude product was purified by Prep-HPLC to afford tert-butyl 4-((6-benzylpyridin-2-yl)oxy)piperidine-1-carboxylate (100 mg, yield: 32%) as a colorless oil. MS Calcd.: 368.4. MS Found: 369.2 [M+H]⁺.

2-({4-[(6-Benzylpyridin-2-yl)oxy]piperidin-1-yl}methyl)-3-{[(2S)-oxetan-2-yl]methyl}-3H-imidazo[4,5-b]pyridine-5-carboxylic acid (34 mg) was then obtained as a white solid by the similar procedure of Compound 109a. MS Calcd.: 513.2; MS Found: 514.2 [M+H]⁺.

$^1$H NMR (400 MHz, DMSO-d$_6$): δ 8.07 (d, J=8.4 Hz, 1H), 7.97 (d, J=8.4 Hz, 1H), 7.54-7.59 (m, 1H), 7.25-7.30 (m, 4H), 7.15-7.20 (m, 1H), 6.81 (d, J=7.2 Hz, 1H), 6.56 (d, J=8.0 Hz, 1H), 5.12-5.19 (m, 1H), 4.95-5.03 (m, 1H), 4.80-4.88 (m, 1H), 4.68-4.75 (m, 1H), 4.46-4.51 (m, 1H), 4.31-4.38 (m, 1H), 3.86-3.99 (m, 4H), 2.61-2.82 (m, 3H), 2.45-2.55 (m, 1H), 2.37 (t, J=6.4 Hz, 2H), 1.90-1.97 (m, 2H), 1.57-1.69 (m, 2H).

Example 39: (S)-2-((4-((6-(4-chlorobenzyl)pyridin-2-yl)oxy)piperidin-1-yl)methyl)-3-(oxetan-2-ylmethyl)-3H-imidazo[4,5-b]pyridine-5-carboxylic acid (Compound 124a)

Compound 124a

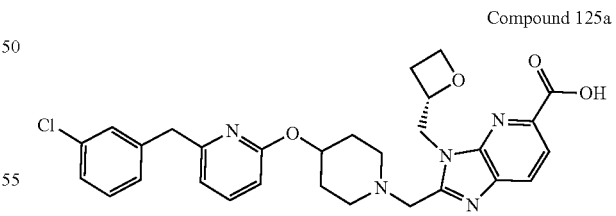

MS Calcd.: 547.2. MS Found: 548.2 (M+H)⁺.

$^1$H NMR (400 MHz, DMSO-d$_6$) δ 13.04 (br.s, 1H), 8.14 (d, J=8.4 Hz, 11H), 8.00 (d, J=8.4 Hz, 1H), 7.58 (dd, J=7.2, 0.8 Hz, 1H), 7.27-7.36 (m, 4H), 6.82 (d, J=7.2 Hz, 1H), 6.58 (d, J=8.0 Hz, 1H), 5.18-5.25 (m, 1H), 4.91-5.01 (m, 1H), 4.85 (dd, J=14.8, 6.4 Hz, 1H), 4.72 (dd, J=14.4, 4.4 Hz, 1H), 4.45-4.52 (m, 1H), 4.33-4.40 (m, 1H), 3.89-4.03 (m, 4H), 2.60-2.85 (m, 3H), 2.35-2.41 (m, 3H), 1.92-2.00 (m, 2H), 1.56-1.68 (m, 2H).

Example 40: (S)-2-((4-((6-(3-chlorobenzyl)pyridin-2-yl)oxy)piperidin-1-yl)methyl)-3-(oxetan-2-ylmethyl)-3H-imidazo[4,5-b]pyridine-5-carboxylic acid (Compound 125a)

Compound 125a

MS Calcd.: 547.2. MS Found: 548.2 (M+H)⁺.

$^1$H NMR (400 MHz, DMSO-d$_6$) δ 13.04 (br.s, 1H), 8.14 (d, J=8.4 Hz, 1H), 7.99 (d, J=8.0 Hz, 1H), 7.55-7.63 (m, 1H), 7.40 (s, 1H), 7.22-7.32 (m, 3H), 6.86 (d, J=7.2 Hz, 1H), 6.58 (d, J=8.0 Hz, 1H), 5.12-5.22 (m, 1H), 4.93-5.01 (m, 1H), 4.84 (dd, J=14.8, 6.4 Hz, 1H), 4.71 (dd, J=14.8, 4.4 Hz, 1H), 4.44-4.52 (m, 1H), 4.32-4.41 (m, 1H), 3.92-4.02 (m, 4H), 2.63-2.86 (m, 3H), 2.32-2.52 (m, 3H), 1.89-2.00 (m, 2H), 1.52-1.70 (m, 2H).

Example 41: (S)-2-((4-((6-(2-chlorobenzyl)pyridin-2-yl)oxy)piperidin-1-yl)methyl)-3-(oxetan-2-ylmethyl)-3H-imidazo[4,5-b]pyridine-5-carboxylic acid (Compound 126a)

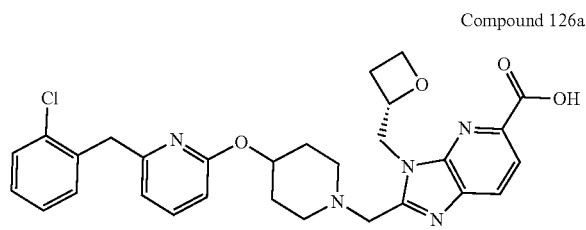 [SMILES: O=C(O)c1ccc2nc(CN3CCC(Oc4cccc(Cc5ccccc5Cl)n4)CC3)n(C[C@@H]3CCO3)c2n1]

Compound 126a

MS Calcd.: 547.2. MS Found: 548.2 (M+H)⁺.

¹H NMR (400 MHz, DMSO-d₆) δ 12.98 (br.s, 1H), 8.15 (d, J=8.4 Hz, 1H), 8.00 (d, J=8.4 Hz, 1H), 7.55-7.61 (m, 1H), 7.36-7.45 (m, 2H), 7.25-7.31 (m, 2H), 6.77 (d, J=7.2 Hz, 1H), 6.57 (d, J=8.0 Hz, 1H), 5.10-5.21 (m, 1H), 4.81-4.91 (m, 2H), 4.71 (dd, J=14.8, 4.4 Hz, 1H), 4.46-4.52 (m, 1H), 4.36-4.41 (m, 1H), 4.11 (s, 2H), 3.96 (q, J=13.6 Hz, 2H), 2.60-2.85 (m, 3H), 2.44-2.50 (m, 1H), 2.25-2.37 (m, 2H), 1.82-1.95 (m, 2H), 1.51-1.68 (m, 2H).

Example 42: 3-{[(2S)-oxetan-2-yl]methyl}-2-({4-[(6-{[4-(trifluoromethyl)phenyl]methyl}pyridin-2-yl)oxy]piperidin-1-yl}methyl)-3H-imidazo[4,5-b]pyridine-5-carboxylic acid (Compound 145a)

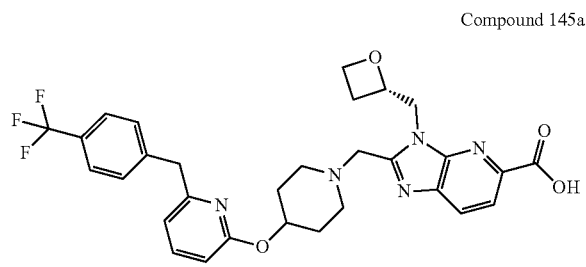 [SMILES: O=C(O)c1ccc2nc(CN3CCC(Oc4cccc(Cc5ccc(C(F)(F)F)cc5)n4)CC3)n(C[C@@H]3CCO3)c2n1]

Compound 145a

MS Calcd.: 581.2. MS Found: 582.2 [M+H]⁺.

¹H NMR (400 MHz, CD₃OD): δ 8.06 (d, J=7.6 Hz, 1H), 8.00 (d, J=8.4 Hz, 1H), 7.57-7.50 (m, 3H), 7.45 (d, J=7.6 Hz, 2H), 6.79 (d, J=7.2 Hz, 1H), 6.55 (d, J=8.0 Hz, 1H), 5.32-5.22 (m, 1H), 5.04-4.92 (m, 2H), 4.89-4.84 (m, 1H), 4.63-4.57 (m, 1H), 4.43-4.38 (m, 1H), 4.08-4.05 (m, 3H), 3.93-3.90 (m, 1H), 2.83-2.72 (m, 3H), 2.60-2.47 (m, 1H), 2.44-2.39 (m, 2H), 2.00-1.93 (m, 2H), 1.78-1.64 (m, 2H).
¹⁹F NMR (377 MHz, CD₃OD): δ 63.79.

Example 43: 2-{[4-({6-[(4-cyclopropylphenyl)methyl]pyridin-2-yl}oxy)piperidin-1-yl]methyl}-3-{[(2S)-oxetan-2-yl]methyl}-3H-imidazo[4,5-b]pyridine-5-carboxylic acid (Compound 146a)

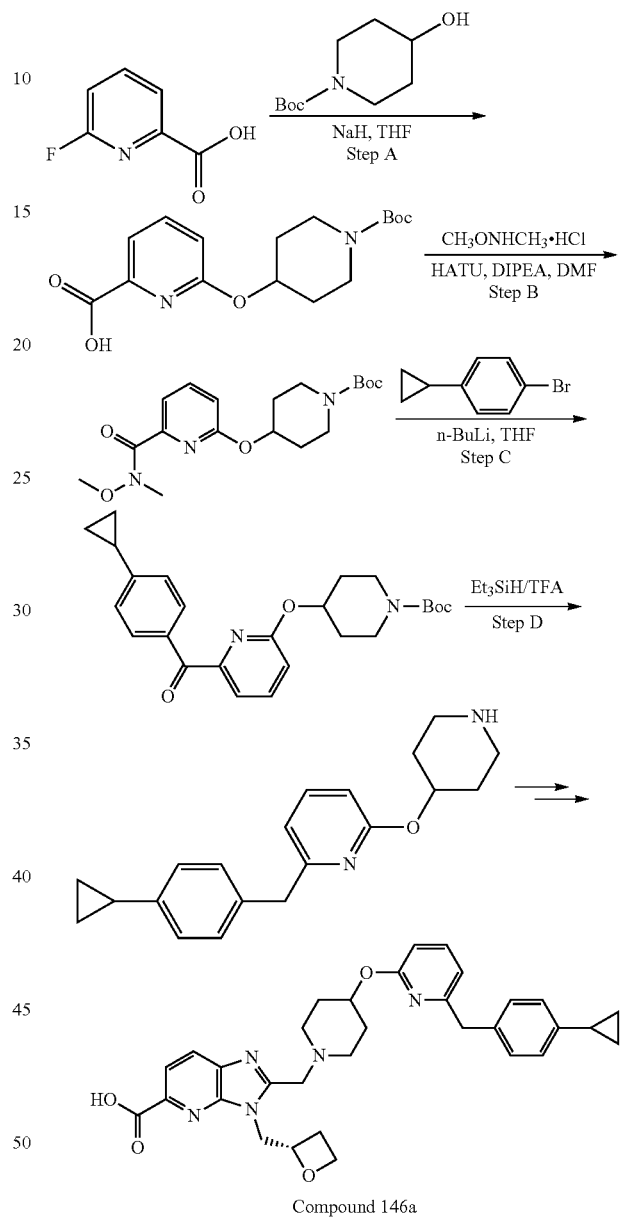

Compound 146a

Step A: The Synthesis of 6-((1-(tert-butoxycarbonyl)piperidin-4-yl)oxy)picolinic acid To a stirred mixture of tert-butyl 4-hydroxypiperidine-1-carboxylate (8.6 g, 35.5 mmol) in dry THF (80 mL) was added NaH (4.3 g, 106.5 mmol) in portions at 0° C. The reaction mixture was stirred at room temperature for 2 hours. To the above reaction mixture was added 6-fluoropicolinic acid (5.0 g, 1.56 mmol) in portions at room temperature. The final reaction mixture was stirred at 80° C. for 18 hours. Upon cooling down, the reaction mixture was quenched with saturated NH₄Cl (200 mL) and extracted with ethyl acetate (100 mL). The combined organic layers were dried over anhydrous $Na_2SO_4$ and then concentrated under vacuum. The residue was purified by reverse-phase chromatography to give 6-((1-(tert-butoxycarbonyl)piperidin-4-yl)oxy)picolinic acid (3.6 g, yield: 31%) as a yellow solid.

MS Calcd.: 322.2. MS Found: 323.2 [M+H]$^+$, 267.1 [M-56+H]$^+$.

Step B: The Synthesis of tert-butyl 4-((6-(methoxy(methyl)carbamoyl)pyridin-2-yl)oxy)piperidine-1-carboxylate A mixture of 6-((1-(tert-butoxycarbonyl)piperidin-4-yl)oxy)picolinic acid (3.58 g, 11.1 mmol), DIPEA (7.76 g, 44.4 mmol), $CH_3ONHCH_3$—HCl (2.17 g, 22.3 mmol), HATU (5.47 g, 16.7 mmol) in DMF (30 mL) was stirred at room temperature for 18 hours. The reaction mixture was diluted with saturated $NaHCO_3$ (150 mL) and extracted with ethyl acetate (80 mL). The combined organic layers were washed with brine (50 mL), dried over anhydrous $Na_2SO_4$ and concentrated under vacuum. The residue was purified by reverse-phase chromatography to give tert-butyl 4-((6-(methoxy(methyl)carbamoyl)pyridin-2-yl)oxy)piperidine-1-carboxylate (2.91 g, yield: 72%) as a yellow oil.

MS Calcd.: 365.2. MS Found: 366.4 [M+H]$^+$.

Step C: The Synthesis of tert-butyl 4-((6-(4-cyclopropylbenzoyl)pyridin-2-yl)oxy)piperidine-1-carboxylate To a stirred solution of 1-bromo-4-cyclopropylbenzene (386 mg, 1.97 mmol) in dry THF (15 mL) was added n-BuLi (1.4 mL, 3.29 mmol, 2.5N in n-hexane) dropwise at −78° C. The reaction mixture was stirred at −78° C. for 1 hour. To the above reaction mixture was added a solution of tert-butyl 4-((6-(methoxy(methyl)carbamoyl)pyridin-2-yl)oxy)piperidine-1-carboxylate (600 mg, 1.64 mmol) in dry THF (5.0 mL) dropwise at −78° C. The final reaction mixture was slowly warm up to room temperature during a period of about 2 hours. The reaction mixture was quenched with saturated $NH_4C_1$ (200 mL) and extracted with ethyl acetate (100 mL). The combined organic layers were dried over anhydrous $Na_2SO_4$ and then concentrated under vacuum. The residue was purified by silica gel column chromatography to give tert-butyl 4-((6-(4-cyclopropylbenzoyl)pyridin-2-yl)oxy)piperidine-1-carboxylate (210 mg, yield: 30%) as a yellow oil.

MS Calcd.: 422.2. MS Found: 423.6 [M+H]$^+$, 367.5 [M-56+H]$^+$.

Step D: The Synthesis of 2-(4-cyclopropylbenzyl)-6-(piperidin-4-yloxy)pyridine and 2-(piperidin-4-yloxy)-6-(4-propylbenzyl)pyridine A mixture of tert-butyl 4-((6-(4-cyclopropylbenzoyl)pyridin-2-yl)oxy)piperidine-1-carboxylate (210 mg, 0.50 mmol) in $Et_3SiH$ (2.0 mL) and TFA (2.0 mL) was stirred at 80° C. for 2 hours in a sealed tube. Upon cooling down, the reaction mixture was adjusted the pH to 9 with saturated $NaHCO_3$. The mixture was then extracted with ethyl acetate (30 mL). The combined organic layers were dried over anhydrous $Na_2SO_4$ and concentrated under vacuum to give 2-(4-cyclopropylbenzyl)-6-(piperidin-4-yloxy)pyridine and 2-(piperidin-4-yloxy)-6-(4-propylbenzyl)pyridine (2.20 g, crude) as a colorless oil. Used directly for the next step.

MS Calcd.: 308.2. MS Found: 309.5 [M+H]$^+$. 2-{[4-({6-[(4-Cyclopropylphenyl)methyl]pyridin-2-yl}oxy)piperidin-1-yl]methyl}-3-{[(2S)-oxetan-2-yl]methyl}-3H-imidazo[4,5-b]pyridine-5-carboxylic acid (48 mg) was then obtained as a white solid by the similar procedure of Compound 109a.

MS Calcd.: 553.3. MS Found: 554.7 [M+H]$^+$.

$^1$H NMR (400 MHz, $CD_3OD$): δ 8.12-8.00 (m, 2H), 7.52 (t, J=8.0 Hz, 1H), 7.13 (d, J=8.0 Hz, 2H), 6.98 (d, J=8.4 Hz, 2H), 6.73 (d, J=7.2 Hz, 1H), 6.54 (d, J=8.0 Hz, 1H), 5.33-5.29 (m, 1H), 5.10-4.97 (m, 2H), 4.98-4.88 (m, 1H), 4.66-4.60 (m, 1H), 4.48-4.40 (m, 1H), 4.10 (d, J=13.6 Hz, 1H), 3.98 (d, J=13.6 Hz, 1H), 3.93 (s, 2H), 2.87-2.75 (m, 3H), 2.62-2.50 (m, 1H) 2.50-2.40 (m, 2H), 2.05-1.95 (m, 2H), 1.90-1.81 (m, 1H), 1.79-1.69 (m, 2H), 0.93-0.84 (m, 2H), 0.63-0.56 (m, 2H).

Example 44: 2-{[4-({6-[(4-chloro-2-oxo-1,2-dihydropyridin-1-yl)methyl]pyridin-2-yl}oxy)piperidin-1-yl]methyl}-3-{[(2S)-oxetan-2-yl]methyl}-3H-imidazo[4,5-b]pyridine-5-carboxylic acid (Compound 149a)

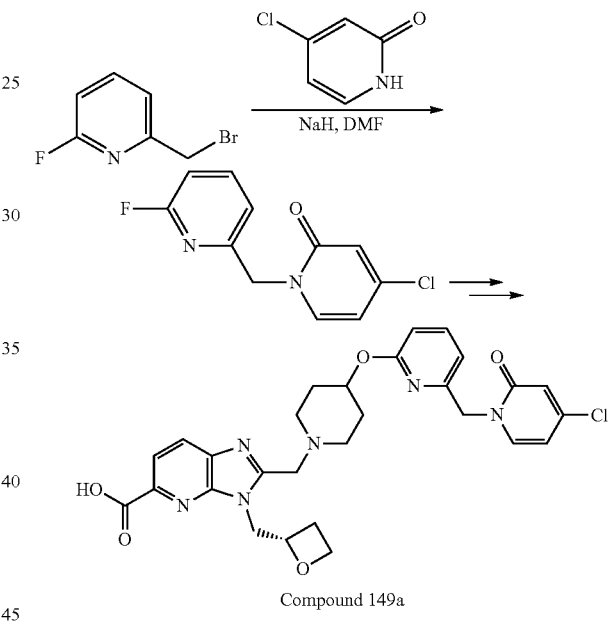

Compound 149a

A mixture of 4-chloropyridin-2(1H)-one (68 mg, 0.53 mmol) in DMF (2 mL) was cooled to 0° C., and NaH (32 mg, 0.79 mmol) was added. The mixture was stirred at 0° C. for 20 min under Ar. 2-(bromomethyl)-6-fluoropyridine (100 mg, 0.53 mmol) in DMF (0.5 mL) was added dropwise. The resulting mixture was stirred at room temperature for 2 hours under Ar, then cooled to 0° C., quenched with $NH_4C_1$ (aq.) (8 mL), extracted with ethyl acetate (2×15 mL). The combined organic layers were dried over $Na_2SO_4$, filtered, and concentrated under reduced pressure to give 4-chloro-1-((6-fluoropyridin-2-yl)methyl)pyridin-2(1H)-one (130 mg) as a yellow solid.

MS Calcd.: 238.0. MS Found: 239.1 [M+H]$^+$. 2-{[4-({6-[(4-Chloro-2-oxo-1,2-dihydropyridin-1-yl)methyl]pyridin-2-yl}oxy)piperidin-1-yl]methyl}-3-{[(2S)-oxetan-2-yl]methyl}-3H-imidazo[4,5-b]pyridine-5-carboxylic acid was then obtained as a white solid by the similar procedure of Compound 109a. MS Calcd.: 564.2. MS Found: 565.2 [M+H]$^+$.

$^1$H NMR (400 MHz, DMSO-d6): δ 7.90-7.95 (m, 2H), 7.85 (d, J=7.2 Hz, 1H), 7.65 (t, J=8.0 Hz, 1H), 6.87 (d, J=7.2

Hz, 1H), 6.64 (d, J=8.0 Hz, 1H), 6.54 (d, J=2.4 Hz, 1H), 6.42 (dd, J=7.2 Hz, 2.4 Hz, 1H), 5.09-5.14 (m, 3H), 4.79-4.87 (m, 1H), 4.60-4.72 (m, 2H), 4.46-4.51 (m, 1H), 4.28-4.34 (m, 1H), 3.94 (d, J=13.6 Hz, 1H), 3.72-3.78 (m, 1H), 2.75-2.83 (m, 1H), 2.59-2.75 (m, 2H), 2.38-2.51 (m, 1H), 2.17-2.25 (m, 2H), 1.79-1.90 (m, 2H), 1.48-1.58 (m, 2H).

Example 45: 3-{[(2S)-oxetan-2-yl]methyl}-2-{[4-({6-[(1-oxo-2,3-dihydro-1H-isoindol-2-yl)methyl]pyridin-2-yl}oxy)piperidin-1-yl]methyl}-3H-imidazo[4,5-b]pyridine-5-carboxylic acid (Compound 148a)

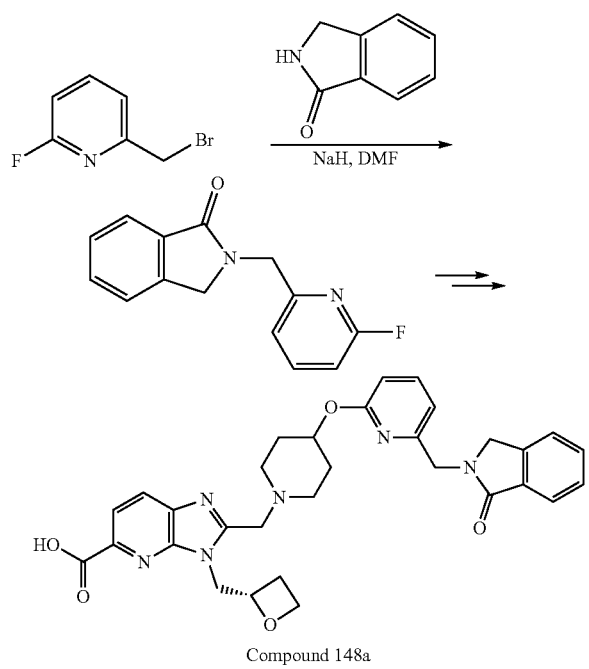

Compound 148a

A mixture of isoindolin-1-one (140 mg, 1.05 mmol) in DMF (5 mL) was cooled to 0° C., NaH (63 mg, 1.57 mmol) was added. The mixture was stirred at 0° C. for 20 min under Ar. 2-(bromomethyl)-6-fluoropyridine (200 mg, 1.05 mmol) in DMF (0.5 mL) was added dropwise. The resulting mixture was stirred at room temperature for 1 hour, cooled to 0° C., quenched with NH$_4$C$_1$ (aq.), extracted with ethyl acetate (2×20 mL). The combined organic layers were dried over Na$_2$SO$_4$, filtered, and concentrated under reduced pressure. The residue was purified by column chromatography to give 2-((6-fluoropyridin-2-yl)methyl)isoindolin-1-one (220 mg, yield: 48%) as a colorless oil. MS Calcd.: 242.1. MS Found: 243.0 [M+H]$^+$. 3-{[(2S)-Oxetan-2-yl]methyl}-2-{[4-({6-[(1-oxo-2,3-dihydro-1H-isoindol-2-yl)methyl]pyridin-2-yl}oxy)piperidin-1-yl]methyl}-3H-imidazo[4,5-b]pyridine-5-carboxylic acid was then obtained as a white solid by the similar procedure of Compound 109a. MS Calcd.: 568.2. MS Found: 569.2 [M+H]$^+$.

$^1$H NMR (400 MHz, DMSO-d6): δ 7.98 (d, J=8.0 Hz, 1H), 7.92 (d, J=8.4 Hz, 1H), 7.72 (d, J=7.6 Hz, 1H), 7.65 (t, J=8.0 Hz, 1H), 7.59 (d, J=4.0 Hz, 2H), 7.47-7.52 (m, 1H), 6.86 (d, J=7.2 Hz, 1H), 6.63 (d, J=8.4 Hz, 1H), 5.08-5.14 (m, 1H), 4.59-4.81 (m, 5H), 4.55 (s, 2H), 4.46-4.51 (m, 1H), 4.29-4.34 (m, 1H), 3.85 (d, J=13.6 Hz, 1H), 3.71 (d, J=13.6 Hz, 1H), 2.51-2.65 (m, 3H), 2.43-2.49 (m, 1H), 1.90-1.99 (m, 2H), 1.71-1.82 (m, 2H), 1.42-1.54 (m, 2H).

Example 46: 2-{[4-({6-[(5-chlorothiophen-2-yl)methyl]pyridin-2-yl}oxy)piperidin-1-yl]methyl}-3-{[(2S)-oxetan-2-yl]methyl}-3H-imidazo[4,5-b]pyridine-5-carboxylic acid (Compound 147a)

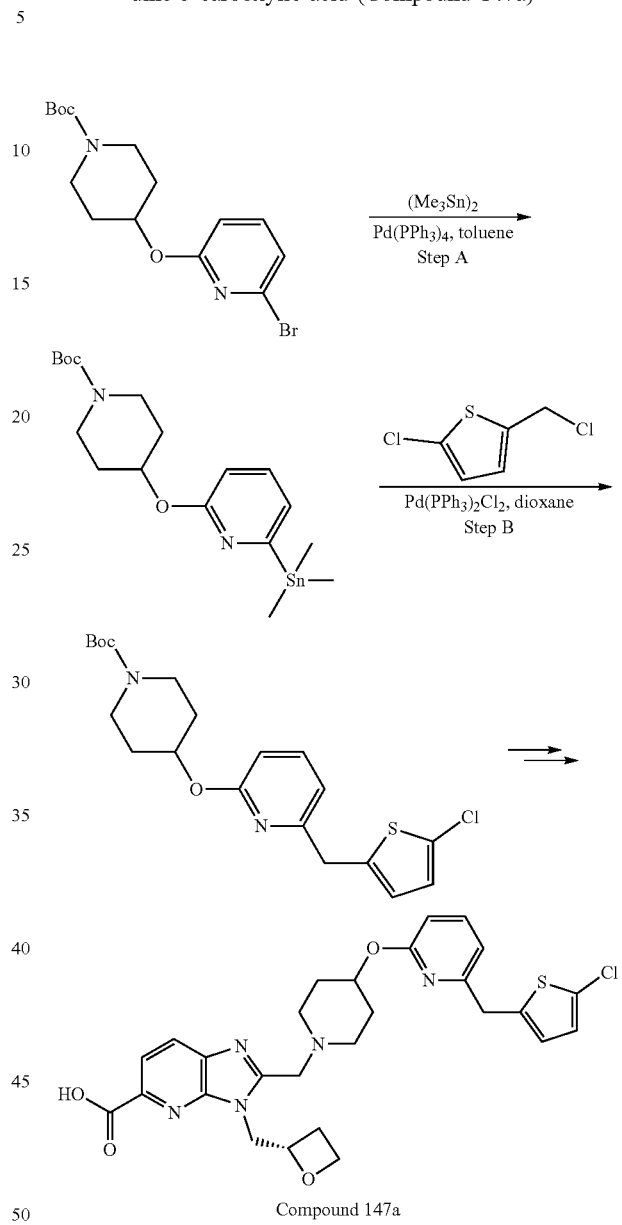

Compound 147a

Step A: The Synthesis of tert-butyl 4-((6-(trimethylstannyl)pyridin-2-yl)oxy)piperidine-1-carboxylate A mixture of tert-butyl 4-((6-bromopyridin-2-yl)oxy)piperidine-1-carboxylate (150 mg, 0.42 mmol), (Me$_3$Sn)$_2$ (206 mg, 0.63 mmol) and Pd(PPh$_3$)$_4$ (48 mg, 0.042 mmol) in toluene (4 mL) was stirred at 110° C. under N$_2$ for 162 hours. The reaction mixture was concentrated, diluted with aq. KF, extracted with DCM. The combined organic layer was concentrated, filtered by a short column chromatography on silica gel (PE/EA=10/1) to give tert-butyl 4-((6-(trimethylstannyl)pyridin-2-yl)oxy)piperidine-1-carboxylate (193 mg) as a brown oil. Used directly for the next step.

Step B: The Synthesis of tert-butyl 4-((6-((5-chlorothiophen-2-yl)methyl)pyridin-2-yl)oxy)piperidine-1-carboxylate A mixture of tert-butyl 4-((6-(trimethylstannyl)pyridin-2-yl)oxy)piperidine-1-carboxylate (193 mg, 0.42 mmol) and 2-chloro-5-(chloromethyl)thiophene (70 mg, 0.42 mmol) and Pd(PPh$_3$)$_2$Cl$_2$ (15 mg, 0.021 mmol) in dioxane (3 mL) was stirred at 90° C. under N$_2$ for 6 hours. The reaction mixture was concentrated in vacuum, purified by prep-TLC (PE/EA=6/1) to give tert-butyl 4-((6-((5-chlorothiophen-2-yl)methyl)pyridin-2-yl)oxy)piperidine-1-carboxylate (100 mg, yield: 58%) as a yellow oil.

MS Calcd.: 408.1. MS Found: 409.1 [M+H]$^+$. 2-{[4-({6-[(5-Chlorothiophen-2-yl)methyl]pyridin-2-yl}oxy)piperidin-1-yl]methyl}-3-{[(2S)-oxetan-2-yl]methyl}-3H-imidazo[4,5-b]pyridine-5-carboxylic acid (59 mg) was then obtained as a white solid by the similar procedure of Compound 109a. MS Calcd.: 553.2. MS Found: 554.1 [M+H]$^+$.

$^1$H NMR (400 MHz, CD$_3$OD): δ 8.11-8.04 (m, 2H), 7.58-7.52 (m, 1H), 6.82 (d, J=7.2 Hz, 1H), 6.76 (d, J=3.6 Hz, 1H), 6.71 (d, J=3.6 Hz, 1H), 6.60 (d, J=8.4 Hz, 1H), 5.33-5.26 (m, 1H), 5.19-5.10 (m, 1H), 5.07-4.97 (m, 1H), 4.86-4.80 (m, 1H), 4.66-4.58 (m, 1H), 4.47-4.40 (m, 1H), 4.19-4.05 (m, 4H), 2.98-2.85 (m, 2H), 2.82-2.70 (m, 1H), 2.61-2.49 (m, 3H), 2.13-2.05 (m, 2H), 1.90-1.77 (m, 2H).

Example 47: 2-{[4-({6-[(4-cyano-2-fluorophenyl)methyl]pyridin-2-yl}oxy)piperidin-1-yl]methyl}-1-{[(2S)-oxetan-2-yl]methyl}-1H-1,3-benzodiazole-6-carboxylic Acid (Compound 135a)

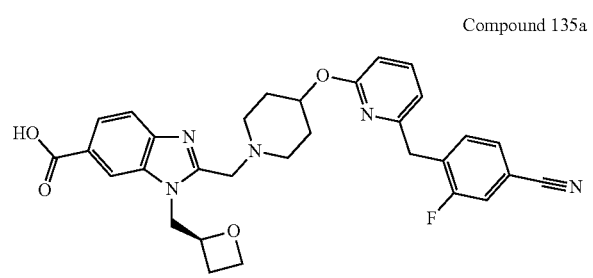 [SMILES: N#Cc1ccc(Cc2cccc(OC3CCN(Cc4nc5ccc(C(=O)O)cc5n4C[C@@H]4CCO4)CC3)n2)c(F)c1]

Compound 135a

Using 4-(bromomethyl)-3-fluorobenzonitrile as the starting material, 2-{[4-({6-[(4-cyano-2-fluorophenyl)methyl]pyridin-2-yl}oxy)piperidin-1-yl]methyl}-1-{[(2S)-oxetan-2-yl]methyl}-1H-1,3-benzodiazole-6-carboxylic acid was obtained as a white solid by the similar procedure of Compound 147a. MS Calcd.: 555.2. MS Found: 556.1 [M+H]$^+$.

$^1$H NMR (400 MHz, CD$_3$OD): δ 8.16 (s, 1H), 7.93 (dd, J=8.8 Hz, 1.6 Hz, 1H), 7.58 (d, J=3.6 Hz, 1H), 7.55 (d, J=3.2 Hz, 1H), 7.53 (d, J=1.6 Hz, 1H), 7.52-7.49 (m, 2H), 6.81 (d, J=7.2 Hz, 1H), 6.55 (d, J=8.0 Hz, 1H), 5.28-5.20 (m, 1H), 4.75-4.68 (m, 2H), 4.68-4.60 (m, 2H), 4.48-4.42 (m, 1H), 4.11 (s, 2H), 3.98 (d, J=13.6 Hz, 1H), 3.88 (d, J=13.6 Hz, 1H), 2.81-2.72 (m, 3H), 2.55-2.48 (m, 1H), 2.39-2.30 (m, 2H), 1.93-1.86 (m, 2H), 1.73-1.62 (m, 2H). $^{19}$F NMR (377 MHz, CD$_3$OD): δ 116.32.

Example 48: 2-{[4-({6-[(4-cyano-2-fluorophenyl)methyl]pyridin-2-yl}oxy)piperidin-1-yl]methyl}-3-{[(2S)-oxetan-2-yl]methyl}-3H-imidazo[4,5-b]pyridine-5-carboxylic acid (Compound 136a)

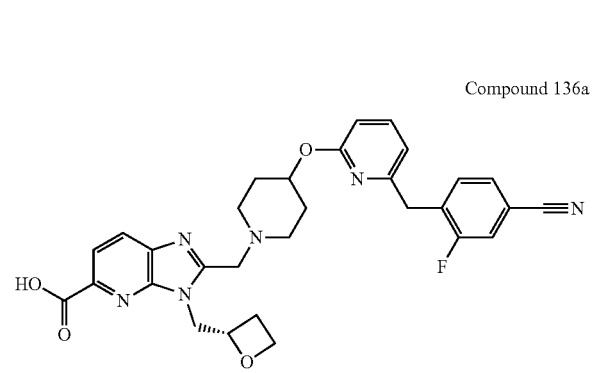 [SMILES: N#Cc1ccc(Cc2cccc(OC3CCN(Cc4nc5ccc(C(=O)O)nc5n4C[C@@H]4CCO4)CC3)n2)c(F)c1]

Compound 136a

MS Calcd.: 556.2. MS Found: 557.0 [M+H]$^+$.

$^1$H NMR (400 MHz, CD$_3$OD): δ 8.05 (d, J=8.0 Hz, 1H), 8.01 (d, J=8.0 Hz, 1H), 7.59-7.47 (m, 4H), 6.82 (d, J=7.2 Hz, 1H), 6.55 (d, J=8.4 Hz, 1H), 5.33-5.20 (m, 1H), 5.08-4.94 (m, 1H), 4.86-4.80 (m, 2H), 4.64-4.57 (m, 1H), 4.46-4.40 (m, 1H), 4.11 (s, 2H), 4.07 (d, J=13.6 Hz, 1H), 3.94 (d, J=13.6 Hz, 1H), 2.85-2.70 (m, 3H), 2.59-2.48 (m, 1H), 2.41-2.31 (m, 2H), 1.95-1.88 (m, 2H), 1.74-1.64 (m, 2H). $^{19}$F NMR (377 MHz, CD$_3$OD): δ 116.32.

Example 49: 2-{[4-({2-[(2,4-dichlorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (Compound 164a)

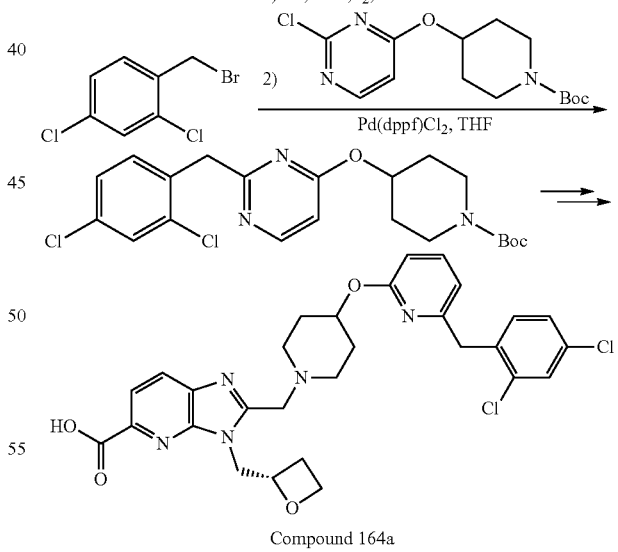

Compound 164a

A mixture of 1-(bromomethyl)-2,4-dichlorobenzene (200 mg, 0.83 mmol), LiCl (18 mg, 0.42 mmol), I$_2$ (11 mg, 0.08 mmol) and Zn (163 mg, 2.5 mmol) in dry THF (18 mL) was heated to 50° C. for 1 hour under an atmosphere of nitrogen (balloon). Then tert-butyl 4-((2-chloropyrimidin-4-yl)oxy)piperidine-1-carboxylate (100 mg, 0.32 mmol) and Pd(dppf)Cl$_2$ (15 mg, 0.02 mmol) was added to the above reaction mixture. The reaction mixture was stirred at 70° C. for 3 hours under nitrogen. The reaction was quenched with water and extracted with ethyl acetate. The organic layer was combined and washed with brine, dried over Na$_2$SO$_4$, filtered, and concentrated in vacuum. The residue was purified by column chromatography to give tert-butyl 4-((2-(2,4-dichlorobenzyl)pyrimidin-4-yl)oxy)piperidine-1-carboxylate (112 mg, 80% yield) as a yellow oil.

MS Calcd.: 437.1. MS Found: 438.2 [M+H]$^+$. 2-{[4-({2-[(2,4-Dichlorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (37 mg) was then obtained as a white solid by the similar procedure of Compound 109a. MS Calcd.: 582.1. MS Found: 583.1 [M+H]$^+$.

$^1$H NMR (400 MHz, DMSO-d$_6$): δ 8.40 (d, J=8.8 Hz, 1H), 8.02 (d, J=8.0 Hz, 1H), 7.93 (d, J=8.4 Hz, 1H), 7.58 (d, J=2.0 Hz, 1H), 7.44 (d, J=8.4 Hz, 1H), 7.41-7.37 (m, 1H), 6.71 (d, J=6.0 Hz, 1H), 5.01-4.96 (m, 1H), 4.86-4.80 (m, 2H), 4.68-4.60 (m, 1H), 4.44-4.37 (m, 1H), 4.37-4.27 (m, 1H), 4.25 (s, 2H), 4.05-4.01 (m, 1H), 3.78 (d, J=13.2 Hz, 1H), 3.30-3.28 (m, 1H), 2.80-2.63 (m, 2H), 2.37-2.20 (m, 3H), 1.90-1.80 (m, 2H), 1.67-1.50 (m, 2H).

Example 50: 2-({4-[(2-{[2-fluoro-4-(trifluoromethyl)phenyl]methyl}pyrimidin-4-yl)oxy]piperidin-1-yl}methyl)-3-{[(2S)-oxetan-2-yl]methyl}-3H-imidazo[4,5-b]pyridine-5-carboxylic acid (Compound 163a)

Compound 163a

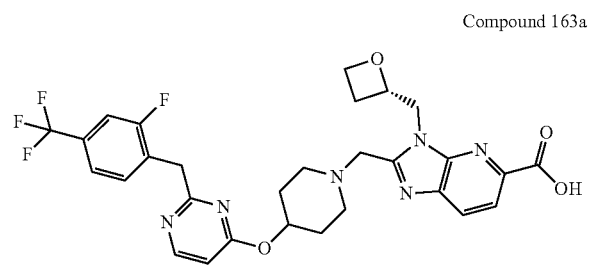

MS Calcd.: 600.2. MS Found: 601.4 [M+H]$^+$.

$^1$H NMR (400 MHz, DMSO-d$_6$): δ 8.42 (d, J=5.6 Hz, 1H), 8.05 (d, J=8.0 Hz, 1H), 7.95 (d, J=8.0 Hz, 1H), 7.60-7.67 (m, 2H), 7.56 (d, J=8.0 Hz, 1H), 6.74 (d, J=6.0 Hz, 1H), 5.10-5.18 (m, 1H), 4.78-4.87 (m, 2H), 4.68 (dd, J=14.4, 4.0 Hz, 1H), 4.46-4.51 (m, 1H), 4.31-4.37 (m, 1H), 4.27 (s, 2H), 3.94 (d, J=13.6 Hz, 1H), 3.86 (d, J=13.6 Hz, 1H), 2.63-2.80 (m, 3H), 2.44-2.51 (m, 1H), 2.20-2.27, (m, 2H), 1.82-1.90 (m, 2H), 1.54-1.66 (m, 2H). $^{19}$F NMR (377 MHz, DMSO-d6): δ −60.92, −114.42.

Example 51: 2-{[4-({2-[(3,4-dichlorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (Compound 167a)

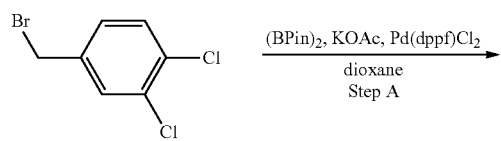

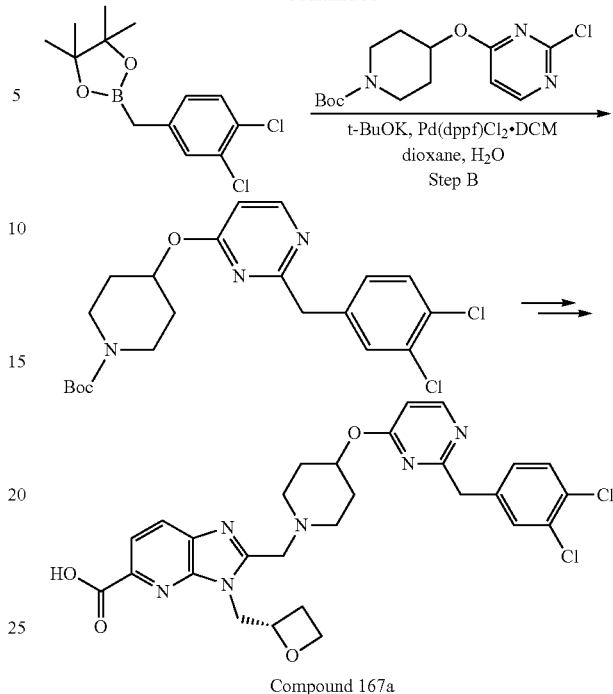

Compound 167a

Step A: The Synthesis of 2-(3,4-dichlorobenzyl)-4,4,5,5-tetramethyl-1,3,2-dioxaborolane A mixture of 4-(bromomethyl)-1,2-dichlorobenzene (2.0 g, 8.3 mmol), Bis(pinacolato)diboron (2.7 g, 12.5 mmol), Pd(dppf)Cl$_2$ (291 mg, 0.4 mmol), KOAc (1.6 g, 16.6 mmol) in dioxane (40 mL) was stirred at 85° C. for 3 hours. After the reaction was completed, the mixture was filtered, and the filtrate concentrated in vacuum. The residue was purified by column chromatography to give 2-(3,4-dichlorobenzyl)-4,4,5,5-tetramethyl-1,3,2-dioxaborolane (1.1 g, yield: 46%) as a colorless oil.

$^1$H NMR (400 MHz, CDCl$_3$):7.27-7.30 (m, 2H), 7.01 (dd, J=8.0 Hz, 2.0 Hz, 1H), 2.24 (s, 2H), 1.23 (s, 12H).

Step B: The Synthesis of tert-butyl 4-((2-(3,4-dichlorobenzyl)pyrimidin-4-yl)oxy)piperidine-1-carboxylate A mixture of tert-butyl 4-((2-chloropyrimidin-4-yl)oxy)piperidine-1-carboxylate (300 mg, 0.96 mmol), 2-(3,4-dichlorobenzyl)-4,4,5,5-tetramethyl-1,3,2-dioxaborolane (548 mg, 1.92 mmol), Pd(dppf)Cl$_2$·DCM (39 mg, 0.048 mmol), t-BuOK (323 mg, 2.88 mmol) in dioxane/H$_2$O (5 mL/0.5 mL) was stirred at 90° C. for 3 hours under Ar. The mixture was extracted with DCM (3×20 mL). The combined organic layer was dried over Na$_2$SO$_4$, filtered, and concentrated under reduced pressure, the residue was purified by silica gel column chromatography to give tert-butyl 4-((2-(3,4-dichlorobenzyl)pyrimidin-4-yl)oxy)piperidine-1-carboxylate (61 mg, yield: 15%) as colorless oil.

MS Calcd.: 437.1. MS Found: 438.1 [M+H]$^+$. 2-{[4-({2-[(3,4-Dichlorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (9.2 mg) was obtained as a white solid by the similar procedure of Compound 109a. MS Calcd.: 582.2. MS Found: 583.4 [M+H]$^+$.

¹H NMR (400 MHz, DMSO-d₆): δ 8.42 (d, J=6.0 Hz, 1H), 8.13 (d, J=8.4 Hz, 1H), 7.99 (d, J=8.4 Hz, 1H), 7.62 (d, J=2.0 Hz, 1H), 7.55 (d, J=8.4 Hz, 1H), 7.30 (dd, J=8.4 Hz, 2.0 Hz, 1H), 6.74 (d, J=6.0 Hz, 1H), 5.13-5.20 (m, 1H), 4.98-5.03 (m, 1H), 4.80-4.86 (m, 1H), 4.68-4.73 (m, 1H), 4.46-4.52 (m, 1H), 4.33-4.38 (m, 1H), 4.12 (s, 2H), 3.99 (d, J=14.0 Hz, 1H), 3.93 (d, J=13.6 Hz, 1H), 2.65-2.82 (m, 3H), 2.47-2.53 (m, 1H), 2.33-2.41 (m, 2H), 1.90-1.97 (m, 2H), 1.63-1.71 (m, 2H).

Example 52: 2-{[4-({2-[(2,4-difluorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (Compound 165a)

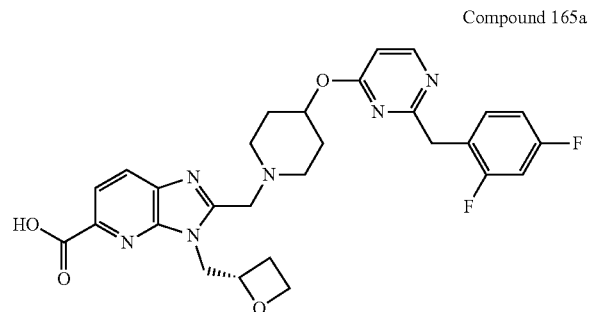 [SMILES: O=C(O)c1ccc2nc(CN3CCC(Oc4ccnc(Cc5ccc(F)cc5F)n4)CC3)n(C[C@@H]3CCO3)c2n1]

Compound 165a

MS Calcd.: 550.2, MS Found: 551.2 [M+H]⁺.
¹H NMR (400 MHz, CD₃OD): δ 8.35 (d, J=6.0 Hz, 1H), 8.16-8.09 (m, 2H), 7.39-7.31 (m, 1H), 6.96-6.87 (m, 2H), 6.67 (d, J=6.0 Hz, 1H), 5.32-5.25 (m, 1H), 5.04-4.95 (m, 2H), 4.86-4.83 (m, 1H), 4.63-4.58 (m, 1H), 4.42-4.37 (m, 1H), 4.15 (s, 2H), 4.14-4.02 (m, 2H), 2.91-2.73 (m, 3H), 2.56-2.40 (m, 3H), 2.01-1.93 (m, 2H), 1.82-1.72 (m, 2H).
¹⁹F NMR (400 MHz, CD₃OD): δ 114.37, −114.39, −114.59, −114.61.

Example 53: 2-({4-[(2-{[4-chloro-2-(trifluoromethyl)phenyl]methyl}pyrimidin-4-yl)oxy]piperidin-1-yl}methyl)-3-{[(2S)-oxetan-2-yl]methyl}-3H-imidazo[4,5-b]pyridine-5-carboxylic acid (Compound 166a)

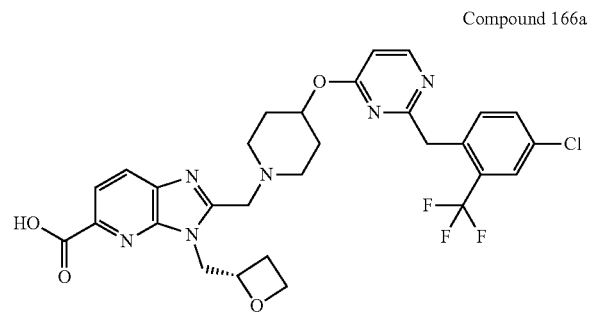 [SMILES: O=C(O)c1ccc2nc(CN3CCC(Oc4ccnc(Cc5ccc(Cl)cc5C(F)(F)F)n4)CC3)n(C[C@@H]3CCO3)c2n1]

Compound 166a

MS Calcd.: 616.2. MS Found: 617.0 [M+H]⁺.
¹H NMR (400 MHz, DMSO-d₆): δ 8.41 (d, J=6.0 Hz, 1H), 7.91-7.97 (m, 2H), 7.71-7.78 (m, 2H), 7.58 (d, J=8.0 Hz, 1H), 6.72 (d, J=5.6 Hz, 1H), 5.05-5.15 (m, 1H), 4.75-4.91 (m, 2H), 4.58-4.63 (m, 1H), 4.43-4.50 (m, 1H), 4.27-4.32 (m, 3H), 3.94 (d, J=13.6 Hz, 1H), 3.72 (d, J=13.2 Hz, 1H), 2.70-2.80 (m, 1H), 2.55-2.70 (m, 2H), 2.45-2.53 (m, 1H), 2.15-2.26 (m, 2H), 1.76-1.88 (m, 2H), 1.49-1.61 (m, 2H).
¹⁹F NMR (377 MHz, DMSO-d6): δ −58.94.

Example 54: 2-{[4-({2-[(4-chlorophenyl)methyl]pyrimidin-4-yl}oxy)piperidin-1-yl]methyl}-3-{[(2S)-oxetan-2-yl]methyl}-3H-imidazo[4,5-b]pyridine-5-carboxylic acid (Compound 152a)

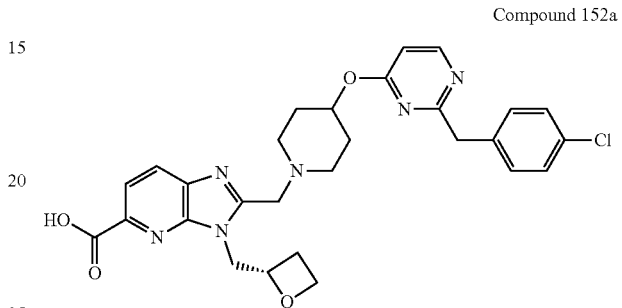

Compound 152a

MS Calcd.: 548.2. MS Found: 549.2 [M+H]⁺.
¹H NMR (400 MHz, CD₃OD): δ 8.33 (d, J=5.6 Hz, 1H), 8.03 (dd, J=21.2 Hz, 8.4 Hz, 2H), 7.31-7.26 (m, 4H), 6.66 (d, J=6.0 Hz, 1H), 5.31-5.26 (m, 1H), 5.15-5.05 (m, 1H), 5.00 (dd, J=14.8 Hz, 6.8 Hz, 1H), 4.88-4.84 (m, 1H), 4.61 (dd, J=14.0 Hz, 7.6 Hz, 1H), 4.44-4.39 (m, 1H), 4.09 (s, 2H), 4.07 (d, J=13.6 Hz, 1H), 3.95 (d, J=13.6 Hz, 1H), 2.86-2.70 (m, 3H), 2.59-2.48 (m, 1H), 2.43 (t, J=8.8 Hz, 2H), 2.05-1.95 (m, 2H), 1.83-1.70 (m, 2H).

Example 55: 2-((4-((2-(4-chlorobenzyl)pyrimidin-4-yl)oxy)piperidin-1-yl)methyl)-3-(2-ethoxyethyl)-3H-imidazo[4,5-b]pyridine-5-carboxylic acid (Compound 194)

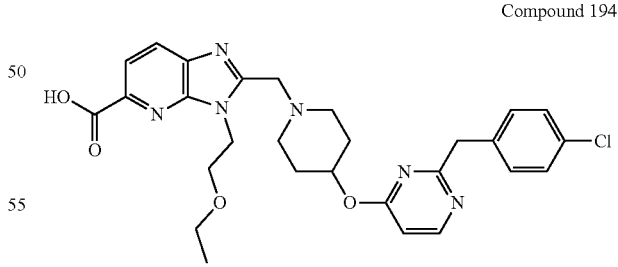

Compound 194

MS Calcd.: 550.2. MS Found: 551.3 [M+H]⁺.
¹H NMR (400 MHz, DMSO-d6): δ 8.41 (d, J=6.0 Hz, 1H), 8.13 (d, J=8.4 Hz, 1H), 7.99 (d, J=8.4 Hz, 1H), 7.31-7.36 (m, 4H), 6.72 (d, J=5.6 Hz, 1H), 4.98-5.05 (m, 1H), 4.63 (t, J=5.6 Hz, 2H), 4.08 (s, 2H), 3.93 (s, 2H), 3.80 (t, J=5.6 Hz, 2H), 3.41-3.48 (m, 2H), 2.72-2.78 (m, 2H), 2.32-2.41 (m, 2H), 1.89-1.98 (m, 2H), 1.58-1.70 (m, 2H), 1.03 (t, J=6.8 Hz, 3H).

Example 56: 2-((4-((2-(4-chlorobenzyl)pyrimidin-4-yl)oxy)piperidin-1-yl)methyl)-3-(2-methoxypropyl)-3H-imidazo[4,5-b]pyridine-5-carboxylic acid (Compound 195)

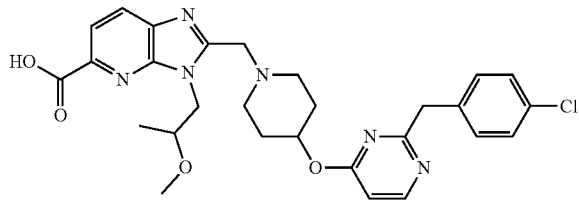

Compound 195

MS Calcd.: 550.2. MS Found: 551.3 [M+H]+.
$^{1}$H NMR (400 MHz, DMSO-d$_{6}$): δ 8.41 (d, J=6.0 Hz, 1H), 8.05 (d, J=8.0 Hz, 1H), 7.94 (d, J=8.4 Hz, 1H), 7.31-7.37 (m, 4H), 6.72 (d, J=6.0 Hz, 1H), 4.98-5.07 (m, 1H), 4.50-4.58 (m, 1H), 4.40-4.47 (m, 1H), 4.08 (s, 2H), 3.89-4.02 (m, 2H), 3.81 (d, J=14.0 Hz, 1H), 3.14 (s, 3H), 2.70-2.79 (m, 2H), 2.30-2.42 (m, 2H), 1.89-1.96 (m, 2H), 1.57-1.70 (m, 2H), 1.14 (d, J=6.0 Hz, 3H).

Example 57: (R)-2-((4-((2-(4-chlorobenzyl)pyrimidin-4-yl)oxy)piperidin-1-yl)methyl)-3-((tetrahydrofuran-3-yl)methyl)-3H-imidazo[4,5-b]pyridine-5-carboxylic acid (Compound 196a)

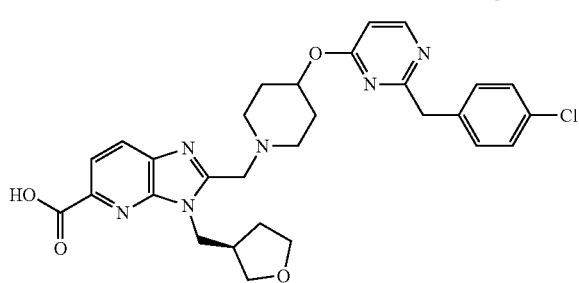

Compound 196a

MS Calcd.: 562.21. MS Found: 563.2 [M+H]+.

$^{1}$H NMR (400 MHz, DMSO-d$_{6}$): δ 8.41 (d, J=6.0 Hz, 1H), 8.12 (d, J=8.4 Hz, 1H), 7.98 (d, J=8.4 Hz, 1H), 7.31-7.38 (m, 4H), 6.73 (d, J=6.0 Hz, 1H), 4.98-5.07 (m, 1H), 4.42 (d, J=7.6 Hz, 2H), 4.08 (s, 2H), 3.85-3.92 (m, 3H), 3.60-3.70 (m, 3H), 3.07-3.16 (m, 1H), 2.74-2.81 (m, 2H), 2.34-2.42 (m, 2H), 1.84-1.97 (m, 3H), 1.70-1.80 (m, 1H), 1.58-1.68 (m, 2H).

Example 58: (R)-2-((4-((2-(4-chlorobenzyl)-5-fluoropyrimidin-4-yl)oxy)piperidin-1-yl)methyl)-3-((tetrahydrofuran-3-yl)methyl)-3H-imidazo[4,5-b]pyridine-5-carboxylic acid (Compound 197a)

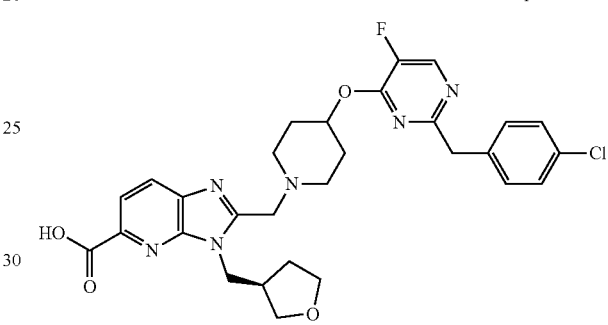

Compound 197a

MS Calcd.: 580.20. MS Found: 581.2 [M+H]+.
$^{1}$H NMR (400 MHz, DMSO-d$_{6}$): δ 8.51 (d, J=3.2 Hz, 1H), 8.13 (d, J=8.4 Hz, 1H), 7.99 (d, J=8.0 Hz, 1H), 7.30-7.37 (m, 4H), 5.07-5.16 (m, 1H), 4.43 (d, J=7.6 Hz, 2H), 4.09 (s, 2H), 3.86-3.94 (m, 3H), 3.62-3.70 (m, 3H), 3.07-3.17 (m, 1H), 2.75-2.82 (m, 2H), 2.38-2.44 (m, 2H), 1.85-2.01 (m, 3H), 1.62-1.80 (m, 3H). $^{19}$F NMR (377 MHz, DMSO-d6): δ −157.46.

Example 59: 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylic Acid (Compound 193)

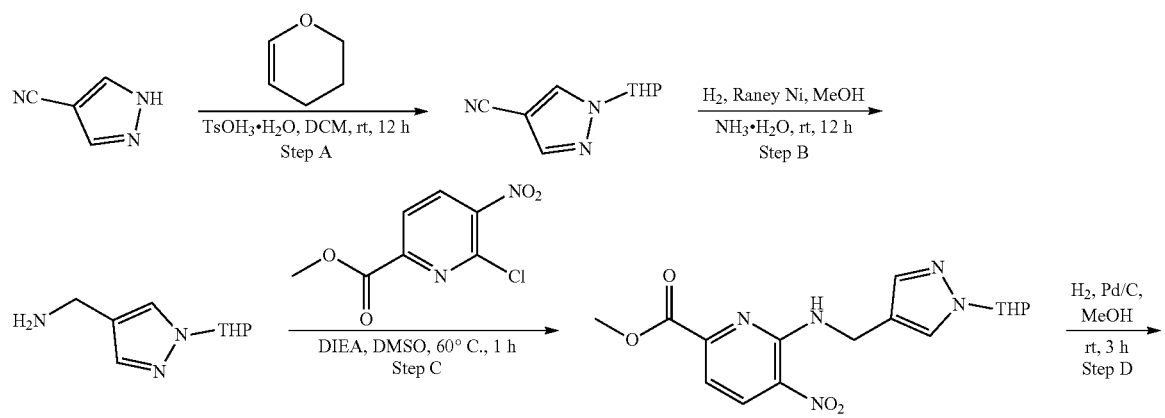

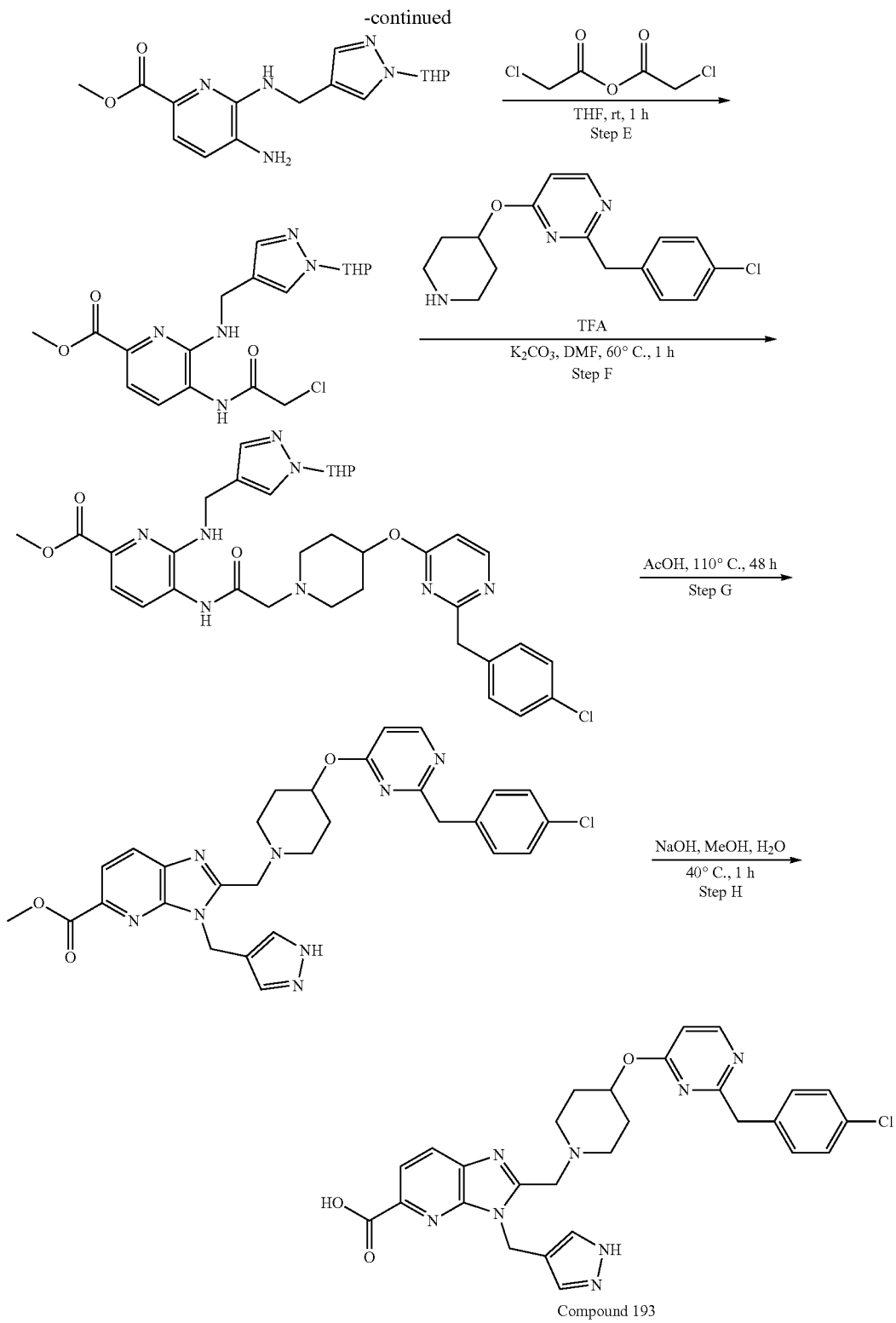

Step A: The Synthesis of 1-(tetrahydro-2H-pyran-2-yl)-1H-pyrazole-4-carbonitrile To a solution of 1H-pyrazole-4-carbonitrile (500 mg, 5.4 mmol) in DCM (10 mL) was added 3,4-dihydro-2H-pyran (542 mg, 6.4 mmol) and p-toluenesulfonic acid monohydrate (102 mg, 0.54 mmol) at 0° C. The resulting mixture was stirred at room temperature for 12 hours. The clear reaction solution was then washed with aqueous sodium carbonate solution. The organic layer was dried over Na₂SO₄, filtered, and concentrated under vacuum. The residue was applied on a silica gel column and eluted with PE:EtOAc=4:1 to give 1-(tetrahydro-2H-pyran-2-yl)-1H-pyrazole-4-carbonitrile (820 mg, 86% yield) as a white solid.

$^1$H NMR (400 MHz, DMSO-d$_6$): δ 8.75 (s, 1H), 8.11 (s, 1H), 5.50 (dd, J=9.6 Hz, 2.4 Hz, 1H), 3.90-3.95 (m, 1H), 3.62-3.68 (m, 1H), 1.88-2.09 (m, 3H), 1.62-1.73 (m, 1 H), 1.52-1.57 (m, 2H).

Step B: The Synthesis of 1-(tetrahydro-2H-pyran-2-yl)-1H-pyrazole-4-carbonitrile To a mixture of 1-(tetrahydro-2H-pyran-2-yl)-1H-pyrazole-4-carbonitrile (600 mg, 3.4 mmol) in MeOH (8 mL) and ammonium hydroxide (2 mL) was added Raney nickel (0.3 mL). The resulting mixture was stirred at room temperature for 12 hours under an atmosphere of hydrogen (balloon). The reaction mixture was filtered through a celite pad. The filtrate was concentrated under vacuum to give (1-(tetrahydro-2H-pyran-2-yl)-1H-pyrazol-4-yl)methanamine (510 mg, 83% yield) as colorless oil.
MS Calcd.: 181.1. MS Found: 182.2 [M+H]$^+$.

Step C: The Synthesis of methyl 5-nitro-6-(((1-(tetrahydro-2H-pyran-2-yl)-1H-pyrazol-4-yl)methyl)amino) picolinate A mixture of (1-(tetrahydro-2H-pyran-2-yl)-1H-pyrazol-4-yl)methanamine (302 mg, 1.7 mmol), methyl 6-chloro-5-nitropicolinate (300 mg, 1.4 mmol) and DIEA (358 mg, 2.8 mmol) in DMSO (6 mL) was heated to 60° C. for 1 hour. The reaction mixture was quenched with water, extracted with DCM. The organic layers were combined, dried over Na$_2$SO$_4$, filtered, and concentrated under vacuum. The residue was applied on a silica gel column and eluted with PE:EtOAc=2:1 to give methyl 5-nitro-6-(((1-(tetrahydro-2H-pyran-2-yl)-1H-pyrazol-4-yl)methyl)amino)picolinate (300 mg, 60% yield) as a yellow solid.
MS Calcd.: 361.1. MS Found: 362.2 [M+H]$^+$.

Step D: The Synthesis of methyl 5-amino-6-(((1-(tetrahydro-2H-pyran-2-yl)-1H-pyrazol-4-yl)methyl)amino) picolinate To a solution of methyl 5-nitro-6-(((1-(tetrahydro-2H-pyran-2-yl)-1H-pyrazol-4-yl)methyl)amino) picolinate (300 mg, 0.83 mmol) in MeOH (6 mL) was added Pd/C (90 mg, 10% wet with water). The resulting mixture was stirred at room temperature for 3 hours under an atmosphere of hydrogen (balloon). The reaction mixture was filtered through a celite pad. The filtrate was concentrated under vacuum to give methyl 5-amino-6-(((1-(tetrahydro-2H-pyran-2-yl)-1H-pyrazol-4-yl)methyl)amino)picolinate (260 mg, 94% yield) as a white solid.
MS Calcd.: 331.2. MS Found: 332.2 [M+H]$^+$.

Step E: The Synthesis of methyl 5-(2-chloroacetamido)-6-((1-(tetrahydro-2H-pyran-2-yl)-1H-pyrazol-4-yl)methyl)amino)picolinate A mixture of methyl 5-amino-6-(((1-(tetrahydro-2H-pyran-2-yl)-1H-pyrazol-4-yl)methyl)amino) picolinate (260 mg, 0.78 mmol) and 2-chloroacetic anhydride (161 mg, 0.94 mmol) in THF (5 mL) was stirred at room temperature for 1 hour. The solvent was removed in vacuo. The residue was applied on a silica gel column and eluted with PE:EtOAc=1:2 to give methyl 5-(2-chloroacetamido)-6-(((1-(tet-rahydro-2H-pyran-2-yl)-1H-pyrazol-4-yl)methyl)amino)picolinate (230 mg, 72% yield) as a brown solid.
MS Calcd.: 407.1. MS Found: 408.1 [M+H]$^+$.

Step F: The Synthesis of methyl 5-(2-(4-(2-(4-chlorobenzyl)pyrimidin-4-yl)oxy)piperidin-1-yl)acet-amido)-6-(((1-(tetrahydro-2H-pyran-2-yl)-1H-pyrazol-4-yl)methyl)amino)picolinate To a solution of 2-(4-chlorobenzyl)-4-(piperidin-4-yloxy)pyrimidine (283 mg, 0.68 mmol, TFA salt) in DMF (6 mL) was added K$_2$CO$_3$ (234 mg, 1.70 mmol). After a few minutes, methyl 5-(2-chloroacetamido)-6-(((1-(tetrahydro-2H-pyran-2-yl)-1H-pyrazol-4-yl)methyl)amino)picolinate (230 mg, 0.56 mmol) was added. The resulting mixture was heated to 60° C. for 1 hour. The reaction mixture was quenched with water, extracted with ethyl acetate. The organic layers were combined, dried over Na$_2$SO$_4$, filtered, and concentrated under vacuum. The residue was applied on a silica gel column and eluted with EtOAc to give methyl 5-(2-(4-((2-(4-chlorobenzyl)pyrimidin-4-yl)oxy)piperidin-1-yl)acetamido)-6-(((1-(tetrahydro-2H-pyran-2-yl)-1H-pyrazol-4-yl)methyl)amino)picolinate (250 mg, 75% yield) as a brown solid.
MS Calcd.: 674.3. MS Found: 675.5 [M+H]$^+$.

Step G: The Synthesis of methyl 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylate A mixture of methyl 5-(2-(4-((2-(4-chlorobenzyl)pyrimidin-4-yl)oxy)piperidin-1-yl)acetamido)-6-(((1-(tetrahydro-2H-pyran-2-yl)-1H-pyrazol-4-yl)methyl)amino)picolinate (230 mg, 0.34 mmol) in AcOH (4 mL) was heated to 110° C. for 48 hours. The solvent was removed in vacuo. The residue was diluted with ethyl acetate and washed with sodium bicarbonate aqueous solution. The organic layers were combined, dried over Na$_2$SO$_4$, filtered, and concentrated under vacuum. The residue was applied on a silica gel column and eluted with DCM:MeOH=20:1 to give methyl 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylate (110 mg, 56% yield) as a white solid.
MS Calcd.: 572.2. MS Found: 573.2 [M+H]$^+$.

Step H: The Synthesis of 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylic acid To a solution of methyl 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylate (110 mg, 0.19 mmol) in MeOH (2 mL) and water (0.5 mL) was added NaOH (15.4 mg, 0.38 mmol). The solution was stirred at 40° C. for 1 hour. The solvent was removed in vacuo. The residue was purified by Prep-HPLC to give 3-((1H-pyrazol-4-yl)methyl)-2-((4-((2-(4-chlorobenzyl)pyrimidin-4-yl)oxy)piperidin-1-yl)methyl)-3H-imidazo[4,5-b]pyridine-5-carboxylic acid (36.7 mg, yield: 34%) as a white solid.
MS Calcd.: 558.2. MS Found: 559.3 [M+H]$^+$.
$^1$H NMR (400 MHz, DMSO-d$_6$): δ 8.50 (d, J=5.6 Hz, 1H), 8.29 (d, J=8.4 Hz, 1H), 8.10 (d, J=8.4 Hz, 1H), 7.74 (s, 2H), 7.33-7.40 (m, 4H), 6.81 (d, J=6.0 Hz, 1H), 5.52 (s, 2H), 5.24-5.36 (m, 1H), 4.95 (s, 2H), 4.11 (s, 2H), 3.42-3.69 (m, 4H), 2.19-2.30 (m, 2H), 1.97-2.16 (m, 2H).

Example 60: 2-{[4-({2-[(4-chloro-2-fluorophenyl)methyl]pyrimidin-4-yl}oxy)-3,3-difluoropiperidin-1-yl]methyl}-3-{[(2S)-oxetan-2-yl]methyl}-3H-imidazo[4,5-b]pyridine-5-carboxylic acid (Compound 168a)

Compound 168a

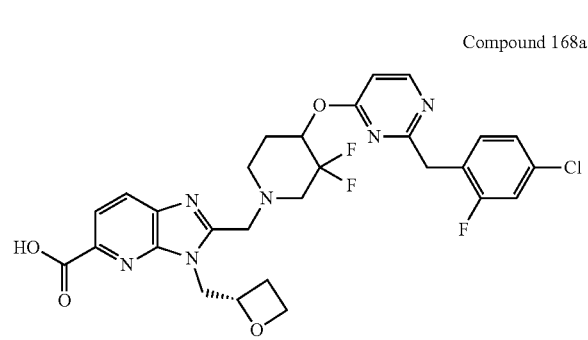 [SMILES: O=C(O)c1ccc2nc(CN3CCC(Oc4ccnc(Cc5ccc(Cl)cc5F)n4)C(F)(F)C3)n(C[C@@H]3CCO3)c2n1]

MS Calcd.: 602.2. MS Found: 603.4 [M+H]$^+$.

$^1$H NMR (400 MHz, DMSO-d$_6$): 8.49 (d, J=6.0 Hz, 1H), 7.91-7.96 (m, 2H), 7.38-7.44 (m, 2H), 7.25 (dd, J=8.0 Hz, 2.0 Hz, 1H), 6.89 (d, J=5.6 Hz, 1H), 5.29-5.39 (m, 1H), 5.05-5.15 (m, 1H), 4.78-4.86 (m, 1H), 4.55-4.65 (m, 1H), 4.45-4.51 (m, 1H), 4.29-4.36 (m, 1H), 4.18 (s, 2H), 4.08-4.14 (m, 1H), 3.91 (t, J=14.4 Hz, 1H), 3.00-3.25 (m, 1H), 2.70-2.93 (m, 2H), 2.57-2.65 (m, 1H), 2.42-2.50 (m, 2H), 1.92-2.01 (m, 1H), 1.68-1.82 (m, 1H). 19F NMR (377 MHz, DMSO-d6): δ −108.50, −108.62, −109.17, −109.25, −114.01.

Example 61: 2-{[3-({6-[(4-chloro-2-fluorophenyl)methyl]pyridin-2-yl}oxy)pyrrolidin-1-yl]methyl}-3-{[(2S)-oxetan-2-yl]methyl}-3H-imidazo[4,5-b]pyridine-5-carboxylic acid (Compound 130a)

Compound 130a

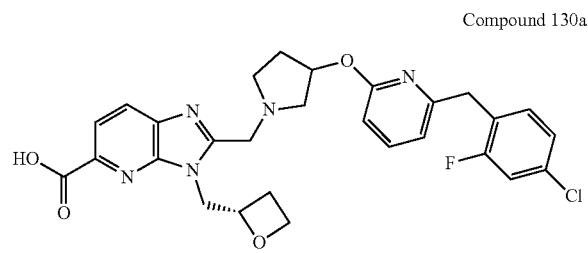 [SMILES: O=C(O)c1ccc2nc(CN3CCC(Oc4cccc(Cc5ccc(Cl)cc5F)n4)C3)n(C[C@@H]3CCO3)c2n1]

MS Calcd.: 551.2. MS Found: 552.1 [M+H]$^+$.

$^1$H NMR (400 MHz, CD$_3$OD): δ 8.16-8.08 (m, 2H), 7.55 (t, J=8.0 Hz, 1H), 7.24 (t, J=8.4 Hz, 1H), 7.10-7.00 (m, 2H), 6.81 (d, J=7.6 Hz, 1H), 6.59 (dd, J=8.4 Hz, 2.0 Hz, 1H), 5.36-5.23 (m, 2H), 4.95-4.77 (m, 2H), 4.58-4.50 (m, 1H), 4.37-4.15 (m, 3H), 3.98 (s, 2H), 3.18-2.65 (m, 4H), 2.52-2.42 (m, 1H), 2.37-2.27 (m, 2H), 2.02-1.93 (m, 1H). $^{19}$F NMR (377 MHz, DMSO-d6): δ −116.70.

Example 62: 2-{[5-({2-[(4-chlorophenyl)methyl]pyrimidin-4-yl}oxy)-octahydrocyclopenta[c]pyrrol-2-yl]methyl}-3-{[(2S)-oxetan-2-yl]methyl}-3H-imidazo[4,5-b]pyridine-5-carboxylic acid (Compound 201a)

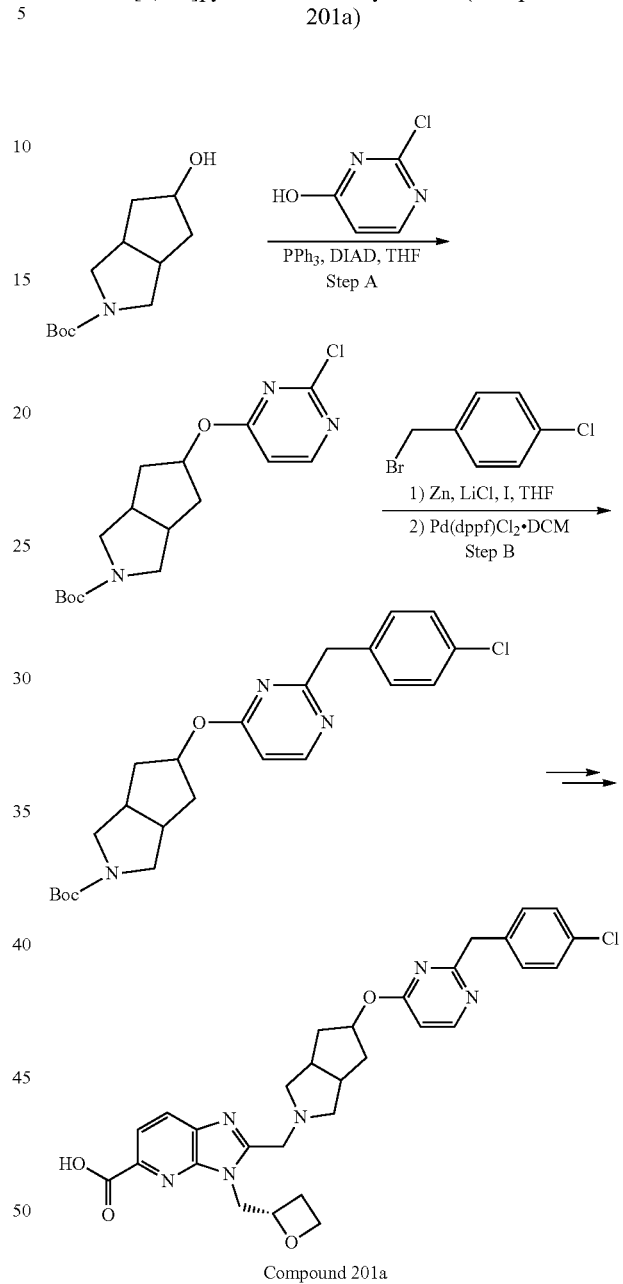

Compound 201a

Step A: The Synthesis of tert-butyl 5-((2-chloropyrimidin-4-yl)oxy)hexahydrocyclopenta[c]pyrrole-2(1H)-carboxylate To a solution of tert-butyl 5-hydroxyhexahydrocyclopenta[c]pyrrole-2(1H)-carboxylate (500 mg, 1.86 mmol) and 2-chloropyrimidin-4-ol (250 mg, 1.94 mmol) in THF (15 mL) was added PPh$_3$ (600 mg, 2.29 mmol) and DIAD (426 mg, 2.29 mmol) at 0° C. The reaction was stirred at room temperature for 3 hours. After the reaction was completed, the reaction was quenched with water (10 mL) and extracted with ethyl acetate (30 mL×3). The organic layer was combined and washed with brine (10 mL×2), dried over sodium sulfate, filtered, and concentrated in vacuum. The residue was purified by column chromatography (EA/PE=1/3) to give tert-butyl 5-((2-chloropyrimidin-4-yl)oxy)hexahydro-cyclopenta[c]pyrrole-2(1H)-carboxylate (400 mg, 59.5%) as a white solid. MS Calcd.: 339.1. MS Found: 340.1 [M+H]$^+$.

Step B: The Synthesis of tert-butyl 5-((2-(4-chlorobenzyl)pyrimidin-4-yl)oxy)hexahydrocyclopenta[c]pyrrole-2(1H)-carboxylate A mixture of 1-(bromomethyl)-4-chlorobenzene (530 mg, 2.58 mmol), Zn (503 mg, 7.74 mmol), LiCl (54 mg, 1.29 mmol) and Iodine (65 mg, 0.256 mmol) in dry THF (30 mL) was stirred at 50° C. for 1 hour. Then, tert-butyl 5-((2-(4-chlorobenzyl)pyrimidin-4-yl)oxy)hexahydrocyclopenta[c]pyrrole-2(1H)-carboxylate (350 mg, 1.03 mmol) and Pd(dppf)Cl$_2$ (100 mg, 0.1 mmol) was added into the mixture. The resulting mixture was stirred at 70° C. for 2 hours. After the reaction was completed, the reaction was filtrated. The filtrate was quenched with water (10 mL) and extracted with ethyl acetate (30 mL×3). The organic layer was combined and washed with brine (10 mL×2), dried over sodium sulfate, filtered, and concentrated in vacuum. The residue was purified by column chromatography (MeOH/DCM=1/20) to give tert-butyl 5-((2-(4-chlorobenzyl)pyrimidin-4-yl)oxy)hexahydrocyclopenta[c]pyrrole-2(1H)-carboxylate (400 mg, 79.1%) as a brown oil. MS Calcd.: 429.2. MS Found: 430.1 [M+H]$^+$. 2-{[5-({2-[(4-chlorophenyl)methyl]pyrimidin-4-yl}oxy)-octahydrocyclopenta[c]pyrrol-2-yl]methyl}-3-{[(2S)-oxetan-2-yl]methyl}-3H-imidazo[4,5-b]pyridine-5-carboxylic acid (117 mg, 30% yield) was obtained as a white solid by the similar procedure of Compound 109a. MS Calcd.: 574.2; MS Found: 575.2 [M+H]$^+$.

$^1$H NMR (400 MHz, DMSO-d$_6$): δ 8.39 (d, J=5.6 Hz, 1H), 8.12 (d, J=8.0 Hz, 1H), 7.98 (d, J=8.4 Hz, 1H), 7.24-7.28 (m, 4H), 6.68 (d, J=6.0 Hz, 1H), 5.43-5.48 (m, 1H), 5.13-5.20 (m, 1H), 4.84-4.90 (m, 1H), 4.69-4.75 (m, 1H), 4.44-4.50 (m, 1H), 4.29-4.35 (m, 1H), 3.96-4.05 (m, 4H), 2.67-2.72 (m, 4H), 2.42-2.48 (m, 4H), 1.84-1.93 (m, 2H), 1.68-1.77 (m, 2H).

Example 63: 3-{[(2S)-oxetan-2-yl]methyl}-2-{[trans-4-({2-[(4-chloro-2-fluorophenyl)methyl]pyrimidin-4-yl}oxy)cyclohexyl]methyl}-3H-imidazo[4,5-b]pyridine-5-carboxylic acid (Compound 175b)

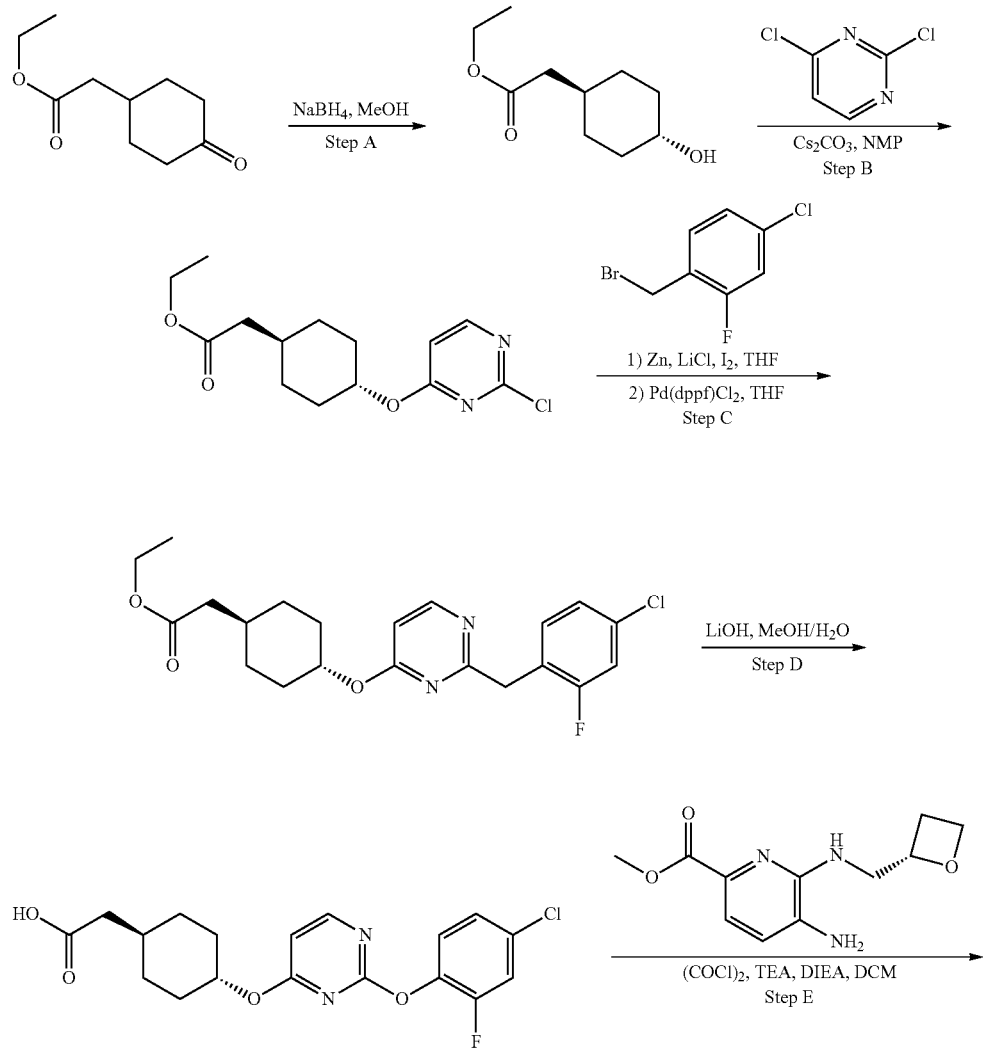

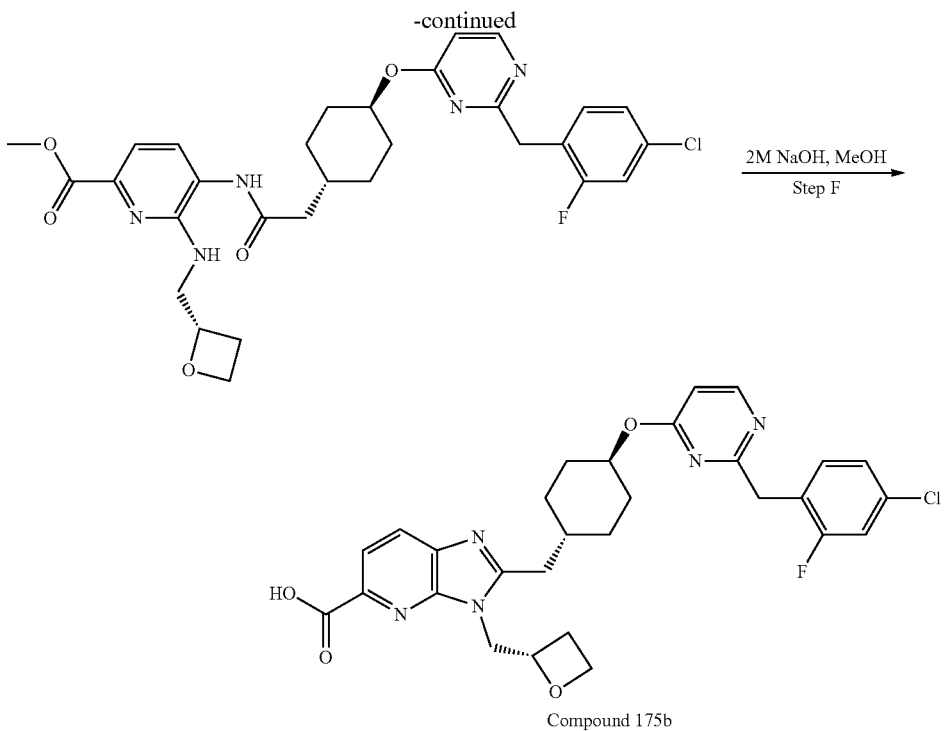

Compound 175b

Step A: The Synthesis of ethyl 2-(trans-4-hydroxycyclohexyl)acetate

To a solution of ethyl 2-(4-oxocyclohexyl)acetate (23.0 g, 125 mmol) in MeOH (300 mL) was added NaBH$_4$ (14.3 g, 375 mmol) at 0° C. The reaction mixture was stirred at 0° C. for 4 hours. After the reaction was completed, the reaction was quenched with water and concentrated under reduced pressure to remove MeOH. The mixture was extracted with ethyl acetate (200 mL*2). The organic layers were combined, dried over Na$_2$SO$_4$ and concentrated. The residue was purified by silica gel column chromatography (PE/EA=5/1) to give ethyl 2-(trans-4-hydroxycyclohexyl)acetate (8.4 g, 34% yield) as colorless oil.

$^1$H NMR (400 MHz, CDCl$_3$): δ 4.05 (q, J=7.2 Hz, 2H), 3.44-3.51 (m, 1H), 2.11 (d, J=6.8 Hz, 2H), 1.88-2.10 (m, 3H), 1.65-1.74 (m, 3H), 1.17-1.27 (m, 5H), 0.93-1.03 (m, 2H).

Step B: The Synthesis of ethyl 2-(trans-4-((2-chloropyrimidin-4-yl)oxy)cyclohexyl)acetate A mixture of ethyl 2-(trans-4-hydroxycyclohexyl)acetate (5.0 g, 26.9 mmol), 2,4-dichloropyrimidine (4.8 g, 32.3 mmol), Cs$_2$CO$_3$ (17.5 g, 53.8 mmol) in NMP (70 mL) was stirred at 70° C. for 16 hours. The reaction was diluted with ethyl acetate (200 mL) and washed with water (200 mL*3). The organic layers were dried over Na$_2$SO$_4$ and concentrated. The residue was purified by silica gel column chromatography (PE/EA=9/1) to give ethyl 2-(trans-4-((2-chloropyrimidin-4-yl)oxy)cyclohexyl)acetate (2.5 g, 31% yield) as colorless oil.

MS Calcd.: 298.1. MS Found: 299.0 [M+H]$^+$.

Step C: The Synthesis of ethyl 2-(trans-4-((2-(4-chloro-2-fluorobenzyl)pyrimidin-4-yl)oxy)cyclohexyl) acetate A mixture of 1-(bromomethyl)-4-chloro-2-fluorobenzene (935 mg, 4.2 mmol), LiCl (88 mg, 2.1 mmol), Zn (819 mg, 12.6 mmol), I$_2$ (203 mg, 0.8 mmol) in THF (15 mL) was stirred at 50° C. for 1 hour under Ar. Then ethyl 2-(trans-4-((2-chloropyrimidin-4-yl)oxy)cyclohexyl)acetate (500 mg, 1.7 mmol) in THF (3 mL) was added followed by the addition of Pd(dppf)Cl$_2$·DCM (164 mg, 0.2 mmol). Then the reaction mixture was stirred at 70° C. for 2 hours under N$_2$ atmosphere. After the reaction was completed, the reaction mixture was filtered, and the filtrate concentrated. The crude product was purified by column chromatography on silica gel (PE:EA=5:1) to give ethyl 2-(trans-4-((2-(4-chloro-2-fluorobenzyl)pyrimidin-4-yl)oxy)cyclohexyl)acetate (320 mg, yield: 46%) as red oil.

MS Calcd.: 406.2. MS Found: 407.0 [M+H]$^+$.

Step D: The Synthesis of 2-(trans-4-((2-(4-chloro-2-fluorobenzyl)pyrimidin-4-yl)oxy)cyclohexyl)acetic acid To a solution of ethyl 2-(trans-4-((2-(4-chloro-2-fluorobenzyl)pyrimidin-4-yl)oxy)cyclohexyl)acetate (320 mg, 0.79 mmol) in MeOH (6 mL)/THF (3 mL)/H$_2$O (3 mL) was added LiOH (166 mg, 3.94 mmol). The reaction was stirred at 50° C. for 3 hours. After the reaction was completed, the mixture was acidified with 1N HCl to pH=6 and extracted with ethyl acetate (50 mL*3). The organic layers were combined, dried over Na$_2$SO$_4$ and concentrated to give 2-(trans-4-((2-(4-chloro-2-fluorobenzyl)pyrimidin-4-yl) oxy)cyclohexyl)acetic acid (280 mg, 94% yield) as a brown solid.

MS Calcd.: 378.1. MS Found: 379.0 [M+H]$^+$.

Step E: The Synthesis of methyl 5-(2-(trans-4-((2-(4-chloro-2-fluorobenzyl)pyrimidin-4-yl)oxy)cyclohexyl) acetamido)-6-((((S)-oxetan-2-yl)methyl)amino)picolinate To a solution of 2-(trans-4-((2-(4-chloro-2-fluorobenzyl)pyrimidin-4-yl)oxy)cyclohexyl)acetic acid (200 mg, 0.53 mmol) in DCM (10 mL) was added (COCl)$_2$ (202 mg, 1.6 mmol) at room temperature. The mixture was stirred at room temperature for 3 hours, concentrated to give a yellow solid. The yellow solid was dissolved in DCM (10 mL), then methyl (S)-5-amino-6-((oxetan-2-ylmethyl)amino)picolinate (126 mg, 0.53 mmol), DIEA (342 mg, 2.7 mmol) was added. The mixture was stirred at room temperature for 2 hours, diluted with ethyl acetate (50 mL). The organic layer was washed with brine (2×20 mL), dried over Na$_2$SO$_4$, filtered, and concentrated under reduced pressure. The residue was purified by silica gel column chromatography to give methyl 5-(2-(trans-4-((2-(4-chloro-2-fluorobenzyl)pyrimidin-4-yl)oxy)cyclohexyl)acetamido)-6-((((S)-oxetan-2-yl)methyl)amino)picolinate (120 mg, yield: 38%) as a red solid.
MS Calcd.: 597.2. MS Found: 598.0 [M+H]$^+$.

Step F: The Synthesis of 3-{[(2S)-oxetan-2-yl]methyl}-2-{[trans-4-({2-[(4-chloro-2-fluorophenyl)methyl]pyrimidin-4-yl}oxy)cyclohexyl]methyl}-3H-imidazo[4,5-b]pyridine-5-carboxylic acid A mixture of methyl 5-(2-(trans-4-((2-(4-chloro-2-fluorobenzyl)pyrimidin-4-yl)oxy)cyclohexyl)acetamido)-6-((((S)-oxetan-2-yl)methyl)amino)picolinate (120 mg, 0.2 mmol), 2 M NaOH (1 mL) in MeOH (4 ml) was stirred at 50° C. for 2 days. The reaction mixture was directly purified by Prep-HPLC to give 3-{[(2S)-oxetan-2-yl]methyl}-2-{[trans-4-({2-[(4-chloro-2-fluorophenyl)methyl]pyrimidin-4-yl}oxy)cyclohexyl]methyl}-3H-imidazo[4,5-b]pyridine-5-carboxylic acid (19.5 mg, yield: 15%) as a white solid. MS Calcd.: 565.2. MS Found: 566.3 [M+H]$^+$.
$^1$H NMR (400 MHz, DMSO-d$_6$): δ 8.40 (d, J=6.0 Hz, 1H), 8.10 (d, J=8.4 Hz, 1H), 7.97 (d, J=8.0 Hz, 1H), 7.38-7.44 (m, 2H), 7.24-7.27 (m, 1H), 6.71 (d, J=6.0 Hz, 1H), 5.05-5.15 (m, 1H), 4.75-4.85 (m, 1H), 4.60-4.70 (m, 1H), 4.44-4.59 (m, 2H), 4.28-4.36 (m, 1H), 4.15 (s, 2H), 2.90-3.05 (m, 2H), 2.61-2.74 (m, 1H), 2.45-2.51 (m, 1H), 1.90-2.10 (m, 3H), 1.81-1.90 (m, 2H), 1.30-1.41 (m, 2H), 1.10-1.25 (m, 2H). $^{19}$F NMR (377 MHz, DMSO-d6): δ −114.08.

Example 64: 3-{[(2S)-oxetan-2-yl]methyl}-2-{[cis-4-({2-[(4-chloro-2-fluorophenyl)methyl]pyrimidin-4-yl}oxy)cyclohexyl]methyl}-3H-imidazo[4,5-b]pyridine-5-carboxylic acid (Compound 175a)

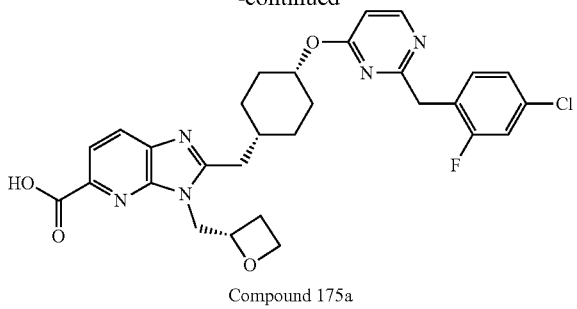

Compound 175a

Step A: The Synthesis of ethyl 2-(cis-4-((2-chloropyrimidin-4-yl)oxy)cyclohexyl)acetate A mixture of ethyl 2-(trans-4-hydroxycyclohexyl)acetate (400 mg, 2.2 mmol), 2-chloropyrimidin-4-ol (337 mg, 2.6 mmol), PPh$_3$ (865 mg, 3.3 mmol), DIAD (667 mg, 3.3 mmol) in THF (10 mL) was stirred at room temperature overnight under N$_2$. The reaction was diluted with ethyl acetate (50 mL) and washed with water (30 mL). The organic layers were dried over Na$_2$SO$_4$ and concentrated. The residue was purified by silica gel column chromatography (PE/EA=20/1) to give ethyl 2-(cis-4-((2-chloropyrimidin-4-yl)oxy)cyclohexyl) acetate (320 mg, 49% yield) as a colorless oil.
$^1$H NMR (400 MHz, CDCl$_3$): δ 8.27 (d, J=5.6 Hz, 1H), 6.64 (d, J=5.6 Hz, 1H), 5.39-5.40 (m, 1H), 4.14 (q, J=6.8 Hz, 2H), 2.26 (d, J=6.8 Hz, 2H), 2.00-2.05 (m, 2H), 1.90-1.96 (m, 1H), 1.61-1.71 (m, 4H), 1.30-1.36 (m, 2H), 1.26 (t, J=7.2 Hz, 3H). 3-{[(2S)-oxetan-2-yl]methyl}-2-{[cis-4-({4-chloro-2-fluorophenyl)methyl]pyrimidin-4-yl}oxy)cyclohexyl]methyl}-3H-imidazo[4,5-b]pyridine-5-carboxylic acid (5.4 mg) was obtained as a white solid by the similar procedure of Compound 175b. MS Calcd.: 565.2. MS Found: 566.2 [M+H]$^+$.
$^1$H NMR (400 MHz, DMSO-d$_6$): δ 8.40 (d, J=5.6 Hz, 1H), 8.05 (d, J=8.0 Hz, 1H), 7.95 (d, J=8.4 Hz, 1H), 7.36-7.41 (m, 2H), 7.24 (dd, J=8.0 Hz, 1.6 Hz, 1H), 6.74 (d, J=5.6 Hz, 1H), 5.05-5.17 (m, 2H), 4.41-4.66 (m, 3H), 4.22-4.30 (m, 1H), 4.13 (s, 2H), 2.91-3.04 (m, 2H), 2.61-2.71 (m, 1H), 2.35-2.49 (m, 1H), 2.15-2.28 (m, 1H), 1.82-1.91 (m, 2H), 1.55-1.66 (m, 4H), 1.38-1.50 (m, 2H). $^{19}$F NMR (377 MHz, DMSO-d6): δ −114.04.

Example 65: 3-{[(2S)-oxetan-2-yl]methyl}-2-{[trans-4-({2-[(4-chlorophenyl)methyl]pyrimidin-4-yl}oxy)cyclohexyl]methyl}-3H-imidazo[4,5-b]pyridine-5-carboxylic acid (Compound 177a)

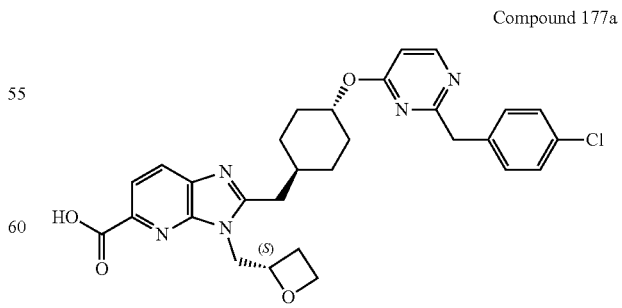

Compound 177a

MS Calcd.: 547.2. MS Found: 548.0 [M+H]$^+$.
$^1$H NMR (400 MHz, DMSO-d6): 8.43 (d, J=5.6 Hz, 1H), 8.13 (d, J=8.4 Hz, 1H), 8.00 (d, J=8.4 Hz, 1H), 7.30-7.37 (m,

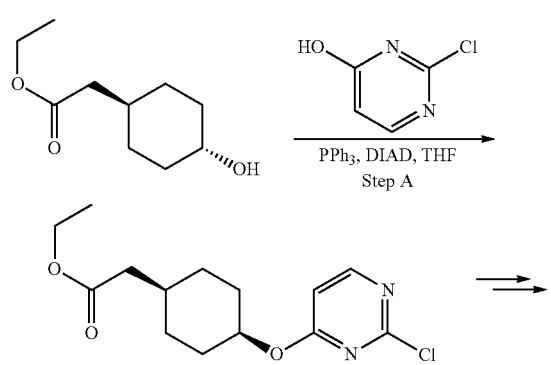

4H), 6.74 (d, J=5.6 Hz, 1H), 5.07-5.16 (m, 1H), 4.89-4.99 (m, 1H), 4.65-4.72 (m, 1H), 4.46-4.59 (m, 2H), 4.31-4.37 (m, 1H), 4.10 (s, 2H), 2.95-3.07 (m, 2H), 2.67-2.77 (m, 1H), 2.41-2.51 (m, 1H), 1.97-2.12 (m, 3H), 1.84-1.91 (m, 2H), 1.32-1.46 (m, 2H), 1.20-1.31 (m, 2H).

Example 66: 1-{[(2S)-oxetan-2-yl]methyl}-2-{[trans-4-({2-[(4-chlorophenyl)methyl]pyrimidin-4-yl}oxy)cyclohexyl]methyl}-1H-1,3-benzodiazole-6-carboxylic acid (Compound 176a)

in DCM (2 mL) was added T₃P (172 mg, 0.54 mmol) at room temperature. The mixture was stirred at room temperature for 1 hour. The mixture was quenched by H₂O, diluted with ethyl acetate (20 mL). The organic layer was washed with brine (2×20 mL), dried over Na₂SO₄, filtered, and concentrated under reduced pressure. The residue was purified by silica gel column chromatography to give methyl 4-(2-(trans-4-((2-(4-chlorobenzyl)pyrimidin-4-yl)oxy)cyclohexyl)acetamido)-3-((((S)-oxetan-2-yl)methyl)amino)benzoate (100 mg, yield: 64%) as a brown oil.

MS Calcd.: 578.2. MS Found: 579.2 [M+H]⁺.

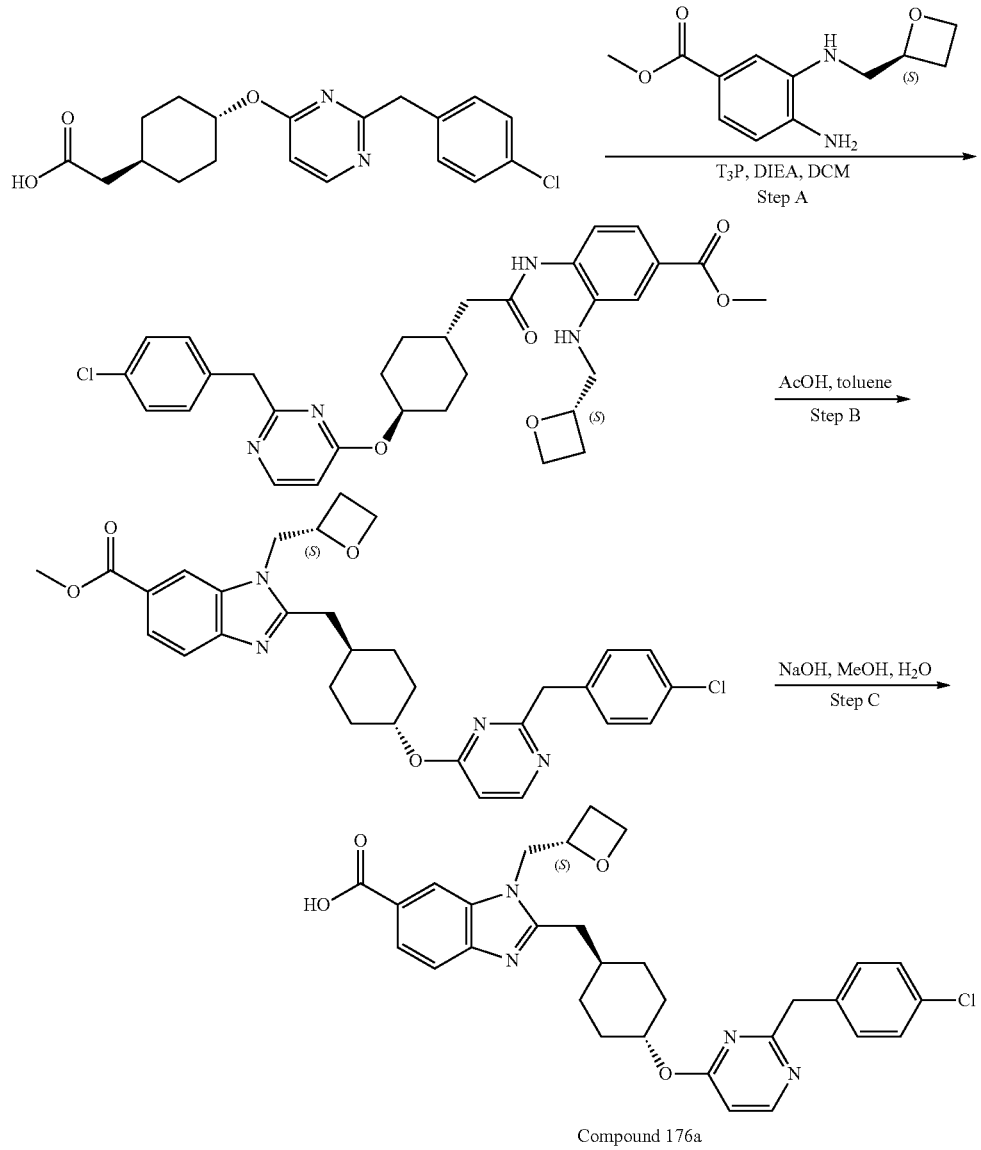

Compound 176a

Step A: The Synthesis of methyl 4-(2-(trans-4-((2-(4-chlorobenzyl)pyrimidin-4-yl)oxy)cyclohexyl) acetamido)-3-((((S)-oxetan-2-yl)methyl)amino)benzoate To a solution of 2-(trans-4-((2-(4-chlorobenzyl)pyrimidin-4-yl)oxy)cyclohexyl)acetic acid (68 mg, 0.27 mmol), DIEA (104 mg, 0.81 mmol) and methyl (S)-4-amino-3-((oxetan-2-ylmethyl)amino)benzoate (100 mg, 0.27 mmol)

Step B: The Synthesis of methyl 2-((trans-4-((2-(4-chlorobenzyl)pyrimidin-4-yl)oxy)cyclohexyl)methyl)-1-(((S)-oxetan-2-yl)methyl)-1H-benzo[d]imidazole-6-carboxylate To a solution of methyl 4-(2-(trans-4-((2-(4-chlorobenzyl)pyrimidin-4-yl)oxy)cyclohexyl)acetamido)-3-((((S)-oxetan- 2-yl)methyl)amino)benzoate (100 mg, 0.17 mmol) in toluene (5 mL) was added AcOH (0.1 mL) at room temperature, the mixture was stirred at 110° C. for 3 hours. The mixture was concentrated under vacuum. The residue was purified by silica gel column chromatography to give methyl 2-((trans-4-((2-(4-chlorobenzyl)pyrimidin-4-yl)oxy)cyclohexyl)methyl)-1-(((S)-oxetan-2-yl)methyl)-1H-benzo[d]imidazole-6-carboxylate (90 mg, yield: 93%) as a brown solid.

MS Calcd.: 560.2. MS Found: 561.3 [M+H]+.

Step C: The Synthesis of 1-{[(2S)-oxetan-2-yl]methyl}-2-{[trans-4-({2-[(4-chlorophenyl)methyl]pyrimidin-4-yl}oxy)cyclohexyl]methyl}-1H-1,3-benzodiazole-6-carboxylic acid A mixture of methyl 2-((trans-4-((2-(4-chlorobenzyl)pyrimidin-4-yl)oxy)cyclohexyl)methyl)-1-(((S)-oxetan-2-yl)methyl)-1H-benzo[d]imidazole-6-carboxylate (90 mg, 0.16 mmol), NaOH (20 mg dissolved in 0.5 mL H2O) in MeOH (1 mL) was stirred at 50° C. for 3 hours. The reaction mixture was directly purified by Prep-HPLC to give 1-{[(2S)-oxetan-2-yl]methyl}-2-{[trans-4-({2-[(4-chlorophenyl)methyl]pyrimidin-4-yl}oxy)cyclohexyl]methyl}-1H-1,3-benzodiazole-6-carboxylic acid (17.0 mg, yield: 19.4%) as a white solid. MS Calcd.: 546.2; MS Found: 547.3 [M+H]+.

1H NMR (400 MHz, DMSO-d6): δ 8.39-8.44 (m, 2H), 7.96 (d, J=8.4 Hz, 1H), 7.76 (d, J=8.8 Hz, 1H), 7.30-7.38 (m, 4H), 6.71 (d, J=5.6 Hz, 1H), 5.03-5.10 (m, 1H), 4.88-4.96 (m, 1H), 4.78-4.86 (m, 1H), 4.64-4.71 (m, 1H), 4.46-4.52 (m, 1H), 4.35-4.42 (m, 1H), 4.09 (s, 2H), 3.04-3.10 (m, 2H), 2.70-2.80 (m, 1H), 2.39-2.53 (m, 1H), 1.94-2.04 (m, 3H), 1.78-1.85 (m, 2H), 1.20-1.42 (m, 4H).

Example 67: 3-{[(2S)-oxetan-2-yl]methyl}-2-{[trans-4-({2-[(4-cyanophenyl)methyl]pyrimidin-4-yl}oxy)cyclohexyl]methyl}-3H-imidazo[4,5-b]pyridine-5-carboxylic acid (Compound 182a)

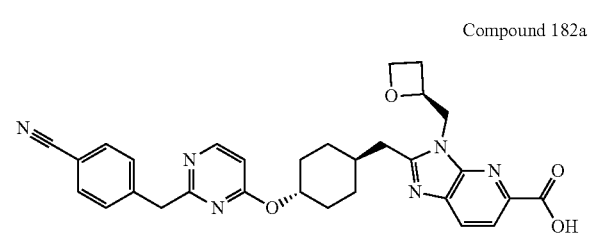 [SMILES: N#Cc1ccc(Cc2nccc(O[C@H]3CC[C@H](Cc4nc5ccc(C(=O)O)nc5n4C[C@@H]4CCO4)CC3)n2)cc1]

Compound 182a

MS Calcd.: 538.23. MS Found: 539.1 [M+H]+.

1H NMR (400 MHz, DMSO-d): 8.40 (d, J=6.0 Hz, 1H), 8.06 (d, J=8.4 Hz, 1H), 7.95 (d, J=8.4 Hz, 1H), 7.75-7.79 (m, 2H), 7.52 (d, J=8.4 Hz, 2H), 6.71 (d, J=5.6 Hz, 1H), 5.08-5.14 (m, 1H), 4.87-4.97 (m, 1H), 4.60-4.68 (m, 1H), 4.45-4.56 (m, 2H), 4.30-4.36 (m, 1H), 4.20 (s, 2H), 2.90-3.04 (m, 2H), 2.65-2.72 (m, 1H), 2.40-2.51 (m, 1H), 1.90-2.12 (m, 3H), 1.83-1.92 (m, 2H), 1.34-1.43 (m, 2H), 1.14-1.29 (m, 2H).

Example 68: 3-{[(2S)-oxetan-2-yl]methyl}-2-{[trans-4-({6-[(4-chloro-2-fluorophenyl)methyl]pyridin-2-yl}oxy)cyclohexyl]methyl}-3H-imidazo[4,5-b]pyridine-5-carboxylic acid (Compound 174b)

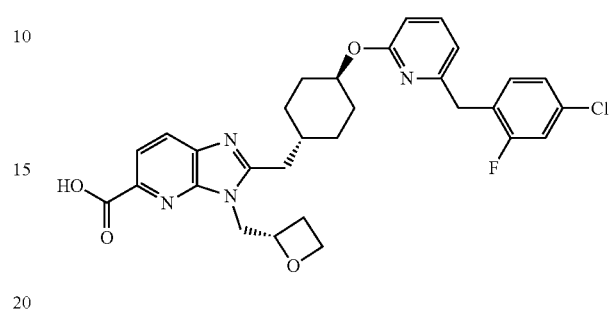

Compound 174b

MS Calcd.: 564.19. MS Found: 565.2 [M+H]+.

1H NMR (400 MHz, DMSO-d6): 12.93 (brs, 1H), 8.11 (d, J=8.4 Hz, 1H), 7.97 (d, J=8.0 Hz, 1H), 7.56-7.60 (m, 1H), 7.34-7.40 (m, 2H), 7.23 (dd, J=8.4 Hz, 2.0 Hz, 1H), 6.80 (d, J=7.2 Hz, 1H), 6.54 (d, J=8.4 Hz, 1H), 5.08-5.15 (m, 1H), 4.60-4.80 (m, 2H), 4.42-4.60 (m, 2H), 4.31-4.40 (m, 1H), 4.01 (s, 2H), 2.90-3.04 (m, 2H), 2.64-2.75 (m, 1H), 2.40-2.47 (m, 1H), 2.00-2.10 (m, 1H), 1.90-2.00 (m, 2H), 1.79-1.87 (m, 2H), 1.10-1.35 (m, 4H). 19F NMR (377 MHz, DMSO-d6): δ −114.58, −114.60.

Example 69: 3-{[(2S)-oxetan-2-yl]methyl}-2-{[cis-4-({6-[(4-chloro-2-fluorophenyl)methyl]pyridin-2-yl}oxy)cyclohexyl]methyl}-3H-imidazo[4,5-b]pyridine-5-carboxylic acid (Compound 174a)

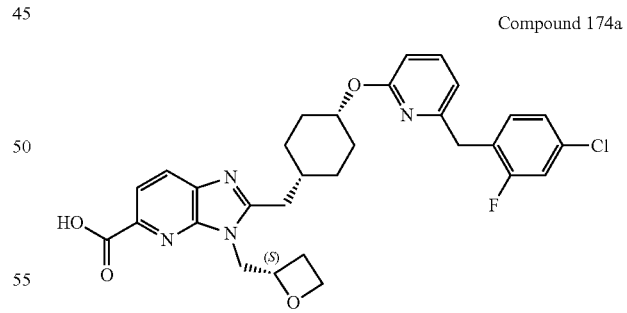

Compound 174a

MS Calcd.: 564.2. MS Found: 565.3 [M+H]+.

1H NMR (400 MHz, DMSO-d6): 8.06 (d, J=8.4 Hz, 1H), 7.95 (d, J=8.0 Hz, 1H), 7.60 (t, J=7.6 Hz, 1H), 7.34-7.40 (m, 2H), 7.23 (dd, J=8.4 Hz, 2.0 Hz, 1H), 6.78 (d, J=6.8 Hz, 1H), 6.61 (d, J=8.4 Hz, 1H), 5.05-5.14 (m, 2H), 4.59-4.65 (m, 1H), 4.40-4.54 (m, 2H), 4.25-4.31 (m, 1H), 3.99 (s, 2H), 2.91-3.04 (m, 2H), 2.62-2.71 (m, 1H), 2.38-2.51 (m, 1H), 2.15-2.30 (m, 1H), 1.80-1.89 (m, 2H), 1.40-1.64 (m, 6H). 19F NMR (377 MHz, DMSO-d6): δ −114.56.

Example 70: 3-{[(2S)-oxetan-2-yl]methyl}-2-{[trans-4-({6-[(4-chlorophenyl)methyl]pyridin-2-yl}oxy)cyclohexyl]methyl}-3H-imidazo[4,5-b]pyridine-5-carboxylic acid (Compound 181a)

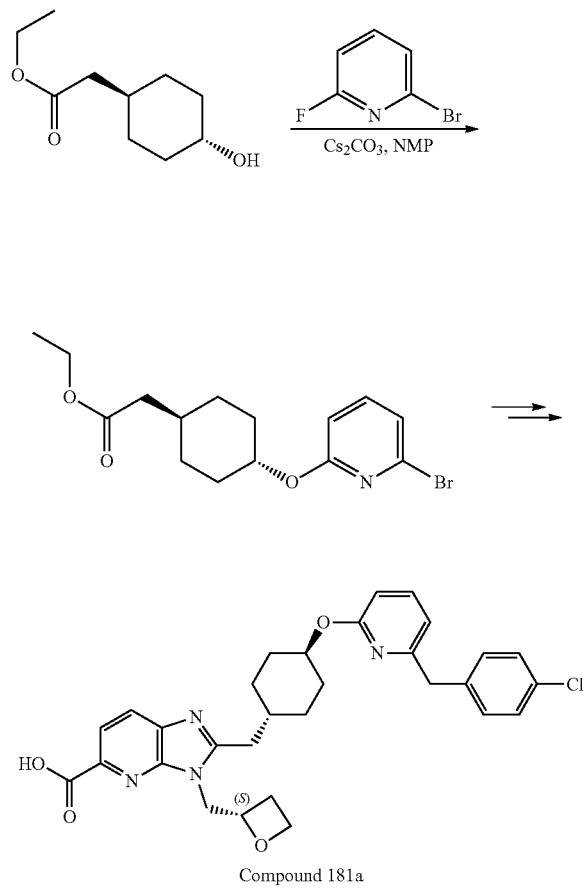

Compound 181a

A mixture of ethyl 2-(trans-4-hydroxycyclohexyl)acetate (1.2 g, 6.4 mmol), 2-bromo-6-fluoropyridine (1.1 g, 6.4 mmol) and $Cs_2CO_3$ (6.3 g, 19.3 mmol) in NMP (20 mL) was heated to 80° C. for 3 days under an atmosphere of nitrogen. The reaction mixture was quenched with water, extracted with ethyl acetate. The organic layers were combined, dried over $Na_2SO_4$, filtered, and concentrated under vacuum. The residue was applied on a silica gel column and eluted with PE:EA=10:1 to give ethyl 2-(trans-4-((6-bromopyridin-2-yl)oxy)cyclohexyl)acetate (1.2 g, 54.5% yield) as colorless oil. MS Calcd.: 341.1. MS Found: 344.2 [M+H]+. 3-{[(2S)-oxetan-2-yl]methyl}-2-{trans-4-({6-[(4-chlorophenyl)methyl]pyridin-2-yl}oxy)cyclohexyl]methyl}-3H-imidazo[4,5-b]pyridine-5-carboxylic acid (63.0 mg) was obtained as a white solid by the similar procedures of Compound 175b. MS Calcd.: 546.2. MS Found: 547.3 [M+H]+.

$^1$H NMR (400 MHz, DMSO-$d_6$): 12.94 (brs, 1H), 8.14 (d, J=8.4 Hz, 1H), 8.01 (d, J=8.0 Hz, 1H), 7.55-7.60 (m, 1H), 7.30-7.35 (m, 4H), 6.81 (d, J=7.6 Hz, 1H), 6.55 (d, J=8.0 Hz, 1H), 5.09-5.16 (m, 1H), 4.84-4.91 (m, 1H), 4.65-4.73 (m, 1H), 4.44-4.60 (m, 2H), 4.32-4.39 (m, 1H), 3.95 (s, 2H), 2.93-3.06 (m, 2H), 2.66-2.76 (m, 1H), 2.40-2.51 (m, 1H), 1.98-2.12 (m, 3H), 1.82-1.90 (m, 2H), 1.20-1.40 (m, 4H).

Example 71: 3-{[(2S)-oxetan-2-yl]methyl}-2-{[trans-4-({2-[(4-chlorophenyl)methyl]-5-fluoropyrimidin-4-yl}oxy)cyclohexyl]methyl}-3H-imidazo[4,5-b]pyridine-5-carboxylic acid (Compound 188a)

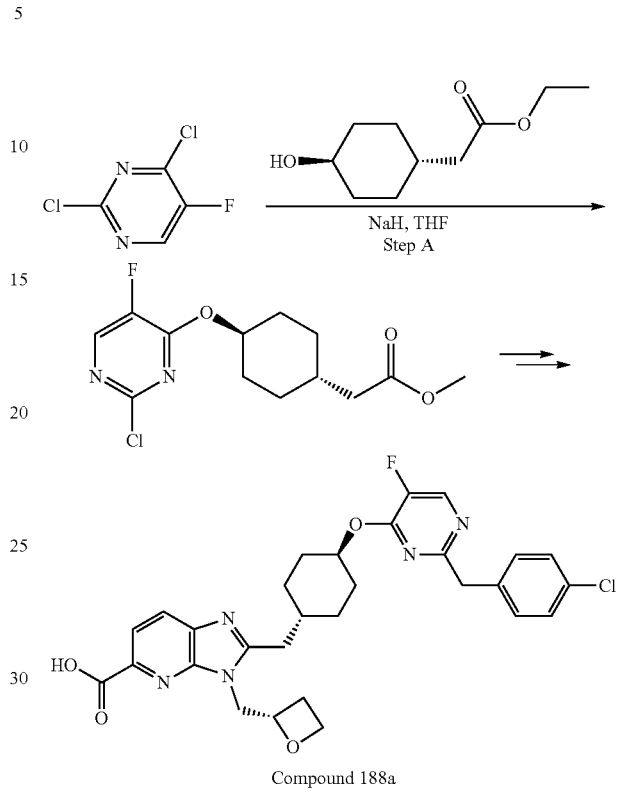

Compound 188a

Step A: The Synthesis of ethyl 2-(trans-4-((2-chloro-5-fluoropyrimidin-4-yl)oxy)cyclohexyl)acetate To a solution 2,4-dichloro-5-fluoropyrimidine (500 mg, 2.7 mmol) in THF (10 mL) was added NaH (129 mg, 3.2 mmol) at 0° C. The reaction mixture was stirred at 30° C. for 30 min. ethyl 2-(trans-4-hydroxycyclohexyl)acetate in THF was added and the mixture was stirred at 50° C. for 2 hours. After the reaction was completed, the reaction mixture was quenched with $NH_4Cl$ (aq.) and extracted with ethyl acetate (20 mL*2). The organic layers were combined, dried over $Na_2SO_4$ and concentrated. The residue was purified by silica gel column chromatography (PE/EA=10/1) to give ethyl 2-(trans-4-((2-chloro-5-fluoropyrimidin-4-yl)oxy)cyclohexyl)acetate (520 mg, 61% yield) as a yellow solid. MS Calcd.: 316.1. MS Found: 358.0 [M+H+41]+. 3-{[(2S)-oxetan-2-yl]methyl}-2-{[trans-4-({2-[(4-chlorophenyl)methyl]-5-fluoropyrimidin-4-yl}oxy)cyclohexyl]methyl}-3H-imidazo[4,5-b]pyridine-5-carboxylic acid (71.7 mg) was obtained as a white solid by the similar procedures of Compound 175b MS Calcd.: 565.2. MS Found: 566.2 [M+H]+.

$^1$H NMR (400 MHz, DMSO-d6): δ 8.49 (d, J=3.6 Hz, 1H), 8.10 (d, J=8.0 Hz, 1H), 7.97 (d, J=8.0 Hz, 1H), 7.30-7.36 (m, 4H), 5.07-5.15 (m, 1H), 4.97-5.04 (m, 1H), 4.62-4.70 (m, 1H), 4.51-4.58 (m, 1H), 4.45-4.51 (m, 1H), 4.30-4.36 (m, 1H), 4.09 (s, 2H), 2.93-3.06 (m, 2H), 2.66-2.74 (m, 1H), 2.40-2.51 (m, 1H), 2.00-2.12 (m, 3H), 1.85-1.92 (m, 2H), 1.40-1.51 (m, 2H), 1.21-1.31 (m, 2H). $^{19}$F NMR (377 MHz, DMSO-d6): δ −157.54.

Example 72: 3-[(1-cyanocyclopropyl)methyl]-2-{[trans-4-({2-[(4-chlorophenyl)methyl]pyrimidin-4-yl}oxy)cyclohexyl]methyl}-3H-imidazo[4,5-b]pyridine-5-carboxylic acid (Compound 178a)

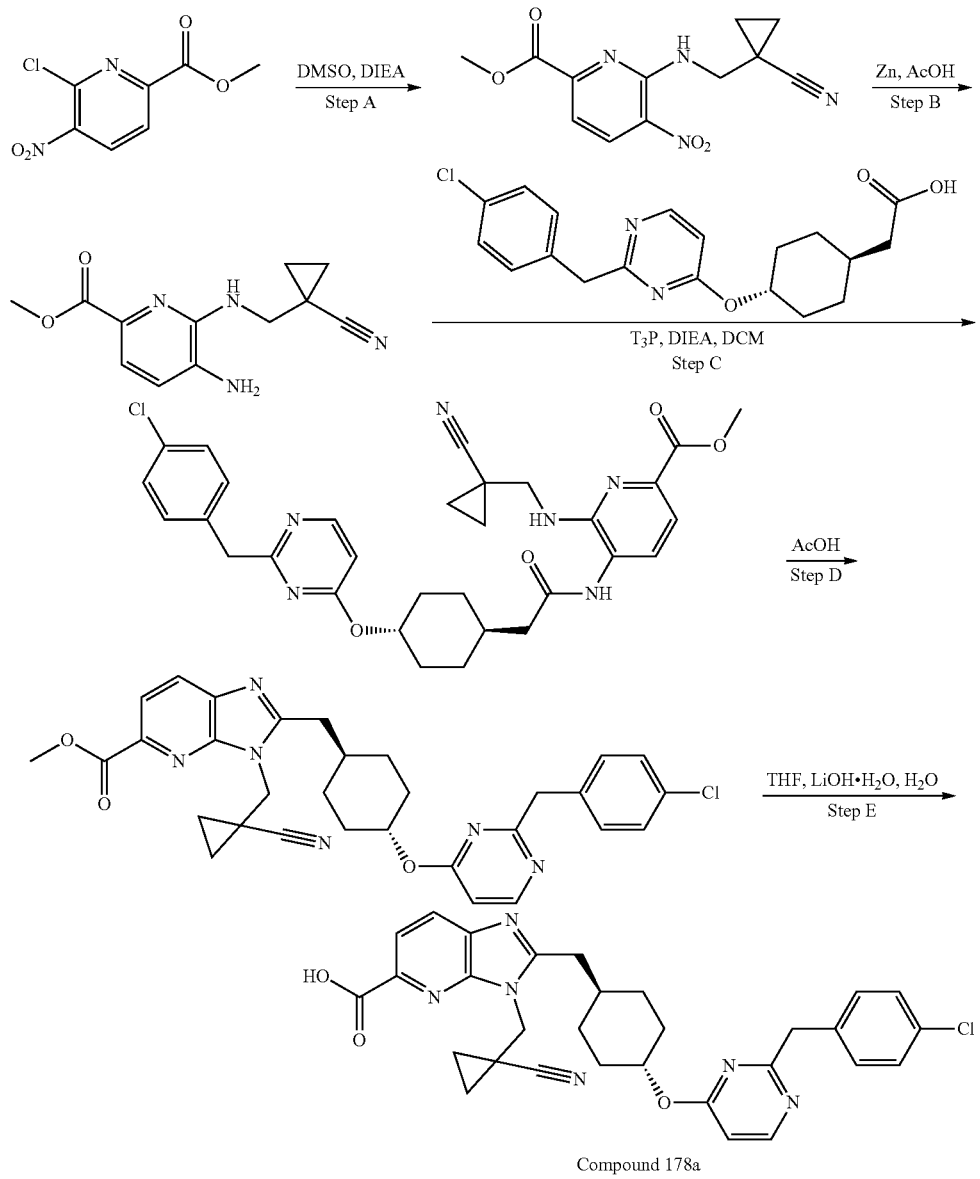

Compound 178a

Step A: The Synthesis of methyl 6-(((1-cyanocyclopropyl)methyl)amino)-5-nitropicolinate To a solution of methyl 6-chloro-5-nitropicolinate (880 mg, 5.3 mmol) and 1-(aminomethyl)cyclopropane-1-carbonitrile (500 mg, 5.8 mmol) in DMSO (60 mL) was added DIEA (2.1 g, 15.9 mmol) at room temperature. The reaction was stirred at 70° C. for 5 hours. After the reaction was completed, the reaction mixture was quenched with water (50 mL) and extracted with ethyl acetate (200 mL×3). The organic layer was combined and washed with brine (100 mL×2), dried over Na$_2$SO$_4$, filtered, and concentrated in vacuum. The residue was purified by column chromatography (PE:EA=3:1) to give methyl 6-(((1-cyanocyclopropyl)methyl)amino)-5-nitropicolinate (800 mg, 57%) as an orange solid.

Step B: The Synthesis of methyl 5-amino-6-(((1-cyanocyclopropyl)methyl)amino)picolinate To a solution of methyl 6-(((1-cyanocyclopropyl)methyl)amino)-5-nitropicolinate (800 mg, 2.7 mmol) in MeOH (10 mL) was added Zn (1.8 g, 27.5 mmol) and AcOH (1.6 g, 27 mmol) at room temperature. The reaction was stirred at room temperature for 3 hours. After the reaction was completed, the reaction mixture was filtered and concentrated in vacuum. The residue was purified by column chromatography (PE:EA=1:1) to give methyl 5-amino-6-(((1-cyanocyclopropyl)methyl)amino)picolinate (500 mg, 71% yield) as brown solid.

MS Calcd.: 246.1. MS Found: 247.0 [M+H]⁺.

Step C: The Synthesis of methyl 5-(2-(trans-4-((2-(4-chlorobenzyl)pyrimidin-4-yl)oxy)cyclohexyl)acetamido)-6-(((1-cyanocyclopropyl)methyl)amino) picolinate To a solution of 2-(trans-4-((2-(4-chlorobenzyl)pyrimidin-4-yl)oxy)cyclohexyl)acetic acid (300 mg, 0.83 mmol) in DCM (5 mL) was added methyl 5-amino-6-(((1-cyanocyclopropyl)methyl) amino) picolinate (205 mg, 0.833 mmol), DIEA (215 mg, 1.67 mmol) and T₃P (1.06 g, 1.67 mmol, 50% wt ethyl acetate). The resulting mixture was stirred at room temperature for 2 hours. The reaction was quenched with water, extracted with DCM. The organic layers were combined, dried over Na₂SO₄, filtered, and concentrated under vacuum. The residue was applied on a silica gel column and eluted with PE:EA=2:1 to give methyl 5-(2-(trans-4-((2-(4-chlorobenzyl)pyrimidin-4-yl)oxy)cyclohexyl)acetamido)-6-(((1-cyanocyclopropyl)methyl)amino) picolinate (230 mg, 47% yield) as a white solid.

MS Calcd.: 588.2. MS Found: 589.4 [M+H]⁺.

Step D: The Synthesis of methyl 2-((trans-4-((2-(4-chlorobenzyl)pyrimidin-4-yl)oxy)cyclohexyl)methyl)-3-((1-cyanocyclopropyl)methyl)-3H-imidazo[4,5-b]pyridine-5-carboxylate Methyl 5-(2-(trans-4-((2-(4-chlorobenzyl)pyrimidin-4-yl)oxy)cyclohexyl)acetamido)-6-(((1-cyanocyclopropyl)methyl)amino)picolinate (230 mg, 0.39 mmol) was dissolved in AcOH (3 mL), then the mixture was heated to 110° C. for 3 hours. The solvent was removed in vacuo. The residue was diluted with sodium bicarbonate aqueous solution, extracted with ethyl acetate. The organic layers were combined, dried over Na₂SO₄, filtered, and concentrated under vacuum. The residue was applied on a silica gel column and eluted with PE:EA=1:1 to give methyl 2-((trans-4-((2-(4-chlorobenzyl)pyrimidin-4-yl)oxy)cyclohexyl)methyl)-3-((1-cyanocyclopropyl)methyl)-3H-imidazo[4,5-b]pyridine-5-carboxylate (160 mg, 72% yield).

MS Calcd.: 570.2. MS Found: 571.3 [M+H]⁺.

Step E: The Synthesis of 3-[(1-cyanocyclopropyl)methyl]-2-{[trans-4-({2-[(4-chlorophenyl)methyl]pyrimidin-4-yl}oxy)cyclohexyl]methyl}-3H-imidazo[4,5-b]pyridine-5-carboxylic acid To a solution of methyl 2-((trans-4-((2-(4-chlorobenzyl)pyrimidin-4-yl)oxy)cyclohexyl)methyl)-3-((1-cyanocyclopropyl)methyl)-3H-imidazo[4,5-b]pyridine-5-carboxylate (160 mg, 0.28 mmol) in THF (2 mL) was added H₂O (0.5 mL) and LiOH H₂O (23.5 mg, 0.561 mmol). The solution was stirred at room temperature for 3 hours. The solvent was removed in vacuo. The residue was purified by Prep-HPLC to give 3-[(1-cyanocyclopropyl)methyl]-2-{[trans-4-({2-[(4-chlorophenyl)methyl]pyrimidin-4-yl}oxy)cyclohexyl]methyl}-3H-imidazo[4,5-b]pyridine-5-carboxylic acid (44.5 mg, yield: 28%) as a white solid. MS Calcd.: 556.2. MS Found: 557.3 [M+H]⁺.

¹H NMR (400 MHz, DMSO-d₆): 8.43 (d, J=6.0 Hz, 1H), 8.15 (d, J=8.4 Hz, 1H), 8.01 (d, J=8.4 Hz, 1H), 7.32-7.39 (m, 4H), 6.75 (d, J=6.0 Hz, 1H), 4.91-4.99 (m, 1H), 4.55 (s, 2H), 4.11 (s, 2H), 3.06 (d, J=6.8 Hz, 2H), 2.00-2.16 (m, 3H), 1.88-1.93 (m, 2H), 1.64-1.70 (m, 2H), 1.22-1.47 (m, 6H).

Example 73: 3-(2-methoxyethyl)-2-{[trans-4-({2-[(4-chlorophenyl)methyl]pyrimidin-4-yl}oxy)cyclohexyl]methyl}-3H-imidazo[4,5-b]pyridine-5-carboxylic Acid (Compound 179a)

Compound 179a

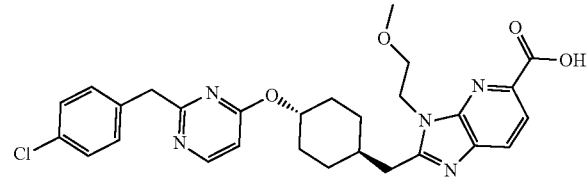

MS Calcd.: 535.2. MS Found: 536.2 [M+H]⁺.

¹H NMR (400 MHz, DMSO-d6): δ 8.39 (d, J=5.6 Hz, 1H), 7.85-7.90 (m, 2H), 7.30-7.35 (m, 4H), 6.69 (d, J=6.0 Hz, 1H), 4.89-4.98 (m, 1H), 4.48 (t, J=5.2 Hz, 2H), 4.08 (s, 2H), 3.67 (t, J=5.2 Hz, 2H), 3.20 (s, 3H), 2.85 (d, J=6.8 Hz, 2H), 1.97-2.05 (m, 3H), 1.83-1.90 (m, 2H), 1.34-1.43 (m, 2H), 1.18-1.30 (m, 2H).

Example 74: 3-methyl-2-{[trans-4-({2-[(4-chlorophenyl)methyl]pyrimidin-4-yl}oxy)cyclohexyl]methyl}-3H-imidazo[4,5-b]pyridine-5-carboxylic Acid (Compound 180a)

Compound 180a

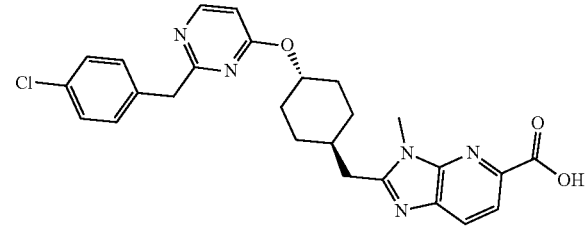

MS Calcd.: 491.2. MS Found: 492.2 [M+H]⁺.

¹H NMR (400 MHz, DMSO-d₆): δ 8.39 (d, J=6.0 Hz, 1H), 8.07 (d, J=8.4 Hz, 1H), 7.96 (d, J=8.4 Hz, 1H), 7.30-7.38 (m, 4H), 6.69 (d, J=6.0 Hz, 1H), 4.87-4.98 (m, 1H), 4.08 (s, 2H), 3.84 (s, 3H), 2.90 (d, J=6.8 Hz, 2H), 1.95-2.05 (m, 3H), 1.80-1.89 (m, 2H), 1.30-1.44 (m, 2H), 1.21-1.31 (m, 2H).

Example 75: 2-{[4-({2-[(4-chlorophenyl)methyl]
pyrimidin-4-yl}oxy)phenyl]methyl}-3-{[(2S)-
oxetan-2-yl]methyl}-3H-imidazo[4,5-b]pyridine-5-
carboxylic acid (Compound 186a)
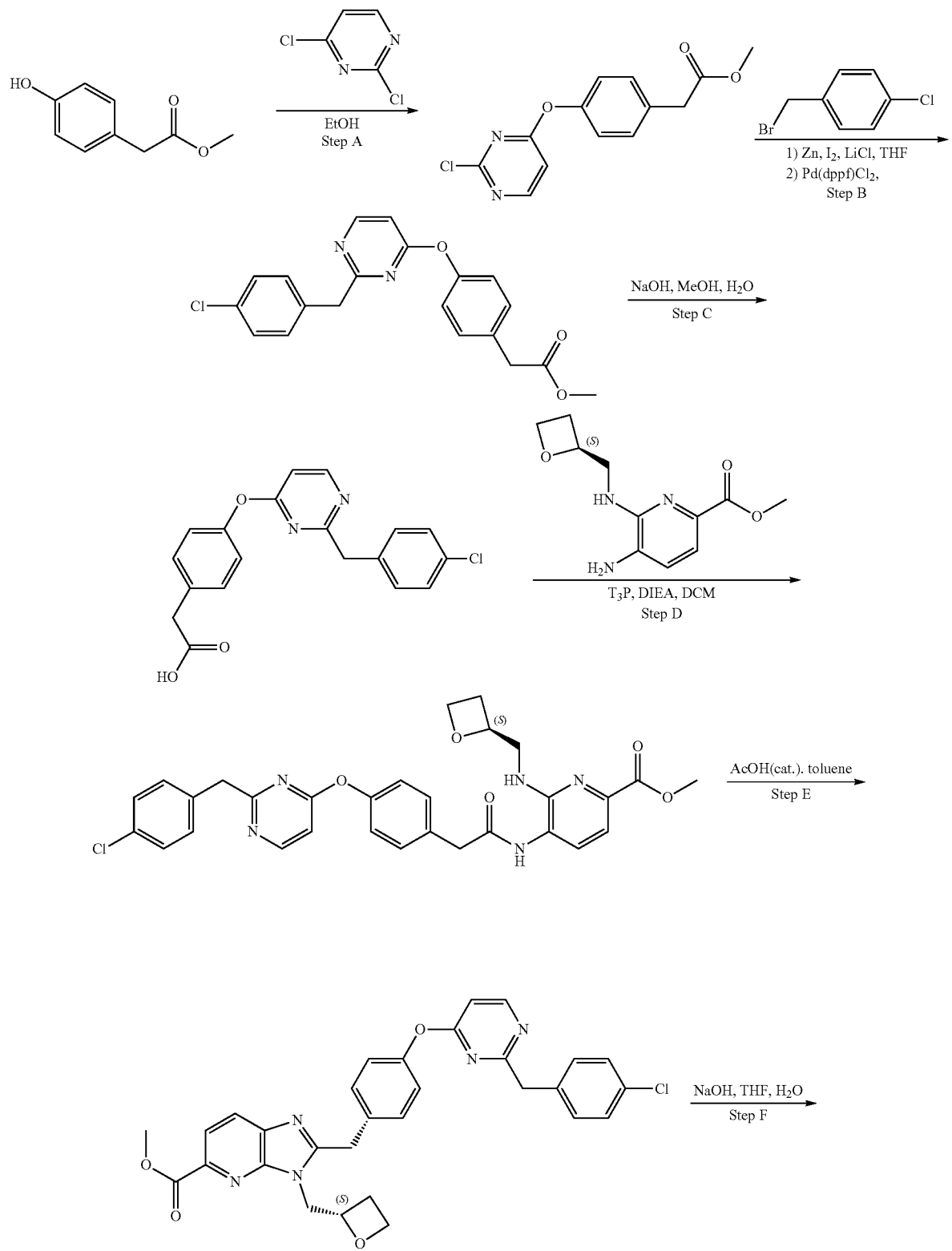

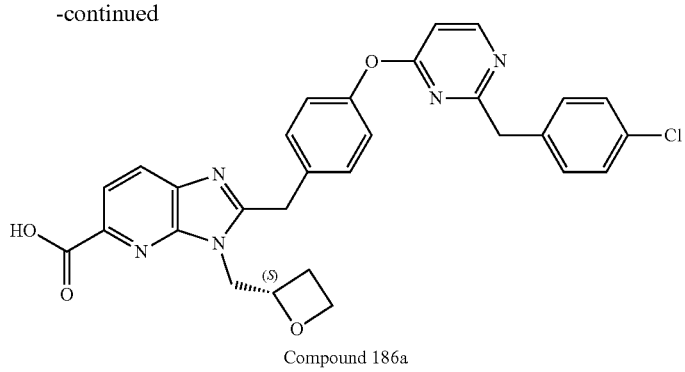

Compound 186a

Step A: The Synthesis of methyl 2-(4-((2-chloropyrimidin-4-yl)oxy)phenyl)acetate To a solution of methyl 2-(4-hydroxyphenyl)acetate (1.0 g, 6.0 mmol) in EtOH (15 mL) was added 2,4-dichloropyrimidine (898 mg, 6.024 mmol) and triethylamine (1.2 g, 12.0 mmol). The resulting mixture was stirred at 80° C. for 12 hours. The solvent was removed in vacuo. The residue was purified by silica gel column chromatography (PE/EA=4/1) to give methyl 2-(4-((2-chloropyrimidin-4-yl)oxy)phenyl)acetate (1.0 g, 59% yield) as a yellow solid.

MS Calcd.: 278.0. MS Found: 279.0 [M+H]$^+$.

Step B: The Synthesis of methyl 2-(4-(2-(4-chlorobenzyl)pyrimidin-4-yl)oxy)phenyl)acetate A mixture of 1-(bromomethyl)-4-chlorobenzene (1.5 g, 7.2 mmol), Zn (1.4 g, 21.6 mmol), I$_2$ (183 mg, 0.7 mmol) and LiCl (151 mg, 3.6 mmol) in dry THF (15 mL) was heated to 50° C. for 1 hour under an atmosphere of nitrogen. Then methyl 2-(4-((2-chloropyrimidin-4-yl)oxy)phenyl)acetate (1.0 g, 3.6 mmol) and Pd(dppf)Cl$_2$ (527 mg, 0.72 mmol) was added to the above reaction mixture. The final mixture was stirred at 70° C. for 3 hours under an atmosphere of nitrogen. The solid was filtered out and the filtrate was concentrated under vacuum. The residue was applied on a silica gel column and eluted with PE:EA=3:1 to give methyl 2-(4-((2-(4-chlorobenzyl)pyrimidin-4-yl)oxy)phenyl)acetate (1.1 g, 83% yield) as an off-white solid.

MS Calcd.: 368.1. MS Found: 369.1 [M+H]$^+$.

Step C: The Synthesis of 2-(4-((2-(4-chlorobenzyl)pyrimidin-4-yl)oxy)phenyl)acetic acid To a solution of methyl 2-(4-((2-(4-chlorobenzyl)pyrimidin-4-yl)oxy)phenyl)acetate (1.1 g, 3.0 mmol) in MeOH (10 mL) and water (2 mL) was added NaOH (239 mg, 6.0 mmol). The solution was stirred at 30° C. for 2 hours. The reaction mixture was concentrated under vacuum. The residue was diluted with water, then adjusted to pH 4-5 with 1 N HCl. The isolated solid was collected by filtration, dried to give 2-(4-((2-(4-chlorobenzyl)pyrimidin-4-yl)oxy)phenyl)acetic acid (0.6 g, 60% yield) as an off-white solid.

MS Calcd.: 354.1. MS Found: 355.0 [M+H]$^+$.

Step D: The Synthesis of methyl (S)-5-(2-(4-((2-(4-chlorobenzyl)pyrimidin-4-yl)oxy)phenyl)acetamido)-6-((oxetan-2-ylmethyl)amino)picolinate To a solution of 2-(4-((2-(4-chlorobenzyl)pyrimidin-4-yl)oxy)phenyl)acetic acid (200 mg, 0.565 mmol) in DCM (4 mL) was added methyl (S)-5-amino-6-((oxetan-2-ylmethyl)amino)picolinate (133 mg, 0.565 mmol), DIEA (146 mg, 1.13 mmol) and T$_3$P (718 mg, 1.13 mmol, 50% wt ethyl acetate). The resulting mixture was stirred at room temperature for 2 hours. The reaction was quenched with water, extracted with DCM. The organic layers were combined, dried over Na$_2$SO$_4$, filtered and concentrated under vacuum. The residue was applied on a silica gel column and eluted with EA to give methyl (S)-5-(2-(4-((2-(4-chlorobenzyl)pyrimidin-4-yl)oxy)phenyl)acetamido)-6-((oxetan-2-ylmethyl)amino)picolinate (210 mg, 65% yield) as a light-yellow solid.

MS Calcd.: 573.2. MS Found: 574.0 [M+H]$^+$.

Step E: The Synthesis of methyl (S)-2-(4-((2-(4-chlorobenzyl)pyrimidin-4-yl)oxy)benzyl)-3-(oxetan-2-ylmethyl)-3H-imidazo[4,5-b]pyridine-5-carboxylate A mixture of methyl (S)-5-(2-(4-((2-(4-chlorobenzyl)pyrimidin-4-yl)oxy)phenyl)acetamido)-6-((oxetan-2-ylmethyl)amino)picolinate (210 mg, 0.37 mmol) and AcOH (1 drop) in toluene (5 mL) was stirred at 110° C. for 16 hours. The solvent was concentrated under vacuum. The residue was applied on a silica gel column and eluted with EA to give methyl (S)-2-(4-((2-(4-chlorobenzyl)pyrimidin-4-yl)oxy)benzyl)-3-(oxetan-2-ylmethyl)-3H-imidazo[4,5-b]pyridine-5-carboxylate (160 mg, 79% yield) as an off-white solid.

MS Calcd.: 555.2. MS Found: 556.2 [M+H]$^+$.

Step F: The Synthesis of 2-{[4-({2-[(4-chlorophenyl)methyl]pyrimidin-4-yl}oxy)phenyl]methyl}-3-{[(2S)-oxetan-2-yl]methyl}-3H-imidazo[4,5-b]pyridine-5-carboxylic acid To a solution of methyl (S)-2-(4-((2-(4-chlorobenzyl)pyrimidin-4-yl)oxy)benzyl)-3-(oxetan-2-ylmethyl)-3H-imidazo[4,5-b]pyridine-5-carboxylate (140 mg, 0.25 mmol) in THF (2 mL) and water (0.5 mL) was added NaOH (20 mg, 0.50 mmol). The solution was stirred at 50° C. for 4 hours. The solvent was removed in vacuo. The residue was purified by Prep-HPLC to give 2-{[4-({2-[(4-chlorophenyl)methyl]pyrimidin-4-yl}oxy)phenyl]methyl}-3-{[(2S)-oxetan-2-yl]methyl}-3H-imidazo[4,5-b]pyridine-5-carboxylic acid (39.3 mg, yield: 29%) as a white solid. MS Calcd.: 541.2. MS Found: 542.4 [M+H]$^+$.

$^1$H NMR (400 MHz, DMSO-d$_6$): 13.00 (s, 1H), 8.58 (d, J=5.6 Hz, 1H), 8.12 (d, J=8.0 Hz, 1H), 7.99 (d, J=8.4 Hz, 1H), 7.43 (d, J=8.4 Hz, 2H), 7.20-7.30 (m, 4H), 7.16 (d,

J=8.4 Hz, 2H), 6.88 (d, J=6.0 Hz, 1H), 5.08-5.14 (m, 1H), 4.67-4.72 (m, 1H), 4.47-4.61 (m, 4H), 4.35-4.40 (m, 1H), 4.03 (s, 2H), 2.65-2.73 (m, 1H), 2.39-2.48 (m, 1H).

Example 76: 2-{[4-({2-[(4-chlorophenyl)methyl]pyrimidin-4-yl}oxy)phenyl]methyl}-1-{[(2S)-oxetan-2-yl]methyl}-1H-1,3-benzodiazole-6-carboxylic acid (Compound 187a)

Compound 187a

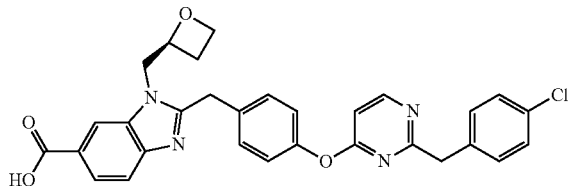

MS Calcd.: 540.2. MS Found: 541.2 [M+H]$^+$.

$^1$H NMR (400 MHz, DMSO-d$_6$): 8.59 (d, J=5.6 Hz, 1H), 8.40 (s, 1H), 7.93 (dd, J=8.4 Hz, 1.6 Hz, 1H), 7.73 (J=8.4 Hz, 1H), 7.45 (d, J=8.4 Hz, 2H), 7.18-7.30 (m, 6H), 6.89 (d, J=6.0 Hz, 1H), 4.94-5.01 (m, 1H), 4.81-4.89 (m, 1H), 4.66-4.72 (m, 1H), 4.57-4.61 (m, 2H), 4.45-4.50 (m, 1H), 4.37-4.42 (m, 1H), 4.03 (s, 2H), 2.62-2.72 (m, 1H), 2.32-2.42 (m, 1H).

Example 77: 2-{[4-({2-[(4-chlorophenyl)methyl]-5-fluoropyrimidin-4-yl}oxy)phenyl]methyl}-3-{[(2S)-oxetan-2-yl]methyl}-3H-imidazo[4,5-b]pyridine-5-carboxylic acid (Compound 189a)

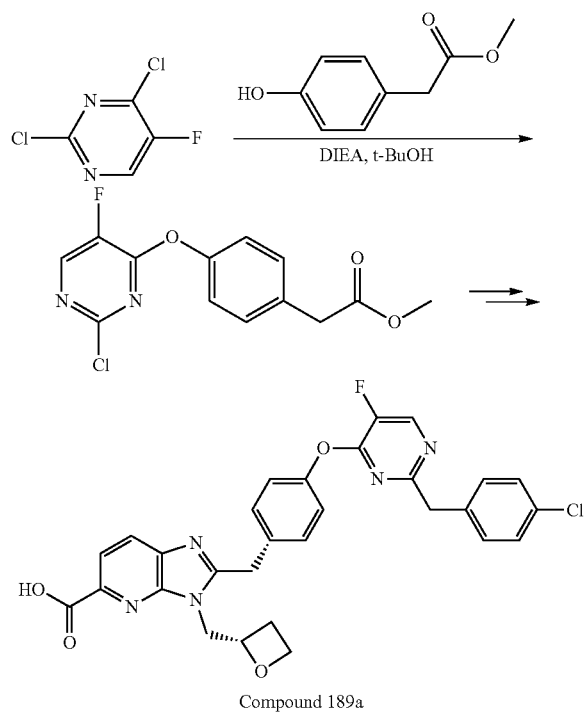

Compound 189a

To a solution 2,4-dichloro-5-fluoropyrimidine (2.0 g, 12.0 mmol) in t-BuOH (30 mL) were added methyl 2-(4-hydroxyphenyl)acetate (2.0 g, 12.0 mmol) and DIEA (4.7 g, 36.1 mmol). The reaction mixture was stirred at 110° C. for 16 hours. After the reaction was completed, the reaction mixture was quenched with water and extracted with ethyl acetate (70 mL*2). The organic layers were combined, dried over Na$_2$SO$_4$ and concentrated. The residue was purified by silica gel column chromatography (PE/EA=8/1) to give methyl 2-(4-((2-chloro-5-fluoropyrimidin-4-yl)oxy)phenyl)acetate (2.2 g, 62% yield) as a yellow solid. MS Calcd.: 296.0; MS Found: 297.0 [M+H]$^+$. 2-{[4-({2-[(4-chlorophenyl)methyl]-5-fluoropyrimidin-4-yl}oxy)phenyl]methyl}-3-{[(2S)-oxetan-2-yl]methyl}-3H-imidazo[4,5-b]pyridine-5-carboxylic acid (39.6 mg) was obtained as a white solid by the similar procedure of Compound 186a. MS Calcd.: 559.1. MS Found: 560.1 [M+H]$^+$.

$^1$H NMR (400 MHz, DMSO-d6): δ 8.69 (d, J=3.2 Hz, 1H), 8.09 (d, J=8.4 Hz, 1H), 7.98 (d, J=8.4 Hz, 1H), 7.43 (d, J=8.8 Hz, 2H), 7.15-7.27 (m, 6H), 5.08-5.15 (m, 1H), 4.67-4.72 (m, 1H), 4.55-4.62 (m, 1H), 4.52-4.54 (m, 2H), 4.46-4.51 (m, 1H), 4.34-4.40 (m, 1H), 3.99 (s, 2H), 2.64-2.73 (m, 1H), 2.37-2.51 (m, 1H). $^{19}$F NMR (377 MHz, DMSO-d6): δ −115.19.

Example 78: 2-{[4-({2-[(4-chlorophenyl)methyl]-5-fluoropyrimidin-4-yl}oxy)-2-fluorophenyl]methyl}-3-{[(2S)-oxetan-2-yl]methyl}-3H-imidazo[4,5-b]pyridine-5-carboxylic acid (Compound 190a)

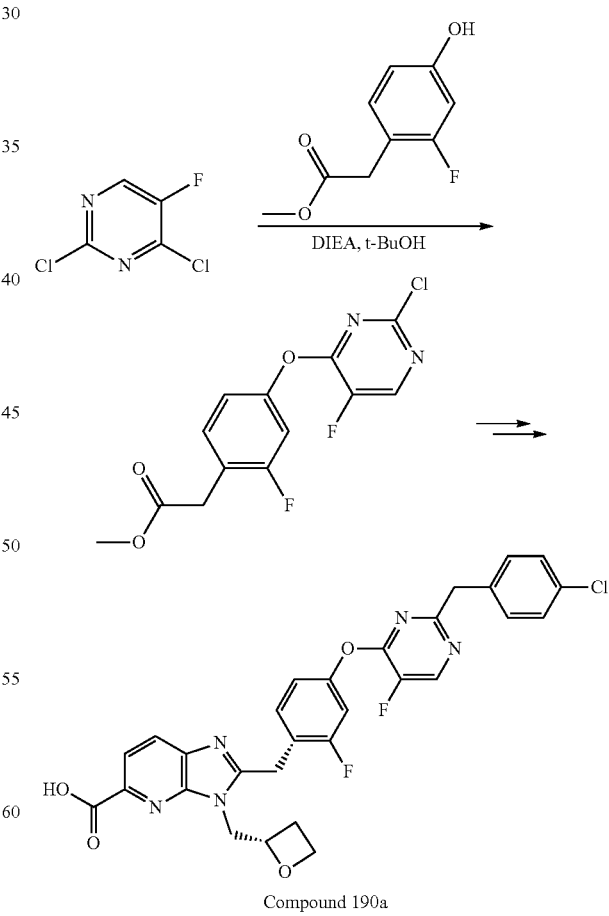

Compound 190a

A mixture of 2,4-dichloro-5-fluoropyrimidine (600 mg, 3.6 mmol), methyl 2-(2-fluoro-4-hydroxyphenyl)acetate (682 mg, 3.7 mmol), DIEA (1.39 g, 10.7 mmol) in t-BuOH (10 mL) was stirred at 110° C. for 2 hours under N₂ atmosphere. After the reaction was completed, the reaction mixture was filtered, and the filtrate concentrated. The crude product was purified by column chromatography on silica gel (PE:EA=15:1) to give methyl 2-(4-((2-chloro-5-fluoropyrimidin-4-yl)oxy)-2-fluorophenyl)acetate (1.0 g, yield: 88%) as a white solid.

MS Calcd.: 314.0. MS Found: 314.9 [M+H]⁺. 2-{[4-({2-[(4-chlorophenyl)methyl]-5-fluoropyrimidin-4-yl}oxy)-2-fluorophenyl]methyl}-3-{[(2S)-oxetan-2-yl]methyl}-3H-imidazo[4,5-b]pyridine-5-carboxylic acid (16.7 mg) was obtained as a white solid by the similar procedure of Compound 186a. MS Calcd.: 577.1. MS Found: 578.4 [M+H]⁺.

¹H NMR (400 MHz, DMSO-d₆): 8.73 (d, J=2.8 Hz, 1H), 7.88 (s, 2H), 7.44 (t, J=8.4 Hz, 1H), 7.25-7.31 (m, 3H), 7.20-7.25 (m, 2H), 7.11 (dd, J=8.4 Hz, 2.0 Hz, 1H), 5.09-5.16 (m, 1H), 4.68-4.73 (m, 1H), 4.57-4.63 (m, 1H), 4.41-4.53 (m, 3H), 4.30-4.35 (m, 1H), 4.04 (s, 2H), 2.60-2.72 (m, 1H), 2.40-2.51 (m, 1H). 19F NMR (377 MHz, DMSO-d6): δ −114.09, −155.95.

Example 79: 2-{[4-({2-[(4-chlorophenyl)methyl]-5-fluoropyrimidin-4-yl}oxy)-2-fluorophenyl]methyl}-1-{[(2S)-oxetan-2-yl]methyl}-1H-1,3-benzodiazole-6-carboxylic acid (Compound 191a)

Compound 191a

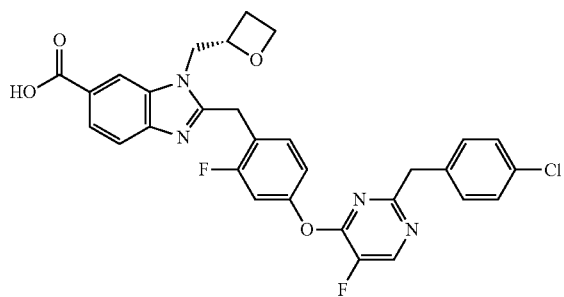

MS Calcd.: 576.1. MS Found: 577.2 [M+H]⁺.

¹H NMR (400 MHz, DMSO-d₆): 8.73 (d, J=2.8 Hz, 1H), 8.25 (d, J=0.8 Hz, 1H), 7.78 (dd, J=8.4 Hz, 1.6 Hz, 1H), 7.58 (d, J=8.8 Hz, 1H), 7.42 (t, J=8.4 Hz, 1H), 7.24-7.30 (m, 3H), 7.19-7.23 (m, 2H), 7.10 (dd, J=8.8 Hz, 4.8 Hz, 1H), 5.00-5.09 (m, 1H), 4.70-4.76 (m, 1H), 4.57-4.63 (m, 1H), 4.42-4.53 (m, 3H), 4.32-4.40 (m, 1H), 4.03 (s, 2H), 2.64-2.75 (m, 1H), 2.30-2.42 (m, 1H). ¹⁹F NMR (377 MHz, DMSO-d6): δ −114.09, −155.96.

Example 80: 2-[(4-{6-[(4-chloro-2-fluorophenyl)methyl]-1H-pyrazolo[3,4-b]pyridin-1-yl}piperidin-1-yl)methyl]-3-{[(2S)-oxetan-2-yl]methyl}-3H-imidazo[4,5-b]pyridine-5-carboxylic acid (Compound 185a)

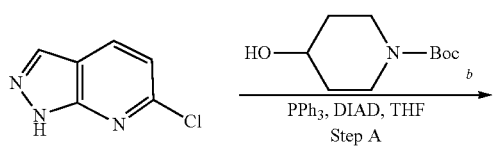

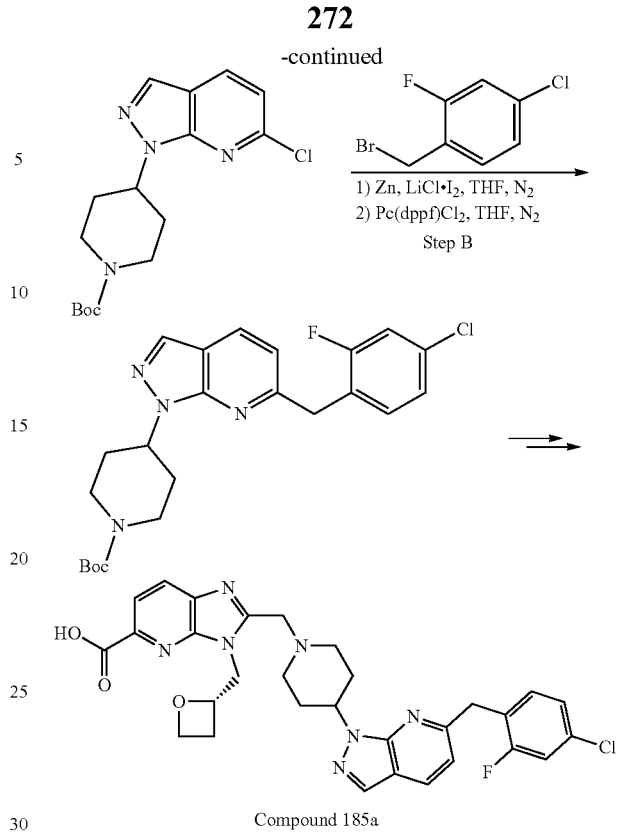

Compound 185a

Step A: The Synthesis of tert-butyl 4-(6-chloro-1H-pyrazolo[3,4-b]pyridin-1-yl)piperidine-1-carboxylate A mixture of 6-chloro-1H-pyrazolo[3,4-b]pyridine (2.0 g, 13.0 mmol), tert-butyl 4-hydroxypiperidine-1-carboxylate (3.1 g, 15.6 mmol), PPh₃ (5.1 g, 19.5 mmol), and DIAD (3.9 g, 19.5 mmol) in THF (20 mL) under N₂ was stirred at room temperature for 2 hours. The mixture was poured into water (150 mL) and extracted with ethyl acetate (250 mL×3), washed with brine (150 mL×2), dried over Na₂SO₄, filtered and concentrated in vacuum. The residue was purified by column chromatography to give tert-butyl 4-(6-chloro-1H-pyrazolo[3,4-b]pyridin-1-yl)piperidine-1-carboxylate (3.4 g, yield: 78%) as a white solid.

Step B: The Synthesis of tert-butyl 4-(6-(4-chloro-2-fluorobenzyl)-1H-pyrazolo[3,4-b]pyridin-1-yl)piperidine-1-carboxylate A mixture of Zn (1.4 g, 22.3 mmol), LiCl (156 mg, 3.72 mmol), I₂ (188 mg, 0.74 mmol), 1-(bromomethyl)-4-chloro-2-fluorobenzene (1.7 g, 7.4 mmol) in dry THF (20 mL) under N₂ was stirred at 50° C. for 1 hour. tert-butyl 4-(6-chloro-1H-pyrazolo[3,4-b]pyridin-1-yl)piperidine-1-carboxylate (1.0 g, 3.0 mmol) and Pd(dppf)Cl₂ was added, and the resulting mixture was stirred at 70° C. for 2 hours. The mixture was poured into cold water and extracted with ethyl acetate (3×150 mL). The organic layer was washed with brine (150 mL), dried over Na₂SO₄, filtered, and concentrated in vacuum. The residue was purified by column chromatography to give tert-butyl 4-(6-(4-chloro-2-fluorobenzyl)-1H-pyrazolo[3,4-b]pyridin-1-yl)piperidine-1-carboxylate (1.0 g, yield: 76%) as a yellow solid.

2-[(4-{6-[(4-chloro-2-fluorophenyl)methyl]-1H-pyrazolo[3,4-b]pyridin-1-yl}piperidin-1-yl)methyl]-3-{[(2S)- oxetan-2-yl]methyl}-3H-imidazo[4,5-b]pyridine-5-carboxylic acid (25 mg) was obtained as white solid by the similar procedure of Compound 109a. MS Calcd.: 589.2. MS Found: 590.3 [M+H]⁺.

¹H NMR (400 MHz, DMSO-d6) δ 8.14 (d, J=8.4 Hz, 1H), 8.10 (s, 1H), 7.99 (d, J=8.4 Hz, 1H), 7.93 (d, J=8.0, 1H), 7.35-7.43 (m, 2H), 7.25 (dd, J=8.0 Hz, 1.6 Hz, 1H), 7.04 (d, J=8.0 Hz, 1H), 5.14-5.22 (m, 1H), 4.70-4.92 (m, 3H), 4.48-4.54 (m, 1H), 4.36-4.41 (m, 1H), 4.25 (s, 2H), 4.03 (d, J=13.6 Hz, 1H), 3.91 (d, J=13.6 Hz, 1H), 3.00-3.07 (m, 1H), 2.90-2.99 (m, 1H), 2.65-2.75 (m, 1H), 2.49-2.58 (m, 1H), 2.32-2.44 (m, 2H), 2.10-2.27 (m, 2H), 1.85-1.95 (m, 2H). ¹⁹F NMR (377 MHz, DMSO-d6): δ −114.13.

Example 81: (S)-2-((4-(2-(4-chloro-2-fluorobenzyl)benzo[d]oxazol-7-yl)piperidin-1-yl)methyl)-3-(oxetan-2-ylmethyl)-3H-imidazo[4,5-b]pyridine-5-carboxylic Acid (Compound 143a)

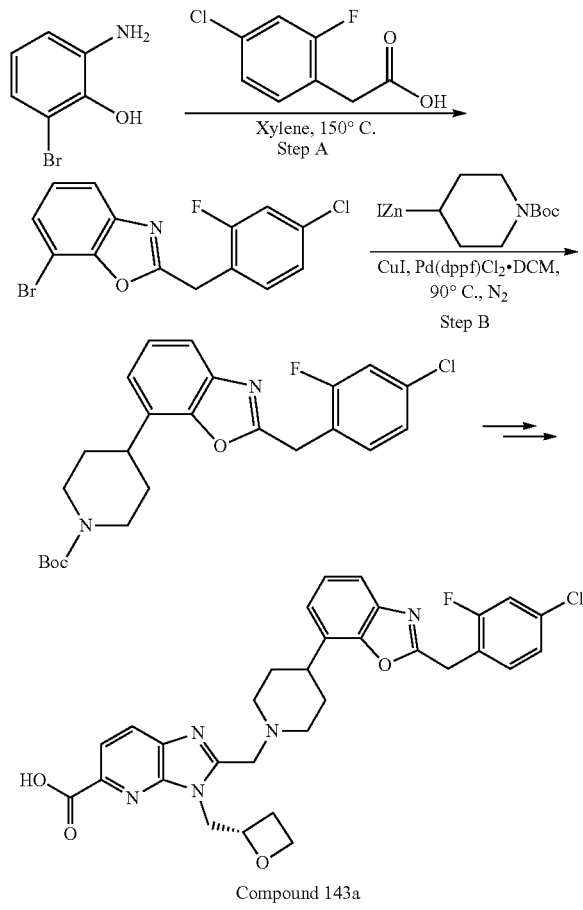

Compound 143a

Step A: 7-bromo-2-(4-chloro-2-fluorobenzyl)benzo[d]oxazole

To a solution of 2-(4-chloro-2-fluorophenyl)acetic acid (2.41 g, 12.7 mmol) in Xylene (50 mL) were added 2-amino-6-bromophenol (2.00 g, 10.6 mmol) and boric acid (790 mg, 12.7 mmol). The mixture was heated to reflux in a flask equipped with a Dean-Stark trap for 8 h. LCMS showed the reaction was completed. The mixture was cooled to room temperature. The mixture was filtered and concentrated to dryness. The residue was purified by silica gel column (PE:EA/10:1) to afford 7-bromo-2-(4-chloro-2-fluorobenzyl)benzo[d]oxazole as a white solid (1.30 g, 36% yield). LC-MS: m/z 340.1, 342.0 (M+H)⁺.

Step B: tert-butyl 4-(2-(4-chloro-2-fluorobenzyl)benzo[d]oxazol-7-yl)piperidine-1-carboxylate To a solution of 7-bromo-2-(4-chloro-2-fluorobenzyl)benzo[d]oxazole (150 mg, 0.440 mmol) in DMA (2 mL) were added Pd(dppf)Cl₂·DCM (22.0 mg, 0.0260 mmol) and CuI (10.0 mg, 0.0520 mmol) at room temperature under N₂ atmosphere. The solution of (1-(tert-butoxycarbonyl)piperidin-4-yl)zinc(II) iodide (2 mL, 1.1 mmol/mL in DMA, 2.2 mmol) was added into the mixture. The mixture was stirred at 90° C. under N₂ atmosphere for 2 h. The mixture was cooled to room temperature. H₂O (10 mL) was added, and the mixture was extracted with ethyl acetate (20 mL*2). The organic layers were washed with brine, dried over Na₂SO₄, concentrated, and purified by column chromatography (petroleum ether/ethyl acetate=4:1) to give tert-butyl 4-(2-(4-chloro-2-fluorobenzyl)benzo[d]oxazol-7-yl)piperidine-1-carboxylate as brown oil (130 mg, 66% yield). LC-MS: m/z 445.3 (M+H)⁺.

(S)-2-((4-(2-(4-chloro-2-fluorobenzyl)benzo[d]oxazol-7-yl)piperidin-1-yl)methyl)-3-(oxetan-2-ylmethyl)-3H-imidazo[4,5-b]pyridine-5-carboxylic acid (20.8 mg, 27% yield) was obtained as a solid by the similar procedure of Compound 109a.

¹H NMR (400 MHz, DMSO-d⁶) δ 8.13 (d, J=8.4 Hz, 1H), 7.99 (d, J=8.0 Hz, 1H), 7.46-7.54 (m, 3H), 7.21-7.32 (m, 3H), 5.17-5.21 (m, 1H), 4.86 (dd, J=14.4, 6.4 Hz, 1H), 4.75 (dd, J=14.8, 4.0 Hz, 1H), 4.47-4.51 (m, 1H), 4.37-4.39 (m, 3H), 3.99 (q, J=14.0 Hz, 2H), 2.90-3.02 (m, 3H), 2.66-2.73 (m, 1H), 2.29-2.35 (m, 3H), 1.84-1.90 (m, 4H). LC-MS: m/z 590.2, 592.3 (M+H)⁺.

Example 82: 2-[(4-{2-[(4-chloro-2-fluorophenyl)methyl]-1,3-benzoxazol-7-yl}-1,2,3,6-tetrahydropyridin-1-yl)methyl]-3-{[(2S)-oxetan-2-yl]methyl}-3H-imidazo[4,5-b]pyridine-5-carboxylic acid (Compound 170a)

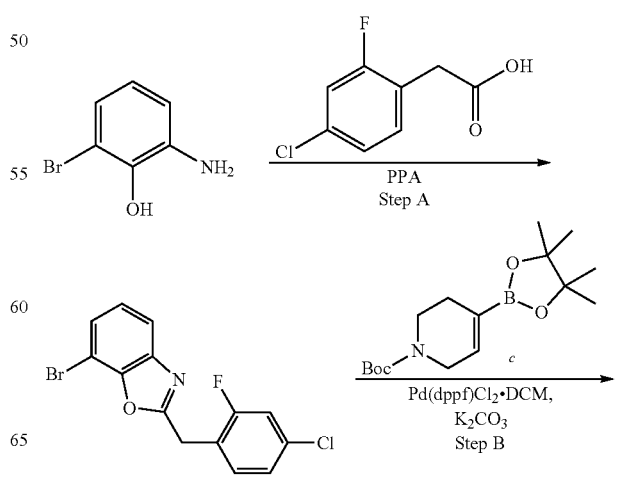

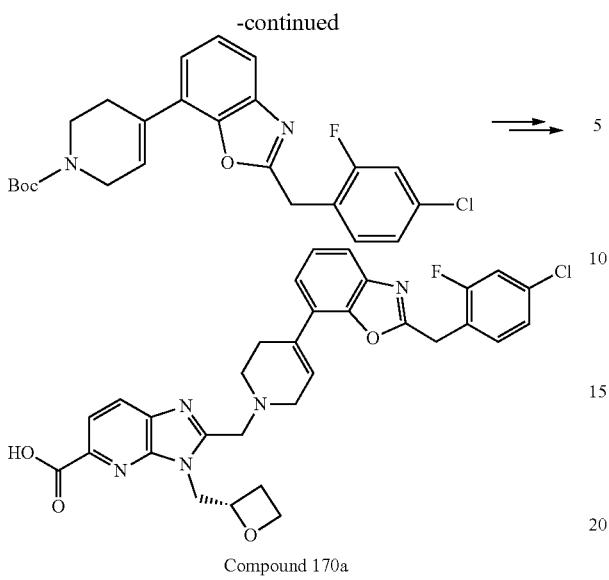

Compound 170a

Step A: The Synthesis of 7-bromo-2-(4-chloro-2-fluorobenzyl)benzo[d]oxazole

A mixture of 2-amino-6-bromophenol (500 mg, 2.65 mmol) and 2-(4-chloro-2-fluorophenyl)acetic acid (500 mg, 2.65 mmol) in PPA (10 mL) was stirred at 140° C. for 3 hours. After the reaction was completed, the reaction mixture was quenched with NaHCO$_3$ solution (100 mL) and extracted with ethyl acetate (100 mL×3). The organic layer was combined and washed with brine (100 mL×2), dried over Na$_2$SO$_4$, and filtered. The filtrate was concentrated in vacuum to give 7-bromo-2-(4-chloro-2-fluorobenzyl)benzo[d]oxazole (400 mg, 67% yield) as a purple oil.

MS Calcd.: 339.0. MS Found: 339.9 [M+H]$^+$.

Step B: The Synthesis of tert-butyl 4-(2-(4-chloro-2-fluorobenzyl)benzo[d]oxazol-7-yl)-3,6-dihydropyridine-1(2H)-carboxylate A mixture of 7-bromo-2-(4-chloro-2-fluorobenzyl)benzo[d]oxazole (400 mg, 1.2 mmol), tert-butyl 4-(4,4,5,5-tetramethyl-1,3,2-dioxaborolan-2-yl)-3,6-dihydropyridine-1(2H)-carboxylate (438 mg, 1.4 mmol), Pd(dppf)Cl$_2$·CH$_2$Cl$_2$ (96 mg, 0.12 mmol) and K$_2$CO$_3$ (828 mg, 3.6 mmol) in dioxane (4 mL) and H$_2$O (0.4 mL) was degassed and charged with N$_2$ three times. The mixture was stirred at 90° C. for 3 hours. After the reaction was completed, the mixture was extracted with ethyl acetate (50 mL×3). The organic layer was washed with brine (50 mL×2), dried over Na$_2$SO$_4$, filtered, and concentrated in vacuum. The residue was purified by column chromatography to give tert-butyl 4-(2-(4-chloro-2-fluorobenzyl)benzo[d]oxazol-7-yl)-3,6-dihydropyridine-1(2H)-carboxylate (600 mg, crude) as a yellow oil.

MS Calcd.: 442.1. MS Found: 443.1 [M+H]$^+$. 2-[(4-{2-[(4-chloro-2-fluorophenyl)methyl]-1,3-benzoxazol-7-yl}-1,2,3,6-tetrahydropyridin-1-yl)methyl]-3-{[(2S)-oxetan-2-yl]methyl}-3H-imidazo[4,5-b]pyridine-5-carboxylic acid (6.4 mg) was obtained as a white solid by the similar procedure of Compound 109a. MS Calcd.: 587.2. MS Found: 588.5 [M+H]$^+$.

$^1$H NMR (400 MHz, DMSO-d$_6$): δ 8.10 (d, J=8.4 Hz, 1H), 7.97 (d, J=8.4 Hz, 1H), 7.50-7.57 (m, 2H), 7.48 (dd, J=10.0 Hz, 2.0 Hz, 1H), 7.28-7.36 (m, 3H), 6.52-6.58 (m, 1H), 5.13-5.20 (m, 1H), 4.79-4.86 (m, 1H), 4.68-4.74 (m, 1H), 4.45-4.51 (m, 1H), 4.40 (s, 2H), 4.33-4.39 (m, 1H), 4.14 (d, J=13.6 Hz, 1H), 4.04 (d, J=13.6 Hz, 1H), 3.26-3.35 (m, 2H), 2.78-2.84 (m, 2H), 2.58-2.71 (m, 3H), 2.44-2.55 (m, 1H).
$^{19}$F NMR (377 MHz, DMSO-d6): δ −113.99.

Example 83: 2-[(4-{2-[(4-chloro-2-fluorophenyl)methyl]-[1,3]oxazolo[4,5-b]pyridin-7-yl}-1,2,3,6-tetrahydropyridin-1-yl)methyl]-3-{[(2S)-oxetan-2-yl]methyl}-3H-imidazo[4,5-b]pyridine-5-carboxylic acid (Compound 171a)

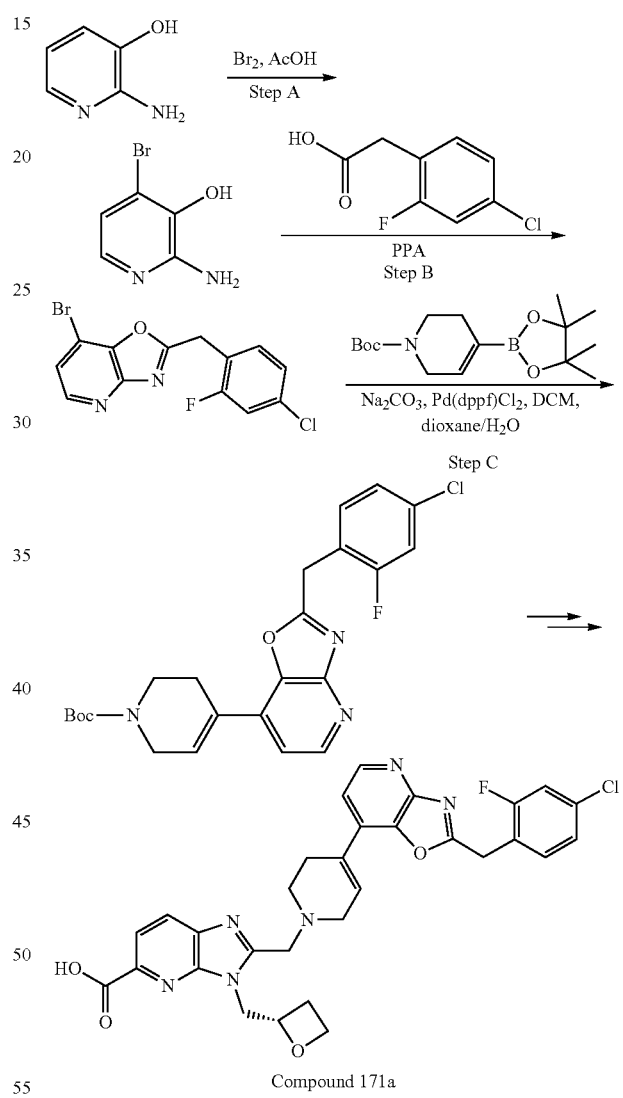

Compound 171a

Step A: The Synthesis of 2-amino-4-bromopyridin-3-ol

Bromine (2.8 mL, 54.6 mmol) was added dropwise to a stirred suspension of 2-aminopyridin-3-ol (5.0 g, 45.5 mmol) in acetic acid (75 mL) at room temperature. The reaction mixture was heated at 120° C. for 4 hours. After the reaction was completed, the reaction mixture was concentrated under reduced pressure. The residue was purified by silica gel column chromatography to give 2-amino-4-bromopyridin-3-ol (3.4 g, 40% yield) as a brown solid.
MS Calcd.: 188.0, MS Found: 188.9 [M+H]⁺.

Step B: The Synthesis of 7-bromo-2-(4-chloro-2-fluorobenzyl)oxazolo[4,5-b]pyridine A mixture of 2-amino-4-bromopyridin-3-ol (500 mg, 2.6 mmol), 2-(4-chloro-2-fluorophenyl)acetic acid (500 mg, 2.6 mmol) in PPA (5 g) was stirred at 140° C. for 5 hours. The reaction mixture was poured into water (200 mL) and stirred for 1 hour, The mixture was filtered, and the filter cake was washed with 10 mL of water. The solid was dried in vacuum to give 7-bromo-2-(4-chloro-2-fluorobenzyl)oxazolo[4,5-b]pyridine (370 mg, 42% yield) as a brown solid.
MS Calcd.: 340.0. MS Found: 340.8 [M+H]+.

Step C: The Synthesis of tert-butyl 4-(2-(4-chloro-2-fluorobenzyl)oxazolo[4,5-b]pyridin-7-yl)-3,6-dihydro pyridine-1(2H)-carboxylate A mixture of 7-bromo-2-(4-chloro-2-fluorobenzyl)oxazolo[4,5-b]pyridine (70 mg, 0.2 mmol), tert-butyl 4-(4,4,5,5-tetramethyl-1,3,2-dioxaborolan-2-yl)-3,6-dihydropyridine-1(2H)-carboxylate (76 mg, 0.24 mmol), Pd(dppf)Cl₂·DCM (8 mg, 0.01 mmol), Na₂CO₃ (64 mg, 0.6 mmol) in dioxane/H₂O (3 mL/0.3 mL) was stirred at 90° C. for 2 hours under Ar. The mixture was extracted with DCM (3×20 mL). The combined organic layer was dried over Na₂SO₄, filtered, and concentrated under reduced pressure. The residue was purified by silica gel column chromatography to give tert-butyl 4-(2-(4-chloro-2-fluorobenzyl)oxazolo[4,5-b]pyridin-7-yl)-3,6-dihydropyridine-1(2H)-carboxylate (74 mg, 83% yield) as a colorless oil.
MS Calcd.: 443.1. MS Found: 444.0 [M+H]⁺. 2-[(4-{2-[(4-chloro-2-fluorophenyl)methyl]-[1,3]oxazolo[4,5-b]pyridin-7-yl}-1,2,3,6-tetrahydropyridin-1-yl)methyl]-3-{[(2S)-oxetan-2-yl]methyl}-3H-imidazo[4,5-b]pyridine-5-carboxylic acid (4.7 mg) was obtained as a white solid by the similar procedure of Compound 109a. MS Calcd.: 588.2. MS Found: 589.4 [M+H]⁺.

¹H NMR (400 MHz, DMSO-d₆): δ 8.43 (d, J=5.2 Hz, 1H), 8.13 (d, J=8.4 Hz, 1H), 7.99 (d, J=8.4 Hz, 1H), 7.56 (t, J=8.4 Hz, 1H), 7.49 (dd, J=10.0 Hz, 2.4 Hz, 1H), 7.31-7.36 (m, 2H), 6.80-6.83 (m, 1H), 5.10-5.20 (m, 1H), 4.78-4.86 (m, 1H), 4.67-4.73 (m, 1H), 4.46-4.51 (m, 3H), 4.32-4.38 (m, 1H), 4.15 (d, J=14.0 Hz, 1H), 4.06 (d, J=13.6 Hz, 1H), 3.30-3.40 (m, 2H), 2.80-2.85 (m, 2H), 2.60-2.70 (m, 3H), 2.43-2.51 (m, 1H). ¹⁹F NMR (377 MHz, DMSO-d6): δ −113.85.

Example 84: 2-[(4-{2-[(4-chloro-2-fluorophenyl)methyl]-4-fluoro-1,3-benzoxazol-7-yl}-1,2,3,6-tetrahydropyridin-1-yl)methyl]-3-{[(2S)-oxetan-2-yl]methyl}-3H-imidazo[4,5-b]pyridine-5-carboxylic acid (Compound 172a)

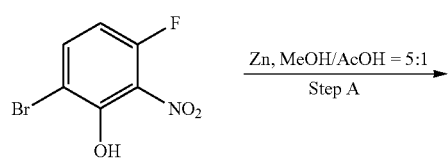

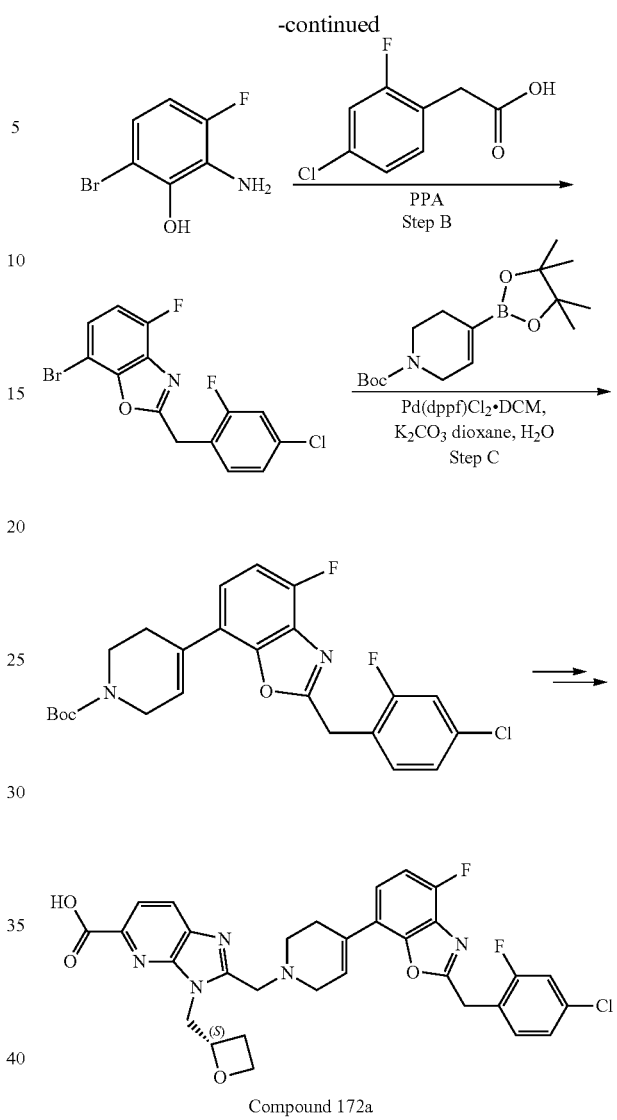

Compound 172a

Step A: The Synthesis of 2-amino-6-bromo-3-fluorophenol

To a solution of 6-bromo-3-fluoro-2-nitrophenol (0.85 g, 3.6 mmol) in MeOH (10 mL) and AcOH (2 mL) was added zinc powder (1.2 g, 18.1 mmol). The resulting mixture was stirred at 60° C. for 2 hours. The solid was filtered out. The filtrate was washed with water and ethyl acetate. The organic layers were combined, dried over Na₂SO₄, filtered, and concentrated under vacuum to give 2-amino-6-bromo-3-fluorophenol (0.81 g) as a light-yellow solid. Used directly for the next step without further purification.
MS Calcd.: 205.0. MS Found: 206.0 [M+H]⁺.

Step B: The Synthesis of 7-bromo-2-(4-chloro-2-fluorobenzyl)-4-fluorobenzo[d]oxazole A mixture of 2-amino-6-bromo-3-fluorophenol (410 mg, 2.0 mmol) and 2-(4-chloro-2-fluoro phenyl)acetic acid (376 mg, 2.0 mmol) in PPA (8 mL) was heated to 140° C. for 3 hours. The reaction mixture was quenched with saturated sodium bicarbonate aqueous solution, extracted with ethyl acetate. The organic layers were combined, dried over Na$_2$SO$_4$, filtered, and concentrated under vacuum. The residue was applied on a silica gel column and eluted with PE:EA=5:1 to give 7-bromo-2-(4-chloro-2-fluorobenzyl)-4-fluorobenzo[d]oxazole (380 mg, 53% yield) as a light-yellow oil.

MS Calcd.: 356.9. MS Found: 358.1 [M+H]$^+$.

Step C: The Synthesis of tert-butyl 4-(2-(4-chloro-2-fluorobenzyl)-4-fluorobenzo[d]oxazol-7-yl)-3,6-dihydro pyridine-1(2H)-carboxylate A mixture of 7-bromo-2-(4-chloro-2-fluorobenzyl)-4-fluorobenzo[d]oxazole (380 mg, 1.07 mmol), tert-butyl 4-(4,4,5,5-tetramethyl-1,3,2-dioxaborolan-2-yl)-3,6-dihydropyridine-1(2H)-carboxylate (396 mg, 1.28 mmol), K$_2$CO$_3$ (442 mg, 3.20 mmol) and Pd(dppf)Cl$_2$·CH$_2$Cl$_2$ (87 mg, 0.10 mmol) in dioxane (8 mL) and water (1 mL) was heated to 90° C. for 4 hours under an atmosphere of nitrogen. The solid was filtered, and the filtrate was concentrated under vacuum. The residue was applied on a silica gel column and eluted with PE:EA=4:1 to give tert-butyl 4-(2-(4-chloro-2-fluorobenzyl)-4-fluorobenzo[d]oxazol-7-yl)-3,6-dihydropyridine-1(2H)-carboxylate (320 mg, 65% yield) as a colorless oil.

MS Calcd.: 460.1, MS Found: 461.0 [M+H]$^+$. 2-[(4-{2-[(4-chloro-2-fluorophenyl)methyl]-4-fluoro-1,3-benzoxazol-7-yl}-1,2,3,6-tetrahydropyridin-1-yl)methyl]-3-{[(2S)-oxetan-2-yl]methyl}-3H-imidazo[4,5-b]pyridine-5-carboxylic acid (26.8 mg) was obtained as a white solid by the similar procedure of Compound 109a. MS Calcd.: 605.2. MS Found: 606.1 [M+H]$^-$.

$^1$H NMR (400 MHz, DMSO-d$_6$): 8.13 (d, J=8.4 Hz, 1H), 7.99 (d, J=8.0 Hz, 1H), 7.54 (t, J=8.4 Hz, 1H), 7.49 (dd, J=10.0 Hz, 2.4 Hz, 1H), 7.31-7.37 (m, 2H), 7.21 (t, J=8.8 Hz, 1H), 6.48-6.52 (m, 1H), 5.12-5.20 (m, 1H), 4.80-4.88 (m, 1H), 4.68-4.73 (m, 1H), 4.45-4.51 (m, 1H), 4.43 (s, 2H), 4.33-4.39 (m, 1H), 4.14 (d, J=13.6 Hz, 1H), 4.05 (d, J=14.0 Hz, 1H), 3.20-3.35 (m, 2H), 2.78-2.84 (m, 2H), 2.64-2.72 (m, 1H), 2.56-2.62 (m, 2H), 2.45-2.51 (m, 1H). $^{19}$F NMR (377 MHz, DMSO-d6): δ −113.93, −128.24.

Example 85: 2-[(4-{5-[(4-chloro-2-fluorophenyl)methyl]thieno[3,2-b]pyridin-3-yl}piperidin-1-yl)methyl]-3-{[(2S)-oxetan-2-yl]methyl}-3H-imidazo[4,5-b]pyridine-5-carboxylic acid (Compound 138a)

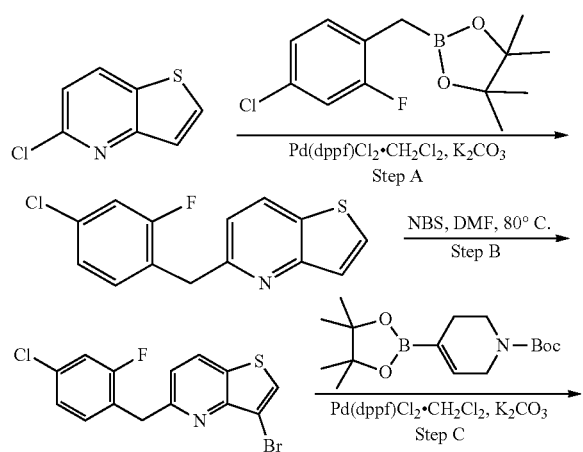

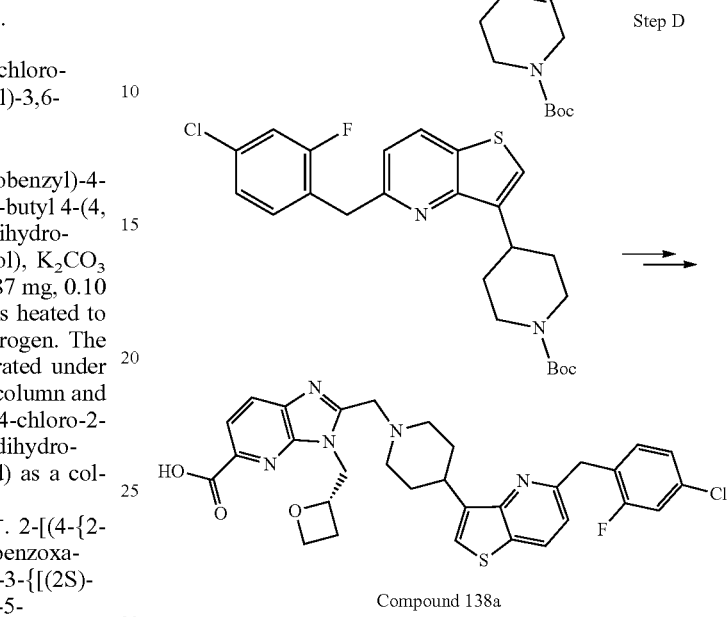

Compound 138a

Step A: The Synthesis of 5-(4-chloro-2-fluorobenzyl)thieno[3,2-b]pyridine

A mixture of 5-chlorothieno[3,2-b]pyridine (200 mg, 1.2 mmol), 2-(4-chloro-2-fluorobenzyl)-4,4,5,5-tetramethyl-1,3,2-dioxaborolane (637 mg, 2.4 mmol), Pd(dppf)Cl$_2$·CH$_2$Cl$_2$ (96 mg, 0.12 mmol) and K$_2$CO$_3$ (488 mg, 3.6 mmol) in dioxane (4 mL) and H$_2$O (1 mL) was degassed and charged with N$_2$ three times. The mixture was stirred at 100° C. for 16 hours. After the reaction was completed, the mixture was extracted with ethyl acetate (30 mL×3). The organic layer was washed with brine (30 mL×2), dried over sodium sulfate, filtered, and concentrated in vacuum. The residue was purified by column chromatography to give 5-(4-chloro-2-fluorobenzyl)thieno[3,2-b]pyridine (150 mg, yield: 46%) as yellow oil.

MS Calcd.: 277.01. MS Found: 278.0 [M+H]$^+$.

Step B: The Synthesis of 3-bromo-5-(4-chloro-2-fluorobenzyl)thieno[3,2-b]pyridine To a solution of 5-(4-chloro-2-fluorobenzyl)thieno[3,2-b]pyridine (150 mg, 0.54 mmol) in DMF (2 mL) was added NBS (144 mg, 0.81 mmol). The mixture was stirred at 80° C. for 3 hours. The reaction was quenched with 10 mL of H$_2$O and extracted with EtOAc (30 mL×3). The combined organic layer was dried over sodium sulfate, filtered, and concentrated. The residue was purified by column chromatography to give 3-bromo-5-(4-chloro-2-fluorobenzyl)thieno[3,2-b]pyridine (80 mg, yield: 42%) as a yellow solid. MS Calcd.: 354.9. MS Found: 355.9 [M+H]$^+$.

Step C: The Synthesis of tert-butyl 4-(5-(4-chloro-2-fluorobenzyl)thieno[3,2-b]pyridin-3-yl)-3,6-dihydropyridine-1(2H)-carboxylate A mixture of 3-bromo-5-(4-chloro-2-fluorobenzyl)thieno[3,2-b]pyridine (70 mg, 0.2 mmol), tert-butyl 4-(4,4,5,5- tetramethyl-1,3,2-dioxaborolan-2-yl)-3,6-dihydropyridine-1 (2H)-carboxylate (73 mg, 0.24 mmol), Pd(dppf)Cl₂CH₂Cl₂ (16 mg, 0.02 mmol) and K₂CO₃ (82 mg, 0.6 mmol) in dioxane (2 mL) and H₂O (0.5 mL) was degassed and charged with N₂ three times. The mixture was stirred at 90° C. for 3 hours. After the reaction was completed, the mixture was extracted with ethyl acetate (30 mL×3). The organic layer was washed with brine (30 mL×2), dried over sodium sulfate, filtered, and concentrated in vacuum. The residue was purified by column chromatography to give tert-butyl 4-(5-(4-chloro-2-fluorobenzyl)thieno[3,2-b]pyridin-3-yl)-3,6-dihydropyridine-1(2H)-carboxylate (70 mg, yield: 78%) as yellow oil. MS Calcd.: 458.1. MS Found: 459.0 [M+H]⁺.

Step D: The Synthesis of tert-butyl 4-(5-(4-chloro-2-fluorobenzyl)thieno[3,2-b]pyridin-3-yl)piperidine-1-carboxylate To a solution of tert-butyl 4-(5-(4-chloro-2-fluorobenzyl) thieno[3,2-b]pyridin-3-yl)-3,6-dihydropyridine-1(2H)-carboxylate (70 mg, 0.15 mmol) in MeOH (2 mL) and THF (0.5 mL) was added PtO₂ (10 mg). The reaction was stirred at 25° C. under H₂ (15 Psi) for 3 h. The reaction was filtered and concentrated under reduced pressure to afford tert-butyl 4-(5-(4-chloro-2-fluorobenzyl)thieno[3,2-b]pyridin-3-yl)piperidine-1-carboxylate (50 mg, yield: 71%) as yellow oil. MS Calcd.: 460.1. MS Found: 461.0 [M+H]⁺.

2-[(4-{5-[(4-chloro-2-fluorophenyl)methyl]thieno[3,2-b] pyridin-3-yl}piperidin-1-yl)methyl]-3-{[(2S)-oxetan-2-yl] methyl}-3H-imidazo[4,5-b]pyridine-5-carboxylic acid (17.2 mg, 35% yield) was obtained as a solid by the similar procedure of Compound 109a. MS Calcd.: 605.2. MS Found: 606.4 [M+H]⁺.

¹H NMR (400 MHz, DMSO-d₆): δ 8.34 (d, J=8.4 Hz, 1H), 8.15 (d, J=8.4 Hz, 1H), 8.01 (d, J=8.4 Hz, 1H), 7.73 (s, 1H), 7.36-7.41 (m, 2H), 7.21-7.25 (m, 2H), 5.15-5.21 (m, 1H), 4.85-4.90 (m, 1H), 4.73-4.78 (m, 1H), 4.47-4.52 (m, 1H), 4.35-4.40 (m, 1H), 4.25 (s, 2H), 4.03 (d, J=13.6 Hz, 1H), 3.96 (d, J=13.6 Hz, 1H), 2.92-3.05 (m, 3H), 2.68-2.72 (m, 1H), 2.47-2.48 (m, 1H), 2.24-2.33 (m, 2H), 1.94-1.98 (m, 2H), 1.66-1.79 (m, 2H). ¹⁹F NMR (377 MHz, DMSO-d6): δ −114.30.

Example 86: 2-[(4-{2-[(4-chloro-2-fluorophenyl) methyl]-1,3-benzothiazol-4-yl}piperidin-1-yl) methyl]-3-{[(2S)-oxetan-2-yl]methyl}-3H-imidazo [4,5-b]pyridine-5-carboxylic acid (Compound 139a)

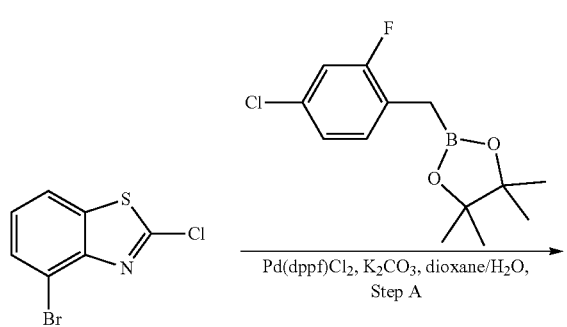

Step A: The Synthesis of 4-bromo-2-(4-chloro-2-fluorobenzyl)benzo[d]thiazole

A mixture of 4-bromo-2-chlorobenzo[d]thiazole (700 mg, 2.83 mmol), 2-(4-chloro-2-fluorobenzyl)-4,4,5,5-tetramethyl-1,3,2-dioxaborolane (765 mg, 2.83 mmol), Pd(dppf) Cl₂ (103 mg, 0.14 mmol) and K₂CO₃ (1.17 g, 8.49 mmol) in 1,4-dioxane/H₂O (10 mL/1 mL) was stirred at 80° C. under Ar for 16 h. After the reaction was completed, the mixture was poured into cold water (200 mL) and extracted with EtOAc (2×200 mL), the combined organic layer was washed

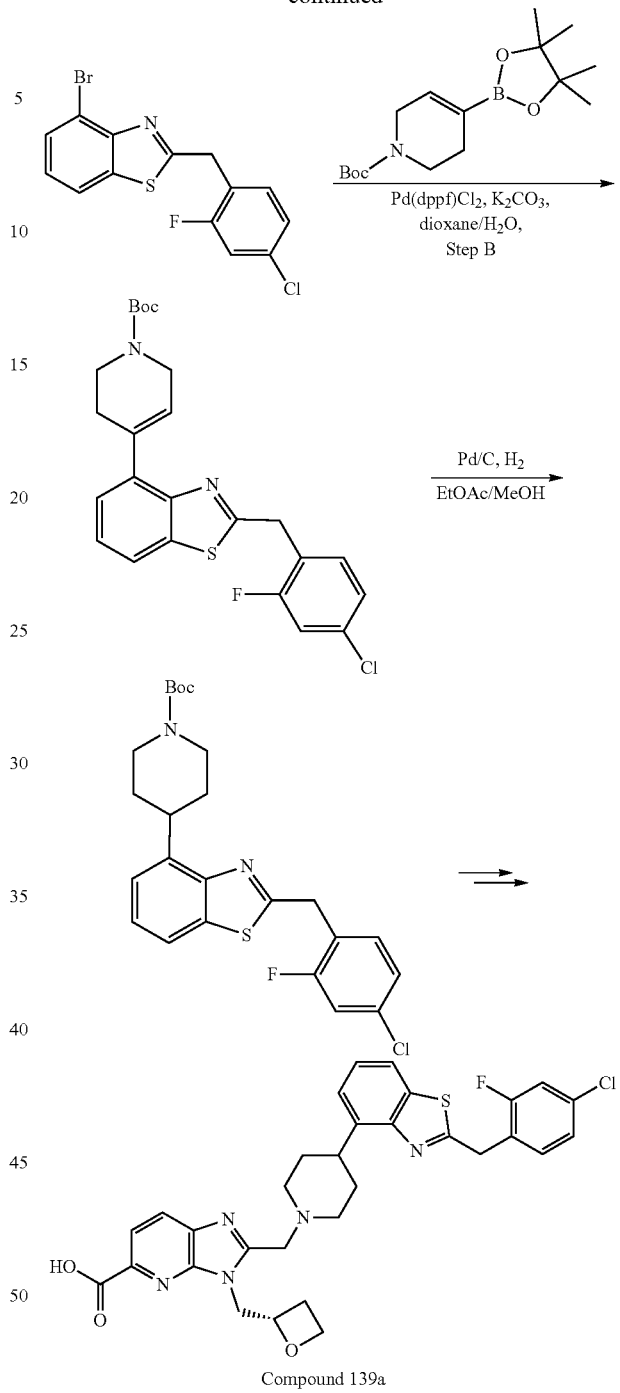

Compound 139a with brine, dried over sodium sulfate, filtered, and concentrated under reduced pressure, the residue was purified by prep-HPLC (TFA) to furnish 4-bromo-2-(4-chloro-2-fluorobenzyl)benzo[d]thiazole (120 mg, yield: 12%) as white solid. MS Calcd.: 354.9. MS Found: 355.9 [M+H]⁺.

Step B: The Synthesis of tert-butyl 4-(2-(4-chloro-2-fluorobenzyl)benzo[d]thiazol-4-yl)-3,6-dihydropyridine-1(2H)-carboxylate A mixture of 4-bromo-2-(4-chloro-2-fluorobenzyl)benzo[d]thiazole (100 mg, 0.28 mmol), tert-butyl 4-(4,4,5,5-tetramethyl-1,3,2-dioxaborolan-2-yl)-3,6-dihydropyridine-1(2H)-carboxylate (174 mg, 0.56 mmol), Pd(dppf)Cl₂ (10 mg, 0.014 mmol) and K₂CO₃ (116 mg, 0.84 mmol) in dioxane/H₂O (10 mL/1 mL) was stirred at 100° C. under Ar for 16 hours. The mixture was poured into water (50 mL) and extracted with EtOAc (2×50 mL), the combined organic layer was washed with brine, dried over sodium sulfate, filtered and concentrated under reduced pressure, the residue was purified by silica gel column chromatography to furnish tert-butyl 4-(2-(4-chloro-2-fluorobenzyl)benzo[d]thiazol-4-yl)-3,6-dihydropyridine-1(2H)-carboxylate (130 mg) as yellow oil. MS Calcd.: 458.1. MS Found: 459.1 [M+H]⁺.

Step C: The Synthesis of tert-butyl 4-(2-(4-chloro-2-fluorobenzyl)benzo[d]thiazol-4-yl)piperidine-1-carboxylate A mixture of tert-butyl 4-(2-(4-chloro-2-fluorobenzyl)benzo[d]thiazol-4-yl)-3,6-dihydropyridine-1(2H)-carboxylate (80 mg, 0.17 mmol) and Pd/C (12 mg) in methanol/ethyl acetate (2 mL/2 mL) was stirred at 25° C. under H₂ for 8 hours. The mixture was filtered, and the filtrate was concentrated under reduced pressure to furnish tert-butyl 4-(2-(4-chloro-2-fluorobenzyl)benzo[d]thiazol-4-yl)piperidine-1-carboxylate (80 mg) as yellow oil. MS Calcd.: 460.1. MS Found: 461.2 [M+H]⁺. 2-[(4-{2-[(4-chloro-2-fluorophenyl)methyl]-1,3-benzothiazol-4-yl}piperidin-1-yl)methyl]-3-{[(2S)-oxetan-2-yl]methyl}-3H-imidazo[4,5-b]pyridine-5-carboxylic acid (11.5 mg, yield: 23%) was obtained as a solid by the similar procedure of Compound 109a. MS Calcd.: 605.2. MS Found: 606.1 [M+H]⁺.

¹H NMR (400 MHz, MeOD) δ 8.15 (s, 2H), 7.76 (dd, J=2.8 Hz, 6.4 Hz, 1H), 7.43 (t, J=8.0 Hz, 1H), 7.37-7.33 (m, 2H), 7.25 (dd, J=2.0 Hz, 9.6 Hz, 1H), 7.22 (dd, J=2.0 Hz, 8.0 Hz, 1H), 5.31 (brs, 1H), 5.01-4.89 (m, 3H), 4.67-4.64 (m, 1H), 4.49 (s, 2H), 4.42 (d, J=9.6 Hz, 2H), 3.66-3.59 (m, 1H), 3.47 (d, J=10.0 Hz, 1H), 3.41 (d, J=11.2 Hz, 1H), 2.89-2.80 (m, 3H), 2.57-2.50 (m, 1H), 2.16-2.03 (m, 4H). 19F NMR (377 MHz, DMSO-d6): δ −115.99.

Example 87: 2-[(4-{6-[(4-chloro-2-fluorophenyl)methyl]-1H-pyrrolo[2,3-b]pyridin-1-yl}piperidin-1-yl)methyl]-3-{[(2S)-oxetan-2-yl]methyl}-3H-imidazo[4,5-b]pyridine-5-carboxylic acid (Compound 140a)

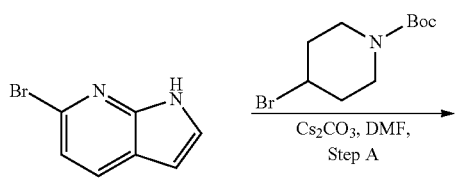

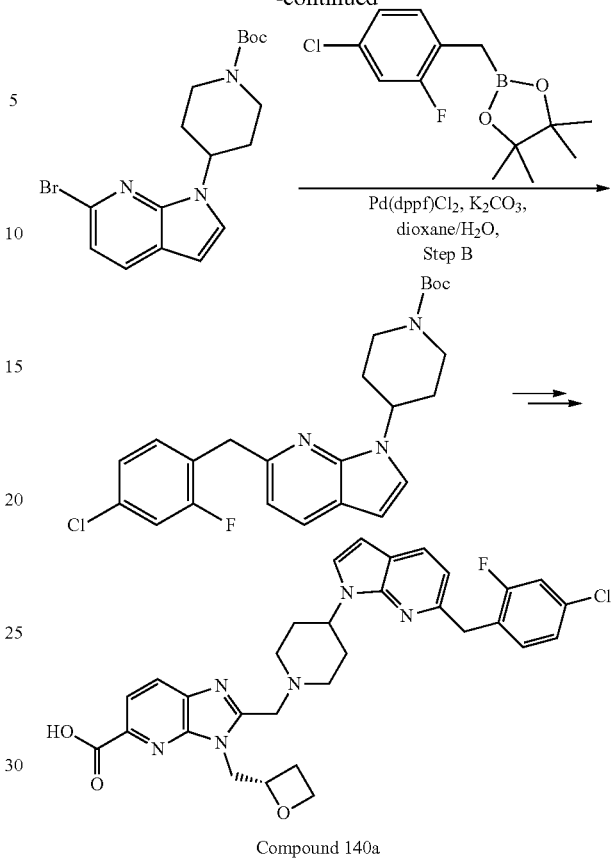

Compound 140a

Step A: The Synthesis of tert-butyl 4-(6-bromo-1H-pyrrolo[2,3-b]pyridin-1-yl)piperidine-1-carboxylate A mixture of 6-bromo-1H-pyrrolo[2,3-b]pyridine (1.2 g, 6.1 mmol), tert-butyl 4-bromopiperidine-1-carboxylate (8.0 g, 30.4 mmol) and Cs₂CO₃ (19.8 g, 60.9 mmol) in DMF (100 mL) was stirred at 95° C. under Ar for 8 h. After the reaction was completed, the mixture was poured into water (400 mL) and extracted with EtOAc (2×200 mL), the combined organic layer was washed with brine, dried over sodium sulfate, filtered and concentrated under reduced pressure, the residue was purified by silica gel column chromatography to furnish tert-butyl 4-(6-bromo-1H-pyrrolo[2,3-b]pyridin-1-yl)piperidine-1-carboxylate (420 mg, yield: 18%) as a yellow solid. MS Calcd.: 379.1. MS Found: 324.1 [M-ᵗ-Bu+H]⁺.

Step B: The Synthesis of tert-butyl 4-(6-(4-chloro-2-fluorobenzyl)-1H-pyrrolo[2,3-b]pyridin-1-yl)piperidine-1-carboxylate A mixture of tert-butyl 4-(6-bromo-1H-pyrrolo[2,3-b]pyridin-1-yl)piperidine-1-carboxylate (420 mg, 1.10 mmol), 2-(4-chloro-2-fluorobenzyl)-4,4,5,5-tetramethyl-1,3,2-dioxaborolane (357 mg, 1.32 mmol), Pd(dppf)Cl₂ (80 mg, 0.11 mmol) and K₂CO₃ (380 mg, 2.75 mmol) in dioxane/H₂O (20 mL/4 mL) was stirred at 80° C. under argon for 16 hours. The mixture was poured into water (50 mL) and extracted with EtOAc (2×50 mL), the combined organic layer was washed with brine, dried over sodium sulfate, filtered and concentrated under reduced pressure, the residue was purified by silica gel column chromatography to furnish tert-butyl 4-(6-(4-chloro-2-fluorobenzyl)-1H-pyrrolo[2,3-b]pyridin-1-yl)piperidine-1-carboxylate (220 mg, yield: 44.9%) as yellow solid. MS Calcd.: 443.2. MS Found: 444.2 [M+H]⁺. 2-[(4-{6-[(4-Chloro-2-fluorophenyl)methyl]-1H-pyrrolo[2,3-b]pyridin-1-yl}piperidin-1-yl)methyl]-3-{[(2S)-oxetan-2-yl]methyl}-3H-imidazo[4,5-b]pyridine-5-carboxylic acid (24.3 mg, yield: 12%) was obtained as a solid by the similar procedure of Compound 109a. MS Calcd.: 588.2. MS Found: 589.2 [M+H]⁺.

¹H NMR (400 MHz, MeOD) δ 8.19-8.12 (m, 2H), 7.83 (d, J=8.0 Hz, 1H), 7.44 (d, J=3.6 Hz, 1H), 7.23 (t, J=8.4 Hz, 1H), 7.16 (dd, J=2.0 Hz, J=10.0 Hz, 1H), 7.10 (dd, J=2.0 Hz, J=8.4 Hz, 1H), 6.92 (d, J=8.0 Hz, 1H), 6.43 (d, J=3.6 Hz, 1H), 5.35-5.30 (m, 1H), 5.08-5.02 (m, 1H), 4.83-4.75 (m, 1H), 4.66-4.61 (m, 1H), 4.47-4.42 (m, 1H), 4.25-4.13 (m, 4H), 3.20 (d, J=10.8 Hz, 2H), 3.14-3.10 (m, 1H), 2.84-2.76 (m, 1H), 2.56 (dd, J=12.4 Hz, J=24.4 Hz, 3H), 2.26-2.13 (m, 2H), 2.06-1.98 (m, 3H). 19F NMR (377 MHz, DMSO-d6): δ -116.70.

Example 88: 2-[(4-{5-[(4-chloro-2-fluorophenyl)methyl]-1H-pyrrolo[3,2-b]pyridin-3-yl}piperidin-1-yl)methyl]-3-{[(2S)-oxetan-2-yl]methyl}-3H-imidazo[4,5-b]pyridine-5-carboxylic acid (Compound 141a)

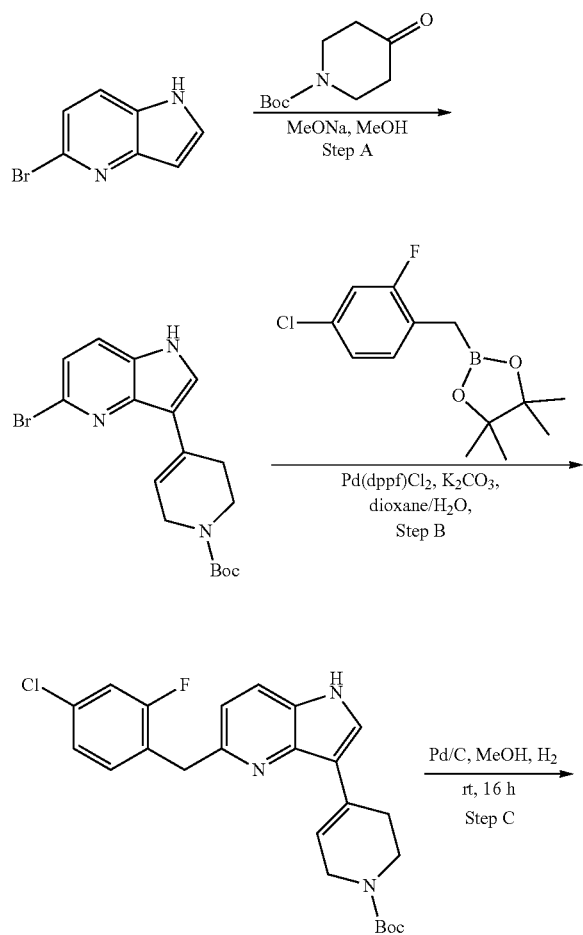

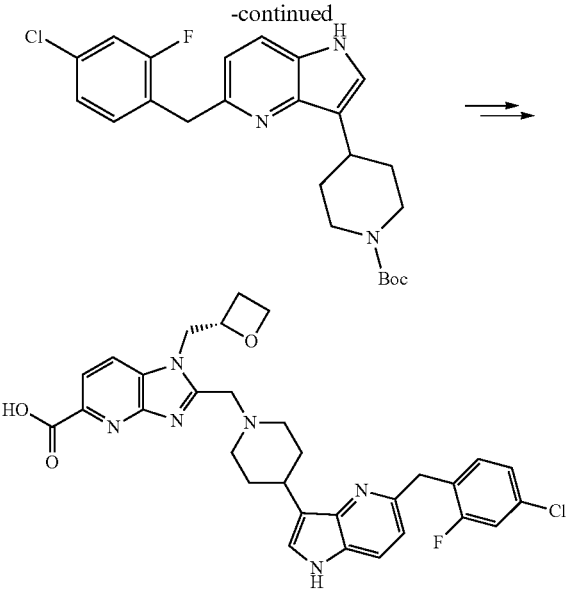

Compound 141a

Step A: The Synthesis of tert-butyl 4-(5-bromo-1H-pyrrolo[3,2-b]pyridin-3-yl)-3,6-dihydropyridine-1(2H)-carboxylate A mixture of 5-bromo-1H-pyrrolo[3,2-b]pyridine (400 mg, 2.04 mmol), tert-butyl 4-oxopiperidine-1-carboxylate (1.22 g, 6.12 mmol) and sodium methoxide (1.21 g, 22.4 mmol) in methanol (20 mL) was stirred at 80° C. for 8 h. After the reaction was completed, the mixture was poured into cold water (100 mL) and extracted with EtOAc (2×100 mL), the combined organic layer was washed with brine, dried over sodium sulfate, filtered and concentrated under reduced pressure, the residue was purified by silica gel column chromatography to furnish tert-butyl 4-(5-bromo-1H-pyrrolo[3,2-b]pyridin-3-yl)-3,6-dihydropyridine-1(2H)-carboxylate (382 mg, yield: 50%) as a yellow solid. MS Calcd.: 377.1. MS Found: 322.0 [M-56+H]⁺.

Step B: The Synthesis of tert-butyl 4-(5-(4-chloro-2-fluorobenzyl)-1H-pyrrolo[3,2-b]pyridin-3-yl)-3,6-dihydropyridine-1(2H)-carboxylate A mixture of tert-butyl 4-(5-bromo-1H-pyrrolo[3,2-b]pyridin-3-yl)-3,6-dihydropyridine-1(2H)-carboxylate (447 mg, 1.19 mmol), 2-(4-chloro-2-fluorobenzyl)-4,4,5,5-tetramethyl-1,3,2-dioxaborolane (320 mg, 1.19 mmol), Pd(dppf)Cl₂ (87 mg, 0.12 mmol) and K₂CO₃ (491 mg, 3.56 mmol) in dioxane/H₂O (5 mL/1 mL) was stirred at 80° C. under Ar for 16 hours. The mixture was poured into water (100 mL) and extracted with EtOAc (2×100 mL), the combined organic layer was washed with brine, dried over sodium sulfate, filtered and concentrated under reduced pressure, the residue was purified by silica gel column chromatography to furnish tert-butyl 4-(5-(4-chloro-2-fluorobenzyl)-1H-pyrrolo[3,2-b]pyridin-3-yl)-3,6-dihydropyridine-1(2H)-carboxylate (95 mg, yield: 18%) as yellow oil. MS Calcd.: 441.2. MS Found: 442.1 [M+H]⁺.

Step C: The Synthesis of tert-butyl 4-(5-(4-chloro-2-fluorobenzyl)-1H-pyrrolo[3,2-b]pyridin-3-yl)piperidine-1-carboxylate A mixture of tert-butyl 4-(5-(4-chloro-2-fluorobenzyl)-1H-pyrrolo[3,2-b]pyridin-3-yl)-3,6-dihydropyridine-1(2H)- carboxylate (95 mg, 0.215 mmol) and Pd/C (20 mg) in methanol (5 mL) was stirred at 25° C. under $H_2$ for 16 hours. The mixture was filtered, and the filtrate was concentrated under reduced pressure, the residue was purified by prep-HPLC to furnish tert-butyl 4-(5-(4-chloro-2-fluorobenzyl)-1H-pyrrolo[3,2-b]pyridin-3-yl)piperidine-1-carboxylate (20 mg, yield: 21.0%) as yellow oil. MS Calcd.: 443.2. MS Found: 444.2 [M+H]$^+$.

2-[(4-{5-[(4-chloro-2-fluorophenyl)methyl]-1H-pyrrolo[3,2-b]pyridin-3-yl}piperidin-1-yl)methyl]-3-{[(2S)-oxetan-2-yl]methyl}-3H-imidazo[4,5-b]pyridine-5-carboxylic acid (4.8 mg, yield: 33%) was obtained as a solid by the similar procedure of Compound 109a. MS Calcd.: 588.2. MS Found: 589.1 [M+H]$^+$.

$^1$H NMR (400 MHz, MeOD) δ8.05 (dd, J1=8.4 Hz, J2=20.4, 2H), 7.65 (d, J=8.4 Hz, 1H), 7.33 (s, 1H), 7.16 (t, J=8.4 Hz, 2H), 7.09 (d, J=8.4 Hz, 1H), 6.92 (d, J=8.4 Hz, 1H), 5.32-5.27 (m, 1H), 5.05 (dd, J1=6.4 Hz, J2=14.8 Hz, 2H), 4.61 (q, J=7.2 Hz, 1H), 4.46-4.41 (m, 1H), 4.23 (s, 2H), 4.12 (d, J=14.0 Hz, 1H), 3.97 (d, J=14.0 Hz, 1H), 3.16-3.06 (m, 2H), 2.98 (d, J=11.2 Hz, 1H), 2.79-2.73 (m, 1H), 2.58-2.49 (m, 1H), 2.47-2.36 (m, 2H), 2.11 (t, J=14.0 Hz, 2H), 1.85-1.72 (m, 2H). $^{19}$F NMR (377 MHz, DMSO-d6): δ −116.66.

Example 89: (S)-2-((4-(2-(4-chloro-2-fluorobenzyl)-2H-indazol-7-yl)piperidin-1-yl)methyl)-3-(oxetan-2-ylmethyl)-3H-imidazo[4,5-b]pyridine-5-carboxylic Acid (Compound 142a)

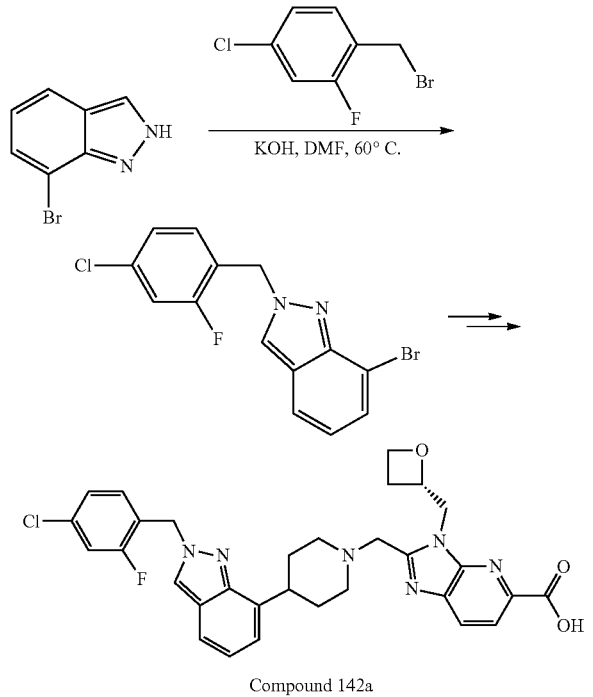

Compound 142a

To a mixture of 7-bromo-2H-indazole (197 mg, 1.00 mmol) in DMF (2 mL) was added KOH (84.0 mg, 1.50 mmol). The mixture was heated at 60° C. for 1 hour. After 1-(bromomethyl)-4-chloro-2-fluorobenzene (268 mg, 1.20 mmol) was slowly added, the reaction mixture was heated at 60° C. for another 4 hours. The mixture was diluted with water (5 mL) and extracted with EA (10 mL*3). The organic layer was dried over $Na_2SO_4$, concentrated, and purified with Prep-TLC (PE/EA=8/1) to afford 7-bromo-2-(4-chloro-2-fluorobenzyl)-2H-indazole as a white solid (150 mg, 44% yield). LCMS: m/z=339.0 (M+H)$^+$.

(S)-2-((4-(2-(4-chloro-2-fluorobenzyl)-2H-indazol-7-yl)piperidin-1-yl)methyl)-3-(oxetan-2-ylmethyl)-3H-imidazo[4,5-b]pyridine-5-carboxylic acid was obtained as a solid by the similar procedure of Compound 109a. MS Calcd.: 588.2. MS Found: 589.2 (M+H)$^+$.

$^1$H NMR (400 MHz, DMSO-d$^6$) δ 8.40 (s, 1H), 8.14 (dd, J=8.4, 2.8 Hz, 1H), 8.00 (d, J=8.4 Hz, 1H), 7.49-7.54 (m, 2H), 7.29 (dd, J=8.4, 1.6 Hz, 1H), 7.20 (t, J=8.4 Hz, 1H), 7.04 (d, J=6.8 Hz, 1H), 6.95-7.01 (m, 1H), 5.72 (s, 2H), 5.19 (dt, J=12.4, 6.4 Hz, 1H), 4.88 (dd, J=14.4, 6.4 Hz, 1H), 4.75 (dd, J=14.4, 4.4 Hz, 1H), 4.49-4.51 (m, 1H), 4.38-4.40 (m, 1H), 4.13 (d, J=13.6 Hz, 1H), 3.96 (d, J=13.6 Hz, 1H), 2.95-3.13 (m, 4H), 2.68-2.73 (m, 1H) 2.25-2.40 (m, 2H), 1.78-1.97 (m, 4H).

Example 90: 2-[(4-{6-[(4-chloro-2-fluorophenyl)methyl]imidazo[1,2-b]pyridazin-3-yl}-1,2,3,6-tetrahydropyridin-1-yl)methyl]-3-{[(2S)-oxetan-2-yl]methyl}-3H-imidazo[4,5-b]pyridine-5-carboxylic acid (Compound 192a)

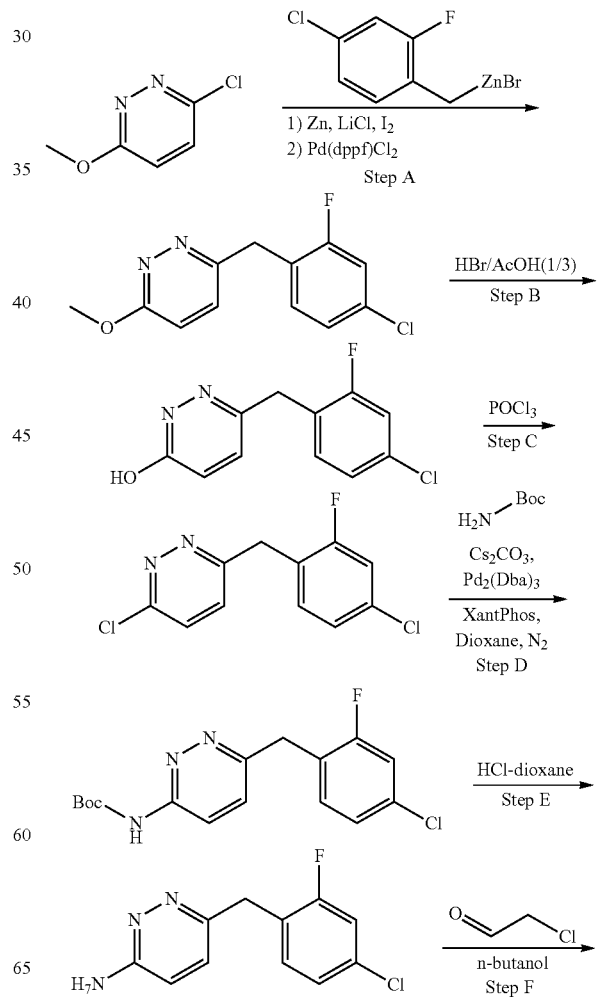

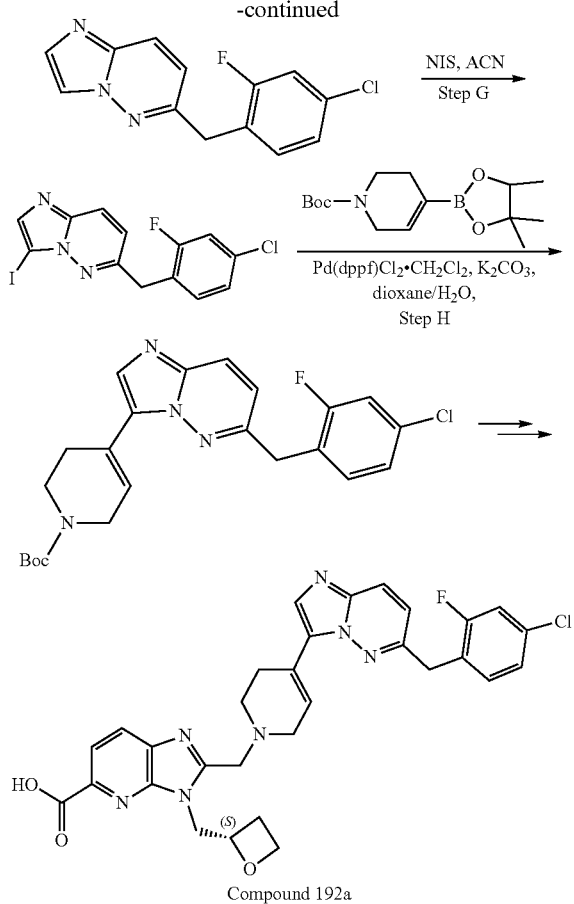

Compound 192a

Step A: The Synthesis of 3-(4-chloro-2-fluorobenzyl)-6-methoxypyridazine

A mixture of 1-(bromomethyl)-4-chloro-2-fluorobenzene (7.7 g, 34.6 mmol), Zn (6.7 g, 103.8 mmol), LiCl (0.73 g, 17.3 mmol) and $I_2$ (0.88 g, 3.46 mmol) in dry THF (30 mL) was stirred at 50° C. for 1 hour. Then, 3-chloro-6-methoxypyridazine (2.0 g, 13.8 mmol) and Pd(dppf)Cl$_2$ (1.3 g, 0.1 mmol) was added into the mixture. The mixture was stirred at 70° C. for 2 hours. After the reaction was completed, the reaction mixture was filtrated. The filtrate was quenched with water (10 mL) and extracted with ethyl acetate (30 mL×3). The organic layer was combined and washed with brine (20 mL×2), dried over $Na_2SO_4$, filtered, and concentrated in vacuum. The residue was purified by column chromatography (PE/EA=3/1) to give 3-(4-chloro-2-fluorobenzyl)-6-methoxypyridazine (2.0 g, 57%) as a yellow solid.

MS Calcd.: 252.0. MS Found: 253.0 [M+H]$^+$.

Step B: The Synthesis of 6-(4-chloro-2-fluorobenzyl)pyridazin-3-ol

A solution of 3-(4-chloro-2-fluorobenzyl)-6-methoxypyridazine (2.0 g, 7.94 mmol) in HBr/AcOH (30%, 10 mL) was stirred at 100° C. for 16 hours. After the reaction was completed, Sat. $Na_2CO_3$ was added until the pH>7. The mixture was extracted with ethyl acetate (50 mL×3). The organic layer was combined and washed with brine (20 mL×2), dried over $Na_2SO_4$, filtered, and concentrated in vacuum. The residue was purified by column chromatography (PE/EA=3/1) to give 6-(4-chloro-2-fluorobenzyl)pyridazin-3-ol (2.0 g, 94% yield) as a white solid.

Step C: The Synthesis of 3-chloro-6-(4-chloro-2-fluorobenzyl)pyridazine

A solution of 6-(4-chloro-2-fluorobenzyl)pyridazin-3-ol (2.0 g, 8.4 mmol) in POCl$_3$ (20 mL) was stirred at 80° C. for 3 hours. After the reaction was completed, Sat. $Na_2CO$ was added until the pH>7. The mixture was extracted with ethyl acetate (50 mL×3). The organic layer was combined and washed with brine (20 mL×2), dried over $Na_2SO_4$, filtered, and concentrated in vacuum. The residue was purified by column chromatography (PE/EA=3/1) to give 3-chloro-6-(4-chloro-2-fluorobenzyl)pyridazine (1.3 g, 60% yield) as a yellow solid. MS Calcd.: 256.0; MS Found: 297.9 [M+1+41]$^+$.

Step D: The Synthesis of tert-butyl (6-(4-chloro-2-fluorobenzyl)pyridazin-3-yl)carbamate To a solution of 3-chloro-6-(4-chloro-2-fluorobenzyl)pyridazine (600 mg, 2.34 mmol) in dioxane (50 mL) was added tert-butyl carbamate (548 mg, 4.68 mmol), $Cs_2CO_3$ (1.5 g, 4.68 mmol), XantPhos (405 mg, 0.702 mmol) and Pd$_2$(dba)$_3$ (207 mg, 0.234 mmol) at room temperature. The reaction was stirred at 90° C. for 16 hours under $N_2$. After the reaction was completed, the reaction mixture was filtered and concentrated in vacuum. The residue was purified by column chromatography (PE/EA=3/1) to give tert-butyl (6-(4-chloro-2-fluorobenzyl)pyridazin-3-yl)carbamate (500 mg, 63% yield) as a yellow solid.

MS Calcd.: 337.1. MS Found: 338.1 [M+H]$^+$.

Step E: The Synthesis of 6-(4-chloro-2-fluorobenzyl)pyridazin-3-amine

A solution of tert-butyl (6-(4-chloro-2-fluorobenzyl)pyridazin-3-yl)carbamate (500 mg, 1.48 mmol) in HCl-dioxane (5 mL) was stirred at room temperature for 48 hours. After the reaction was completed, the reaction mixture was concentrated in vacuum to give the crude 6-(4-chloro-2-fluorobenzyl)pyridazin-3-amine (400 mg) as a yellow solid. Used directly for the next step.

MS Calcd.: 237.0. MS Found: 238.0[M+H]$^+$.

Step F: The Synthesis of 6-(4-chloro-2-fluorobenzyl)imidazo[1,2-b]pyridazine A mixture of 6-(4-chloro-2-fluorobenzyl)pyridazin-3-amine (400 mg, 1.69 mmol) and 2-chloroacetaldehyde (40%, 5 mL) in n-butanol (6 mL) was stirred at 120° C. for 12 hours. After the reaction was completed, the reaction mixture was concentrated and purified by column chromatography (MeOH/DCM=5/1) to give 6-(4-chloro-2-fluorobenzyl)imidazo[1,2-b]pyridazine (200 mg, 45% yield) as a white solid.

MS Calcd.: 261.0. MS Found: 262.1 [M+H]$^+$.

Step G: The Synthesis of 6-(4-chloro-2-fluorobenzyl)-3-iodoimidazo[1,2-b]pyridazine A solution of 6-(4-chloro-2-fluorobenzyl)imidazo[1,2-b]pyridazine (180 mg, 0.69 mmol) and NIS (187 mg, 0.83 mmol) in ACN (10 mL) was stirred at 40° C. for 48 hours. After the reaction was completed, the reaction mixture was quenched with water (10 mL) and extracted with ethyl acetate (20 mL×3). The organic layer was combined and washed with brine (10 mL×2), dried over Na₂SO₄, filtered, and concentrated in vacuum. The residue was purified by column chromatography (PE/EA=3/1) to give 6-(4-chloro-2-fluorobenzyl)-3-iodoimidazo[1,2-b]pyridazine (120 mg, 45%) as a white solid.

MS Calcd.: 386.9. MS Found: 387.9 [M+H]⁺.

Step H: The Synthesis of tert-butyl 4-(6-(4-chloro-2-fluorobenzyl)imidazo[1,2-b]pyridazin-3-yl)-3,6-dihydropyridine-1(2H)-carboxylate To a solution of 6-(4-chloro-2-fluorobenzyl)-3-iodoimidazo[1,2-b]pyridazine (100 mg, 0.258 mmol) in dioxane (5 mL) and H₂O (0.5 mL) was added tert-butyl 4-(4,4,5-trimethyl-1,3,2-dioxaborolan-2-yl)-3,6-dihydropyridine-1(2H)-carboxylate (103 mg, 0.336 mmol), K₂CO₃ (1.06 mg, 0.775 mmol) and Pd(dppf)Cl₂·DCM (21 mg, 0.0259 mmol). The reaction was stirred at 90° C. for 3 hours. After the reaction was completed, the reaction mixture was quenched with water and extracted with ethyl acetate (10 mL×3). The organic layer was combined and washed with brine (5 mL×2), dried over Na₂SO₄, filtered, and concentrated in vacuum. The residue was purified by column chromatography (PE/EA=2/1) to give tert-butyl 4-(6-(4-chloro-2-fluorobenzyl)imidazo[1,2-b]pyridazin-3-yl)-3,6-dihydropyridine-1(2H)-carboxylate (150 mg, 91% yield) as a colorless oil.

MS Calcd.: 442.2. MS Found: 443.1 [M+H]⁺. 2-[(4-{6-[(4-chloro-2-fluorophenyl)methyl]imidazo[1,2-b]pyridazin-3-yl}-1,2,3,6-tetrahydropyridin-1-yl)methyl]-3-{[(2S)-oxetan-2-yl]methyl}-3H-imidazo[4,5-b]pyridine-5-carboxylic acid (3.5 mg) was obtained as a yellow solid by the similar procedure of Compound 109a. MS Calcd.: 587.2. MS Found: 588.2 [M+H]⁺.

¹H NMR (400 MHz, DMSO-d₆): 8.09 (d, J=9.2 Hz, 1H), 7.90-7.95 (m, 2H), 7.78 (s, 1H), 7.44 (t, J=8.4 Hz, 1H), 7.38 (dd, J=10.0 Hz, 2.0 Hz, 1H), 7.20-7.24 (m, 2H), 6.70-6.74 (m, 1H), 5.03-5.12 (m, 1H), 4.78-4.86 (m, 1H), 4.61-4.67 (m, 1H), 4.42-4.49 (m, 2H), 4.28-4.33 (m, 4H), 4.07 (d, J=13.6 Hz, 1H), 3.88 (d, J=13.2 Hz, 1H), 3.09-3.15 (m, 2H), 2.70-2.79 (m, 2H), 2.53-2.57 (m, 2H). ¹⁹F NMR (377 MHz, DMSO-d6): δ −114.09.

Example 91: N-(2-{[4-({6-[(4-chloro-2-fluorophenyl)methyl]pyridin-2-yl}oxy)piperidin-1-yl]methyl}-1-{[(2S)-oxetan-2-yl]methyl}-1H-1,3-benzodiazol-6-yl)acetamide (Compound 134a)

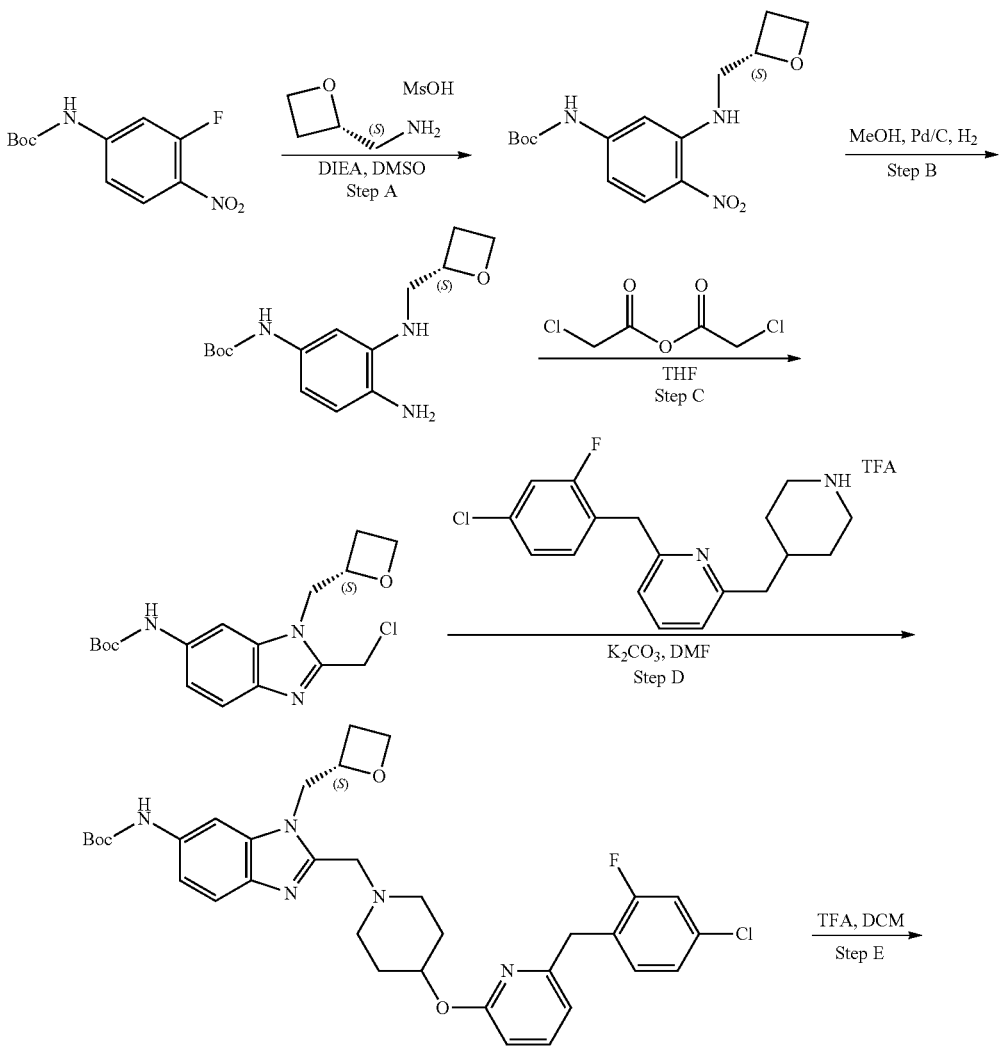

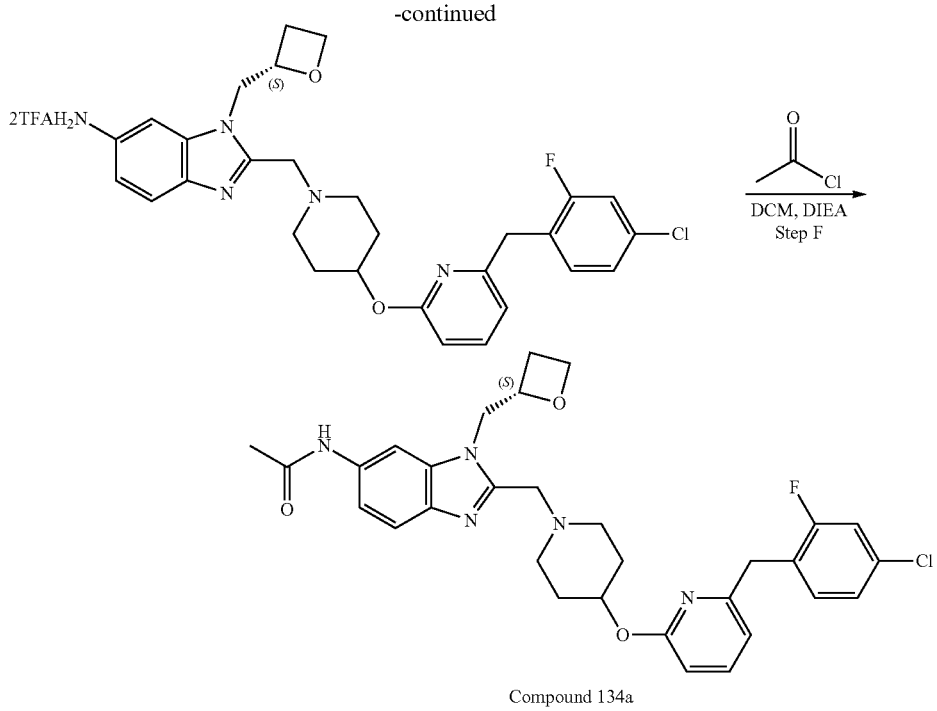

Compound 134a

Step B: Synthesis of tert-butyl (S)-(4-amino-3-((oxetan-2-ylmethyl)amino)phenyl)carbamate A mixture of tert-butyl (S)-(4-nitro-3-((oxetan-2-ylmethyl)amino)phenyl)carbamate (1.1 g, 3.4 mmol), and Pd/C (110 mg, 50% in water) in MeOH (15 mL) was stirred at room temperature under H₂ atmosphere for 2 hours. The mixture was filtered and concentrated under reduced pressure to give tert-butyl (S)-(4-amino-3-((oxetan-2-ylmethyl)amino)phenyl)carbamate (0.83 g, yield: 83%).

MS Calcd.: 293.2. MS Found: 294.1 [M+H]⁺.

Step C: Synthesis of tert-butyl (S)-(2-(chloromethyl)-1-(oxetan-2-ylmethyl)-1H-benzo[d]imidazol-6-yl)carbamate A mixture of tert-butyl (S)-(4-amino-3-((oxetan-2-ylmethyl)amino)phenyl)carbamate (0.83 g, 2.8 mmol) and 2-chloroacetic anhydride (0.53 g, 3.1 mmol) in THF (15 mL) was stirred at 60° C. for 12 hours. The mixture was concentrated under reduced pressure and the residue purified by column chromatography to give tert-butyl (S)-(2-(chloromethyl)-1-(oxetan-2-ylmethyl)-1H-benzo[d]imidazol-6-yl)carbamate (0.87 g, yield: 72%).

MS Calcd.: 351.1. MS Found: 352.0 [M+H]⁺.

Step D: Synthesis of tert-butyl (S)-(2-((4-((6-(4-chloro-2-fluorobenzyl)pyridin-2-yl)oxy)piperidin-1-yl)methyl)-1-(oxetan-2-ylmethyl)-1H-benzo[d]imidazol-6-yl)carbamate A mixture of tert-butyl (S)-(2-(chloromethyl)-1-(oxetan-2-ylmethyl)-1H-benzo[d]imidazol-6-yl)carbamate (0.87 g, 2.5 mmol), 2-(4-chloro-2-fluorobenzyl)-6-(piperidin-4-yloxy)pyridine TFA salt (1.1 g, 2.5 mmol) and K₂CO₃ (1.03 g, 7.4 mmol) in DMF (12 mL) was stirred at 60° C. for 3 hours. The mixture was diluted with ethyl acetate (10 mL) and washed with water and brine. The organic layer was separated and dried over Na₂SO₄, filtered, and concentrated in vacuum. The residue was purified by column chromatography to give tert-butyl (S)-(2-((4-((6-(4-chloro-2-fluorobenzyl)pyridin-2-yl)oxy)piperidin-1-yl)methyl)-1-(oxetan-2-ylmethyl)-1H-benzo[d]imidazol-6-yl)carbamate (1.1 g, yield: 75%).

MS Calcd.: 635.3. MS Found: 636.0 [M+H]⁺.

Step E: Synthesis of (S)-2-((4-((6-(4-chloro-2-fluorobenzyl)pyridin-2-yl)oxy)piperidin-1-yl)methyl)-1-(oxetan-2-ylmethyl)-1H-benzo[d]imidazol-6-amine TFA Salt To a solution of tert-butyl (S)-(2-((4-((6-(4-chloro-2-fluorobenzyl)pyridin-2-yl)oxy)piperidin-1-yl)methyl)-1-(oxetan-2-ylmethyl)-1H-benzo[d]imidazol-6-yl)carbamate (35 mg, 0.056 mmol) in DCM (1 mL) was added TFA (0.4 mL). The resulting mixture was stirred at room temperature for 1 hours. The solvent was removed under vacuum to give (S)-2-((4-((6-(4-chloro-2-fluorobenzyl)pyridin-2-yl)oxy)piperidin-1-yl)methyl)-1-(oxetan-2-ylmethyl)-1H-benzo[d]imidazol-6-amine TFA salt (40 mg, crude) as brown oil. The crude product was directly used for next step without further purification.

MS Calcd.: 535.2. MS Found: 536.0 [M+H]⁺.

Step F: Synthesis of N-(2-{[4-({6-[(4-chloro-2-fluorophenyl)methyl]pyridin-2-yl}oxy)piperidin-1-yl]methyl}-1-{[(2S)-oxetan-2-yl]methyl}-1H-1,3-benzodiazol-6-yl)acetamide To a solution of (S)-2-((4-((6-(4-chloro-2-fluorobenzyl)pyridin-2-yl)oxy)piperidin-1-yl)methyl)-1-(oxetan-2-ylmethyl)-1H-benzo[d]imidazol-6-amine TFA salt (30 mg, 0.056 mmol) and DIEA (21.6 mg, 0.17 mmol) in DCM (1 mL) was added acetyl chloride (4.8 mg, 0.062 mmol). The reaction mixture was stirred at room temperature for 2 hours. After the reaction was completed, the solvent was removed in vacuo. The residue was purified by Prep-HPLC to give N-(2-{[4-({6-[(4-chloro-2-fluorophenyl)methyl]pyridin-2-yl}oxy)piperidin-1-yl]methyl}-1-{[(2S)-oxetan-2-yl]methyl}-1H-1,3-benzodiazol-6-yl)acetamide (8 mg, yield: 25%) as a white solid.

MS Calcd.: 577.2. MS Found: 578.0 [M+H]⁺.

$^1$H NMR (400 MHz, DMSO-d$_6$): 9.96 (s, 1H), 7.98 (d, J=1.2 Hz, 1H), 7.60 (t, J=8.0 Hz, 1H), 7.47 (d, J=8.4 Hz, 1H), 7.33-7.40 (m, 2H), 7.19-7.25 (m, 2H), 6.81 (d, J=7.2 Hz, 1H), 6.57 (d, J=8.0 Hz, 1H), 5.03-5.10 (m, 1H), 4.77-4.84 (m, 1H), 4.56-4.62 (m, 1H), 4.46-4.53 (m, 2H), 4.33-4.39 (m, 1H), 4.00 (s, 2H), 3.84 (d, J=13.6 Hz, 1H), 3.71 (d, J=13.2 Hz, 1H), 2.62-2.79 (m, 3H), 2.40-2.51 (m, 1H), 2.18-2.28 (m, 2H), 2.05 (s, 3H), 1.80-1.90 (m, 2H), 1.48-1.60 (m, 2H). 19F NMR (377 MHz, DMSO-d6): δ −114.58.

Example 92: (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carboxamide (Compound 200a)

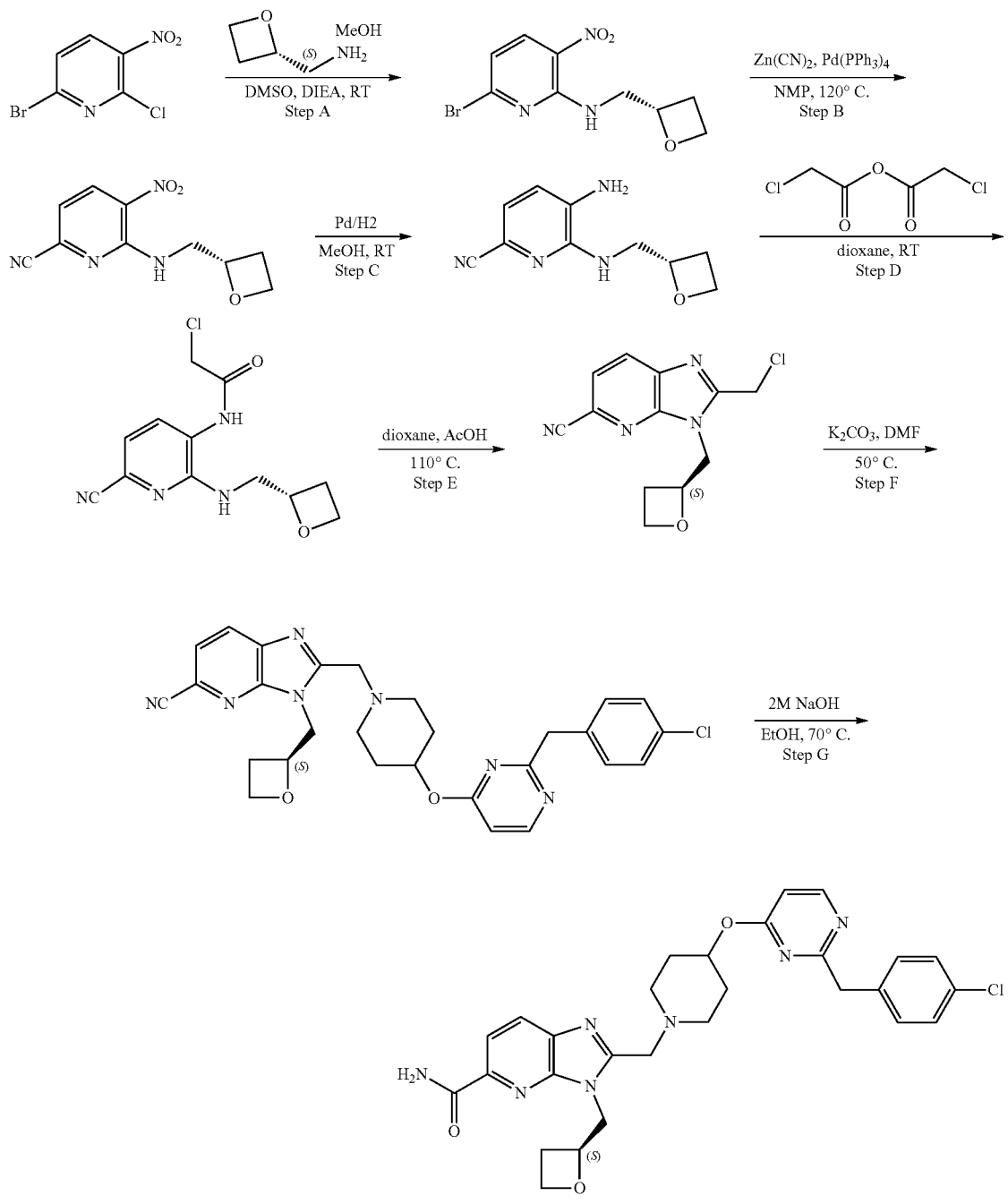

Compound 200a

Step A: Synthesis of (S)-6-bromo-3-nitro-N-(oxetan-2-ylmethyl)pyridin-2-amine A mixture of 6-bromo-2-chloro-3-nitropyridine (1.0 g, 4.24 mmol), (S)-oxetan-2-ylmethanamine MsOH salt and DIEA (615 mg, 4.24 mmol) in DMSO (10 mL) was stirred at room temperature for 2 hours. The reaction mixture was diluted with DCM (50 mL), washed with $H_2O$ (20 mL×3). The organic layer was dried over anhydrous sodium sulfate, filtered, and evaporated to dryness. The residue was purified by column chromatography (PE/EA=20/1) to give (S)-6-bromo-3-nitro-N-(oxetan-2-ylmethyl)pyridin-2-amine (600 mg, yield: 49%) as a white solid.

MS Calcd.: 287.0, MS Found: 288.0 $[M+H]^+$.

Step B: Synthesis of (S)-5-nitro-6-((oxetan-2-ylmethyl)amino)picolinonitrile A mixture of (S)-6-bromo-3-nitro-N-(oxetan-2-ylmethyl)pyridin-2-amine (600 mg, 2.09 mmol) and $Zn(CN)_2$ (734 mg, 6.27 mmol), sPhos (172 mg, 0.42 mmol) and $Pd(PPh_3)_4$ (192 mg 0.21 mmol) in NMP (8 mL) was stirred at 120° C. for 2 hours. After the reaction was completed, the mixture was filtered. The filtrate was diluted with ethyl acetate (50 mL), washed with $H_2O$ (20 mL×3). The organic layer was dried over anhydrous $Na_2SO_4$, filtered and evaporated in vacuo to dryness. The residue was purified by column chromatography (PE/EA=10/1) to give (S)-5-nitro-6-((oxetan-2-ylmethyl)amino)picolinonitrile (300 mg, yield: 61%).

MS Calcd.: 234.1. MS Found: 235.1$[M+H]^+$.

Step C: Synthesis of (S)-5-amino-6-((oxetan-2-ylmethyl)amino)picolinonitrile A mixture of (S)-5-nitro-6-((oxetan-2-ylmethyl)amino)picolinonitrile (300 mg, 1.28 mmol) and Pd/C (678 mg, 6.4 mmol) in MeOH (5 mL) was stirred at room temperature under $H_2$ (1 atm) for 1 hour. After the reaction was completed, the reaction mixture was filtered and dried to give (S)-5-amino-6-((oxetan-2-ylmethyl)amino)picolinonitrile (200 mg, yield: 77%).

MS Calcd.: 204.1. MS Found: 205.2 $[M+H]^+$.

Step D: Synthesis of (S)-2-chloro-N-(6-cyano-2-((oxetan-2-ylmethyl)amino)pyridin-3-yl)acetamide A mixture of (S)-5-amino-6-((oxetan-2-ylmethyl)amino)picolinonitrile (200 mg, 0.98 mmol) and chloroacetic anhydride (330 mg, 1.18 mmol) in dioxane (3 mL) was stirred at room temperature for 16 hours. After the reaction was completed, the reaction mixture was diluted with ethyl acetate (50 mL), washed with $H_2O$ (10 mL×3). The residue was purified by column chromatography (PE/EtOAc=1/1) to give (S)-2-chloro-N-(6-cyano-2-((oxetan-2-ylmethyl)amino)pyridin-3-yl)acetamide (240 mg, yield: 88%).

MS Calcd.: 280.1. MS Found: 281.1 $[M+H]^+$.

Step E: Synthesis of (S)-2-(chloromethyl)-3-(oxetan-2-ylmethyl)-3H-imidazo[4,5-b]pyridine-5-carbonitrile A mixture of (S)-2-chloro-N-(6-cyano-2-((oxetan-2-ylmethyl)amino)pyridin-3-yl)acetamide (240 mg, 0.86 mmol) and AcOH (0.1 mL) in dioxane (5 mL) was stirred at 100° C. for 5 hours. After the reaction was completed, the reaction mixture was diluted with ethyl acetate (20 mL), washed with $H_2O$ (10 mL×3). The organic layer was dried over anhydrous $Na_2SO_4$, filtered and evaporated in vacuo to dryness. The residue was purified by column chromatography (PE/EtOAc=1/2) to give (S)-2-(chloromethyl)-3-(oxetan-2-ylmethyl)-3H-imidazo[4,5-b]pyridine-5-carbonitrile (60 mg, yield: 27%).

MS Calcd.: 262.1. MS Found: 263.0 $[M+H]^+$.

Step F: Synthesis of (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carbonitrile A mixture of (S)-2-(chloromethyl)-3-(oxetan-2-ylmethyl)-3H-imidazo[4,5-b]pyridine-5-carbonitrile (60 mg, 0.23 mmol) and 2-(4-chlorobenzyl)-4-(piperidin-4-yloxy)pyrimidine (84 mg, 0.28 mmol) in DMF (3 mL) was stirred at 50° C. for 1 hour. After the reaction was completed, the mixture was diluted with ethyl acetate (10 mL), washed with $H_2O$ (20 mL×3). The organic layer was dried over anhydrous $Na_2SO_4$ and evaporated in vacuo to dryness. The residue was purified by column chromatography (DCM/MeOH=20/1) to give (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carbonitrile (60 mg, yield: 50%).

MS Calcd.: 529.2. MS Found: 530.2 $[M+H]^+$.

Step G: Synthesis of (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carboxamide A mixture of (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carbonitrile (50 mg, 0.09 mmol) and 2 M NaOH (0.05 mL, 0.27 mmol) in EtOH (1 mL) was stirred at 50° C. for 2 hours. After the reaction was completed, the solvent was removed in vacuo. The reaction mixture was purified by prep-HPLC to give (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carboxamide (2.8 mg, yield: 5.7%). MS Calcd.: 547.2; MS Found: 548.2 $[M+H]^+$.

$^1$H NMR (400 MHz, DMSO-$d_6$): δ 8.41 (d, J=5.6 Hz, 1H), 8.20 (brs, 1H), 8.13 (d, J=8.0 Hz, 1H), 7.95 (d, J=8.4 Hz, 1H), 7.58 (brs, 1H), 7.31-7.36 (m, 4H), 6.72 (d, J=6.0 Hz, 1H), 5.14-5.20 (m, 1H), 4.80-5.07 (m, 1H), 4.84-4.90 (m, 1H), 4.72-4.79 (m, 1H), 4.43-4.51 (m, 1H), 4.37-4.42 (m, 1H), 4.08 (s, 2H), 3.98 (d, J=13.6 Hz, 1H), 3.92 (d, J=13.6 Hz, 1H), 2.66-2.80 (m, 3H), 2.32-2.45 (m, 3H), 1.90-1.97 (m, 2H), 1.58-1.71 (m, 2H).

Example 93: (S)-2-((4-((2-(4-chlorobenzyl)pyrimi-din-4-yl)oxy)piperidin-1-yl)methyl)-3-(oxetan-2-ylmethyl)-5-(1H-tetrazol-5-yl)-3H-imidazo[4,5-b]pyridine (Compound 199a)

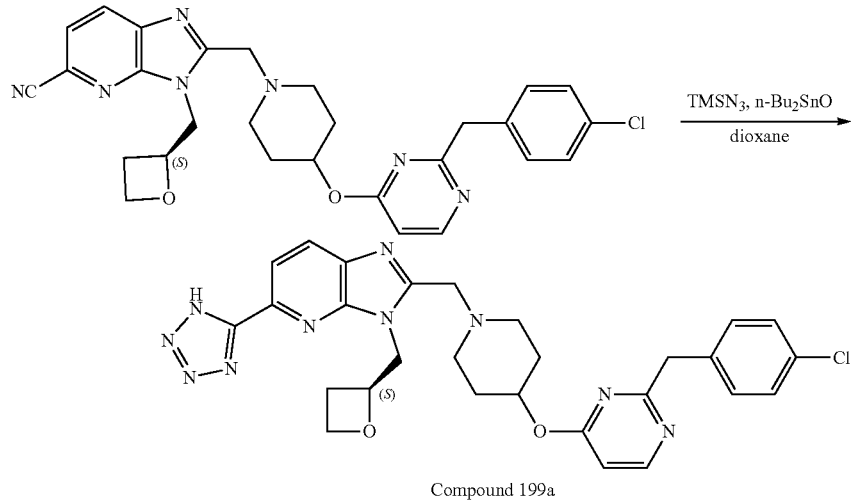

Compound 199a

To a mixture of (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carbonitrile (30 mg, 0.06 mmol) and TMSN$_3$ (35 mg, 0.31 mmol) in dioxane (2 mL) was added dibutyl(oxo)tin (30 mg, 0.12 mmol), the reaction mixture was stirred at 90° C. for 3 hours. After the reaction was completed, the solvent was removed in vacuo. The reaction mixture was purified by Prep-HPLC to give (S)-2-((4-((2-(4-chlorobenzyl)pyrimidin-4-yl)oxy)piperidin-1-yl)methyl)-3-(oxetan-2-ylmethyl)-5-(1H-tetrazol-5-yl)-3H-imidazo[4,5-b]pyridine (5.8 mg, yield: 18%). MS Calcd.: 572.2. MS Found: 573.2 [M+H]$^+$.

$^1$H NMR (400 MHz, DMSO-d$_6$): δ 8.41 (d, J=6.0 Hz, 1H), 8.13-8.20 (m, 1H), 8.06 (d, J=8.0 Hz, 1H), 7.30-7.37 (m, 4H), 6.73 (d, J=5.6 Hz, 1H), 5.18-5.27 (m, 1H), 4.98-5.08 (m, 1H), 4.80-4.90 (m, 1H), 4.70-4.80 (m, 1H), 4.45-4.55 (m, 1H), 4.38-4.44 (m, 1H), 4.08 (s, 2H), 3.90-4.02 (m, 2H), 2.65-2.85 (m, 3H), 2.30-2.51 (m, 3H), 1.91-2.00 (m, 2H), 1.60-1.73 (m, 2H).

Example 94: (S)-3-(2-((4-((2-(4-chlorobenzyl)py-rimidin-4-yl)oxy)piperidin-1-yl)methyl)-3-(oxetan-2-ylmethyl)-3H-imidazo[4,5-b]pyridin-5-yl)-1,2,4-oxadiazol-5(4H)-one (Compound 198a)

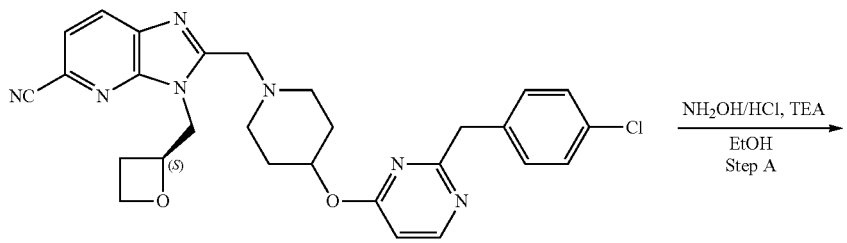

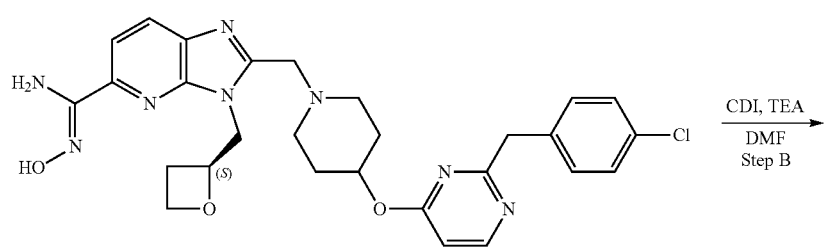

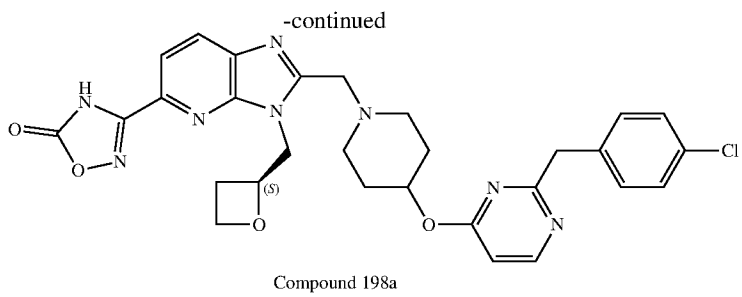

Compound 198a

Step A: Synthesis of (S,Z)-2-((4-((2-(4-chlorobenzyl)pyrimidin-4-yl)oxy)piperidin-1-yl)methyl)-N'-hydroxy-3-(oxetan-2-ylmethyl)-3H-imidazo[4,5-b]pyridine-5-carboximidamide To a mixture of (S)-2-((4-((2-(4-chlorobenzyl)pyrimidin-4-yl)oxy)piperidin-1-yl)methyl)-3-(oxetan-2-ylmethyl)-3H-imidazo[4,5-b]pyridine-5-carbonitrile (50 mg, 0.09 mmol) and hydroxylamine hydrochloride (13 mg, 0.18 mmol) in EtOH (2 mL) was added TEA (0.04 ml, 0.27 mmol), the reaction mixture was stirred at 90° C. for 1 hours. After the reaction was completed, the solvent was removed in vacuo. The reaction mixture was purified by prep-HPLC to give (S,Z)-2-((4-((2-(4-chlorobenzyl)pyrimidin-4-yl)oxy)piperidin-1-yl)methyl)-N'-hydroxy-3-(oxetan-2-ylmethyl)-3H-imidazo[4,5-b]pyridine-5-carboximidamide (50 mg, yield: 94%).

MS Calcd.: 562.2. MS Found: 563.2 [M+H]$^+$.

Step B: Synthesis of (S)-3-(2-((4-((2-(4-chlorobenzyl)pyrimidin-4-yl)oxy)piperidin-1-yl)methyl)-3-(oxetan-2-ylmethyl)-3H-imidazo[4,5-b]pyridin-5-yl)-1,2,4-oxadiazol-5(4H)-one To a mixture of (S,Z)-2-((4-((2-(4-chlorobenzyl)pyrimidin-4-yl)oxy)piperidin-1-yl)methyl)-N'-hydroxy-3-(oxetan-2-ylmethyl)-3H-imidazo[4,5-b]pyridine-5-carboximidamide (50 mg, 0.09 mmol) and CDI (22 mg, 0.14 mmol) in DMF (2 mL) was added TEA (0.04 ml, 0.27 mmol), the reaction mixture was stirred at 50° C. for 3 hours. After the reaction was completed, the solvent was removed in vacuo. The reaction mixture was purified by prep-HPLC to give (S)-3-(2-((4-((2-(4-chlorobenzyl)pyrimidin-4-yl)oxy)piperidin-1-yl)methyl)-3-(oxetan-2-ylmethyl)-3H-imidazo[4,5-b]pyridin-5-yl)-1,2,4-oxadiazol-5(4H)-one (6.7 mg, yield: 13%). MS Calcd.: 588.2. MS Found: 589.1 [M+H]$^+$.

$^1$H NMR (400 MHz, DMSO-d$_6$): δ 8.41 (d, J=6.0 Hz, 1H), 8.20 (br s, 1H), 8.03-8.10 (m, 1H), 7.75-7.81 (m, 1H), 7.31-7.36 (m, 4H), 6.73 (d, J=5.6 Hz, 1H), 5.11-5.21 (m, 1H), 4.95-5.08 (m, 1H), 4.75-4.85 (m, 1H), 4.60-4.75 (m, 1H), 4.46-4.53 (m, 1H), 4.34-4.41 (m, 1H), 4.08 (s, 2H), 3.85-4.00 (m, 2H), 2.65-2.80 (m, 3H), 2.32-2.46 (m, 3H), 1.90-1.97 (m, 2H), 1.60-1.72 (m, 2H).

Example A: cAMP Assays

Activation of GLP-1 receptor is known to stimulate cyclic AMP (cAMP) production in cells which indicates primary coupling to the $G_{\alpha S}$ subunit of the G protein heterotrimeric complex. Evidence suggests signaling through $G_{\alpha S}$ induced cAMP stimulation elicits the desired pharmacological response regarding insulin release from pancreatic β-cells.

To optimize functional activity directed toward $G_{\alpha S}$ coupling, a HEK293/CRE-Luc cell line developed by HDB stably expressing the GLP-1 Receptor was used. 200× concentration of compound working solutions were prepared (Agilent Technologies Bravo) with 1/2 log serial dilution in 384-well Echo LDV plate (Labcyte, Cat #LP-0200). 50 nL/well 200× concentration of compound working solutions were moved to 384-well white low volume plate (Greiner, Cat #784075) using Labcyte ECHO550. 1×10$^5$ cells/mL HEK293/GLP1R/CRE-LUC(HD Biosciences) cell suspensions prepared with assay buffer[DPBS containing 0.5 mM IBMX(Sigma, Cat #15879) and 0.1% BSA (GENVIEW, Cat #FA016-100g)], 10 uL cell suspensions were added to each well of previous generated assay plate which already contains 50n1 compound at 200× concentration using ThermoFisher Multidrop Combi (1000 cells/well). Seal the plate and incubate at 37° C. with 5% CO$_2$ for 30 min.

After incubation the cAMP assay signal was generated using cAMP dynamic 2 Kit (Cisbio). 5 µL cAMP-d2 working solution was added to each well, followed with 5 µL Anti-cAMP antibody-cryptate working solution added to each well using ThermoFisher Multidrop Combi. Incubate at room temperature for 1 hour protected from light. Read the fluorescence at 665 and 615 nm with Reader PerkinElmer EnVision.

% Activity =

100%×(mean *RLU* of test sample − mean *RLU* of vehicle control)/

(mean *RLU* of MAX control − mean *RLU* of vehicle control))

Table 1 shows the biological activity of compounds in GLP-1R agonist cAMP stimulation assay (EC$_{50}$)

| Compound No. | GLP1R cAMP Stimulation DR: EC$_{50}$ (nM) | GLP1R cAMP Stimulation DR: pEC$_{50}$ |
|---|---|---|
| 101a | 290 | 6.54 |
| 102a | 179 | 6.75 |
| 103a | 19.6 | 7.71 |
| 104a | 725 | 6.14 |
| 105a | 497 | 6.3 |
| 106a | 463 | 6.33 |
| 107a | 201 | 6.7 |
| 108a | 1.2 | 8.92 |
| 109a | 0.051 | 10.3 |
| 111a | 0.29 | 9.5 |
| 113a | 0.038 | 10.4 |
| 114a | 1.7 | 8.8 |
| 116a | 2.8 | 8.6 |
| 118a | 30 | 7.5 |

| Compound No. | GLP1R cAMP Stimulation DR: $EC_{50}$ (nM) | GLP1R cAMP Stimulation DR: $pEC_{50}$ |
|---|---|---|
| 121a | 6.5 | 8.2 |
| 123a | 1.7 | 8.8 |
| 124a | 0.043 | 10.4 |
| 125a | 1.4 | 8.9 |
| 126a | 1 | 9 |
| 127a | 13 | 7.9 |
| 128a | 1.2 | 8.9 |
| 129a | 0.91 | 9 |
| 130a | 53 | 7.3 |
| 133a | 2.4 | 8.6 |
| 134a | 58 | 7.2 |
| 135a | 1.8 | 8.7 |
| 136a | 0.44 | 9.4 |
| 137a | 51 | 7.3 |
| 138a | 1.6 | 8.8 |
| 139a | 1.9 | 8.7 |
| 140a | 1.2 | 8.9 |
| 141a | 5 | 8.3 |
| 142a | 1.7 | 8.8 |
| 143a | 0.53 | 9.3 |
| 144a | 4.8 | 8.3 |
| 145a | 3.4 | 8.5 |
| 146a | 0.62 | 9.2 |
| 147a | 0.2 | 9.7 |
| 148a | 4.4 | 8.4 |
| 149a | 5.6 | 8.3 |
| 150a | 68 | 7.2 |
| 151a | 0.085 | 10.1 |
| 152a | 0.038 | 10.4 |
| 153a | 0.14 | 9.8 |
| 154a | 24 | 7.6 |
| 155a | 3.8 | 8.4 |
| 156a | 40 | 7.4 |
| 157a | 42 | 7.4 |
| 158a | >1000 | <6.0 |
| 159a | 2.3 | 8.6 |
| 160a | 0.12 | 9.9 |
| 161a | 0.18 | 9.7 |
| 162 | 0.075 | 10.1 |
| 163a | 0.11 | 10 |
| 164a | 0.11 | 10 |
| 165a | 0.4 | 9.4 |
| 166a | 1 | 9 |
| 167a | 0.13 | 9.9 |
| 168a | 1.2 | 8.9 |
| 169a | 80 | 7.1 |
| 170a | 0.79 | 9.1 |
| 171a | 6 | 8.2 |
| 172a | 0.81 | 9.1 |
| 173a | 3.8 | 8.4 |
| 174a | 29 | 7.5 |
| 174b | 0.14 | 9.9 |
| 175a | 230 | 6.6 |
| 175b | 0.063 | 10.2 |
| 176a | 0.37 | 9.4 |
| 177a | 0.042 | 10.4 |
| 178a | 0.1 | 10 |
| 179a | 2.8 | 8.6 |
| 180a | 2.3 | 8.6 |
| 181a | 0.083 | 10.1 |
| 182a | 0.07 | 10.2 |
| 183a | 0.85 | 9.1 |
| 184a | 90 | 7 |
| 185a | 0.47 | 9.3 |
| 186a | 0.6 | 9.2 |
| 187a | 1.3 | 8.9 |
| 188a | 0.045 | 10.3 |
| 189a | 0.69 | 9.2 |
| 190a | 0.41 | 9.4 |
| 191a | 0.29 | 9.5 |
| 192a | 130 | 6.9 |
| 193 | 0.19 | 9.7 |
| 194 | 2.9 | 8.5 |
| 195 | 0.6 | 9.2 |
| 196a | 1.3 | 8.9 |
| 197a | 2.5 | 8.6 |
| 198a | 0.7 | 9.2 |
| 199a | 0.95 | 9 |
| 200a | 85 | 7.1 |
| 201a | 360 | 6.4 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I:

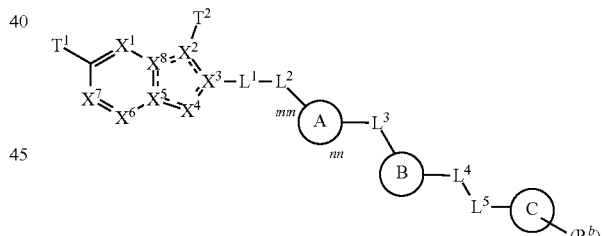

Formula I or a pharmaceutically acceptable salt or solvate thereof, wherein the moiety:

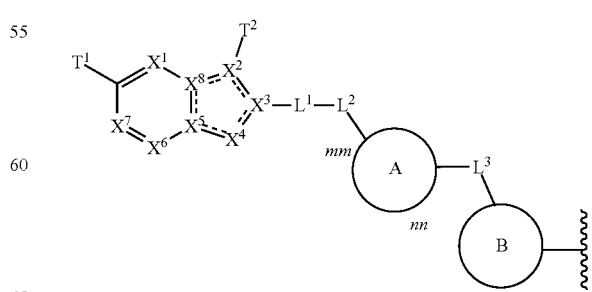

is represented by the moiety of Formula (I-A):

Formula I-A

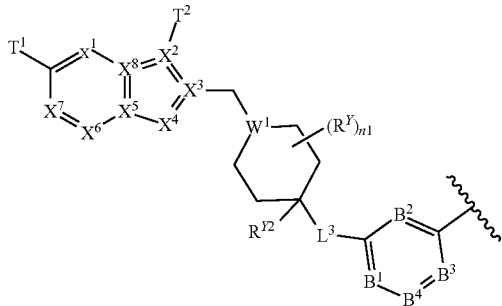

wherein:
L³ is —O—;
⌒ indicates an optional single or double bond, as allowed by valence;
X³, X⁵, and X⁸ are C; X² and X⁴ are N; X⁶ and X¹ are CH; and X¹ is CH or N;
T¹ is C(=O)OH;
T² is hydrogen or (C₁-C₆) alkyl which is optionally substituted with (C₁-C₆) alkoxy, (C₁-C₆) thioalkoxy, (C₁-C₆) haloalkoxy, S(O)₂(C₁-C₆ alkyl), (C₃-C₆) cycloalkyl, 3- to 6-membered heterocycloalkyl, phenyl, or 5- to 6-membered heteroaryl, wherein each of the (C₃-C₆) cycloalkyl, 3- to 6-membered heterocycloalkyl, phenyl, or 5- to 6-membered heteroaryl is optionally substituted with 1-4 R$^T$;
each R$^T$ is independently selected from the group consisting of OH, SH, CN, NO₂, halogen, (C₁-C₆)alkyl, (C₂-C₆)alkenyl, (C₂-C₆)alkynyl, (C₁-C₆)haloalkyl, (C₁-C₆)cyanoalkyl, (C₁-C₆)hydroxyalkyl, (C₁-C₆) alkoxy, (C₁-C₆)haloalkoxy, (C₃-C₆)cycloalkyl, amino, (C₁-C₆)alkylamino, and di(C₁-C₆)alkylamino;
n1 is 0, 1, or 2;
W¹ is CR$^{Y1}$ or N;
each occurrence of R$^Y$ is independently selected from the group consisting of halogen, CN, —OH, oxo, (C₁-C₆) alkyl, (C₁-C₃)haloalkyl, (C₁-C₃)alkoxy, and (C₁-C₃) haloalkoxy;
R$^{Y1}$ and R$^{Y2}$ are independently selected from the group consisting of hydrogen, halogen, CN, —OH, (C₁-C₆) alkyl, (C₁-C₃)haloalkyl, (C₁-C₃)alkoxy, and (C₁-C₃) haloalkoxy; or
when W¹ is CR$^{Y1}$; the R$^{Y1}$ and R$^{Y2}$ groups taken together form (C₁-C₄)alkylene, wherein one of the CH₂ units of the (C₁-C₄)alkylene is optionally replaced by a heteroatom selected from the group consisting of O, S, NH, and N(C₁-₃)alkyl;
each of B¹, B², B³, and B⁴ is independently selected from the group consisting of CR¹ and N;
each R¹ is selected from the group consisting of hydrogen, halogen, CN, (C₁-C₆)alkyl, (C₁-C₆)haloalkyl; (C₁-C₃) alkyl(C₃-C₆)cycloalkyl, (C₁-C₃)alkyl(3- to 5-membered heterocycloalkyl), and —C(O)NR²R³;
each R² and R³ is independently selected from the group consisting of hydrogen and (C₁-C₆)alkyl;
L⁴ is selected from the group consisting of: —C(R$^c$R$^c$)—; —O—; —S—; —N(C₁-₃ alkyl)-; —C(=O)—; and —S(O)₁₋₂—,
L⁵ is selected from the group consisting of: a bond; —C(R$^c$R$^c$)—; —O—; —S—; —N(H)—; —N(C₁-₃ alkyl)-; —C(=O)—; and —S(O)₁₋₂—, provided that when L⁴ is —O—, —S—, or —N(C₁-₃ alkyl)-, then L⁵ is a bond, —C(R$^c$R$^c$)—, —C(=O), or —S(O)₁₋₂—, and
provided that when L⁵ is —O—, —S—, —N(H)—, or —N(C₁-₃ alkyl)-, then L⁴ is —C(R$^c$R$^c$)—, —C(=O), or —S(O)₁₋₂—;
each occurrence of R$^c$ is independently selected from the group consisting of: hydrogen, halogen, CN, —OH, (C₁-C₆)alkyl, (C₁-C₃)haloalkyl, (C₃-C₈)cycloalkyl, (C₁-C₃)alkoxy, and (C₁-C₃)haloalkoxy; or
a pair of R$^c$ taken together with the carbon atom to which each is attached forms a (C₃-C₈)cycloalkyl ring;
Ring C is selected from the group consisting of phenyl, 5- to 6-membered heteroaryl, (C₃-C₆)cycloalkyl, (C₅-C₁₀) bicycloalkyl, 5- to 10-membered bicycloheteroaryl, and 3- to 6-membered heterocycloalkyl;
each R$^b$ is independently selected from the group consisting of (C₁-C₆)alkyl, (C₁-C₆)haloalkyl, (C₁-C₆)alkoxy, (C₁-C₆)haloalkoxy, halogen, (C₃-C₆)cycloalkyl, and CN; and
b is an integer selected from 0-3.

2. The compound of claim 1, or a pharmaceutically acceptable salt or solvate thereof, wherein the compound is selected from the group consisting of:

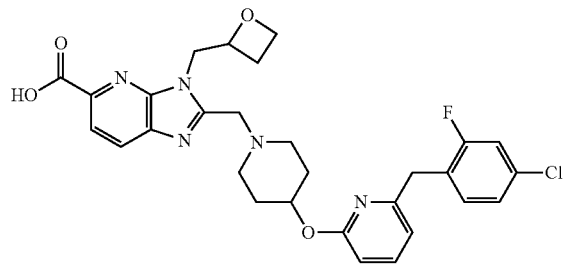

109

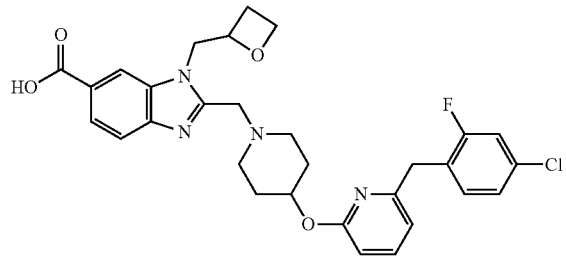

110

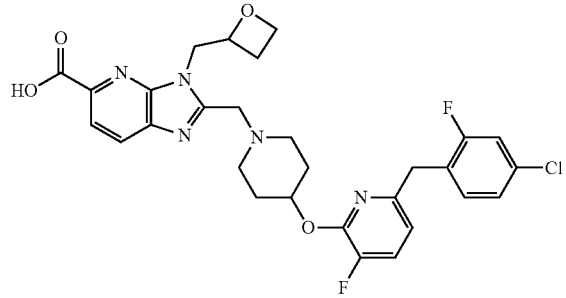

111

112
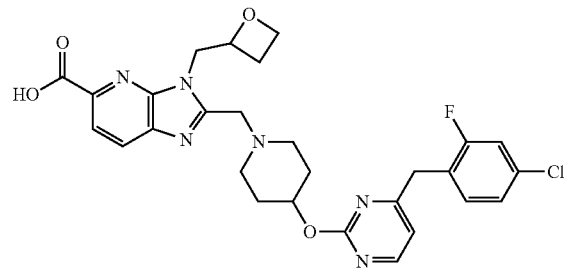
113
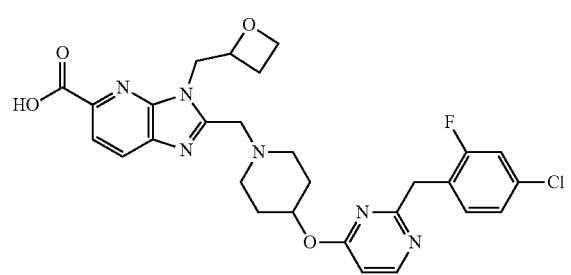
114
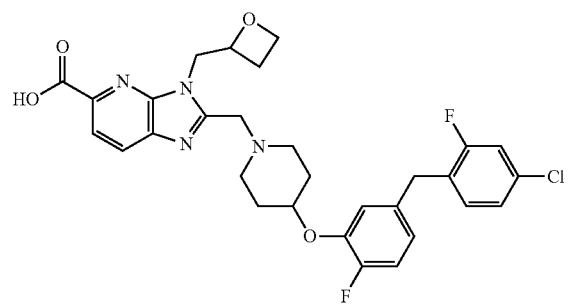
118
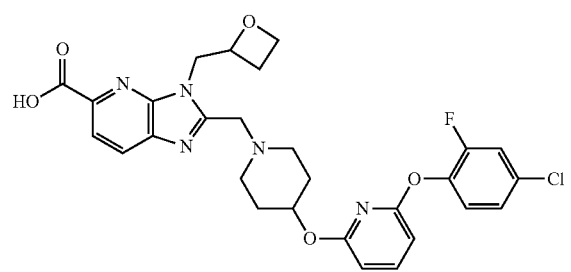
123
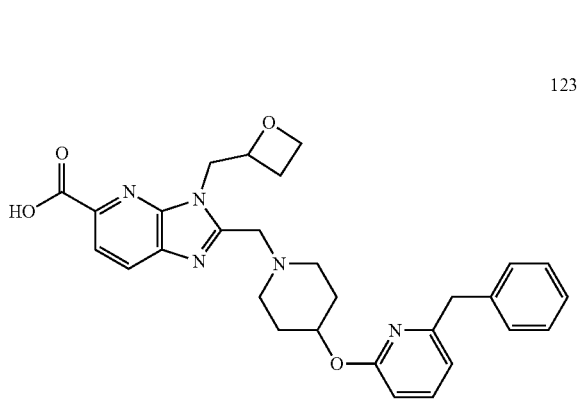
124
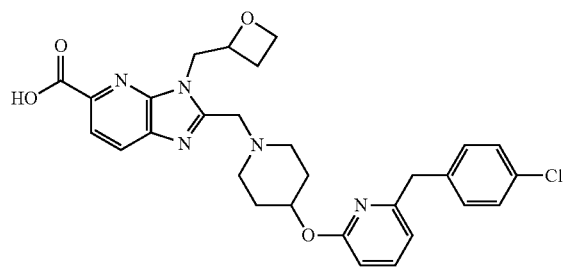
125
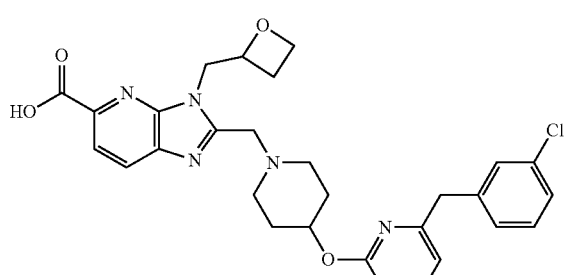
126
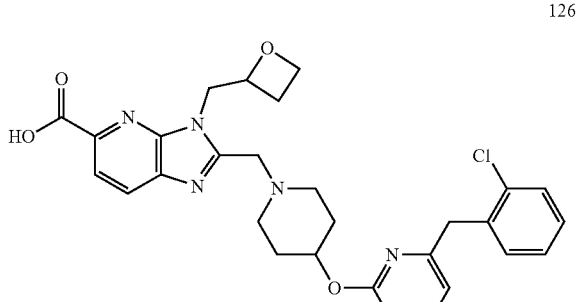
127
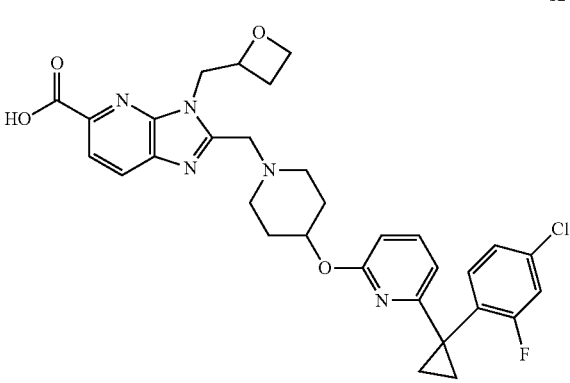
128
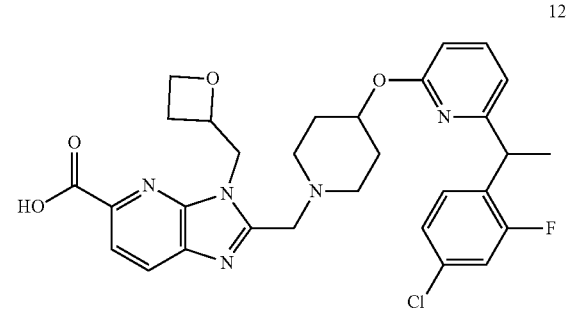

129
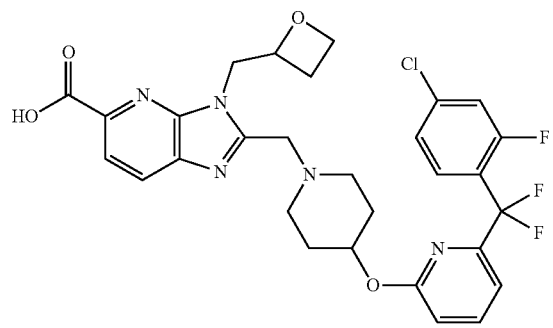
132
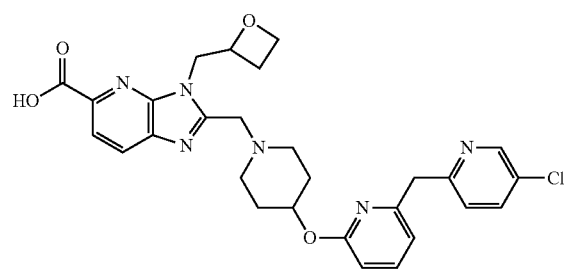
3. The compound of claim 1, or a pharmaceutically acceptable salt or solvate thereof, wherein the compound is selected from the group consisting of:
109a
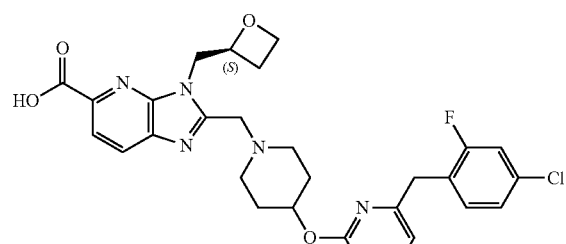
110a
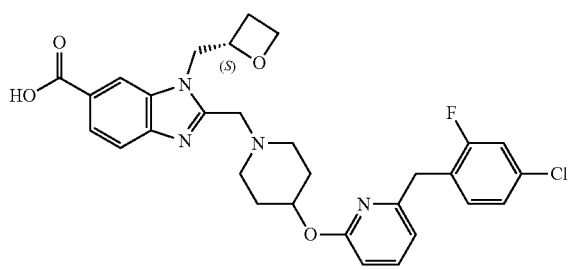
111a
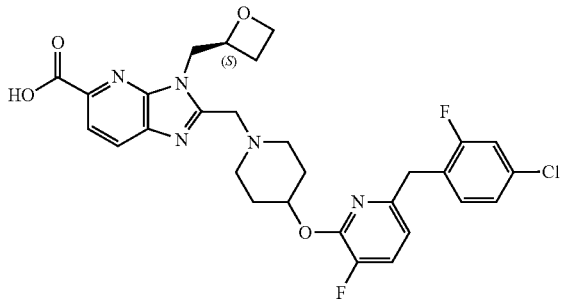
112a
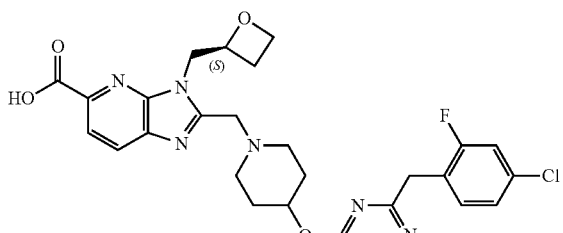
113a
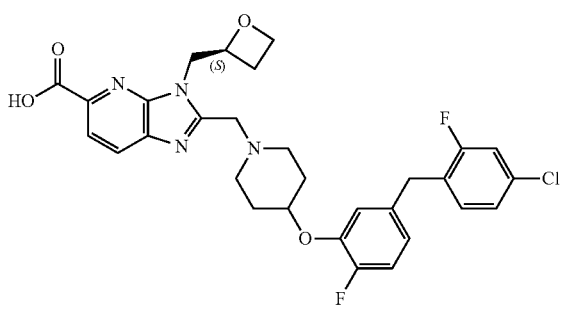
114a
118a
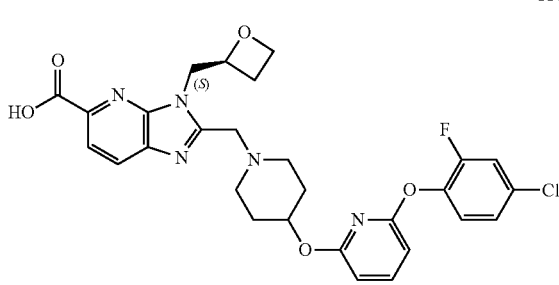

311
-continued
123a
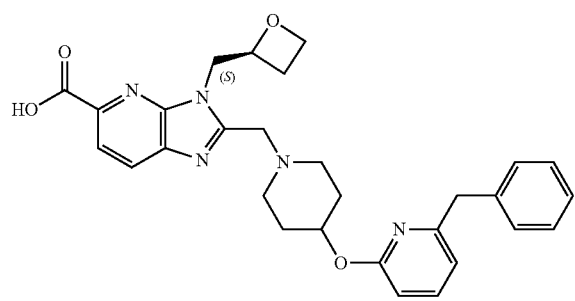
124a
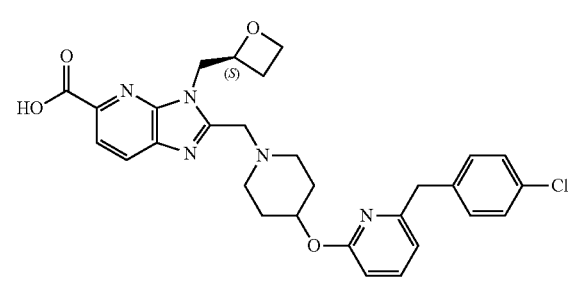
125a
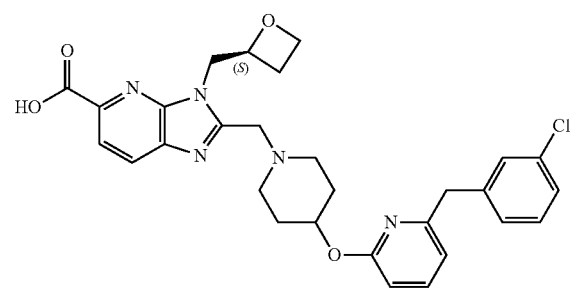
126a
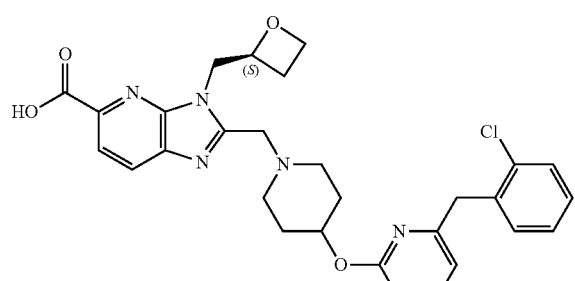
312
-continued
127a
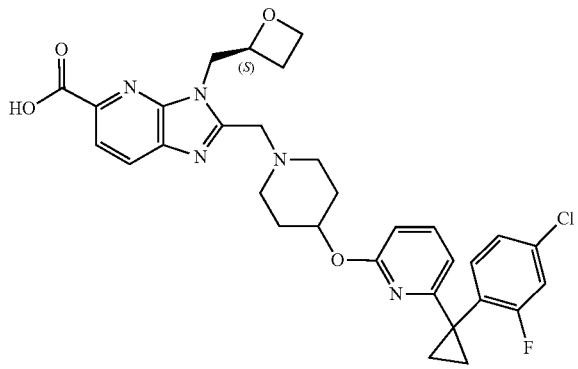
128a
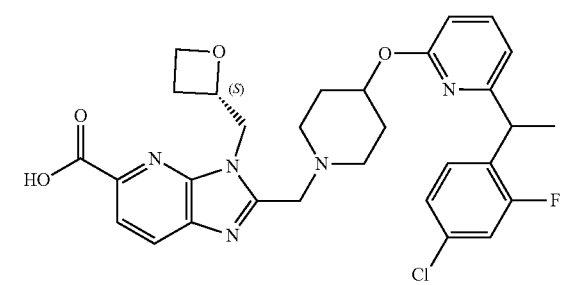
129a
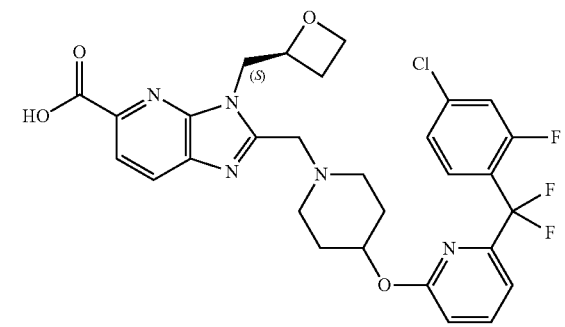
132a
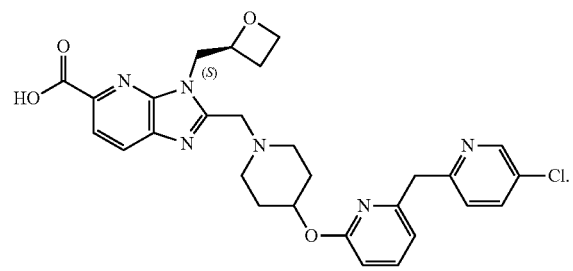
4. A pharmaceutical composition comprising a compound of claim 1, or a pharmaceutically acceptable salt or solvate thereof, and a pharmaceutically acceptable excipient.
* * * * *

UNITED STATES PATENT AND TRADEMARK OFFICE
CERTIFICATE OF CORRECTION

PATENT NO. : 12,221,442 B2
APPLICATION NO. : 18/424580
DATED : February 11, 2025
INVENTOR(S) : Qinghua Meng et al.

Page 1 of 3

It is certified that error appears in the above-identified patent and that said Letters Patent is hereby corrected as shown below:

In the Claims

In Claim 2, Column 309, Line 15, please replace " 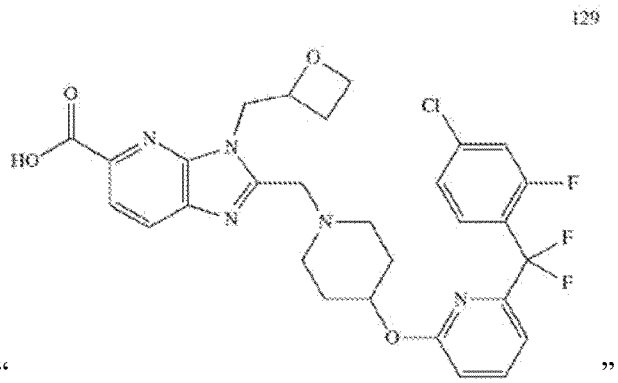  "

with -- 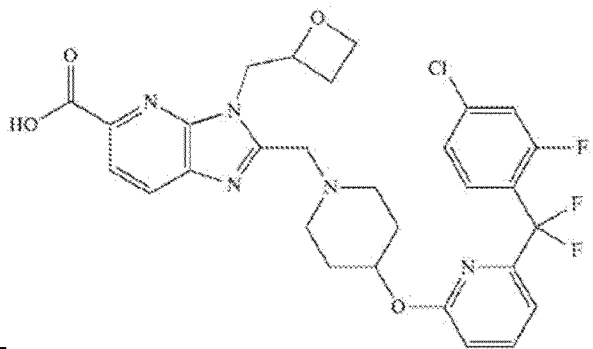 and --

Signed and Sealed this
Fifteenth Day of April, 2025

Coke Morgan Stewart
*Acting Director of the United States Patent and Trademark Office*

CERTIFICATE OF CORRECTION (continued)
U.S. Pat. No. 12,221,442 B2

In Claim 2, Column 309, Line 25, please replace " 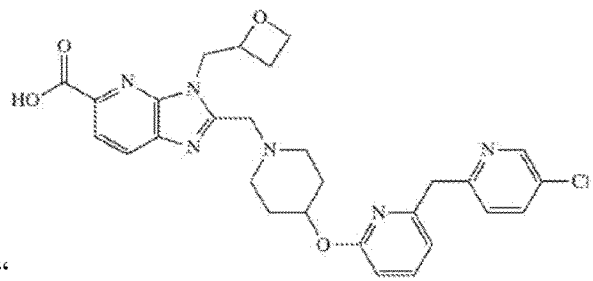 "

with -- 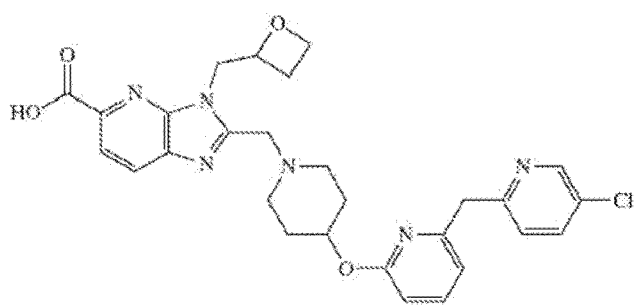 --

In Claim 3, Column 312, Line 40, please replace " 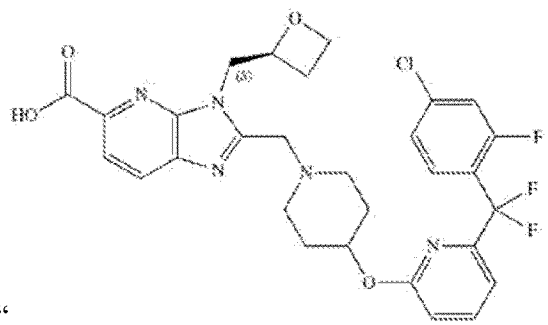 "

with -- 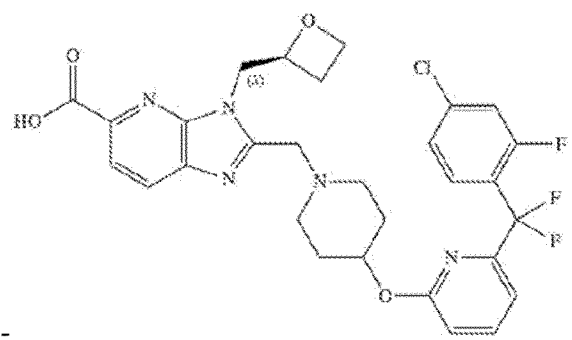 and --

CERTIFICATE OF CORRECTION (continued)
U.S. Pat. No. 12,221,442 B2

In Claim 3, Column 312, Line 50, please replace " 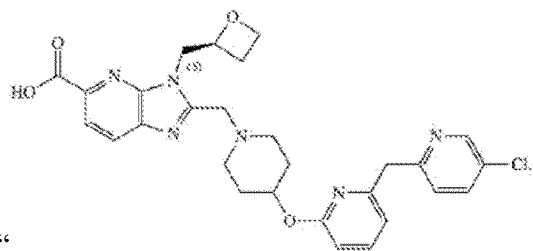 " with

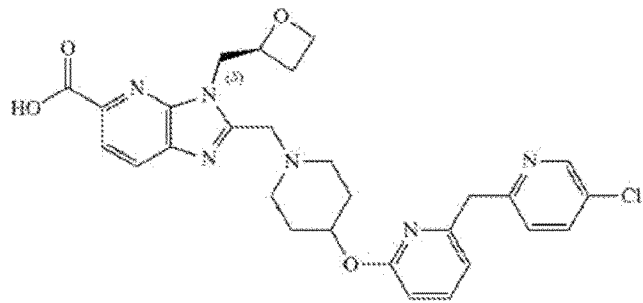

--